US006846802B2

(12) United States Patent
Chen et al.

(10) Patent No.: US 6,846,802 B2
(45) Date of Patent: Jan. 25, 2005

(54) MACROCYCLIC NS3-SERINE PROTEASE INHIBITORS OF HEPATITIS C VIRUS COMPRISING N-CYCLIC P2 MOIETIES

(75) Inventors: Kevin X. Chen, Piscataway, NJ (US); Ashok Arasappan, Bridgewater, NJ (US); Srikanth Venkatraman, Fords, NJ (US); Tejal Parekh, Woodbridge, NJ (US); Haining Gu, Minhang (CN); George F. Njoroge, Union, NJ (US); Viyyoor Moopil Girijavallabhan, Parsippany, NJ (US); Ashit Ganguly, Upper Montclair, NJ (US); Anil Saksena, Upper Montclair, NJ (US); Edwin Jao, Warren, NJ (US); Nanhua Hugh Yao, Edison, NJ (US); Andrew Joseph Prongay, Stewartsville, NJ (US); Vincent Stewart Madison, Mountain Lakes, NJ (US); Bancha Vibulbhan, Kenilworth, NJ (US)

(73) Assignee: Schering Corporation, Kenilworth, NJ (US)

( * ) Notice: Subject to any disclaimer, the term of this patent is extended or adjusted under 35 U.S.C. 154(b) by 459 days.

(21) Appl. No.: 09/825,399

(22) Filed: Apr. 3, 2001

(65) Prior Publication Data

US 2002/0107181 A1 Aug. 8, 2002

Related U.S. Application Data

(60) Provisional application No. 60/194,607, filed on Apr. 5, 2000.

(51) Int. Cl.[7] ............................................... A16K 38/12
(52) U.S. Cl. .......................... 514/9; 514/411; 540/469; 530/317
(58) Field of Search ................................ 514/9, 8, 7, 2, 514/411, 412, 357, 307, 255, 263, 311, 424; 540/469; 530/317, 350, 321, 323; 546/140; 548/338.1, 518

(56) References Cited

U.S. PATENT DOCUMENTS 5,712,145 A    1/1998   Houghton et al.

FOREIGN PATENT DOCUMENTS

| EP | 381 216 | 8/1990 |
|---|---|---|
| WO | WO 89/04669 | 6/1989 |
| WO | WO 98/17679 | 4/1998 |
| WO | WO 98/22496 | 5/1998 |
| WO | WO 99/07734 | 2/1999 |
| WO | WO 99 07734 | 2/1999 |
| WO | WO00/05245 | * 2/2000 |
| WO | WO 00/09543 | 2/2000 |
| WO | WO 00/09558 | 2/2000 |
| WO | WO 00 09558 | 2/2000 |

OTHER PUBLICATIONS

Pizzi, (1994) *Proc. Natl. Acad. Sci(USA)* 91:888–892.
Failla (1996) *Folding & Design*, 1:35–42.
Kollykhalov(1994) *J. Virol.*, 68:7525–7533.
Komoda(1994) *J. Virol* . 68:7351–7357.
Landro (1997) *Biochem.* 36:9340–9348.
Ingallinella (1998) *Biochem.* 37:8906–8914.
Llinas–Brunet(1998)*Bioorg. Med. Chem. Lett.* 8:1713–1718.
Martin (1998) *Biochem.* 37:37:11459–11468.
Dimasi(1997) *J. Virol.* 71:7461–7469.
Martin(1997) *Protein Eng.* 10:607–614.
Elzoukl(1997) *J. Hepat.* 27:42–48.
*BioWorld Today* 9(217): 4(Nov. 10, 1998).
Berenguer(1998)*Proc. Assoc. Am. Physicians*, 110(2):98–112.
Hoofnagle(1997) *New England Journal of Medicine* 336:347.
Zhang (1999) *Analytical Biochemistry* 270:268–275.
Sali(1998) *Biochemistry* 37:3392–3401.
Barlos (1991) *Int. J. Pept. Protein Res.* 37:513–520.
Holmberg(1979)*Acta Chem. Scand* B33:410–412.
Agrawal(1999) *Hepatology* Supplement to vol. 30"Development and Characterization of Hepatitis C Virus Serine Protease Cell–based Trans–Cleavage Assay".
Hughes (1992) *Org. Reactions* 42:335.
Heck (1989) *Org. Reactions* 27:345–390.

* cited by examiner

*Primary Examiner*—Robert A. Wax
*Assistant Examiner*—Robert B Mondesi
(74) *Attorney, Agent, or Firm*—Palaiyur S. Kalyanaraman

(57) ABSTRACT

The present invention discloses novel macrocyclic compounds which have HCV protease inhibitory activity as well as methods for preparing such compounds. In another embodiment, the invention discloses pharmaceutical compositions comprising such macrocycles as well as methods of using them to treat disorders associated with the HCV protease.

21 Claims, No Drawings

MACROCYCLIC NS3-SERINE PROTEASE INHIBITORS OF HEPATITIS C VIRUS COMPRISING N-CYCLIC P2 MOIETIES

This application claims priority from U.S. provisional patent application, Ser. No. 60/194,607 filed Apr. 5, 2000. The present invention relates to novel hepatitis C virus ("HCV") protease inhibitors, pharmaceutical compositions containing one or more such inhibitors, methods of preparing such inhibitors and methods of using such inhibitors to treat hepatitis C and related disorders. This invention specifically discloses novel macrocyclic compounds as inhibitors of the HCV NS3/NS4a serine protease.

FIELD OF INVENTION

BACKGROUND OF THE INVENTION

Hepatitis C virus (HCV) is a (+)-sense single-stranded RNA virus that has been implicated as the major causative agent in non-A, non-B hepatitis (NANBH), particularly in blood-associated NANBH (BB-NANBH)(see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliary cirrhosis.

Recently, an HCV protease necessary for polypeptide processing and viral replication has been identified, cloned and expressed; (see, e.g., U.S. Pat. No. 5,712,145). This approximately 3000 amino acid polyprotein contains, from the amino terminus to the carboxy terminus, a nucleocapsid protein (C), envelope proteins (El and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys>Thr substitution at NS3/NS4a is postulated to account for the requirement of cis rather than trans processing at this junction. See, e.g., Pizzi et al. (1994) *Proc. Natl. Acad. Sci (USA)* 91:888–892, Failla et al. (1996) *Folding & Design* 1:35–42. The NS3/NS4a cleavage site is also more tolerant of mutagenesis than the other sites. See, e.g., Kollykhalov et al. (1994) *J. Virol.* 68:7525–7533. It has also been found that acidic residues in the region upstream of the cleavage site are required for efficient cleavage. See, e.g., Komoda et al. (1994) *J. Virol.* 68:7351–7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) *Biochem.* 36:9340–9348, Ingallinella et al. (1998) *Biochem.* 37:8906–8914, Llinàs-Brunet et al. (1998) *Bioorg. Med. Chem. Lett.* 8:1713–1718), inhibitors based on the 70-amino acid polypeptide eglin c (Martin et al. (1998) *Biochem.* 37:11459–11468, inhibitors affinity selected from human pancreatic secretory trypsin inhibitor (hPSTI-C3) and minibody repertoires (MBip) (Dimasi et al. (1997) J. Virol. 71:7461–7469), cV$_H$E2 (a "camelized" variable domain antibody fragment) (Martin et al.(1997) *Protein Eng.* 10:607–614), and α1-antichymotrypsin (ACT)(Elzouki et al.) (1997) *J. Hepat.* 27:42–28). A ribozyme designed to selectively destroy hepatitis C virus RNA has recently been disclosed (see, *BioWorld Today* 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche AG); and WO 99/07734, published Feb. 18, 1999 (Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10–30%, whereas those with localized unresectable hepatocellular carcinoma have a five-year survival rate of less than Reference is also made to WO 00/09558 (Assignee: Boehringer Ingelheim Limited; Published Feb. 24, 2000) which discloses peptide derivatives of the formula:

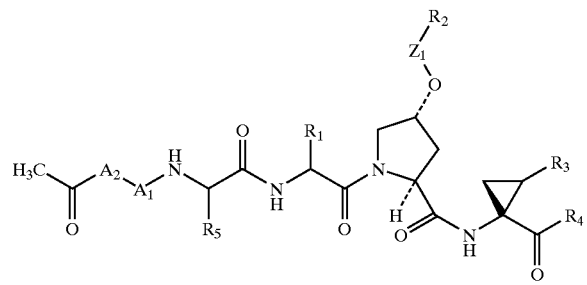

where the various elements are defined therein. An illustrative compound of that series is:

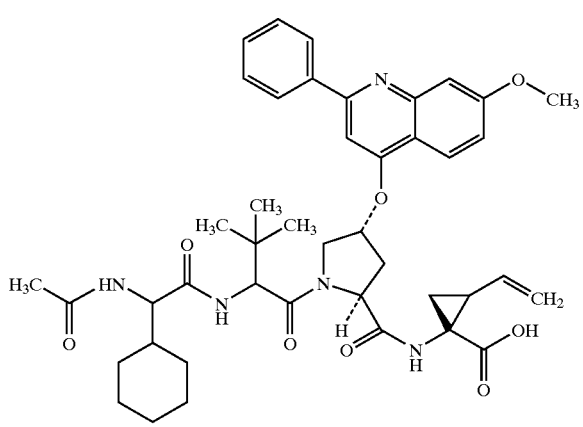

Reference is also made to WO 00/09543 (Assignee: Boehringer Ingelheim Limited; Published Feb. 24, 2000) which discloses peptide derivatives of the formula:

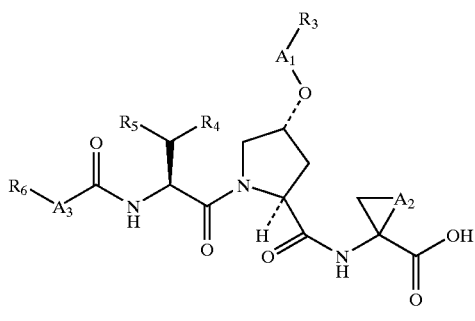

where the various elements are defined therein. An illustrative compound of that series is:

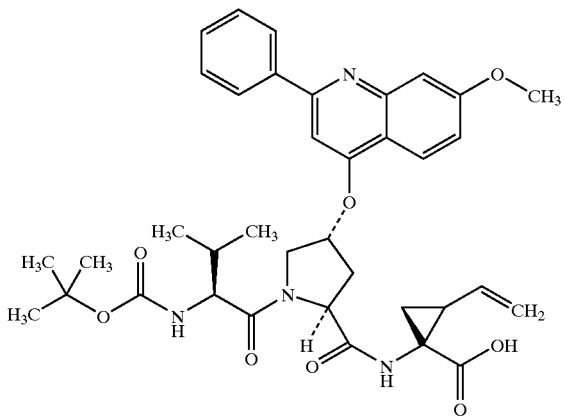

Current therapies for hepatitis C include interferon-α (INF$_\alpha$) and combination therapy with ribavirin and interferon. See, e.g., Beremguer et al. (1998) *Proc. Assoc. Am. Physicians* 110(2):98–112. These therapies suffer from a low sustained response rate and frequent side effects. See, e.g., Hoofnagle et al. (1997) *N. Engl. J. Med.* 336:347. Currently, no vaccine is available for HCV infection.

There is a need for new treatments and therapies for HCV infection. It is, therefore, an object of this invention to provide compounds useful in the treatment or prevention or amelioration of one or more symptoms of hepatitis C.

It is a further object herein to provide methods of treatment or prevention or amelioration of one or more symptoms of hepatitis C.

A still further object of the present invention is to provide methods for modulating the activity of serine proteases, particularly the HCV NS3/NS4a serine protease, using the compounds provided herein.

Another object herein is to provide methods of modulating the processing of the HCV polypeptide using the compounds provided herein.

SUMMARY OF THE INVENTION

In its many embodiments, the present invention provides a novel class of macrocyclic inhibitors of the HCV protease, pharmaceutical compositions containing one or more of the compounds, methods of preparing pharmaceutical formulations comprising one or more such compounds, and methods of treatment, prevention or amelioration or one or more of the symptoms of hepatitis C. Also provided are methods of modulating the interaction of an HCV polypeptide with HCV protease. Among the compounds provided herein, compounds that inhibit HCV NS3/NS4a serine protease activity are preferred. The presently disclosed compounds generally contain about three or more amino acid residues and less than about twelve amino acid residues.

In its principal embodiment, the present invention provides a macrocyclic compound of Formula I:

Formula I

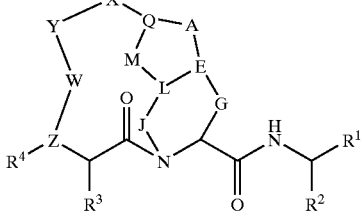

wherein:

X and Y are independently selected from the moieties: alkyl, alkyl-aryl, heteroalkyl, heteroaryl, aryl-heteroaryl, alkyl-heteroaryl, cycloalkyl, alkyl ether, alkyl-aryl ether, aryl ether, alkyl amino, aryl amino, alkyl-aryl amino, alkyl sulfide, alkyl-aryl sulfide, aryl sulfide, alkyl sulfone, alkyl-aryl sulfone, aryl sulfone, alkyl-alkyl sulfoxide, alkyl-aryl sulfoxide, alkyl amide, alkyl-aryl amide, aryl amide, alkyl sulfonamide, alkyl-aryl sulfonamide, aryl sulfonamide, alkyl urea, alkyl-aryl urea, aryl urea, alkyl carbamate, alkyl-aryl carbamate, aryl carbamate, alkyl-hydrazide, alkyl-aryl hydrazide, alkyl hydroxamide, alkyl-aryl hydroxamide, alkyl sulfonyl, aryl sulfonyl, heteroalkyl sulfonyl, heteroaryl sulfonyl, alkyl carbonyl, aryl carbonyl, heteroalkyl carbonyl, heteroaryl carbonyl, alkoxycarbonyl, aryloxycarbonyl, heteroaryloxycarbonyl, alkylaminocarbonyl, arylaminocarbonyl, heteroarylaminocarbonyl or a combination thereof, with the proviso that X and Y may optionally be additionally substituted with moieties selected from the group consisting of aromatic, alkyl, alkyl-aryl, heteroalkyl, aryl-heteroaryl, alkyl-heteroaryl, cycloalkyl, alkyl ether, alkyl-aryl ether, alkyl sulfide, alkyl-aryl sulfide, alkyl sulfone, alkyl-aryl sulfone, alkyl amide, alkyl-aryl amide, alkyl sulfonamide, alkyl amines, alkyl-aryl amines, alkyl-aryl sulfonamide, alkyl urea, alkyl-aryl urea, alkyl carbamate and alkyl-aryl carbamate;

$R^1$=COR$^5$ or B(OR)$_2$, wherein R$^5$=H, OH, OR$^8$, NR$^9$R$^{10}$, CF$_3$, C$_2$F$_5$, C$_3$F$_7$, CF$_2$R$^6$, R$^6$, COR$^7$ wherein R$^7$=H, OH, OR$^8$, CHR$^9$R$^{10}$, or NR$^9$R$^{10}$, wherein R$^6$, R$^8$, R$^9$ and R$^{10}$ are independently selected from the group consisting of H, alkyl, aryl, heteroalkyl, heteroaryl, cycloalkyl, cycloalkyl, arylalkyl, heteroarylalkyl, CH(R$^{1'}$)COOR$^{11}$, CH(R$^{1'}$)CONR$^{12}$R$^{13}$, CH(R$^{1'}$)CONHCH(R$^{2'}$)COO R$^{11}$, CH(R$^{1'}$)CONHCH(R$^{2'}$)CONR$^{12}$R$^{13}$, CH(R$^{1'}$)CONHCH(R$^{2'}$)R', CH(R$^{1'}$)CONHCH(R$^{2'}$)CONHCH(R$^{3'}$)COO R$^{11}$, CH(R$^{1'}$)CONHCH(R$^{2'}$)CONHCH(R$^{3'}$)CONR$^{12}$R$^{13}$, CH(R$^{1'}$)CONHCH(R$^{2'}$)CONHCH(R$^{3'}$)CONHCH(R$^{4'}$)COO R$^{11}$, CH(R$^{1'}$)CONHCH(R$^{2'}$)CONHCH(R$^{3'}$)CONHCH(R$^{4'}$)CONR$^{12}$R$^{13}$, CH(R$^{1'}$)CONHCH(R$^{2'}$)CONHCH(R$^{3'}$)CONHCH(R$^{4'}$)CONHCH(R$^{5'}$)COO R$^{11}$, CH(R$^{1'}$)CONHCH(R$^{2'}$)CONHCH(R$^{3'}$)CONHCH(R$^{4'}$)CONHCH(R$^{5'}$)CONR$^{12}$R$^{13}$, wherein R$^{1'}$, R$^{2'}$, R$^{3'}$, R$^{4'}$, R$^{5'}$, R$^{11}$, R$^{12}$, R$^{13}$, and R' are independently selected from a group consisting of H, alkyl, aryl, heteroalkyl, heteroaryl, cycloalkyl, alkyl-aryl, alkyl-heteroaryl, aryl-alkyl and heteroaralkyl;

Z is selected from O, N, or CH;

W may be present or absent, and if W is present, W is selected from C=O, C=S, or SO$_2$;

Q maybe present or absent, and when Q is present, Q is CH, N, P, (CH$_2$)$_p$, (CHR)$_p$, (CRR')$_p$, O, NR, S, or SO$_2$; and when Q is absent, M is also absent, and A is directly linked to X;

A is O, CH$_2$, (CHR)$_p$, (CHR-CHR')$_p$, (CRR')$_p$, NR, S, SO$_2$ or a bond;

E is CH, N or CR, or a double bond towards A, L or G;

G may be present or absent, and when G is present, G is (CH$_2$)$_p$, (CHR)$_p$, or (CRR')$_p$'; and when G is absent, J is present and E is directly connected to the carbon atom where G was connected to;

J maybe absent or present, and when J is present, J is (CH$_2$)$_p$, (CHR)$_p$, or (CRR')$_p$, SO$_2$, NH, NR or O; and when J is absent, G is present and E is directly linked to N;

L may be present or absent, and when L is present, L is CH, CR, O, S or NR; and when L is absent, then M may be absent or present, and if M is present with L being absent, then M is directly and independently linked to E, and J is directly and independently linked to E;

M may be present or absent, and when M is present, M is O, NR, S, SO$_2$, (CH$_2$)$_p$, (CHR)$_p$ (CHR-CHR')$_p$, or (CRR')$_p$;

p is a number from 0 to 6; and

R, R', R$^2$, R$^3$ and R$^4$ are independently selected from the group consisting of H; C1–C10 alkyl; C2–C10 alkenyl; C3–C8 cycloalkyl; C3–C8 heterocycloalkyl, alkoxy, aryloxy, alkylthio, arylthio, amino, amido, ester, carboxylic acid, carbamate, urea, ketone, aldehyde, cyano, nitro; oxygen, nitrogen, sulfur, or phosphorus atoms with said oxygen, nitrogen, sulfur, or phosphorus atoms numbering zero to six;

(cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl;

with said alkyl, heteroalkyl, alkenyl, heteroalkenyl, aryl, heteroaryl, cycloalkyl and heterocycloalkyl moieties may be optionally substituted, with said term "substituted" referring to optional and suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamide, sulfoxide, sulfone, sulfonyl urea, hydrazide, and hydroxamate.

Unless defined otherwise, all technical and scientific terms used herein have the same meaning as is commonly understood by one of skill in the art to which this invention belongs. Thus, for example, the term alkyl (including the alkyl portions of alkoxy) refers to a monovalent group derived from a straight or branched chain saturated hydrocarbon by the removal of a single atom having from 1 to 8 carbon atoms, preferably from 1 to 6;

aryl—represents a carbocyclic group having from 6 to 14 carbon atoms and having at least one benzenoid ring, with all available substitutable aromatic carbon atoms of the carbocyclic group being intended as possible points of attachment. Preferred aryl groups include phenyl, 1-naphthyl, 2-naphthyl and indanyl, and especially phenyl and substituted phenyl;

aralkyl—represents a moiety containing an aryl group linked vial a lower alkyl;

alkylaryl—represents a moiety containing a lower alkyl linked via an aryl group;

cycloalkyl—represents a saturated carbocyclic ring having from 3 to 8 carbon atoms, preferably 5 or 6, optionally substituted.

heterocyclic—represents, in addition to the heteroaryl groups defined below, saturated and unsaturated cyclic organic groups having at least one O, S and/or N atom interrupting a carbocyclic ring structure that consists of one ring or two fused rings, wherein each ring is 3 to 9-membered and may or may not have double bonds that lack delocalized pi electrons, which ring structure has from 2 to 8, preferably from 3 to 6 carbon atoms, e.g., 2- or 3-piperidinyl, 2- or 3-piperazinyl, 2- or 3-morpholinyl, or 2- or 3-thiomorpholinyl;

halogen—represents fluorine, chlorine, bromine and iodine;

heteroaryl—represents a cyclic organic group having at least one O, S and/or N atom interrupting a carbocyclic ring structure and having a sufficient number of delocalized pi electrons to provide aromatic character, with the aromatic heterocyclic group having from 2 to 14, preferably 4 or 5 carbon atoms, e.g., 2-, 3- or 4-pyridyl, 2- or 3-furyl, 2- or 3-thienyl, 2-, 4- or 5-thiazolyl, 2- or 4-imidazolyl, 2-, 4- or 5-pyrimidinyl, 2-pyrazinyl, or 3- or 4-pyridazinyl, etc. Preferred heteroaryl groups are 2-, 3- and 4-pyridyl; Such heteroaryl groups may also be optionally substituted.

Also included in the invention are tautomers, enantiomers and other optical isomers of compounds of Formula I, as well as pharmaceutically acceptable salts and solvates thereof.

A further feature of the invention is pharmaceutical compositions containing as active ingredient a compound of Formula I (or its salt, solvate or isomers) together with a pharmaceutically acceptable carrier or excipient.

The invention also provides methods for preparing compounds of Formula I, as well as methods for treating diseases such as, for example, HCV and related disorders. The methods for treating comprise administering to a patient suffering from said disease or diseases a therapeutically effective amount of a compound of Formula I, or pharmaceutical compositions comprising a compound of Formula I.

Also disclosed is the use of a compound of Formula I for the manufacture of a medicament for treating HCV and related disorders.

DETAILED DESCRIPTION OF PREFERRED EMBODIMENTS

In one embodiment, the present invention discloses compounds of Formula I as inhibitors of HCV protease, especially the HCV NS3/NS4a serine protease. Among the compounds encompassed by Formula I, preferred compounds are those which have the Formula II:

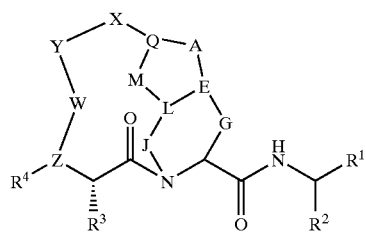

Formula II or a pharmaceutically acceptable derivative thereof, where the various definitions are given above. Some of the preferred embodiments include, but are not limited to, the following definitions of the various functionalities in the above-noted general formulas I and II. Thus, for example, $R^2$ in formula I may be selected from the following moieties:

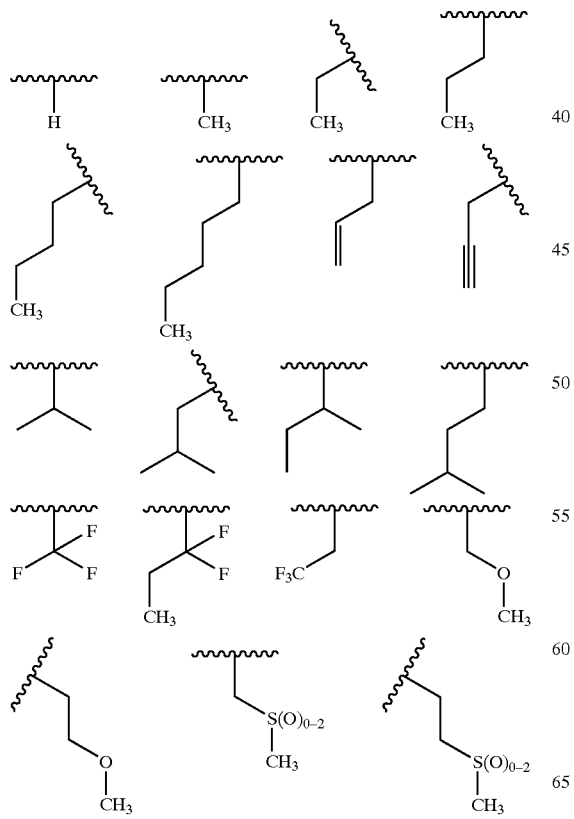

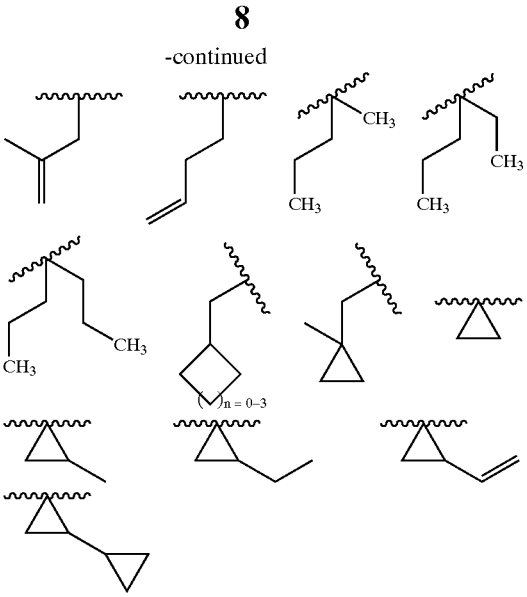

Some preferred representations for the moiety

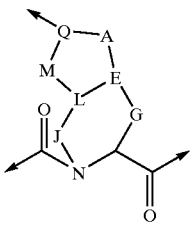

are, for example, the following structures a, b, or c:

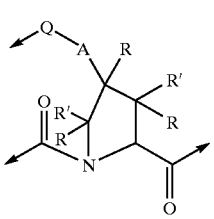

a

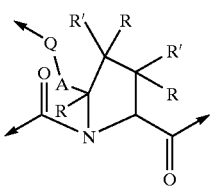

b

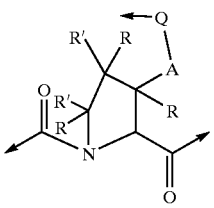

c

The structure a may be selected from the following non-limiting types of structures:

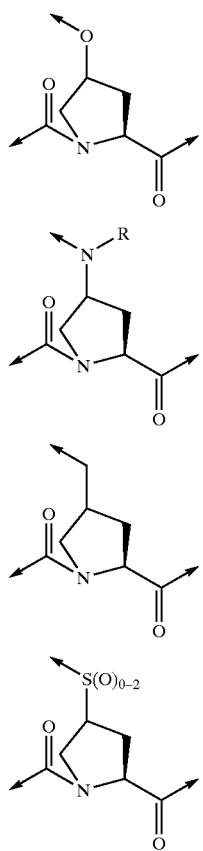

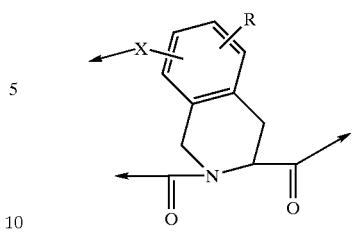

In some more preferred compounds, the moieties G and J are independently selected from $(CH_2)_p$, $(CHR)_p$, $(CHR\text{-}CHR')_p$, and $(CRR')_p$, and the moiety A-E-L-M-Q is an aromatic ring consisting of two to eight carbon atoms, zero to six hetero atoms with X and J being ortho, para or meta with respect to each other.

In other preferred embodiments, $R^3$ in formula I is selected from the following structures:

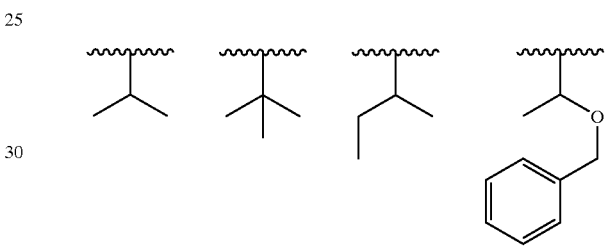

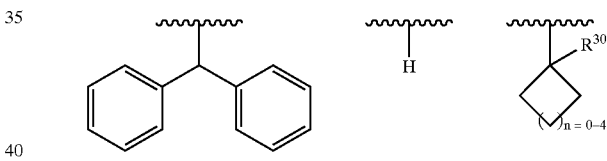

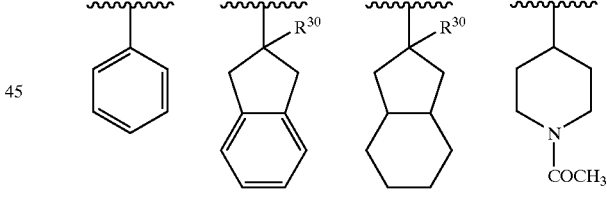

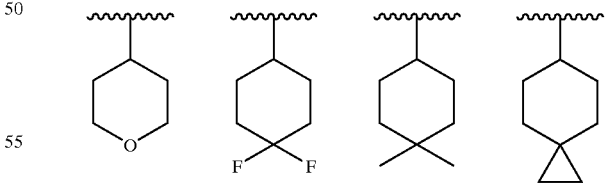

Other additional preferred embodiments are, for example, where the moiety:

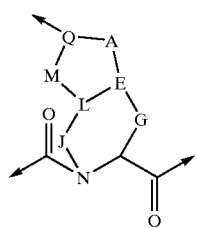

is sometimes the following structures, where the definitions for the various positions are exemplified in the structures of compounds shown later in this section:

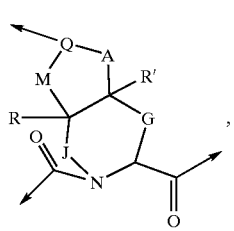 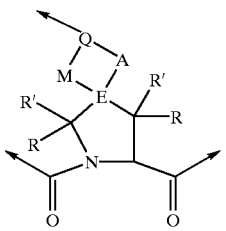

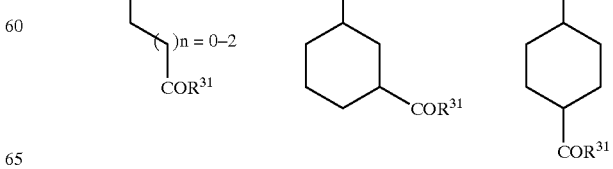

-continued

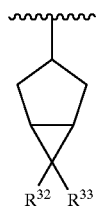

wherein $R^{30}$=H, $CH_3$ or other alkyl groups;

$R^{31}$=OH, O-alkyl, $NH_2$ or N-alkyl;

$R^{32}$ and $R^{33}$ may be the same or different and are independently selected from H, F, Cl, Br and $CH_3$;

and the moiety X-Y is selected from the following structures:

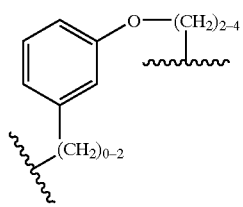
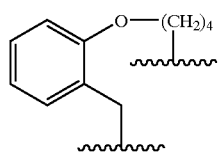
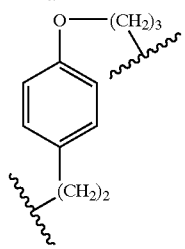
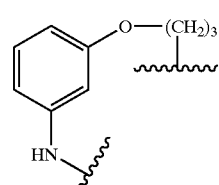
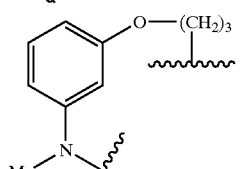
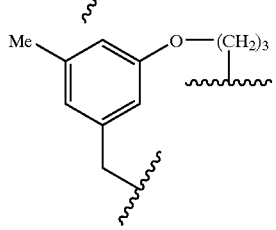
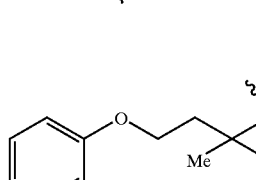
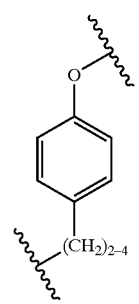

-continued

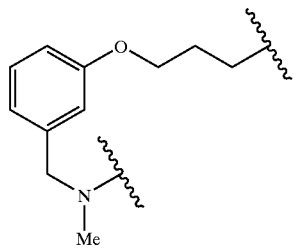
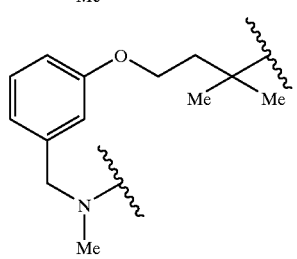
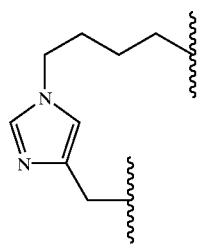
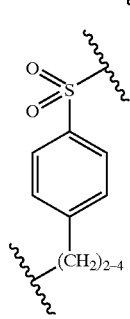
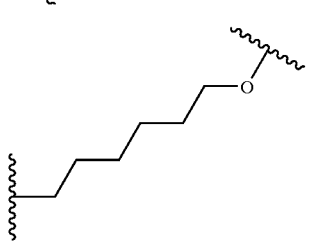

Several additional and further refinements of the above-noted various definitions for the compounds represented by Formula I are noted in the Claims section of this application. They are also represented by the various compounds listed in the specification and claims. Such refinements, definitions and limitations are to be considered as representing the entire invention of this application.

Representative compounds of the invention which exhibit excellent HCV protease inhibitory activity are listed below along with their activity (ranges of $K_i$ values in nanomolar, nM). The Example numbers refer to the numbers for the various structures in the EXAMPLES section found in the later parts of this application.

TABLE 1

HCV protease continuous assay results

| Example Number | Ki* (nM) |
|---|---|
| 1A | a |
| 1B | b |
| 2 | b |
| 3 | b |
| 4A | a |
| 4B | b |
| 5 | b |
| 6 | b |
| 7A | a |
| 7B | b |
| 8 | a |
| 9 | b |
| 10A | a |
| 10B | b |
| 11 | a |
| 12A | a |
| 12B | b |
| 13A | a |
| 13B | b |
| 14 | b |
| 15 | b |
| 16 | b |
| 17 | b |
| 18 | b |
| 19 | b |
| 20A | a |
| 20B | b |
| 21 | a |
| 22 | b |
| 23 | a |
| 24 | a |
| 25 | a |
| 26A | a |
| 26B | a |
| 27A | a |
| 27B | b |
| 28A | a |
| 28B | b |
| 29A | a |
| 29B | b |
| 30 | b |
| 31 | b |
| 37A | a |
| 37B | a |
| 38A | a |
| 38B | a |
| 39 | a |
| 40 | a |
| 41 | a |
| 42 | a |
| 43 | b |
| 44A | a |
| 44B | a |
| 46 | a |
| 53A | a |
| 53B | a |
| 56A | a |
| 56B | a |
| 57A | a |
| 57B | b |
| 58 | a |
| 59A | b |
| 59B | b |
| 60 | a |
| 61 | a |
| 62 | a |
| 63 | a |
| 64 | a |
| 65 | b |
| 66A | a |
| 66B | b |
| 67A | a |
| 67B | b |
| 68 | b |
| 69A | a |

TABLE 1-continued

HCV protease continuous assay results

| Example Number | Ki* (nM) |
|---|---|
| 69B | b |
| 70A | a |
| 70B | b |
| 71 | b |
| 72 | b |
| 73 | a |
| 74A | a |
| 74B | b |
| 75A | a |
| 75B | b |
| 76 | b |
| 77 | a |
| 78 | a |
| 79 | a |
| 80 | b |
| 81 | a |
| 82 | a |
| 83 | b |
| 84 | a |
| 85 | a |
| 86 | a |
| 87 | a |
| 88 | a |
| 89 | a |
| 90 | a |
| 91 | a |
| 92 | b |
| 93 | a |
| 94 | a |
| 95 | b |
| 96 | a |
| 97 | a |
| 98 | b |
| 99 | a |
| 100 | a |
| 101 | b |
| 102 | a |
| 103 | a |
| 104 | a |
| 105 | a |
| 106 | a |
| 107 | a |
| 108 | a |
| 109 | a |
| 110 | b |
| 111 | b |

HCV continuous assay Ki* range:
Category b = 1–100 nM;
Category a = 101 nM–100 μM Some of the inventive compounds and the methods of synthesizing the various types of the inventive compounds are listed below, then schematically described, followed by the illustrative Examples.

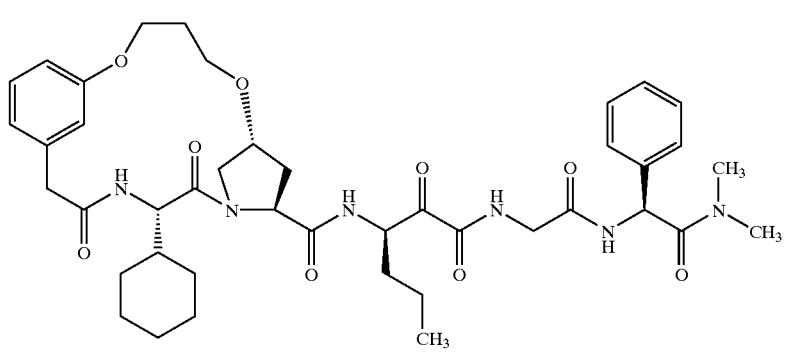
1A
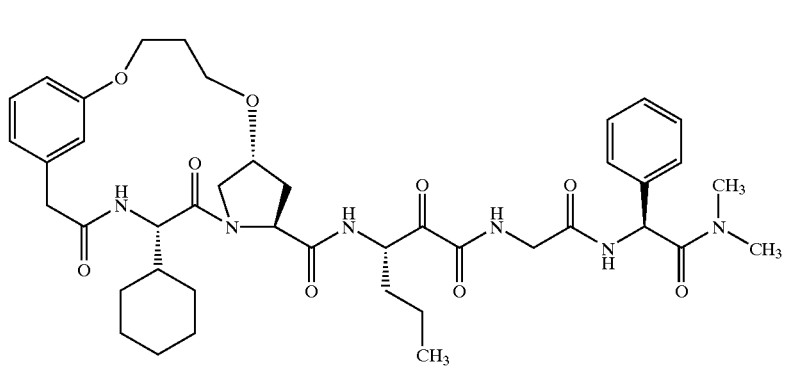
1B
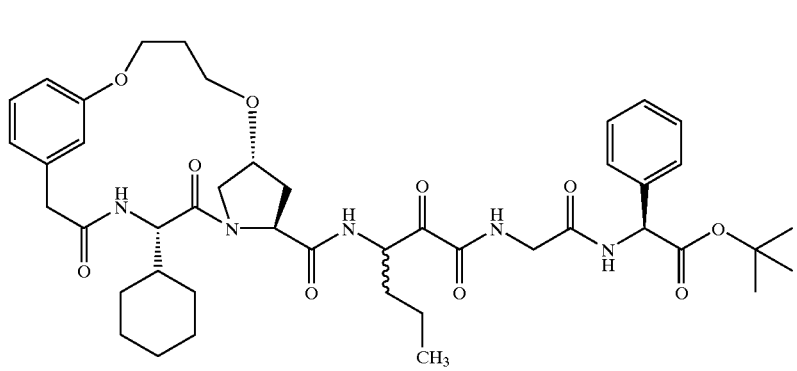
2
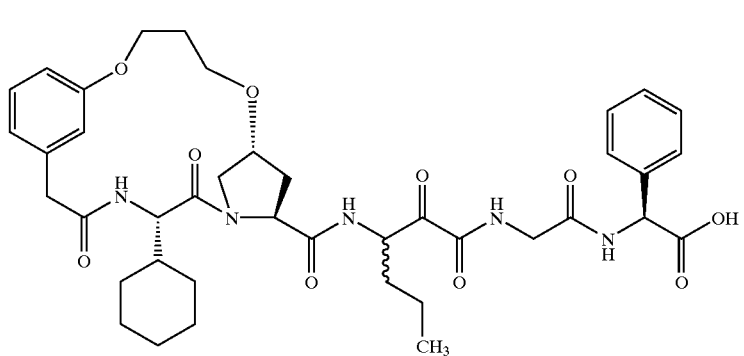
3

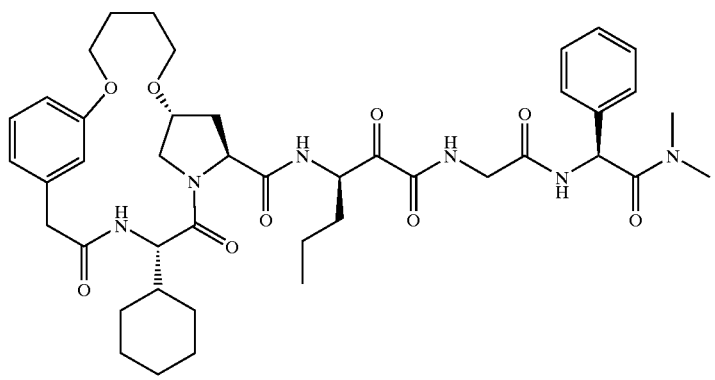
4A
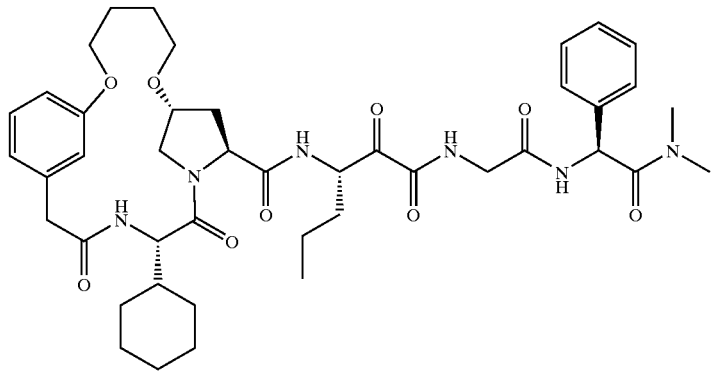
4B
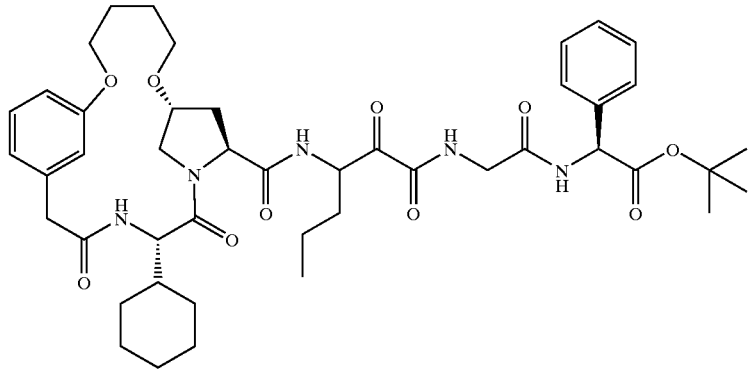
5
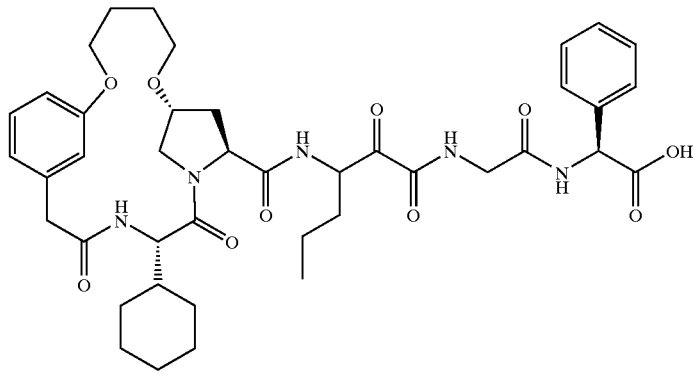
6

-continued
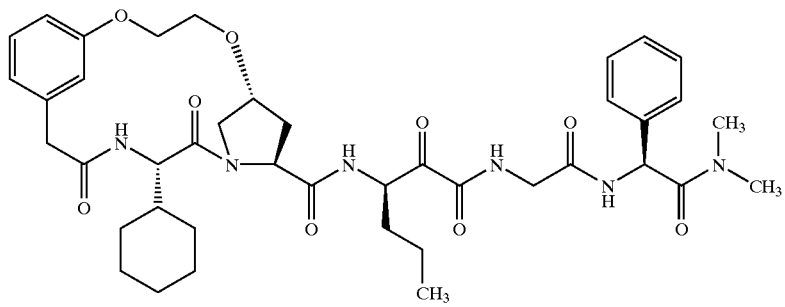
7A
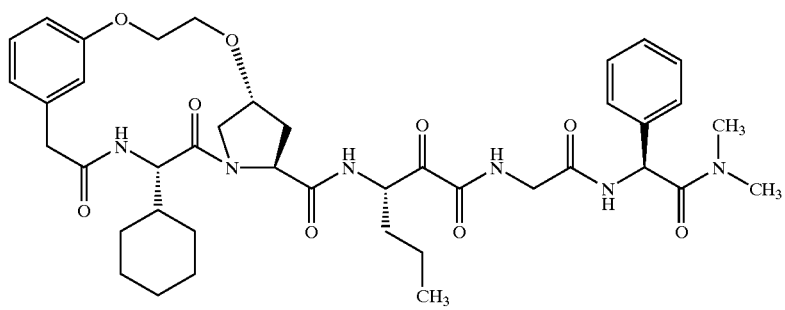
7B
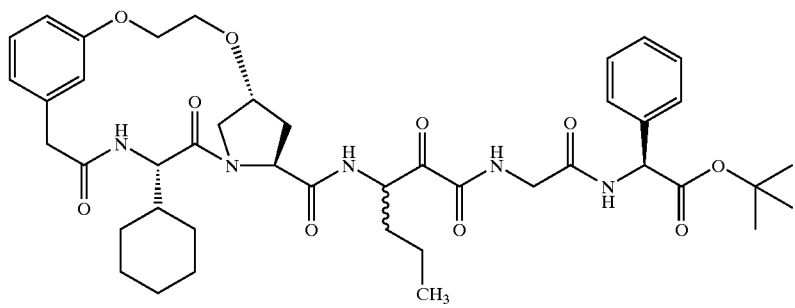
8
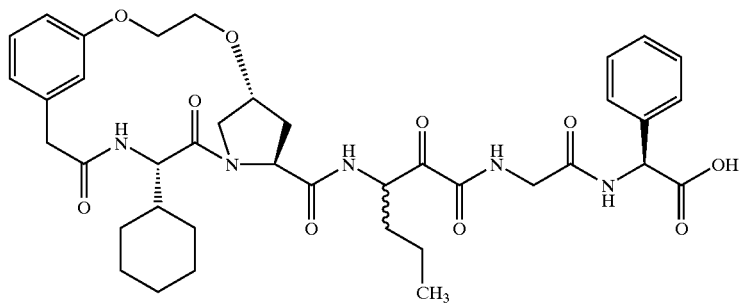
9
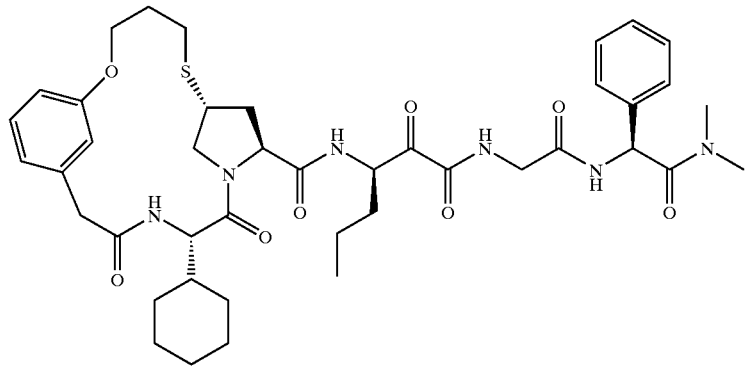
10A

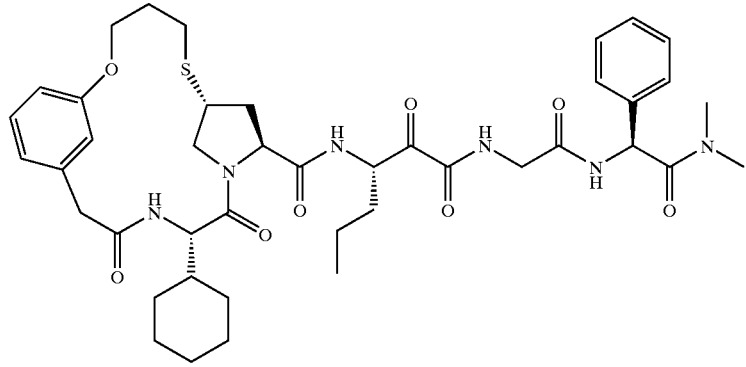
10B
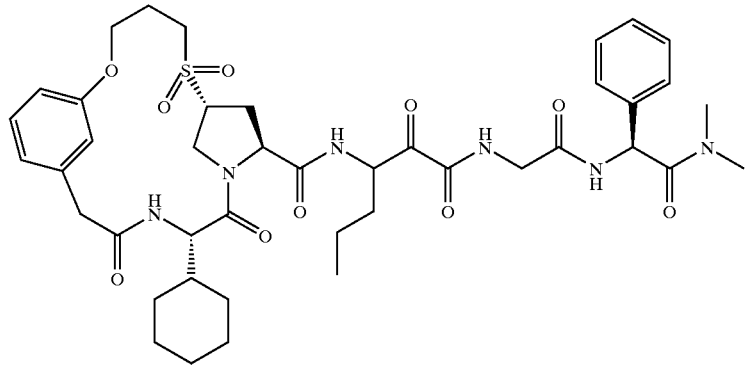
11
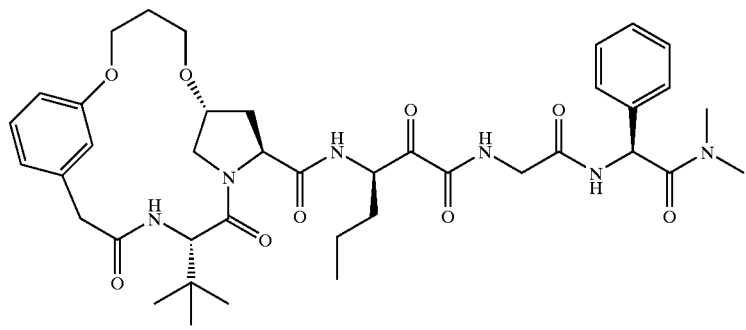
12A
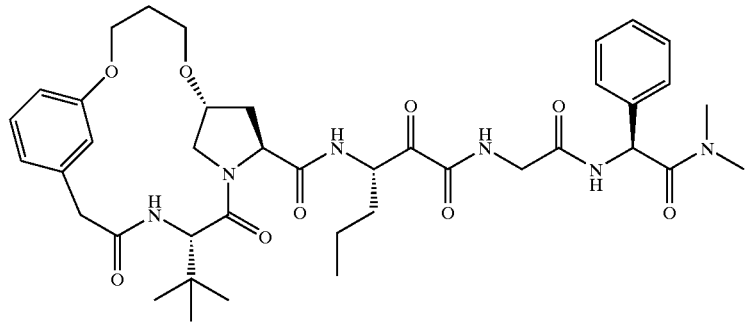
12B

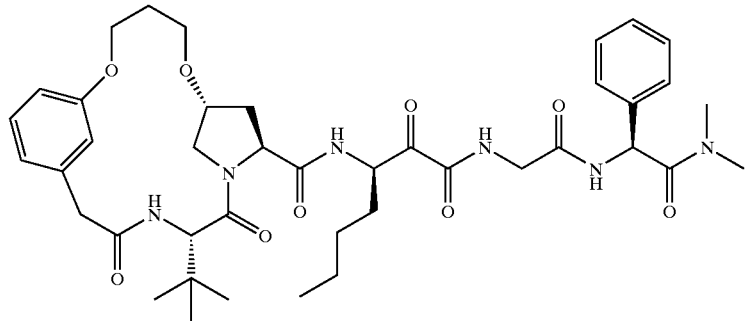
13A
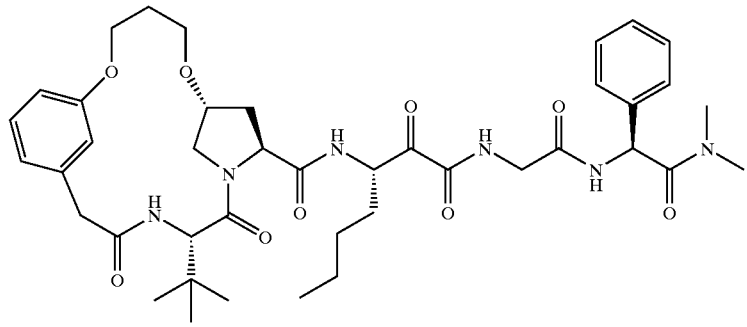
13B
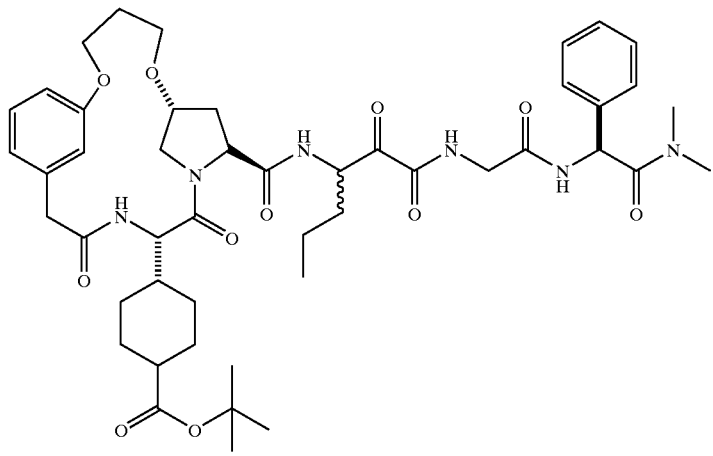
14
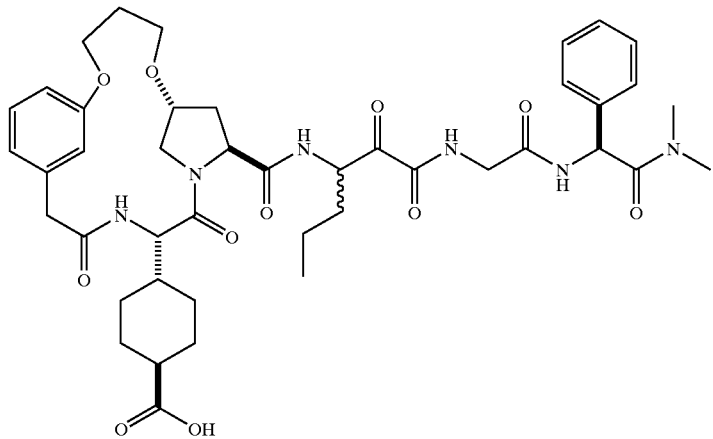
15

16
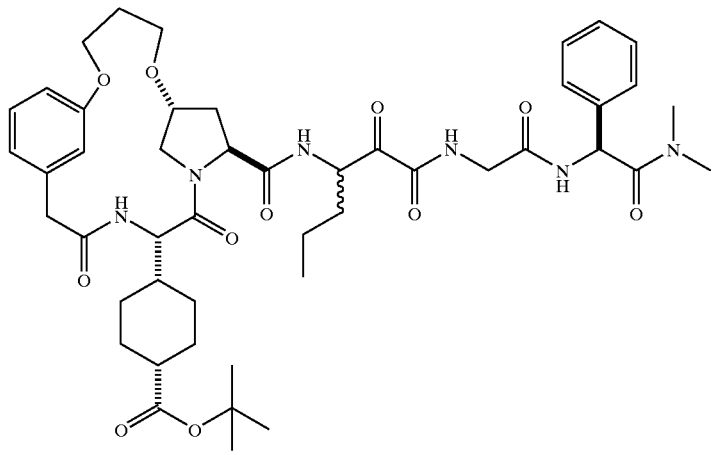
17
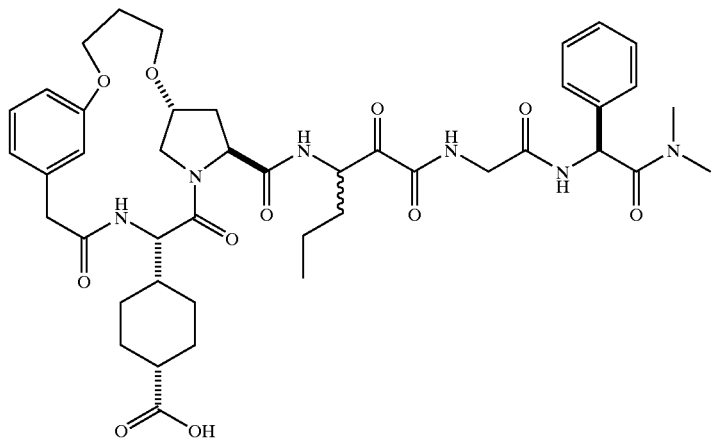
18
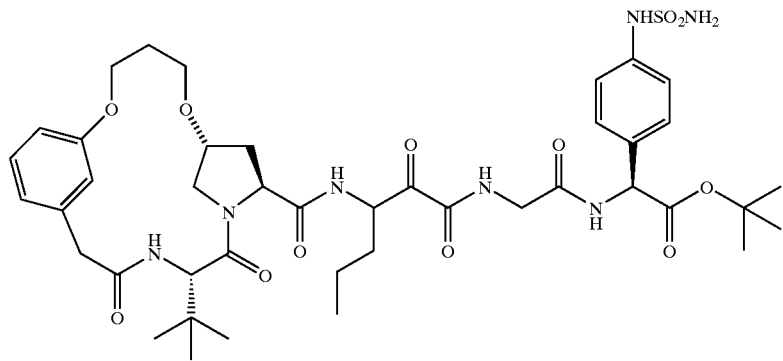
19
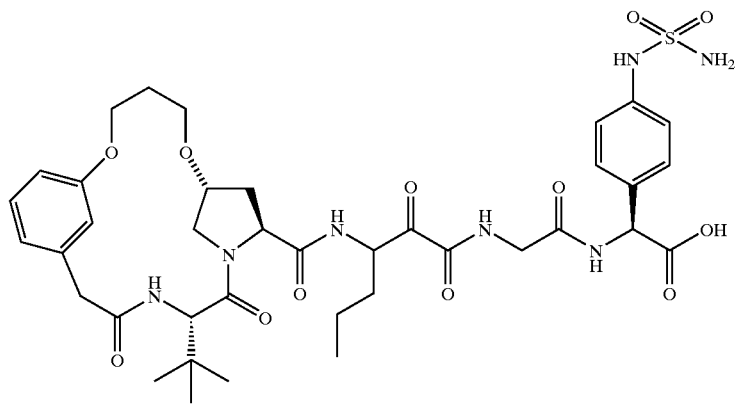

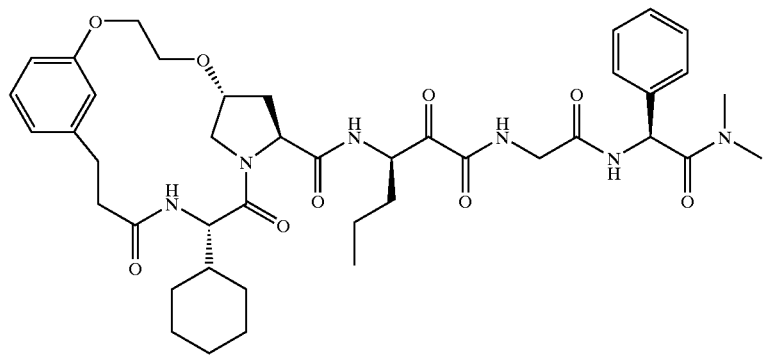
20A
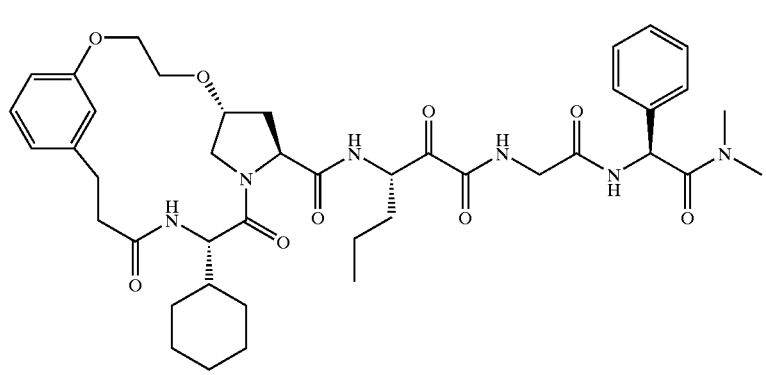
20B
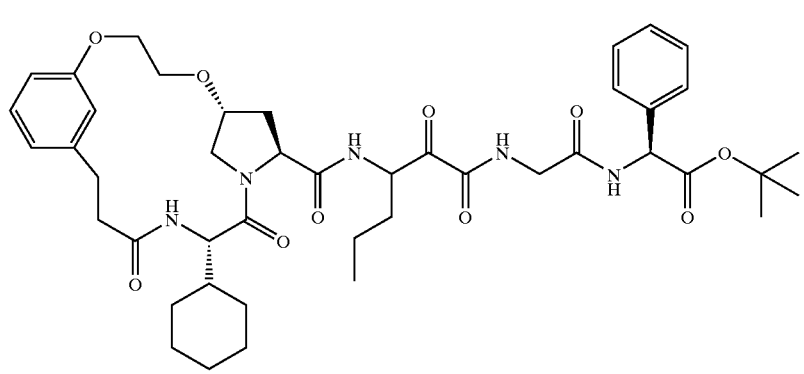
21
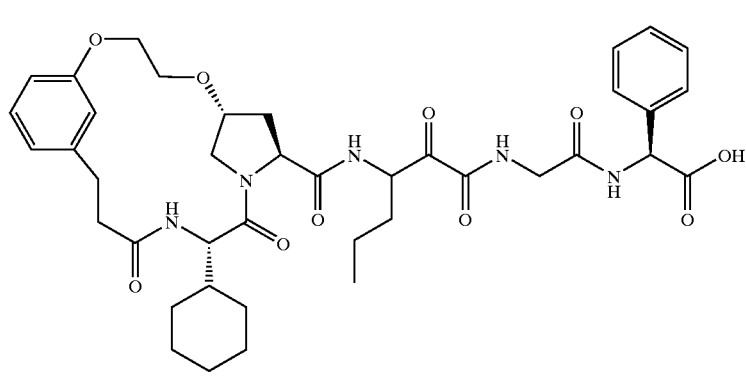
22

23
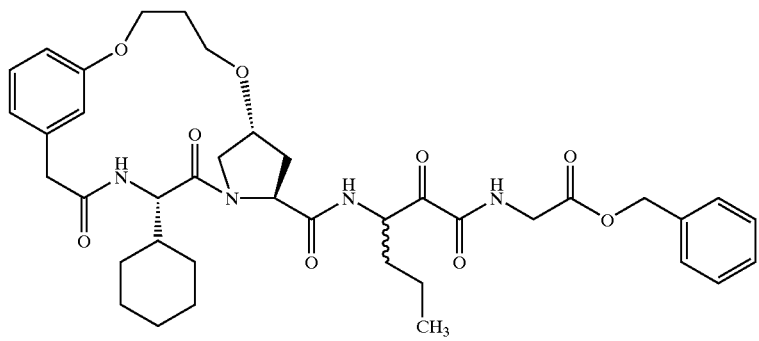
24
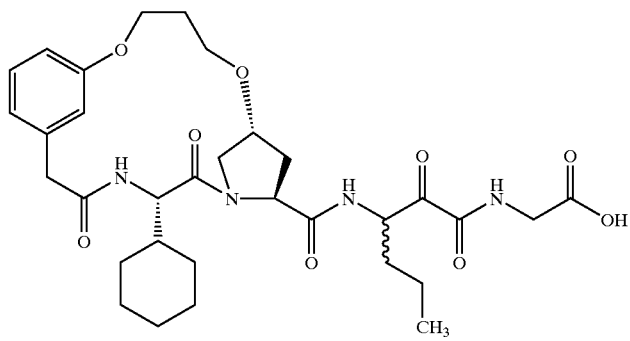
25
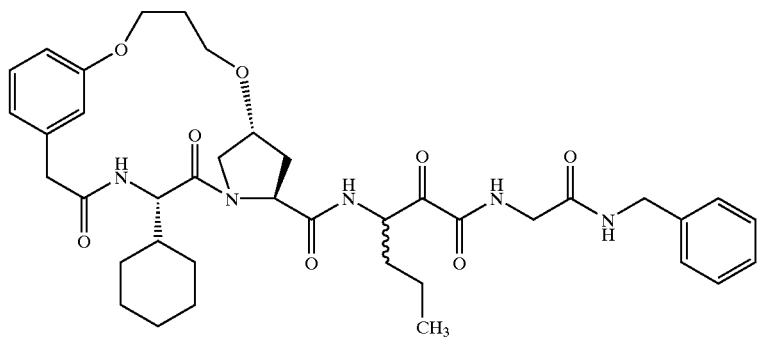
26A
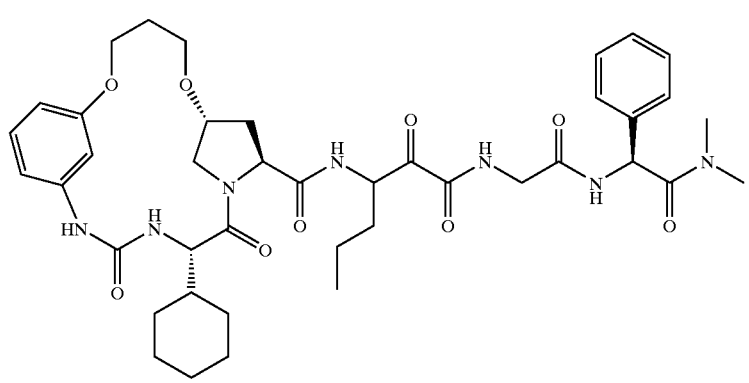

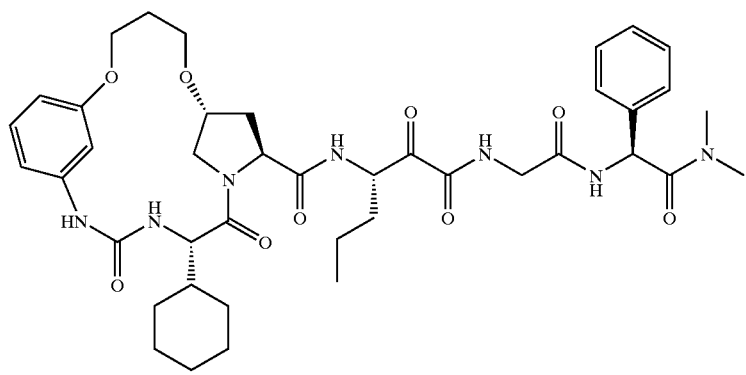
26B
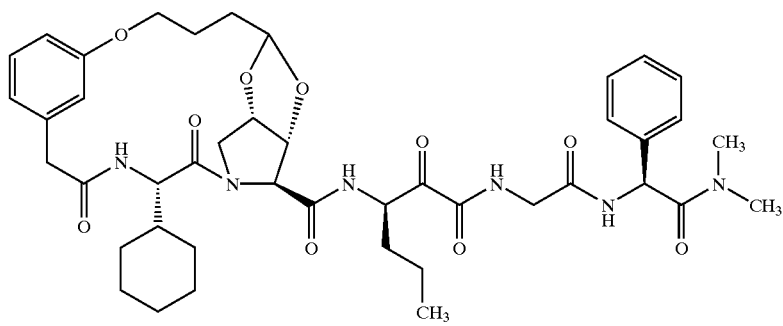
27A
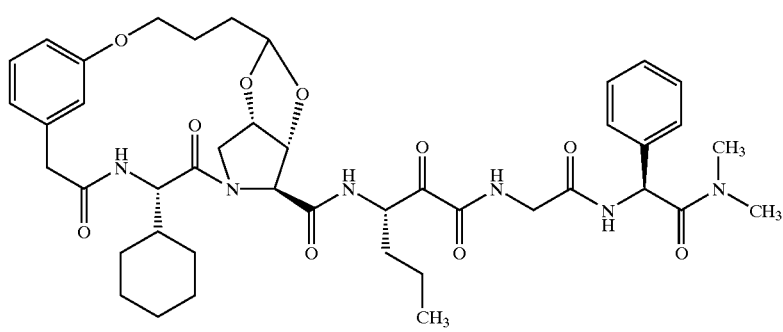
27B
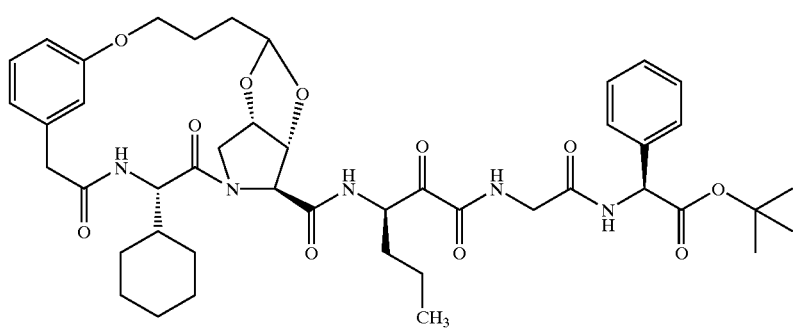
28A

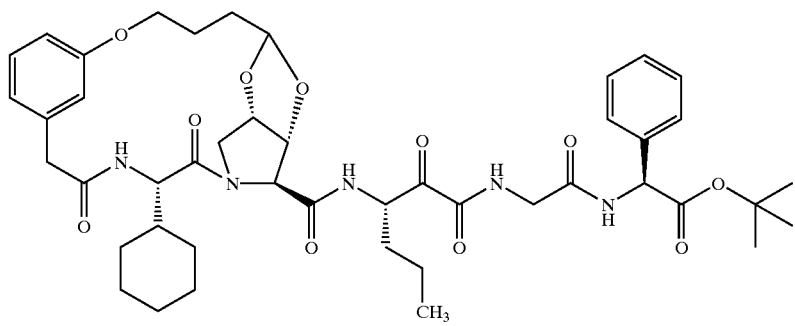
28B
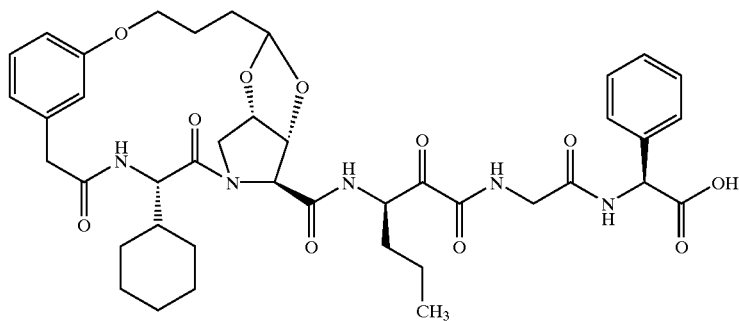
29A
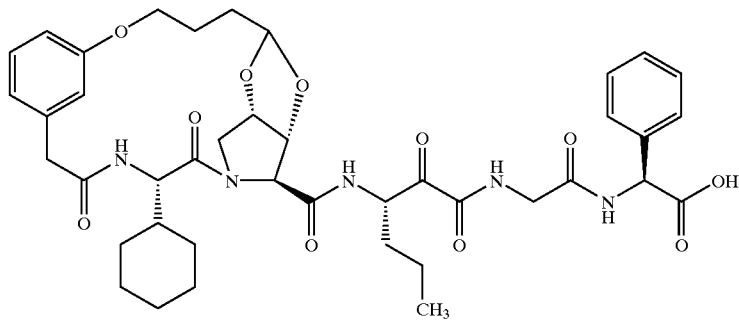
29B
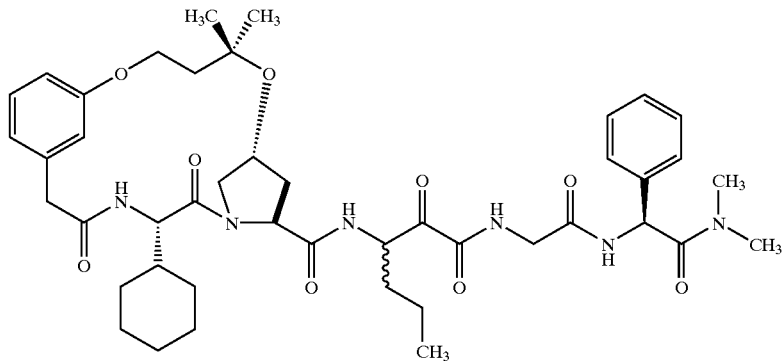
30

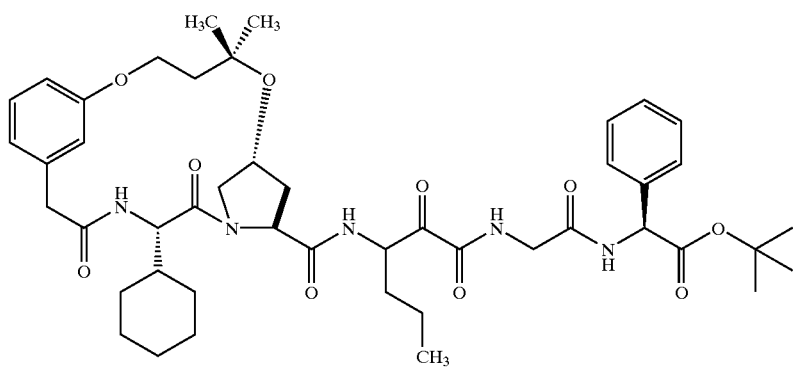
31
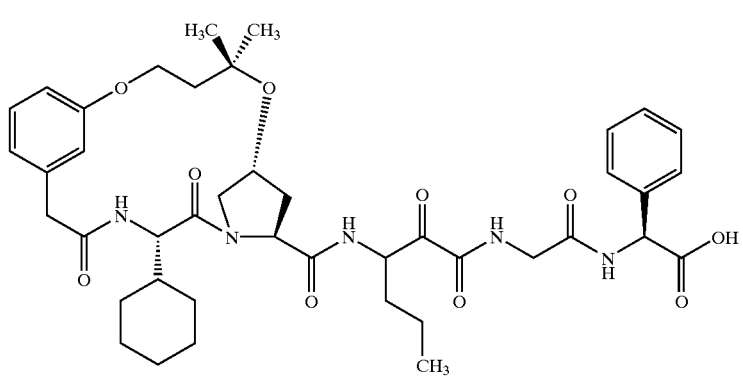
32
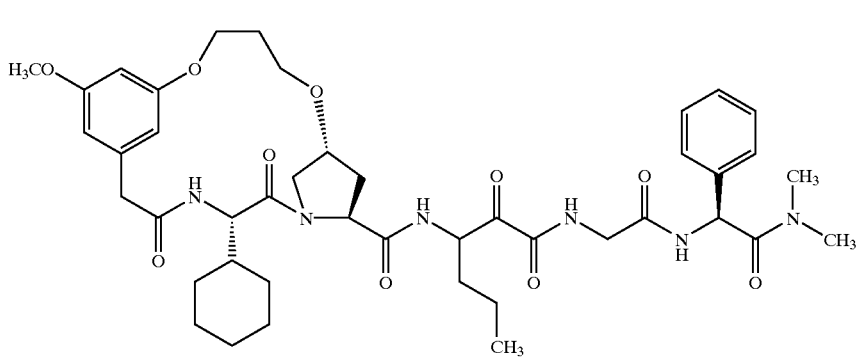
33
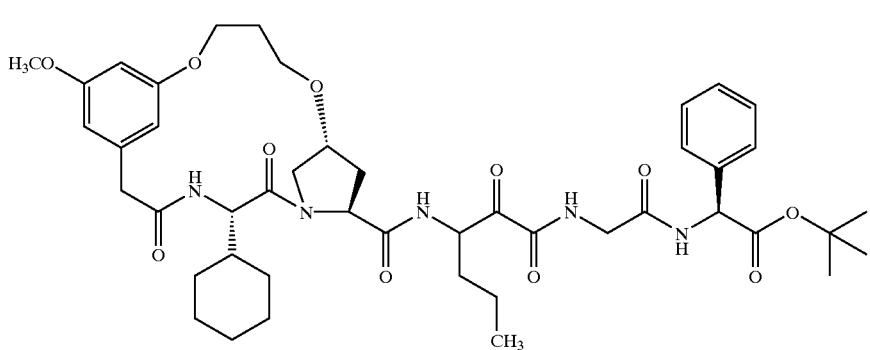
34

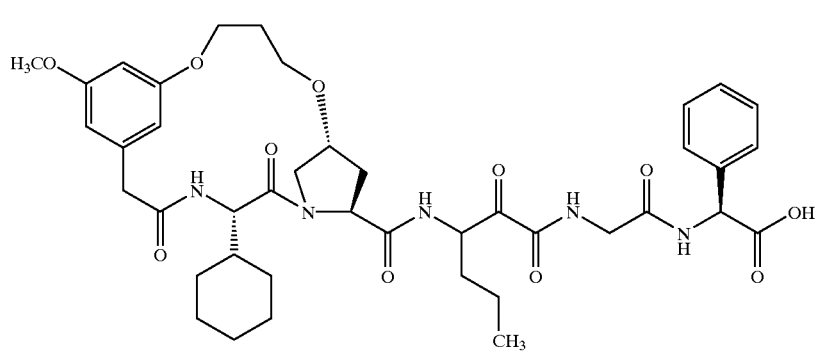
35
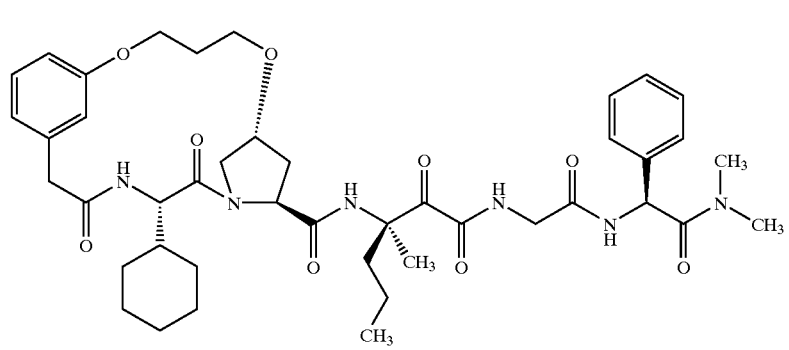
36A
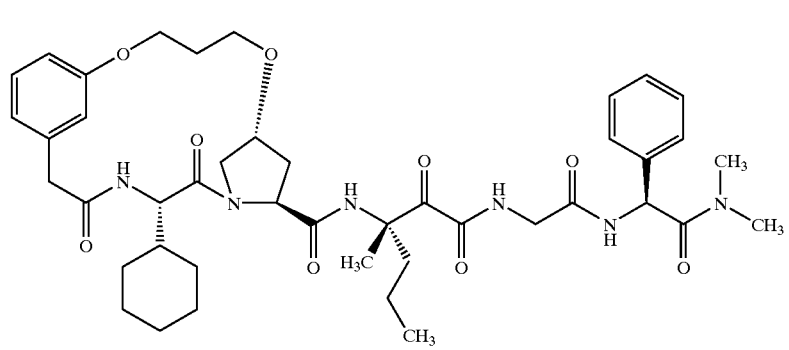
36B
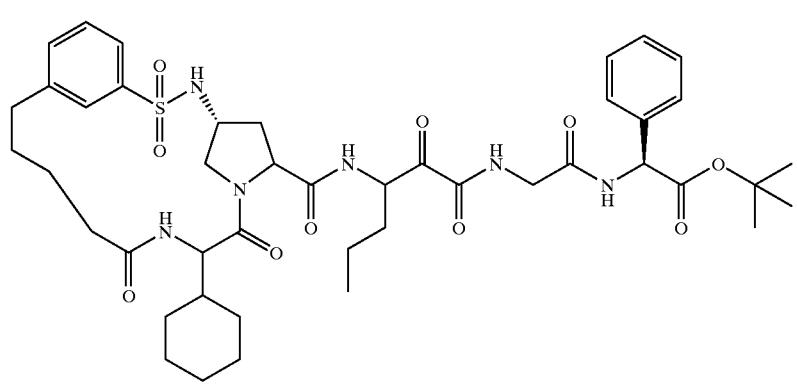
37A

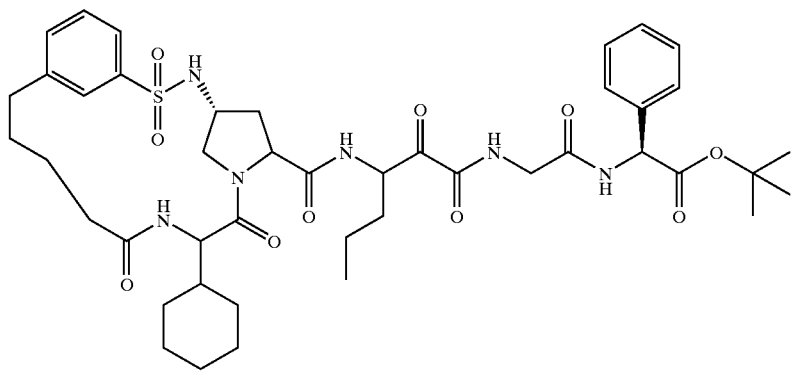
37B
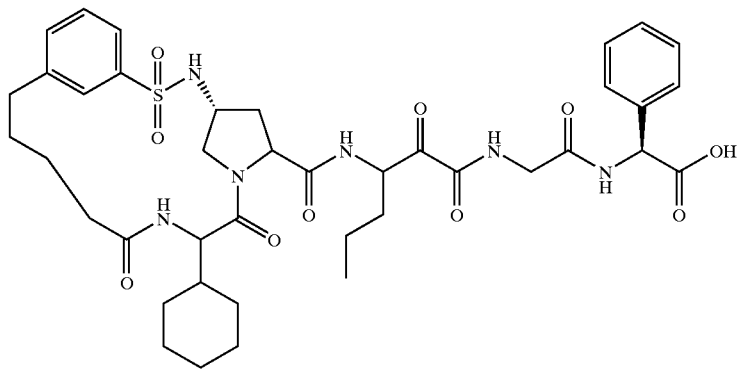
38A
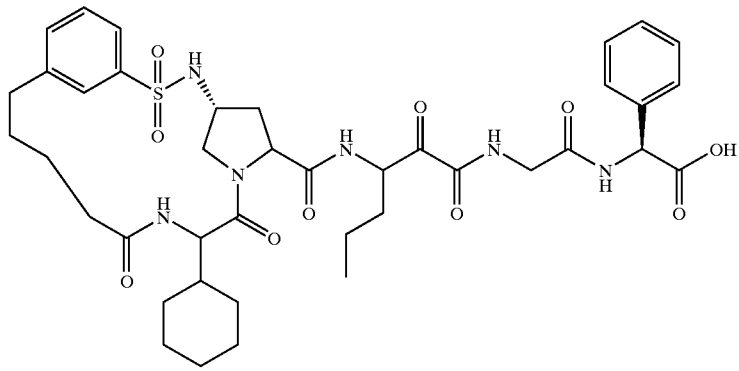
38B
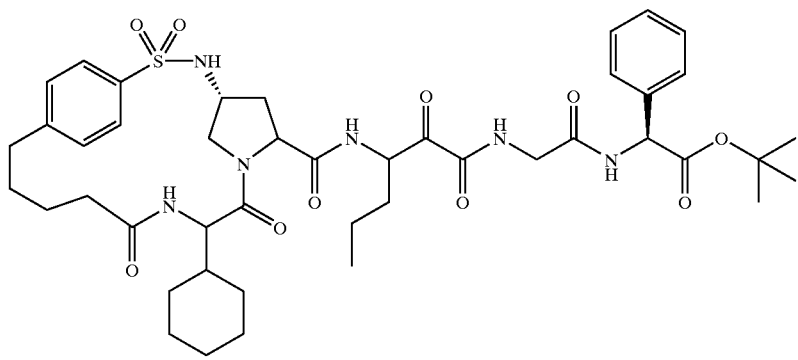
39

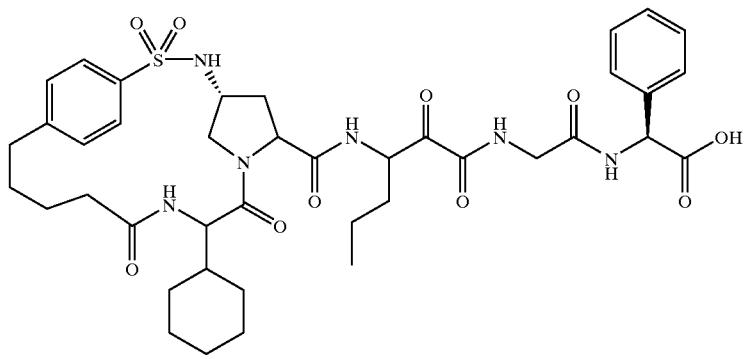
40
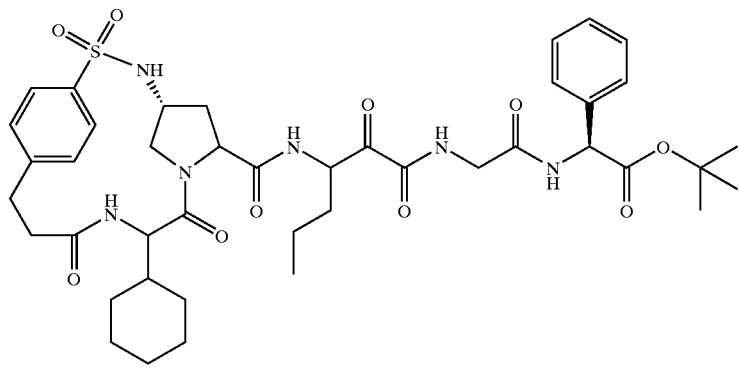
41
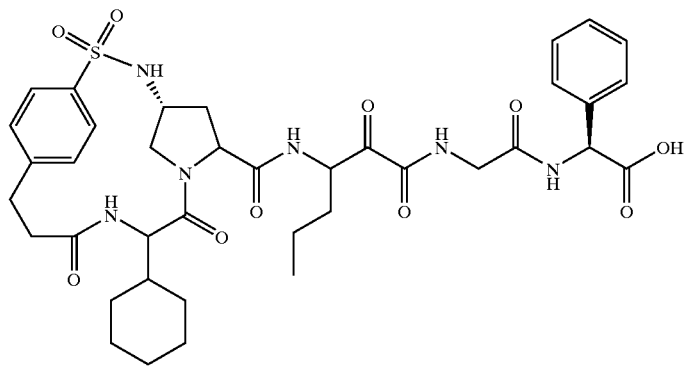
42
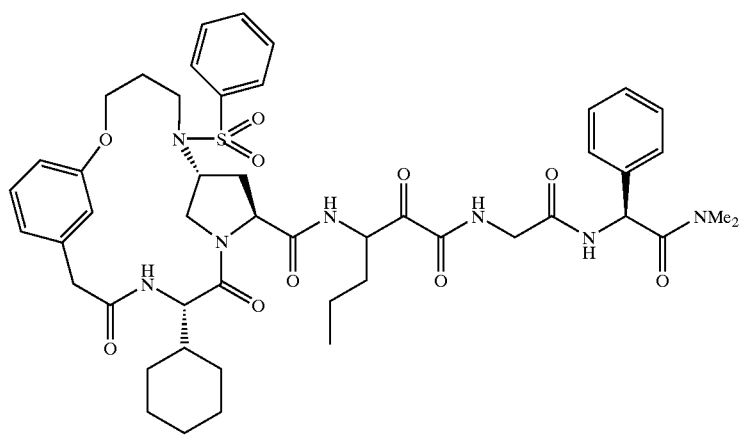
43

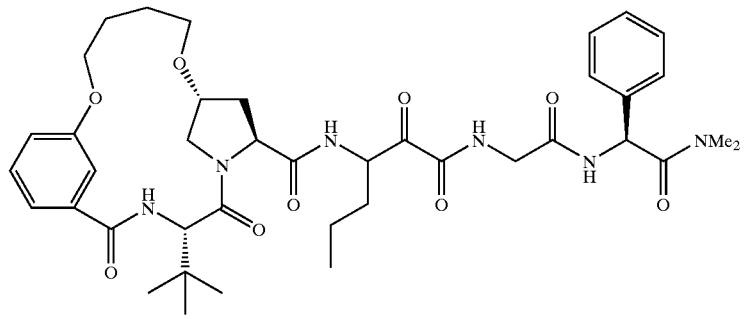
44
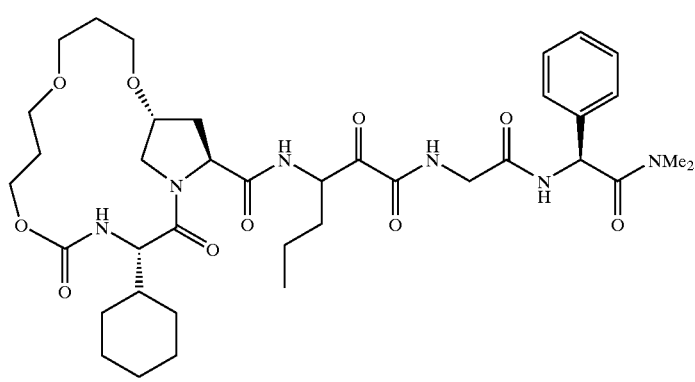
45
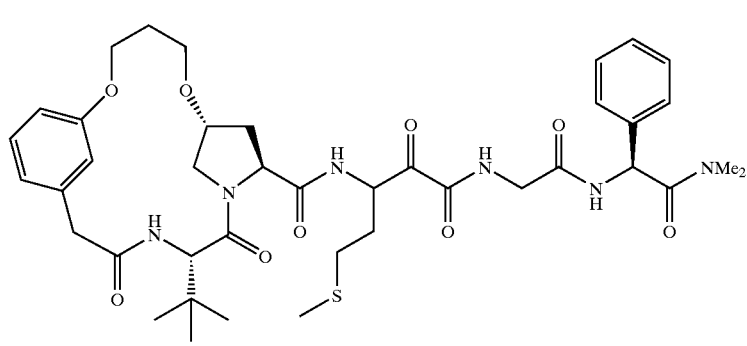
46
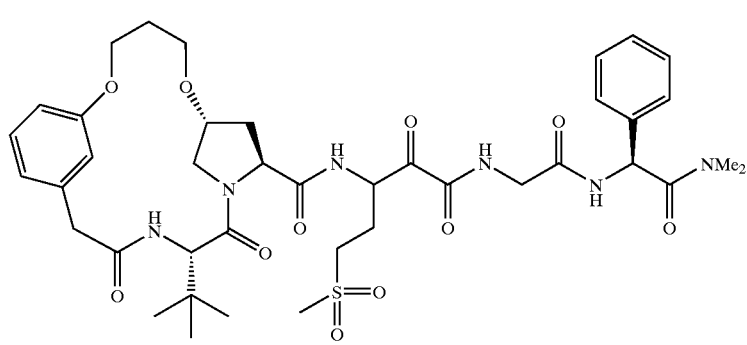
47

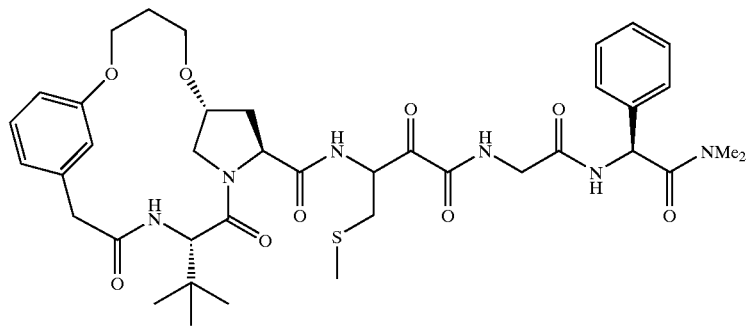
48
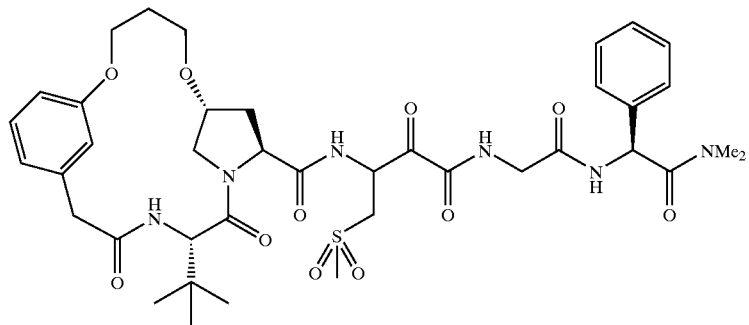
49
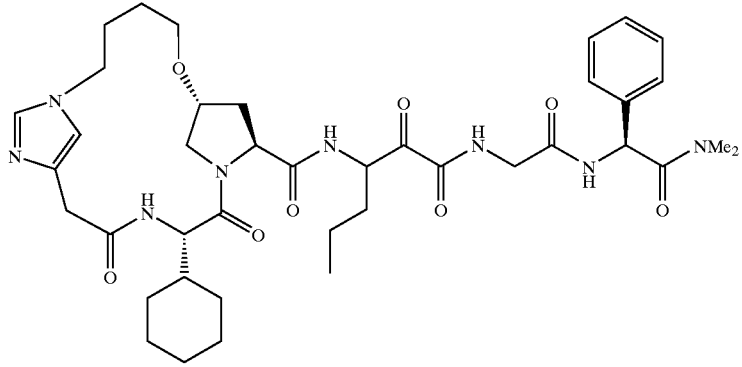
50
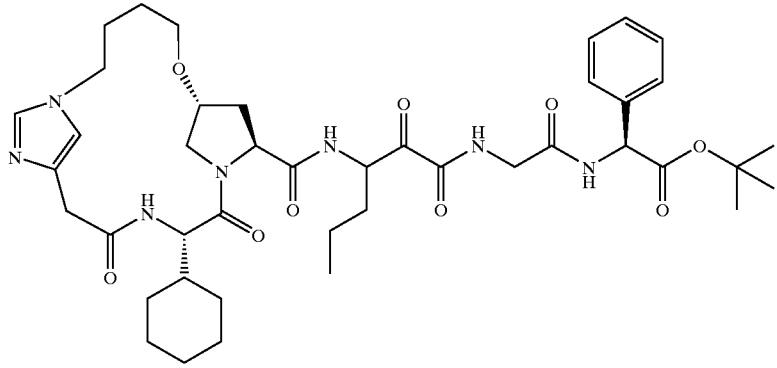
51

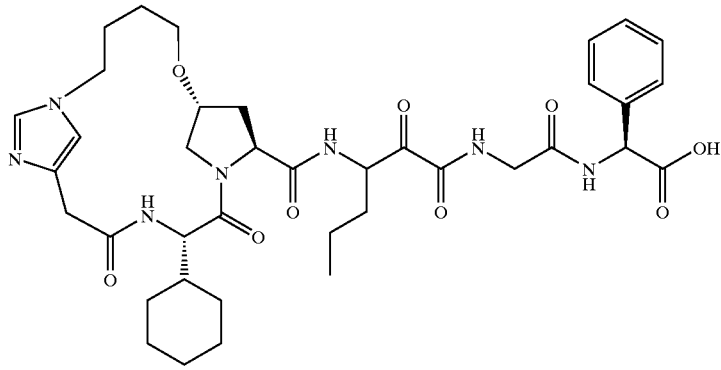
52
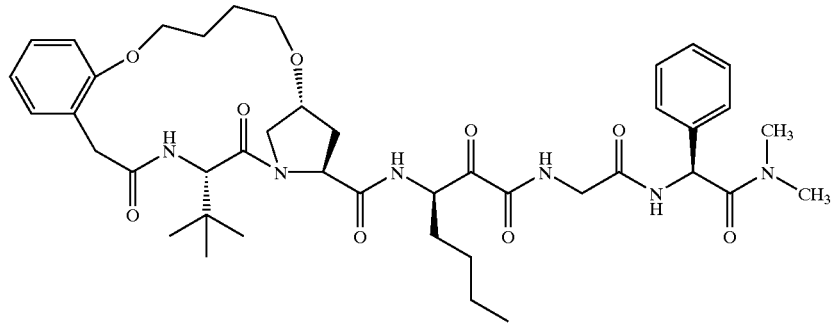
53A
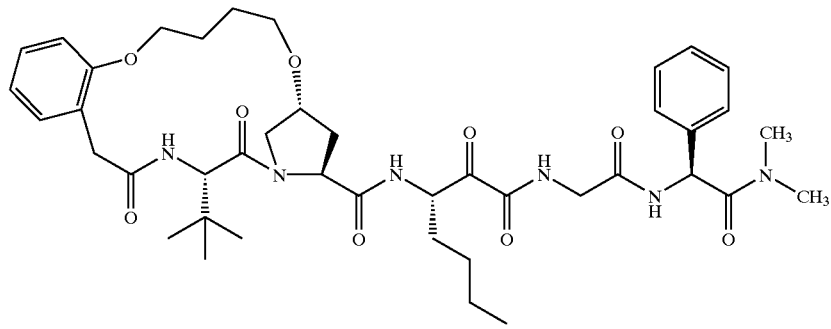
53B
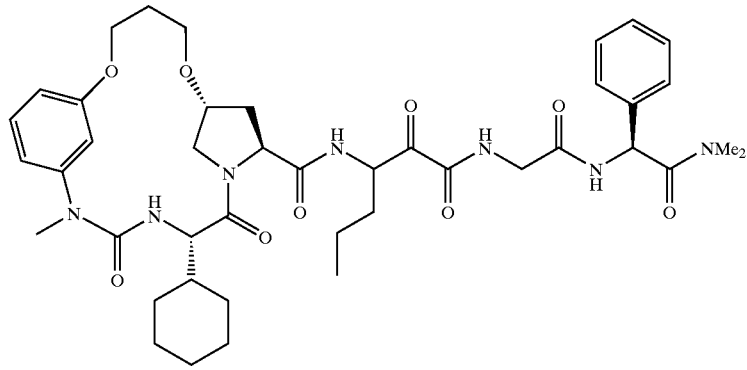
54

-continued
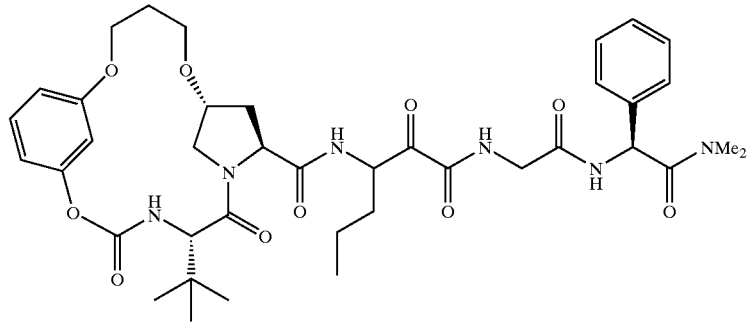
55
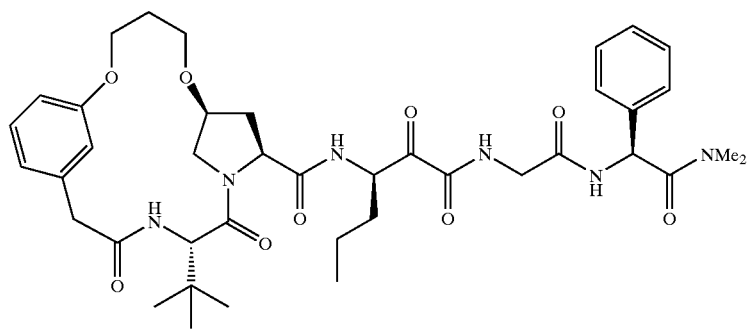
56A
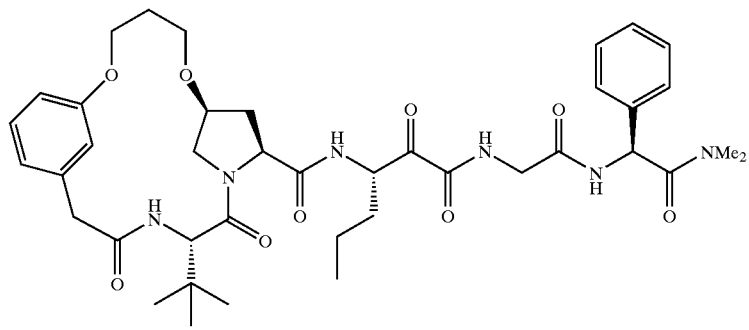
56B
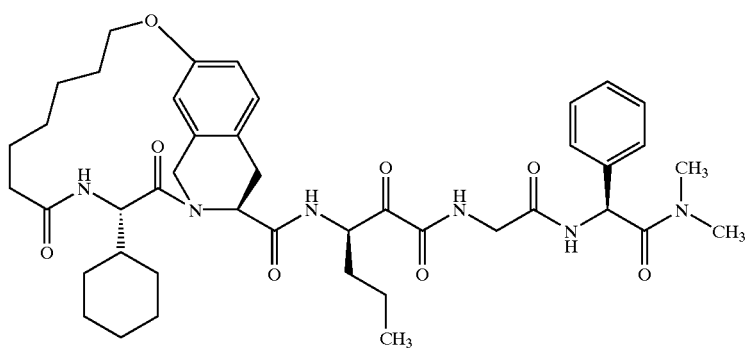
57A

57B
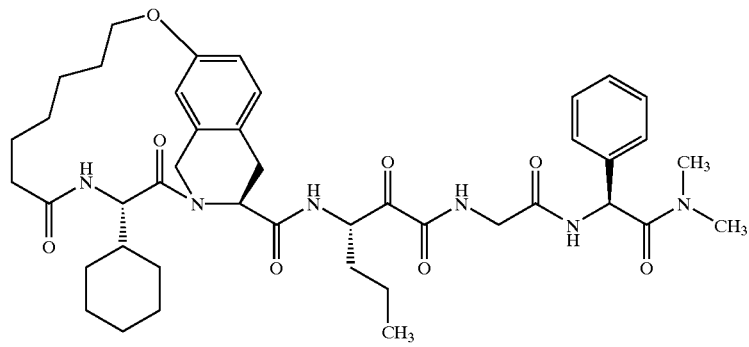
58
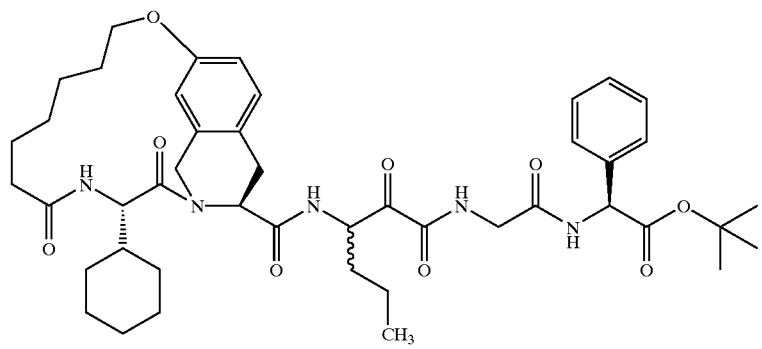
59A
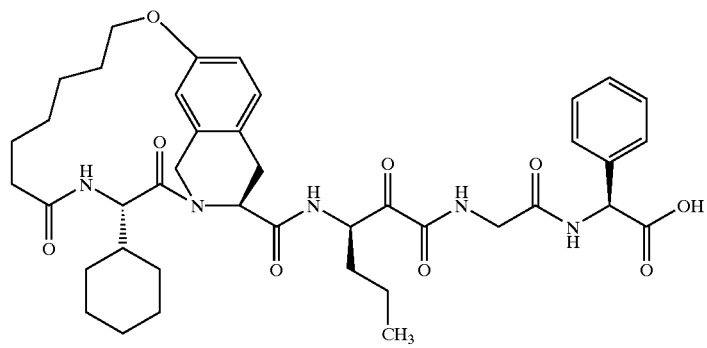
59B
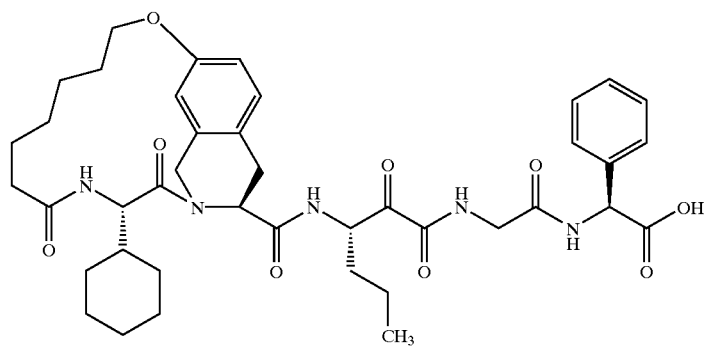

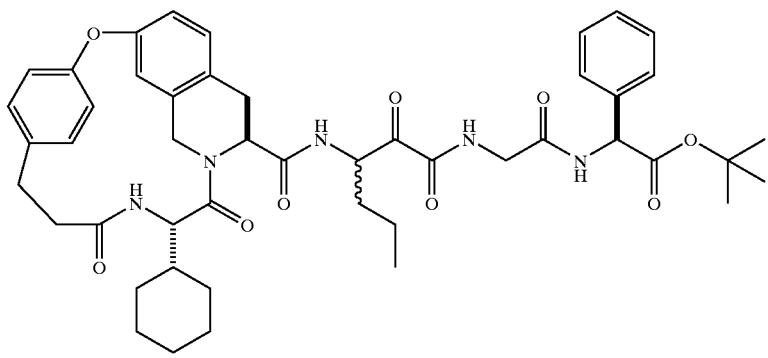
60
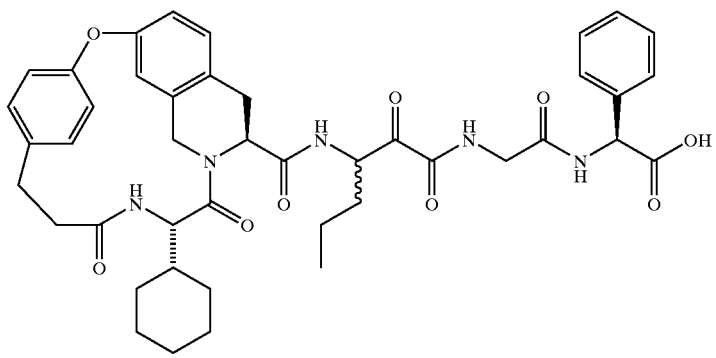
61
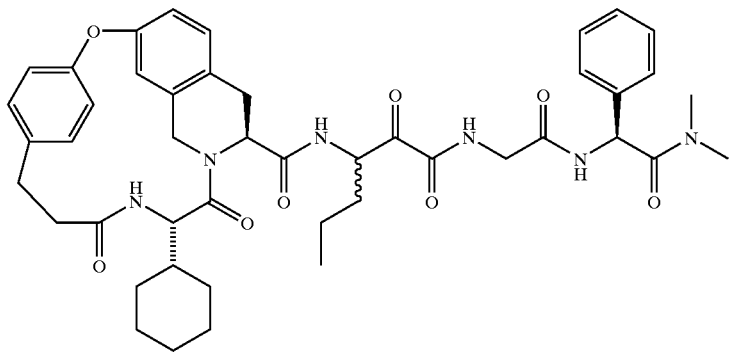
62
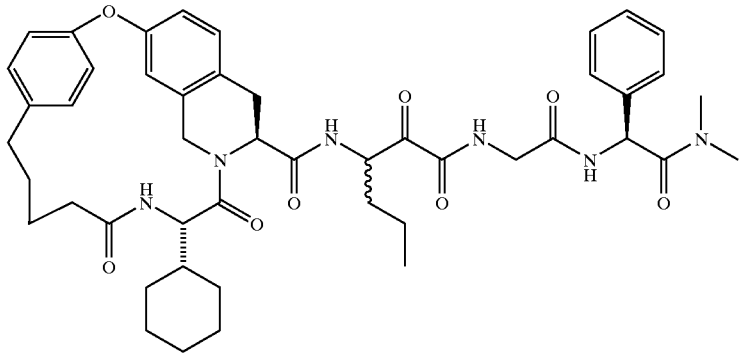
63

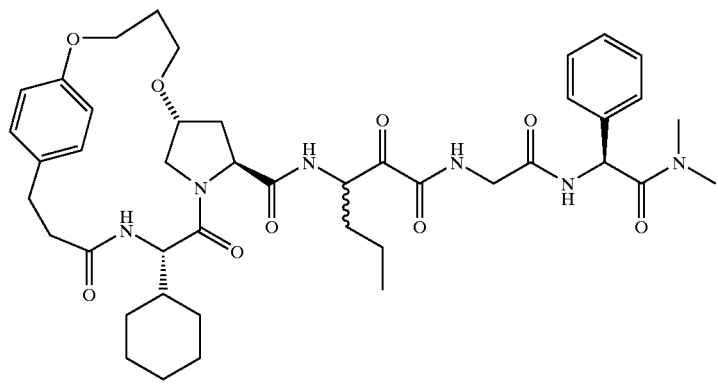
64
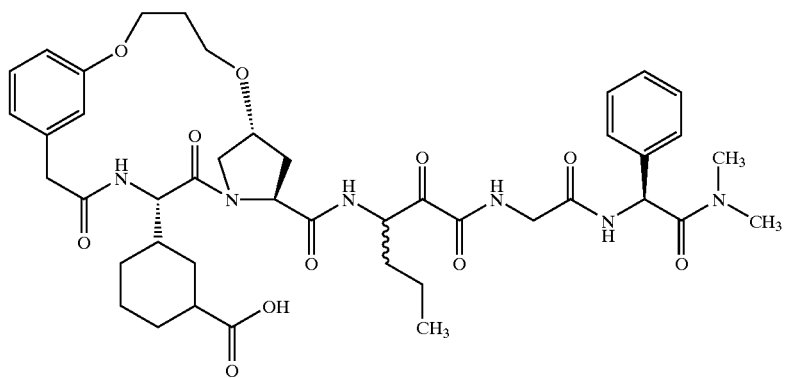
65
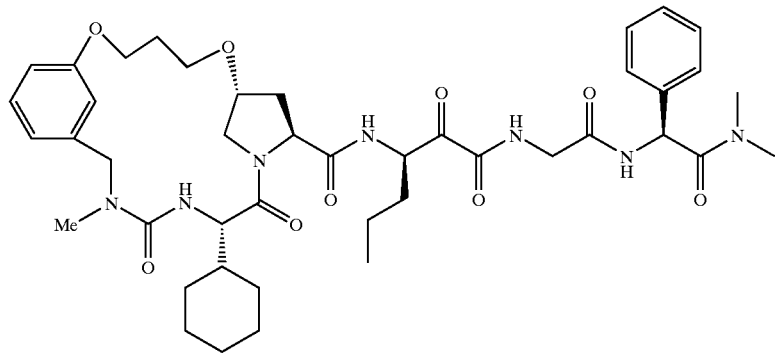
66A
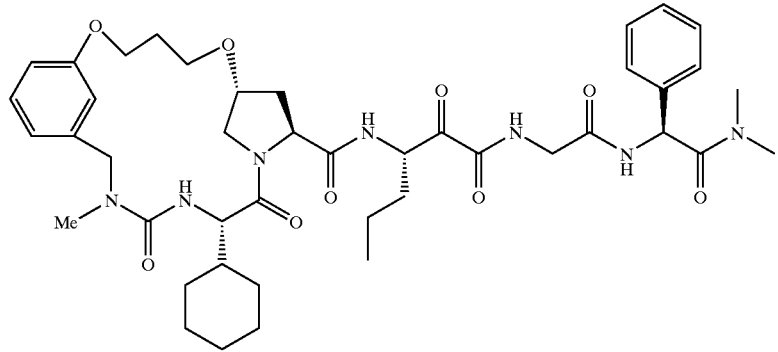
66B

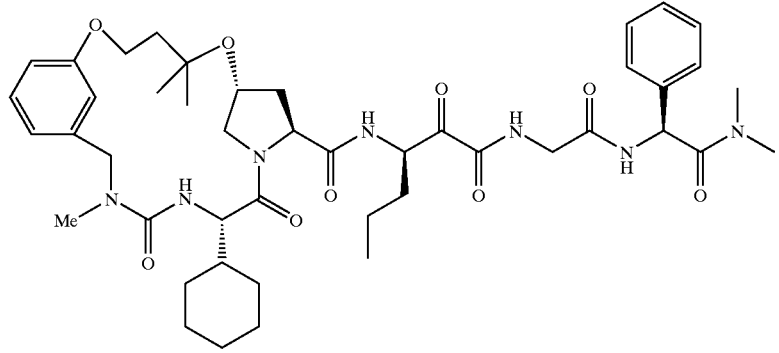
67A
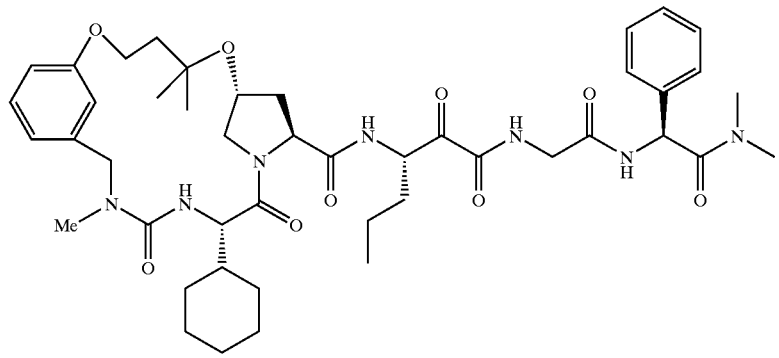
67B
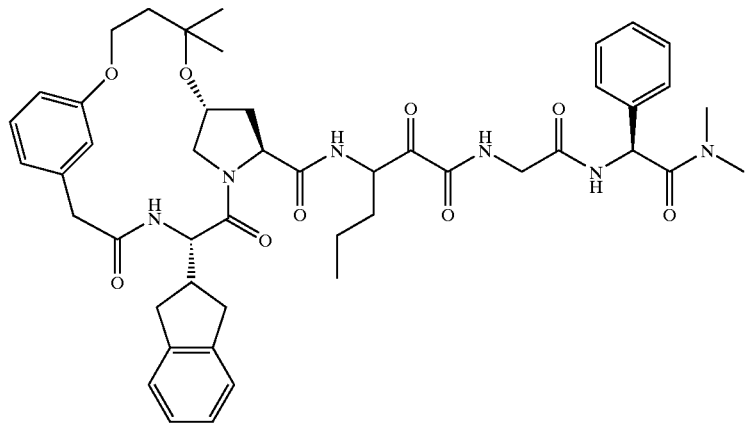
68
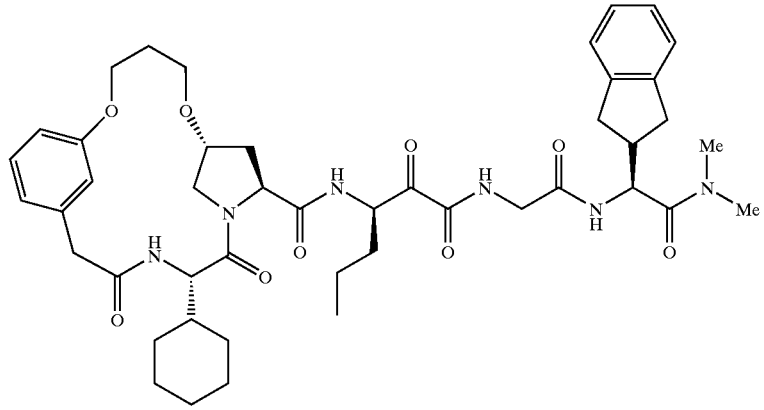
69A

69B
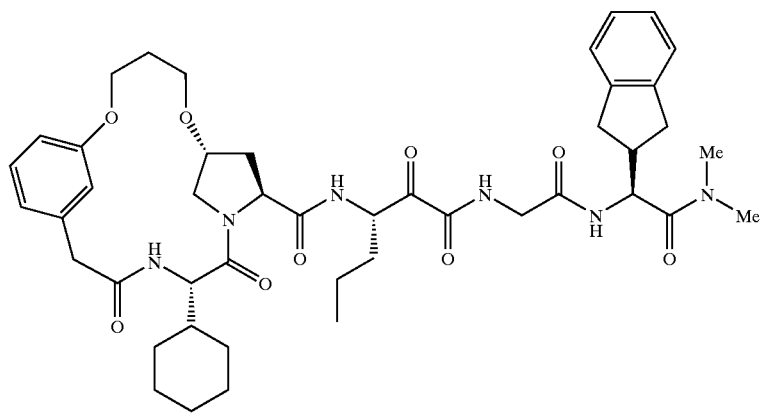
70A
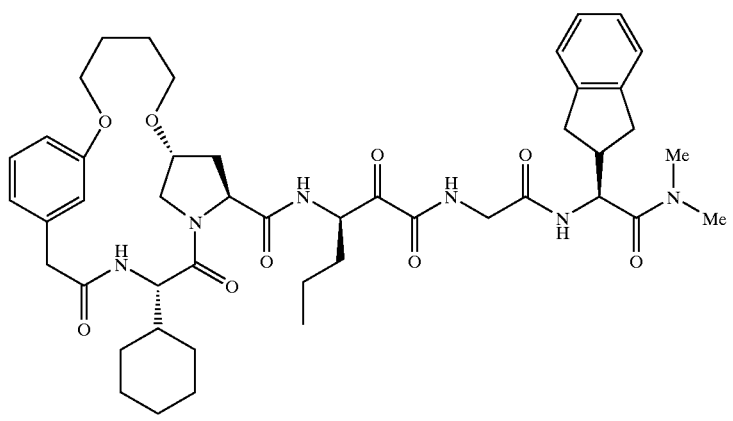
70B
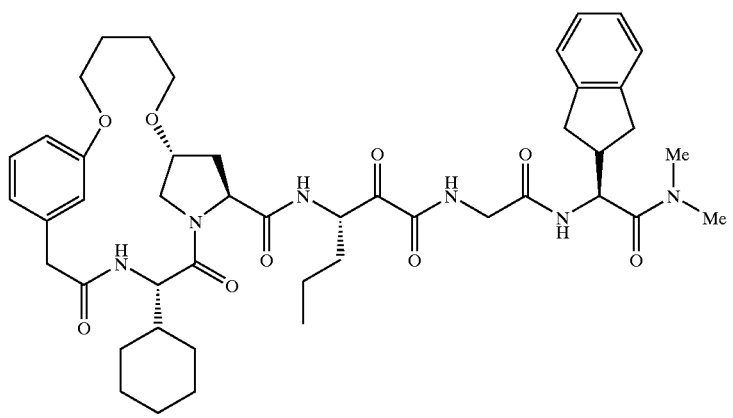
71
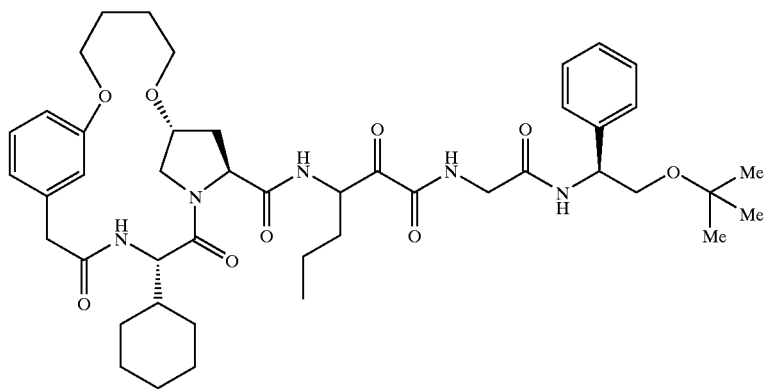

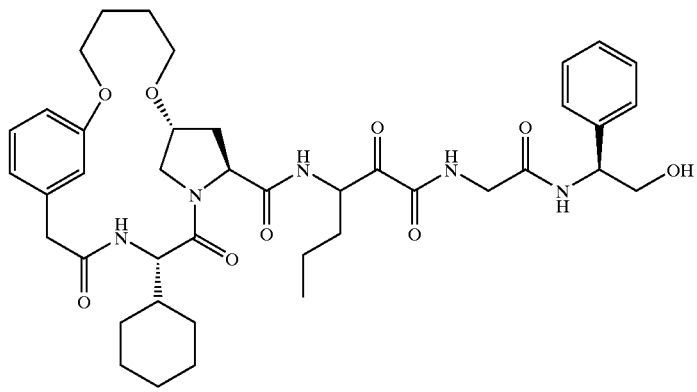
72
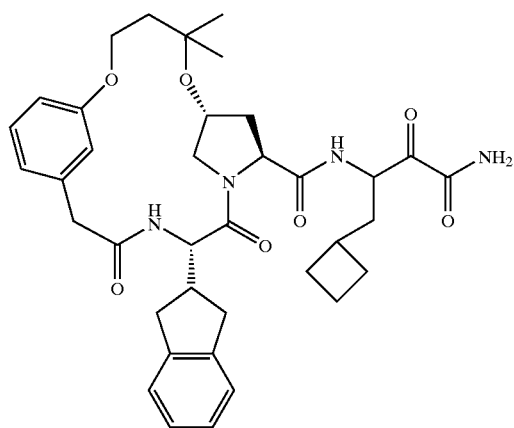
73
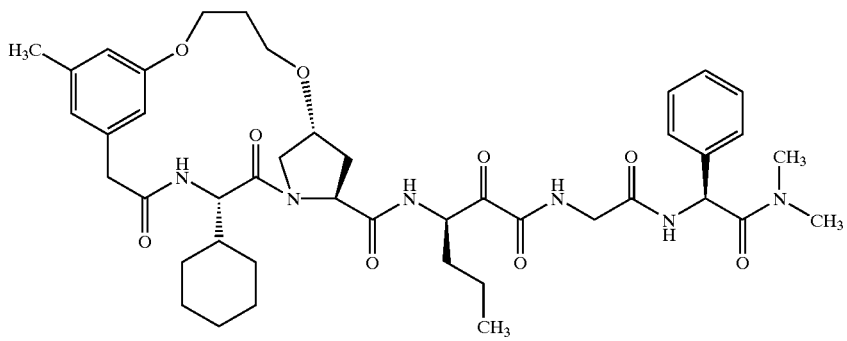
74A
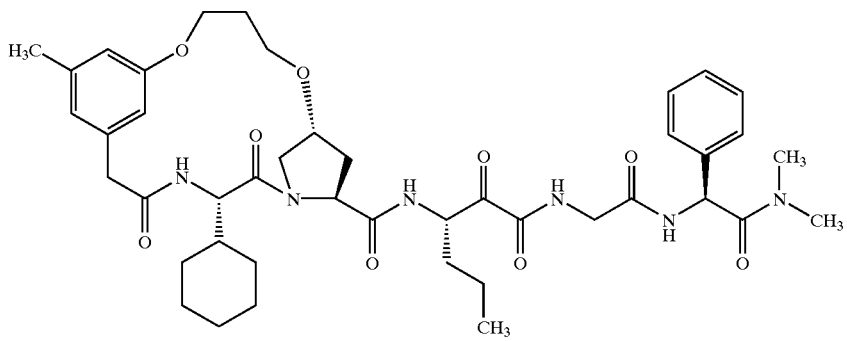
74B

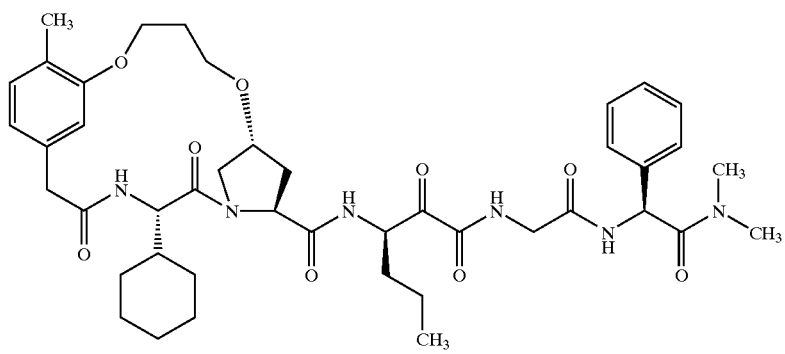
75A
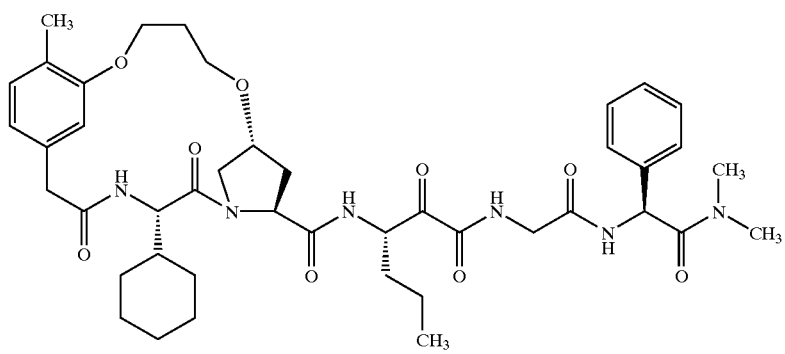
75B
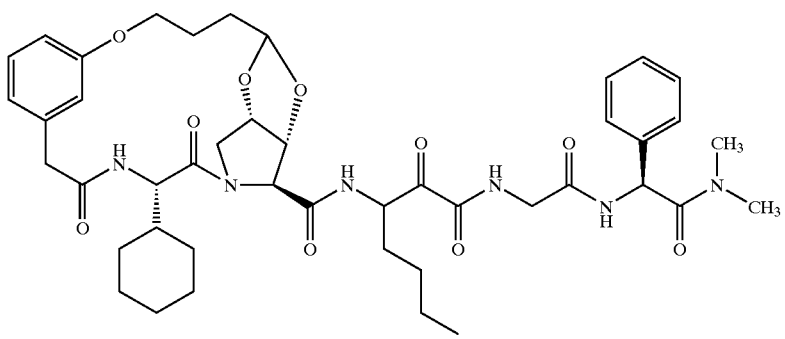
76
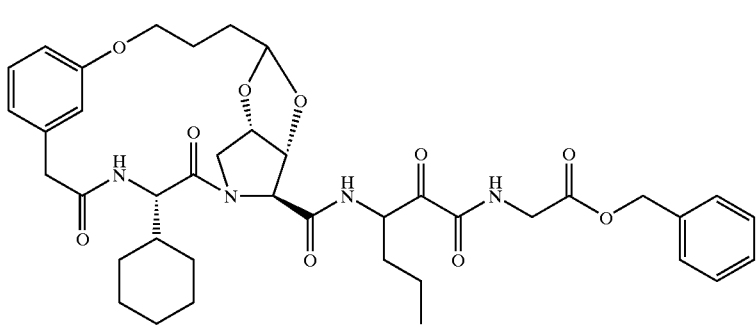
77

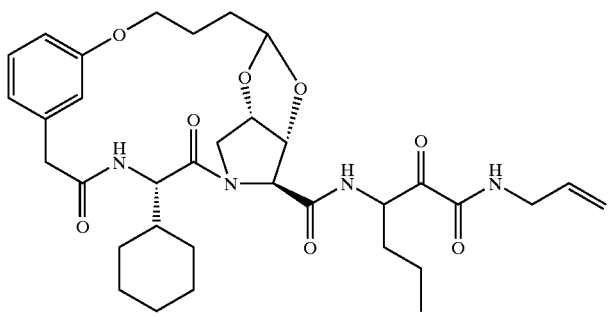
78
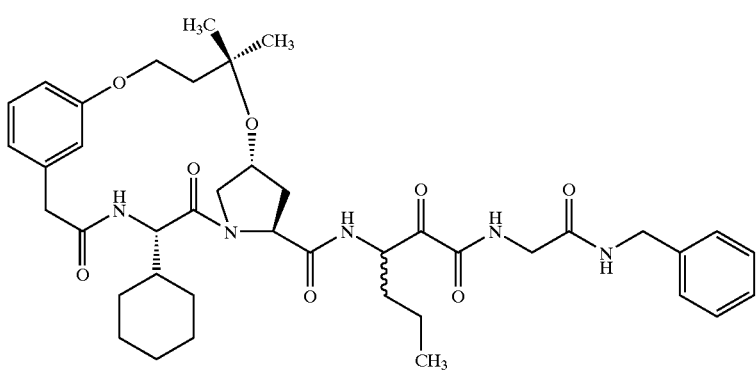
79
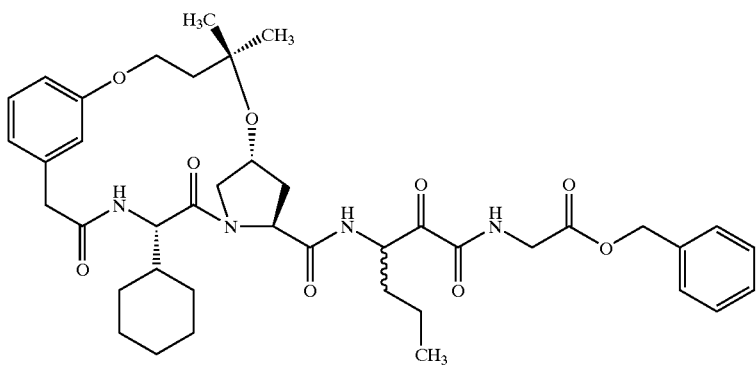
80
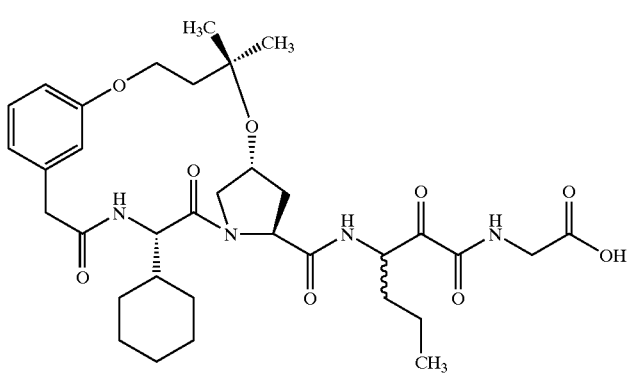
81

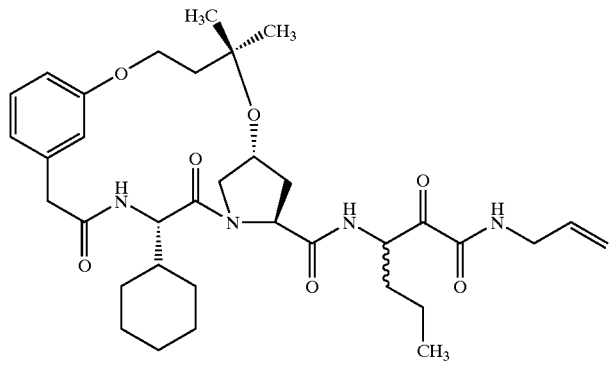
82
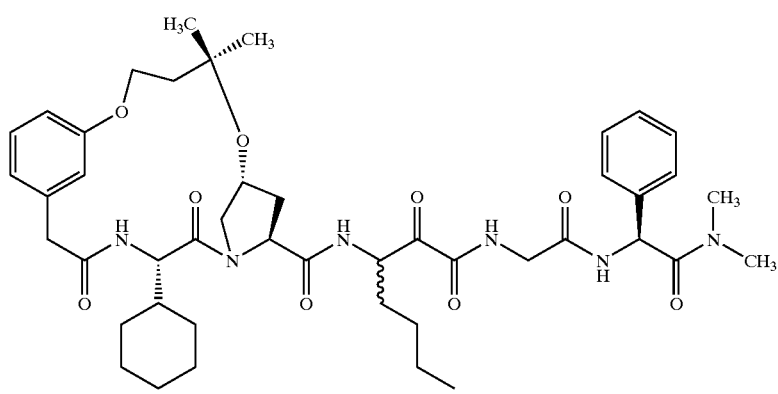
83
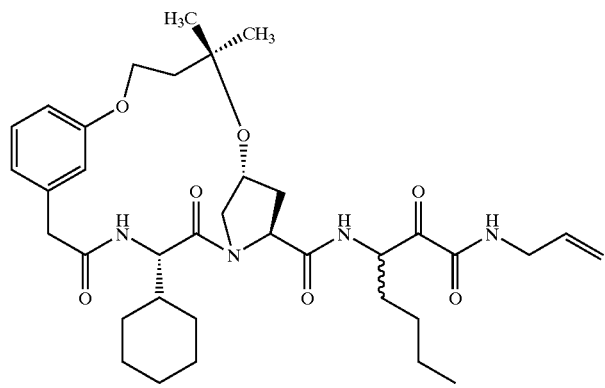
84
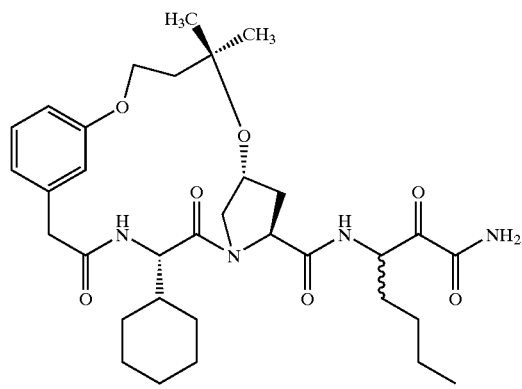
85

86
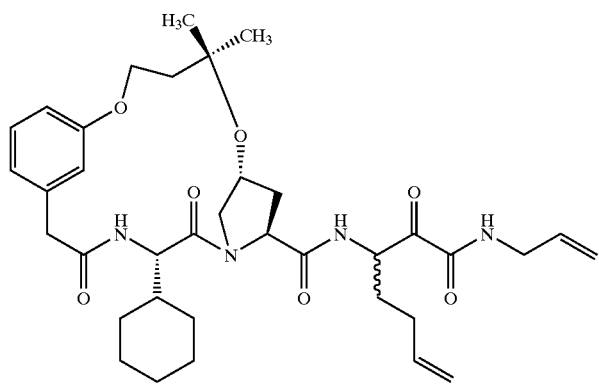
87
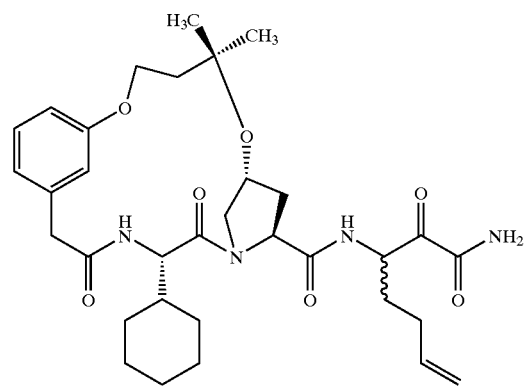
88
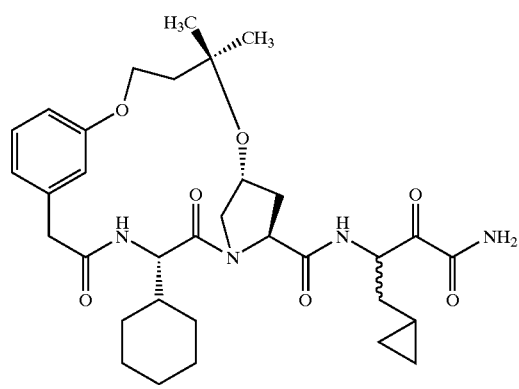
89
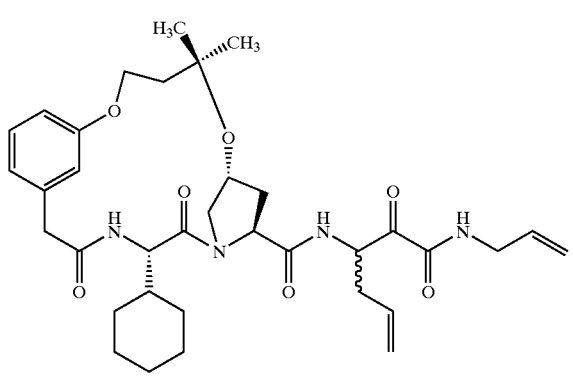
90
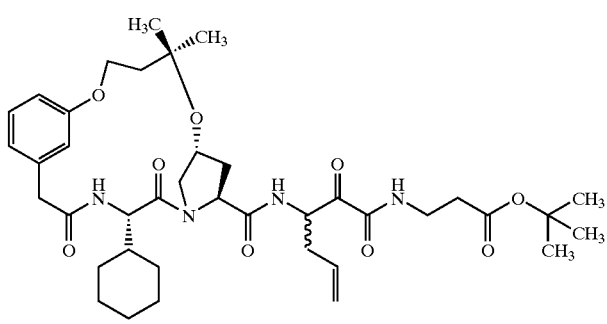
91
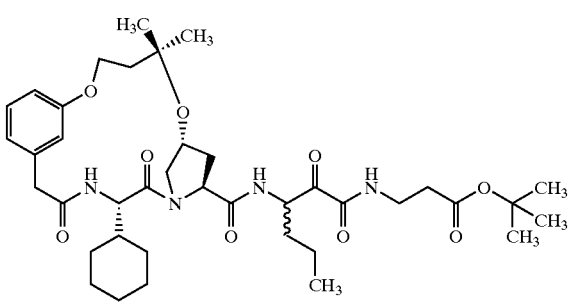
92
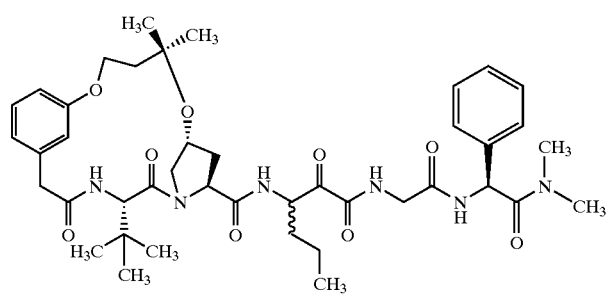
93
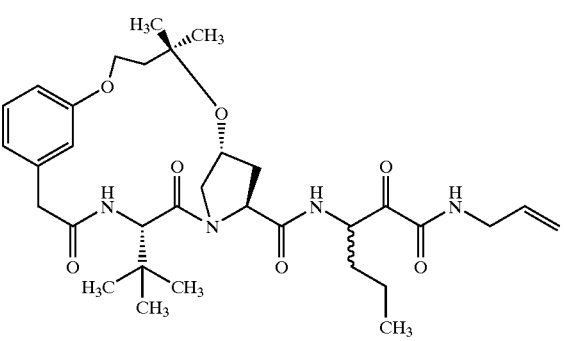

94
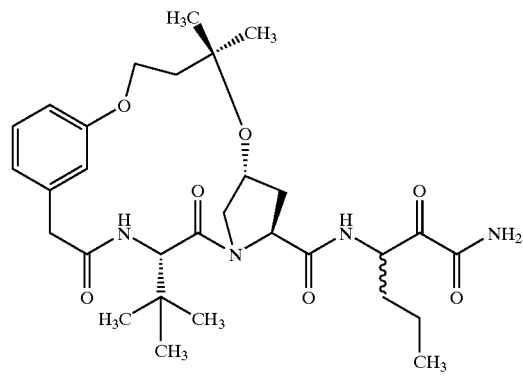
95
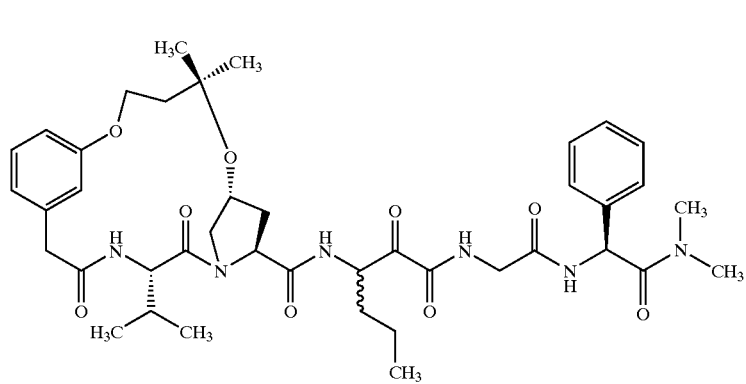
96
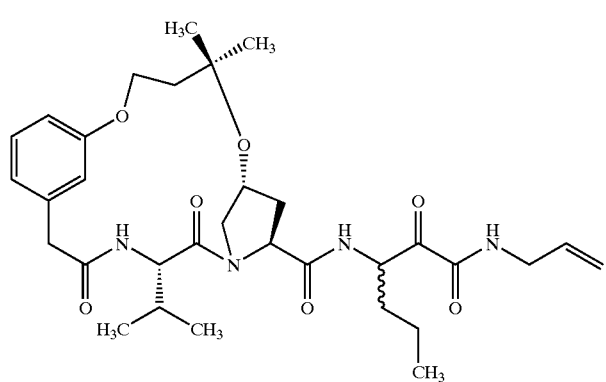
97
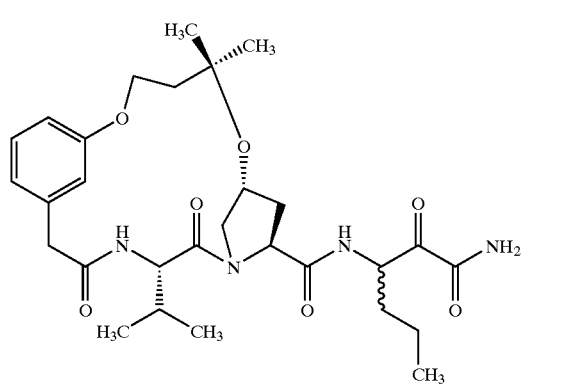

-continued
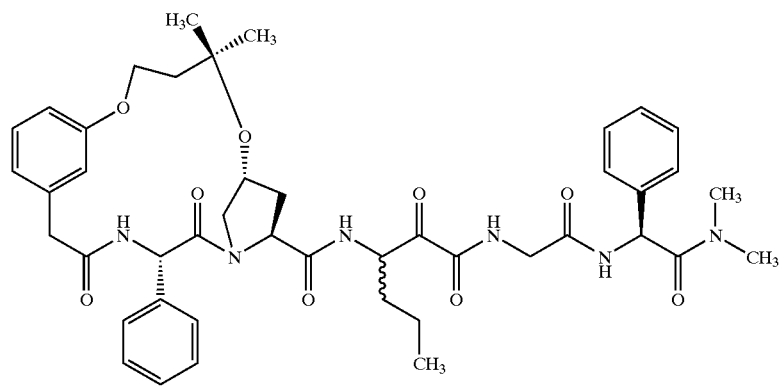
98
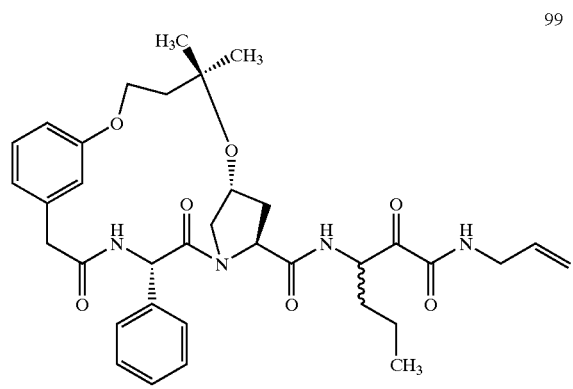
99
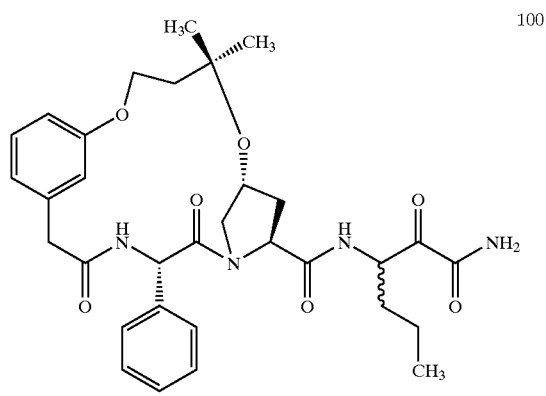
100
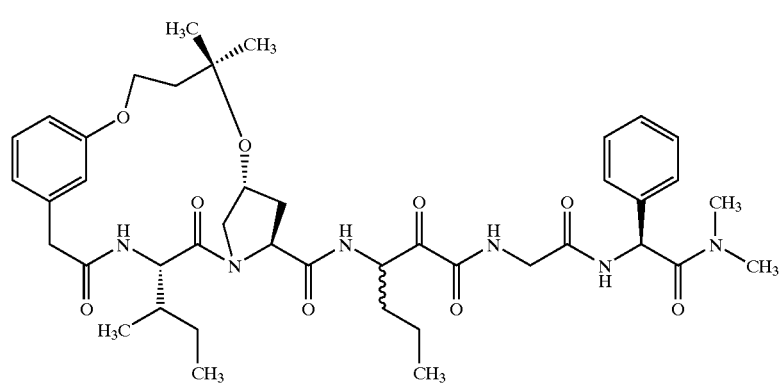
101
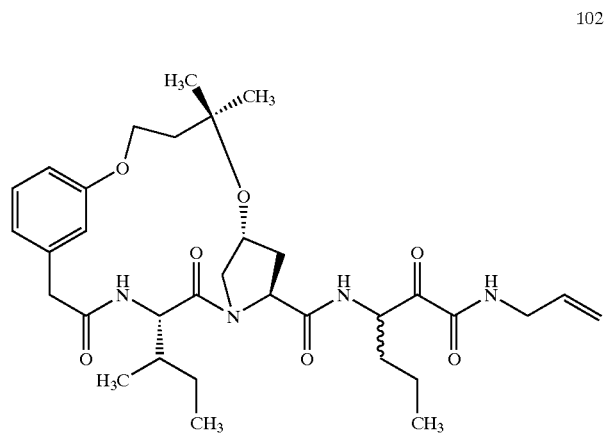
102
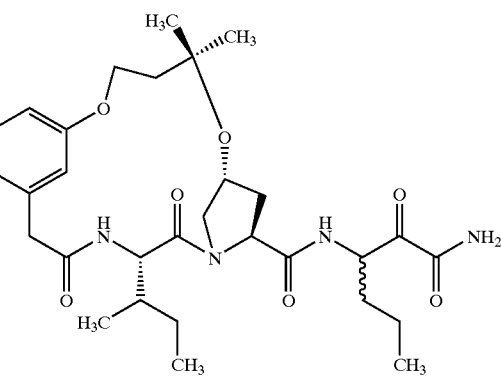
103

104
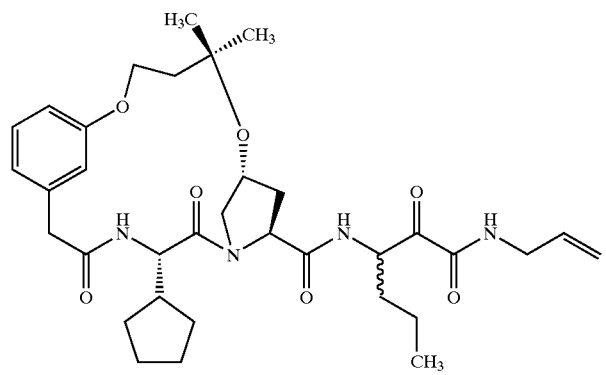
105
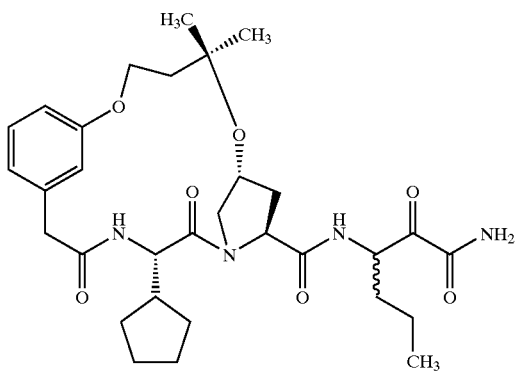
106
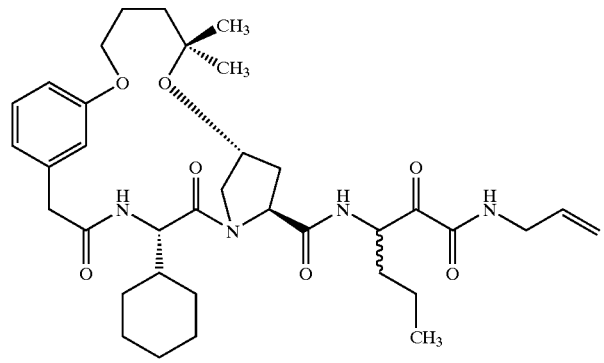
107
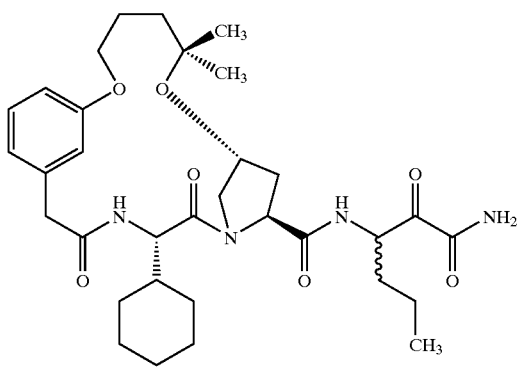
108
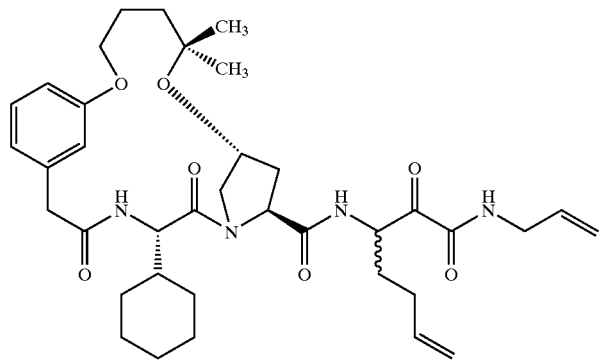
109
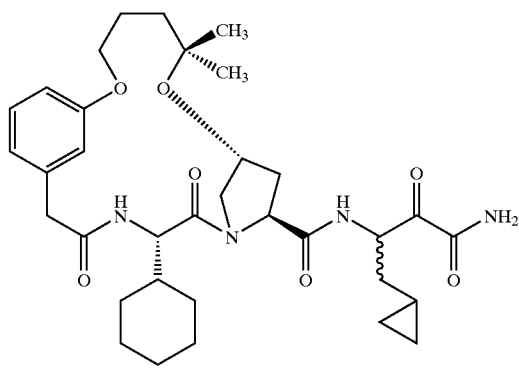
110
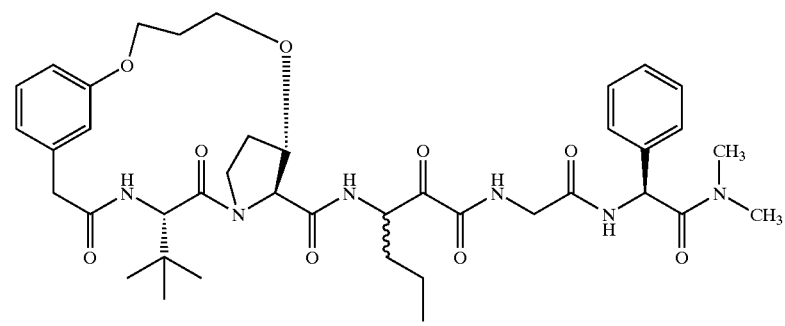

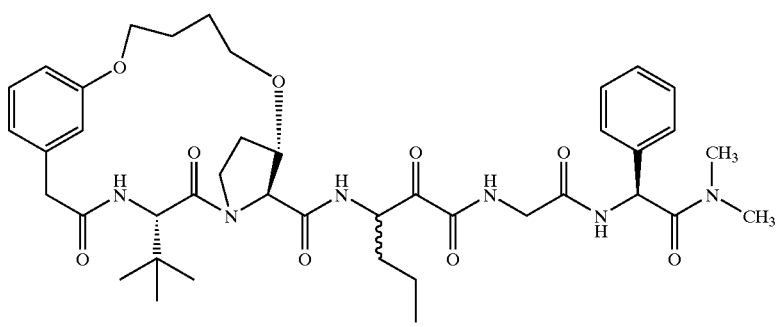

111

Depending upon the structure, the compounds of the invention may form pharmaceutically acceptable salts with organic or inorganic acids, or organic or inorganic bases. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. For formation of salts with bases, suitable bases are, for example, NaOH, KOH, $NH_4OH$, tetraalkylammonium hydroxide, and the like.

In another embodiment, this invention provides pharmaceutical compositions comprising the above-described inventive macrocycles as an active ingredient. The pharmaceutical compositions generally additionally comprise a pharmaceutically acceptable carrier diluent, excipient or carrier (collectively referred to herein as carrier materials). Because of their HCV inhibitory activity, such pharmaceutical compositions possess utility in treating hepatitis C and related disorders.

In yet another embodiment, the present invention discloses methods for preparing pharmaceutical compositions comprising the inventive macrocycle compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the pharmaceutical compositions disclosed above for treatment of diseases such as, for example, hepatitis C the like. The method comprises administering a therapeutically effective amount of the inventive pharmaceutical composition to a patient having such a disease or diseases and in need of such a treatment.

As stated earlier, the invention includes tautomers, enantiomers and other stereoisomers of the compounds also. Thus, as one skilled in the art knows, some of the inventive compounds may exist in isomeric forms. Such variations are contemplated to be within the scope of the invention.

Another embodiment of the invention discloses a method of making the macrocyclic compounds disclosed herein. The compounds may be prepared by several techniques known in the art. Representative illustrative procedures are outlined in the following reaction schemes. It is to be understood that while the following illustrative schemes describe the preparation of macrocycles predominately derived from 4-cishydroxyproline ("cis-HYP") or 7-hydroxytetrahydroisoquinoline-3-carboxylic acid ("TIC"), suitable substitution of any of both the natural and unnatural amino acids will result in the formation of the desired macrocycles based on such substitution.

Abbreviations which are used in the descriptions of the schemes, preparations and the examples that follow are:
THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCl: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
MeOH: Methanol
EtOH: Ethanol
Et$_2$O: Diethyl ether
Bn: Benzyl
Boc: tert-Butyloxycarbonyl
Cbz: Benzyloxycarbonyl
Cp: Cyclopentylidene
Ts: p-toluenesulfonyl
Me: Methyl
PyBrOP: Tris(pyrolidino)bromophosphonium hexafluorophosphate
DMSO: Dimethyl sulfoxide
TFA: Trifluoroacetic acid
HOBt: Hydroxybezotriazole
Hünigs base: Diisoprpylethyl amine
BOP: Benzotrizaol-1-yloxytris(dimethylamino) phosphonium hexafluorophosphate
LDA: Lithium diisopropyl amide
Ph$_3$P: Triphenyl phosophine
LAH: Lithium Aluminum Hydride
DMAP: 4-Dimethyl aminopyridine
DCC: Dicyclohexylcarbodiimide
MCPBA: meta-Chloroperbenzoic acid
BINAP: 2,2'-Bis(diphenylphosphino)-1,1'-binaphtol
MeCN: acetonitrile
Pr: Propyl
Ac: Acetyl
Ph: Phenyl General Preparative Schemes The preparation of the compound of formula 1h, wherein R$^1$, R$^2$, R$^3$ are defined above, R' is alkyl, heteroalkyl (OR", SR''', NR"R''' wherein R" and R''' are alkyl groups), halo substituent at ortho, meta, or para -position to oxygen atom; R is alkyl, aryl, or alkylaryl groups; n is from zero to five; X is (CH$_2$)$_m$ where m is one to five, oxygen atom, NY where Y is hydrogen atom, alkyl, aryl group; and PG$^1$ and PG$^2$ are appropriate protecting groups (PG$^1$=t-boc, cbz and PG$^2$=H, Bn etc) is outlined in Scheme 1. The protected 4-hydroxyproline acid (1a) is alkylated at the 4-position by an alkyl bromide in the presence of sodium hydride. The product 1b is then converted to an ester either with an alcohol under acidic conditions, or with trimethylsilyldiazamethane. After deprotection, the resulting amine is coupled to a Boc-protected amino acid in the presence of HOOBt, EDCl.HCl and NMM. After removal of the Boc group from product 1d, the dipeptide is reacted with a substituted hydroxyphenyl acetic acid using the same coupling conditions. Catalytic hydrogenation of the benzyl ether gives the precursor for the macrocyclization. The macrocyclization is achieved under Mitsunobu conditions by using triphenylphosphine and ADDP. (The *Mitsunobu* reaction is reviewed by D. L. Hughes, *Org. Reactions*, 42 (1992) 335, John Wiley & Sons, New York, L. Paquette, ed.) After the ester is hydrolyzed to an acid with lithium hydroxide, it is coupled to an amine intermediate to afford 1h.

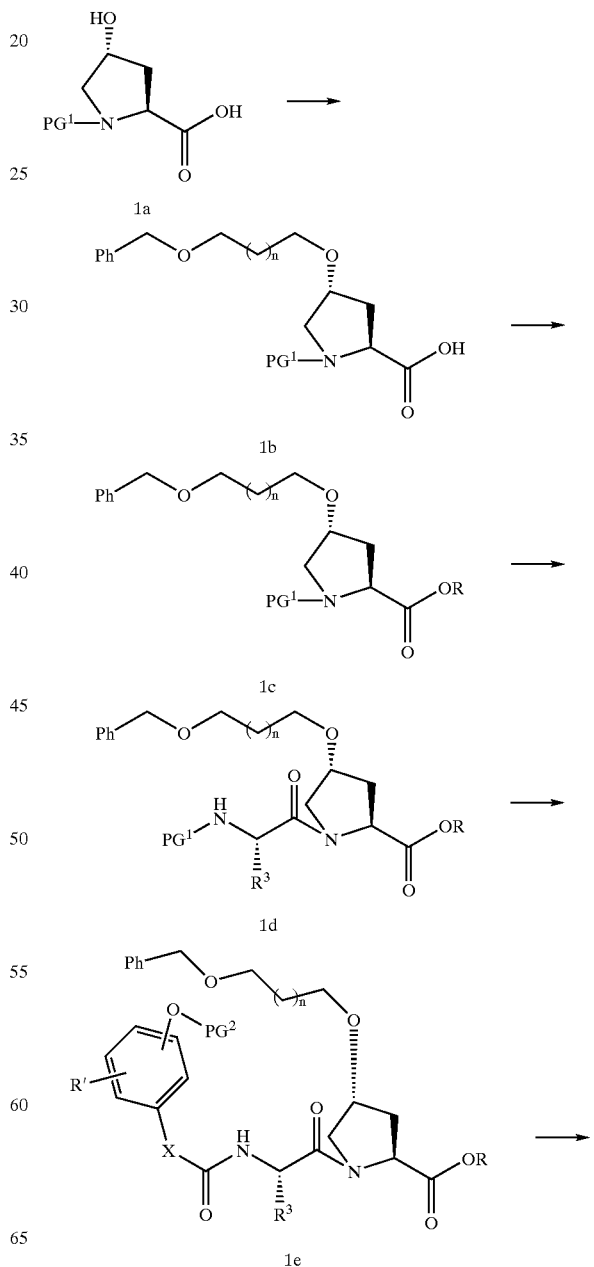

Scheme 1

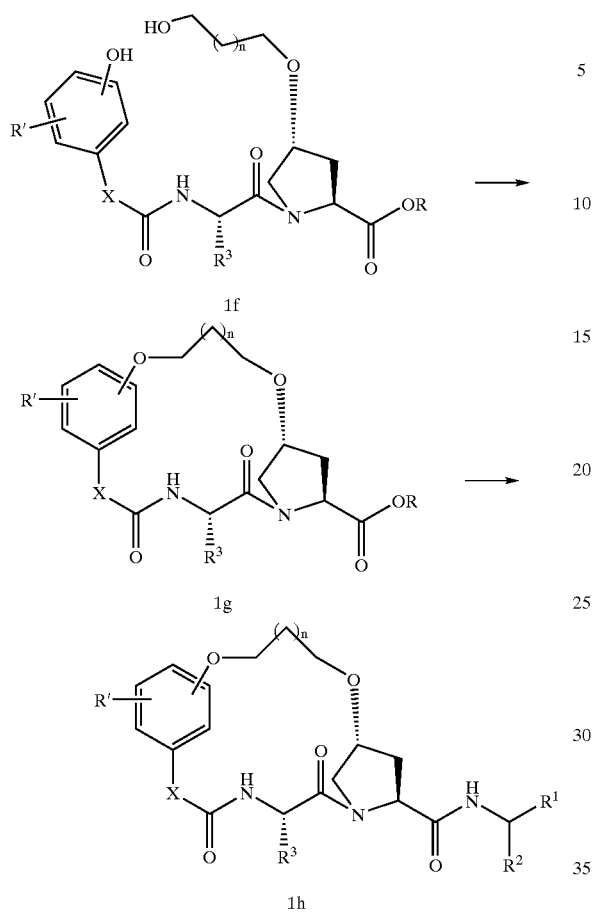

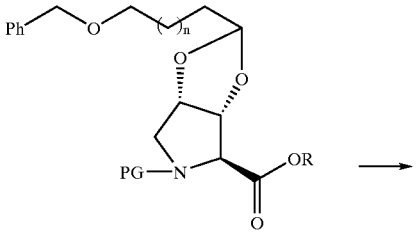

The preparation of the compound of Formula 2e, wherein $R^1, R^2, R^3, R$ and $R'$ are defined above, is outlined in Scheme 2. The protected 3,4-dehydroproline 2a is diastereoselectively dihydroxylated to afford cis-diol 2b. The acetal formation between 2b and an aldehyde can be accomplished in the presence of catalytic amount of p-toluenesulfonic acid. The bicyclic proline derivative 2c is converted to the macrocyclic ester 2d and subsequently to HCV inhibitor 2e according to the sequence outlined in Scheme 1.

The preparation of the compound of Formula 3f, wherein $R^1$, $R^2$, $R^3$, R, R' and n are defined above, is outlined in Scheme 3. When treated with trifluoroboron diethyletherate, the protected 4-hydroxyproline 3a and alkene 3b are converted to proline ether 3c, which undergoes the same sequence of transformations outlined in Scheme 1 to give the macrocyclic ester 3e and subsequently, to the desired final product 3f.

Scheme 2

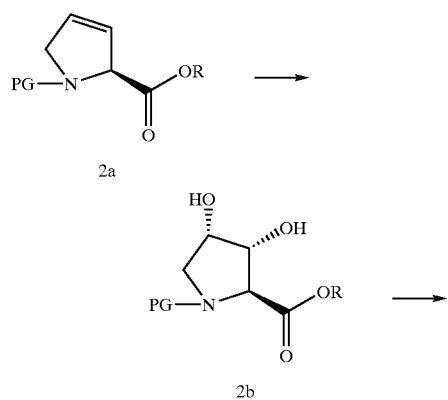

Scheme 3

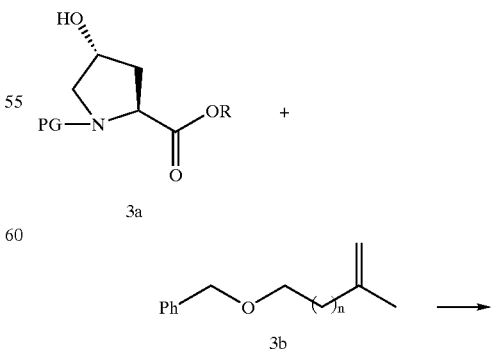

Scheme 4

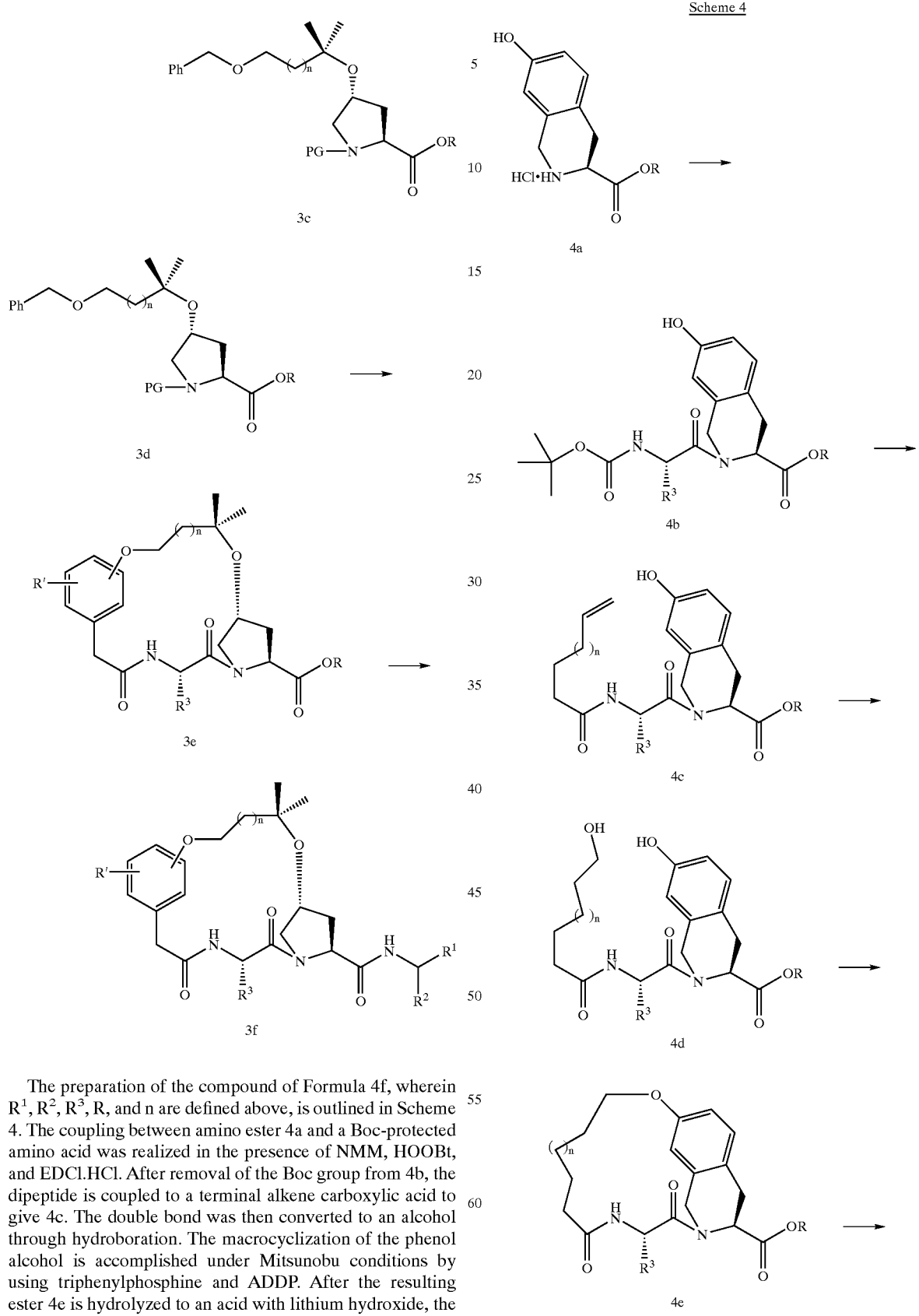

The preparation of the compound of Formula 4f, wherein $R^1$, $R^2$, $R^3$, R, and n are defined above, is outlined in Scheme 4. The coupling between amino ester 4a and a Boc-protected amino acid was realized in the presence of NMM, HOOBt, and EDCl.HCl. After removal of the Boc group from 4b, the dipeptide is coupled to a terminal alkene carboxylic acid to give 4c. The double bond was then converted to an alcohol through hydroboration. The macrocyclization of the phenol alcohol is accomplished under Mitsunobu conditions by using triphenylphosphine and ADDP. After the resulting ester 4e is hydrolyzed to an acid with lithium hydroxide, the acid is coupled to an amine intermediate to afford 4f.

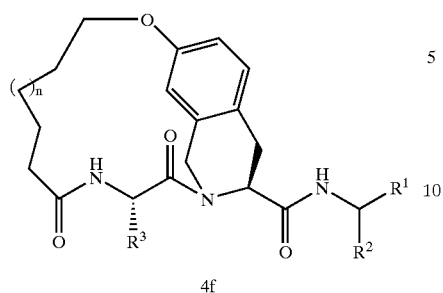

4f

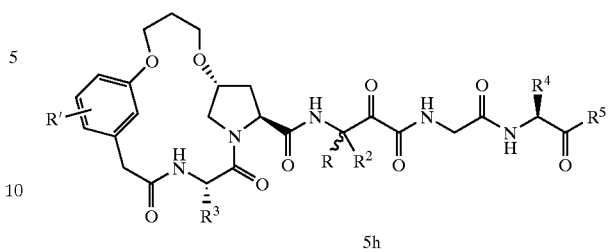

5h

The preparation of the compound of Formula 5h in Scheme 5 where in R, R², R³, R' are defined in Scheme 1, R⁴ being alkyl, cycloalkyl, aryl, heteroaryl, and heteroalkyl and R⁵ is OR, NR₂, or OH. The compound 5b was obtained by a Wittig reaction of 5a with tert-butyl phosphonoacetate and NaH. The compound 5b was converted to 5c by the treatment of MCPBA. The epoxide 5c was further opened with NaN₃ to give compound 5d which was reduced with Pd/C/H₂ to the amine and Cbz protected using Cbz-Cl, Et₃N to obtain compound of the formula 5e. The compound 5e was deprotected with TFA and further elaborated to 5f. The Cbz group of 5f was hydrogenolyzed and then coupled with compound of formula 1g using EDCl, HOOBt, NMM to obtain 5g. The compound of the type 5g is oxidized with Dess-Martin reagent to generate compounds of formula 5h.

The compound of formula 6m is synthesized as outlined in Scheme 6 wherein R¹, R², R' and n are defined in Scheme 1 and R⁶ being alkyl, aryl, ester, carboxylic acid and carboxylamides. The compound of type 6b is synthesized from 6a by a Wittig olefination using Ph₃PCH₃I and BuLi. The compound 6b is further aminohydroxylated to synthesize compound of the type 6c, which was reduced using Rh/C, and H₂ to afford compound of type 6d. The compound 6d was oxidized to compound of type 6e using RuCl₃ and H₅IO₆. The compound 6e was elaborated to compound 6i by coupling it with deprotected 6h using NMM, EDCl, and HOOBt. Extension of compound 6i to 6j was again achieved by coupling deprotected 6i and appropriately substituted phenyl acetic acid using EDCl, HOOBt and NMM. The compound 6k obtained after hydrogenolysis of benzyl group in 6j was cyclized to 6l using the Mitsunobu conditions. 6l was further elaborated to compounds of type 6m as outlined in Scheme 1.

Scheme 6

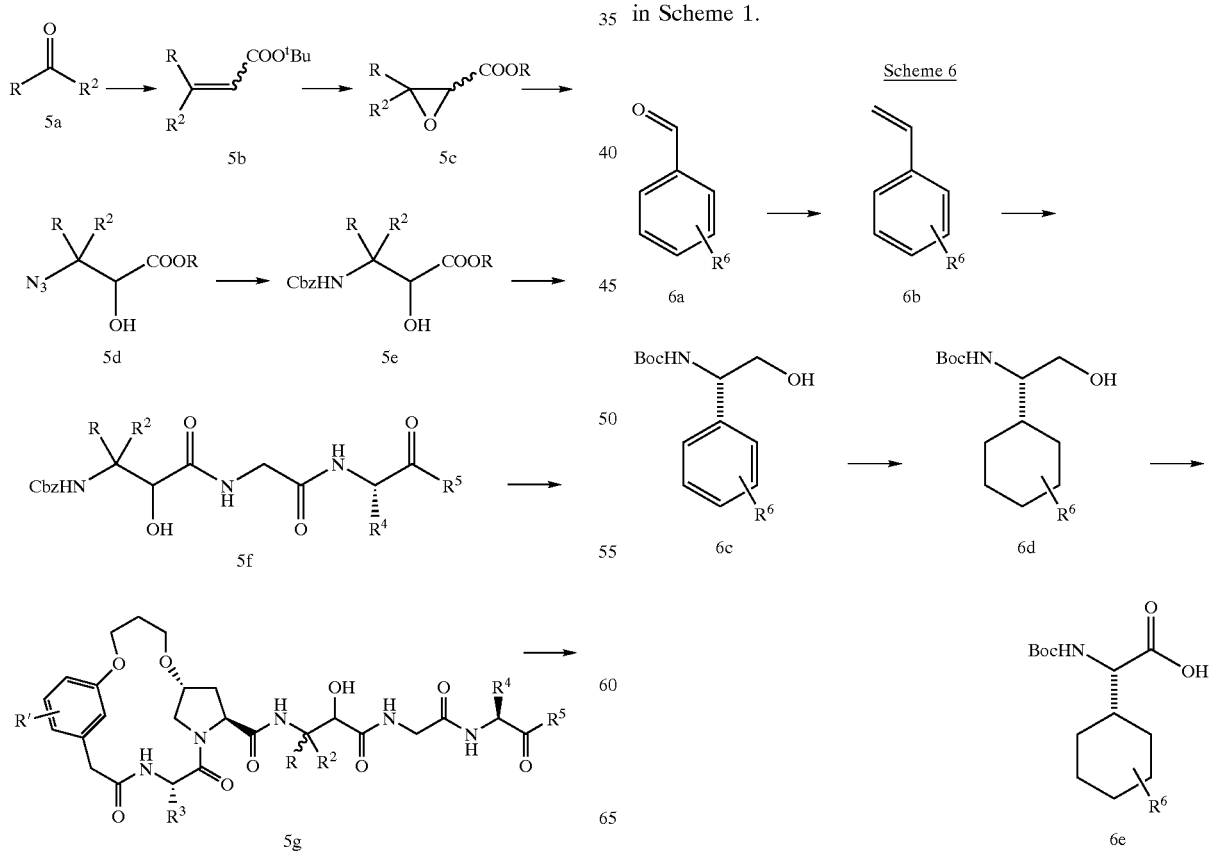

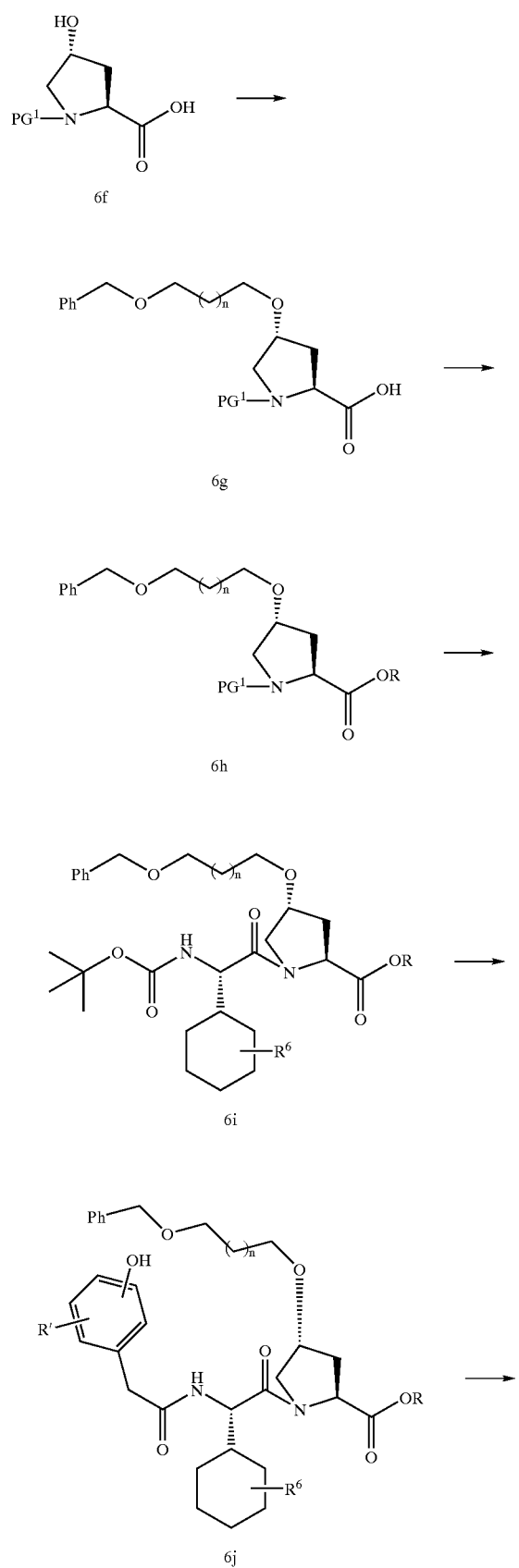
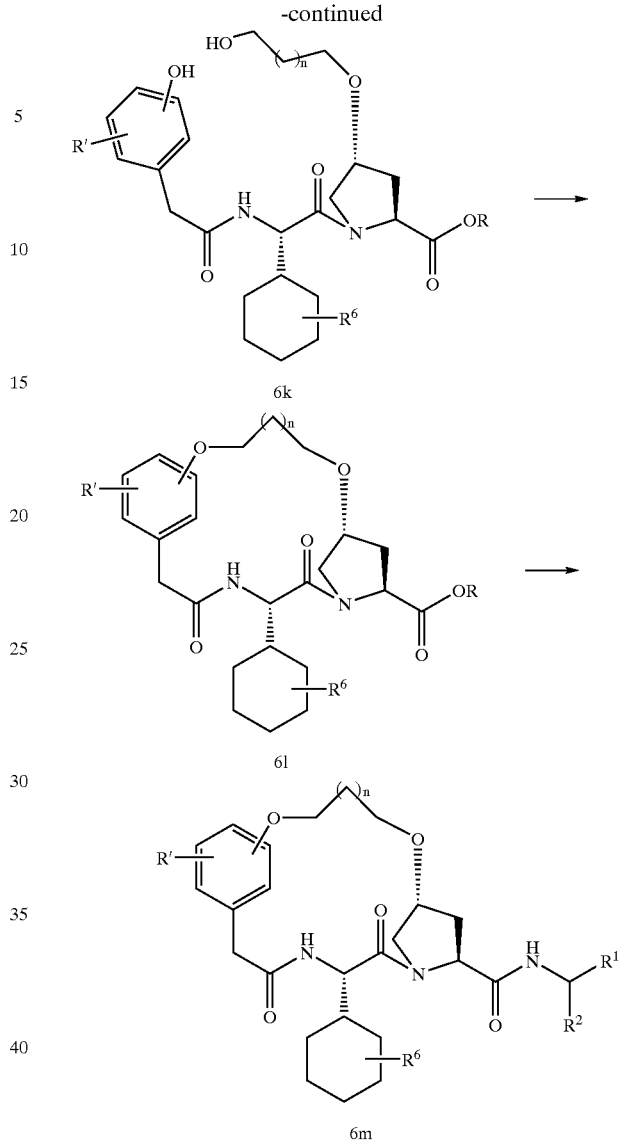

The compounds of type 7d are synthesized using the arene ruthenium chemistry wherein the substituents $R^1$, R2, $R^3$, R' are defined in Scheme 1, and n=0 to 3. The synthesis of the compound of formula 7b was obtained from compound of type 7a by an EDCl, HOBt, Hünigs base coupling. The treatment of 7b with $Cs_2CO_3$ and photolytic removal of ruthenium converted the compound of type 7b to type 7c, which was further elaborated to compounds 7d as outlined in Scheme 1.

Scheme 7

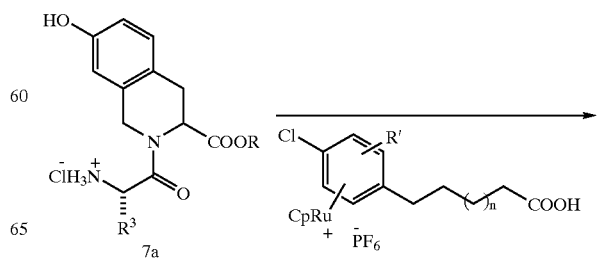

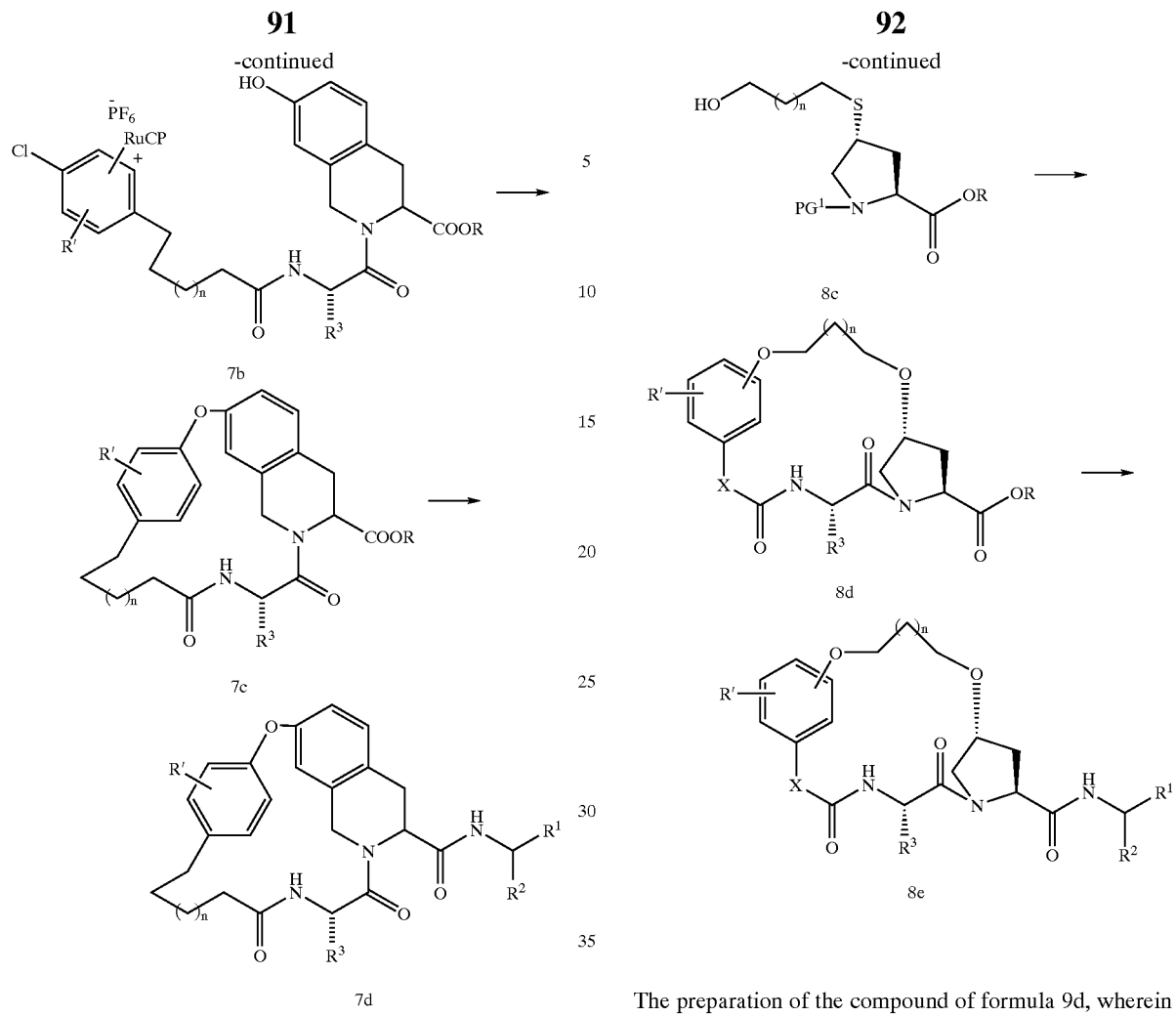

7b

7c

7d

The preparation of the compound of formula 8e, wherein $R^1$, $R^2$, $R^3$ are defined above, R' is alkyl, heteroalkyl (OR", SR'", NR"R'" wherein R" and R'" are alkyl groups), halo substituent at ortho, meta, or para-position to oxygen atom; R is alkyl, aryl, or alkylaryl groups; n is from zero to five; and X is $(CH_2)_m$ where m is one to five, oxygen atom, NY where Y is hydrogen atom, alkyl, aryl group is outlined in Scheme 8. The protected cis-4-hydroxyproline derivative 8a is converted to the brosylate (Bs=4-bromobenzenesulfonyl) derivative 8b which was displaced with the appropriate mercaptoalcohol under sodium hydride conditions to give 8c. Conversion to the macrocyclic ester 8d and subsequently to the desired target 8e was accomplished as outlined in Scheme 1.

8c

8d

8e

The preparation of the compound of formula 9d, wherein $R^1$, $R^2$, $R^3$ are defined above, R' is alkyl, heteroalkyl (OR", SR'", NR"R'" wherein R" and R'" are alkyl groups), halo substituent at ortho, meta, or para-position to oxygen atom; R is alkyl, aryl, or alkylaryl groups; n is from zero to five; X is $(CH_2)_m$ where m is one to five, oxygen atom, NY where Y is hydrogen atom, alkyl, aryl group; and LG is leaving group (e.g., OTs, Br) is outlined in Scheme 9. The protected 4-hydroxyproline derivative 1a is converted to 9a via formation of 11d (which is described in Scheme 1). Removal of the benzyl ether followed by conversion to an appropriate leaving group and unravelling the N protecting group provided 9b. Conversion to the macrocyclic ester 9c was carried out by treatment with sodium carbonate/sodium iodide in refluxing acetone. Subsequent processing to the desired target 9d was accomplished as outlined in Scheme 1.

Scheme 8

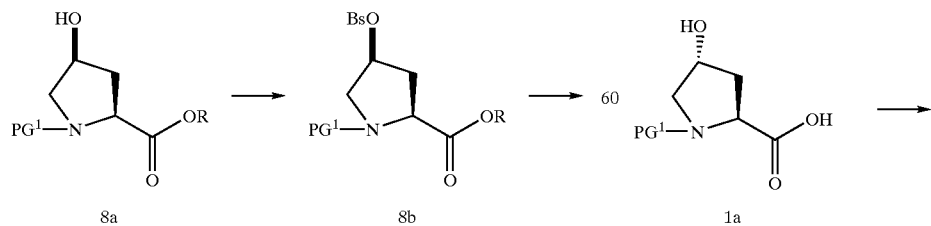

8a

8b

Scheme 9

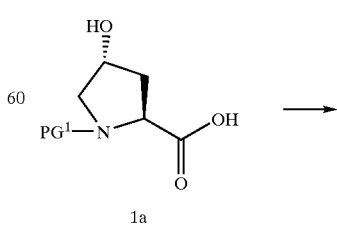

1a

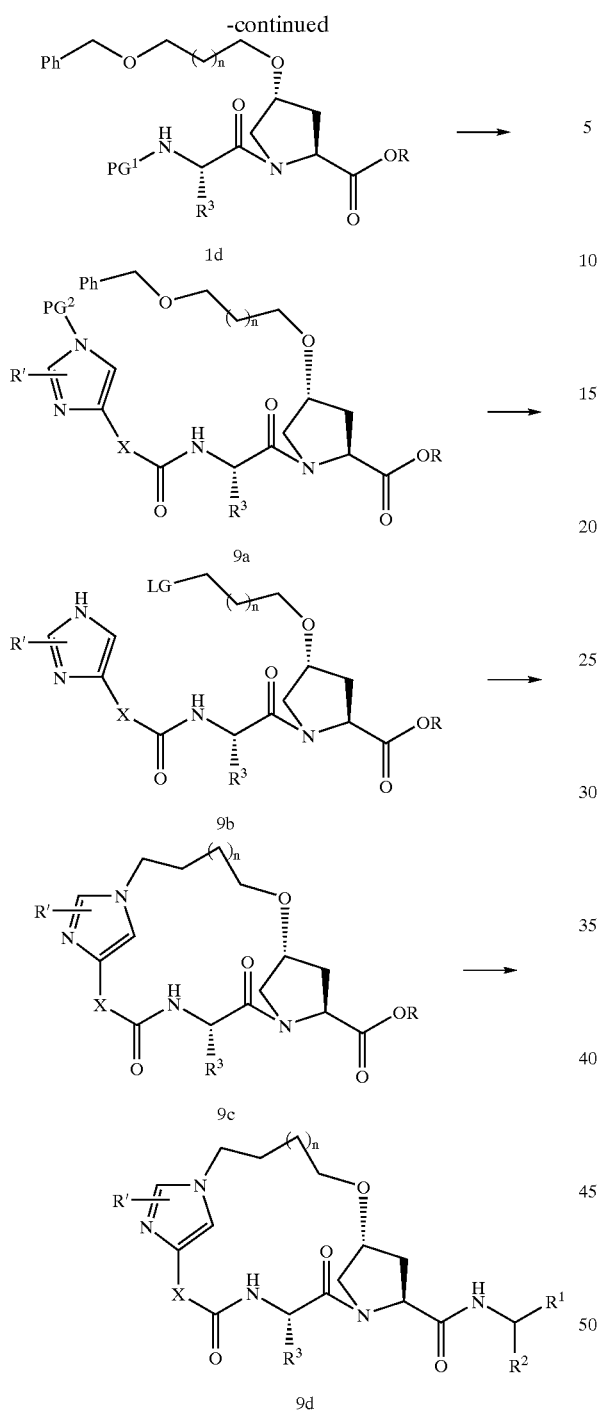

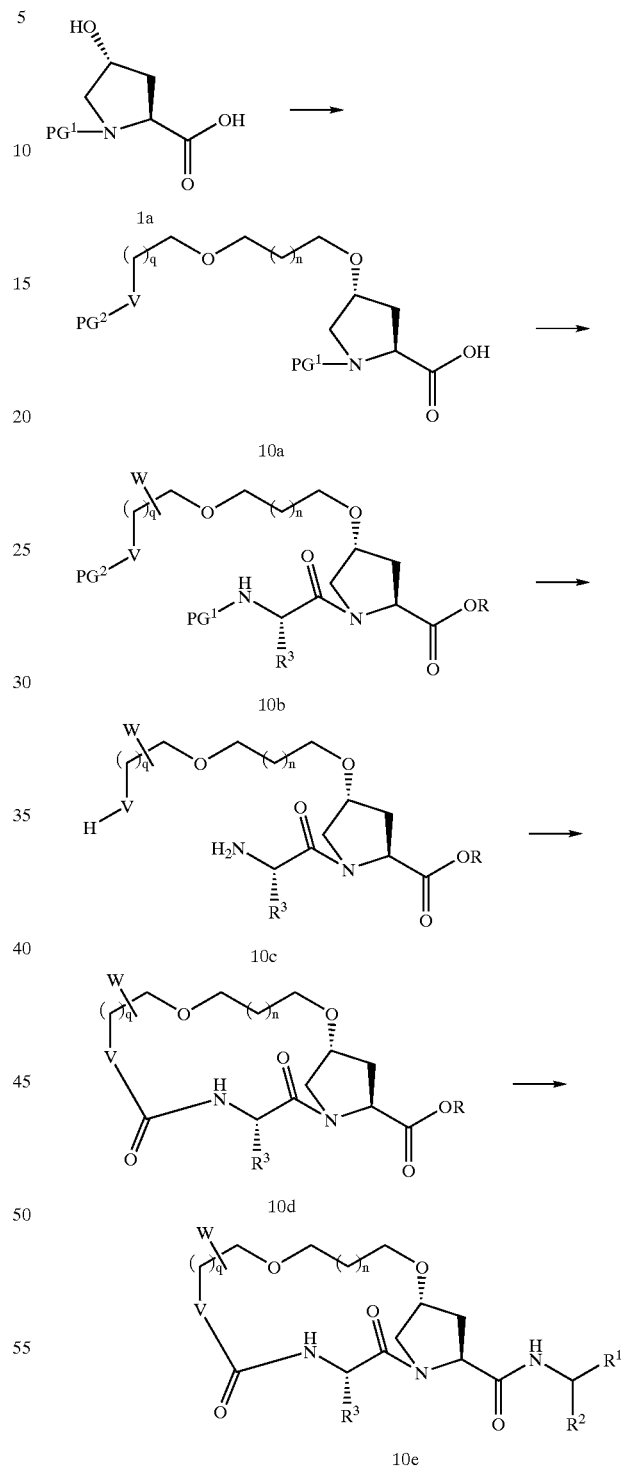

to the desired target 10e was accomplished as outlined in Scheme 1.

The preparation of the compound of formula 10e, wherein $R^1$, $R^2$, $R^3$ are defined above, R' is alkyl, heteroalkyl (OR", SR'", NR"R'" wherein R" and R'" are alkyl groups), halo substituent at ortho, meta, or para -position to oxygen atom; R is alkyl, aryl, or alkylaryl groups; n and q is any combination of zero to five; V is oxygen atom, NY where Y is hydrogen atom, alkyl, aryl group; W is alkyl, aryl, alkylaryl, heteroaryl; PG' and PG² are appropriate protecting groups ($PG^1$=t-boc, cbz and $PG^2$=H, Bn, etc) is outlined in Scheme 10. The protected 4-hydroxyproline derivative 1a is converted to 10b as described in Scheme 1. Removal of the protecting group (10c) followed by treatment with phosgene equivalent results in the macrocyclic ester 10d. Conversion The preparation of the compound of formula 11g, wherein $R^1$, $R^2$, $R^3$ are defined above, R is alkyl, aryl, or alkylaryl groups; X is $(CH_2)_m$, $(CH_2)_mO$, $(CH_2)_mNY$ where m is one to five, and Y is hydrogen atom, alkyl, aryl group; A is hydrogen atom or appropriately positioned halogen atom; $PG^1$ is appropriate protecting groups ($PG^1$=t-boc, cbz, etc) is outlined in Scheme 11. The protected 4-aminoproline derivative 11a is converted to 11b by treatment with suitable benzenesulfonyl chloride and a base. Removal of protecting group and coupling with a protected aminoacid derivative gave 11c. This was converted to 11d using similar deprotection, coupling strategy. Palladium(0) catalyzed cyclization afforded 11e as a mixture of isomers which was hydrogenated to provide macrocyclic ester 11f. Subsequent conversion to the desired target 11g was accomplished as outlined in Scheme 1.

Scheme 11

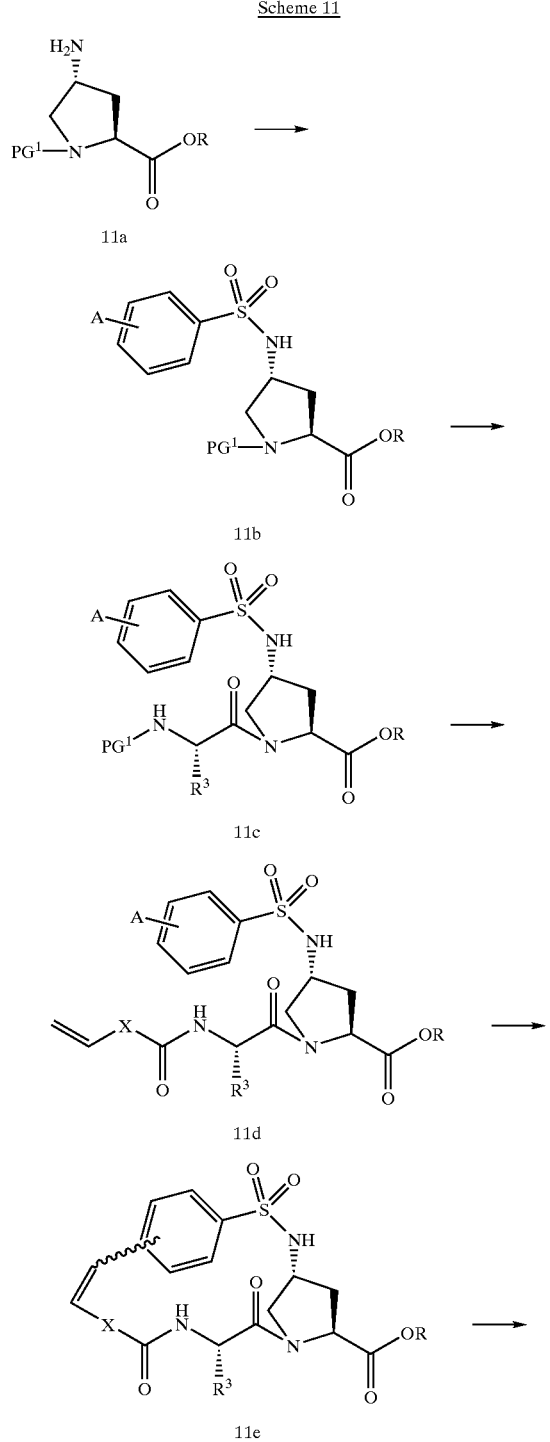

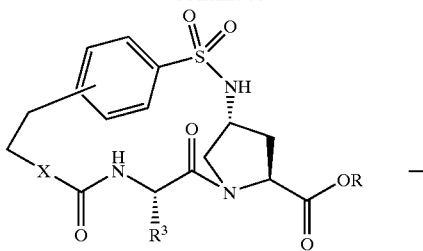

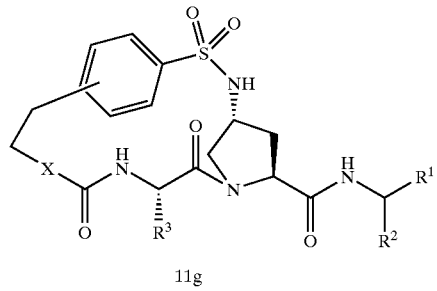

The preparation of the compound of formula 12d, wherein $R^1$, $R^2$, $R^3$ are defined above, R is alkyl, aryl, or alkylaryl groups; n is from zero to five; X is $(CH_2)_m$ where m is one to five, oxygen atom, NY where Y is hydrogen atom, alkyl, aryl group; A is hydrogen atom or appropriately positioned halogen atom; and $PG^1$ and $PG^2$ are appropriate protecting groups ($PG^1$=t-boc, cbz and $PG^2$=H, Bn etc) is outlined in Scheme 12. The protected 4-aminoproline derivative 11a is converted to 11c as described in Scheme 11. Conversion of 11c to the macrocyclic ester 12c and subsequent conversion to the desired target 12d was accomplished as outlined in Scheme 1.

Scheme 12

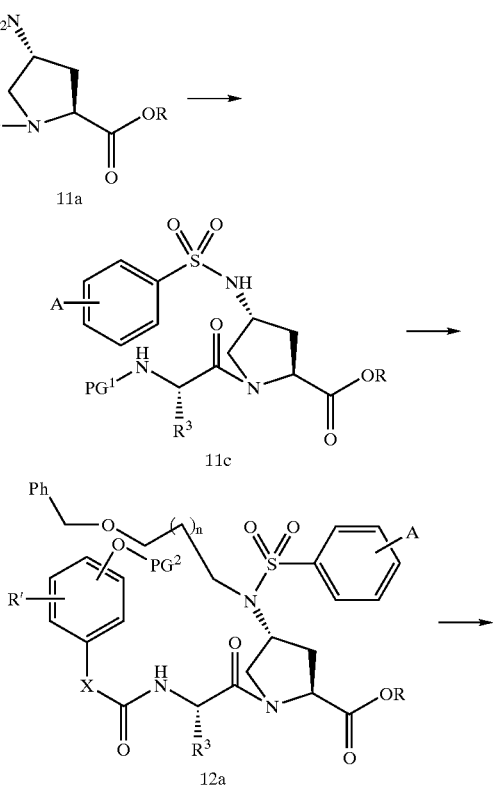

-continued

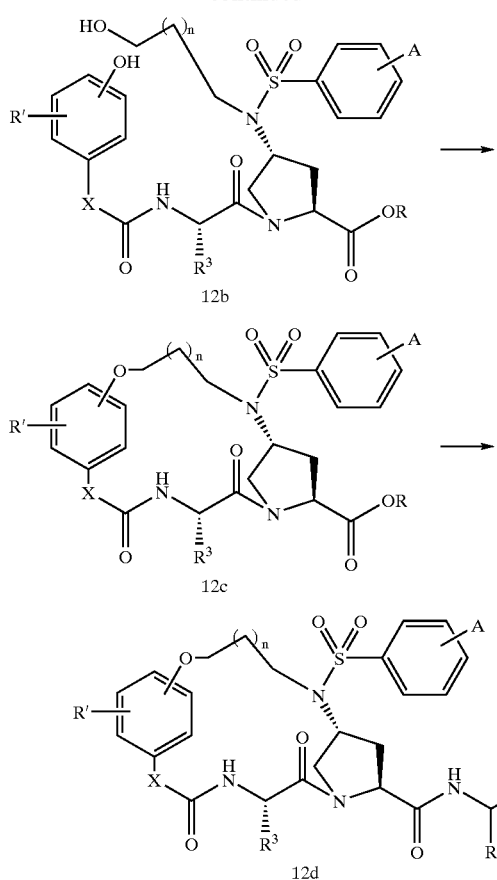

12b

12c

12d

Preparation of Intermediates

Intermediate A

Step 1:

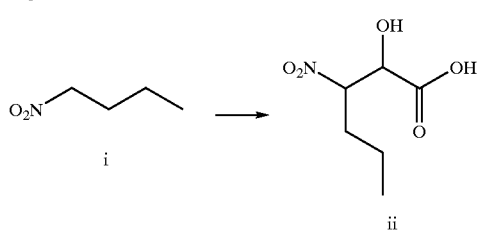

i ii

To a stirred solution of 1-nitrobutane (16.5 g, 0.16 mol) and glyoxylic acid in H$_2$O (28.1 g, 0.305 mol) and MeOH (122 mL) at 0° C.-5° C., was added dropwise triethyl amine (93 mL, 0.667 mol) over 2 hrs. The solution was warmed to room temperature, stirred overnight and concentrated to dryness to give an oil. The oil was then dissolved in H$_2$O and acidified to pH=1 with 10% HCl, followed by extraction with EtOAc. The combined organic solution was washed with brine, dried over Na$_2$SO$_4$, filtered and concentrated to dryness to give the product ii (28.1 g, 99% yield)

Step 2:

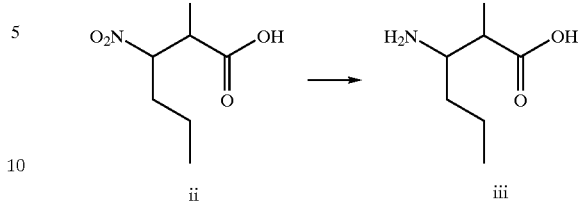

ii iii

To a stirred solution of starting material ii (240 g, 1.35 mol) in acetic acid (1.25 L) was added 10% Pd/C (37 g). The resulting solution was hydrogenated at 59 psi for 3 hrs and then at 60 psi overnight. The acetic acid was then evaporated and azeotroped 3 times with toluene, then triturated with MeOH and ether. The solution was then filtered and azeotroped twice with toluene to give an off white solid (131 g, 0.891 mol, 66%).

Step 3:

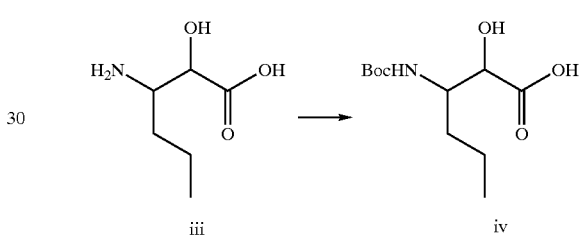

iii iv

To a stirred solution of the amino acid iii (2.0 g, 13.6 mmol) in dioxane (10 mL) and H$_2$O (5 mL) at 0° C., was added 1N NaOH solution (4.3 mL, 14.0 mmol). The resulting solution was stirred for 10 minutes, followed by addition of di-t-butyldicarbonate (0.110 g, 14.0 mmol) and stirred at 0° C. for 15 minutes. The solution was then warmed to room temperature, stirred for 45 minutes and kept at refrigerator overnight and concentrated to dryness to give a crude material. To the solution of this crude material in EtOAc (100 mL) and ice, was added KHSO$_4$ (3.36 g) and H$_2$O (32 mL) and stirred for 4–6 minutes. The organic layer was then separated and the aqueous layer was extracted twice with EtOAc and the combined organic layer was washed with water, brine, dried over Na$_2$SO$_4$, filtered and concentrated to dryness to give the product as a clear gum (3.0 g, 89% yield).

Step 4:

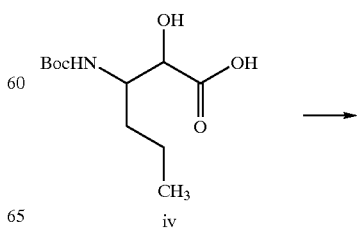

iv

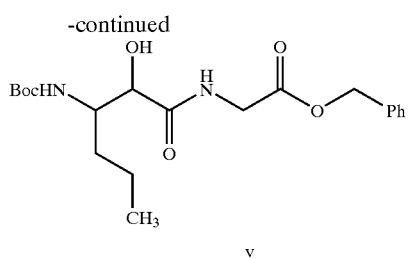

v

To a stirred solution of starting material (3.00 g, 12.0 mmol) in DMF (15 mL) and $CH_2Cl_2$ (15 mL) at −20° C. was added HOOBt (1.97 g, 12.0 mmol), N-methyl morpholine (4.0 mL, 36.0 mmol) and EDCl (2.79 g, 14.5 mmol) and stirred for 10 minutes, followed by addition of $HCl \cdot H_2N$-Gly-OBn (2.56 g, 13.0 mmol). The resulting solution was stirred at −20° C. for 2 hrs, then kept at refrigerator overnight and concentrated to dryness, followed by dilution with EtOAc (150 mL). The EtOAc solution was then washed twice with saturated $NaHCO_3$, $H_2O$, 5% $H_3PO_4$, brine, dried over $Na_2SO_4$, filtered and concentrated to dryness to give the product (4.5 g, 94%). LRMS m/z $MH^+$=395.1.

Step 5:

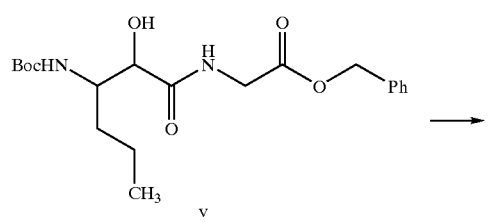

The solution of starting material v (7.00 g, 17.8 mmol) in absolute ethanol (300 mL) was stirred at room temperature under a hydrogen atmosphere in the presence of Pd-C (300 mg, 10%). The reaction progress was monitored by TLC. After 2h, the mixture was filtered through a celite pad and the resulting solution was concentrated in vacuo to give the product vi (5.40 g, quantitative). LRMS m/z $MH^+$=305.1.

Step 6:

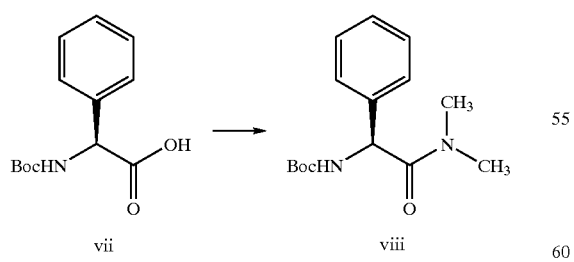

To a solution of dimethylamine hydrochloride (1.61 g, 19.7 mmol), N-Boc-phenylglycine (4.50 g, 17.9 mmol), HOOBt (3.07 g, 18.8 mmol) and EDCl (4.12 g, 21.5 mmol) in anhydrous DMF (200 mL) and $CH_2Cl_2$ (150 mL) at −20° C. was added NMM (5.90 mL, 53.7 mmol). After being stirred at this temperature for 30 min, the reaction mixture was kept in a freezer overnight (18 h). It was then allowed to warm to rt., and EtOAc (450 mL), brine (100 mL) and 5% $H_3PO_4$ (100 mL) were added. After layers were separated, the organic solution was washed with 5% $H_3PO_4$ (100 mL), saturated aqueous sodium bicarbonate solution (2×150 mL), water (150 mL), and brine (150 mL), dried ($MgSO_4$), filtered and concentrated in vacuo to afford crude product viii (4.86 g) as a white solid, which was used without further purification.

Step 7:

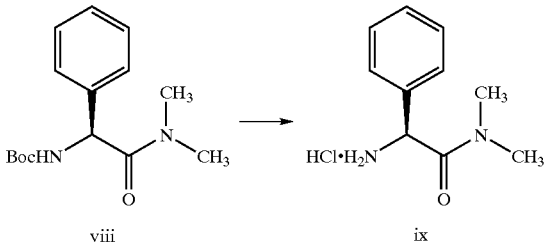

The N-Boc-phenylglycine dimethylamide viii (4.70 g, crude) was dissolved in 4 N HCl (60 mL, 240 mmol) and the resulting solution was stirred at room temperature. The progress of the reaction was monitored by TLC. After 4 h, the solution was concentrated in vacuo to yield a white solid which was used in the next reaction without further purification. LRMS m/z $MH^+$=179.0.

Step 8:

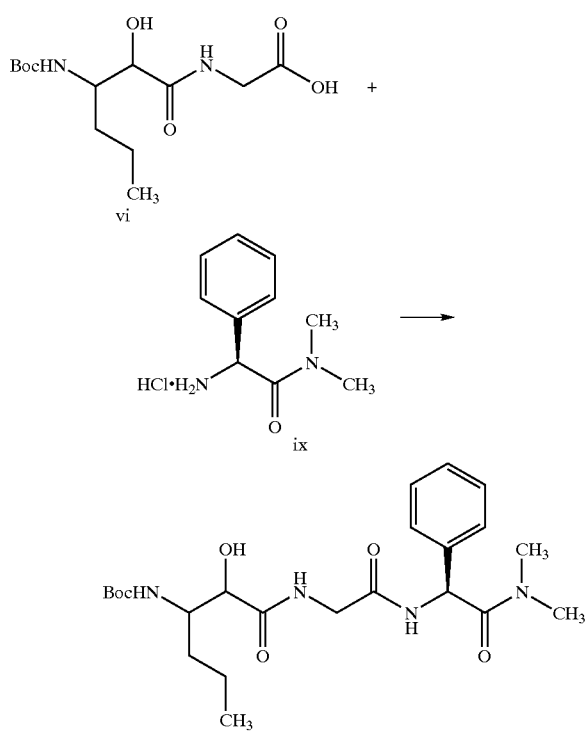

The desired compound x was prepared according to the coupling procedures described in Step 4. LRMS m/z $MH^+$= 465.1.

Step 9:

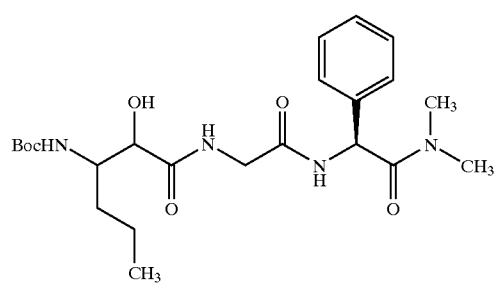

x

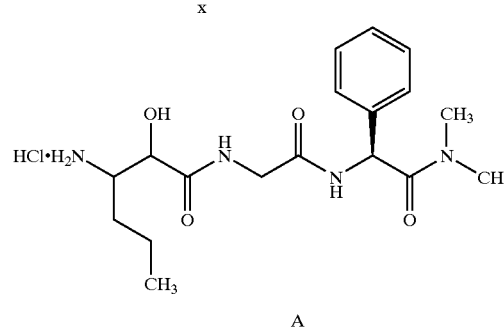

A

The desired intermediate A was prepared from tripeptide x according to the procedures described in Step 7. LRMS m/z MH⁺=365.1.

Intermediate B

Step 1:

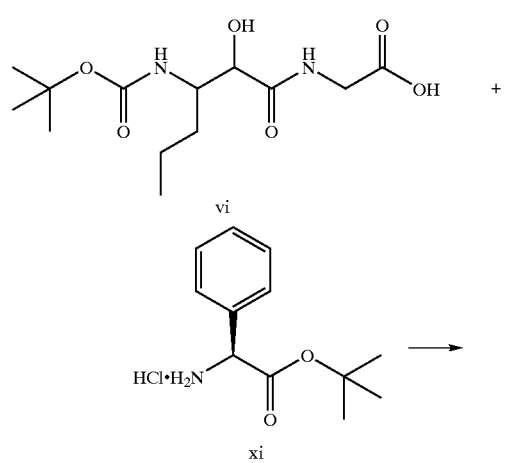

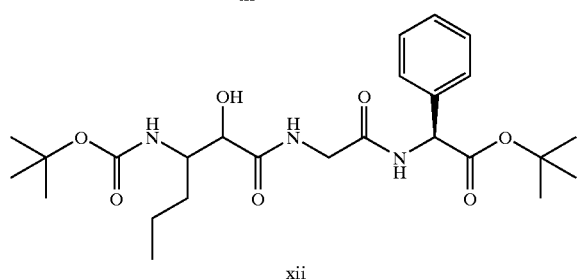

xii

The desired product xii was obtained by the procedure described for Intermediate A, Step 8 using commercially available xi as the coupling partner. The crude material was sufficiently pure for further studies. A portion of the product was purified by flash chromatography using 97/3 dichloromethane/MeOH. HRMS (FAB) Calcd for $C_{25}H_{40}N_3O_7$: 494.2866 (M+H)⁺. Found: 494.2863.

Step 2:

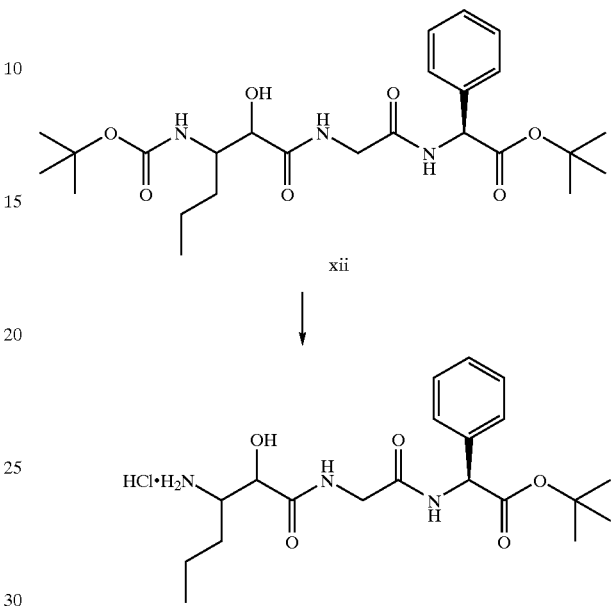

The desired product B was obtained by the procedure described for Intermediate A, Step 7. The crude material was used without further purification.

Intermediate C

Step 1:

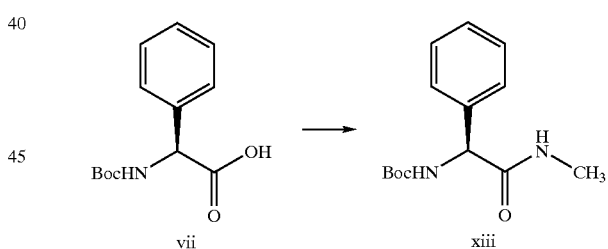

The desired compound xiii was prepared similar to the coupling procedures described in Step 6 for intermediate A except for substituting methylamine for dimethylamine.

Step 2:

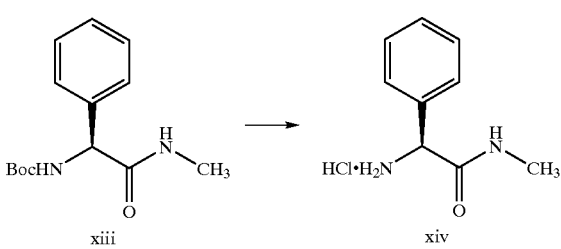

The desired compound xiv was prepared from xiii according to the procedures described in Step 7 for intermediate A.

Step 3:

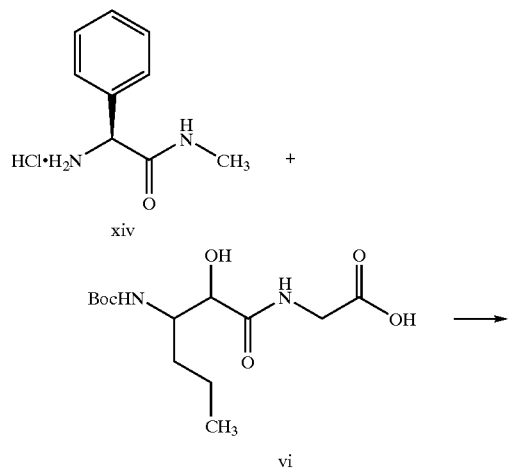

xiv vi

The desired compound xv was prepared according to the coupling procedures described in Step 6 for intermediate A, except for substituting amine xiv for amine ix. LRMS m/z MH$^+$=451.1.

Step 4:

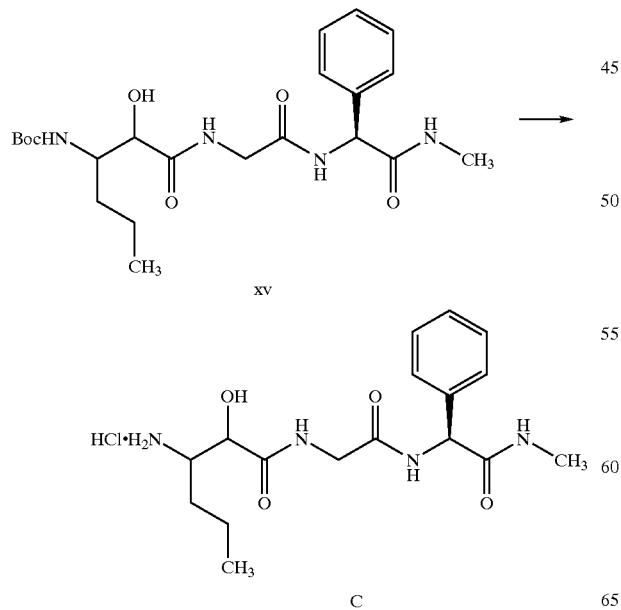

xv

C

The desired intermediate C was prepared according to the procedures described in Step 7 for intermediate A. LRMS m/z MH$^+$=351.1. It was used without further purification.

Intermediate D

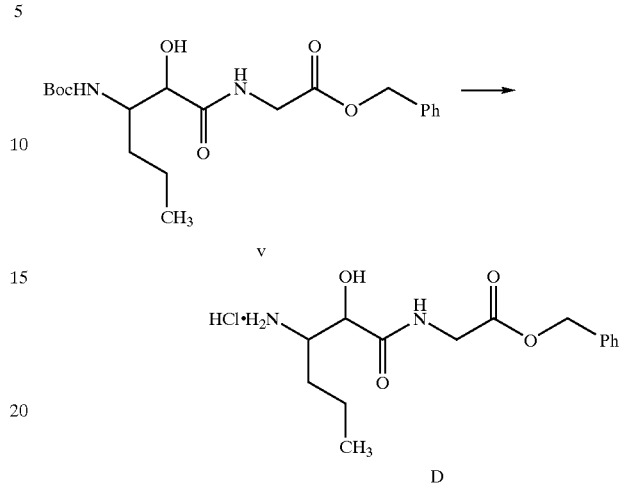

v

D

The desired intermediate D was prepared from compound v according to the procedures described in Step 7 for intermediate A. It was used without further purification.

Intermediate E

Step 1

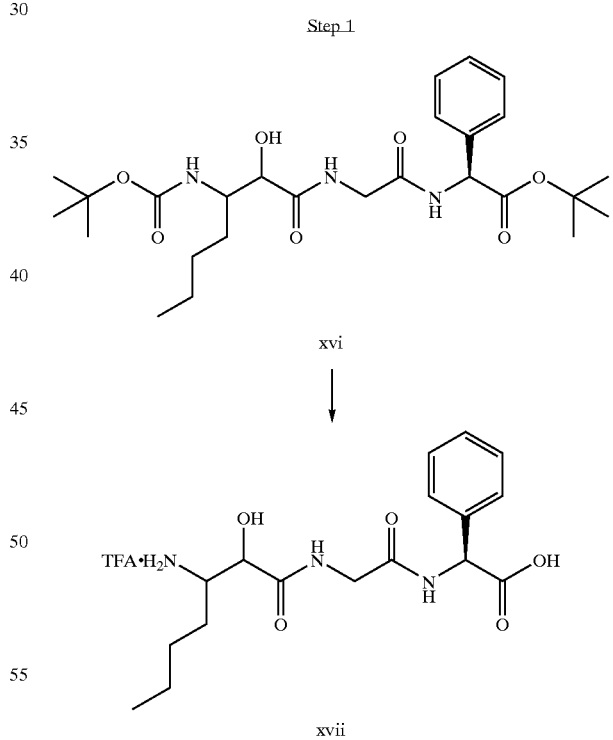

xvi xvii

To a solution of xvi (5g) in dichloromethane (20 mL) was added TFA (20 ML) and stirred at ambient temperature for 4 hrs. Another portion of TFA (10 mL) was added and left standing for additional 3 hrs. All the volatiles were evaporated and it was dried in vacuo to provide quantitative yield of xvii. This material was carried further. (Note: The starting material xvi was obtained by a similar protocol described for B, using nitropentane as precursor).

Step 2

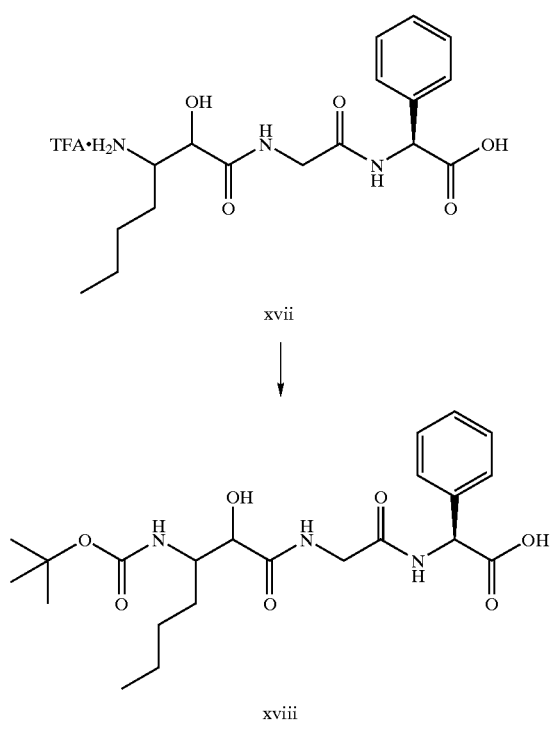

The desired compound xviii was obtained by the method described for Intermediate A, Step 3. Sodium carbonate was used as the base instead of NaOH. The crude material xviii was carried further without purification.

Step 3

To a cold (−20° C.) solution of xviii (4.8 g, 10.7 mmol) in dichloromethane/DMF (4/1, 25 mL) was added dimethylamine hydrochloride (959 mg, 11.77 mmol), diisopropylethylamine (4.2 mL, 24.1 mmol) and BOP (6.14 g, 13.89 mmol). It was left standing at −8° C. overnight. The reaction mixture was diluted with dichloromethane and washed with 10% citric acid solution, saturated $NaHCO_3$ solution and brine. The organic layer was dried ($Na_2SO_4$) and concentrated. The residue was purified by flash column chromatography using 97.5/2.5 dichloromethane/MeOH to afford 2.4 g of xix (47% yield). HRMS (FAB) Calcd for $C_{24}H_{39}N_4O_6$: 479.2870 $(M+H)^+$. Found: 479.2862.

Step 4

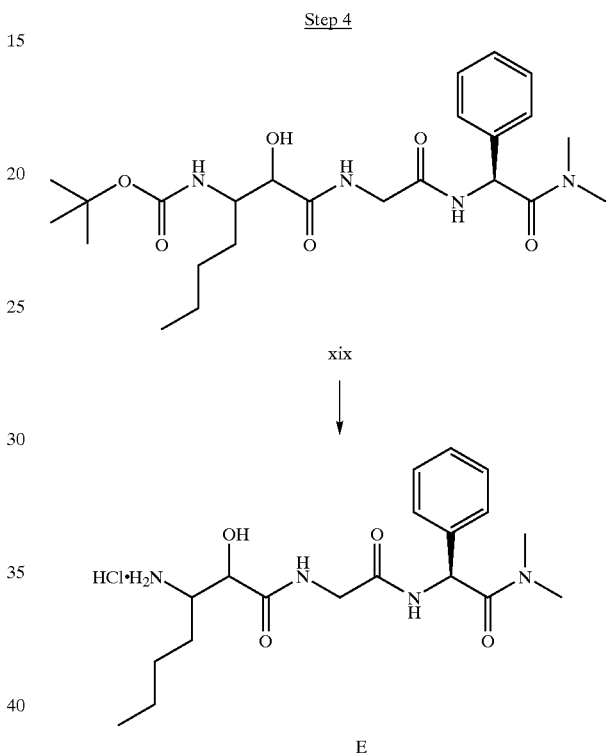

The desired product E was obtained by the procedure described for Intermediate A, Step 7. The crude material was used without further purification.

Intermediate F

Step 1

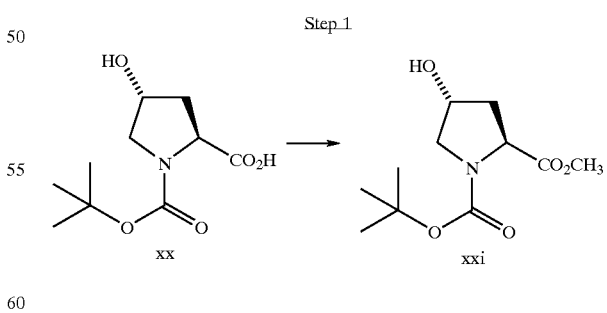

To a cold (0° C.) solution of xx (20.0 g, 86.5 mmol) in benzene (300 mL) and MeOH (50 mL) was added trimethylsilyl diazomethane (2M in hexanes, 56 mL, 112 mmol) dropwise till the solution remained yellow. The reaction mixture was concentrated to provide 21 g of xxi (99% yield) which was pure enough to be carried further. HRMS (FAB) Calcd for $C_{11}H_{20}NO_5$: 246.1341 $(M+H)^+$. Found: 246.1347.

Step 2

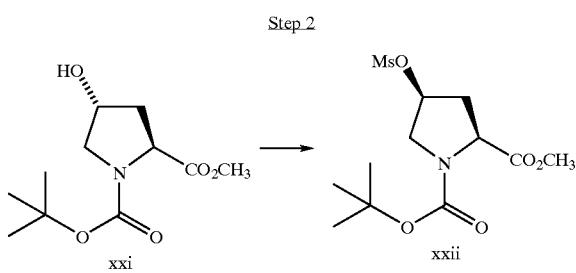

To a cold (~5° C.) mechanically stirred mixture of triphenylphosphine (31.97 g, 121.9 mmol) and methanesulfonic acid (7.66 mL, 118.1 mmol) in toluene was added DEAD (26.47 g, 152 mmol) slowly while maintaining the reaction temperature below 35° C. After the addition was complete, the reaction mixture was cooled to 20° C. and a solution of xxi (23.71 g, 96.8 mmol) in toluene was added followed by triethylamine (5.39 mL, 38.7 mmol). The mixture was heated to 70–75° C. for 6 hrs and cooled to 5–10° C. for 1 hr. All the solid material were filtered off and the filtrate was washed with 5% $KH_2PO_4$ solution and brine. The organic layer was dried ($Na_2SO_4$), and concentrated. Flash column chromatography of the residue using 95/5 dichloromethane/EtOAc provided 26 g of xxii (83% yield). HRMS (FAB) Calcd for $C_{12}H_{22}NO_7S$: 324.1117 $(M+H)^+$. Found: 324.1115.

Step 3

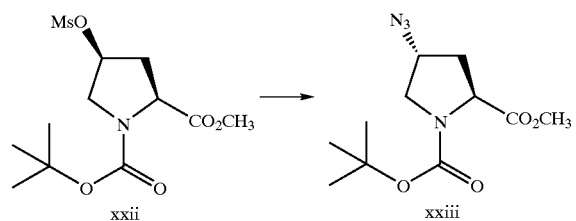

The mesylate xxii (26 g, 80.4 mmol) was dissolved in DMF and all the volatiles were evaporated in vacuo. (CAUTION: Trace amounts of dichloromethane must be removed by this process). To the remaining solution was added sodium azide (5.75 g, 88.4 mmol) and warmed to 70° C. over 5 hrs. The reaction mixture was cooled, diluted with EtOAc and washed with saturated $NaHCO_3$. The organic layer was dried ($Na_2SO_4$) and concentrated to afford 18 g (83% yield) of xxiii which was sufficiently pure for further studies.

Step 4

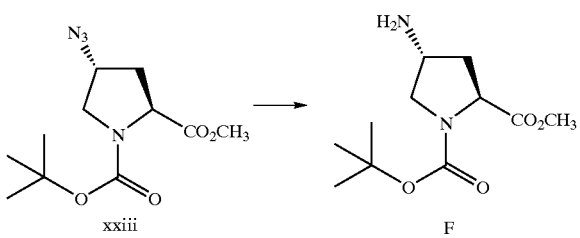

The desired product F was obtained by the procedure described for Intermediate A, Step 5. The crude material was used without further purification.

EXAMPLES

Example 1

Preparation of Compounds of Formulas 1A and 1B

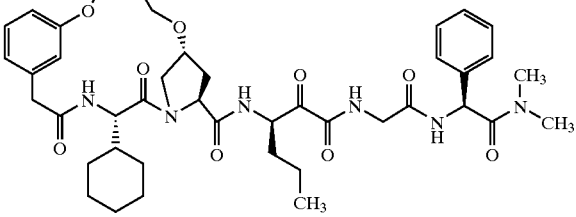

1A

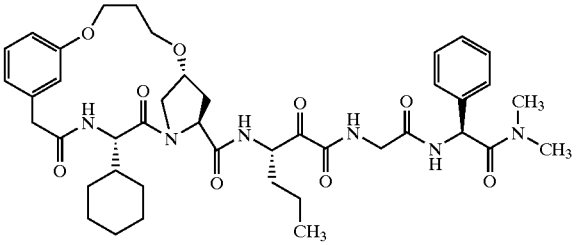

1B

Step A:

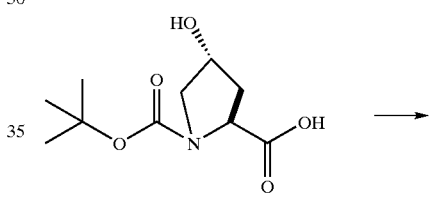

1a

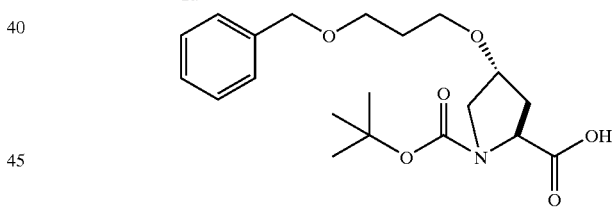

1b

To a solution of Boc-Hyp-OH (7.0 g, 30.3 mmol) and benzyl 3-bromopropyl ether (7.8 g, 34.0 mmol) in anhydrous DMF (400 mL) at room temperature was added sodium hydride (3.5 g, 60% dispersion in mineral oil, 87.5 mmol) and sodium iodide (0.5 g, 3.33 mmols) with stirring. The resulting suspension was vigorously stirred at room temperature overnight (18 h). The reaction was quenched carefully with a slow addition of water (50 mL) and acidified with 6 N HCl solution (20 mL). After addition of ethyl acetate (800 mL), brine (150 mL) and more water (150 mL), the formed two layers were separated and the organic layer was washed with 5% $H_3PO_4$ (3×200 mL). It was then dried with $MgSO_4$, filtered and concentrated in vacuo to afford I b as an oil which was used in Step B without further purification.

Step B:

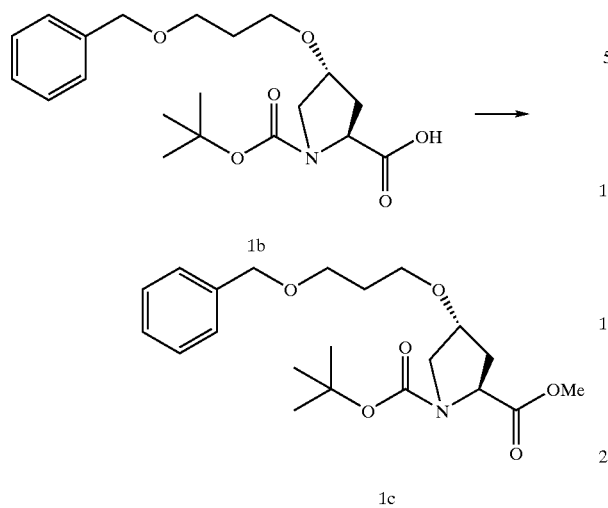

The acid 1b from Step A was dissolved in benzene (25 mL) and methanol (28 mL). To this solution at room temperature was added a solution of trimethylsilyl diazomethane (27 mL, 2.0 M in cyclohexane) with caution. After being stirred at room temperature for 1 h, it was concentrated in vacuo to yield the methyl ester. Flash chromatography (8 to 20% EtOAc-CH$_2$Cl$_2$) afforded 1c (5.15 g; 13.1 mmol, 43%, 2 steps) as an oil.

Step C:

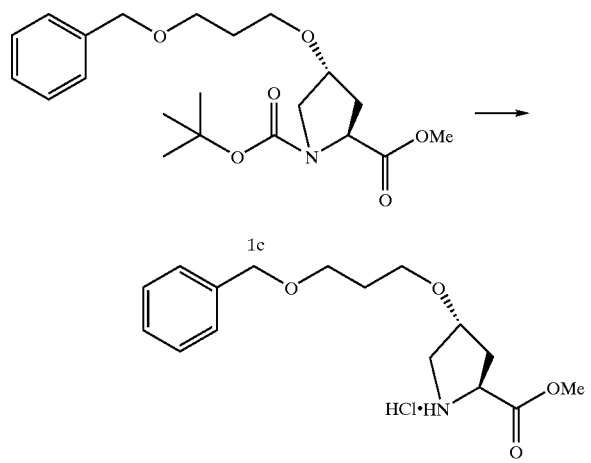

The Boc-amino methyl ester 1c (5.83 g, 14.8 mmol) was dissolved in 4 N HCl in dioxane (80 mL, 320 mmol) and the resulting solution was stirred at room temperature. The progress of the reaction was monitored by TLC. After 5 h, the solution was concentrated in vacuo and the residue was kept under vacuum overnight to yield a white solid which was used in the next coupling reaction without further purification.

Step D:

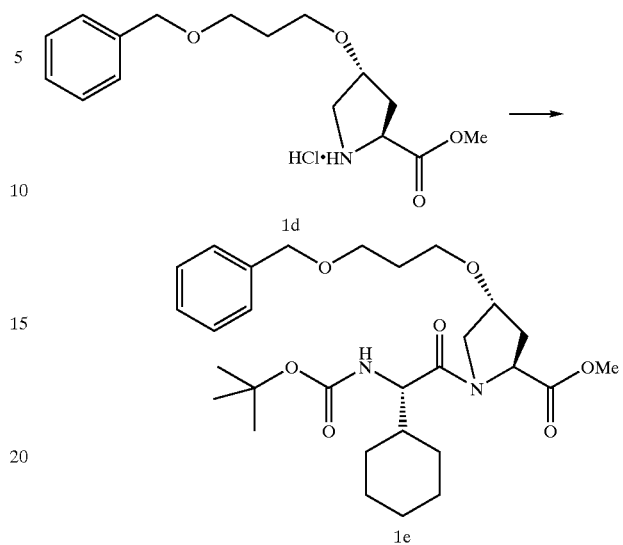

To a solution of the amine ester 1d (from Step 1B), N-Boc-cyclohexylglycine (4.10 g, 14.9 mmol), HOOBt (2.60 g, 15.9 mmol) and EDCl (3.41 g, 17.8 mmol) in anhydrous DMF (150 mL) and CH$_2$Cl$_2$ at −20° C., was added NMM (6.50 mL, 59.1 mmol). After being stirred at this temperature for 30 min, the reaction mixture was kept in a freezer overnight (18 h). It was then stirred in air and allowed to warm to room temperature in 1 h. EtOAc (450 mL), brine (100 mL) and 5% H$_3$PO$_4$ (100 mL) were added. The separated organic solution was washed with 5% H$_3$PO$_4$ (100 mL), saturated aqueous sodium bicarbonate solution (2×150 mL), water (150 mL), and brine (150 mL), dried with magnesium sulfate, filtered and concentrated in vacuo. Flash chromatography (10 to 20% EtOAc-CH$_2$Cl$_2$) afforded 1e (6.60 g, 84% 2 steps) as a white solid. $^1$H NMR (400 MHz, d$_6$-DMSO) δ 7.36–7.25 (m, 5H), 6.87 (d, J=8.9 Hz, 1H), 4.46–4.40 (m, 2H), 4.25 (t, J=8.3 Hz, 1H), 4.11 (s, 1H), 4.05–4.04 (m, 1H), 4.03–3.94 (m, 1H), 3.60 (s, 3H), 3.50–3.41 (m, 4H), 2.25–2.20 (m, 1H), 1.95–1.88 (m, 1H), 1.77–1.55 (m, 9H), 1.35 (s, 9H), 1.19–0.90 (m, 4H); $^{13}$C NMR (100 MHz, d$_6$-DMSO) δ 172.0, 170.7, 155.6, 138.8, 128.2, 127.4, 127.3, 78.0, 77.1, 71.9, 66.6, 65.1, 57.4, 56.3, 51.8, 34.5, 29.6, 28.6, 28.2, 25.9, 25.6, 25.5.

Step E:

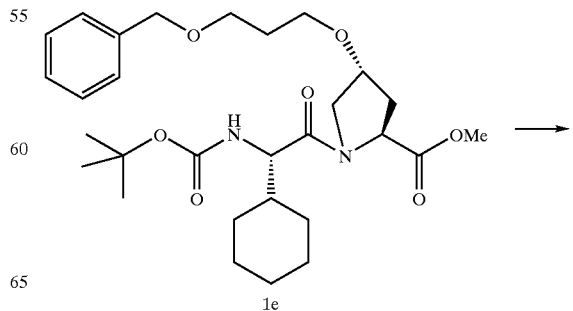

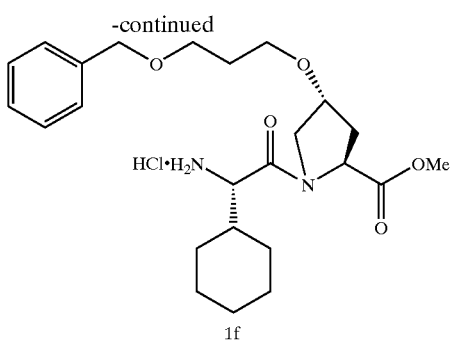

1f

The Boc-amino methyl ester 1e (6.53 g, 12.3 mmol) was dissolved in 4 N HCl (60 mL, 240 mmol) and the resulting solution was stirred at room temperature. The progress of the reaction was monitored by TLC. After 4 h, the solution was concentrated in vacuo and the residue was kept under vacuum overnight to give a white solid which was used in the next coupling reaction without further purification. $^1$H NMR (400 MHz, $d_6$-DMSO) δ 7.36–7.27 (m, 5H), 4.43 (s, 2H), 4.35–4.31 (m, 1H), 3.88 (d, J =11.7 Hz, 1H), 3.62 (s, 3H), 3.62–3.57 (m, 2H), 3.53–3.41 (m, 3H), 2.32–2.27 (m, 1H), 1.97–1.91 (m, 1H), 1.79–1.60 (m, 8H), 1.17–1.07 (m, 5H); $^{13}$C NMR (100 MHz, $d_6$-DMSO) δ 171.5, 167.4, 138.6, 133.3, 129.1, 128.8, 128.2, 127.4, 77.1, 71.9, 66.5, 65.3, 57.8, 54.9, 52.4, 52.0, 34.0, 29.6, 27.7, 27.0, 25.6, 25.5, 25.48; HRMS m/z 433.2702 [calcd for $C_{24}H_{36}N_2O_5$, 433.2702].

Step F:

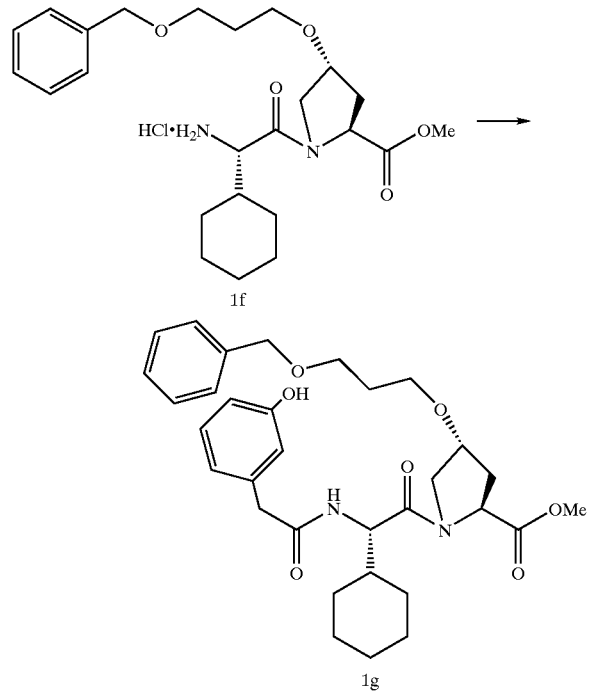

To a solution of the amine 1f (from Step 1 D), 3-hydroxy phenylacetic acid (1.90 g, 12.5 mmol), HOOBt (2.10 g, 12.9 mmol) and EDCl (2.85 g, 14.9 mmol) in anhydrous DMF (250 mL) and $CH_2Cl_2$ (100 mL) at −20° C., was added NMM (4.20 mL, 38.2 mmol). After being stirred at this temperature for 30 min, the reaction mixture was kept in a freezer overnight (18 h). It was then stirred in air and allowed to warm to room temperature in 1 h. EtOAc (500 mL), brine (100 mL) and 5% $H_3PO_4$ (100 mL) were added. The separated organic solution was washed with 5% $H_3PO_4$ (100 mL), saturated aqueous sodium bicarbonate solution (2×150 mL), water (150 mL), and brine (150 mL), dried with magnesium sulfate, filtered and concentrated in vacuo. Flash chromatography (10 to 20% EtOAc-$CH_2Cl_2$) afforded 1g (6.30 g, 11.1 mmol, 90% (2 steps)) as a white solid. $^1$H NMR (400 MHz, $d_6$-DMSO) δ 9.26 (s, 1H), 8.19 (d, J =8.5 Hz, 1H), 7.36–7.25 (m, 5H), 7.05–7.01 (m, 1H), 6.66–6.64 (m, 1H), 6.60–6.57 (m, 1H), 4.46–4.39 (m, 2H), 4.34 (t, J=8.3 Hz, 1H), 4.29–4.25 (m, 1H), 4.09–4.08 (m, 1H), 3.91 (d, J=11.0 Hz, 1H), 3.66–3.58 (m, 1H), 3.61 (s, 3H), 3.50–3.39 (m, 5H), 3.30 (d, J=13.7 Hz, 1H), 2.24–2.18 (m, 1H), 1.95–1.89 (m, 1H), 1.74–1.57 (m, 8H), 1.18–0.89 (m, 5H); $^{13}$C NMR (100 MHz, $d_6$-DMSO) δ 172.0, 170.3, 170.0, 157.1, 138.6, 137.6, 128.9, 128.2, 127.4, 127.3, 119.6, 116.1, 113.2, 76.9, 71.8, 66.6, 65.2, 57.4, 54.7, 51.9, 51.8, 41.8, 34.4, 29.6, 28.5, 28.0, 25.5, 25.5; HRMS m/z 567.3073 [calcd for $C_{32}H_{42}N_2O_7$, 567.3070].

Step G:

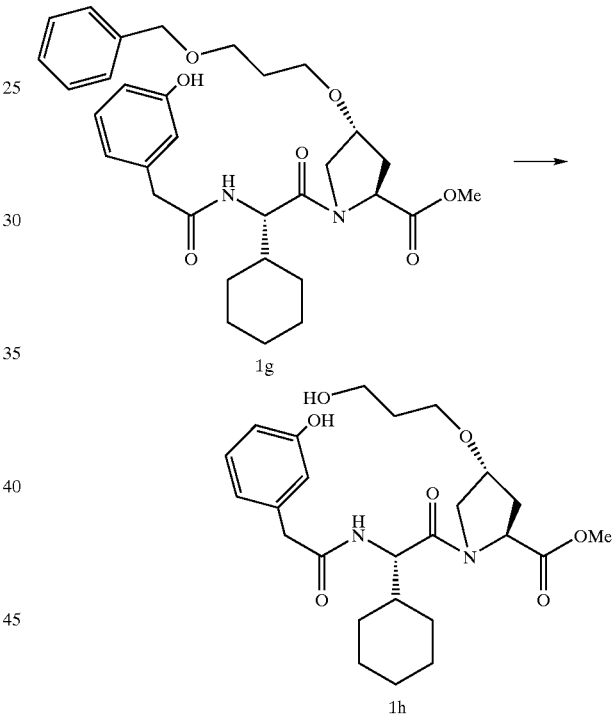

To a solution of the benzyl ether 1g (6.23 g, 11.0 mmol) in ethanol (200 mL) under nitrogen at room temperature was added 10% Pd-C (1.5 g) cautiously. The resulting suspension was vigorously stirred at room temperature under hydrogen for 23 h. After careful filtration, the solution was concentrated in vacuo. Flash chromatography (2 to 5% MeOH—$CH_2Cl_2$) afforded 1 h (4.54 g, 9.52 mmol, 87%) as a colorless oil. $^1$H NMR (400 MHz, $d_6$-DMSO) δ 9.26 (s, 1H), 8.22 (d, J=8.6 Hz, 1H), 7.06–7.02 (m, 1H), 6.66–6.58 (m, 3H), 4.42–4.40 (m, 1H), 4.35–4.31 (s, 1H), 4.27 (t, J=8.3 Hz, 1H), 4.10–4.09 (m, 1H), 3.92 (d, J=11.2 Hz, 1H), 3.64 (dd, J=11.2, 4.3 Hz, 1H), 3.61 (s, 3H), 3.59–3.43 (m, 5H), 3.40–3.38 (m,1H), 2.26–2.21 (m, 1H), 1.97–1.90 (m, 1H), 1.74–1.55 (m, 8H), 1.18–0.89 (m, 5H); $^{13}$C NMR (100 MHz, $d_6$-DMSO) δ 172.0, 170.3, 170.1, 157.1, 137.6, 129.0, 119.6, 116.0, 113.3, 76.9, 65.2, 57.6, 57.4, 54.8, 51.9, 51.8, 41.7, 34.4, 32.6, 28.5, 28.0, 25.9, 25.52, 25.49; HRMS m/z 477.2606 [calcd for $C_{25}H_{36}N_2O_7$, 477.2601].

Step H:

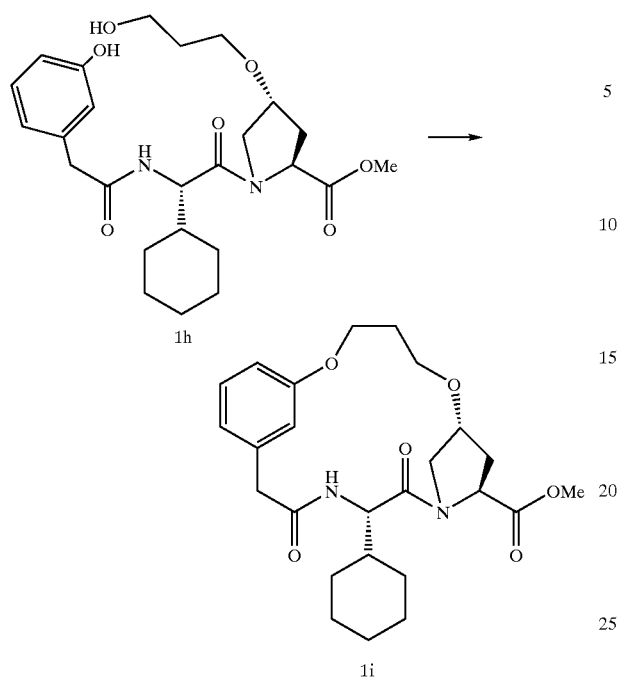

A solution of the phenol alcohol 1h (4.50 g, 9.43 mmol) and ADDP (6.60 g, 26.2 mmol) in anhydrous $CH_2Cl_2$ was bubbled with argon through a frit glass bubbler for 20 min. To this solution at 0° C. was added triphenylphosphine (4.10 g, 16.3 mmol). After stirring at 0° C. for 20 min, a second portion of triphenylphosphine (3.40 g, 13.5 mmol) was added. The solution was then warmed to room temperature and stirred overnight (24 h) under nitrogen until TLC indicated the complete consumption of the starting material. After removal of solvent in vacuo, the residue was partially purified by flash chromatography (1 to 2% MeOH in $CH_2Cl_2$) to afford a mixture of the macrocycle 1i and triphenylphosphine oxide. $^1H$ NMR (400 MHz, $d_6$-DMSO) δ 8.47 (d, J=9.7 Hz, 1H), 7.17–7.13 (m, 1H), 6.79 (s, 1H), 6.73 (d, J=1.8 Hz, 1H), 6.71 (d, J=1.8 Hz, 1H), 4.50–4.45 (m, 1H), 4.24 (dd, J=10.3, 7.6 Hz, 1H), 4.17–4.06 (m, 4H), 3.68 (d, J=15.1 Hz, 1H), 3.63 (s, 3H), 3.60–3.51 (m, 2H), 3.37 (d, J=15.1 Hz, 1H), 3.35–3.27 (m, 1H), 2.51–2.43 (m, 1H), 1.85–1.47 (m, 9H), 1.22–1.12 (m, 3H), 0.97–0.88 (m, 2H); $^{13}C$ NMR (100 MHz, $d_6$-DMSO) δ 172.0, 170.0, 169.8, 158.4, 138.1, 129.1, 121.8, 115.4, 112.2, 77.0, 64.9, 63.6, 57.0, 54.3, 53.4, 51.8, 41.3, 33.2, 28.9, 28.5, 28.2, 26.0, 25.2; HRMS m/z 459.2495 [calcd for $C_{25}H_{34}N_2O_6$, 459.2495].

Step I:

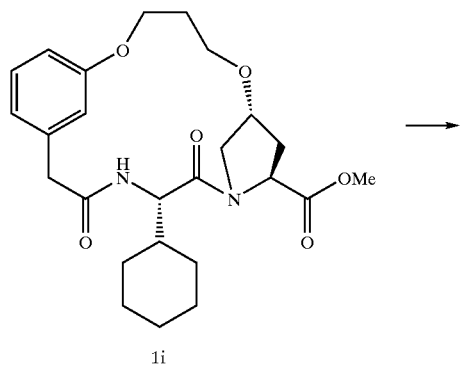

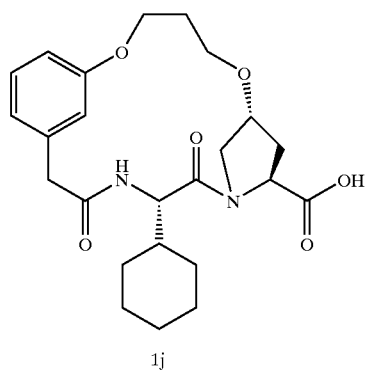

An aqueous lithium hydroxide solution (0.45 g in 30 mL $H_2O$) was added to a 0° C. solution of the methyl ester 1i in THF (30 mL) and methanol (30 mL). The mixture was stirred in an ice bath and warmed to room temperature along with it in 4 h. The progress of the reaction was monitored by TLC. After the volatiles were removed in vacuo, EtOAc (150 mL) and water (30 mL) were added and the two layers separated. The aqueous solution was extracted again with $CH_2Cl_2$ (150 mL), after which it was acidified to pH=1. EtOAc (200 mL) was then added and the aqueous solution was saturated with solid sodium chloride. After separation of the layers, the aqueous layer was extracted with EtOAc (2×150 mL). Organic solutions were combined, dried with magnesium sulfate, filtered and concentrated in vacuo to afford 1j (1.45 g, 3.26 mmol, 35%, 2 steps) as a pale yellow foam. $^1H$ NMR (400 MHz, $d_6$-DMSO) δ 12.32 (bs, 1H), 8.45 (d, J=9.5 Hz, 1H), 7.17–7.13 (m, 1H), 6.73–6.70 (m, 1H), 6.79 (s, 1H), 6.73–6.70 (m, 2H), 4.47 (t, J=9.7 Hz, 1H), 4.17–4.00 (m, 5H), 3.68 (d, J=15.1 Hz, 1H), 3.58–3.45 (m, 2H), 3.39–3.21 (m, 2H), 2.47–2.41 (dd, J=13.4, 7.6 Hz, 1H), 1.85–1.56 (m, 9H), 1.19–1.11 (m, 3H), 0.93–0.87 (m, 2H); $^{13}C$ NMR (100 MHz, $d_6$-DMSO) δ 173.2, 170.2, 170.0, 158.4, 138.1, 129.3, 122.0, 115.5, 112.2, 77.3, 65.1, 63.8, 57.3, 54.2, 53.7, 41.5, 33.6, 29.0, 28.6, 28.4, 26.1, 25.4; HRMS m/z 445.2335 [calcd for $C_{24}H_{32}N_2O_6$, 445.2339].

Step J:

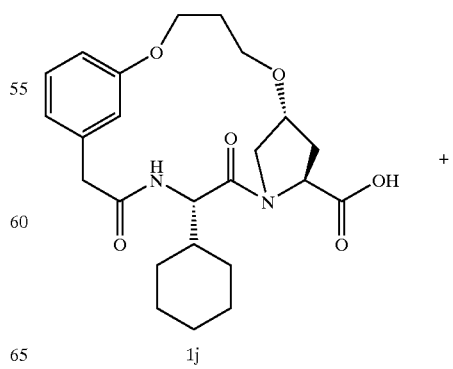 +

-continued

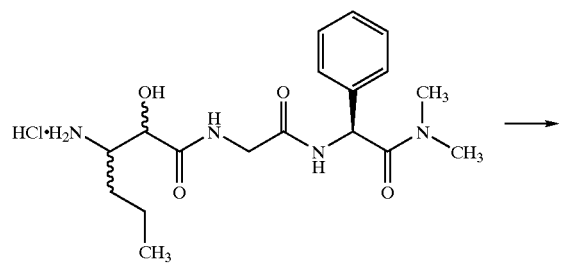

A

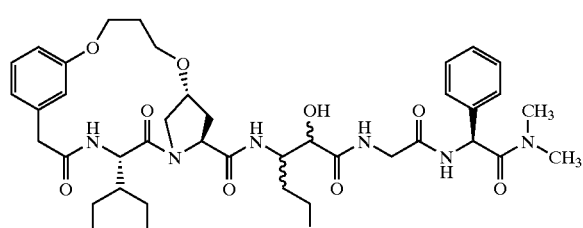

1k

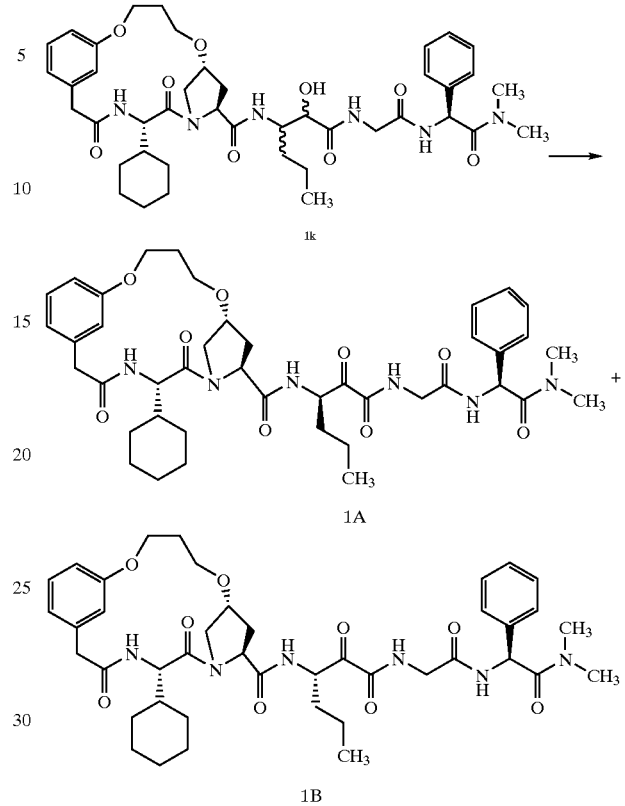

Step K:

1k

1A

1B

To a solution of the acid 1j (0.59 g, 1.33 mmol), amine A (H$_2$N-NVa-CH(OH)-CO-Gly-Phg-NMe$_2$, 0.55 g, 1.37 mmol), HOOBt (250 mg, 1.53 mmol) and EDCl (315 mg, 1.64 mmol) in anhydrous DMF (50 mL) and CH$_2$Cl$_2$ (50 mL) at −20° C. was added NMM (0.50 mL, 4.55 mmol). After stirred at this temperature for 30 min, the reaction mixture was kept in a freezer for 40 h. Then EtOAc (200 mL), brine (50 mL) and 5% H$_3$PO$_4$ (50 mL) were added. The separated organic solution was washed, successively, with 5% H$_3$PO$_4$ (80 mL), saturated aqueous sodium bicarbonate solution (2×80 mL), water (80 mL), and brine (80 mL), dried with magnesium sulfate, filtered and concentrated in vacuo. Flash chromatography (4 to 7.5% MeOH—CH$_2$Cl$_2$) afforded 1k as a mixture of four diastereomers (0.59 g, 0.75 mmol, 56%) as a white solid. $^1$H NMR (400 MHz, d$_6$-DMSO) δ 8.54–8.35 (m, 2H), 7.95–6.98 (m, 8H), 6.79–6.77 (m, 1H), 6.72–6.70 (m, 2H), 5.96–5.73 (m, 2H), 4.53–4.45 (m, 1H), 4.35–3.61 (m, 11H), 3.54–3.41 (m, 1H), 3.40–3.22 (m, 1H), 2.93–2.92 (m, 3H), 2.84 (s, 3H), 2.42–2.17 (m, 1H), 1.87–1.55 (m, 10H), 1.49–1.06 (m, 7H), 0.98–0.75 (m, 5H); $^{13}$C NMR (100 MHz, d$_6$-DMSO) δ 172.1, 171.9, 171.8, 170.8, 170.7, 170.4, 170.4, 170.3, 170.0, 169.8, 169.7, 169.6, 169.2, 169.2, 167.9, 167.8. 167.8, 158.4, 158.3, 138.2, 138.15, 138.11, 138.07, 137.6, 137.50, 137.48, 129.1, 128.5, 128.3, 127.8, 127.7, 121.7, 121.6, 115.4, 115.3, 112.09, 112.07, 112.0, 111.9, 76.9, 76.8, 73.3, 72.1, 71.9, 64.9, 64.8, 63.2, 58.7, 58.5, 57.9, 57.8, 54.6, 54.5, 54.48, 53.8, 53.78, 53.7, 53.66, 53.0, 52.9, 51.0, 50.8, 50.7, 41.6, 41.5, 41.4, 41.3, 36.6, 35.3, 33.9, 33.86, 33.5, 32.9, 32.1, 29.9, 29.0, 28.9, 28.5, 28.4, 28.3, 26.0, 25.9, 25.3, 25.25, 25.2, 18.6, 18.56, 18.5, 13.8, 13.7; HRMS m/z 791.4339 [calcd for C$_{42}$H$_{58}$N$_6$O$_9$, 791.4344, error=1 ppm].

To a mixture of the hydoxy amide 1k (0.57 g, 0.72 mmol) and Des-Martin reagent (0.76 g, 1.8 mmol) at 0° C. was added anhydrous CH$_2$Cl$_2$. The resulting white suspension was vigorously stirred at 0° C. and warmed to room temperature along with the ice bath in 4 h. Saturated aqueous sodium bicarbonate and sodium bisulfite solutions (50 mL each) were added and the mixture was vigorously stirred for 10 min before layers were separated. The aqueous solution was extracted with (2×150 mL). Combined organic solution was dried with magnesium sulfate, filtered and concentrated in vacuo. Flash chromatography (2 to 4% MeOH—CH$_2$Cl$_2$) afforded two diastereomers 1A (250 mg, 0.32 mmol) and 1 B (217 mg, 0.28 mmol, 82% combined yield) as white solids.

Example 2

Preparation of Compound 2

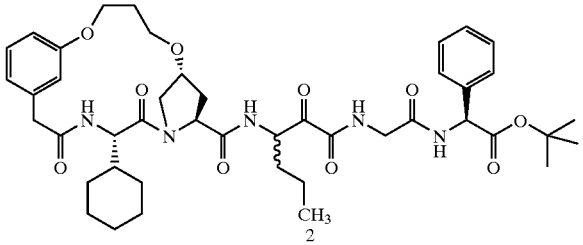

2

Step A:

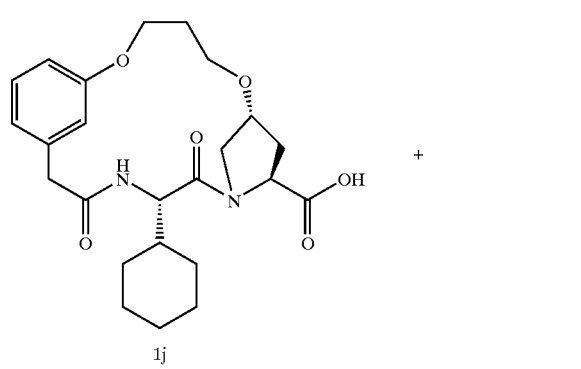

1j

+

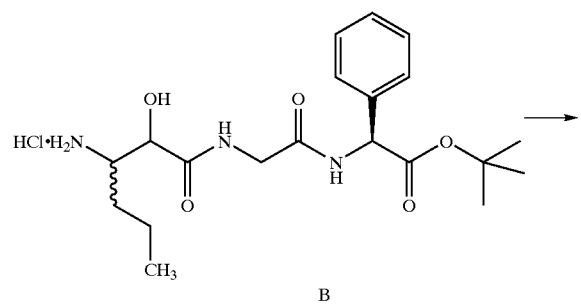

B

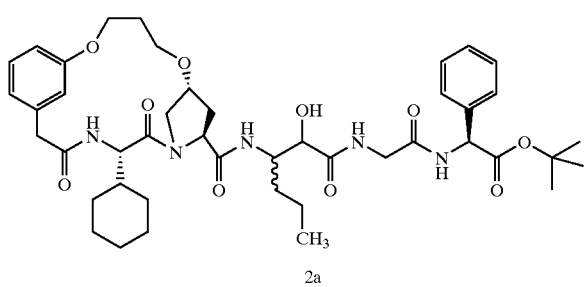

2a

The desired compound 2a was prepared according to the method of Example 1, Step J, except for substituting the amine B for the amine A. The hydoxy amide was obtained as a mixture of inseparable diastereomers in the form of a white solid in 60% yield.

Step B:

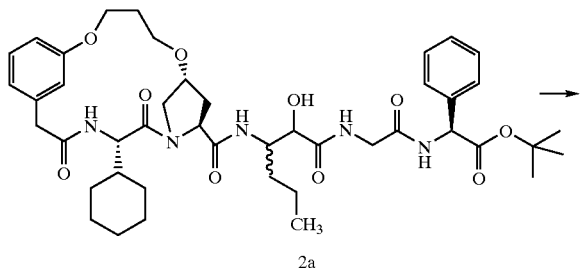

2a

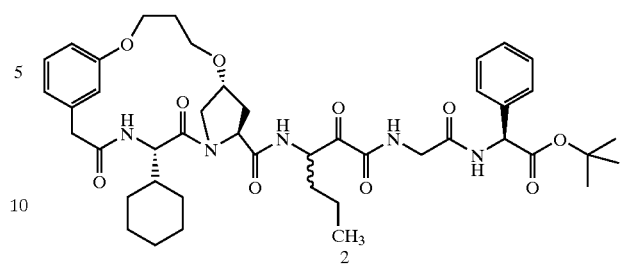

2

The desired ketoamide was prepared from the hydroxy amide 2a according to the method of Example 1, Step K. The product was obtained as a mixture of inseparable diastereomers in the form of a white solid in 78% yield. [1] H NMR (400 MHz, $d_6$-DMSO) δ 8.69–8.57 (m, 1H), 8.45–8.36 (m, 1H), 7.95–7.72 (m, 1H), 7.64–7.53 (m, 1H), 7.41–7.31 (m, 5H), 7.16–6.97 (m, 1H), 6.79–6.70 (m, 3H), 5.97–5.75 (m, 1H), 5.31–5.27 (m, 1H), 4.52–4.44 (m, 1H), 4.35–3.61 (m, 11H), 3.54–3.41 (m, 1H), 3.39–3.21 (m, 1H), 2.42–2.16 (m, 1H), 1.85–1.54 (m, 9H), 1.49–1.05 (m, 16H), 0.95–0.70 (m, 5H); $^{13}$C NMR (100 MHz, $d_6$-DMSO) δ 172.3, 172.2, 172.0, 171.9, 170.9, 170.7, 170.5, 170.5, 170.4, 170.1,1 69.9, 169.7, 169.5, 168.6, 168.5, 158.5, 158.4, 138.2, 138.2, 138.1, 136.7, 132.1, 131.6, 131.5, 129.2, 129.1, 128.8, 128.7, 128.1, 127.7, 127.6, 127.6, 127.5, 127.4, 127.4, 121.7, 116.4, 115.4, 115.4, 113.3, 112.1, 112.1, 112.0, 81.3, 77.0, 76.9, 76.9, 73.4, 72.3, 72.0, 64.9, 64.8, 63.3, 58.8, 56.9, 56.8, 54.7, 54.6, 54.6, 53.9, 53.9, 53.8, 51.1, 50.8, 41.6, 41.4, 41.3, 34.0, 33.9, 29.1, 29.0, 28.6, 28.5, 28.4, 28.4, 28.3, 27.5, 26.0, 26.0, 25.4, 25.3, 25.2, 18.7, 18.6, 18.5, 13.9, 13.8; HRMS m/z 820.4493 [calcd for $C_{44}H_{61}N_5O_{10}$, 820.4497].

Example 3

Preparation of the Compound of Formula 3 below

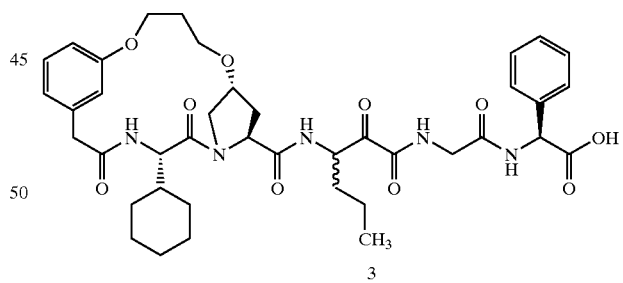

3

Step A:

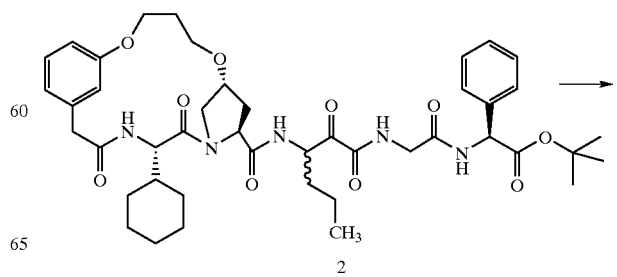

2

-continued

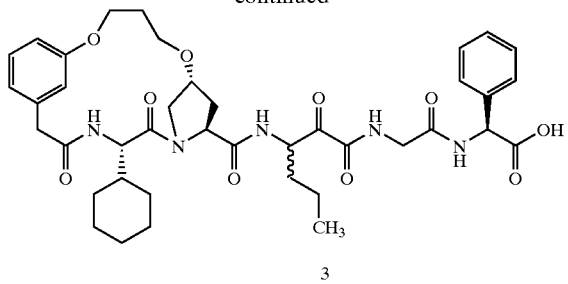

3

A solution of the t-Butyl ester 2 (26 mg, 0.032 mmol) in trifluoroacetic acid (2 mL) and $CH_2Cl_2$ (2 mL) was stirred at room temperature for 3h. After the volatiles were removed in vacuo, the residue was dissolved in 50% MeOH—$CH_2Cl_2$, and concentrated to dryness in vacuo to afford an off-white solid (24 mg, 0.032 mmol, quant.). $^1H$ NMR (400 MHz, $d_6$-DMSO) δ 8.73–8.65 (m, 2H), 8.40 (dd, J=9.5, 2.6 Hz, 1H), 8.24–8.05 (1H), 7.64–7.55 (m, 1H), 7.41–7.32 (m, 5H) 7.15 (t, J=7.8 Hz, 1H), 6.80–6.71 (m, 3H), 5.35 (dd, J=7.5, 1.9 Hz, 1H), 5.04–4.96 (m, 1H), 4.48–4.43 (m, 1H), 4.37–4.22 (m, 1H), 4.16–3.27 (m, 11H) 2.35–2.31 (m, 1H), 1.84–0.70 (m, 21H); $^{13}C$ NMR (100 MHz, $d_6$-DMSO) δ 196.7, 171.7, 171.4, 171.3, 170.0, 169.7, 167.5, 161.0, 160.7, 158.5, 158.5, 158.4, 138.2, 138.2, 137.1, 137.0, 132.1, 132.1, 131.6, 131.5, 131.5, 129.2, 128.8, 128.7, 128.7, 128.6, 128.0, 127.7, 127.5, 127.5, 121.8, 115.4, 112.2, 76.9, 76.8, 10 65.0, 64.9, 63.4, 63.3, 58.2, 5 7.4, 56.3, 56.2, 56.2, 54.6, 54.5, 53.8, 53.4, 53.2, 41.5, 41.5, 41.4, 40.2, 33.9, 33.7, 31.9, 31.7, 29.2, 29.0, 28.6, 28.3, 26.1, 25.3, 18.7, 18.6, 13.5; HRMS m/z 762.3705 [calcd for $C_{40}H_{51}N_5O_{10}$, 762.3714].

Example 4

Preparation of Compounds of Formulas 4A and 4B

4A

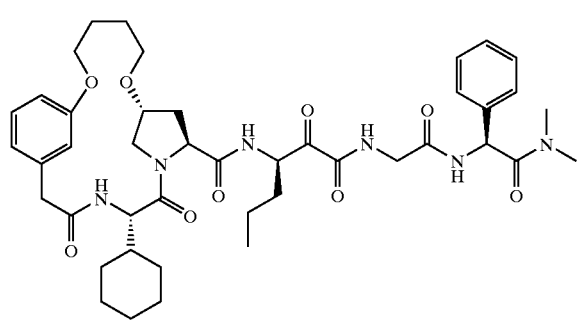

4B

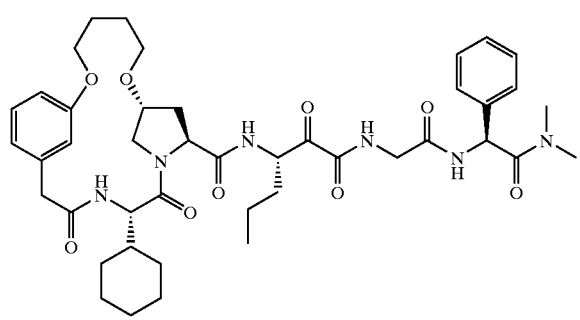

Step A:

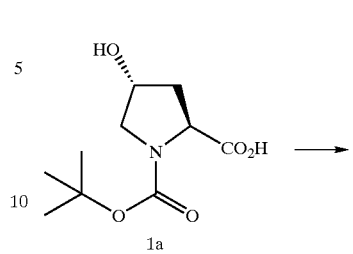

1a

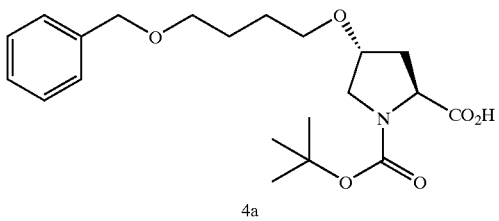

4a

The desired product 4a was obtained by the method described for Example 1, Step A. The crude material was carried to the next step as it was.

Step B:

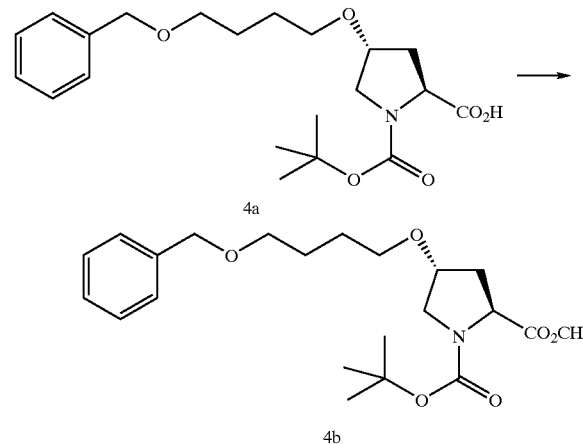

The desired product 4b was obtained by the method described for Example 1, Step B. The material was purified by flash column chromatography using 80/20 to 75/25 hexanes/ethyl acetate to provide 4b in 50% yield as a colorless oil.

Step C:

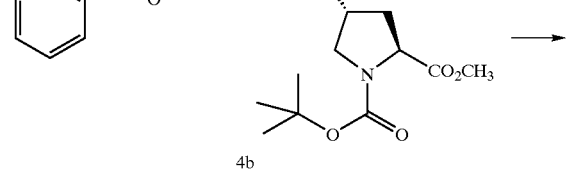

4b

-continued

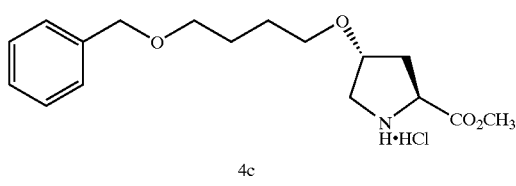
4c

The desired compound 4c was prepared by the protocol described for Example 1, Step C. The material was carried forward as it was.

Step D:

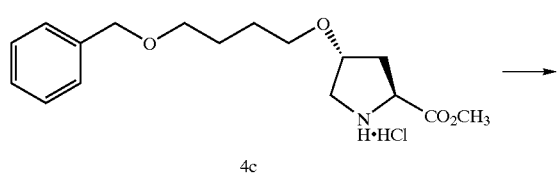
4c

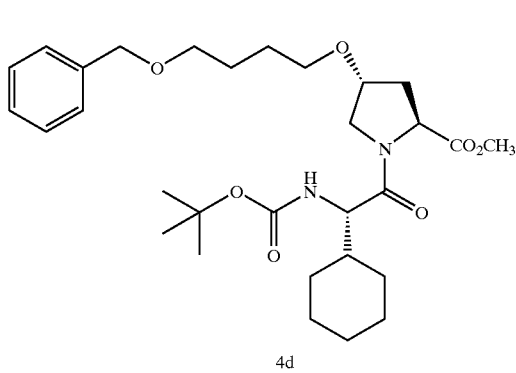
4d

The desired product 4d was obtained by the method described in Example 1, Step D. The material after work-up was sufficiently pure to be carried to the next step. HRMS (FAB) Calcd for $C_{30}H_{47}N_2O_7$: 547.3383 $(M+H)^+$. Found: 547.3372.

Step E:

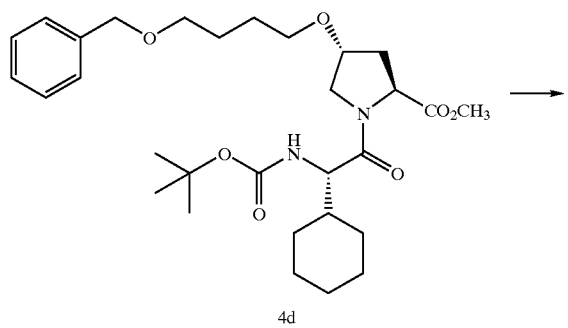
4d

-continued

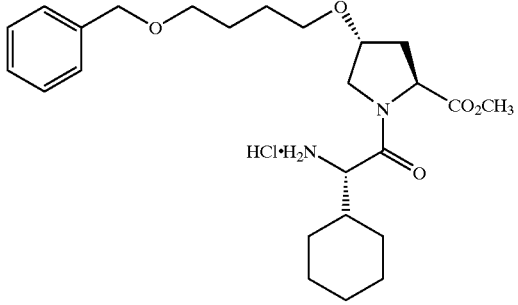
4e

The desired product 4e was obtained by the method described in Example 1, Step E. The crude material was carried to the next step as was.

Step F:

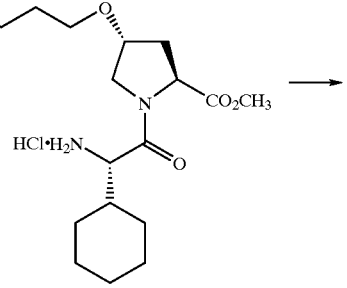
4e

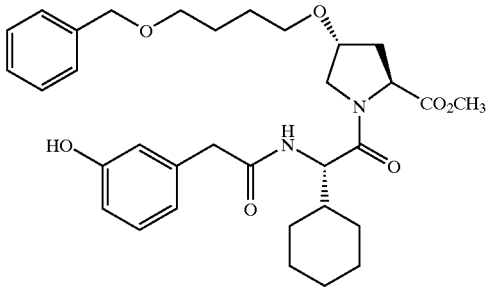
4f

The desired product 4f was obtained by the method described in Example 1, Step F. The material was purified by flash column chromatography using 80/20 to 60/40 dichloromethane/ethyl acetate to provide 4f in 85% yield. HRMS (FAB) Calcd for $C_{33}H_{45}N_2O_7$: 581.3227 $(M+H)^+$. Found: 581.3222.

Step G:

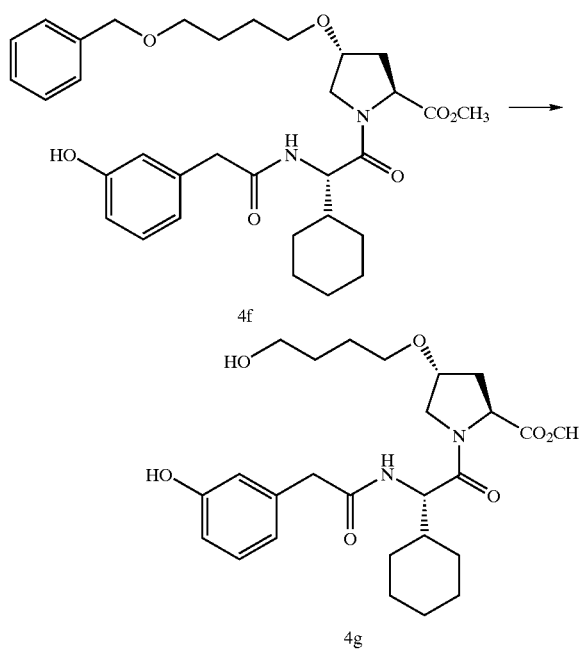

The desired product 4g was obtained by the method described in Example 1, Step G. The crude material was carried to the next step as was. HRMS (FAB) Calcd for $C_{26}H_{39}N_2O_7$: 491.2757 $(M+H)^+$. Found: 491.2761.

Step H:

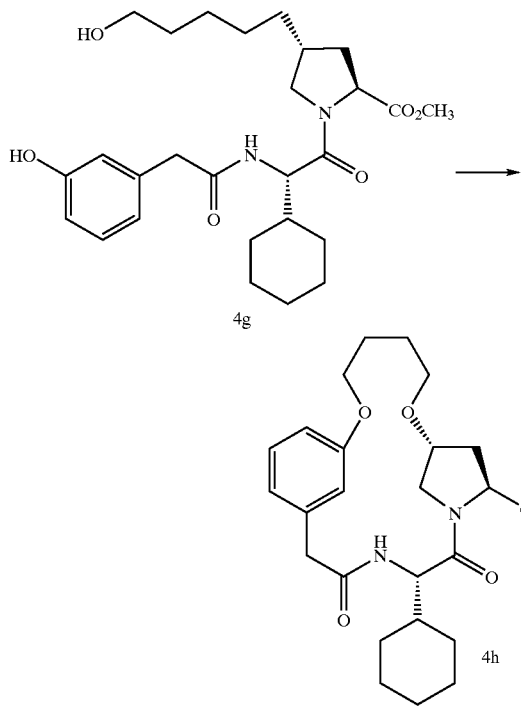

The desired product 4h was obtained by the method described in Example 1, Step H. Purification by column chromatography using 99/1 dichloromethane/methanol afforded 4h along with triphenylphosphine oxide. This mixture was taken to the next step.

Step I:

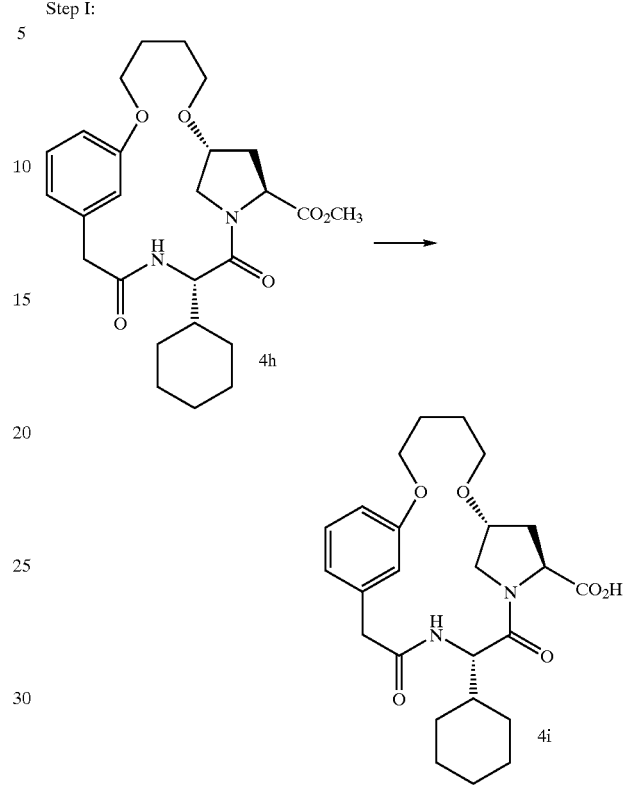

The desired product was obtained by the method described in Example 1 Step I. Yield of 4i (for 2 steps)=24%. $^1$H NMR (DMSO-$d_6$) δ 0.90–0.95 (m, 2H), 1.10–1.16 (m, 3H), 1.51–1.79 (m, 11H), 2.43 (dd, 1H), 3.29–3.32 m, 2H), 3.50–3.54 (m,1H), 3.62–3.68 (m, 2H), 3.91–3.99 (m, 3H), 4.04–4.08 (m, 2H), 4.46 (t, 1H), 6.67–6.72 (m, 3H), 7.13 (app. t, 1H), 8.36 (d, 1H), 12.40 (br. s, 1H); $^{13}$C NMR (DMSO-$d_6$) δ 25.26, 25.31, 25.97, 26.62, 28.42, 33.28, 39.75, 41.49, 53.50, 54.28, 57.45, 67.57, 67.98, 77.25, 111.07, 115.23, 121.48, 129.11, 137.99, 158.33, 170.07, 172.92; HRMS (FAB) Calcd for $C_{25}H_{35}N_2O_6$: 459.2495 $(M+H)^+$. Found: 459.2494.

Step J:

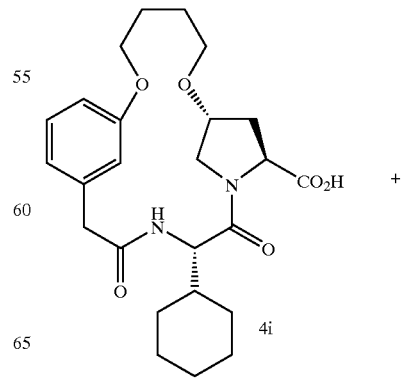 +

-continued

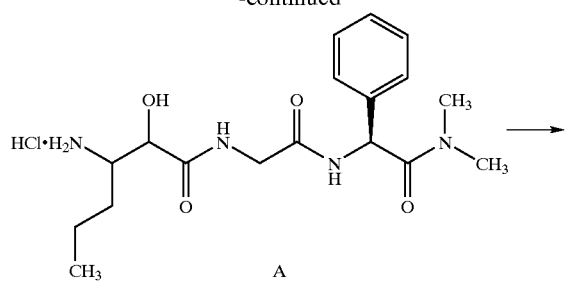

A

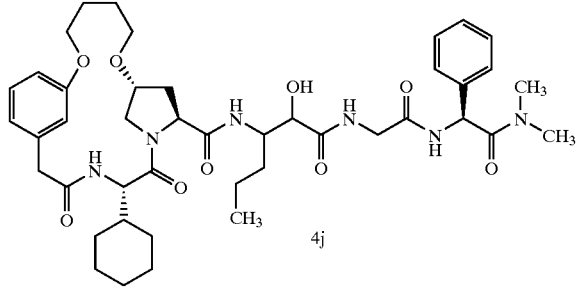

4j

The expected product 4j was synthesized as described earlier for the Example 1 Step J. The material after work-up was of sufficient purity to be carried forward to the next step. HRMS (FAB) Calcd for $C_{43}H_{61}N_6O_9$: 805.4500 (M+H)$^+$. Found: 805.4492.

Step K:

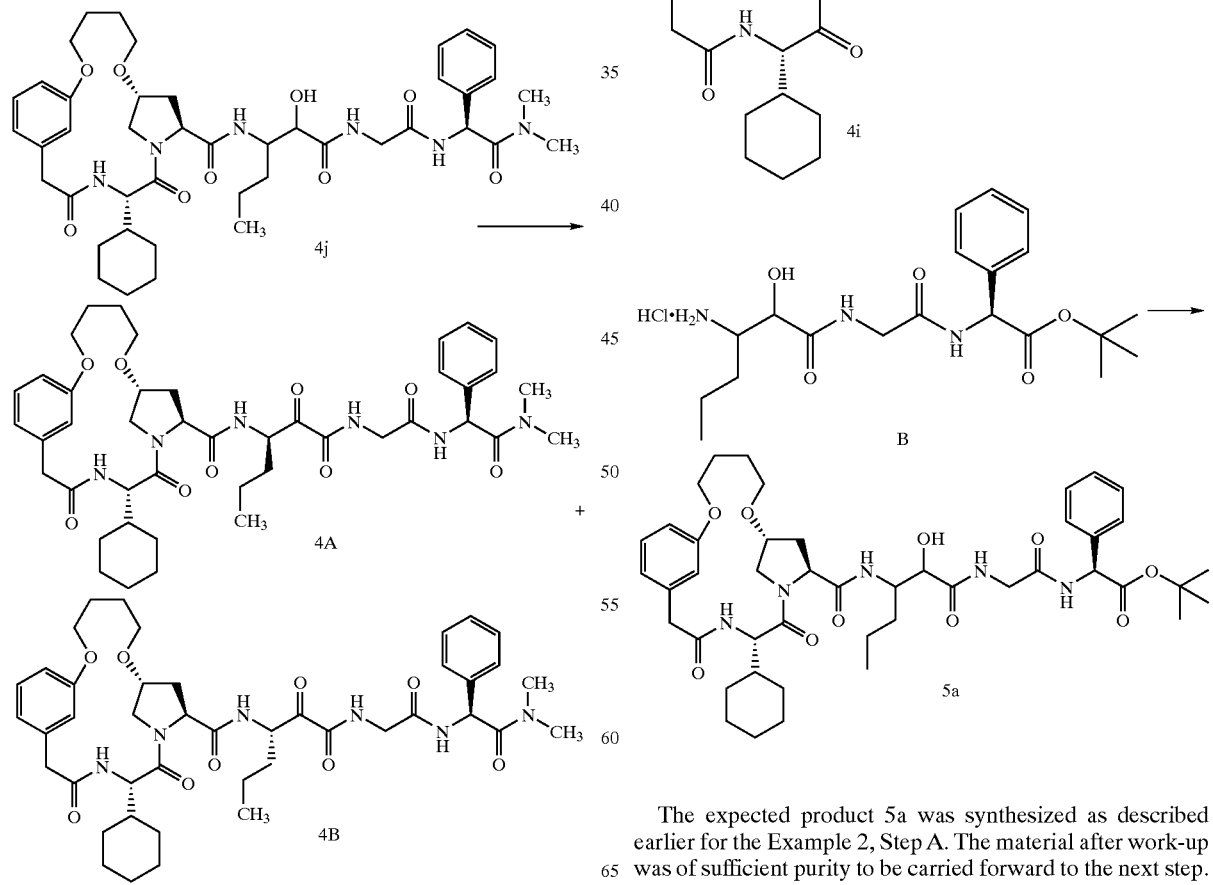

4j

4A

4B

The desired products 4A and 4B were obtained by the oxidation protocol described previously for Example 1 Step K. Purification by flash column chromatography using 100/0 to 99/1 dichloromethane/methanol afforded separate isomers 4A and 4B, and some mixture. Combined yield=34% (for 2 steps). HRMS (FAB) Calcd for $C_{43}H_{59}N_6O_9$: 803.4344 (M+H)$^+$. Found: 803.4339 (4A), 803.4347 (4B).

Example 5

Preparation of Compound 5

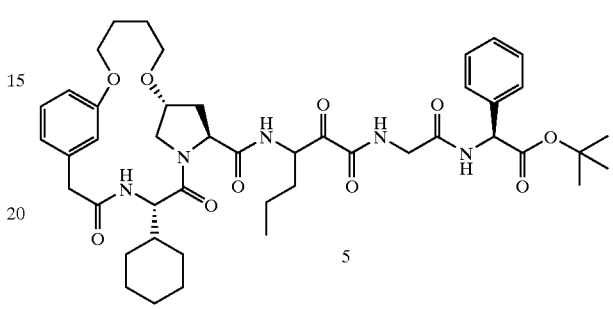

5

Step A:

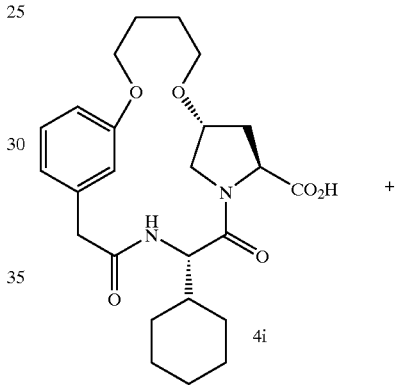

4i

+

B

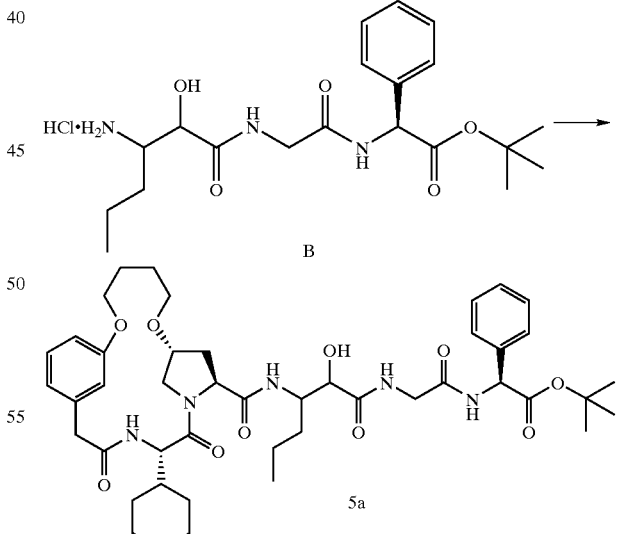

5a

The expected product 5a was synthesized as described earlier for the Example 2, Step A. The material after work-up was of sufficient purity to be carried forward to the next step. HRMS (FAB) Calcd for $C_{45}H_{64}N_5O_{10}$: 834.4653 (M+H)$^+$. Found: 834.4648.

Step B:

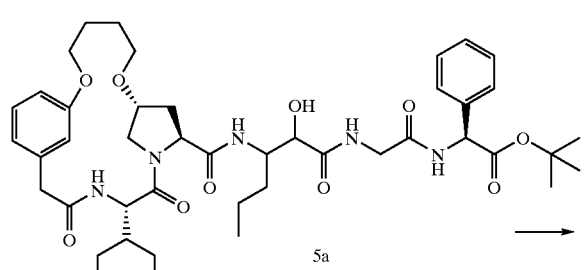

5a

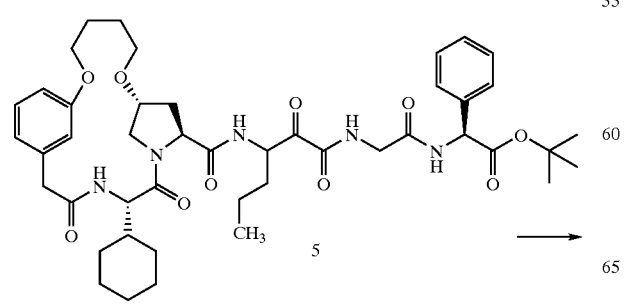

5

The desired product 5 was obtained by the oxidation protocol described previously for Example 1, Step K. Purification by flash column chromatography using 99/1 dichloromethane/methanol afforded 5 as a mixture of diastereomers in 31% yield (for 2 steps). HRMS (FAB) Calcd for $C_{45}H_{62}N_5O_{10}$: 832.4497 (M+H)$^+$. Found: 832.4497.

Example 6

Preparation of Compound 6

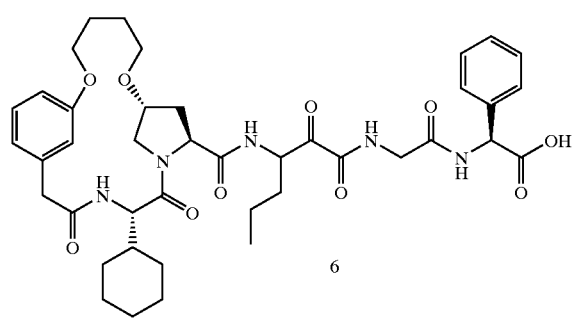

6

Step A:

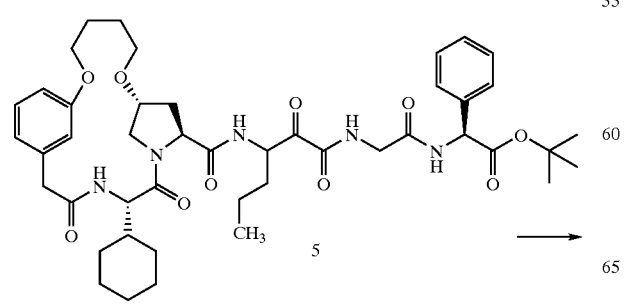

5

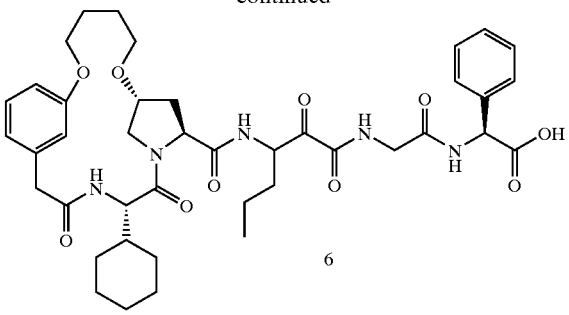

6

The expected product 6 was synthesized as described earlier for the Example 3, Step A in quantitative yield. HRMS (FAB) Calcd for $C_{41}H_{54}N_5O_{10}$: 776.3871 (M+H)$^+$. Found: 776.3865.

Example 7

Preparation of compounds 7A and 7B

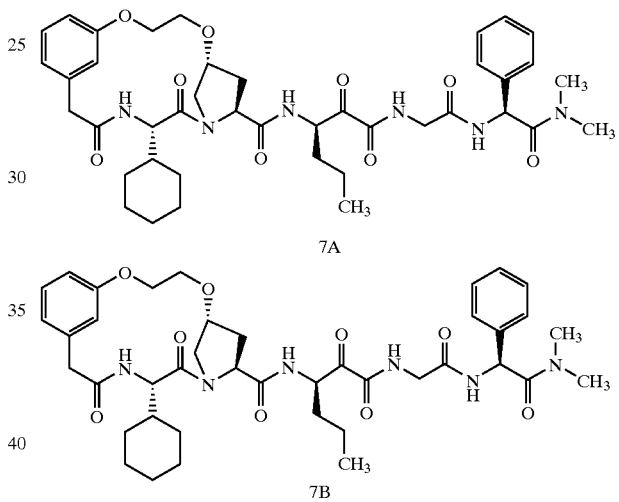

Step A:

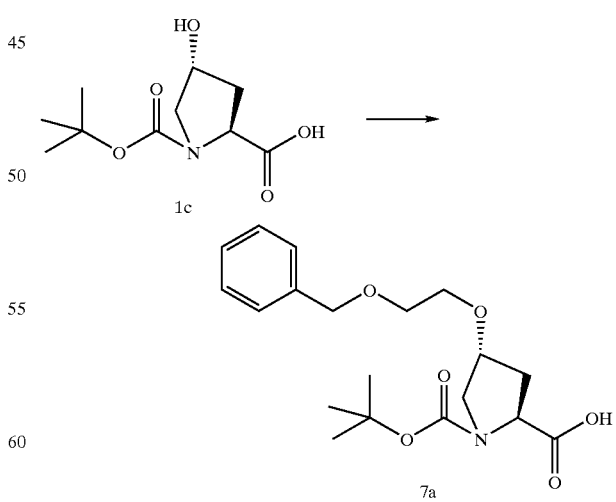

The desired compound 7a was prepared from 1c according to the procedure of Example 1, Step A. The crude product was used in Step B without further purification.

Step B:

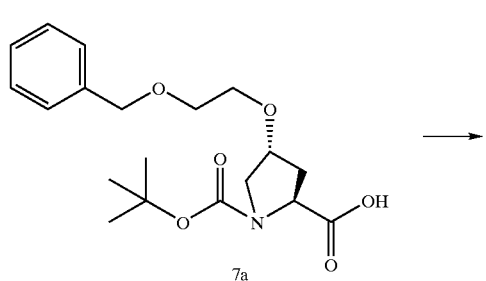

The desired compound 7b was prepared from 7a according to the procedure of Example 1, Step B.

Step C:

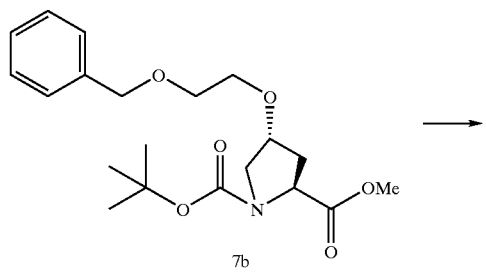

The desired compound 7c was prepared from 7b according to the procedure of Example 1, Step C. The product was used in Step D without further purification.

Step D:

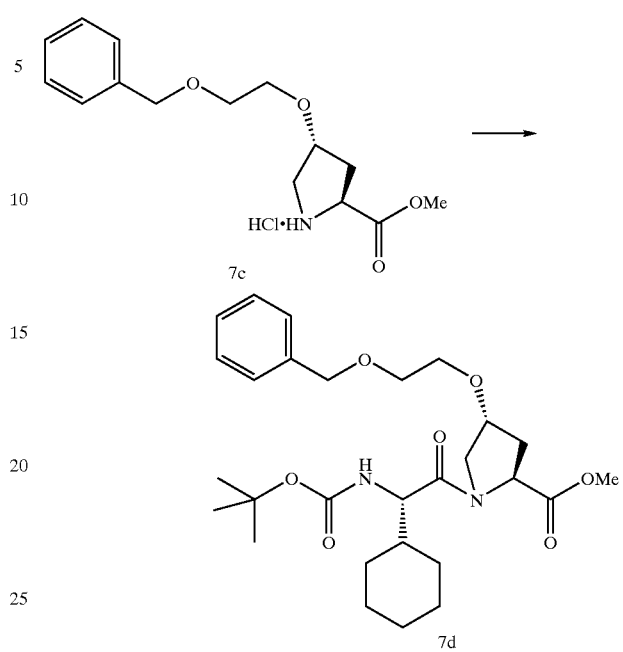

The desired compound 7d was prepared from 7c according to the procedure of Example 1, Step D.

Step E:

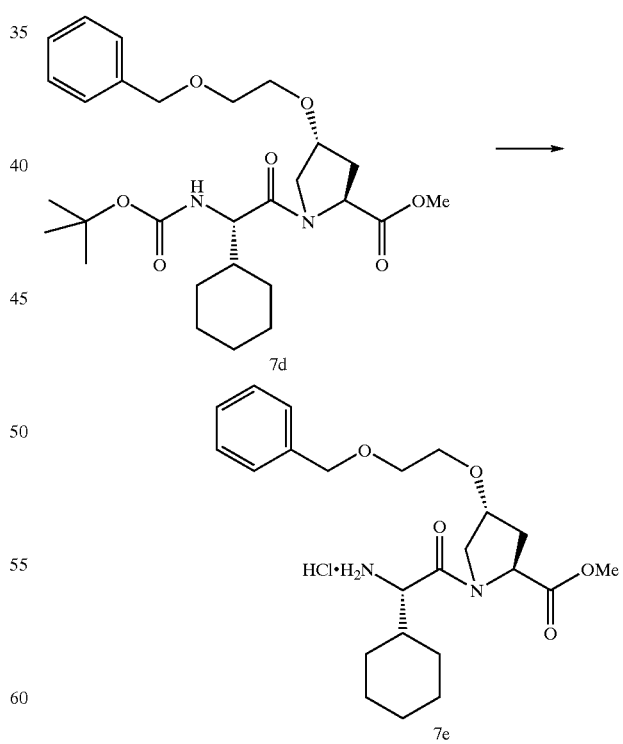

The desired compound 7e was prepared from 7d according to the procedure of Example 1, Step E. The product was used in Step F without further purification.

Step F:

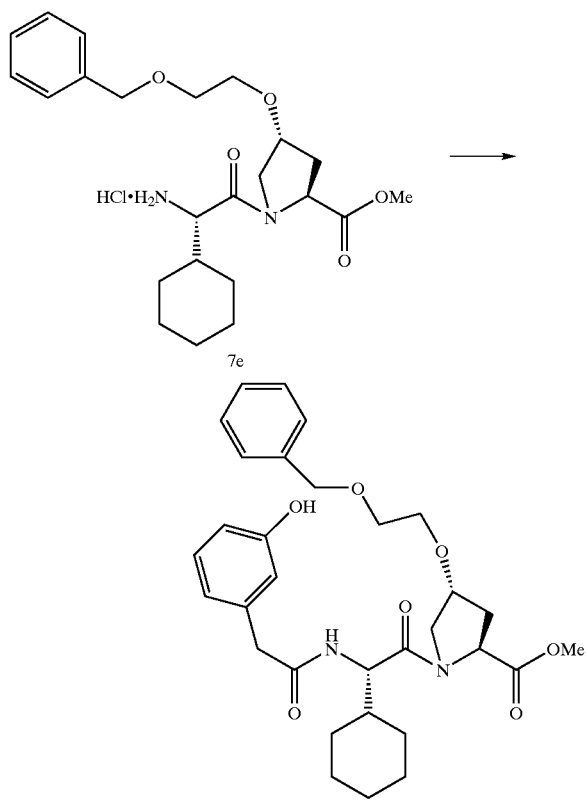

The desired compound 7f was prepared from 7e according to the procedure of Example 1, Step F.

Step G:

The desired compound 7g was prepared from 7f according to the procedure of Example 1, Step F.

Step H:

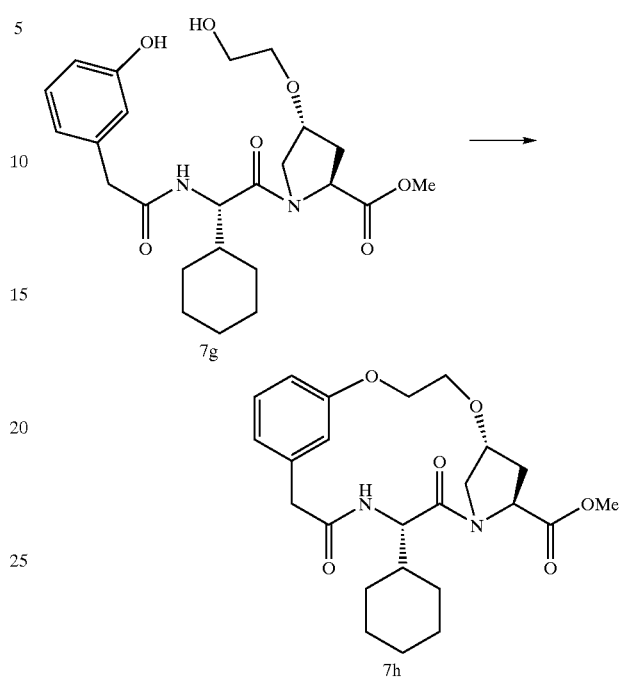

A solution of the phenol alcohol 7g (830 mg, 1.79 mmol) and ADDP (1.36 g, 5.39 mmol) in anhydrous $CH_2Cl_2$ (200 mL) was bubbled with Argon through a frit glass bubbler for 20 min. To this solution at 0° C. was added triphenylphosphine (1.41 g, 5.38 mmol). After stirring at 0° C. for 20 min, the solution was warmed to room temperature and stirred overnight (20 h) under nitrogen. After removal of solvent in vacuo, the residue was purified by flash chromatography (1 to 3% MeOH in $CH_2Cl_2$) to afford a mixture of the desired product 7 h and triphenylphosphine oxide, which was used in Step I without further purification.

Step I:

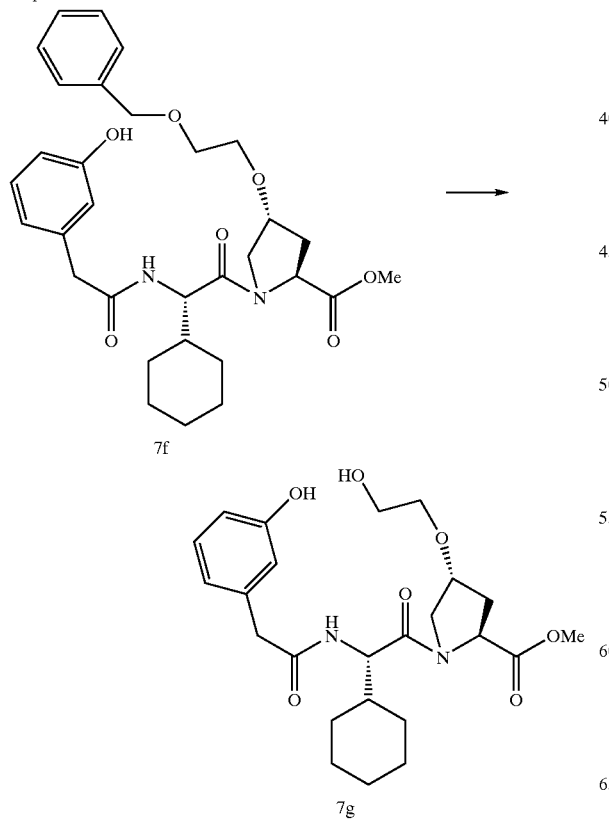

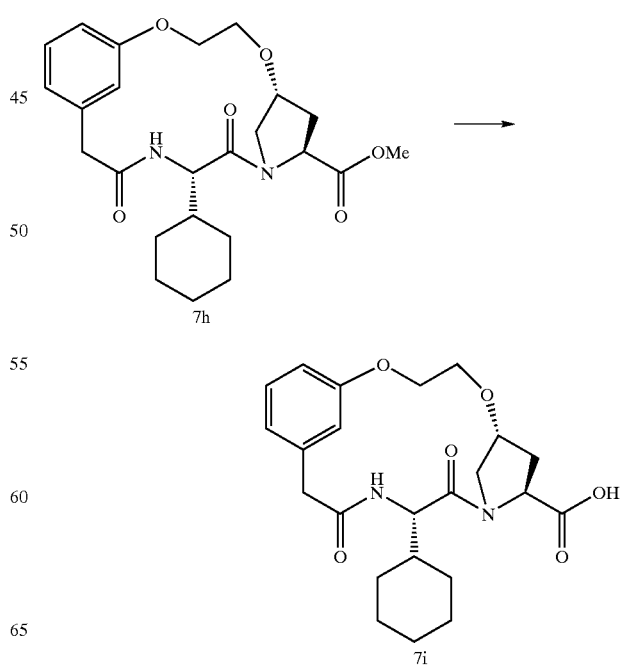

The desired compound 7i was prepared from 7h in 36% yield (2 steps) according to the procedure of Example 1, Step I.
Step J:
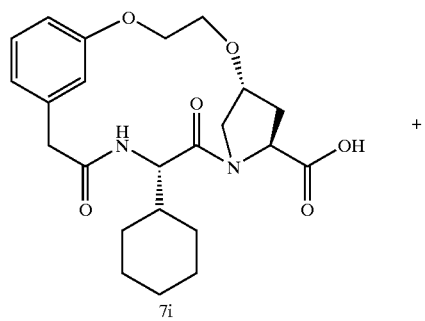
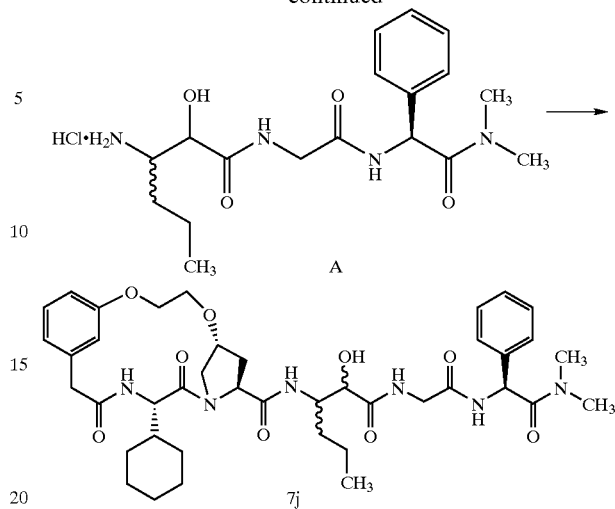
The desired compound 7j was prepared from 7i and A in 56% yield according to the procedure of Example 1, Step J.
Step K:
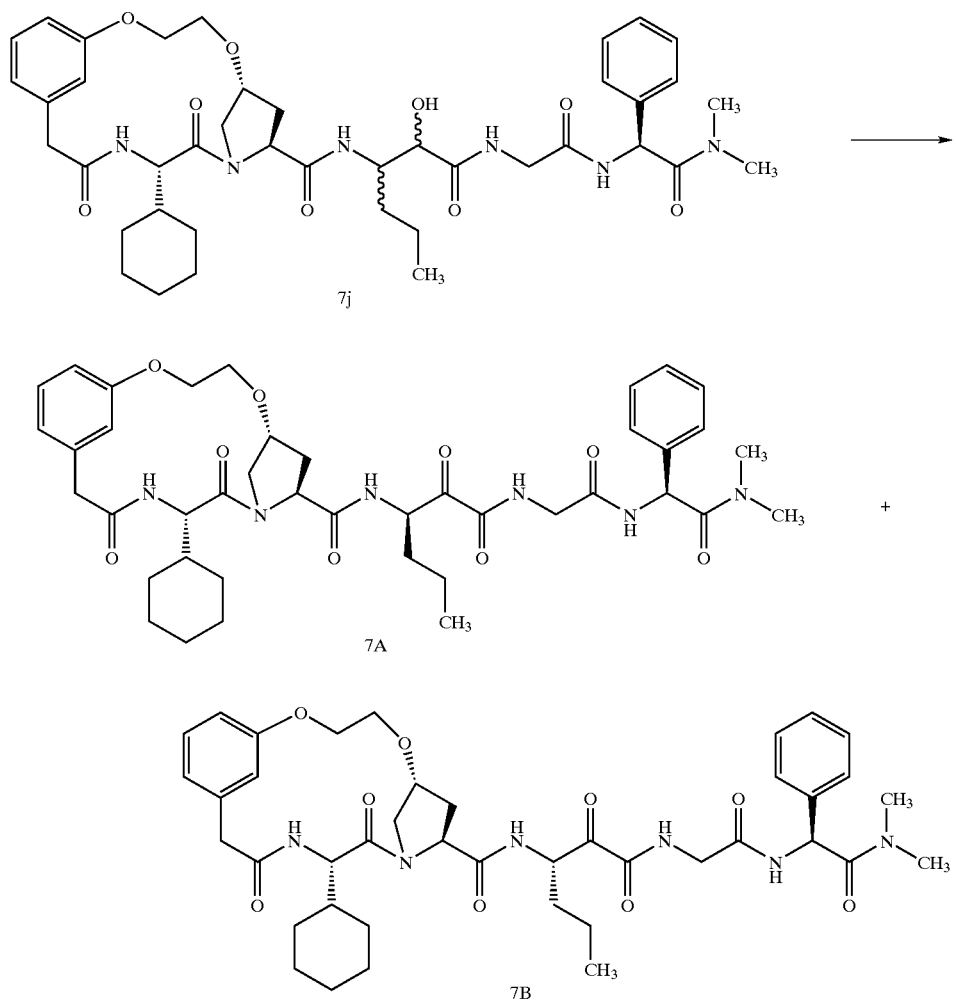

The desired compound 7A and 7B were prepared from 7j according to the procedure of Example 1, Step K.

Example 8

Preparation of Compound of Formula 8

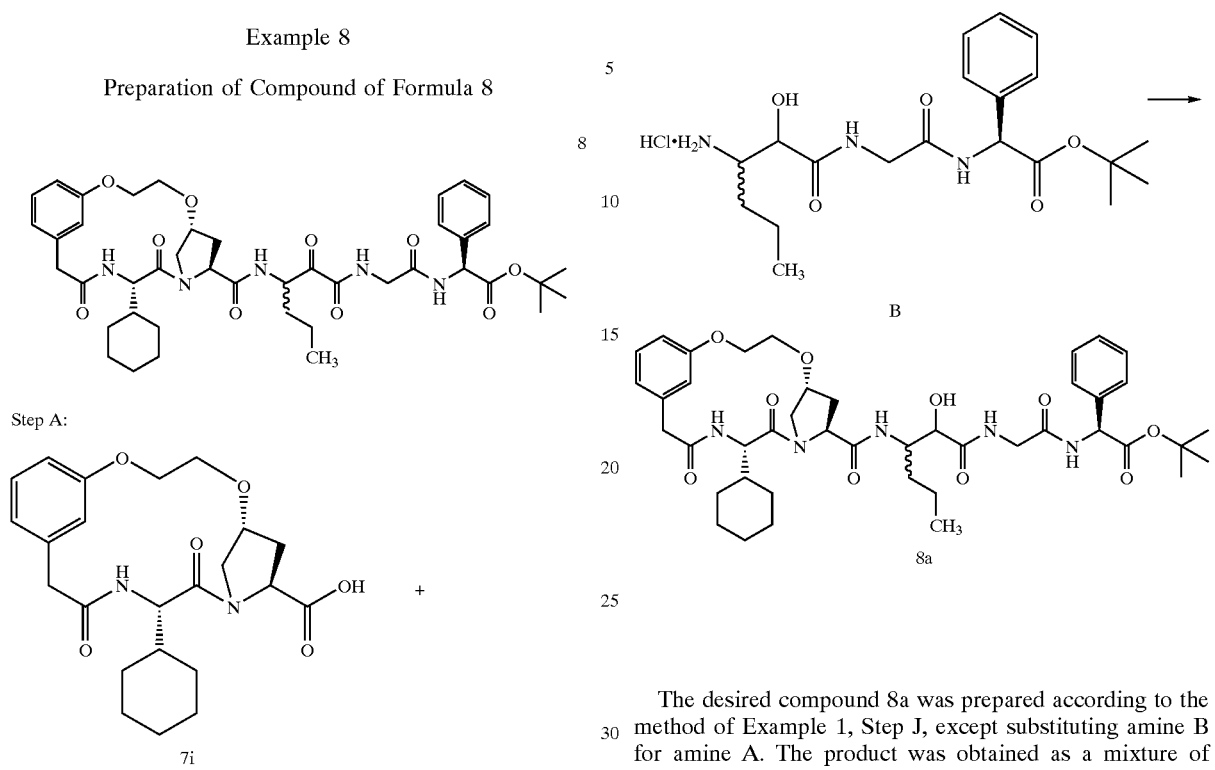

Step A:

Step B:

The desired compound 8a was prepared according to the method of Example 1, Step J, except substituting amine B for amine A. The product was obtained as a mixture of inseparable diastereomers in the form of a white solid in 57% yield.

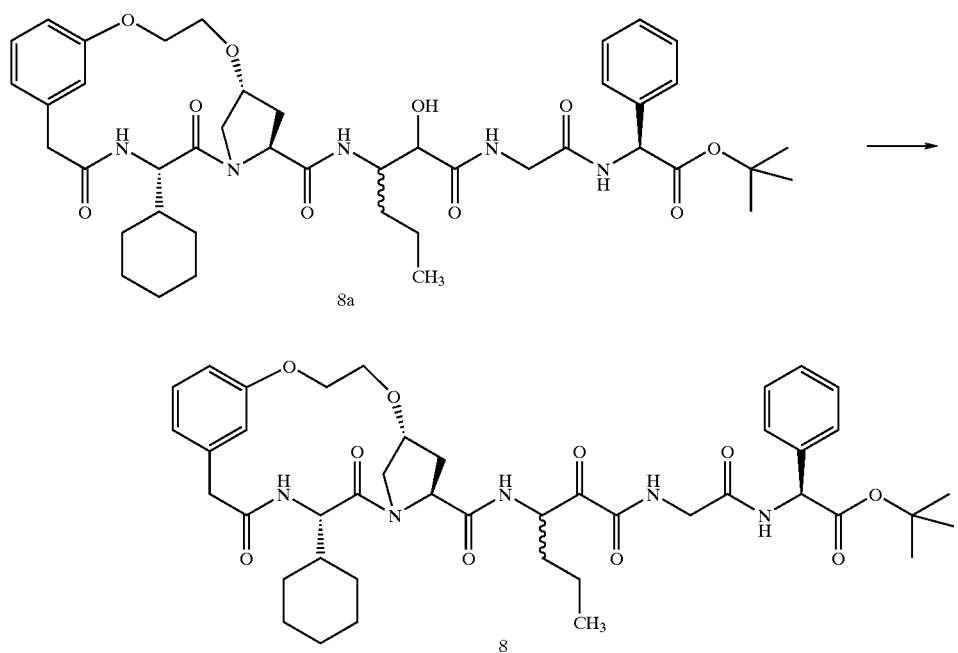

The desired compound 8 was prepared in 72% yield from 8a according to the method of Example 1 Step K.

Example 9

Preparation of Compound of Formula 9

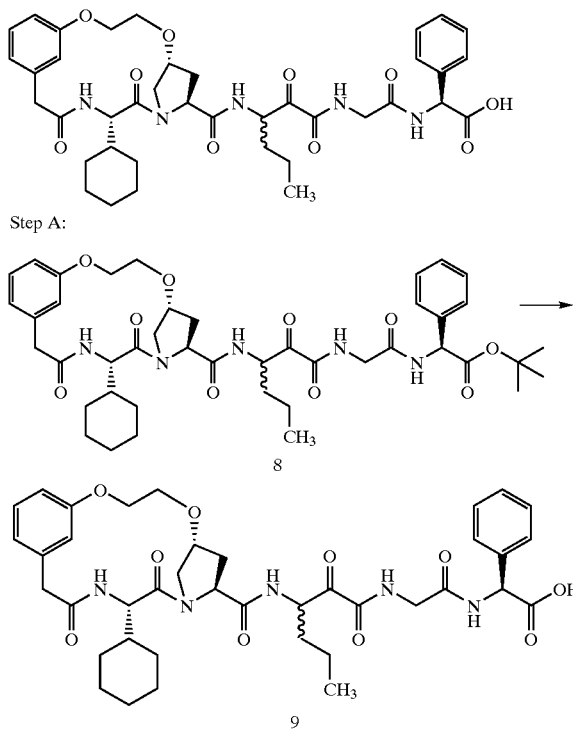

The desired compound 9 was prepared quantitatively from 8 according to the method of Example 3, Step A.

Example 10 preparation of Compounds of Formula 10A and 10B

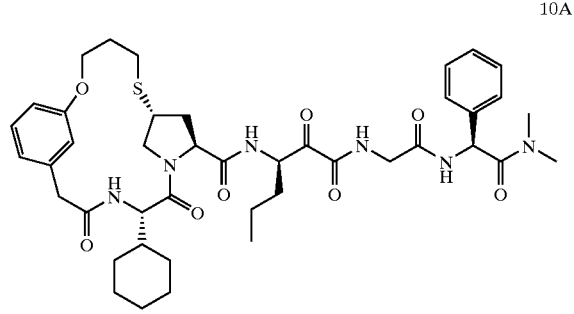

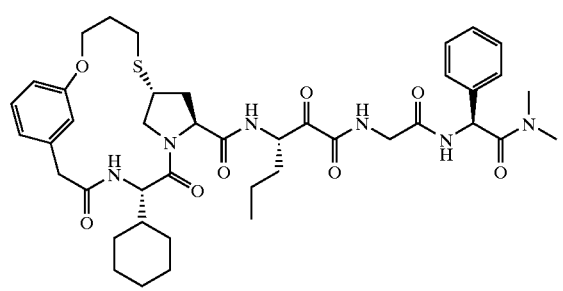

Step A:

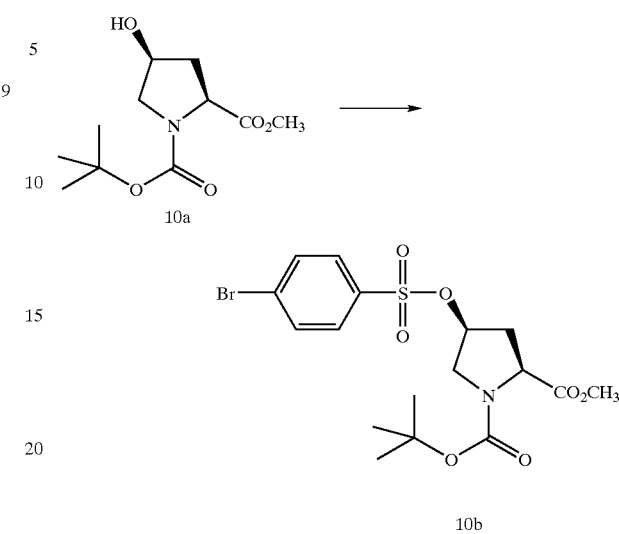

To a 0° C. solution of 10a (10 g, 41 mmol) in dichloromethane (60 mL) was added triethylamine (28.68 mL, 204 mmol) slowly. 4-bromobenzenesulfonyl chloride (20.91 g, 82 mmol) and DMAP (few crystals) were then added and the temperature was maintained at 0° C. for 30 min. The reaction mixture was left standing in the refrigerator (~5° C.) overnight followed by slow warming to ambient temperature over two hours. At this time TLC analysis revealed complete consumption of the starting material. The reaction mixture was diluted with dichloromethane, washed with saturated sodium bicarbonate solution, and 10% aqueous citric acid solution. The organic layer was dried ($Na_2SO_4$) and concentrated. The crude mixture was purified by flash column chromatography using 100/0 to 95/5 dichloromethane/ethyl acetate to provide 18.4 g (97% yield) of the brosylate 10b as a white solid; $^1$H NMR (mixture of rotamers, $CDCl_3$) δ 1.41 and 1.45 (2s, 9H), 2.40–2.50 (m, 2H), 3.59–3.69 (m, 5H), 4.33–4.37 and 4.46 (2 dd, 1H), 5.11 (m, 1H), 7.72–7.74 (m, 4H); $^{13}$C NMR (mixture of rotamers, $CDCl_3$) δ 28.18, 28.27, 36.01, 36.98, 51.59, 52.03, 52.20, 52.35, 56.95, 57.22, 57.28, 78.35, 79.53, 80.66, 129.10, 129.26, 132.66, 135.66, 135.81, 153.25, 153.64, 171.45, 171.78; HRMS (FAB) Calcd for $C_{17}H_{23}NO_7SBr$: 464.0379 (M+H)$^+$. Found: 464.0375.

Step B:

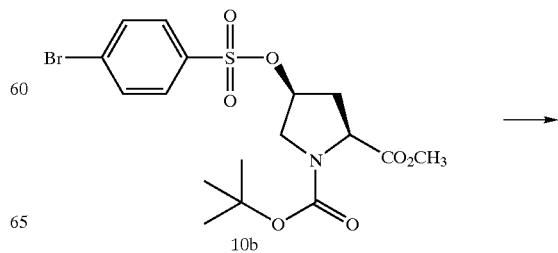

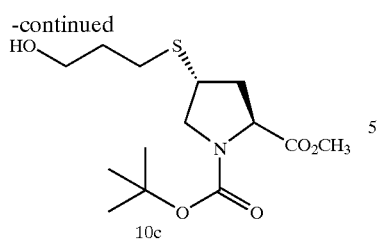

10c

To a suspension of sodium hydride (60% dispersion in mineral oil, 187 mg, 4.68 mmol) in DMF at 0° C. was added 3-mercaptopropanol (0.42 mL, 4.85 mmol) under argon atmosphere. The mixture was stirred for 30 min while maintaining the temperature. A solution of brosylate 101b (1.5 g, 3.23 mmol) in DMF (total volume=10 mL) was added slowly and the mixture was warmed to ambient temperature over 2 hrs. The reaction was quenched by pouring into cold 10% citric acid solution. The aqueous layer was extracted with ethyl acetate, the organic layer was dried ($Na_2SO_4$) and concentrated. The crude material was purified by flash column chromatography using 85/15 dichloromethane/ethyl acetate to provide 800 mg (78% yield) of the sulfide 10c as an oil; $^1$H NMR (mixture of rotamers, $CDCl_3$) δ 1.41 and 1.47 (2s, 9H), 1.83–1.89 (m, 2H), 2.13–2.34 (m, 2H), 2.69 (t, 2H), 3.23–3.49 (m, 2H), 3.73–3.78 (m, 5H), 3.86–3.95 (m, 1H), 4.33–4.37 and 4.42–4.46 (2dd, 1H); $^{13}$C NMR (mixture of rotamers, $CDCl_3$) δ 28.21, 28.30, 32.15, 32.23, 36.65, 37.27, 40.45, 40.89, 52.16, 52.35, 52.50, 52.84, 58.32, 58.55, 61.22, 61.41, 80.35, 153.49, 153.99, 173.05, 173.23; HRMS (FAB) Calcd for $C_{14}H_{26}NO_5S$: 320.1532 $(M+H)^+$. Found: 320.1528.

Step C:

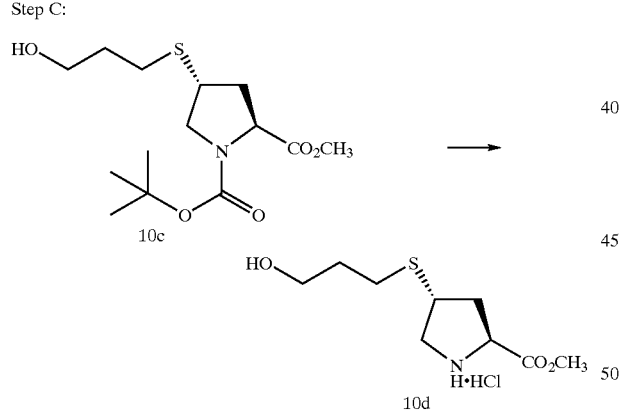

The desired compound 10d was prepared by the protocol described for Example 1, Step C. Reaction conditions were 0° C., 1 hr. The material was carried to the next step as it was.

Step D:

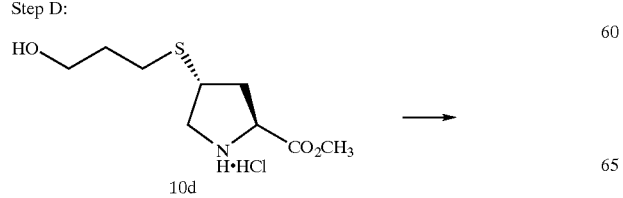

10d

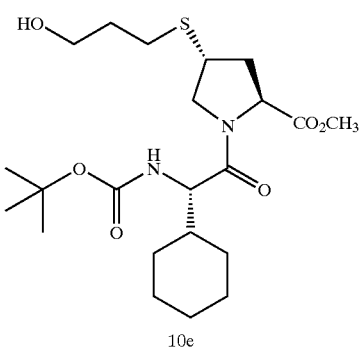

10e

The desired compound 10e was prepared by the method described for Example 1, Step D. The coupling reaction was carried out at −8° C. for 2 days. After workup the product 10e was sufficiently pure by TLC and was obtained in 80% yield; HRMS (FAB) Calcd for $C_{22}H_{39}N_2O_6S$: 459.2529 $(M+H)^+$. Found: 459.2523.

Step E:

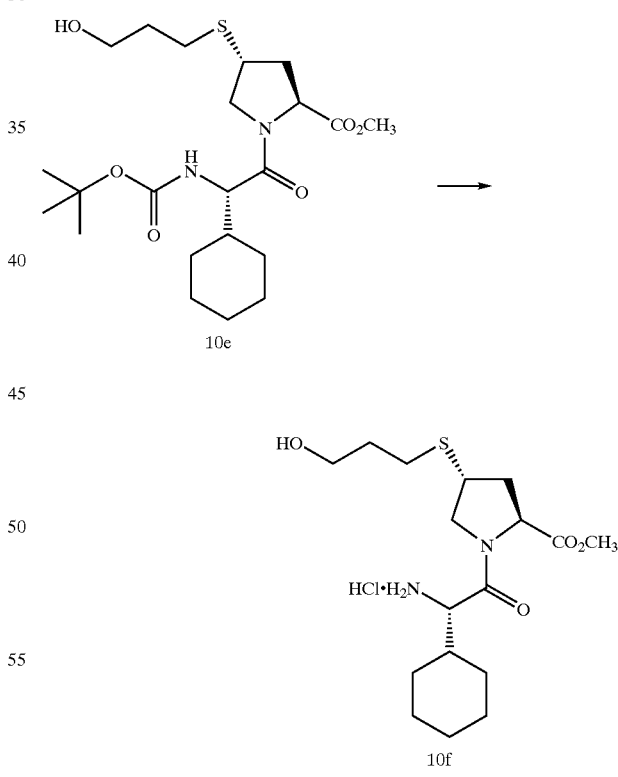

The desired compound 10f was prepared by the protocol described for Example 1, Step E. The material was carried forward as it was.

Step F:

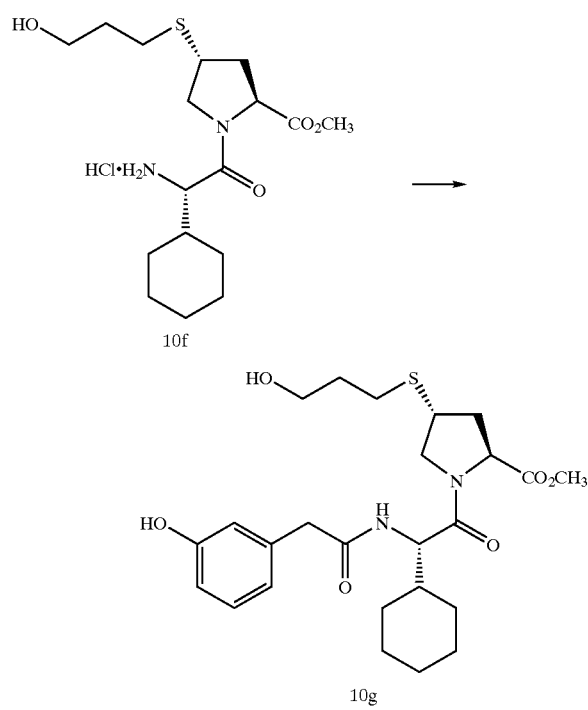

The desired compound 10g was prepared by the procedure described for Example 1, Step F. The crude product was purified by flash column chromatography using 98/2 of dichloromethane/methanol to provide 10 g in 40% yield as a white solid; $^1$H NMR (mixture of rotamers, CDCl$_3$) δ 0.90–1.26 (m), 1.66–1.88 (m), 2.22–2.31 (m, 2H), 2.73 (t, 2H), 3.47 (s), 3.5–3.55 (m), 3.65–3.75 (m), 3.88–3.94 (dd, 1H), 4.07–4.12 (dd, 1H), 4.53 (t, 1H), 4.62 (t, 1H), 6.73–6.80 (m, 4H), 7.17 (t, 1H); $^{13}$C NMR (mixture of rotamers, CDCl$_3$) δ 25.80, 25.89, 26.14, 27.71, 28.55, 29.22, 31.88, 35.46, 40.58, 42.44, 43.16, 52.32, 52.90, 55.49, 58.46, 60.30, 114.59, 116.27, 121.01, 130.02, 135.90, 156.73, 171.25, 171.87, 171.96; HRMS (FAB) Calcd for C$_{25}$H$_{37}$N$_2$O$_6$S: 493.2372 (M+H)$^+$. Found: 493.2364.

Step G:

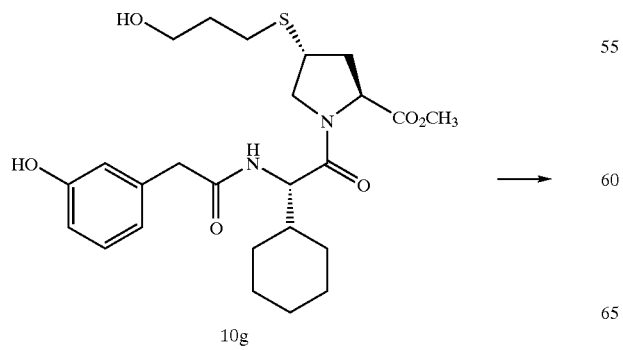

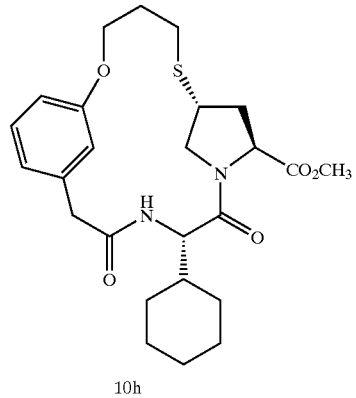

The desired compound 10h was prepared by the protocol described for Example 1, Step G. The crude product was suspended in 80/20 ethyl acetate/hexane, and the solid material was filtered off. The filtrate was concentrated and purified by flash column chromatography using 80/20 hexane/acetone to yield 22% of 10h as a solid. $^1$H NMR (CDCl$_3$) δ 0.98–1.30 (m), 1.64–1.90 (m), 2.06–2.14 (m, 1H), 2.16–2.21 (dd, 2H), 2.62–2.70 (m, 2H), 3.38–3.46 (m, 2H), 3.60–3.66 (m, 3H), 3.71 (s, 3H), 3.88–3.94 (dd, 1H), 4.07–4.15 (m, 1H), 4.22–4.29 (m,1H), 4.48 (t,1H), 4.60 (t,1H), 5.97 (br t,1H), 6.76–6.81 (m, 2H), 6.99 (br s,1H), 7.20 (dd, 1H); HRMS (FAB) Calcd for C$_{25}$H$_{35}$N$_2$O$_5$S: 475.2267 (M+H)$^+$. Found: 475.2260.

Step H:

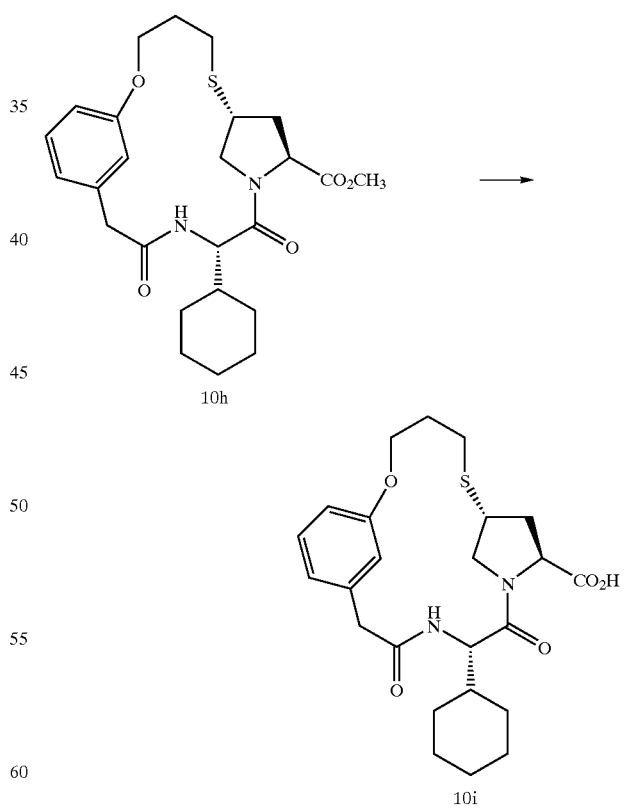

The advanced intermediate 10i was synthesized as described for Example 1, Step H, in quantitative yield as a white solid; $^1$H NMR (DMSO-d$_6$) δ 0.88–0.96 (m, 2H), 1.10–1.14 (m, 3H), 1.59–1.76 (m, 7H), 1.88–1.94 (m, 1H), 2.09 (app. t, 1H), 2.61 (dd,1H), 3.32 (app. d,1H), 3.40–3.45 (m, 2H), 3.61 (app. d, 1H), 3.83 (q, 1H), 4.13 (app. t, 1H), 4.19 (t, J=7.32Hz, 1H), 4.40 (t, J=9.52Hz, 1H), 6.76–6.79 (m, 2H), 6.89 (s, 1H), 7.16 (app. t, 1H), 8.39 (d, 1H), 12.5 (br. s, 1H); $^{13}$C NMR (DMSO-d$_6$) δ 25.33, 25.41, 26.01, 26.44, 28.09, 28.62, 29.24, 34.90, 39.50, 41.40, 42.30, 53.18, 54.44, 58.06, 66.94, 114.88, 115.25, 122.28, 129.20, 137.84, 157.90, 169.25, 170.29, 172.59; HRMS (FAB) Calcd for $C_{24}H_{33}N_2O_5S$: 461.2110 (M+H)$^+$. Found: 461.2104.

Step I:

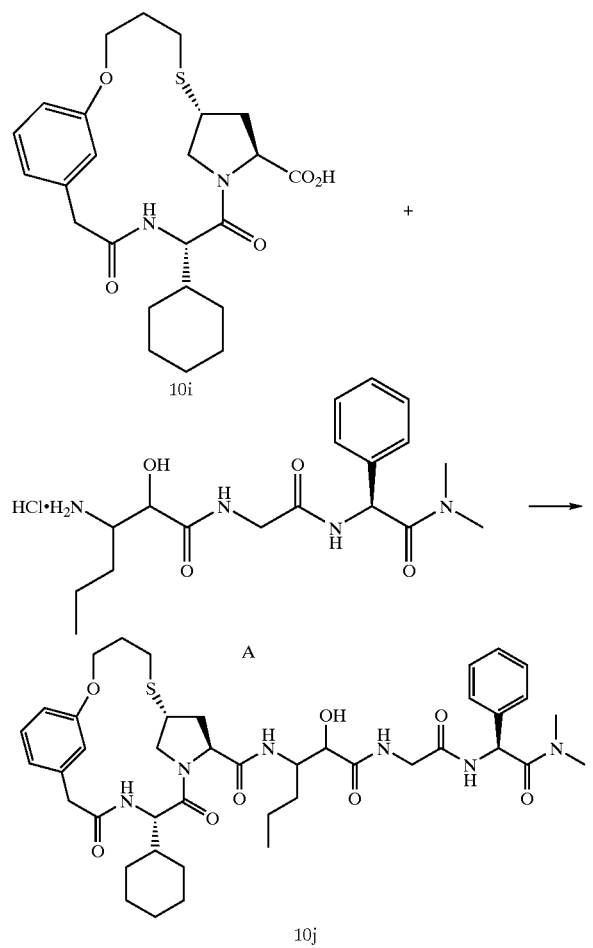

10i

A

10j

The desired compound 10j was prepared as described earlier for Example 1, Step I, in quantitative yield as a pale yellow solid. The material obtained after workup was sufficiently pure by TLC for further manipulations; HRMS (FAB) Calcd for $C_{42}H_{59}N_6O_8S$: 807.4115 (M+H)$^+$. Found: 807.4103.

Step J:

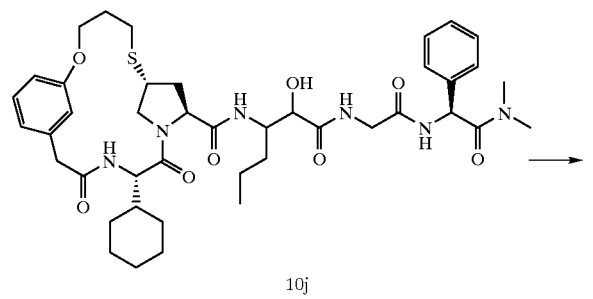

10j

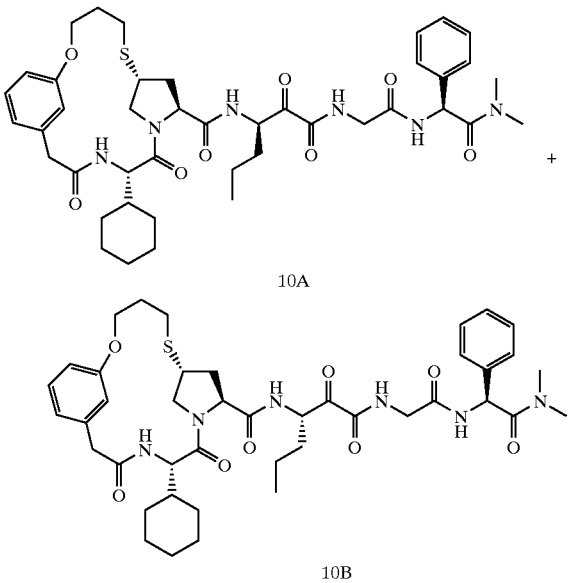

10A

10B

To a solution of 10j (180 mg, 0.22 mmol) in dichloromethane was added sequentially DMSO (0.313 mL, 4.4 mmol), DCC (908 mg, 4.4 mmol), and dichloroacetic acid (36.4 µL, 0.44 mmol). The reaction mixture was stirred overnight at ambient temperature. It was quenched by addition of aqueous 5% citric acid solution (5 mL) and MeOH (1 mL) and stirred for 30 min. The solid material was filtered off, and the filtrate washed with saturated sodium bicarbonate solution and brine. The organic layer was dried over Na$_2$SO$_4$ and solvent removed in vacuo. The crude material was purified by flash column chromatography using 100/0 to 98/2 dichloromethane/methanol to yield 105 mg (60%) of 10A and 10B as a mixture of diastereomers. A part of the mixture (36 mg) was subjected to column chromatography again to provide pure isomer 10A (more polar, white solid, 8 mg) and pure isomer 10B (less polar, white solid, 6 mg), the rest being mixture. HRMS (FAB) Calcd for $C_{42}H_{57}N_6O_8S$: 805.3959 (M+H)$^+$. Found: 805.3958 (10A), 805.3950 (10B).

Example 11

Preparation of Compound of Formula 11

11

Step A:

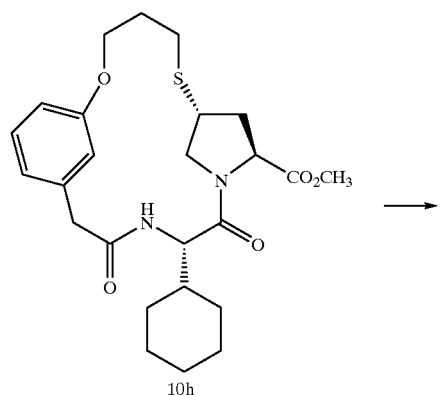
10h

To a cold (0° C.) solution of 10h (200 mg, 0.42 mmol) in dichloromethane (10 mL) was added MCPBA (60%, 364 mg, 1.26 mmol). The reaction mixture was slowly warmed to ambient temperature over 16 hrs. The reaction mixture was diluted with dichloromethane and washed with saturated sodium bicarbonate and sodium bisulfite solution. The organic layer was dried ($Na_2SO_4$), and concentrated. Purification by flash column chromatography using 98/2 dichloromethane/methanol provided 11a (138 mg, 65% yield). HRMS (FAB) Calcd for $C_{25}H_{35}N_2O_7S$: 507.2165 $(M+H)^+$. Found: 507.2158.

Step B:

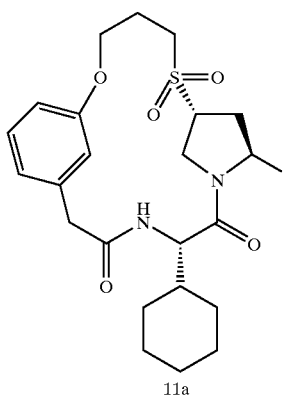
11a

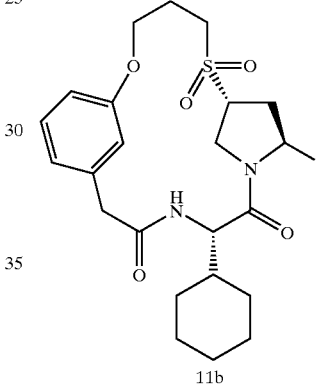
11a

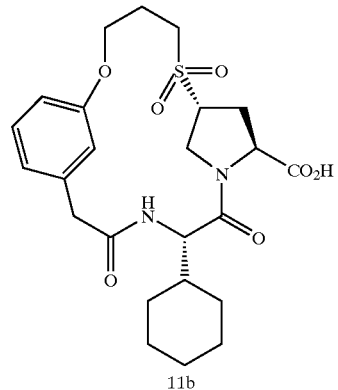
11b

The expected product 11b was synthesized as described for Example 1, Step I in 90% yield as a white solid; HRMS (FAB) Calcd for $C_{24}H_{33}N_2O_7S$: 493.2008 $(M+H)^+$. Found: 493.2012.

Step C:

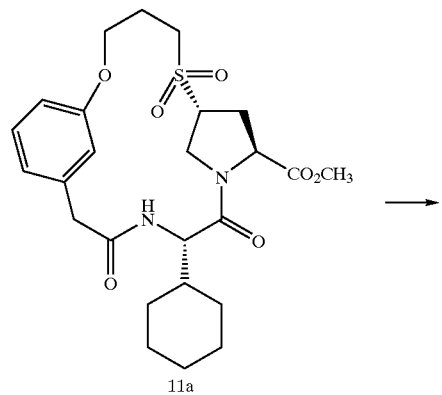
11b

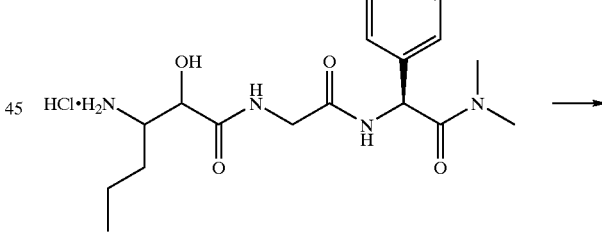
A

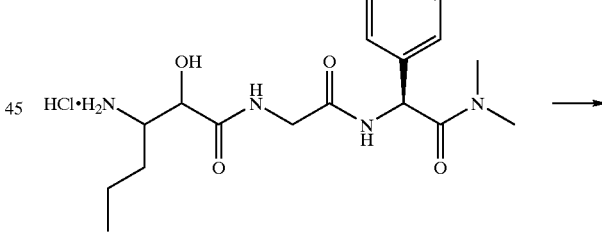
11c

The desired compound 11c was prepared as described earlier for Example 1, Step J, in quantitative yield. The material obtained after workup was sufficiently pure by TLC for further manipulations. HRMS (FAB) Calcd for $C_{42}H_{59}N_6O_{10}S$: 839.4013 $(M+H)^+$. Found: 839.4019.

Step D:

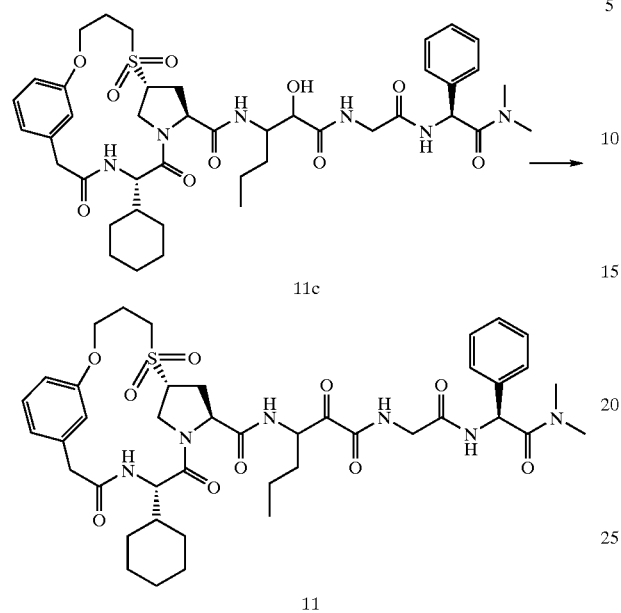

11c

11

The desired product 11 was obtained by the oxidation protocol described earlier for Example 1, Step K. Purification by flash column chromatography using 98/2 dichloromethane/methanol afforded 11 in 4% yield (2 steps). HRMS (FAB) Calcd for $C_{42}H_{57}N_6O_{10}S$: 837.3857 $(M+H)^+$. Found: 837.3865.

Example 12

Preparation of Compounds of Formulas 12A and 12B

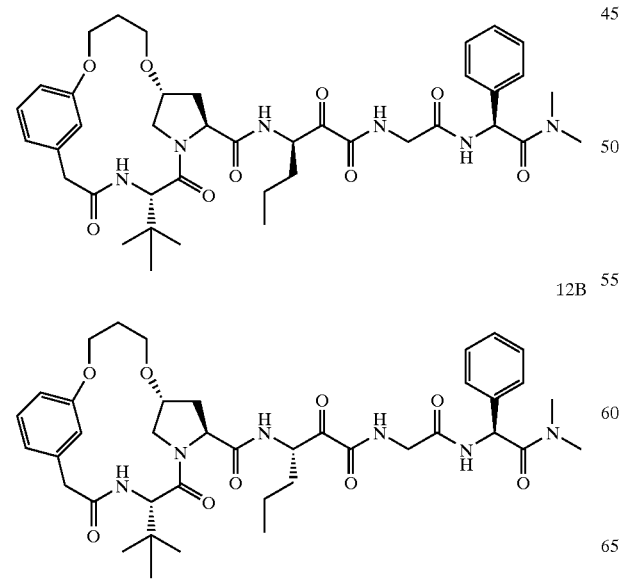

12A

12B

Step A:

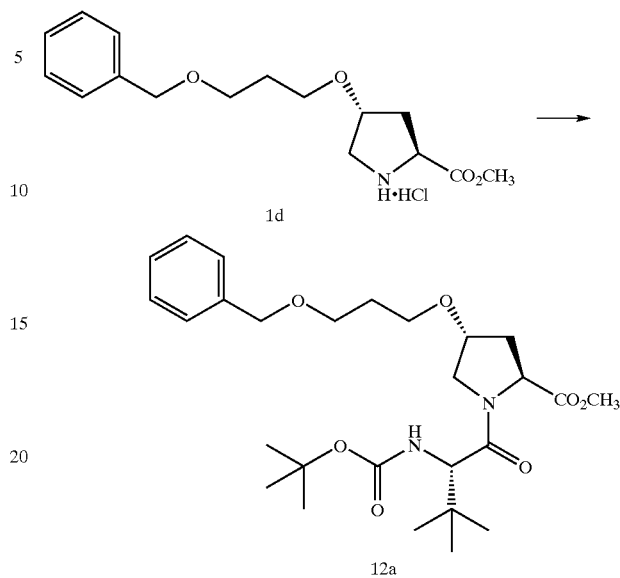

1d

12a

The desired product 12a was obtained by the method described for Example 1, Step D using N-boc-tert-butylglycine as the coupling partner. The material was purified by flash column chromatography using 90/10 dichloromethane/ethyl acetate to provide 12a in 73% yield. $^{13}C$ NMR (mixture of rotamers, CDCl$_3$) δ 26.20, 28.31, 29.07, 30.06, 34.94, 35.86, 37.06, 51.21, 52.16, 52.84, 57.78, 58.33, 65.95, 66.92, 72.97, 75.48, 79.45, 127.55, 127.66, 128.35, 138.45, 155.62, 165.06, 171.13, 172.54; HRMS (FAB) Calcd for $C_{27}H_{43}N_2O_7$: 507.3070 $(M+H)^+$. Found: 507.3077.

Step B:

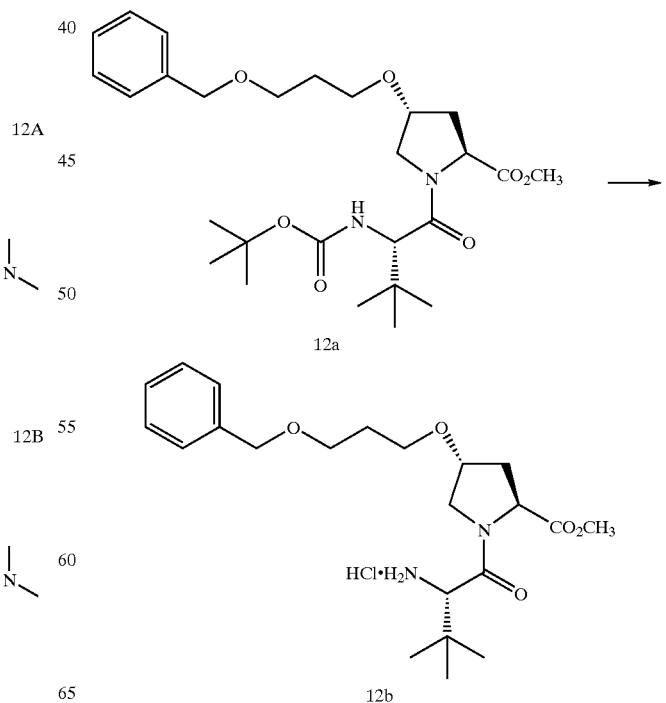

12a

12b

The desired compound 12b was prepared by the protocol described for Example 1, Step E. The material was carried forward to the next step.

Step C:

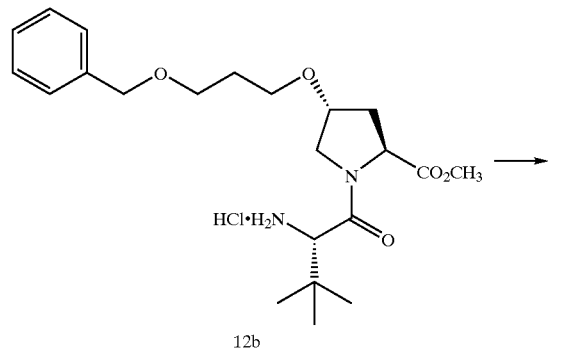

The desired product 12c was obtained by the procedure described for Example 1, Step F. The material was purified by flash column chromatography using 99/1 dichloromethane/methanol to yield 12c in 91%. $^{13}$C NMR (CDCl$_3$) δ 26.24, 29.93, 34.95, 35.96, 43.48, 52.18, 53.09, 57.06, 58.06, 66.10, 66.92, 72.93, 77.43, 114.59, 116.14, 120.87, 127.58, 127.64, 127.74, 128.37, 130.02, 135.95, 138.39, 156.90, 170.65, 171.06, 172.38; HRMS (FAB) Calcd for C$_{30}$H$_{41}$N$_2$O$_7$: 541.2914 (M+H)$^+$. Found: 541.2921.

Step D:

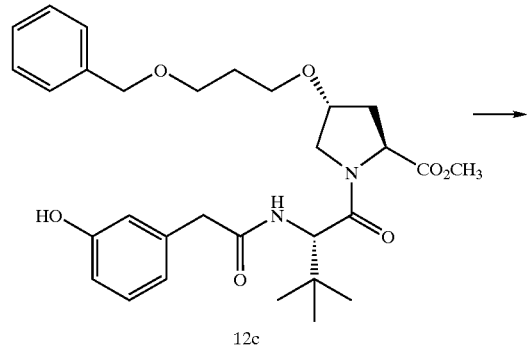

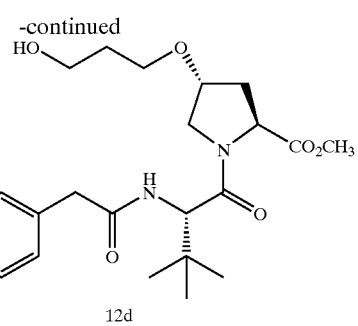

The desired product 12d was obtained by the procedure described for Example 1, Step G. The product obtained after filtering off the catalyst was pure enough for subsequent manipulations. $^{13}$C NMR (CDCl$_3$) δ 26.27, 32.09, 35.44, 35.67, 43.19, 52.21, 52.74, 57.60, 58.21, 58.75, 65.78, 77.74, 114.74, 116.02, 120.68, 130.07, 135.66, 157.11, 170.59, 172.05, 172.51; HRMS (FAB) Calcd for C$_{23}$H$_{35}$N$_2$O$_7$: 451.2444 (M+H)$^+$. Found: 451.2436.

Step E:

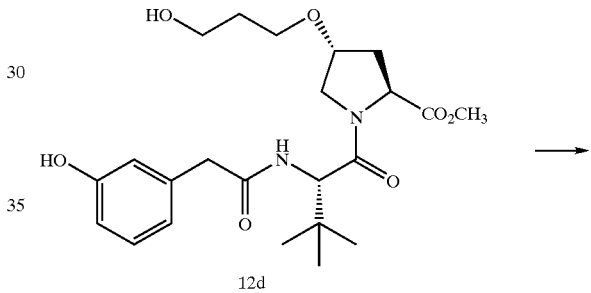

The desired product 12e was obtained by the procedure described for Example 1, Step H. The crude material was suspended in ethyl acetate/hexane (approx. 1/1) and the undissolved solid material was filtered off. Repeated this process once again, the filtrate was concentrated and applied on the column as a dichloromethane solution. The column was eluted with 75/25 hexane/acetone to yield 29% of 12e. HRMS (FAB) Calcd for C$_{23}$H$_{33}$N$_2$O$_6$: 433.2339 (M+H)$^+$. Found: 433.2339.

Step F:

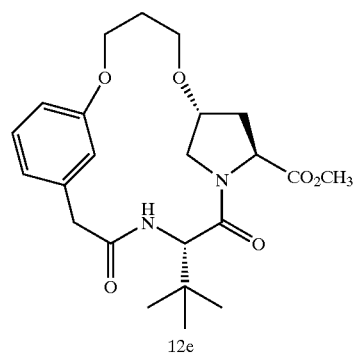 

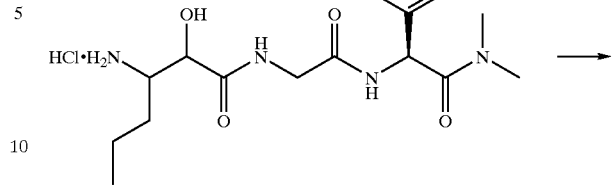

The expected product 12g was synthesized as described earlier for the Example 1, Step J. The material after work-up was of sufficient purity to be carried forward to the next step. HRMS (FAB) Calcd for $C_{40}H_{57}N_6O_9$: 765.4187 (M+H)$^+$. Found: 765.4175.

Step H:

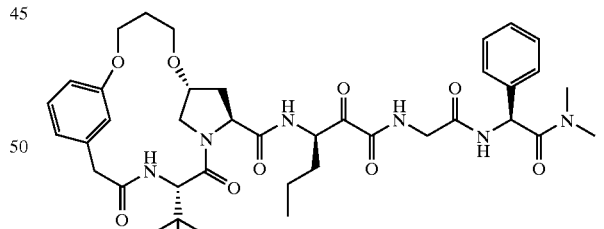

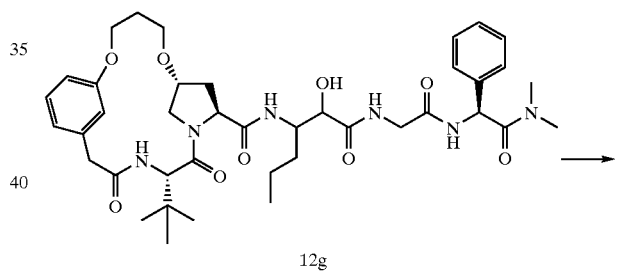

The advanced intermediate 12f was synthesized as described for Example 1, Step I, in quantitative yield; $^1$H NMR (DMSO-d$_6$) δ 0.96 (s, 9H), 1.66–1.70 (m, 1H), 1.75–1.82 (m, 2H), 2.43 (dd,1H), 3.32–3.36 (m, 2H), 3.48–3.52 (m, 1H), 3.55 (dd, 1H), 3.84 (app. d, 1H), 3.99 (app. d, 1H), 4.06–4.10 (m, 3H), 4.16 (dd, 1H), 4.69 (d, 1H), 6.70–6.72 (m, 3H), 7.15 (app. t, 1H), 8.42 (d, 1H), 12.43 (br. s, 1H), $^{13}$C NMR (DMSO-d$_6$) δ 26.25, 28.54, 33.31, 34.97, 41.22, 53.96, 56.11, 56.97, 63.36, 64.96, 76.84, 111.94, 115.25, 121.73, 129.13, 138.36, 158.27, 169.85, 170.15, 173.04; HRMS (FAB) Calcd for $C_{22}H_{31}N_2O_6$: 419.2182 (M+H)$^+$. Found: 419.2180.

Step G:

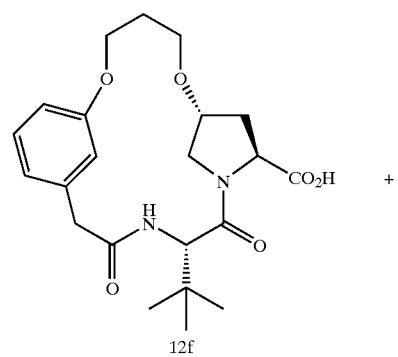 +

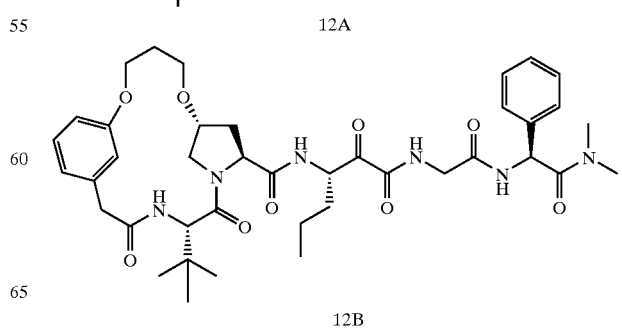

The desired products 12A and 12B were obtained by the oxidation protocol described previously for Example 1, Step K. Purification by flash column chromatography using 98/2 to 96/4 of dichloromethane/methanol afforded separate isomers 12A and 12B, and some mixture. Combined yield= 57% (for 2 steps). HRMS (FAB) Calcd for $C_{40}H_{55}N_6O_9$: 763.4031 (M+H)$^+$. Found: 763.4040 (12A), 763.4047 (12B).

Example 13

Preparation of Compounds of Formulas 13A and 13B

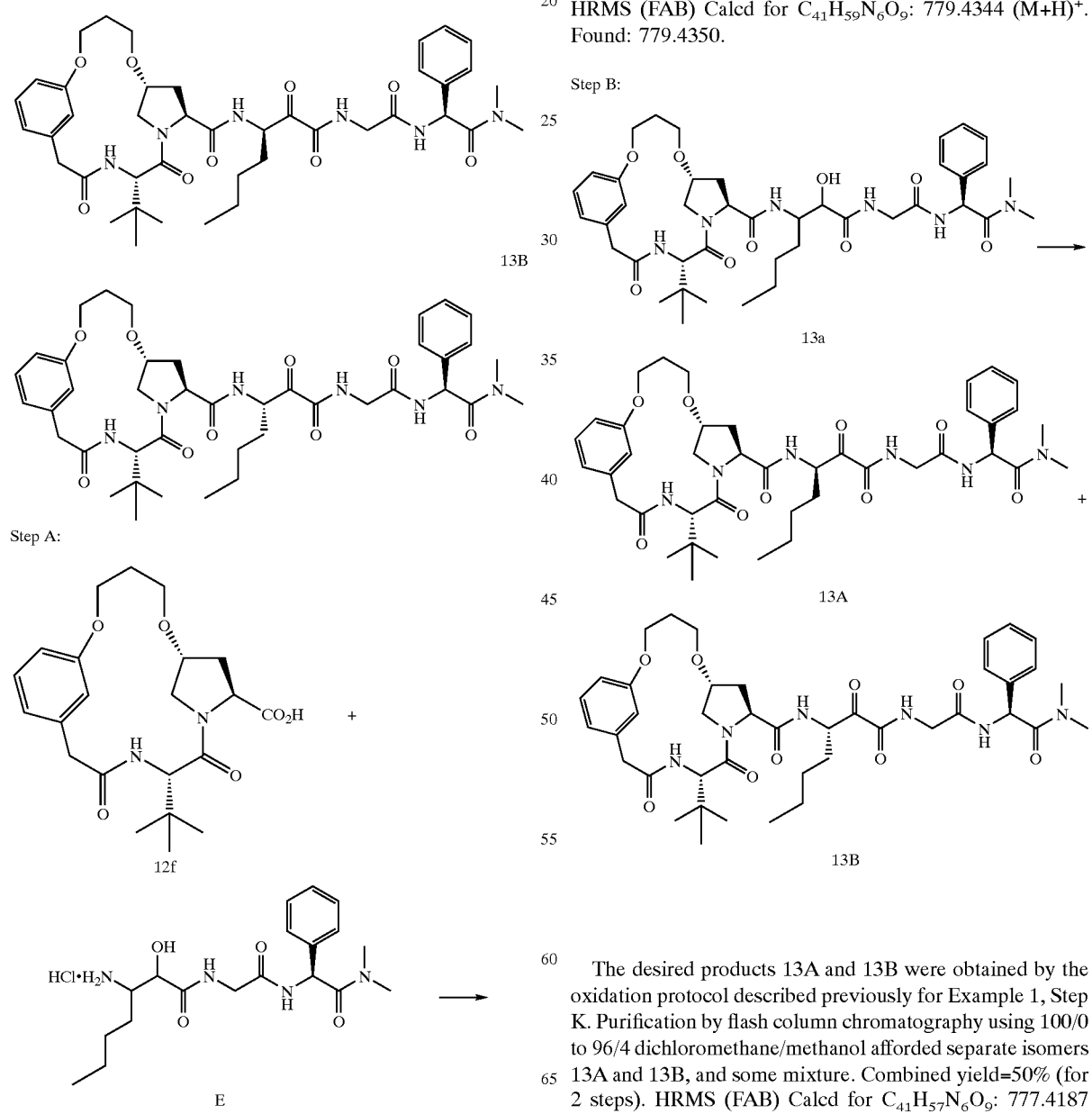

The expected product 13a was synthesized as described earlier for the Example 1, Step J. The material after work-up was of sufficient purity to be carried forward to the next step. HRMS (FAB) Calcd for $C_{41}H_{59}N_6O_9$: 779.4344 (M+H)$^+$. Found: 779.4350.

Step B:

The desired products 13A and 13B were obtained by the oxidation protocol described previously for Example 1, Step K. Purification by flash column chromatography using 100/0 to 96/4 dichloromethane/methanol afforded separate isomers 13A and 13B, and some mixture. Combined yield=50% (for 2 steps). HRMS (FAB) Calcd for $C_{41}H_{57}N_6O_9$: 777.4187 (M+H)$^+$. Found: 777.4177 (13A), 777.4185 (13B).

Example 14

Preparation of Compound 14

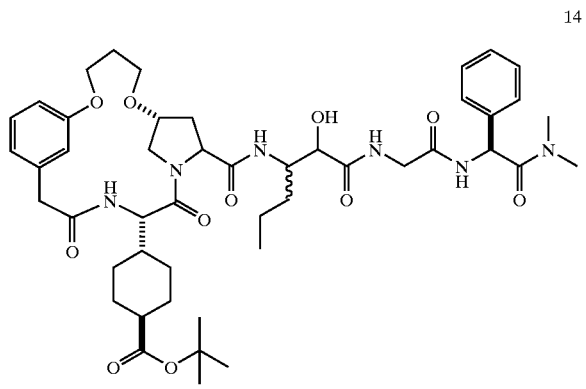

Step A:

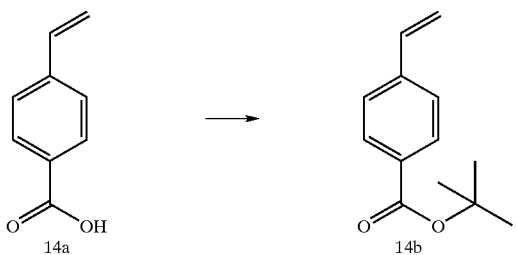

A solution of vinyl benzoic acid 14a (10 g, 68 mmol) in dry benzene (150 mL) was treated with ditert-butylacetal of DMF (69 g, 340 mmol, 5.0 equiv.) and heated at reflux for 4 h. The reaction mixture was concentrated in vacuo and diluted with aq. NaOH (1M, 300 mL). The reaction mixture was extracted in diethyl ether (3×100 mL). The combined organic layer was extracted with aq. NaOH (1M, 100 mL), $H_2O$ (2×100 mL), brine (1×100 mL) dried ($Na_2SO_4$), filtered and concentrated in vacuo. The residue was distilled under reduced pressure to yield 14b 9.2 g (66.2%) of a colorless oil.

Step B:

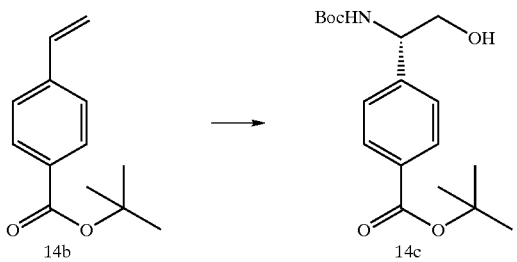

A solution of tert-butyl carbamate (5.96 g, 50.9 mmol) in 1-PrOH (68 mL) was treated with aq. NaOH (128 mL, 0.41 M) and tert-butyl hypochlorite (5.5g, 50.9 mmol). The reaction mixture was cooled to 0° C. and $(DHQ)_2Phal$ (780 mg, 1.00 mmol) in 1-PrOH (64 mL) was added. A solution of tert-butyl-4-vinylbenzoate 14b in 1-PrOH (119 mL) was added followed by $K_2OsO_4 \cdot H_2O$ (248 mg, 0.7 mmol) and the reaction mixture was stirred at 0° C. for 4–5 h. The reaction turns green and all the starting material disappears with a new product formed. The reaction mixture was concentrated in vacuo and the residue was diluted with $H_2O$ (300 mL) and extracted with EtOAc (3×100 mL). The combined organic layer was extracted with aq. HCl (200 mL), brine(100 mL) dried ($Na_2SO_4$) filtered conc. in vacuo and purified by chromatography ($SiO_2$, EtOAc/Hexanes 1:2) to yield 14c as a colorless solid (4.6 g, 82%). $^1H$ NMR ($CD_3OD$, δ) 7.90 (d, 2H, J=6.0 Hz), 7.40 (d, 2H, J=6.3 Hz), 7.22 (bd, 1H, J=5.7 Hz), 4.69 (bs, 1H), 3.71–3.62 (m, 2H) 1.58 (s, 9H), 1.39 (s, 9 Hz); $^{13}C$ NMR ($CD_3OD$, 75 MHz) 169.7, 160.5, 149.8, 134.5, 132.9, 130.4, 84.7, 82.9, 68.7, 60.7, 31.25, 30.9-MS (FAB) 675.2 ([2M+1]$^+$, 15), 338 ([M+1]$^+$, 15), 282 (65), 225 (50), 165 (100); HRMS calcd for $C_{18}H_{28}NO_5$ (M+1): 338.1887; found 338.1967.

Step C:

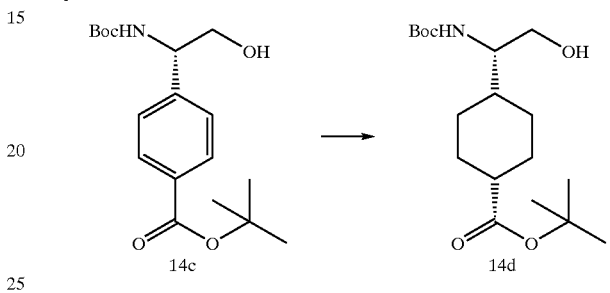

A solution of aromatic compound 14c (1.0 g, 2.96 mmol) in $CH_3OH$ (20 mL) was treated with Rh/C (10% w/w 100 mg) and hydrogenated (60 psi) for 2d. The reaction mixture was filtered through a plug of celite and the residue was concentrated in vacuo to yield 14d. The crude product was purified by chromatography ($SiO_2$, EtOAc/Hex 2:3) to yield the cis compound 14d (830 mg, 83%) which was further purified by crystallizing from hexanes. $^1H$ NMR ($CD_3OD$, δ) 6.31 (d, 1H, J=6.9 Hz), 3.58–3.49 (s, 2H), 3.40 (bd, 1H, J=4.8 Hz), 2.48–2.46 (m, 1H), 2.1–1.98(m, 2H), 1.61–1.2 (m, 7H), 1.45 (s, 9H), 1.42 (s, 9H), $^{13}C$ NMR ($CD_3OD$, 75 MHz) 176.2, 158.5, 81.2, 79.8, 63.1, 57.2, 41.8, 38.8, 28.8, 28.3, 27.7, 27.5, 25.9. MS (FAB) 687.2 ([2M+1]$^+$, 5), 344 ([M+1]$^+$, 20), 232 (40), 188(100),107 (13); HRMS calcd for $C_{18}H_{34}NO_5$ (M+1): 344.2437; Found: 344.2444. CHN calcd for $C_{18}H_{33}NO_5$ C=64.07%, H=8.07%,N=4.15% Found C=64.32%, H=8.21%, N=4.32%.

Step E:

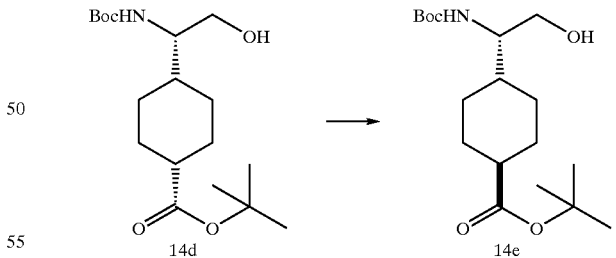

A solution of amino alcohol 14d (3.3 g, 11.08 mmol) in dry THF (200 mL) was cooled to −78° C. (dry ice/acetone, internal temperature −68° C.) was treated with LDA (44 mL, 2M soln in heptanes, 88 mmol, 8.0 equiv.). The reaction mixture was stirred at −78° C. for 2 h and quenched with $CH_3OH$ (20 mL). The reaction mixture was treated with aq. HCl (150 mL, 1 M) and extracted with ether (3×100 mL). The combined ether layer was extracted with brine (50 mL) dried ($MgSO_4$), concentrated in vacuo and purified by crystallization from boiling hexanes. The solid separating out from the mother liquor was predominantly cis stereo isomer, where concentration of the mother liquor gave the pure trans isomer. The above sequence was repeated twice more to obtain 2.7 g of the trans compound and 600 mg of cis/trans mixture. $^{13}$C NMR (CDCl3, 75 MHz) 175.3, 156.6, 79.8, 63.6, 57.0, 44.1, 38.3, 37.7, 28.9, 28.6, 28.4, 28.1, 26.6, 26.1. MS (electron spray) 344 (M$^+$, 50), 288 (50) 232 (90), 188 (100).

Step F:

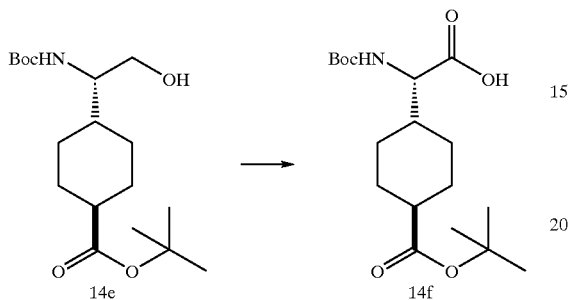

A solution of alcohol 14e (2.6 g, 7.6 mmol) in CH3CN (150 mL) and CCl$_4$ (150 mL) was treated with H$_2$O (22 mL), cooled to 0° C., treated with periodic acid (7.05 g, 30.92 mmol, 4.0 equiv.) and RuCl$_3$•3H$_2$O (60 mg, 0.3 mmol, 4 mol %). The reaction mixture was stirred at rt. for 3h, and concentrated in vacuo. The residue was diluted with water (150 mL) and extracted with EtOAc (3×100 mL). The combined organic layer was extracted with H$_2$O (100 mL) and with aq. NaOH (1M, 3×100 mL).The combined aq. layers were acidified with HCl (6M, pH ~1) and extracted with EtOAc (3×100 mL). The ethyl acetate layers were pooled, extracted with brine (100 mL) dried (Na$_2$SO$_4$) filtered concentrated in vacuo to yield acid 14f (1.8 g, 66%) used for further couplings without further purification. MS (FAB) 380.2 ([M+Na]$^+$, 30)358 ([M+1]$^+$, 5), 302 (20), 258(20), 246 (100), 202 (70), 200 (20)

Step G:

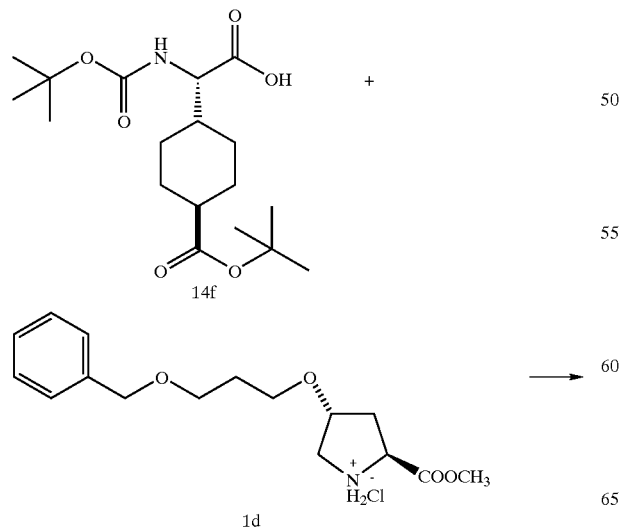

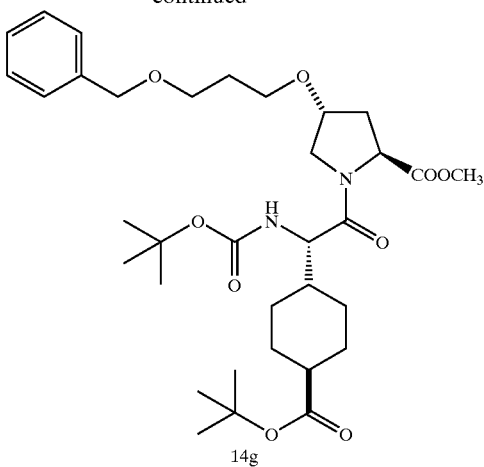

A solution of Boc-trans-4-tertbutylcarboxyl-cyclohexylgylcine 14f (1.9 g, 5.3 mmol) in CH$_2$Cl$_2$ (30 mL) was treated with proline compound 1d (1.92 g, 5.85 mmol, 1.1 equiv.) and cooled to 0° C. The reaction mixture was treated with Hünigs base (1.51 g, 11.7 mmol, 2.2 equiv., 2.15 mL) followed by the addition of BOP reagent (2.6 g, 5.85 mmol, 1.1 equiv.) The reaction mixture was stirred at rt. for 12 h diluted with aq. HCl (1M, 100 mL) and extracted with EtOAc (3×100 mL). The combined ethyl acetate layers were extracted with aq. NaOH (1M, 100 mL) brine (100 mL) dried (Na$_2$SO$_4$), filtered concentrated in vacuo and purified by chromatography (SiO$_2$, EtOAc/Hexanes 2:3) to yield 14g as colorless foam (1.8 g, 54%); $^1$H NMR (CD$_3$OD, δ, mixture of rotomers) 7.32–7.23 (m, 5H), 6.64 (d, 1H, J=9.0 Hz), 4.47–4.39 (m, 3H), 4.19–4.04 (m, 3H), 3.74 (s, 3H), 3.66–3.56 (m, 4 H), 2.55–2.10 (m, 2H), 1.99–1.00 (m, 12H), 1.42 (s, 9H), 1.40 (s, 9H). $^{13}$C NMR (CD$_3$OD, δ, mixture of rotomers), 175.6, 174.6, 172.4, 172.0, 156.4, 138.5, 128.1, 127.5, 127.4, 127.3, 79.8, 79.7, 79.0, 77.5, 72.5, 66.7, 65.4, 58.1, 56.6, 52.1, 51.3, 43.9, 40.4, 39.4, 38.6, 34.6, 29.8, 28.4, 27.9, 27.3, 26.1, 25.4, 24.5; MS (FAB) 633 ([M+1]+, 11), 533 (55), 477 (24), 428 (5), 294 (100), 234 (12) 156 (40), 128 (39); CHN Calcd. for C$_{34}$H$_{52}$NO$_9$ C 64.53% H 8.28% N 4.43%; Found C 64.41% H 8.00% N 4.19%.

Step H:

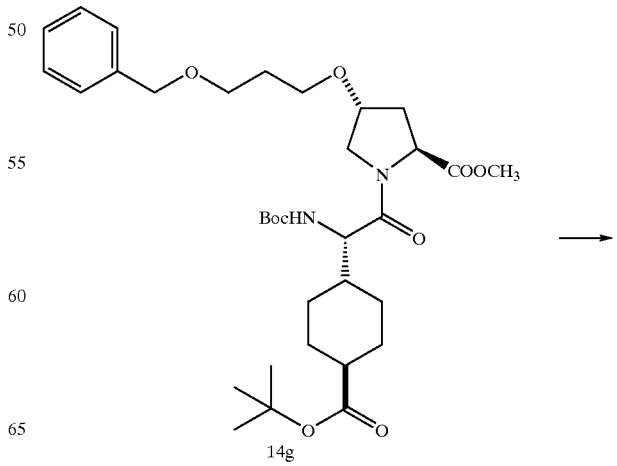

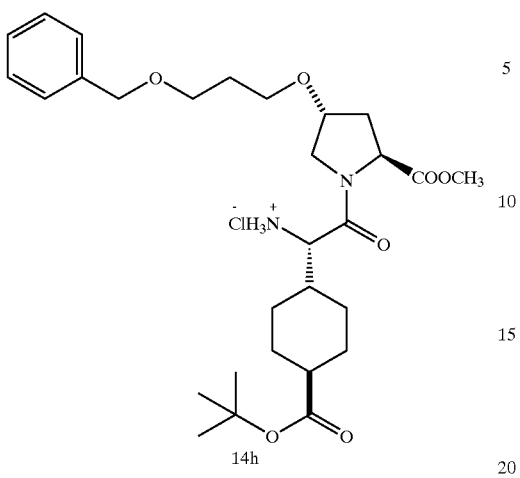

14h

A solution of Boc-trans-4-tertbutylcarboxycyclohexyl glycine 14g (1.8 g) in HCl (4M soln in dioxane, 60 mL) was stirred at rt. for 4–5 h. The reaction was followed by TLC (EtOAc/Hex 3:7) for the disappearance of starting material and the appearance of base line product. The reaction mixture was concentrated in vacuo and the residue was dried in the pump overnight. The solid 14h was used for couplings without further purification.

Step I

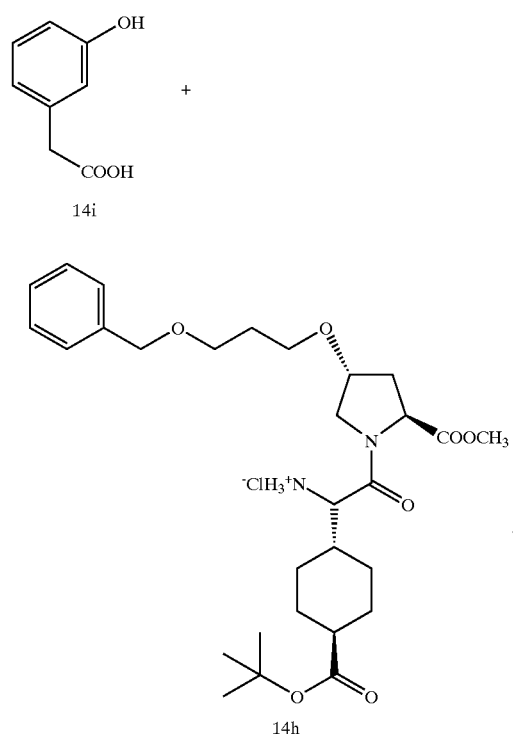

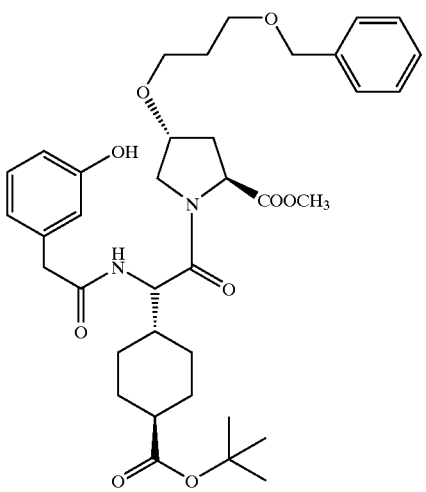

14j

A solution of 3-hydroxyphenylacetic acid 14i (501 mg, 3.29 mmol, 1.8 equiv.) and amine hydrochloride 14h (1.79 g, 2.99 mmol) in dry CH$_2$Cl$_2$ (30 mL) was treated with Hünigs base (850 mg, 6.59 mmol, 2.20 equiv., 1.2 mL) and BOP reagent (1.5 g, 3.29 mmol, 1.1 equiv.) at 0° C. and stirred at rt. for 24 h. The reaction mixture was concentrated in vacuo and diluted with aq. HCl (1 M, 250 mL). The aq. layer was extracted with EtOAc (3×100 mL). The combined organic layers were extracted with aq. NaOH (1×100 mL), brine (1×100 mL) dried (Na$_2$SO$_4$) filtered, concentrated in vacuo and purified by chromatography (EtOAc/Hexanes 1:1) to yield 14j as a colorless solid (710 mg, 36%).

Step J

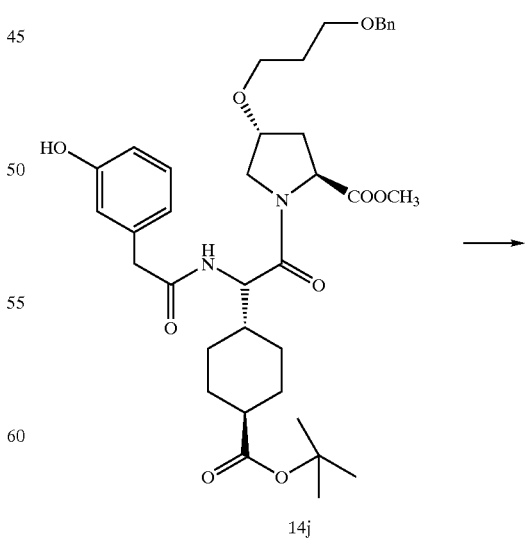

14j

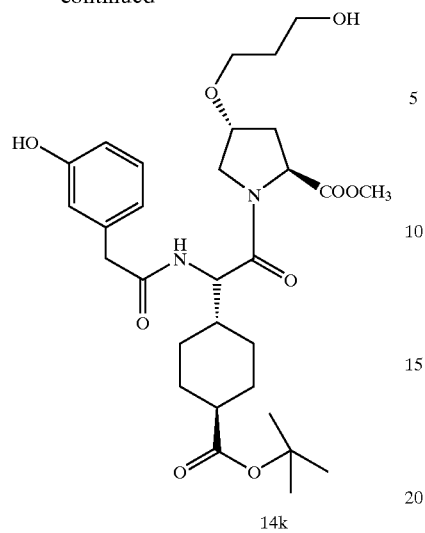

14k

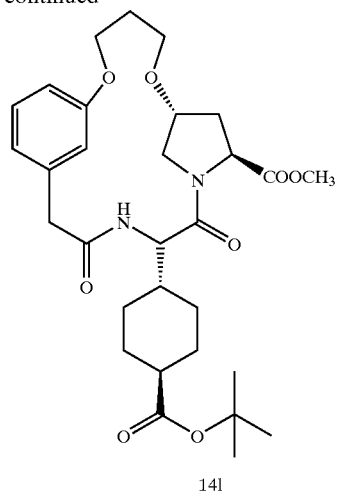

14l

A solution of the coupled compound 14j (710 mg, 1.1 mmol) in CH3OH (50 mL) was treated with Pearlmans catalyst (10% Pd(OH)$_2$/C) and hydrogenated (H$_2$, 40 psi) for 12 h. The Pd/C was filtered off through a plug of celite and filtrate was concentrate and used for the next cyclization without further purification R$_f$ 0.12 (acetone/Hexanes 3:7); $^1$H NMR (CD$_3$OD, δ, mixture of rotomers) 8.25 (bs, 1H), 7.01 (bt, 1H, J=7.2 Hz), 6.72 (bs, 1H), 6.65 (d, 2H, J=7.8 Hz), 4.79–4.70 (bs, 3H), 4.55–4.41 (bs, 2H), 4.20–4.12 (bs, 2H), 3.77 (s, 3H), 3.66–3.44 (bm, 6H) 2.43–1.04 (bm, 14H) 1.40 (s, 9H); $^{13}$C NMR (CD$_3$OD, δ, mixture of rotomers): 175.5, 174.6, 172.6, 172.4, 171.3, 161.1, 157.3, 136.8, 136.7, 129.3, 120.0, 115.7, 113.6, 100.0, 94.8, 79.9, 79.8, 77.5, 65.1, 58.5, 58.2, 55.6, 55.5, 54.3, 5.2, 51.5, 43.9, 42.1, 39.4, 35.0, 32.4, 28.6, 28.4, 27.5, 27.2, 27.1, 26.1, 25.2, 25.0; MS (FAB): 577 ([M+1]$^+$, 70), 521(10), 443 (10), 387 (10), 374 (10), 318 (15), 290 (100), 248 (30); HRMS calcd. for C$_{30}$H$_{45}$N$_2$O$_9$ (M+H)$^+$: 577.3125; Found 577.3133.

Step K:

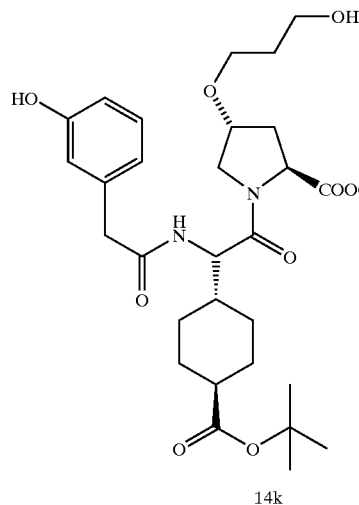

14k

A solution of alcohol 14k (600 mg, 1.05 mmol) and ADDP (787 mg, 3.12 mmol, 3.0 equiv.) in CH$_2$Cl$_2$ (30 mL) was treated with Ph$_3$P (818 mg, 3.12 mmol, 3.0 equiv.) under positive pressure of dry N$_2$ at 0° C. The reaction mixture was stirred at rt. for 24 h, concentrated in vacuo and the residue was purified by chromatography (SiO$_2$, acetone/Hexanes 2:3) to yield a colorless solid 14l (120 mg, 22%) of cyclic product; R$_f$ 0.73 (acetone/Hexanes 1:1); $^1$H NMR (CD$_3$OD, δ) 7.13 (t, 1H J=7.8 Hz), 6.76 (s, 1H), 6.71 (t, 2H, J=8.1 Hz), 4.58 (d, 1H, J=9.9 Hz), 4.37 (dd, 1H, J=7.8, 2.7 Hz), 4.23–4.11 (m, 4H), 3.74–3.61 (m, 2H), 3.66 (s, 3H), 3.59–3.40 (m, 2H), 2.54–2.41 (m, 1H), 2.19–2.10 (m, 1H), 1.98–1.42 (m, 10H), 1.43 (s, 9H); $^{13}$C NMR (CD$_3$OD, δ) 175.6, 172.4, 172.1, 170.8, 159.0, 137.0, 129.1, 121.7, 115.7, 112.2, 94.8, 79.8, 77.4, 65.2, 64.0, 57.6, 55.2, 53.8, 51.3, 44.0, 41.5, 39.1, 33.3, 28.7, 28.1, 26.9; MS (electron spray) 559 ([M+1]$^+$, 100) 327 (10), 189 (20); HRMS calcd. for C$_{30}$H$_{43}$N$_2$O$_8$ (M+1)$^+$: 559.3019; Found: 559.3025; CHN calcd for C$_{30}$H$_{42}$N$_2$O$_8$·0.5H$_2$O C=63.47%, H=7.63%, N=4.93%; Found C=63.57%, H=7.46%, N=4.93%.

Step L

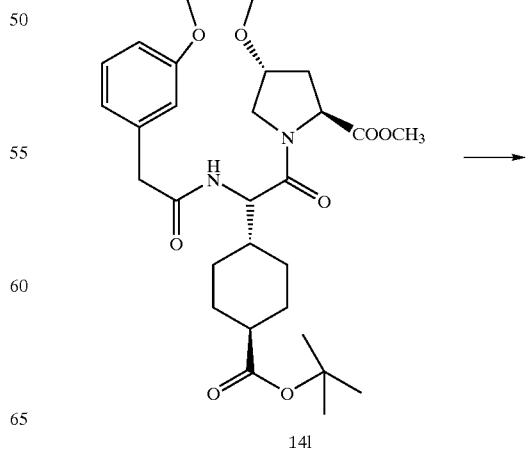

14l

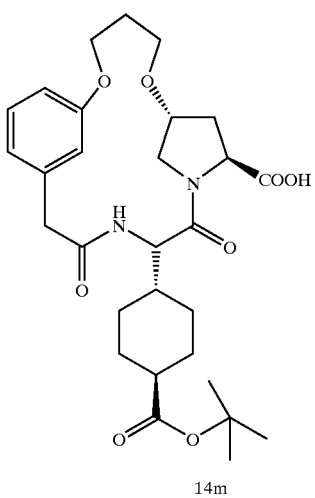

14m

A solution of methyl ester 14l (120 mg, 0.22 mmol) in THF (5.0 mL) and H$_2$O (1.0 mL) was treated with LiOH (20 mg, 0.5 mmol, 2.0 equiv.). The reaction mixture was stirred at rt. for 3 h and CH$_3$OH (1.0 mL) was added and stirred for an additional 1 h. The reaction mixture was stirred with HCl (4.0 M in Dioxane, 1 mL) and concentrated in vacuo and the water was lyophilized to yield a colorless solid 14m which was used for next coupling.

Step M

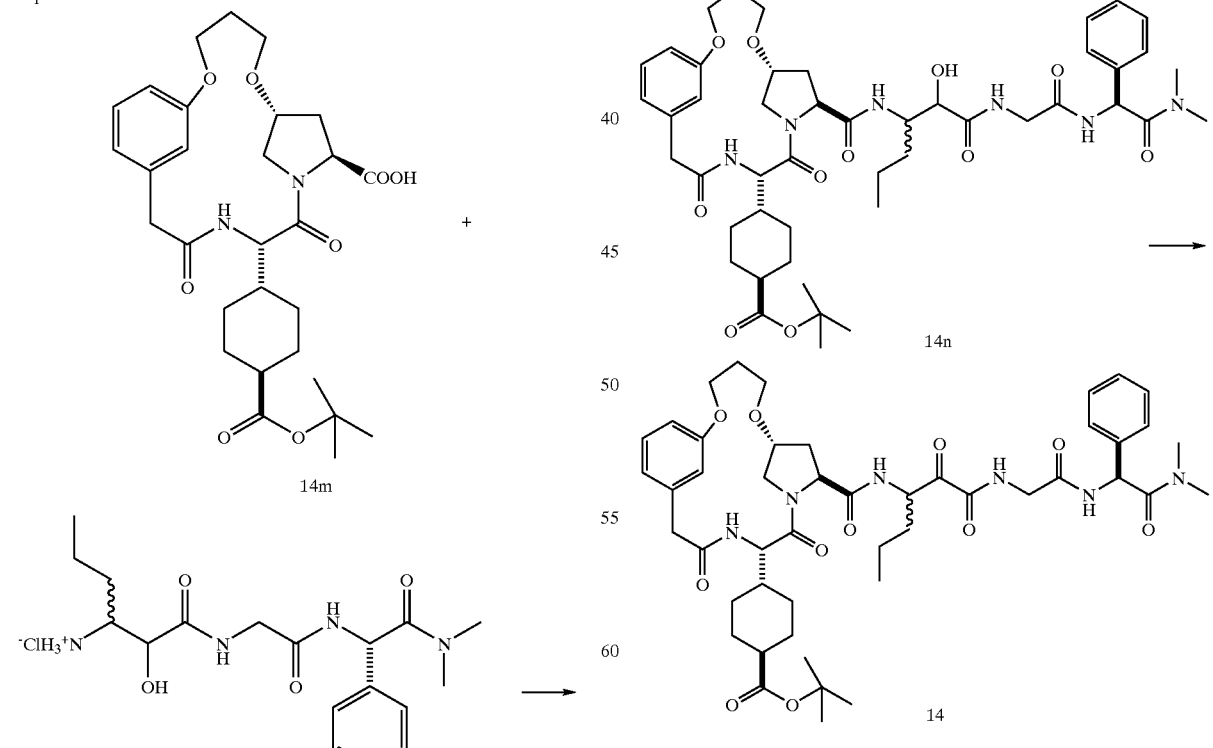

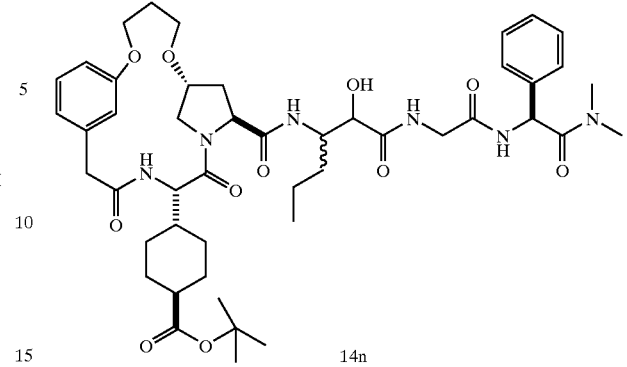

A solution of carboxylic acid 14m (110 mg, 0.21 mmol) in DMF (3.0 mL) and CH$_2$Cl$_2$ (5.0 mL) was treated with Hünigs base (109 mg, 0.84 mmol, 4.0 equiv. 155.0 µL) and HOOBt (52 mg, 0.315 mmol, 1.5 equiv.). The reaction mixture was cooled to 0° C. and treated with EDCl (61 mg, 0.31 mmol, 1.5 equiv.) The reaction mixture was stirred at 0° C. and treated with amine hydrochloride A after 30 min. The reaction mixture was stirred at rt. for 24 h and concentrated in vacuo to remove DMF and CH$_2$Cl$_2$. The residue was diluted with aq. HCl (100 mL) and extracted with CH$_2$Cl$_2$ (3×75 mL) The combined organic layers were extracted with aq. NaOH (1M, 3×50 mL), brine (100 mL) and concentrated in vacuo. The residue 14n (79 mg) was oxidized without further purification.

Step N

A solution of alcohol 14n (79 mg, 88 µmol) in CH$_2$Cl$_2$ (4.0 mL) was treated with Dess-Martin reagent (110 mg, 0.25 mmol, 2.5 equiv.) The reaction mixture was stirred at rt. for 3 h and the mixture was concentrated in vacuo. The residue was purified by chromatography (SiO$_2$, acetone/hexanes 1:1) to yield oxidized product 14 (29 mg, 38%) as a colorless solid; MS (FAB) 889 [(M+1)$^+$, 100), 844 (20), 833 (60), 788 (30), 760 (10), 655 (10), 527 (20); HRMS calcd. for C$_{47}$H$_{65}$N$_6$O$_{11}$; 889.471 1; Found: 889.4732.

Example 15

Preparation of Compound 15

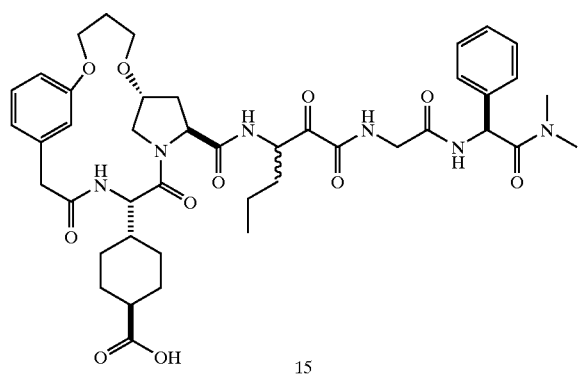

Step A

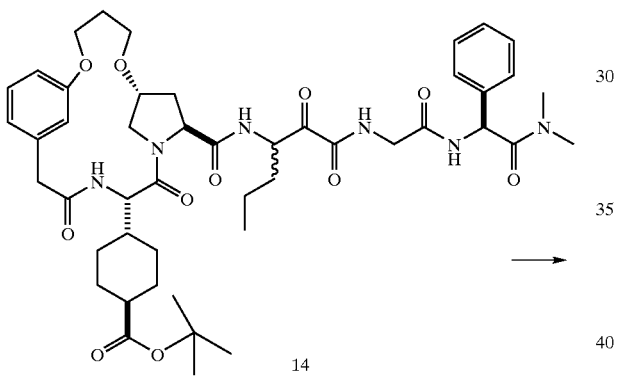

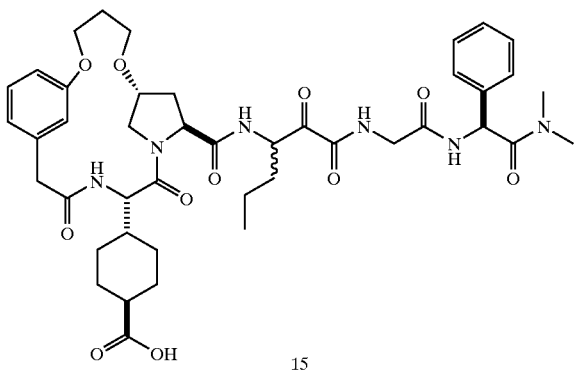

A solution of tert-butyl ester 14 (20.0 mg, 22.0 μmol) was treated with TFA/CH$_2$Cl$_2$ (1:1, 4 mL) and stirred at rt. for 4 h. The disappearance of the ester to the base line was followed by TLC (CH$_3$OH/CH$_2$Cl$_2$ 1:24). After the deprotection was complete the reaction mixture was concentrated in vacuo and the residue was repeatedly treated with CH$_2$Cl$_2$/Hexanes and concentrated to yield a white solid 15 (19 mg, 100%); MS (Electron spray) 833 ([M+1]$_+$, 60), 661 (10), 530 (40), 391 (75), 279 (100).

Example 16

Preparation of Compound 16

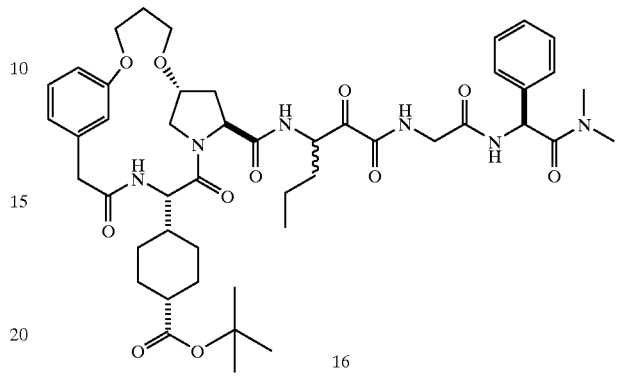

Step A

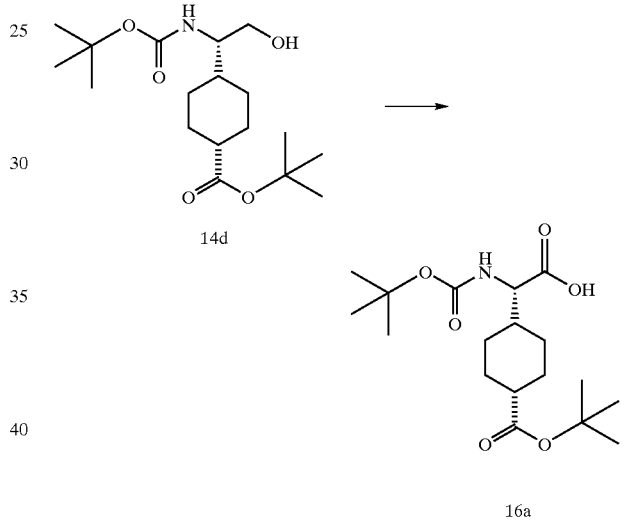

The desired compound 16a was prepared from 14d in 70% yield according to the procedure of Example 14, Step F. It was used for the couplings without further purification's; MS (FAB): 380.2 ([M+Na]$^+$, 30) 358 ([M+1]$^+$5), 302 (20), 258(20), 246 (100), 202 (70), 200 (20); HRMS calcd. for C$_{18}$H$_{32}$NO$_6$ (M+1)$^+$: 358.2230; Found: 358.2237.

Step B

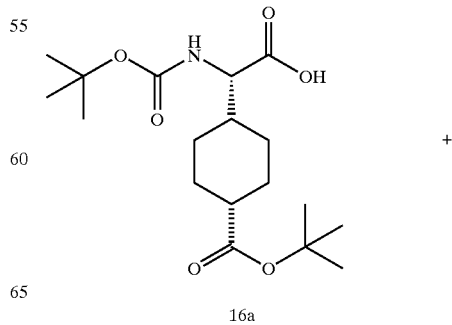

+

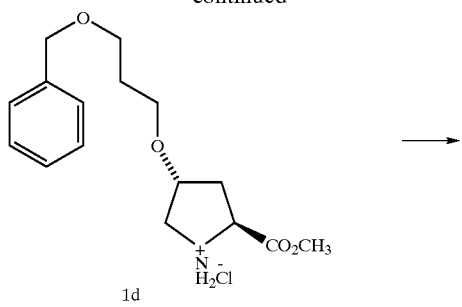

1d

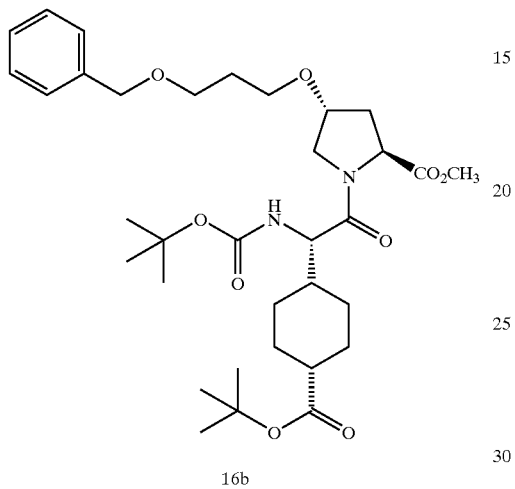

16b

The desired compound 16b was prepared from 16a in 41% yield according to the procedure of Example 14, Step G; $[\alpha]_D$ −52.7 (c 0.3 CHCl$_3$, 25); $^1$H NMR (CDCl$_3$, δ) 7.35–7.21 (m, 5H), 6.63 (d, 1H, J=9.3 Hz), 4.46 (d, 2H, J=4.3 Hz), 4.41 (t, 1H, J=9.3 Hz), 4.38–4.07 (m, 3H), 3.68 (s, 3H), 3.66–3.43 (m, 5H), 2.45 (p, 1H, J=4.2 Hz), 2.32 (dd, 1H, J=7.8, 5.7 Hz), 2.02–1.90 (m, 3H), 1.90–1.56 (m, 3H), 1.56–1.24 (m, 24H); $^{13}$C NMR (CD$_3$OD, δ)174.7, 172.4, 172.0, 156.4, 138.4, 128.0, 127.5, 127.4, 79.8, 79.0, 77.5, 72.5, 66.6, 65.3, 58.0, 55.3, 52.1, 51.3, 40.4, 38.6, 34.7, 29.7, 27.4, 27.03, 26.1, 24.5. MS (FAB) 633.2 [(M+1)$^+$, 100]; HRMS calcd for C$_{34}$H$_{53}$N$_2$O$_9$ (M+1)$^+$: 633.3751; Found 633.3759.

Step C

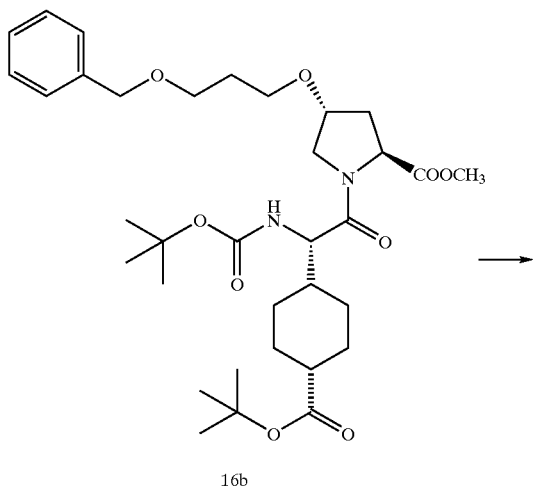

16b

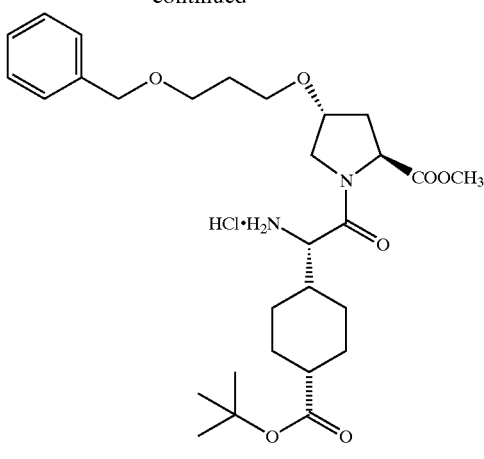

16c

The desired compound 16c was prepared from 16b according to the procedure of Example 14, Step H. The product was used without further purification.

Step D

16c

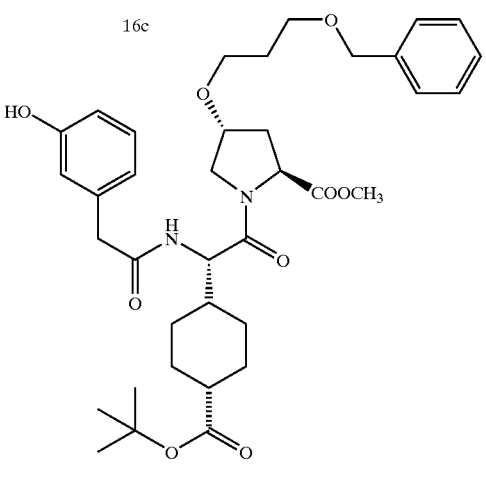

16d

The desired compound 16d was prepared from 16c in 41% yield according to the procedure of Example 14, Step I. $^1$H NMR (CHCl$_3$, δ) 7.34–7.26 (m, 5H), 7.12 (t, 1H, J=7.5 Hz), 6.72–6.67 (m, 3H), 4.76–4.64 (m, 1H), 4.47 (s, 2H), 4.51–4.42 (m, 1H), 4.11–4.02 (m, 2H), 3.68 (s, 3H), 3.70–3.65 (m, 1H), 3.55–3.43 (m, 6H), 2.54–2.42 (m, 1H), 2.28–2.39 (m, 1H), 2.1–1.9 (m, 3H), 1.86–1.64 (4), 1.50–1.38 (m, 14H); $^{13}$C NMR (CDCl$^3$, δ) 175.0, 172.4, 171.5, 171.1, 157.1, 138.5, 136.0, 130.1, 128.5, 127.9, 127.7, 121.0, 116.0, 114.8, 80.5, 77.6, 73.0, 66.9, 66.2, 58.2, 54.3, 52.5, 52.3, 43.4, 39.4, 39.9, 34.9, 30.0, 28.2, 26.8, 26.6, 26.0, 24.0; MS (FAB) 689 [(M+Na)$^+$, 35), 667 [(M+H)$^+$, 23), 633 (5), 294 (100), 204 (39), 156 (63).

Step E:

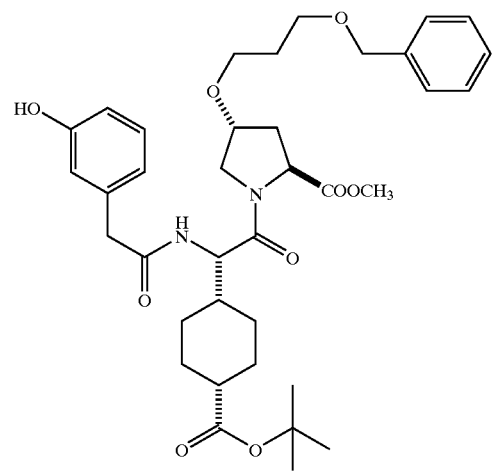

16d

The desired compound 16e was prepared from 16d according to the procedure of Example 14, Step J. The product was used without further purification.

Step F

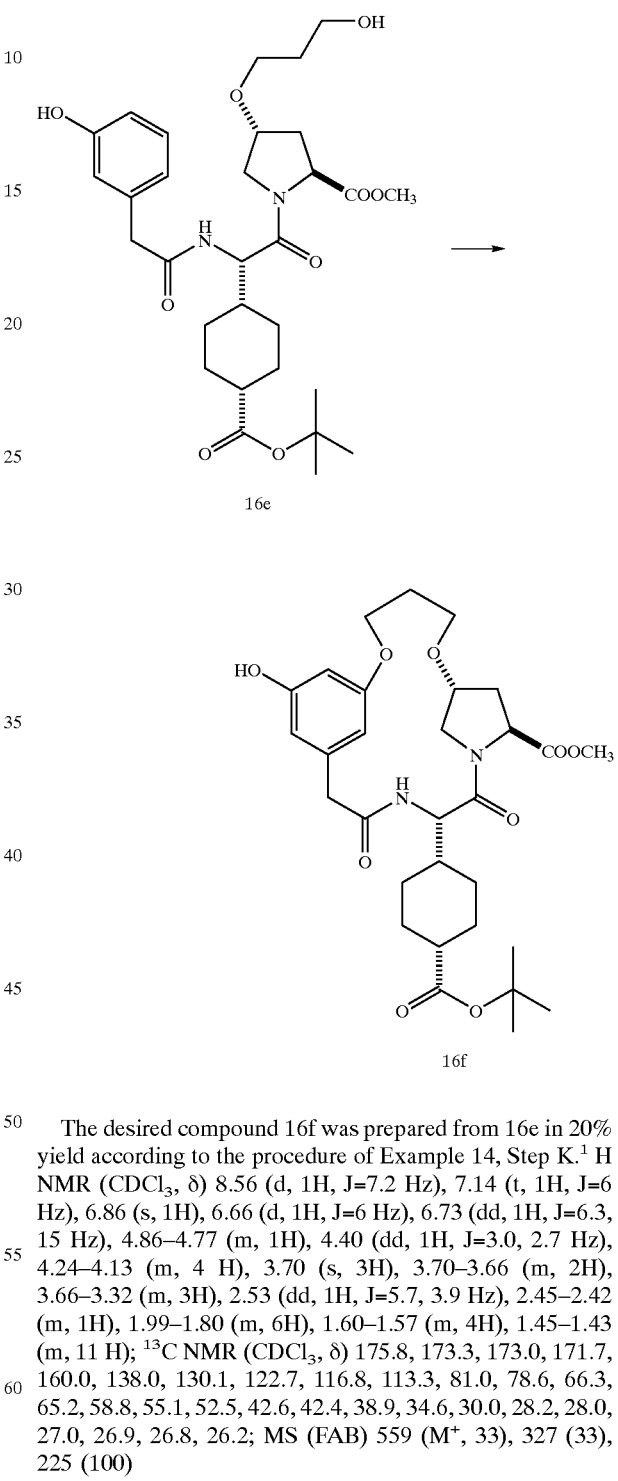

16e

16f

The desired compound 16f was prepared from 16e in 20% yield according to the procedure of Example 14, Step K. $^1$H NMR (CDCl$_3$, δ) 8.56 (d, 1H, J=7.2 Hz), 7.14 (t, 1H, J=6 Hz), 6.86 (s, 1H), 6.66 (d, 1H, J=6 Hz), 6.73 (dd, 1H, J=6.3, 15 Hz), 4.86–4.77 (m, 1H), 4.40 (dd, 1H, J=3.0, 2.7 Hz), 4.24–4.13 (m, 4 H), 3.70 (s, 3H), 3.70–3.66 (m, 2H), 3.66–3.32 (m, 3H), 2.53 (dd, 1H, J=5.7, 3.9 Hz), 2.45–2.42 (m, 1H), 1.99–1.80 (m, 6H), 1.60–1.57 (m, 4H), 1.45–1.43 (m, 11 H); $^{13}$C NMR (CDCl$_3$, δ) 175.8, 173.3, 173.0, 171.7, 160.0, 138.0, 130.1, 122.7, 116.8, 113.3, 81.0, 78.6, 66.3, 65.2, 58.8, 55.1, 52.5, 42.6, 42.4, 38.9, 34.6, 30.0, 28.2, 28.0, 27.0, 26.9, 26.8, 26.2; MS (FAB) 559 (M$^+$, 33), 327 (33), 225 (100)

Step G:

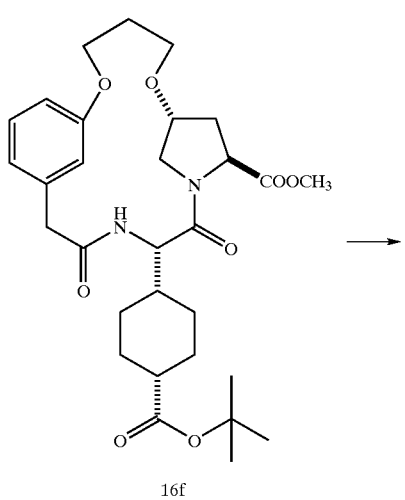
16f

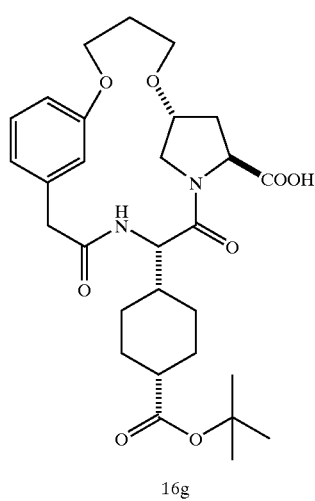
16g

The desired compound 16g was prepared from 16f according to the procedure of Example 14, Step H. The product was used without further purification.

Step H:

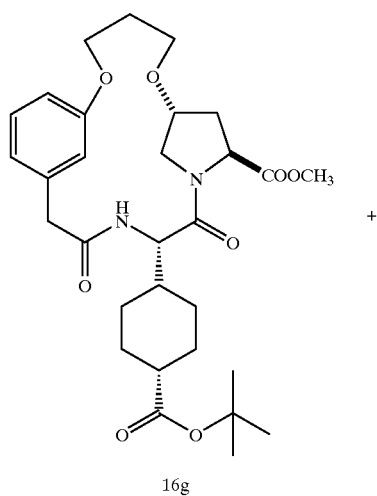
16g

+

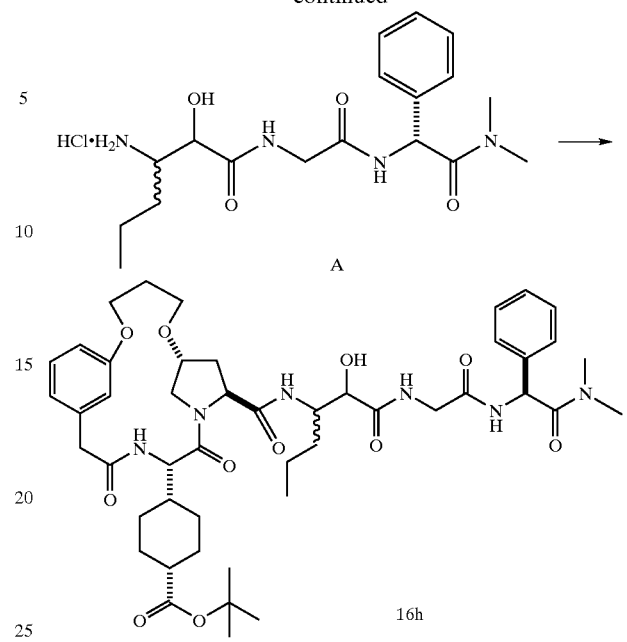
A

16h

The desired compound 16h was prepared from 16g and A according to the procedure of Example 14, Step L. The product was used without further purification.

Step I

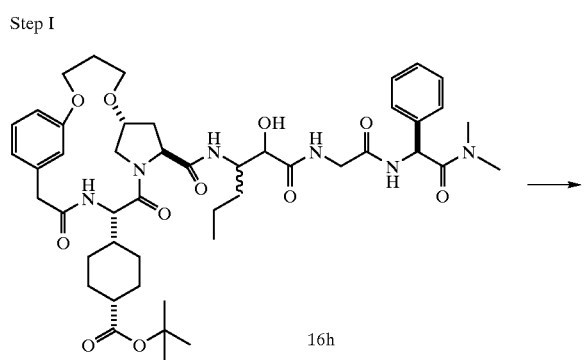
16h

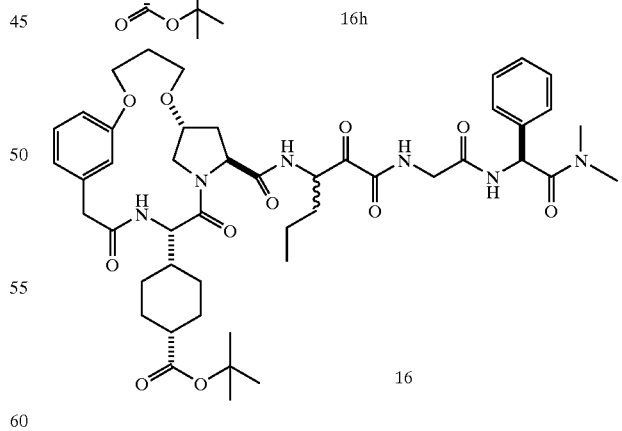
16

The desired compound 16 was prepared as a colorless solid from 16h in 40% yield according to the procedure of Example 14, Step N. MS (electron spray) 889 [(M+1)$^+$, 85), 637 (20), 530 (75), 265 (100); HRMS calcd. for $C_{47}H_{65}N_6O_{11}$: 889.4711; Found 889.4699.

Example 17

Preparation Of Compound 17

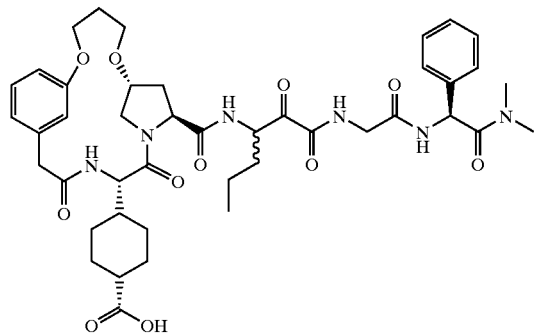

Step A:

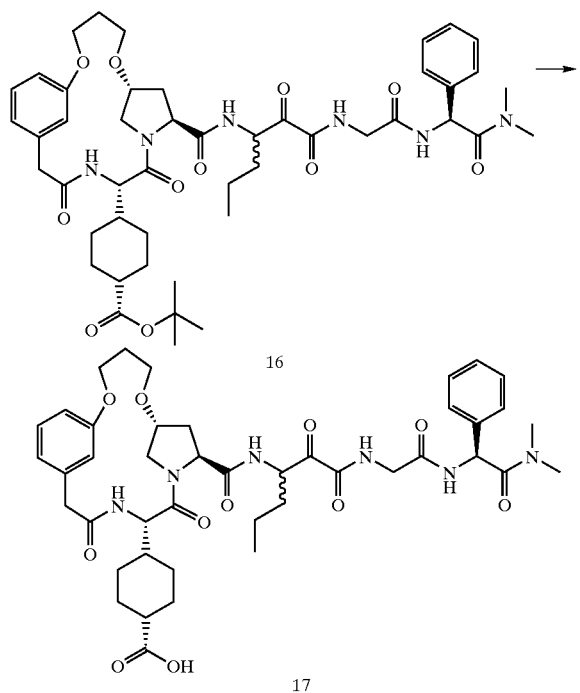

The desired compound 17 was prepared from 16 quantitatively according to the procedure of Example 15, Step A. MS (FAB) 833 [(M+1)+, 100], 788 (10), 723 (5), 308 (100).

Example 18

Preparation of Compound of Formula 18

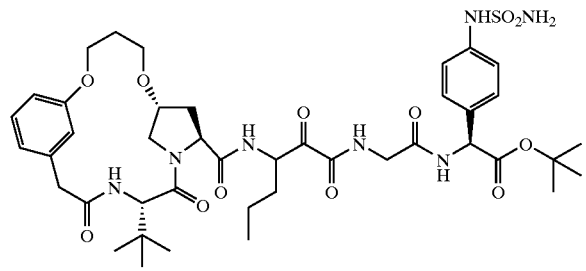

Step A:

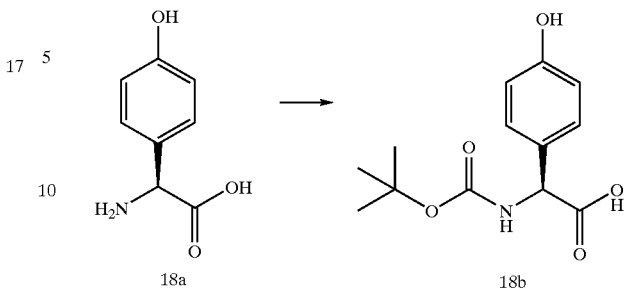

To a cold (0° C.) slurry of 18a (15.0 g, 90 mmol) in dioxane (100 mL), water (100 mL), and saturated sodium bicarbonate (100 mL) was added a solution of tert-butoxycarbonyl anhydride (7.2 g, 33 mmol) in dioxane (100 mL). The reaction mixture was slowly warmed to ambient temperature over 6 hr. The reaction mixture was concentrated in vacuo. The residue was diluted with water and extracted with diethylether (2×150 mL). The ether layer was discarded. The aqueous layer was acidified slowly with solid citric acid (pH~4) and extracted with ethyl acetate (3×150 mL). The organic layer was dried ($Na_2SO_4$) and concentrated in vacuo to afford 18b (14.6 g, 61% yield) as a white foam.

Step B:

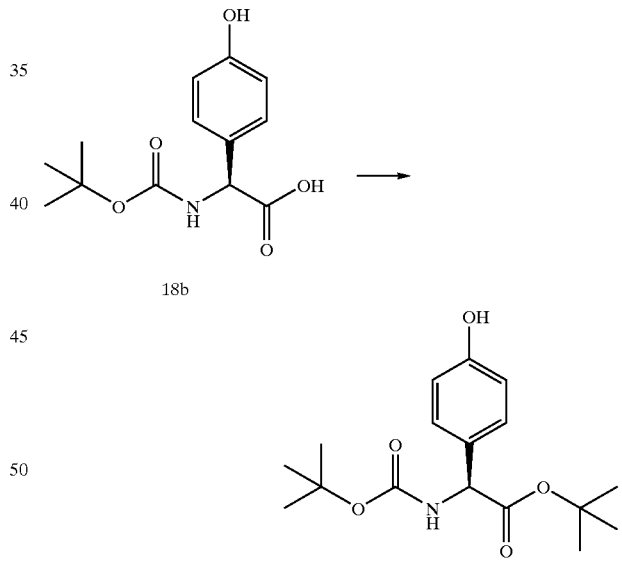

To a 80° C. solution of 18b (14.6 g, 54.68 mmol) in toluene (230 mL) was added DMF-di-tert-butyl acetal (53 mL, 218.72 mmol) dropwise over 2 hrs. The reaction mixture was maintained at the same temperature for 1 hr after the addition was complete. It was then cooled to ambient temperature and concentrated. The residue was purified by flash column chromatography using 96/4 to 90/10 dichloromethane/ethyl acetate to provide the required compound 18c (7.53 g, 43% yield). HRMS (FAB) Calcd for $C_{17}H_{26}NO_5$: 324.1811 (M+H)+. Found: 324.1807.

Step C:

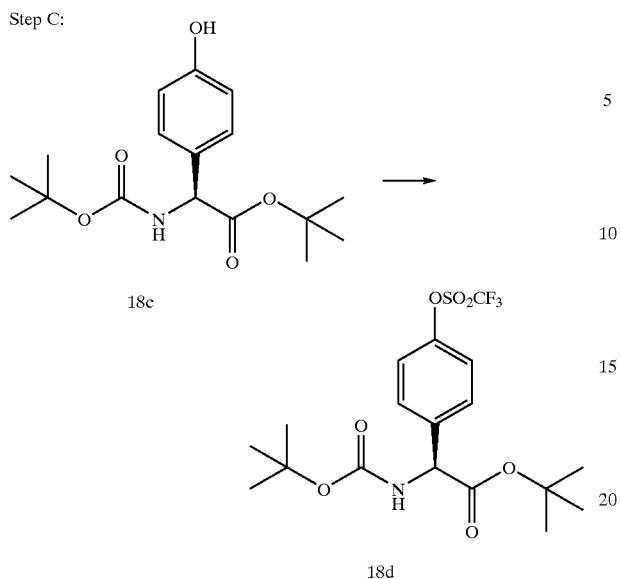

To a cold (0° C.) solution of 18c (7.5 g, 23.22 mmol) in dichloromethane (100 mL) was added triethylamine (7.12 mL, 51.08 mmol) followed by triflic anhydride (4.30 mL, 25.54 mmol) dropwise. The reaction mixture was slowly warmed to ambient temperature over 4 hrs. It was quenched with saturated bicarbonate solution and extracted into dichloromethane. The combined organic layer was washed with saturated bicarbonate and brine, dried ($Na_2SO_4$) and concentrated. The brown residue was purified by flash column chromatography using dichloromethane to provide 7.74 g of 18d (73% yield).

Step D:

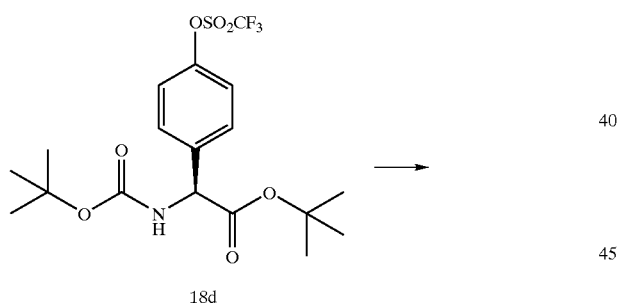

1e;.5qTo an oven dried flask was added THF (75 mL, previously deoxygenated by bubbling argon), palladium acetate (74 mg, 0.33 mmol), R-(+)-BINAP (311 mg, 0.495 mmol), and cesium carbonate (5.38 g, 16.5 mmol) under argon atmosphere. To this mixture was added 18d (5.0 g, 11 mmol) followed by diphenylketimine (2.77 mL, 16.5 mmol). The flask was flushed with argon and heated to reflux for 12 hrs (overnight). Cooled the reaction mixture to ambient temperature and diluted with ether (500 mL). The organic layer is washed with saturated ammonium chloride solution (2×300 mL), dried ($Na_2SO_4$) and concentrated. Purification by flash chromatography using 100/0 to 90/10 dichloromethane/ethyl acetate provided the required product 18e (3.58 g) in 67% yield.

Step E:

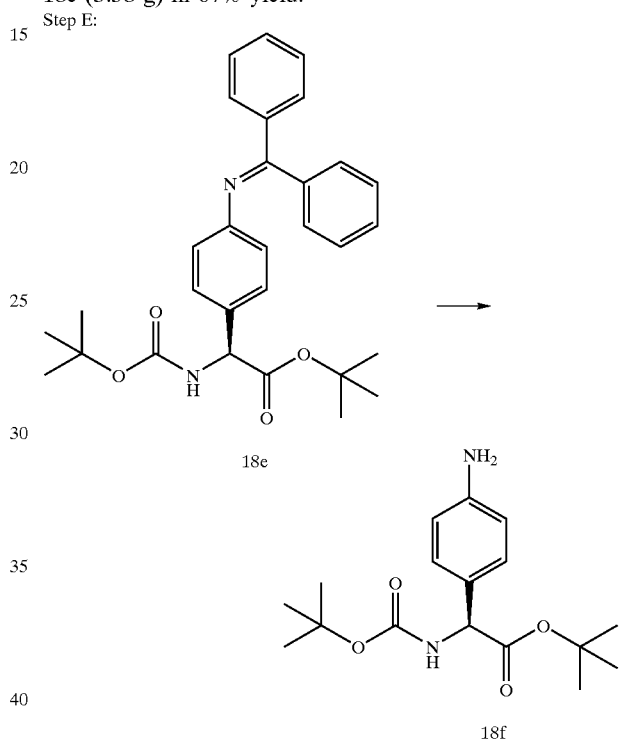

To a solution of 18e (3.0 g, 6.17 mmol) in methanol (62 mL) was added sodium acetate (1.218 g, 14.8 mmol), and hydroxylamine hydrochloride (0.774 g, 1 1.1 1 mmol). The reaction mixture was stirred at ambient temperature for 3 hrs. The reaction mixture was concentrated, diluted with dichloromethane and washed with 0. 1 N NaOH solution. The organic layer was dried ($Na_2SO_4$) and concentrated. Purification by flash column chromatography using 95/5 to 92/8 dichloromethane/ethyl acetate afforded 18f (1.31 g) in 66% yield.

Step F:

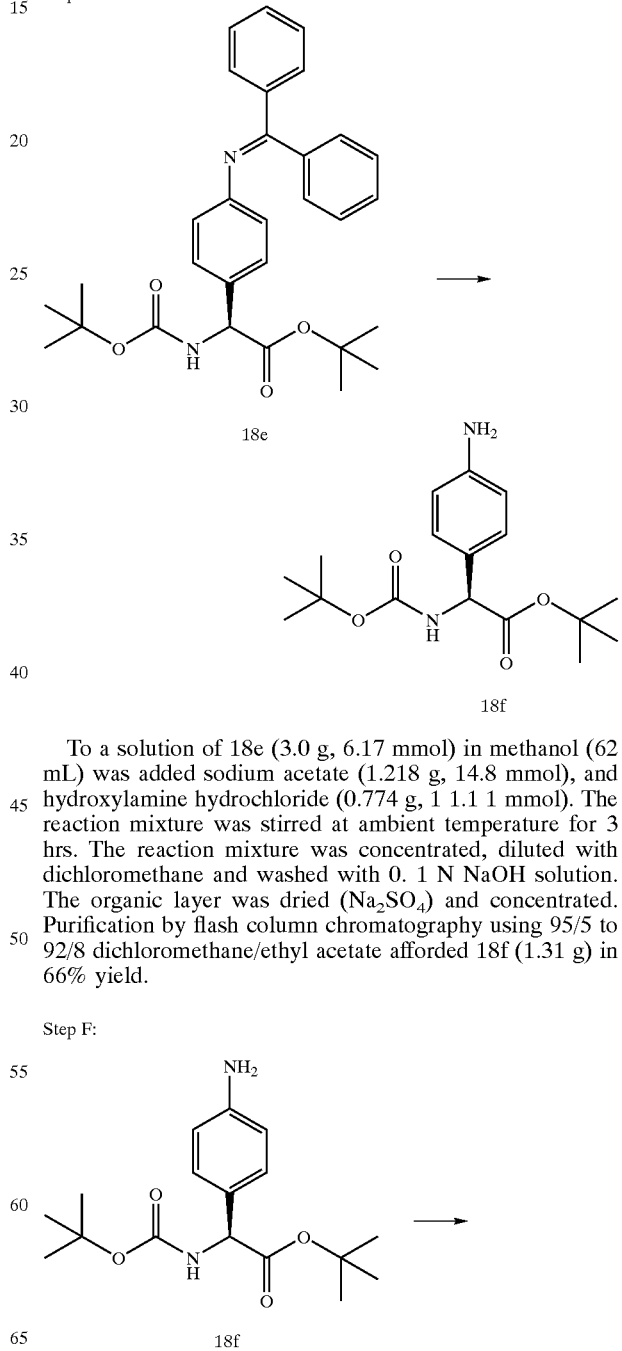

Step H:

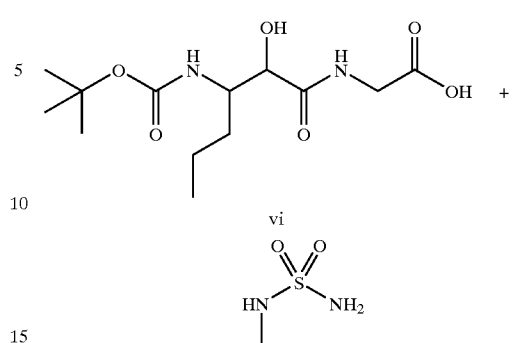

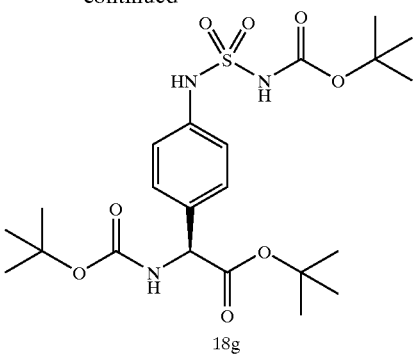
18g

To a cold (−20° C.) solution of dichloromethane (2 mL) was added chlorosulfonyl isocyanate (0.16 mL, 1.87 mmol). To this was added tert-butanol (0.18 mL, 1.87 mmol) in dichloromethane (2 mL) and slowly warmed to 0° C. over 2.5 hrs. At this time a solution of 18f (0.6 g, 1.87 mmol) in dichloromethane (6 mL) containing triethylamine (0.52 mL, 3.73 mmol) was added dropwise. The reaction mixture was warmed to ambient temperature over 12 hrs (overnight). Added saturated bicarbonate and dichloromethane and the organic layer was separated, dried (Na$_2$SO$_4$) and concentrated. Purification by flash chromatography using 95/5 to 90/10 dichloromethane/ethyl acetate provided 18g (0.59 g) in 63% yield.

Step G:

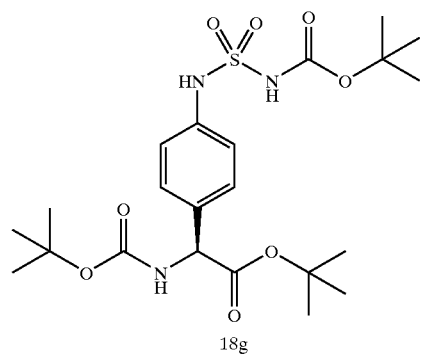

The expected product 18i was synthesized as described earlier for the Example 1, Step D. The crude material was purified by flash chromatography using 98/2 to 90/10 dichloromethane/methanol to afford 18i in 34% yield.

Step I:

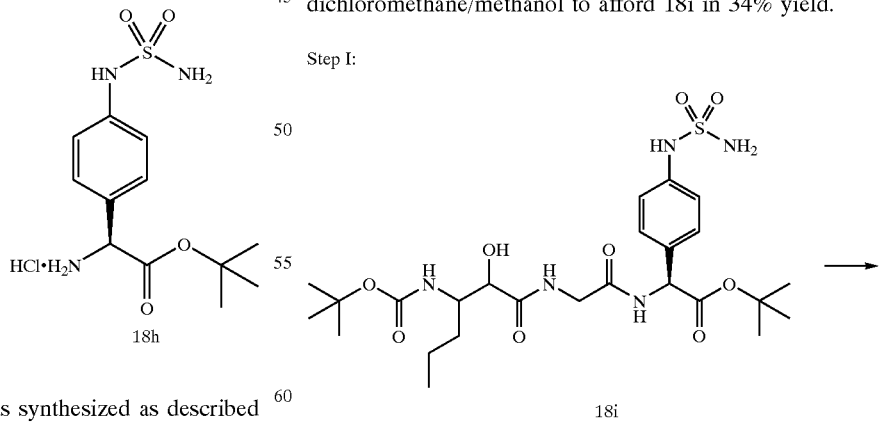
18i

The expected product 18h was synthesized as described earlier for the Example 1, Step C. The material was carried to the next step as it was.

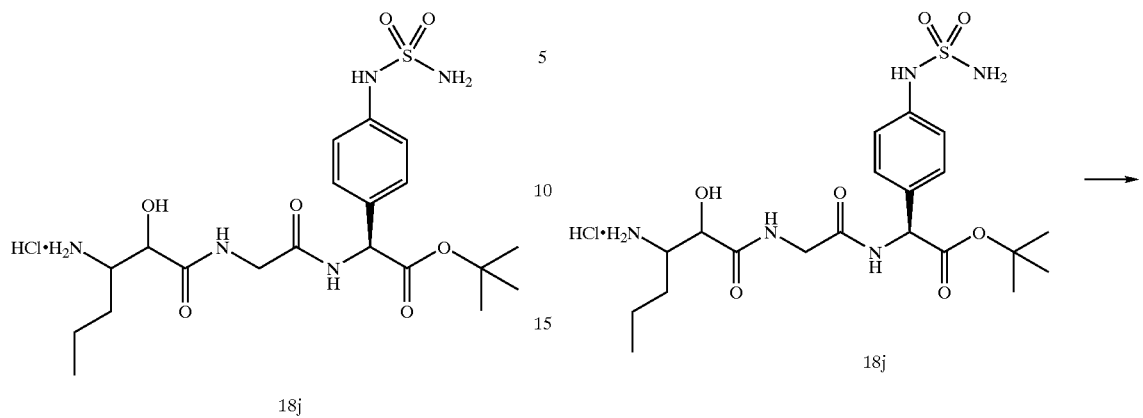
18j
The expected product 18j was synthesized as described earlier for the Example 1, Step C. The material was carried to the next step as it was.
Step J:
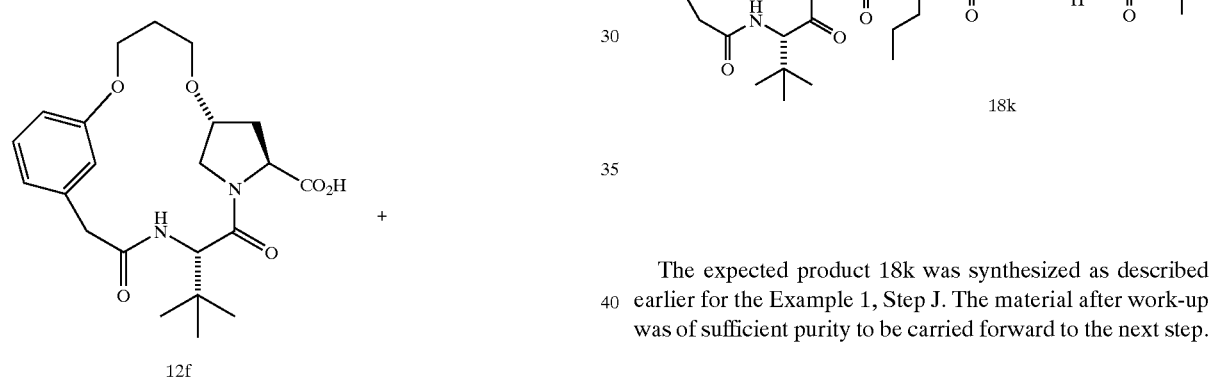
18k
The expected product 18k was synthesized as described earlier for the Example 1, Step J. The material after work-up was of sufficient purity to be carried forward to the next step.
Step K:
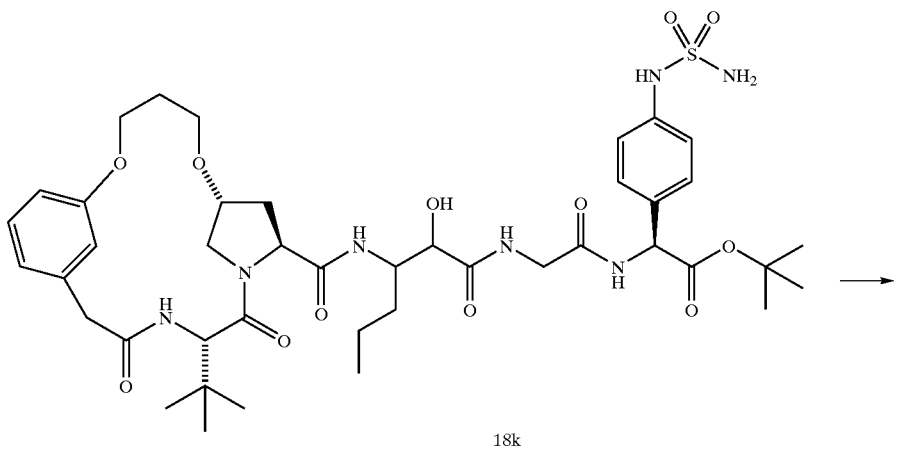
18k

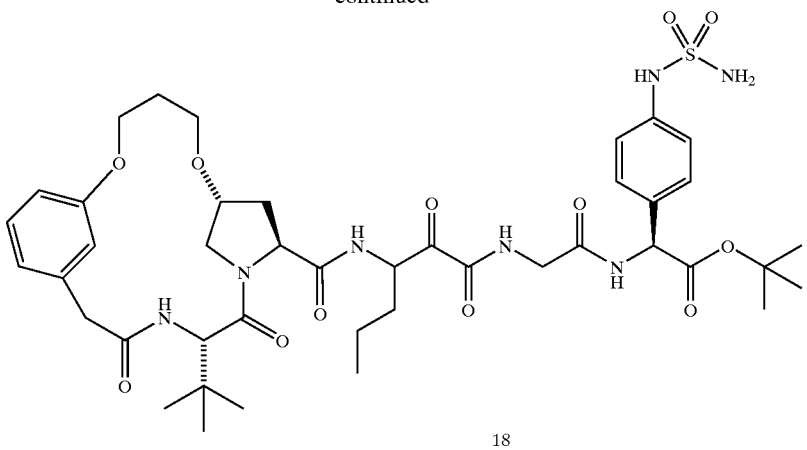

18

The desired product 18 was obtained by the oxidation protocol described previously for Example 1, Step K. Purification by flash column chromatography using 98/2 to 92/8 dichloromethane/MeOH afforded 11 as a mixture of diastereomers in 13% yield (for 2 steps).

Example 19

Preparation of Compound of Formula 19

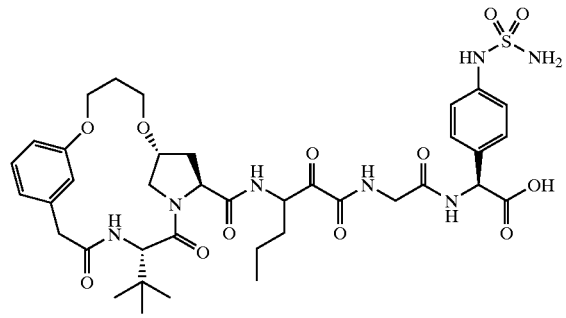

19

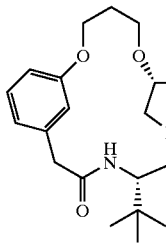

19

The expected product 19 was synthesized as described earlier for the Example 3, Step A, in quantitative yield.

Example 20

Preparation of Compounds of Formulas 20A and 20B

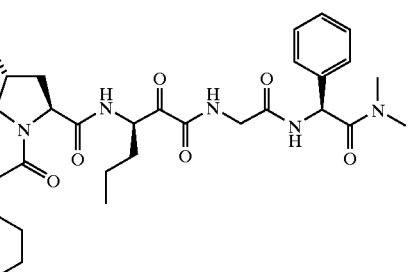

20A

Step A:

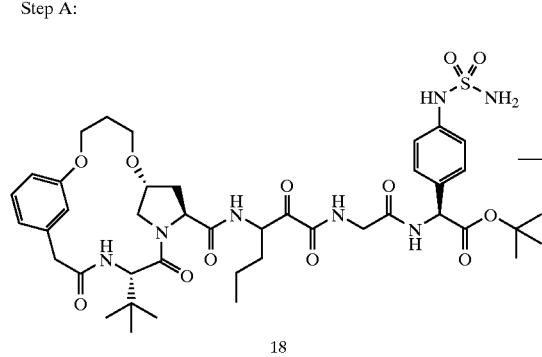

18

-continued

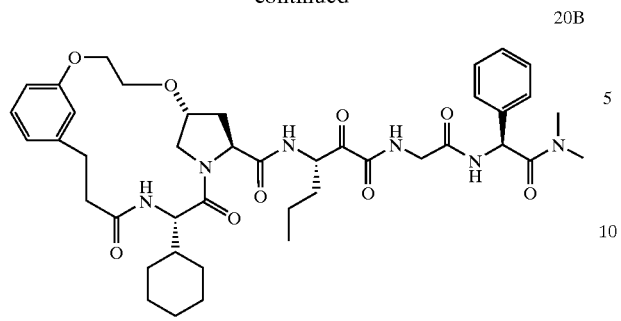

20B

Step A:

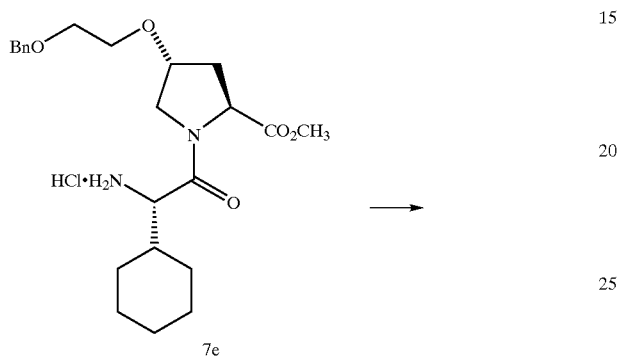

7e

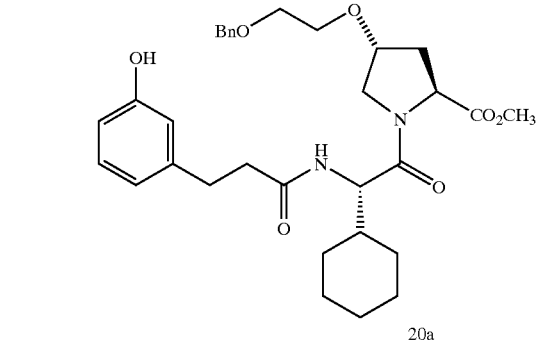

20a

The desired product 20a was obtained by the method described for Example 1, Step F. The material was purified by flash column chromatography using 98/2 dichloromethane/methanol to provide 20a in 97% yield. HRMS (FAB) Calcd for $C_{32}H_{43}N_2O_7$: 567.3070 $(M+H)^+$. Found: 567.3073.

Step B:

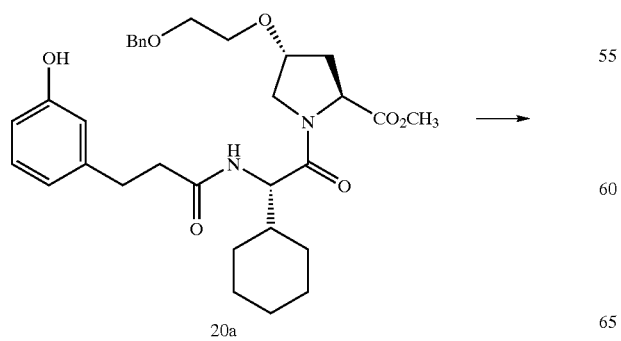

20a

-continued

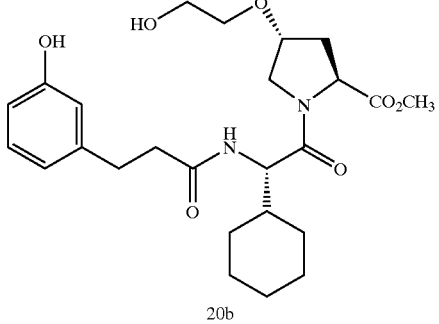

20b

The desired product 20b was obtained by the method described for Example 1, Step G. The material was purified by flash column chromatography using 98/2 to 96/4 dichloromethane/methanol to provide 20b in 81% yield. HRMS (FAB) Calcd for $C_{25}H_{37}N_2O_7$: 477.2601 $(M+H)^+$. Found: 477.2606.

Step C:

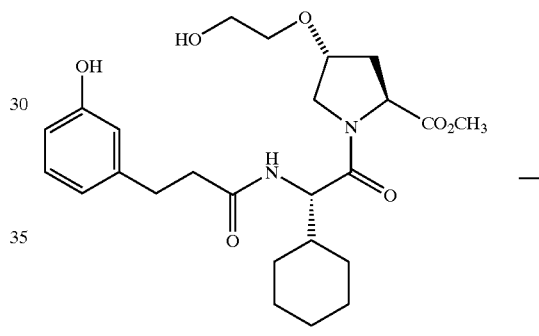

20b

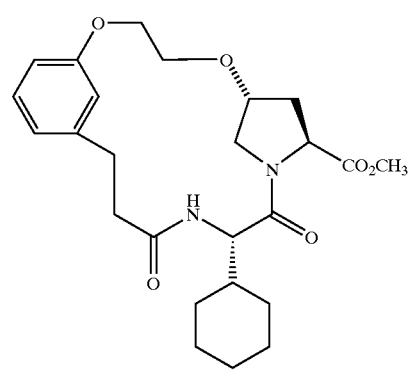

20c

The desired product 20c was obtained by the method described for Example 1, Step H. Purification by column chromatography using 99/1 dichloromethane/methanol afforded 20c along with triphenylphosphine oxide. This mixture was taken to the next step. HRMS (FAB) Calcd for $C_{25}H_{35}N_2O_6$: 459.2495 $(M+H)^+$. Found: 459.2490.

Step D:

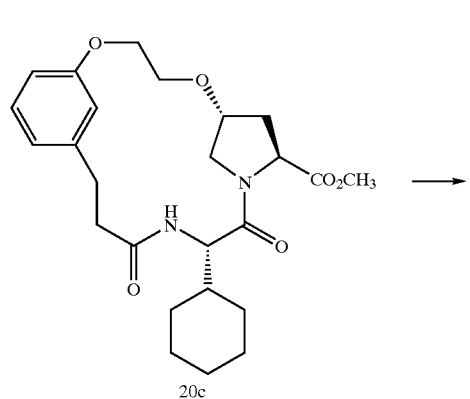

20c

↓

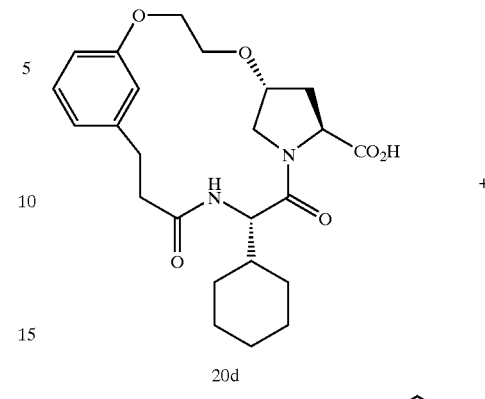

20d

Step E:

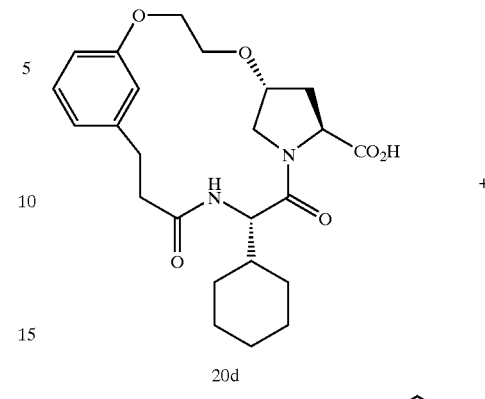

20d

+

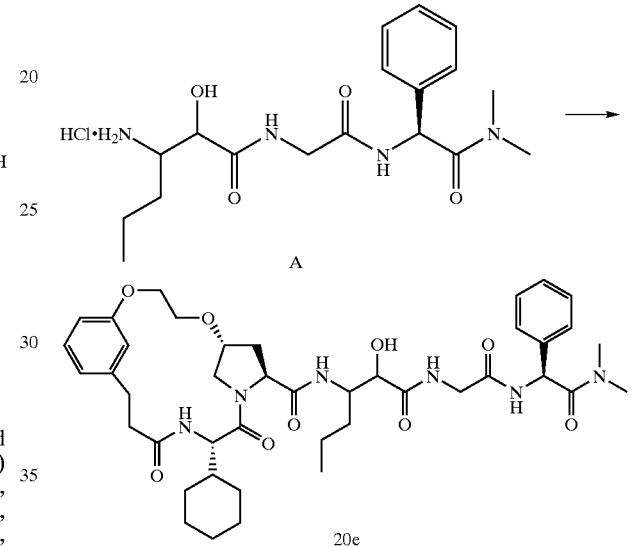

A

↓

20e

The desired product 20d was obtained by the method described for Example 1, Step I. Yield of 20d (for 2 steps) 23%. $^1$H NMR (DMSO-$d_6$). 0.84 (m, 2H), 1.10 (m, 3H), 1.56–1.67 (m, 6H), 1.75–1.81 (m, 1H), 2.32–2.49 (m, 3H), 2.55–2.59 (m,1H), 2.94 (dt,1H), 3.50 (dd,1H), 3.56–3.65 (m, 2H), 3.99 (dd,1H), 4.06–4.23 (m, 4H), 4.37 (t,1H), 6.64–6.74 (m, 3H), 7.08 (app. t, 1H), 7.95 (d, 1H), 12.30 (br. s, 1H); $^{13}$C NMR δ (DMSO-$d_6$) 25.25, 25.97, 28.30, 28.55, 30.61, 33.77, 36.04, 39.41, 52.52, 54.02, 57.22, 66.38, 68.03, 77.49, 114.75, 115.37, 121.14, 128.86, 142.66, 158.92, 169.87, 170.83, 172.99; HRMS (FAB) Calcd for $C_{24}H_{33}N_2O_6$: 445.2339 (M+H)$^+$. Found: 445.2343.

The expected product 20e was synthesized as described earlier for the Example 1, Step J. The material after work-up was of sufficient purity to be carried forward to the next step.

Step F:

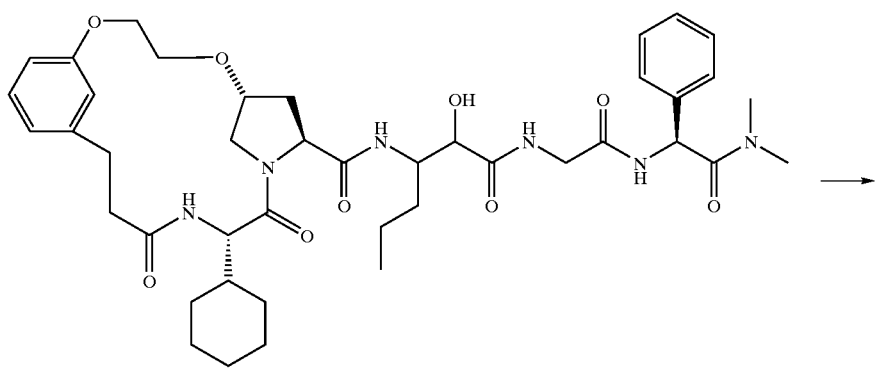

20e

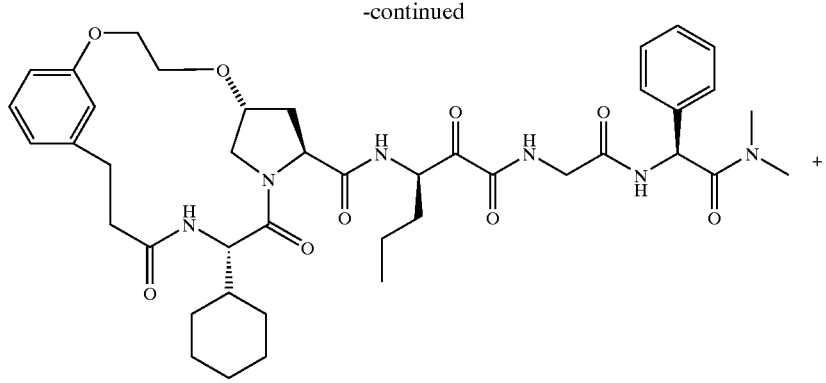

20A

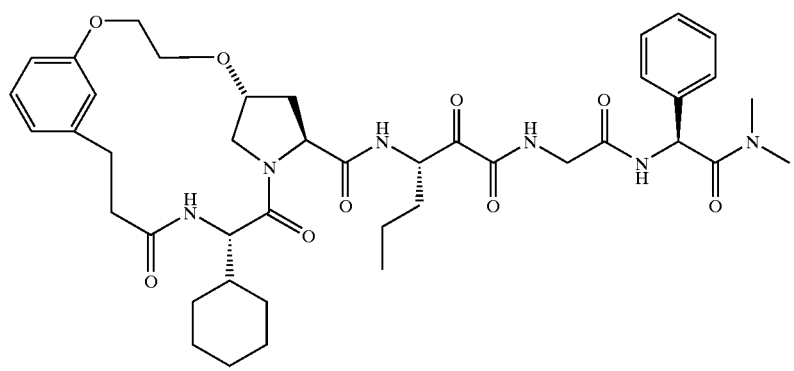

20B

The desired products 20A and 20B were obtained by the oxidation protocol described previously for Example 1, Step K. Purification by flash column chromatography using 100/0 to 98/2 dichloromethane/methanol afforded separate isomers 20A and 20B, and some mixture. Combined yield=50% (for 2 steps). HRMS (FAB) Calcd for $C_{42}H_{57}N_6O_9$: 789.4187 (M+H)$^+$. Found: 789.4179 (20A) and 789.4187 (20B).

Example 21

Preparation of Compound of Formula 21

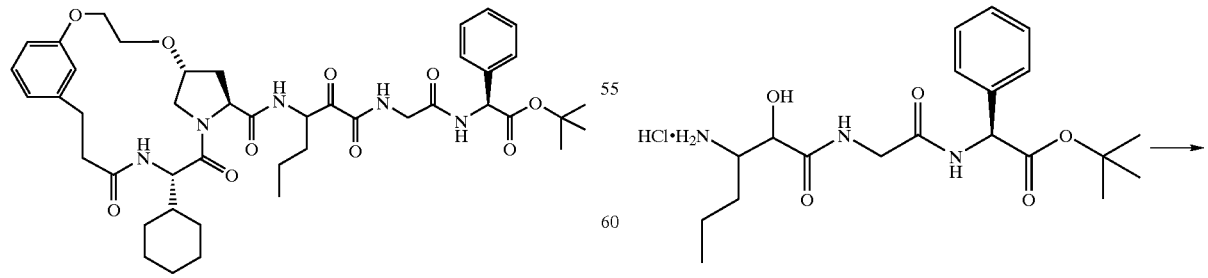

21

Step A:

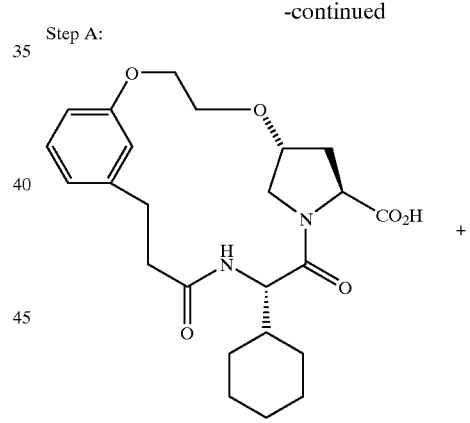

20d

189

-continued

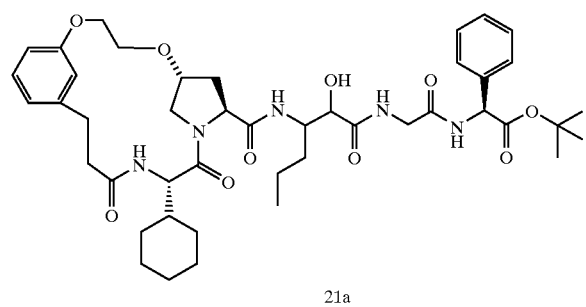

21a

The expected product 21a was synthesized as described earlier for the Example 2, Step A. The material after work-up was of sufficient purity to be carried forward to the next step.

Step B:

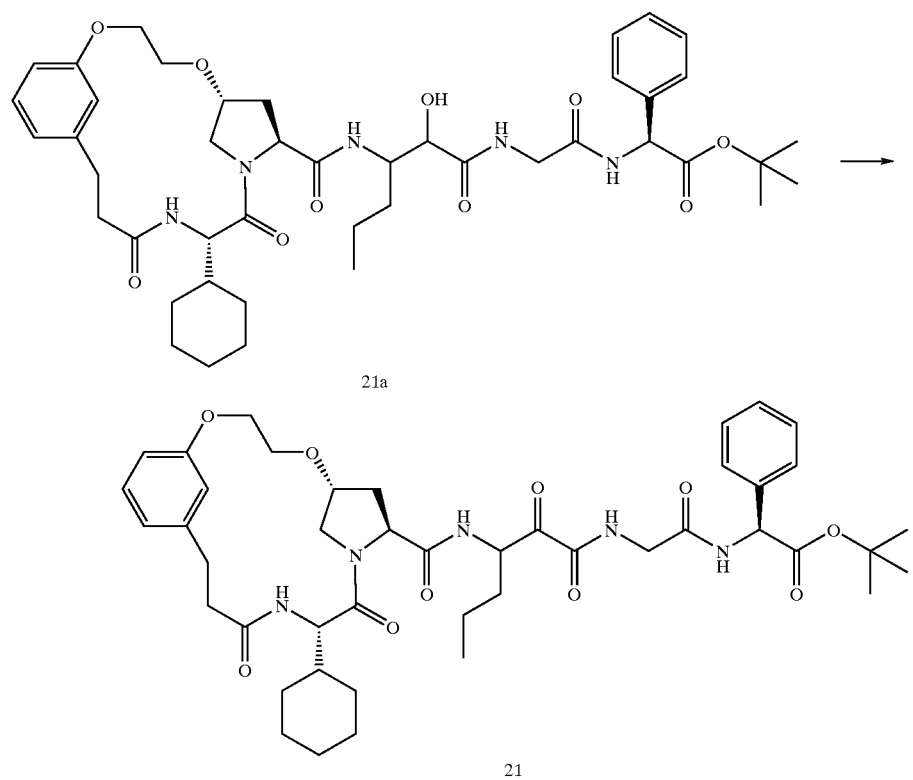

21a

21

The desired product 21 was obtained by the oxidation protocol described previously for Example 2, Step B. Purification by flash column chromatography using 100/0 to 98/2 dichloromethane/methanol afforded 21 in 38% yield. HRMS (FAB) Calcd for $C_{44}H_{60}N_5O_{10}$: 818.4340 (M+H)$^+$. Found: 818.4329.

190

Example 22

Preparation of Compound of Formula 22

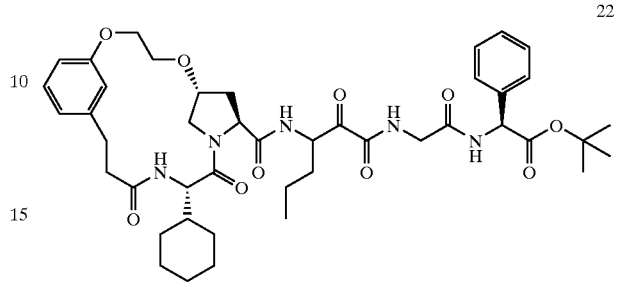

22

-continued

Step A:

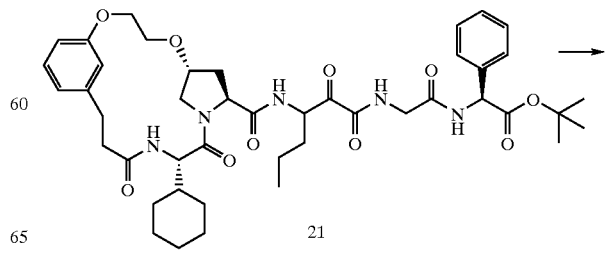

21

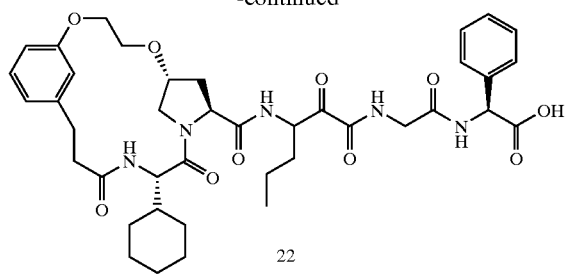
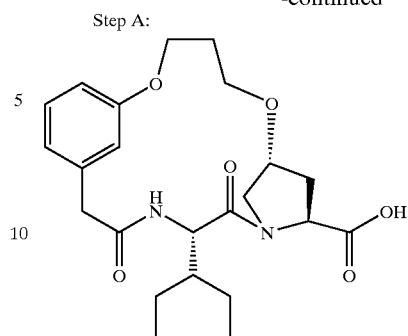
The expected product 22 was synthesized as described earlier for the Example 3 Step A in quantitative yield. HRMS (FAB) Calcd for $C_{40}H_{52}N_5O_{10}$ 762.3714 $(M+H)^+$. Found: 762.3722.
Example 23
Preparation of Compound of Formula 23
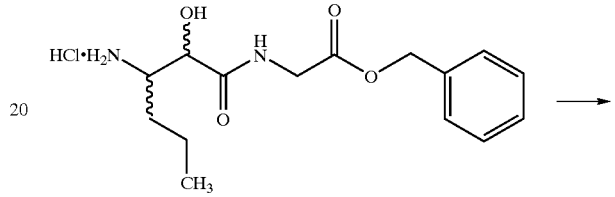
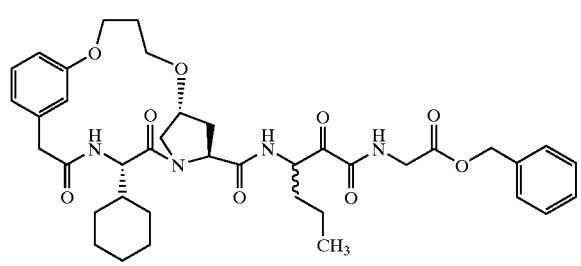
Step A:
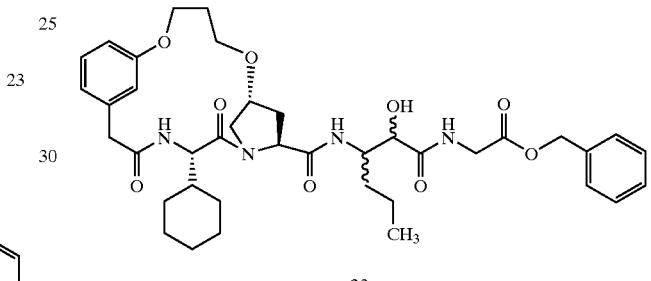
The desired compound 23a was prepared in 58% yield from 1I and D according to the method of Example 1, Step J.
Step B:
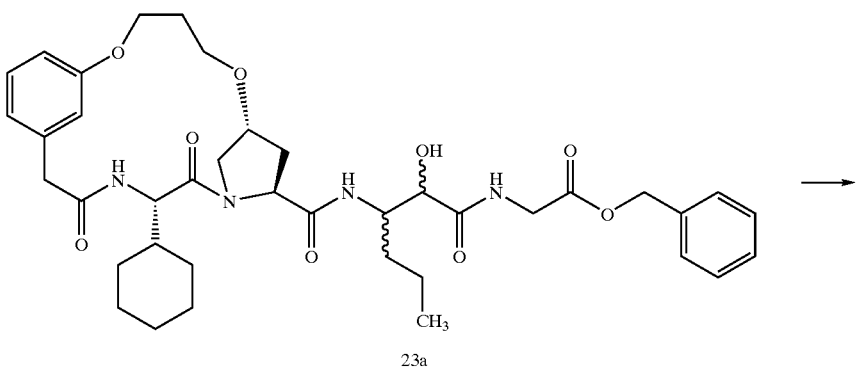

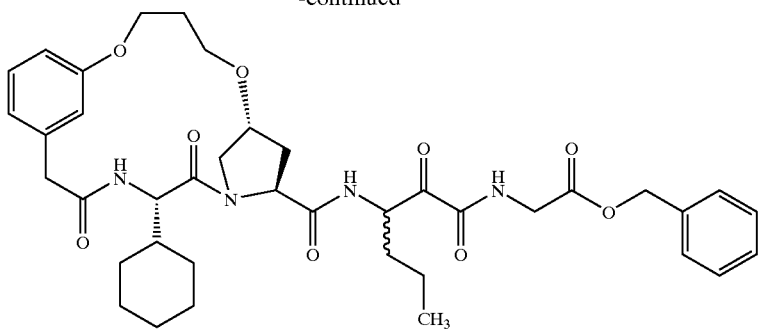

23

The desired compound 23 was prepared in 79% yield from 23a according to the method of Example 1, Step K.

Example 24

Preparation of Compound of Formula 24

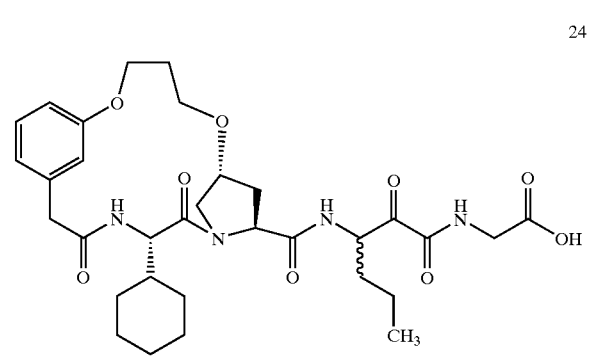

24

Step A:

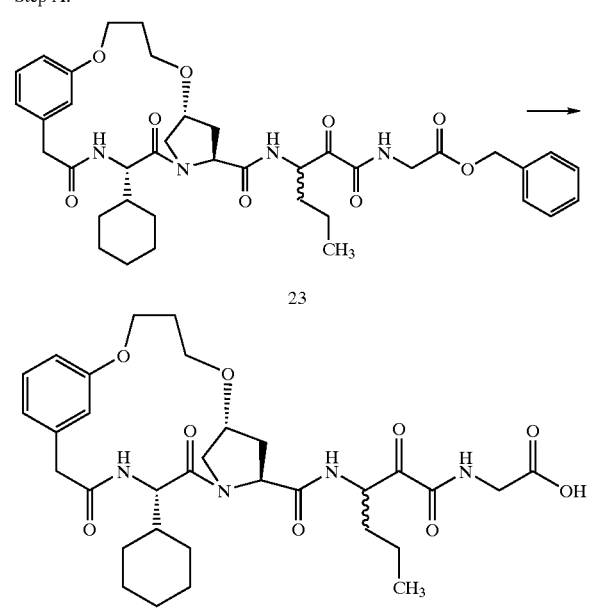

The solution of the benzyl ester 23 (80 mg, 0.11 mmol) in ethanol (30 mL) and methanol (15 mL) was stirred at rt. for 3 h under hydrogen in the presence of palladium on carbon (50 mg). The reaction progress was monitored by TLC. After careful filtration through a celite pad, solvents were then removed in vacuo to give a white solid (67 mg, quant.).

Example 25

Preparation of Compound of Formula 25

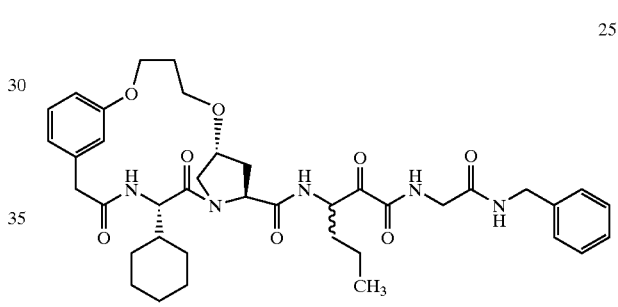

25

Step A:

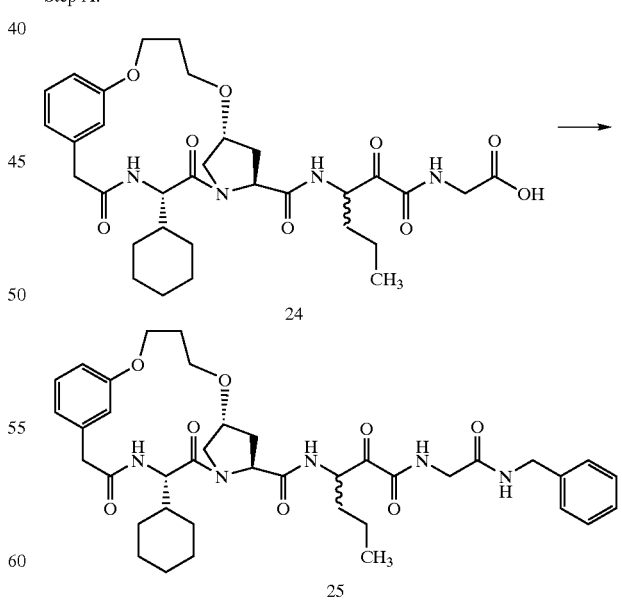

The desired compound 25 was prepared in 53% yield from 24 according to the method of Example 1, Step J, except substituting benzyl amine for amine A.

Example 26

Preparation of Compounds of Formulas 26A and 26B

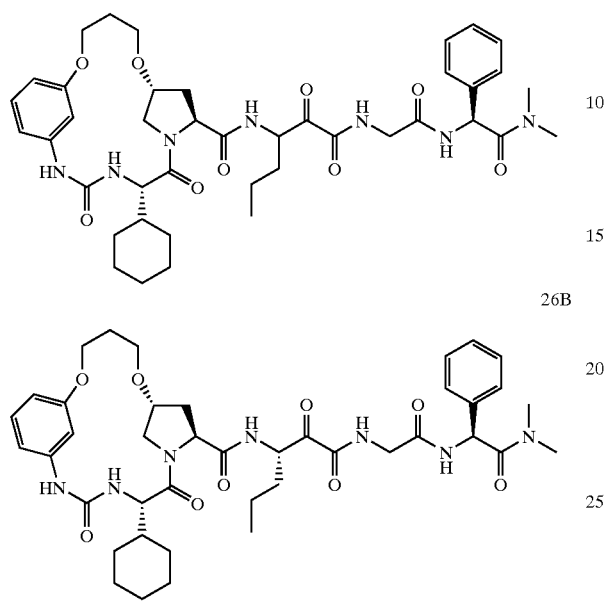

Step A:

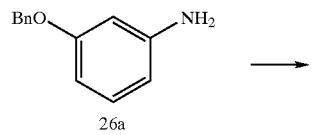

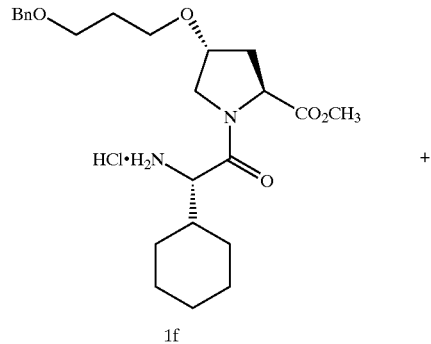

To a cold (0° C.) solution of 26a (4.0 g, 20 mmol) in THF/MeCN (35/5 mL) was added 4-nitrophenyl chloroformate (4.86 g, 24 mmol) and then pyridine (1.9 mL, 24 mmol). The reaction mixture was warmed to ambient temperature over 4.5 hrs. Reaction was monitored till consumption of 26a (needed to add some more of other two reagents). The reaction was quenched by adding water, the organics were separated, washed with brine, dried ($Na_2SO_4$), and evaporated in vacuo to afford the product 26b. This material was sufficiently pure for further studies.

Step B:

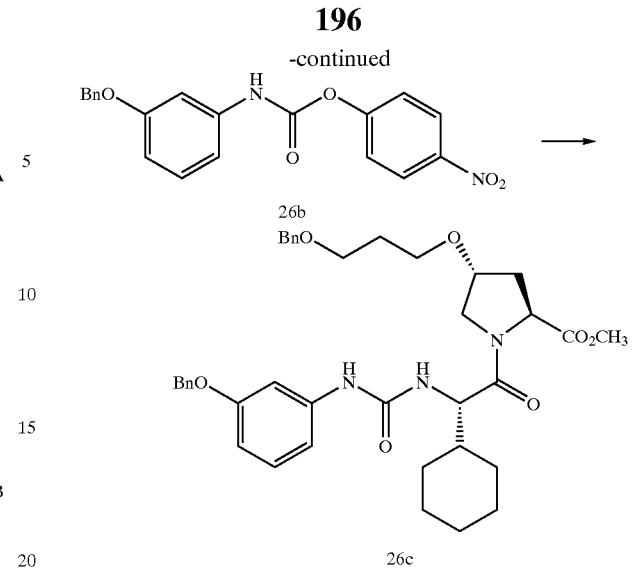

To a solution of 1f (2.3 g, 5.1 mmol) in dichloromethane/DMF (25/5 mL) at 0° C. was added 26b (2.24 g, 6.1 mmol) followed by triethylamine (0.86 mL, 6.1 mmol). Few crystals of imidazole were added and the reaction mixture stored at −8° C. for 16 hrs. The reaction mixture was diluted with dichloromethane, washed with saturated sodium bicarbonate, 10% aqueous citric acid solution, dried ($Na_2SO_4$), and evaporated in vacuo. The crude material was purified by flash column chromatography using 100/0 to 70/30 dichloromethane/ethyl acetate to provide 26c (1.2 g, 38% yield). HRMS (FAB) Calcd for $C_{38}H_{48}N_3O_7$: 658.3492 (M+H)$^+$. Found: 658.3483.

Step C:

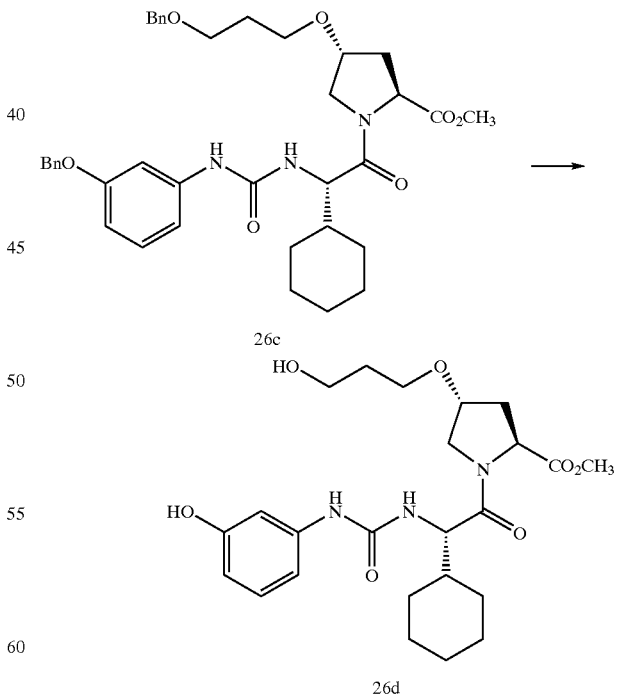

The desired product 26d was obtained by the method described for Example 1, Step G. The crude material was carried to the next step as it was. HRMS (FAB) Calcd for $C_{24}H_{36}N_3O_7$: 478.2553 (M+H)$^+$. Found: 478.2547.

Step D:

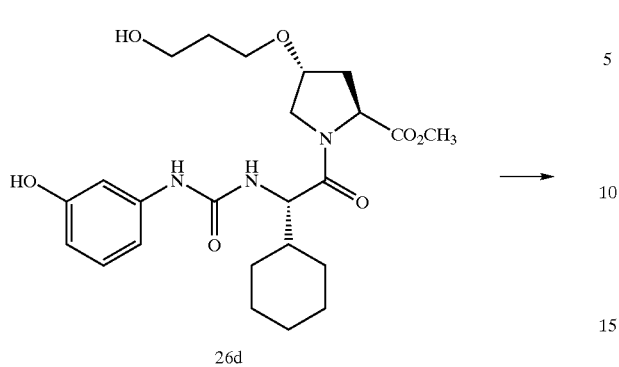

26d

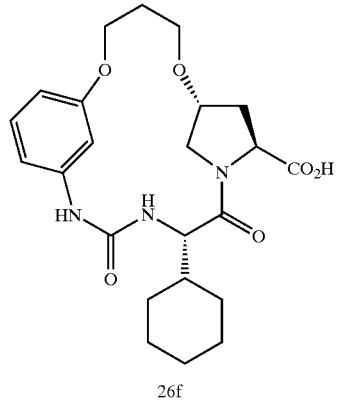

26f

The desired product 26f was obtained by the method described for Example 1, Step I. HRMS (FAB) Calcd for $C_{23}H_{32}N_3O_6$: 446.2291 (M+H)$^+$. Found: 446.2290.

Step F:

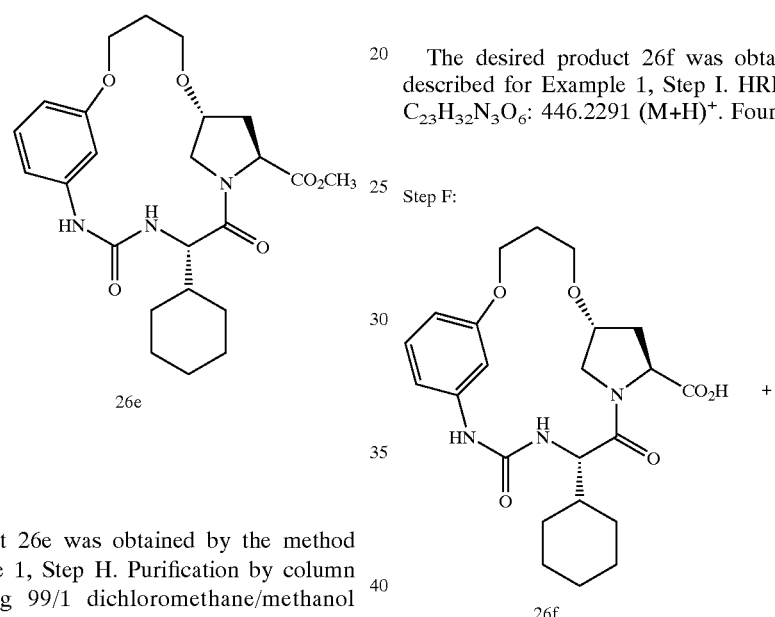

26e

The desired product 26e was obtained by the method described for Example 1, Step H. Purification by column chromatography using 99/1 dichloromethane/methanol afforded 26e along with triphenylphosphine oxide. This mixture was taken to the next step.

Step E:

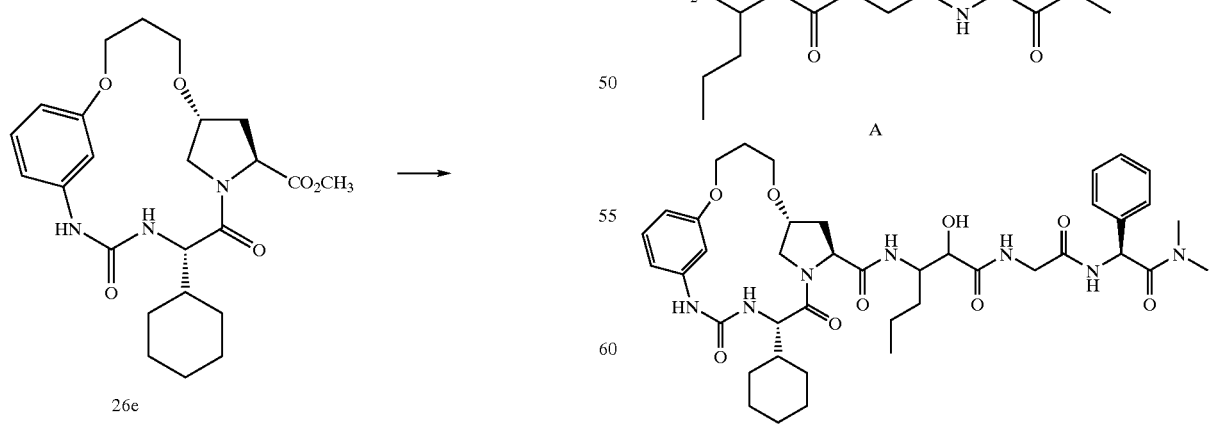

26g

The desired product 26g was obtained by the method described for Example 1, Step J. The crude material was purified by flash column The desired product 21 was obtained by the oxidation protocol described previously for Example 2, Step B. Purification by flash column chromatography using 100/0 to 98/2 dichloromethane/methanol afforded 21 in 38% yield. HRMS (FAB) Calcd for $C_{44}H_{60}N_5O_{10}$: 818.4340 $(M+H)^+$. Found: 818.4329. chromatography using 98/2 dichloromethane/methanol to provide 26g in 31% yield (3 steps). HRMS (FAB) Calcd for $C_{41}H_{58}N_7O_9$: 792.4296 $(M+H)^+$. Found: 792.4284.

Step G

26g

26A

26B

The desired products 26A and 26B were obtained by the method described for Example 1, Step K. Purification by column chromatography using 99/1 to 95/5 dichloromethane/methanol provided 26A (as a mixture) and 26B (pure lower Rf isomer). Combined yield=25%.

Example 27

Preparation of Compound 27

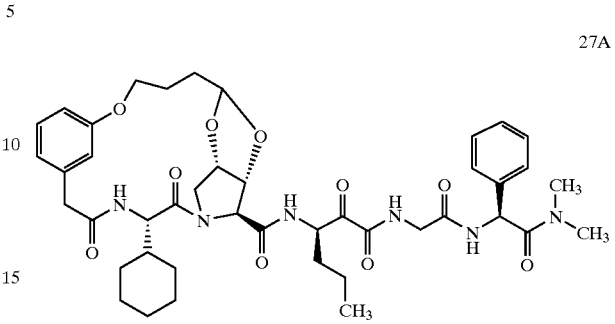

27A

27B

Step A

27a

27b

To the mixture of Boc-3,4-didehydroproline-OMe (27a, 5.30 g, 23.4 mmol), N-methylmorpholine-N-oxide (4.75 g, 35.1 mmol) in acetone (10 mL) and water (15 mL) at rt. was added an Osmium tetroxide solution in tert-butanol (2.5% w/w, 3.5 mL, 0.344 mmol). To this cloudy solution was added THF until the mixture became almost homogeneous. After stirred at rt. overnight, saturated aqueous sodium thiosulfate solution (30 mL) was added and 10 min later, followed by addition of EtOAc (300 mL) and brine (80 mL). After layers were separated, aqueous solution was extracted with EtOAc (2×100 mL). Organic solutions were combined, dried (MgSO$_4$), filtered and concentrated in vacuo to give a dark liquid. Flash chromatography (4 to 8% MeOH/CH$_2$Cl$_2$) afforded 27b (4.73 g, 18.1 mmol, 77%) as an oil.

Step B

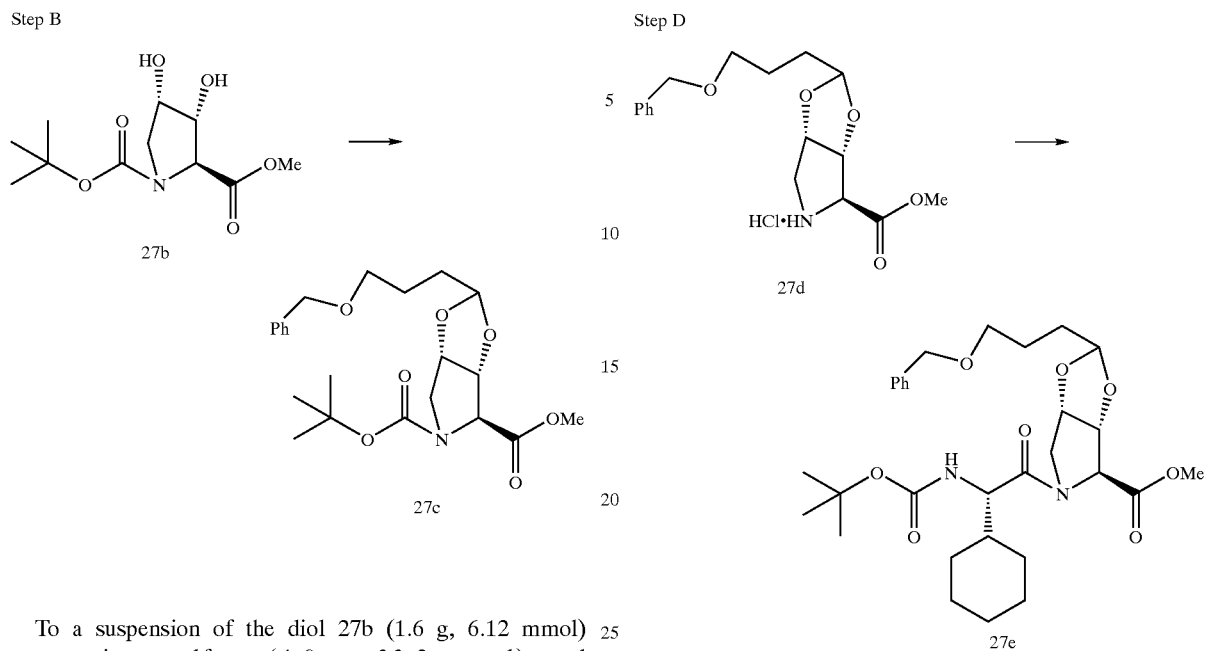

To a suspension of the diol 27b (1.6 g, 6.12 mmol) magnesium sulfate (4.0 g, 33.2 mmol) and 3-benzyloxypropionaldehyde (2.32 g, 13.0 mmol) in anhydrous $CH_2Cl_2$ (60 mL) at 0° C. was added p-toluenesulfonic acid (150 mg, 1.01 mmol). The resulting mixture was stirred vigorously and allowed to warm to rt. along with the ice-bath overnight (18 h). Saturated sodium bicarbonate solution (60 mL), water (30 mL) and CH2Cl2 (100 mL) were added and the layers were separated. The aqueous solution was extracted with $CH_2Cl_2$ (2×100 mL) and combined organic solution was dried (MgSO4), filtered and concentrated in vacuo to give a colorless oil. Flash chromatography (5 to 15 % EtOAc/$CH_2Cl_2$) afforded 27c (2.35 g, 5.57 mmol, 91%) as an oil.

Step C

The desired compound 27d was prepared from 27c according to the method of Example 1, Step C. It was used in the next reaction without further purification.

Step D

The desired compound was prepared from 27d according to the method of Example 1, Step D. Flash chromatography (8 to 20% EtOAc/$CH_2C_{12}$) afforded 27e.

Step E

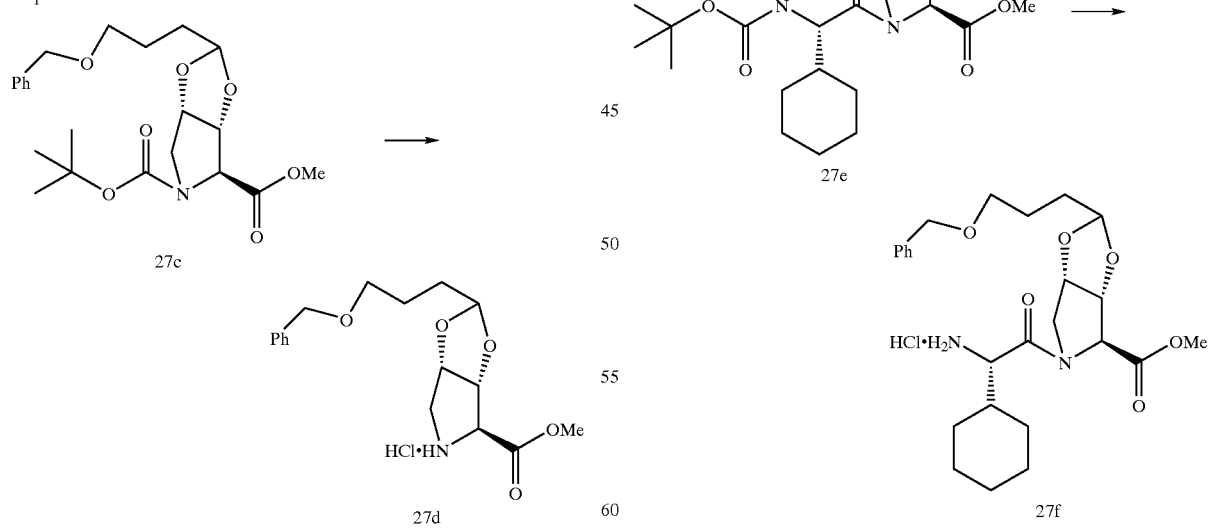

The desired compound 27f was prepared from 27e according to the method of Example 1, Step E. It was used in the next reaction without further purification.

Step F

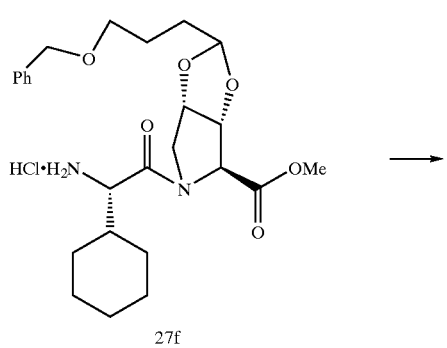

27f

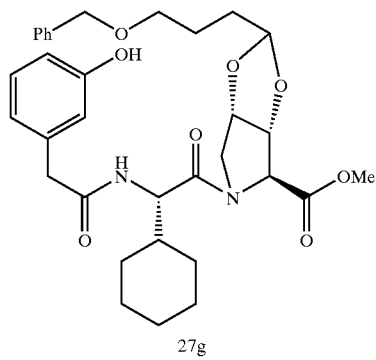

27g

The desired compound was prepared from 27f according to the method of Example 1, Step F. Flash chromatography (8 to 20% EtOAc/CH$_2$Cl$_2$) afforded 27g (36%, 4 steps). HRMS m/z 595.3014 [calcd for C$_{33}$H$_{42}$N$_2$O$_8$, 595.3019].

Step G

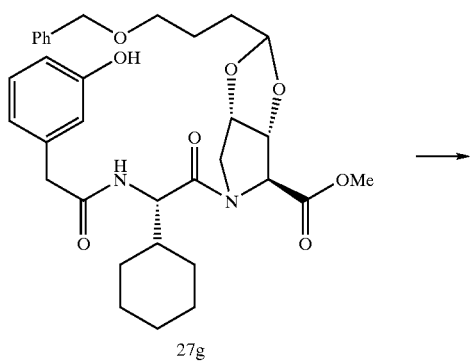

27g

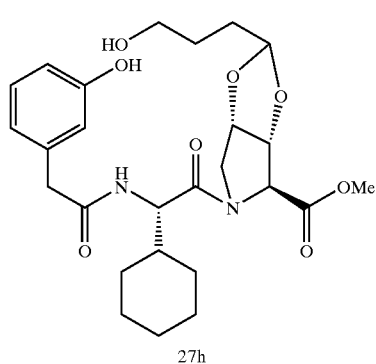

27h

The desired compound was prepared quantitatively from 27g according to the method of Example 1, Step G. Flash chromatography (3 to 5% MeOH/CH$_2$Cl$_2$) afforded 27h as a white solid. HRMS m/z 595.2553 [calcd for C$_{26}$H$_{36}$N$_2$O$_8$, 595.2550].

Step H

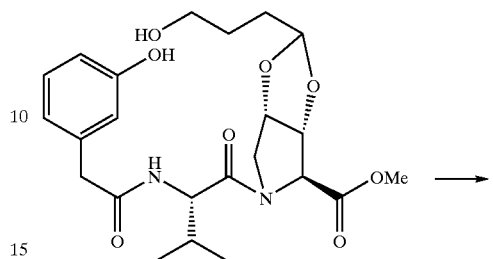

27h

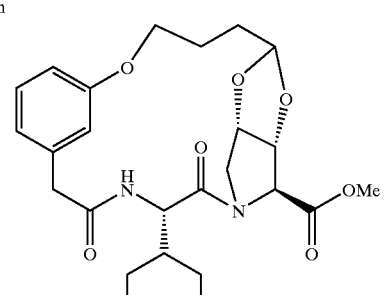

27i

The desired compound was prepared from 27h according to the method of Example 1, Step H. Flash chromatography (3 to 5% MeOH/CH$_2$Cl$_2$) afforded 27i as a mixture with triphenylphosphine oxide which was hydrolyzed.

Step I

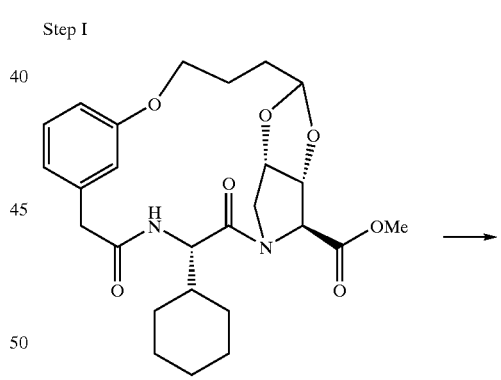

27i

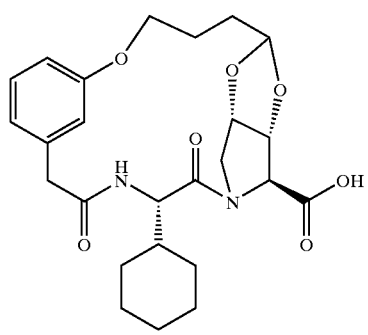

27j

The desired compound was prepared (72%, 2 steps) from 27i according to the method of Example 1, Step I.
Step J
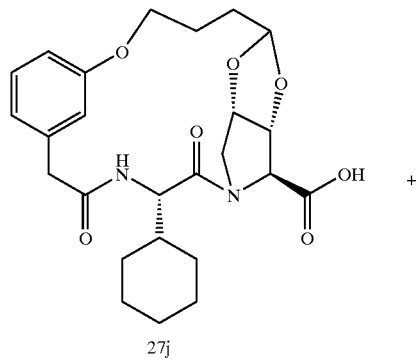
27j
+
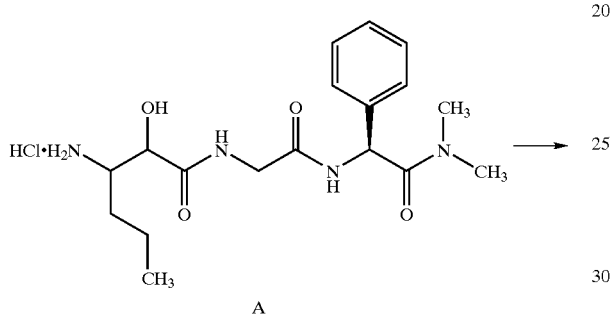
A
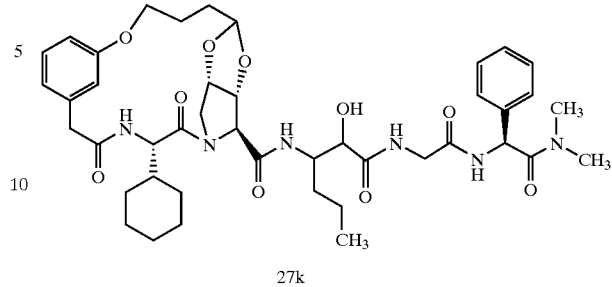
27k
The desired compound was prepared from 27j according to the method of Example 1, Step J. Flash chromatography (3 to 6% MeOH/CH$_2$Cl$_2$) afforded 27k (69%) as a mixture of diastereomers.
Step K
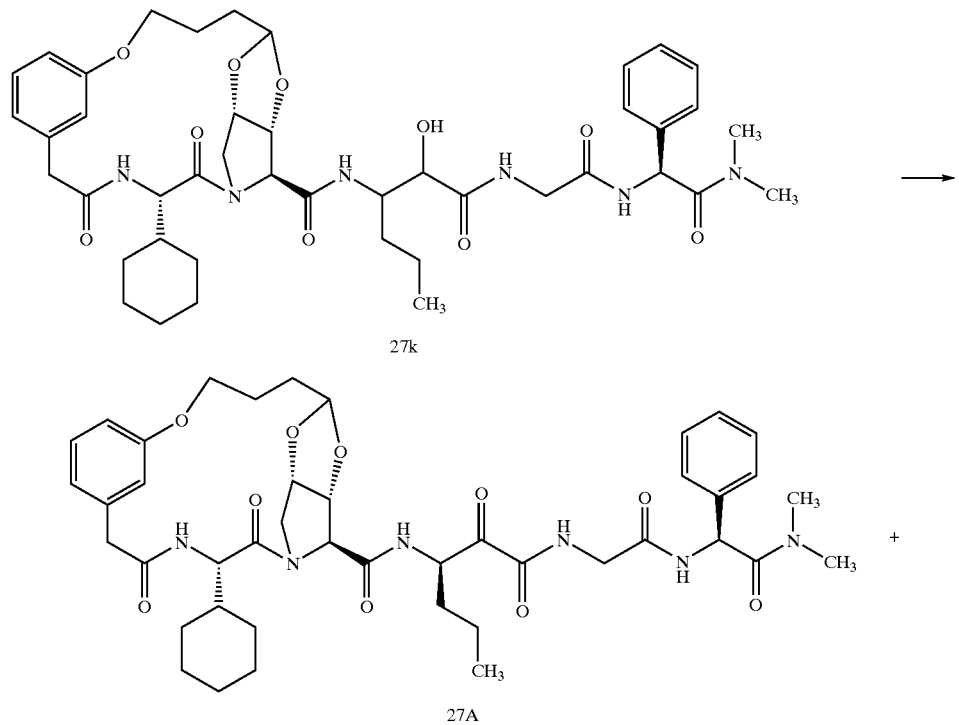

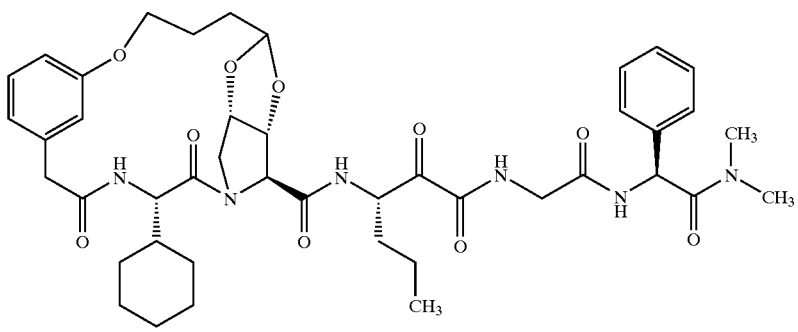
27B
The desired compound was prepared from 27k according to the method of Example 1, Step K. Flash chromatography (2 to 5% MeOH/CH$_2$Cl$_2$) afforded pure 27A and 27B.
Example 28
Preparation of Compound 28
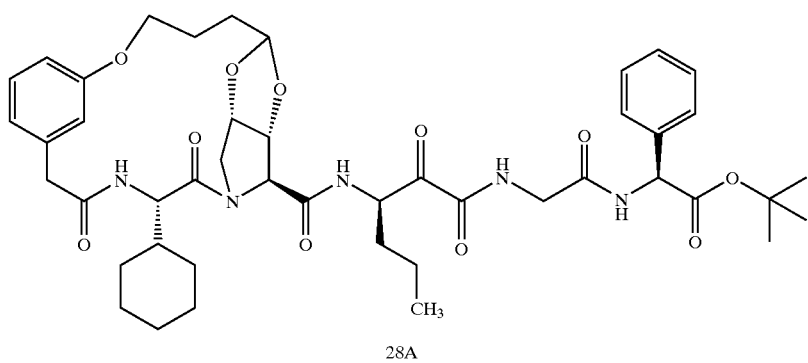
28A
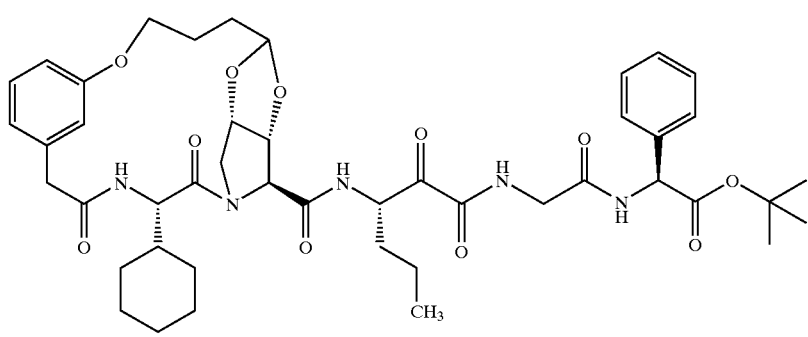
28B Step A
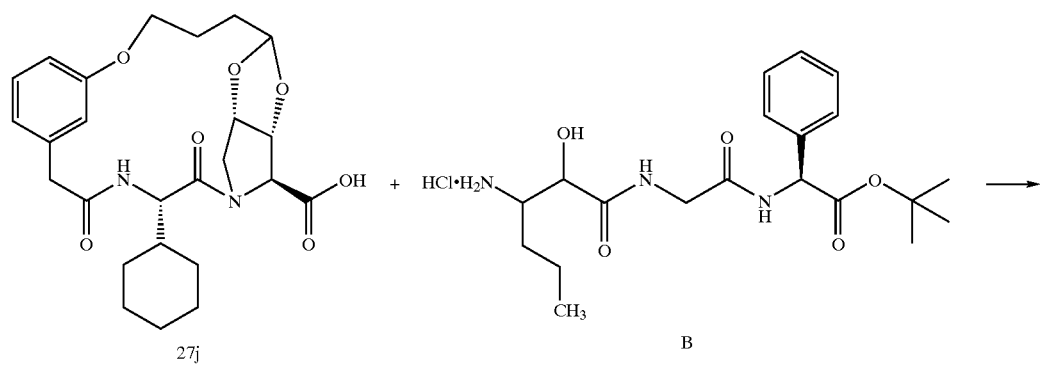
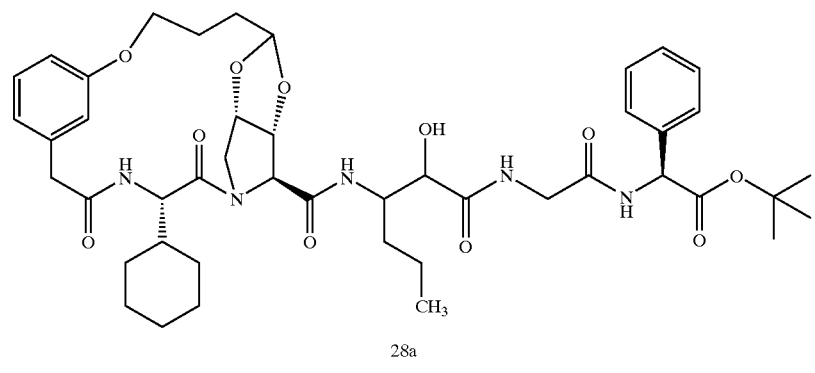
The desired compound was prepared from 27j according to the method of Example 2, Step A. Flash chromatography (3 to 6% MeOH/CH$_2$Cl$_2$) afforded 28a (50%) as a mixture of inseparable diastereomers.
Step B
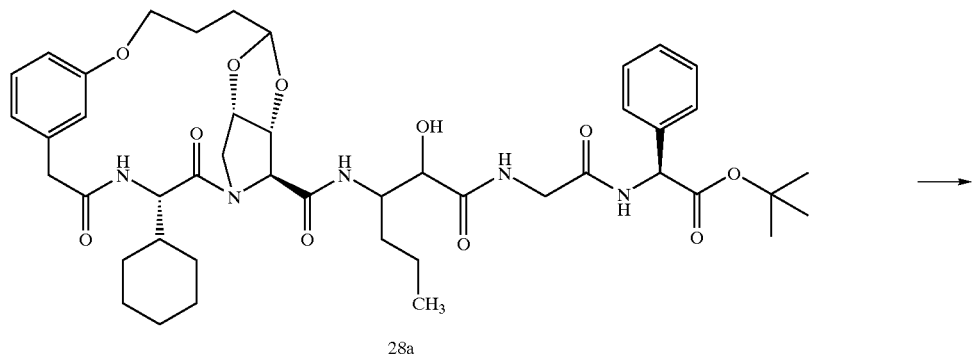
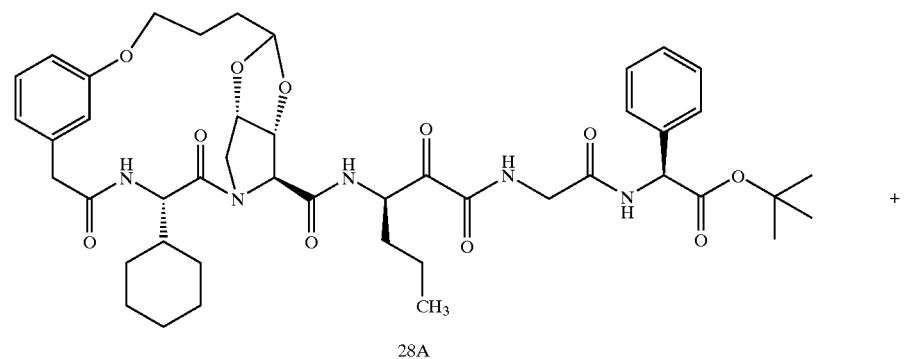

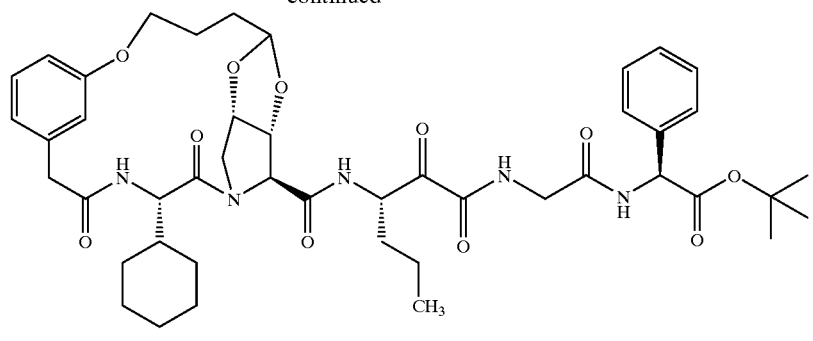
28B
The desired compound was prepared from 28a according to the method of Example 2, Step Flash chromatography (2 to 5% MeOH/CH$_2$Cl$_2$, afforded 28A and 28B.
Example 29
Preparation of Compound 29
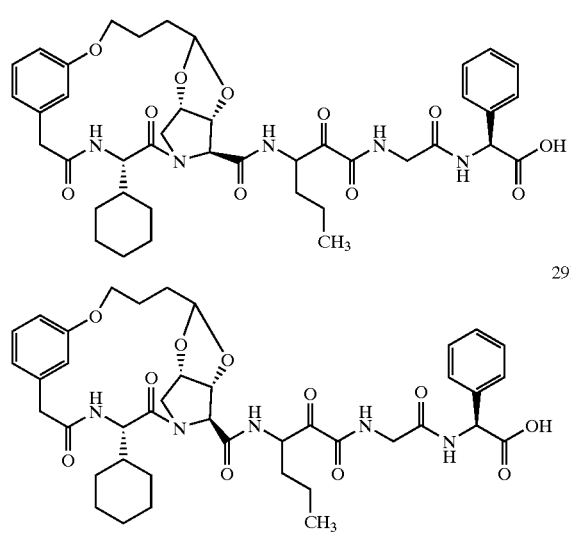
29A
29B
Step A:
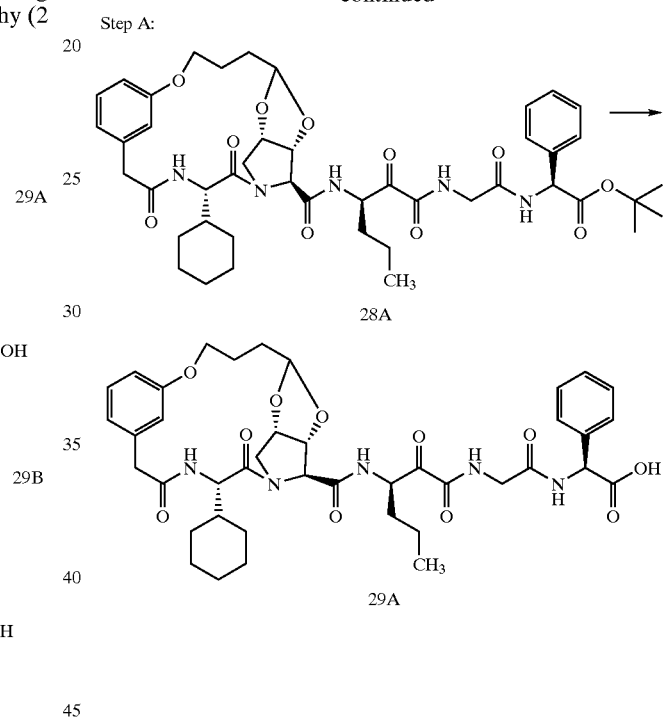
28A
29A
The desired compound 29A was prepared from 28A according to the method of Example 3, Step A.
Step B
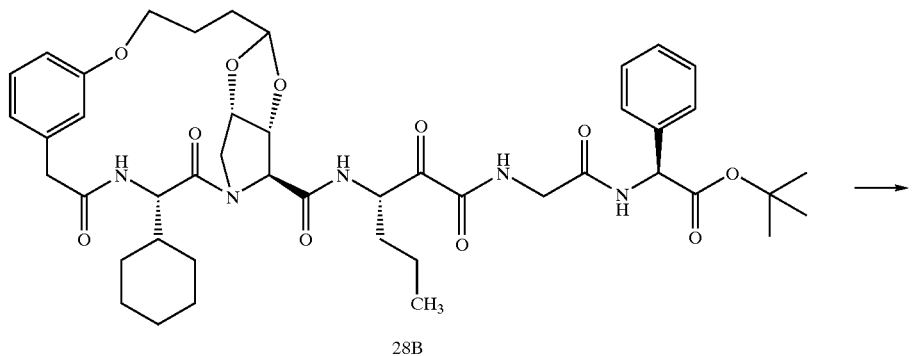
28B

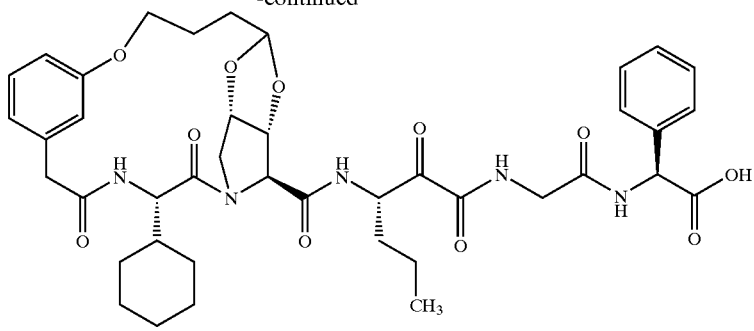

29B

The desired compound 29B was prepared from 28B according to the method of Example 3, Step A.

Example 30

Preparation of Compound 30

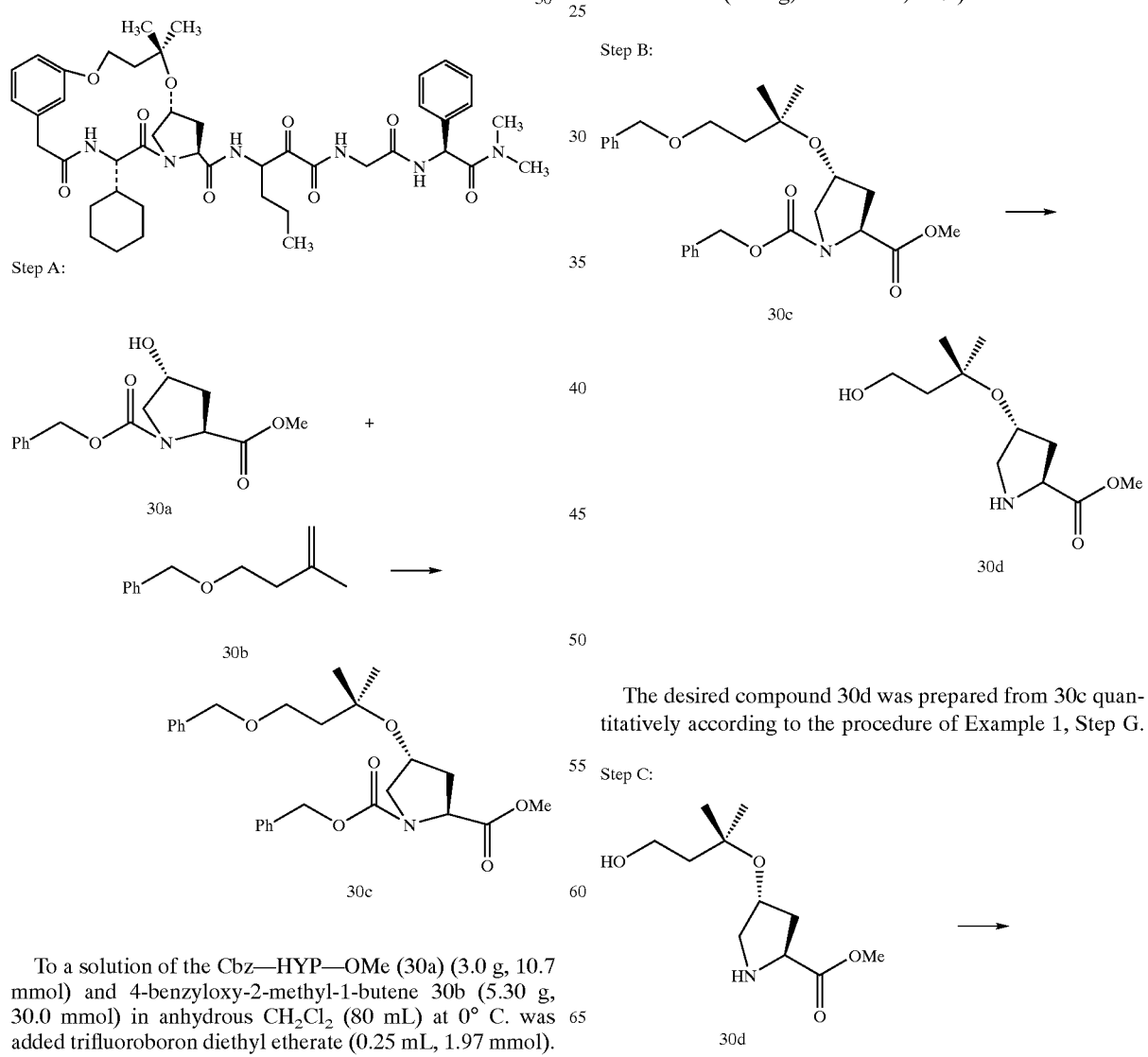

To a solution of the Cbz—HYP—OMe (30a) (3.0 g, 10.7 mmol) and 4-benzyloxy-2-methyl-1-butene 30b (5.30 g, 30.0 mmol) in anhydrous CH₂Cl₂ (80 mL) at 0° C. was added trifluoroboron diethyl etherate (0.25 mL, 1.97 mmol). The resulting mixture was stirred at rt. overnight (18 h). Saturated sodium bicarbonate solution (30 mL), brine (50 mL) and EtOAc (300 mL) were added and the layers were separated. The aqueous solution was extracted with EtOAc (2×100 mL) and the combined organic solution was dried (MgSO₄), filtered and concentrated in vacuo to give a yellow oil. Flash chromatography (5 to 20% EtOAc/CH₂Cl₂) afforded 30c (2.00 g, 4.39 mmol, 41%) as an oil.

Step B:

The desired compound 30d was prepared from 30c quantitatively according to the procedure of Example 1, Step G.

Step C:

Step E:

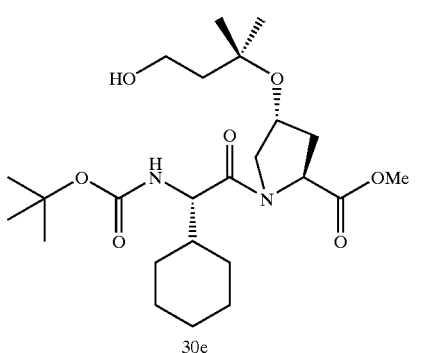
30e

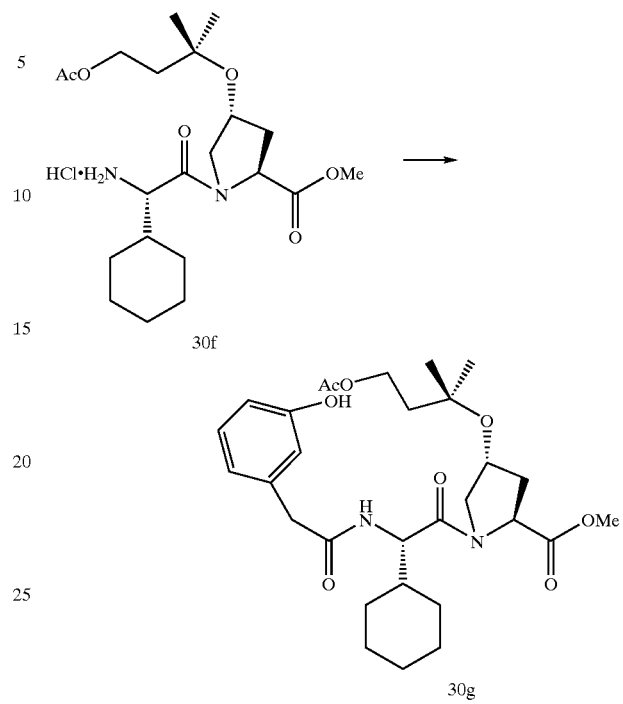
30f

30g

The desired compound 30e was prepared from 30d and Boc-cyclohexylglycine-OH according to the procedure of Example 1, Step D. Flash chromatography (3 to 5% MeOH/CH$_2$Cl$_2$) afforded 30e (61%).

Step D:

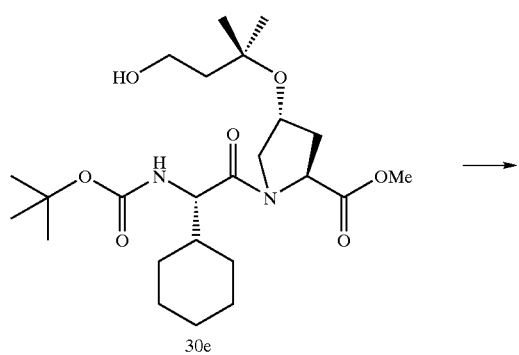
30e

30f

The desired compound 30g was prepared from 30f according to the procedure of Example 1, Step F. Flash chromatography (2 to 5% MeOH/CH$_2$Cl$_2$) afforded 30g (48%, 2 steps).

Step F:

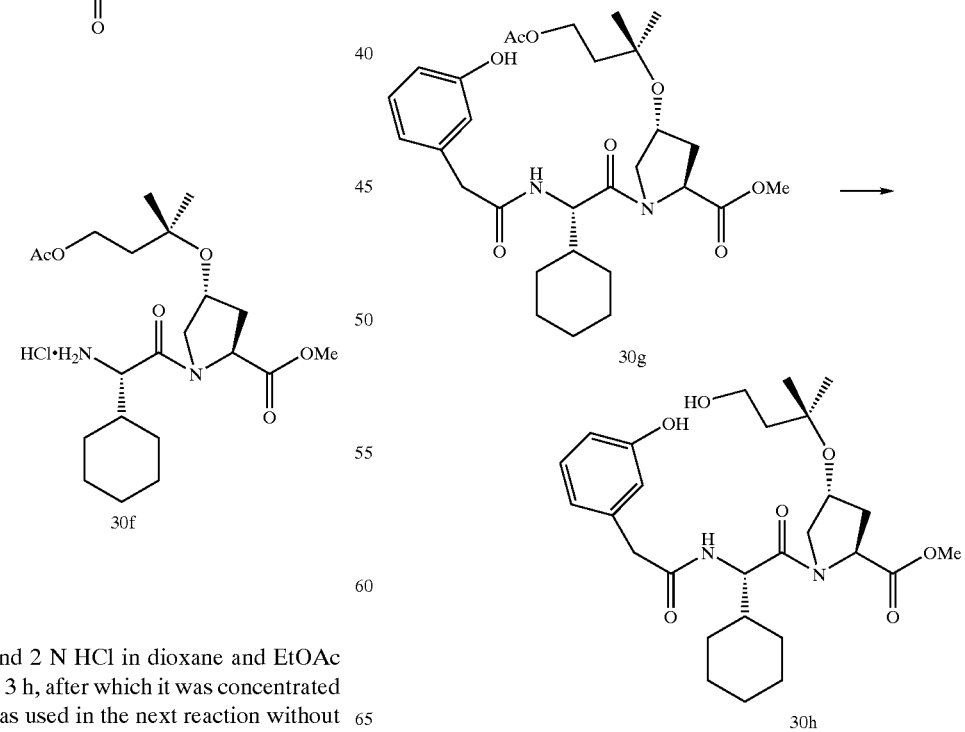
30g

30h

The solution of 30e and 2 N HCl in dioxane and EtOAc (1:1) was stirred at rt. for 3 h, after which it was concentrated in vacuo. The product was used in the next reaction without further purification.

The mixture of 30g (700 mg, 1.28 mmol) and potassium carbonate (530 mg, 3.84 mmol) in anhydrous methanol (80 mL) was vigorously stirred at rt. The reaction progress was monitored by TLC. After 3 h, it was concentrated in vacuo before EtOAc (200 mL) and water (100 mL) were added and layers were separated. The aqueous solution was extracted with EtOAc (2×100 mL). The organic solutions were combined, dried (MgSO₄), filtered and concentrated in vacuo. The product was used in the next reaction without further purification.

Step G:

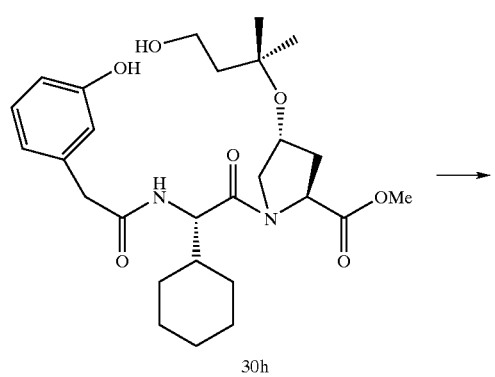

30h

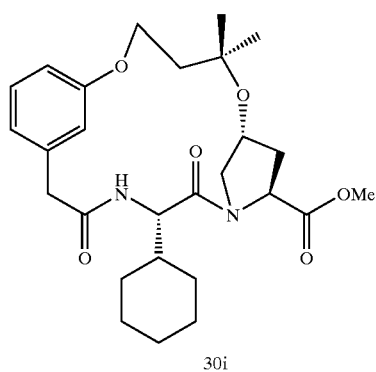

30i

The desired compound 30i was prepared from 30h according to the procedure of Example 1, Step H.

Step H:

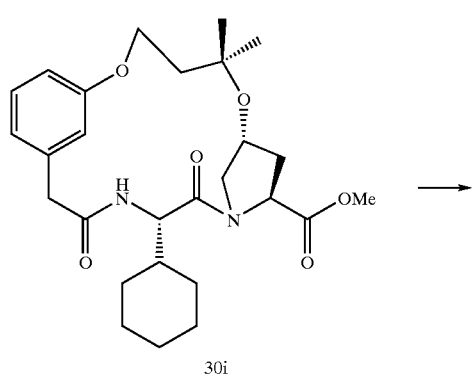

30i

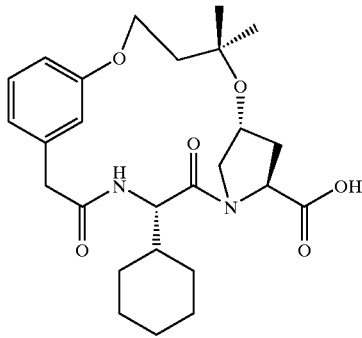

30j

The desired compound 30j was prepared from 30i according to the procedure of Example 1, Step I (23%, 3 steps).

Step I:

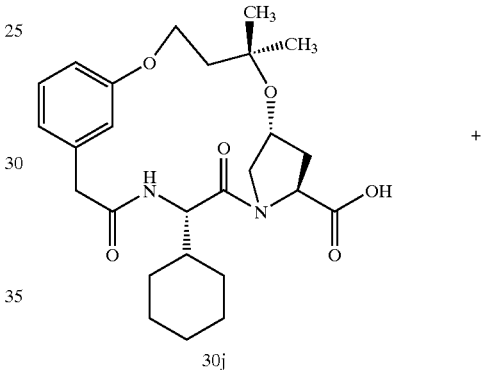

30j

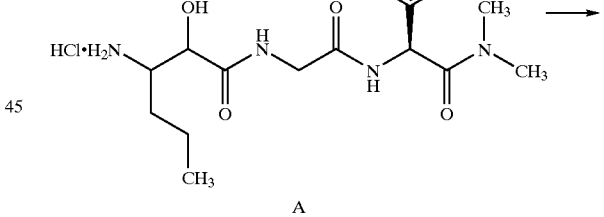

A

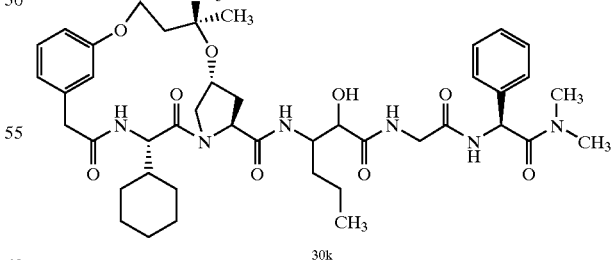

30k

The desired compound was prepared from 30j according to the procedure of Example 1, Step J. Flash chromatography (3 to 6% MeOH/CH₂Cl₂) afforded 30k (58%).

Step J:

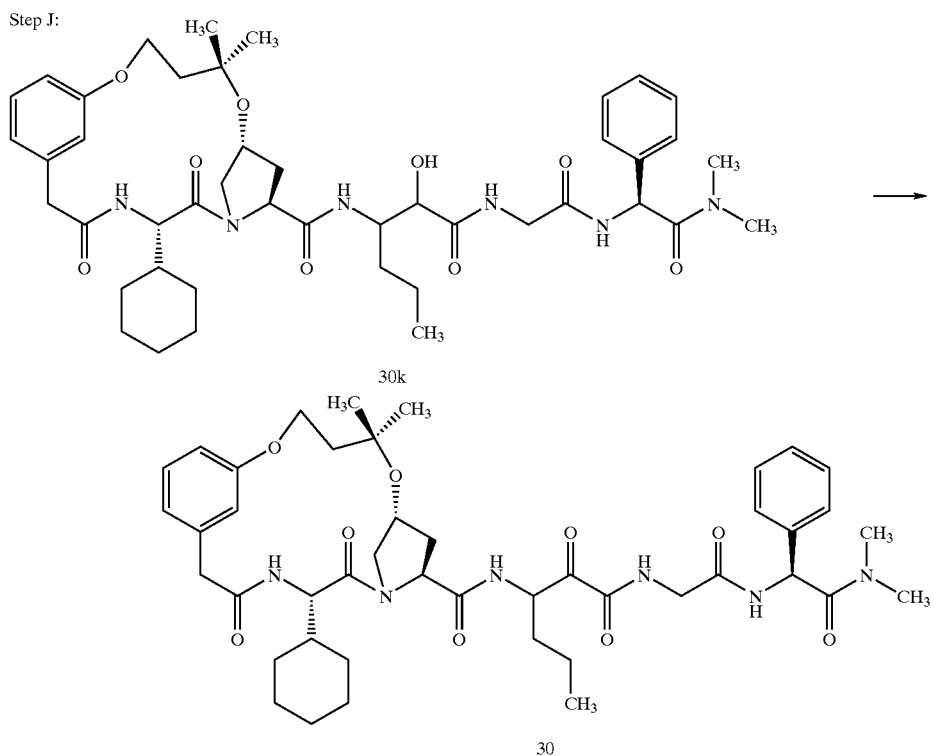

The desired compound 30 was prepared from 30k according to the procedure of Example 1, Step K. Flash chromatography (3 to 5% MeOH/CH$_2$Cl$_2$) afforded 30 as a mixture of inseparable diastereomers.

Example 31

Preparation of Compound 31

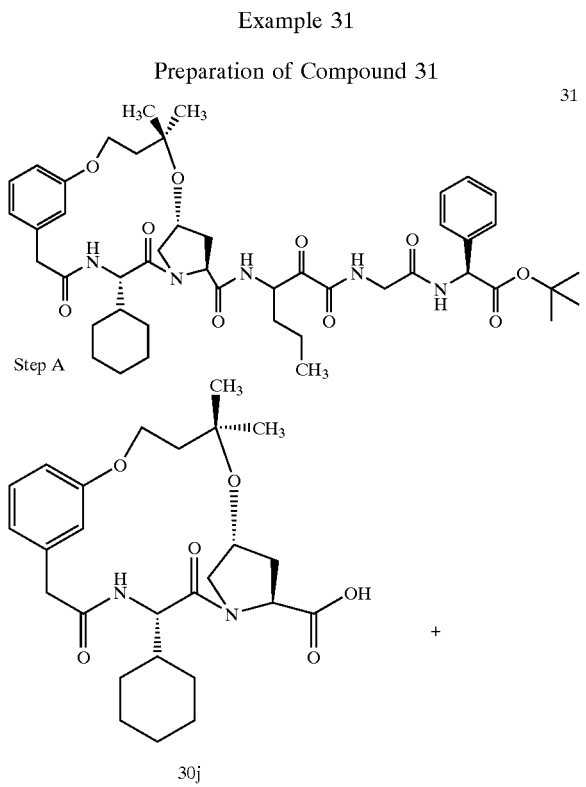

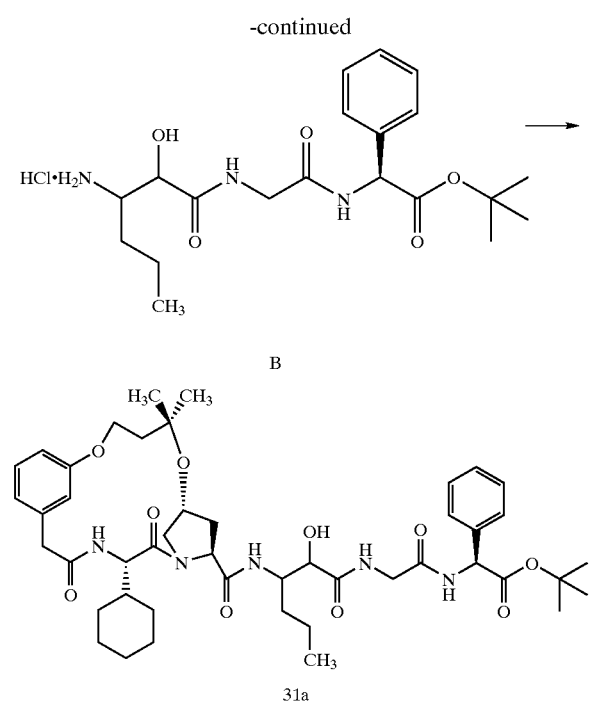

The desired compound was prepared from 30j and B according to the procedure of Example 1, Step J. Flash chromatography (2 to 5% MeOH/CH$_2$Cl$_2$) afforded 31a (73%).

Step B
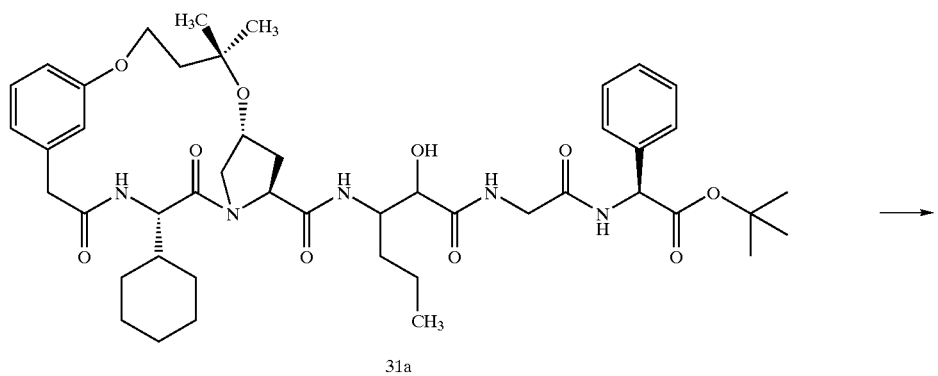
The desired compound was prepared from 31a according to the procedure of Example 1, Step K. Flash chromatography (2 to 5% MeOH/CH$_2$Cl$_2$) afforded 31 as a mixture of inseparable diastereomers.
Example 32
Preparation of Compound 32
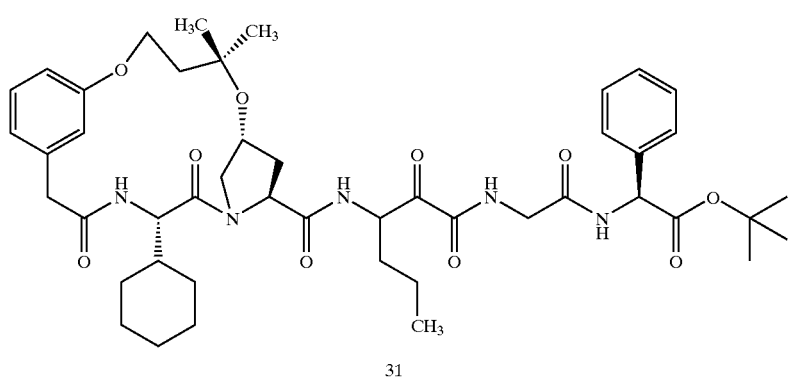
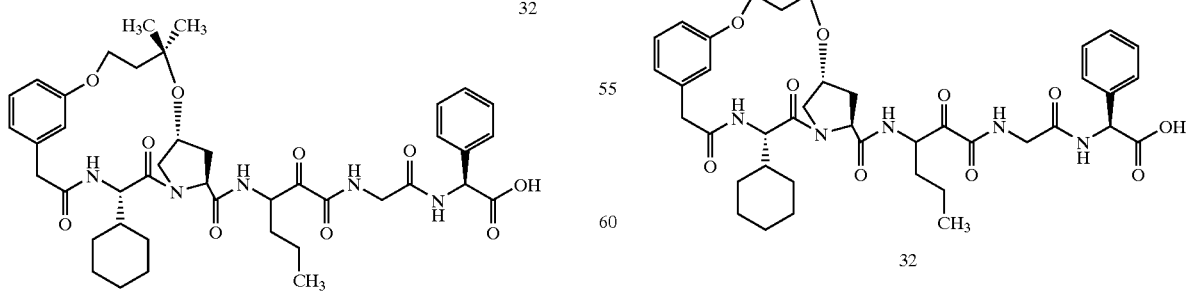
The desired compound 32 can be prepared from 31 according to the procedure of Example 3, Step A.

Example 33

Preparation of Compound 33

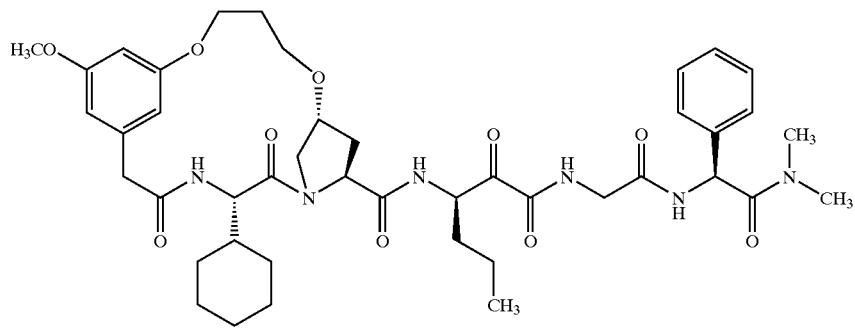

33A

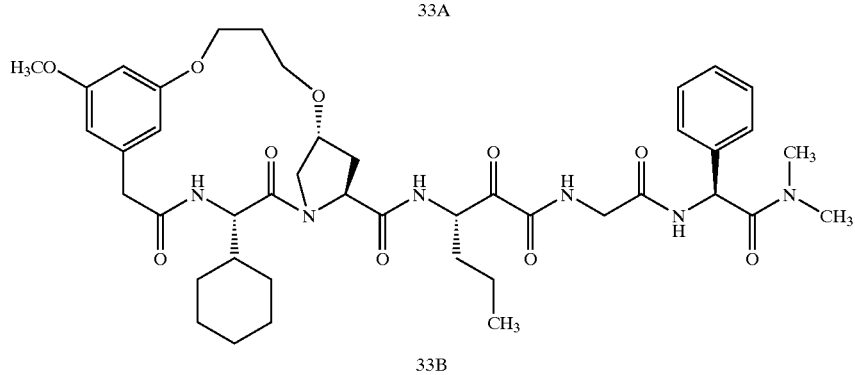

33B

Step A

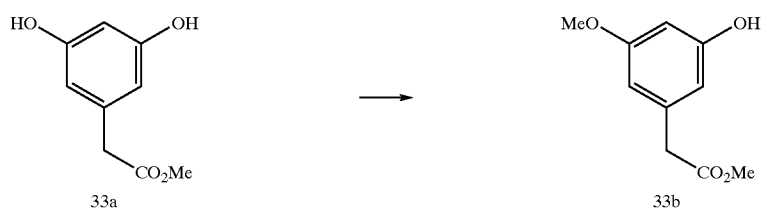

The suspension of methyl 3,5-dihydroxyphenylacetate (33a) (5.0 g, 27.4 mmol) methyl iodide (4.6 g, 32.9 mmol), potassium carbonate (5.69 g, 41.2 mmol) in DMF (30 mL) was heated to 55° C. and stirred overnight. After cooling to rt., saturated aqueous sodium bicarbonate solution (100 mL) and EtOAc (200 mL) were added and layers were separated. The aqueous solution was extracted with EtOAc (2×100 mL). The combined organic solution was dried (MgSO$_4$), filtered and concentrated in vacuo. Flash chromatography (2 to 5% MeOH/CH$_2$Cl$_2$) afforded 33b (1.11 g, 29%) as a white liquid.

Step B

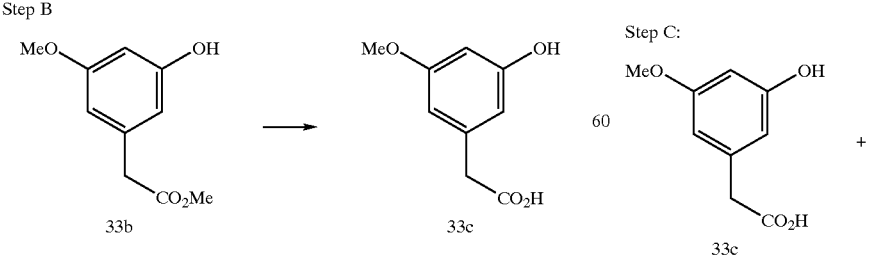

An aqueous lithium hydroxide solution (0.342 g in 10 mL H$_2$O) was added to a solution of the methyl ester 33b in THF (10 mL) and methanol (10 mL) at rt. The progress of the reaction was monitored by TLC. After 4 hr., the volatiles were removed in vacuo, EtOAc (150 mL) and water (30 mL) were added and the aqueous solution was acidified to pH=1 and saturated with solid sodium chloride. After separation of the layers, the aqueous layer was extracted with EtOAc (2×150 mL). Organic solutions were combined, dried with sodium sulfate, filtered and concentrated in vacuo to afford 33c (1.6 g).

Step C:

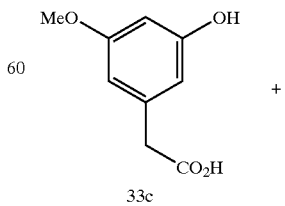

-continued

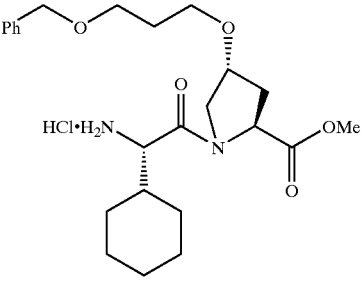

1f

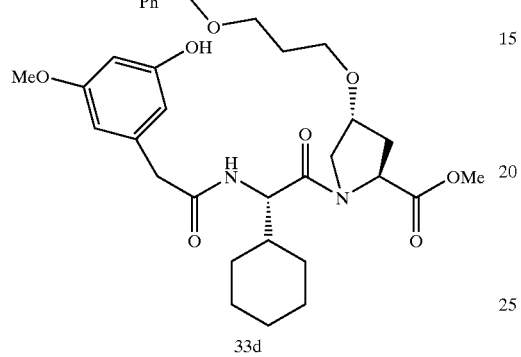

33d

The desired compound 33d was prepared from 33c and 1f according to the procedure of Example 1, Step F. Flash chromatography (2 to 5% MeOH/CH$_2$Cl$_2$) afforded 33d in 90% yield.

Step D:

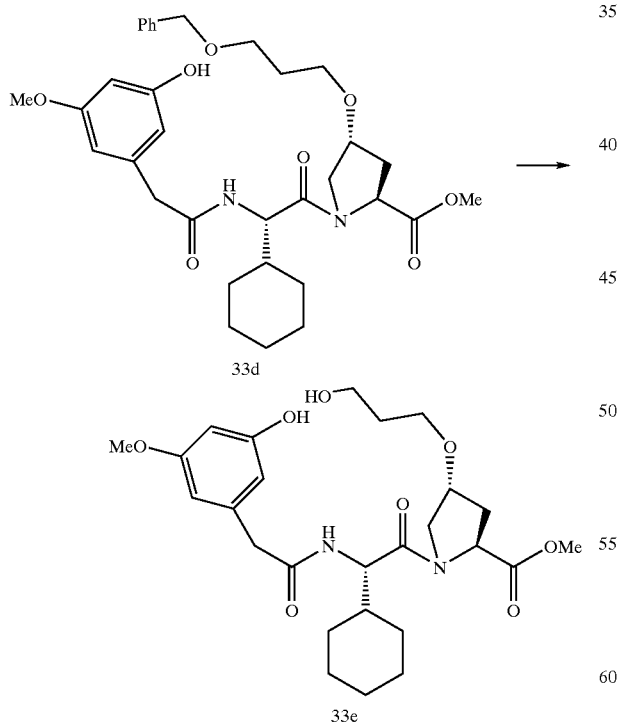

The desired compound 33e was prepared from 33d according to the procedure of Example 1, Step G. Flash chromatography (2 to 5% MeOH/CH$_2$Cl$_2$) afforded 33e in 56% yield.

Step E:

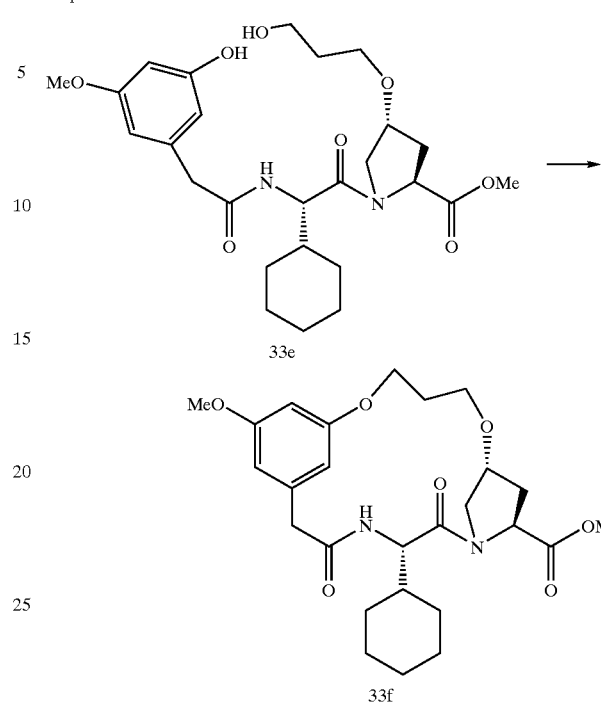

33e

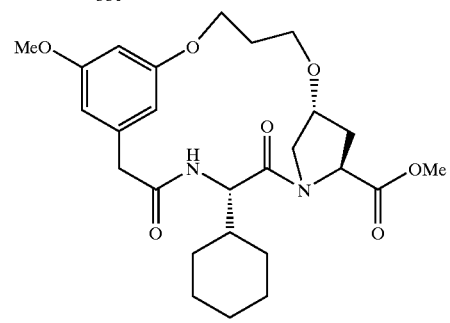

33f

The desired compound 33f was prepared from 33e according to the procedure of Example 1, Step H. Flash chromatography (2 to 5% MeOH/CH$_2$Cl$_2$) afforded 33e as a mixture with triphenylphosphine oxide which was used in the next reaction without further purification.

Step F:

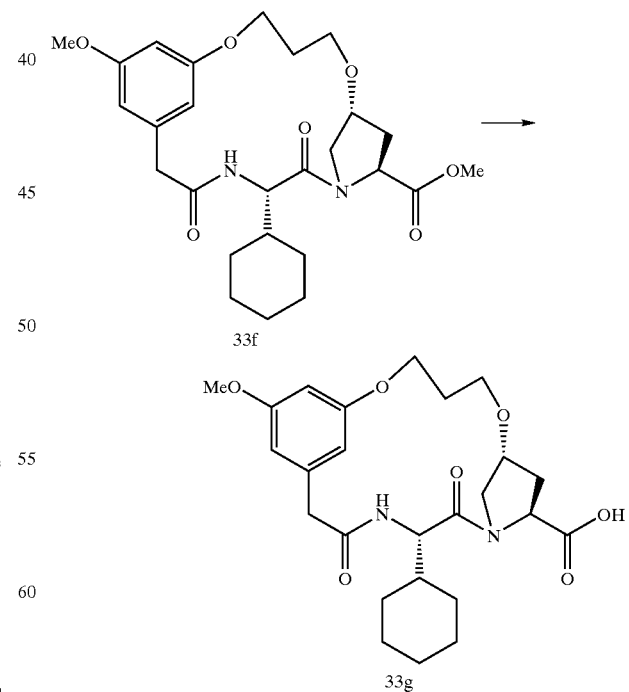

The desired compound 33g was prepared from 33f in 45% yield (2 steps) according to the procedure of Example 1, Step I.
Step G:
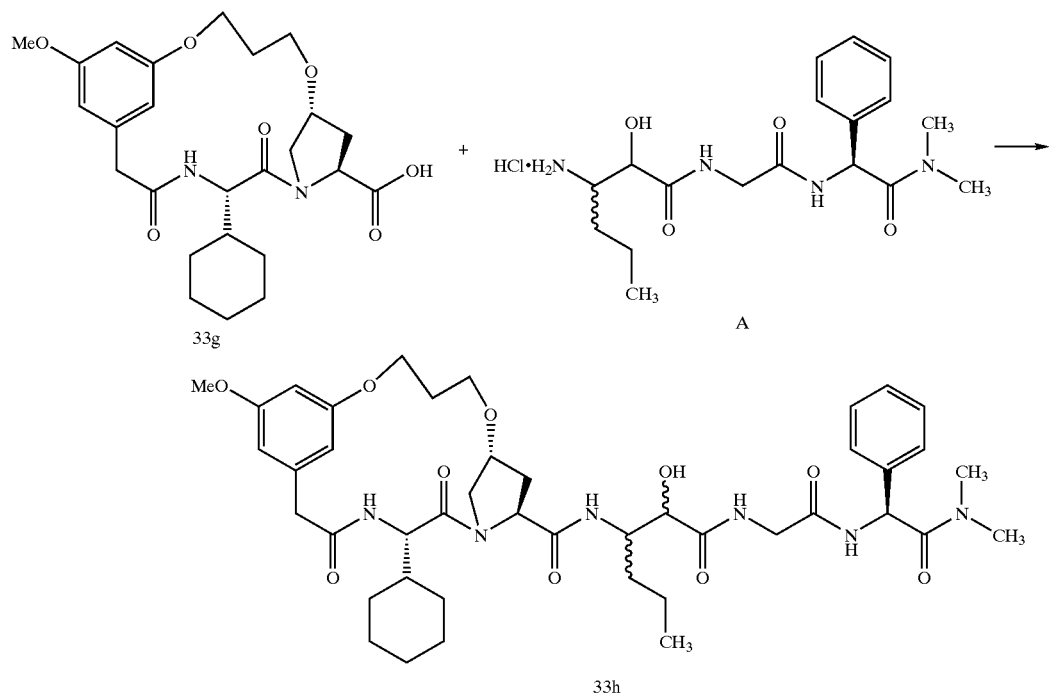
The desired compound 33h is prepared from 33g and A according to the procedure of Example 1, Step J.
Step H:
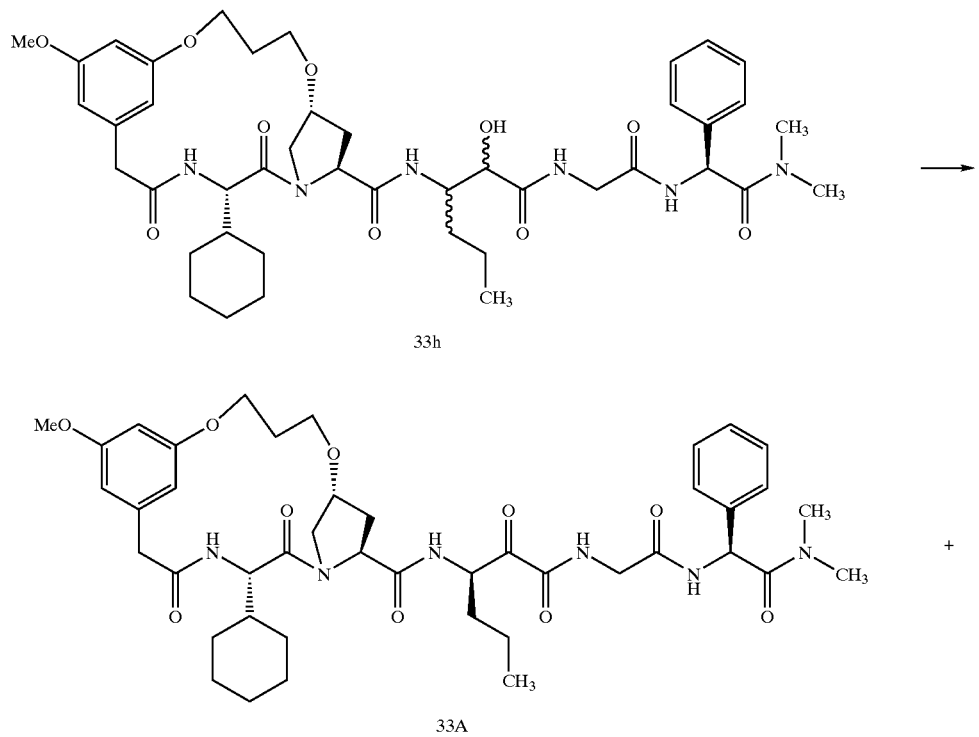

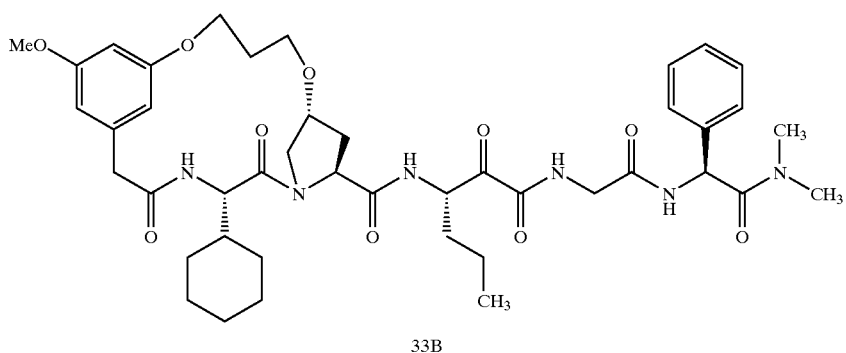
33B
The desired compounds are prepared from 33h according to the procedure of Example 1, Step K.
Example 34
Preparation of Compound 34
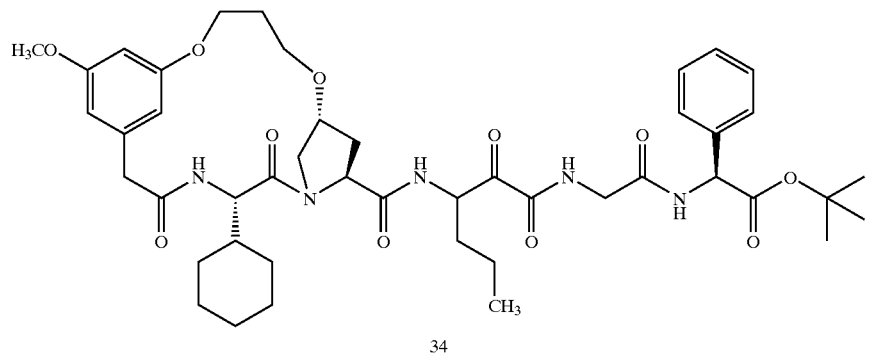
34
Step A:
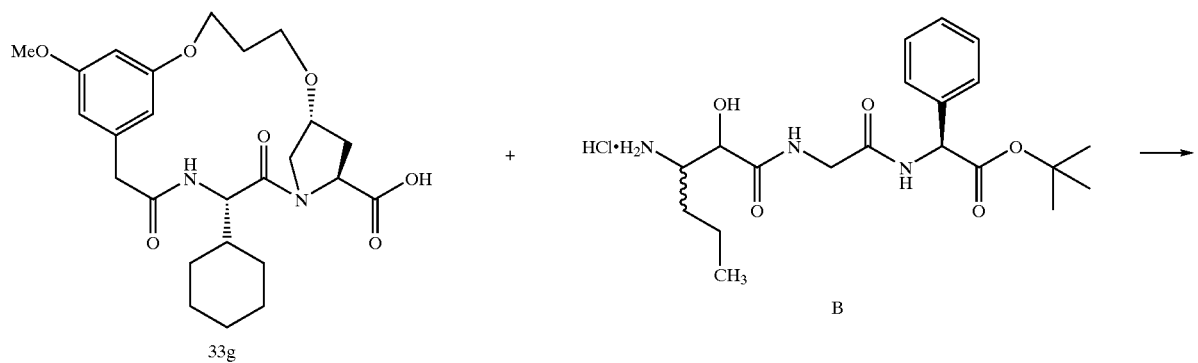

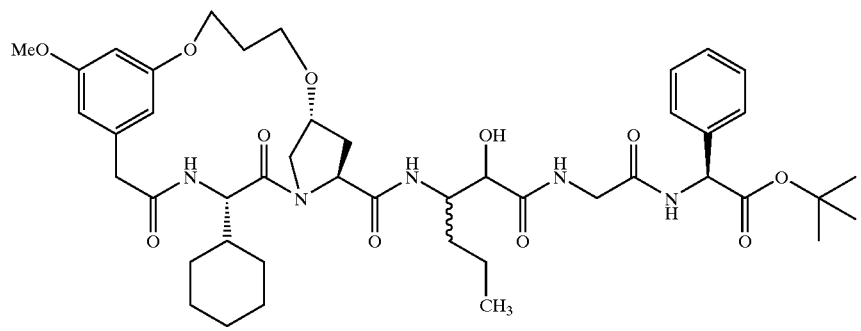
34a
The desired compound 34a is prepared according to the method of Example 1, Step J, except substituting amine B for amine A. The product is obtained as a mixture of inseparable diastereomers.
Step B:
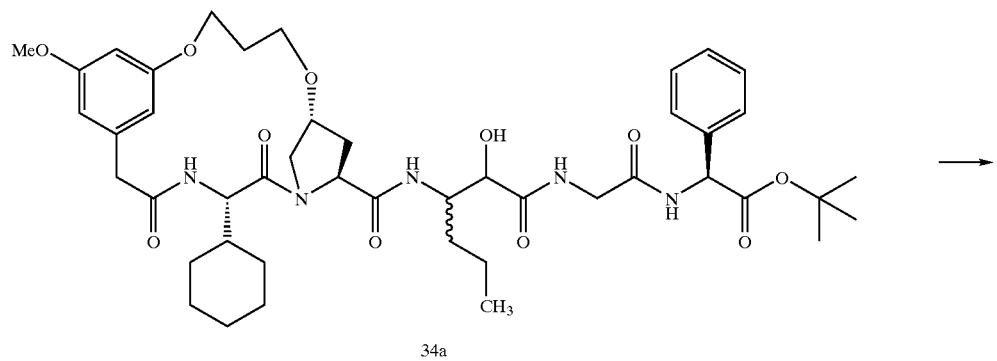
34a
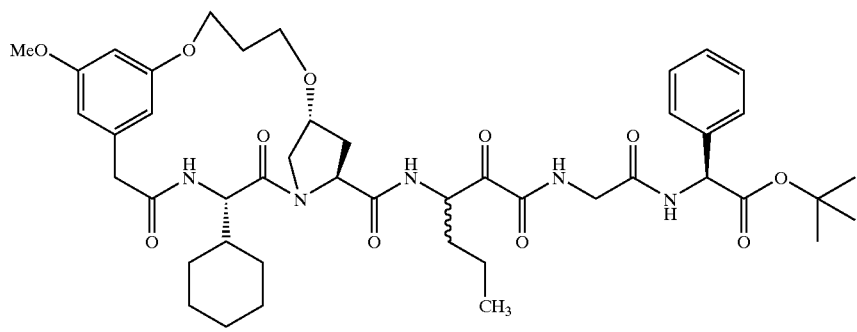
34
The desired compound is prepared from 34a according to the method of Example 1, Step K.

Example 35

Preparation of Compound 35

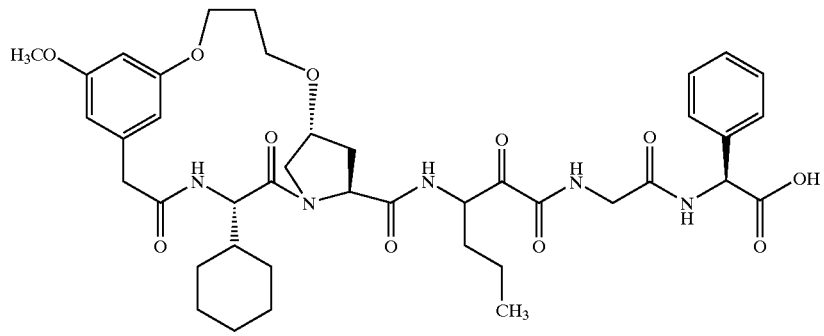

Step A:

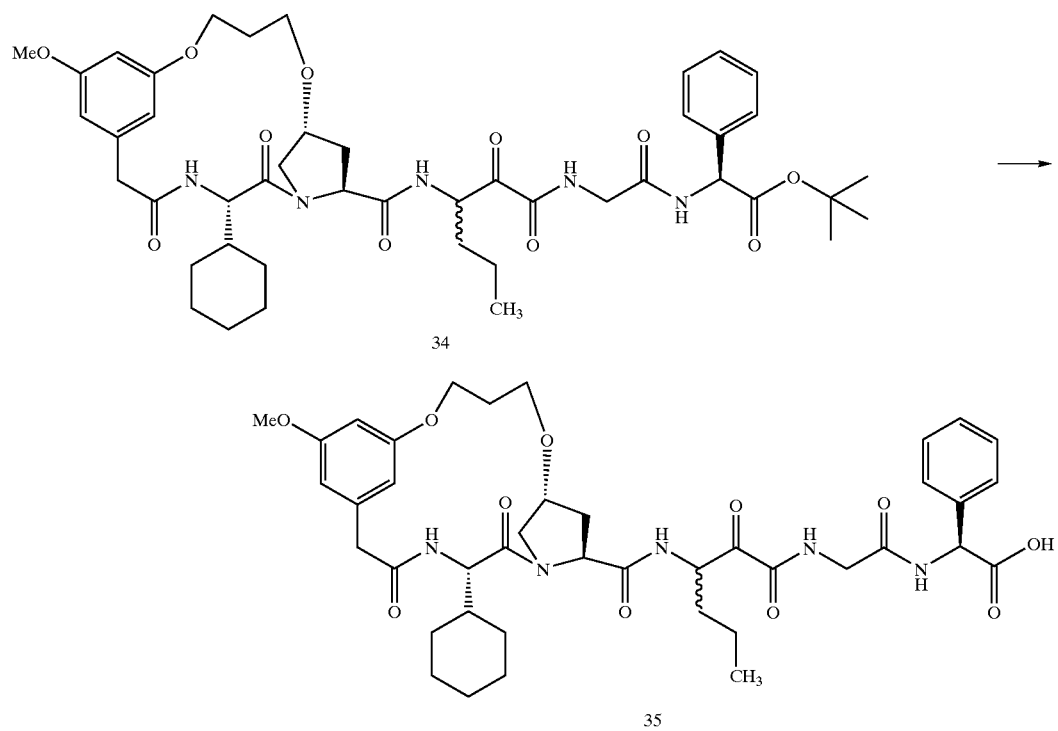

The desired compound 35 is prepared from 34 according to the method of Example 3, Step A.

Example 36

Preparation of Compound 36

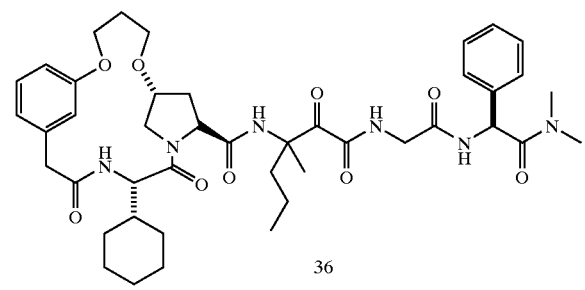

-continued

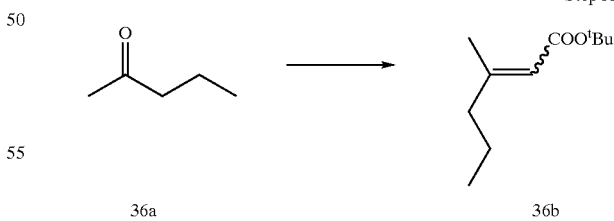

A solution of tert-butyl phosphonoacetate (15.1 g, 50.0 mmol) in dry THF was cooled to 0° C. and treated with NaH (60%, 2.5 g, 62.5 mmol, 1.25 equiv.) and stirred for 20 min. The reaction mixture was treated with 2-pentanone (4.3 g, 50 mmol) and stirred at rt. for 24 h. The reaction mixture was diluted with aq. NaHCO$_3$ and extracted into ether (3×100 mL). The combined ether layer were extracted with brine, dried (MgSO$_4$), concentrated in vacuo and distilled to yield 8.2 g (88%) of 36b (stereochemical ratio 2:1).

Step B

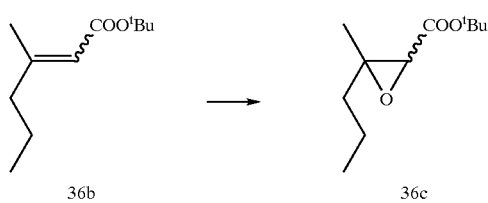

A solution of 36b (5.0 g, 27.1 mmol) was dissolved in dichloroethane and treated with 4,4'-thiobis-(2-tert-butyl-5-methylphenol) (100 mg) and MCPBA (60–80%, 7.76 g, 27.1 mmol) and heated at reflux for 4 h. The reaction mixture was concentrated in vacuo and the residue was diluted with ether (200 mL) The ether layer was washed twice with satd aq $Na_2S_2O_3$, aq. NaOH and brine (100 ml). The reaction mixture was concentrated in vacuo to yield 4.2 g (77%) of 36c which was used as it is in the next step.

Step C

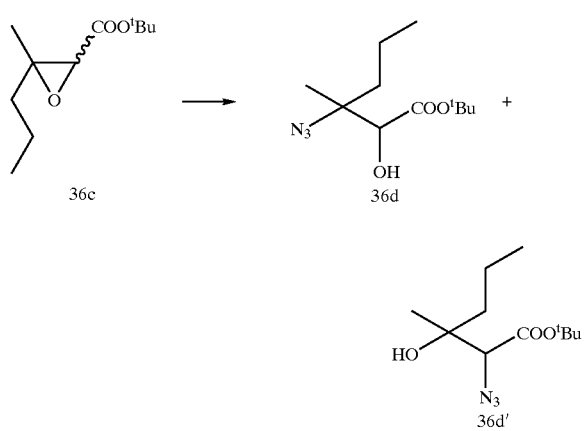

A solution of epoxide (4.0 g, 18.4 mmol) in dry ethanol (100 mL) was treated with $NaN_3$ (12 g, 184 mmol) and $NH_4Cl$ (9.6 g. 184 mmol) and heated at reflux for 36 h. The reaction mixture was diluted with water and the reaction mixture was extracted with ether (300 mL). The combined organic layers were dried with $Na_2SO_4$ and concentrated. The residue was purified by $SiO_2$ chromatography (EtOAc/Hex 1:19) to yield 1.1 g (28%) of 36d and 731 mg (18%) of 36d' as a colorless liquid.

Step D

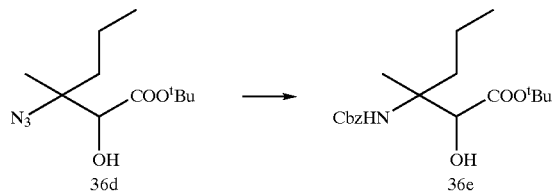

A solution of azide 36d (2.1 g, 8.7 mmol) was dissolved in $CH_3OH$ (100 mL) and treated with Pd/C (50 mg) and hydrogenated (40 psi) for 24 h. The reaction mixture was filtered through a plug of celite and the filtrate was concentrated in vacuo. The residue was used for next reaction without further purification.

A solution of Cbz—Cl (1.48 g, 8.7 mmol, 1.23 mL) was added dropwise to a mixture of amine and Et3N (878 mg, 1.25 mL) at −78° C. in $CH_2Cl_2$ (30 mL). The reaction mixture was warmed to rt. and concentrated in vacuo. The residue was chromatographed on $SiO_2$ (EtOAc/Hex 8:2) to 36e (450 mg, 15%) as a colorless solid.

Step E

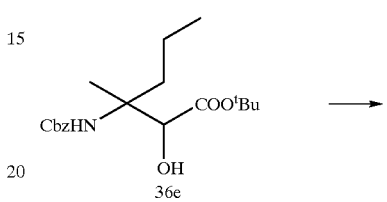

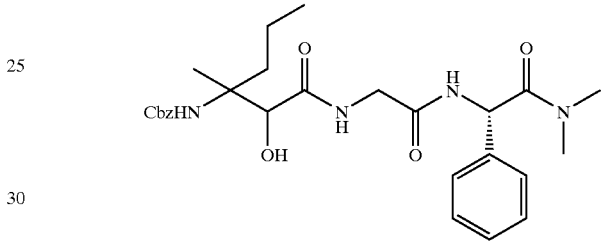

A solution of 36e (450 mg, 1.29 mmol) in $CH_2Cl_2$/TFA (10 mL, 1:1) was stirred at rt. for 4 h. The reaction mixture was concentrated in vacuo to obtain the acid (250 mg) which was used in the next step without further purification.

The acid obtained by hydrolysis of 36e was dissolved in $CH_2Cl_2$ (10 mL) at −20° C. and treated with H-Glycyl-Phenylglycycl-N$(CH_3)_2$ (281 mg, 0.93 mmol), HOOBt (208 mg, 1.27 mmol, 1.25 equiv.) EDCl (244 mg, 1.27 mmol) and NMM (343 mg, 3.4 mmol, 490 μL). The reaction mixture was stored in the freezer for 24 h and diluted with aq. HCl (1 M, 50 mL). The reaction mixture was extracted with $CH_2Cl_2$ (3×50 mL). The combined organic layers were extracted with aq. HCl (1M, 100 mL), aq. $NaHCO_3$ (1M, 100 mL), brine (100 ml), dried ($MgSO_4$), filtered and concentrated in vacuo and chromatographed on $SiO_2$ (acetone/Hexanes 1:3) to yield 36f (330 mg, 75%) as a colorless solid.

Step F

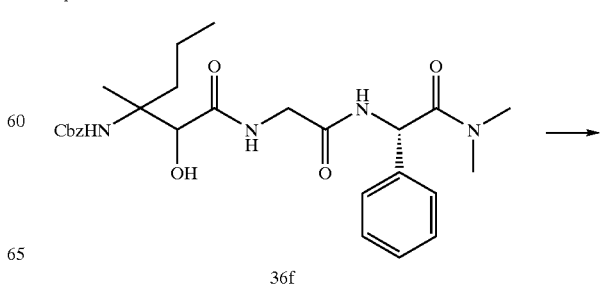

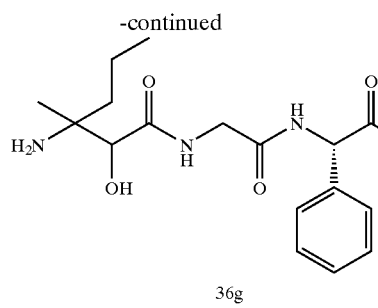

36g

A solution of 36f is dissolved in CH₃OH (20 mL) and treated with Pd/C reaction mixture will be hydrogenated at 40 psi for 12 filtered through a plug of Celite and the filtrate is directly used in the next step.

Step G

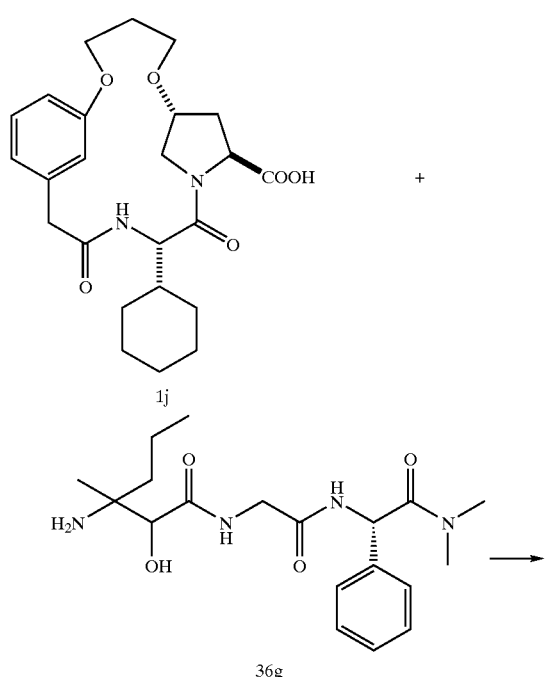

The expected product 36h is synthesized as described earlier for the Example 1, Step J. The coupled material will be used directly for the next step to synthesize 36A and 36 B.

Step H

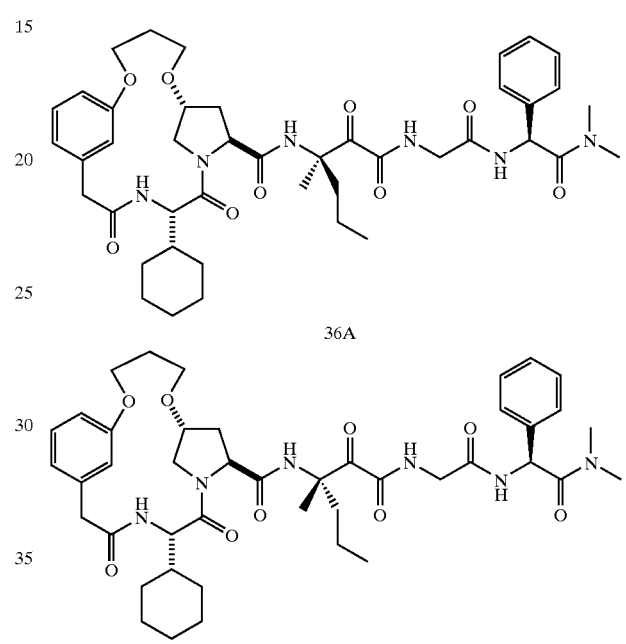

The desired products 36A and 36B are obtained by the oxidation protocol described previously for Example 1, Step K.

Example 37

Preparation of Compound 37

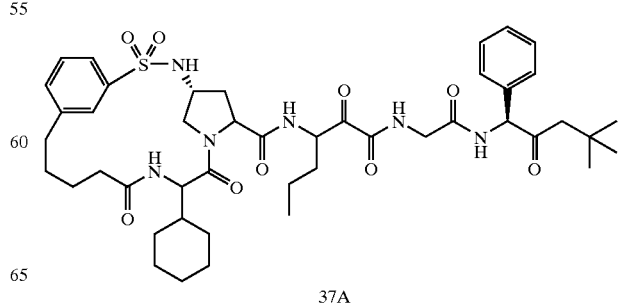

37A

-continued

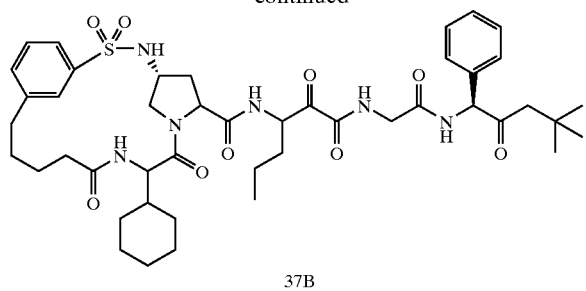

37B

Step A

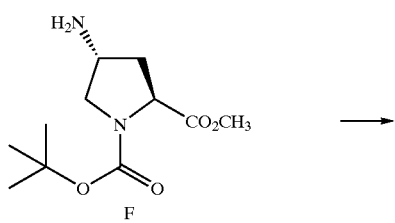

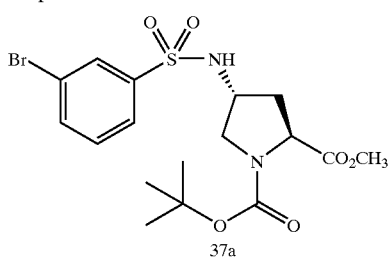

37a

To a cold (0° C.) solution of F (2.3 g g, 9.43 mmol) in dichloromethane (20 mL) was added triethylamine (3.97 mL, 28.28 mmol), DMAP (few crystals) and 3-bromobenzenesulfonyl chloride (3.61 g, 14.14 mmol). The reaction mixture was left standing in the refrigerator (0°–5° C.) overnight. The reaction mixture was washed with saturated NaHCO$_3$, and 10% citric acid solution. The organic layer was dried (Na$_2$SO$_4$) and concentrated. The residue was purified by flash chromatography using 95/5 to 90/10 dichloromethane/EtOAc to afford 2.7 g (62% yield) of 37a. HRMS (FAB) Calcd for C$_{17}$H$_{24}$N$_2$O$_6$SBr: 465.0518 (M+H)$^+$. Found: 465.0497.

Step B

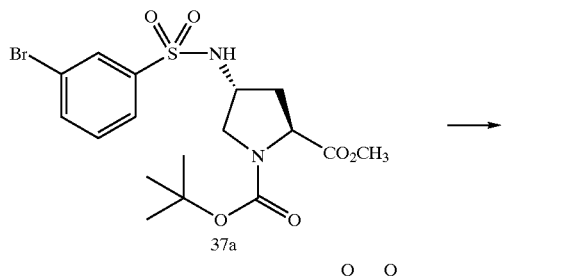

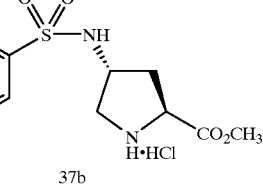

37b

The desired product 37b was obtained by the method described for Example 1, Step C. The crude material was used in the next step without purification.

Step C

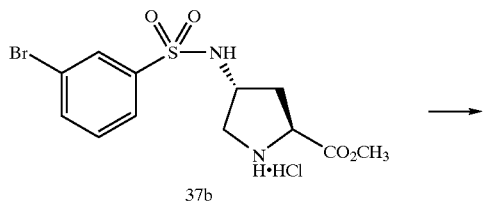

37b

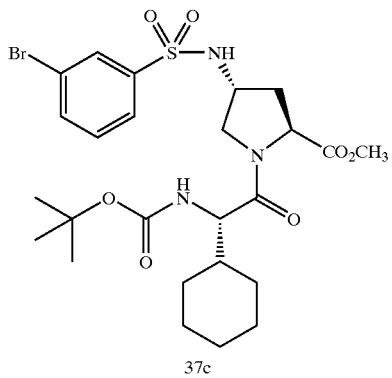

37c

The desired product 37c was obtained by the method described for Example 1, Step D in 97% yield. The material after workup was pure enough to be carried forward.

Step D

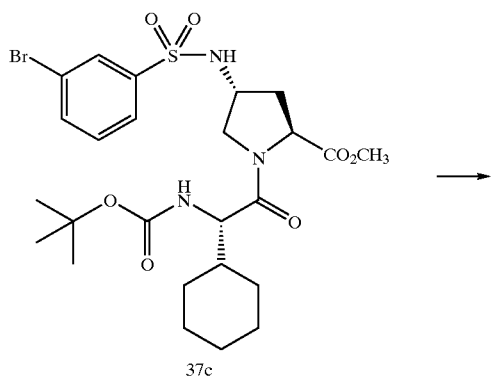

37c

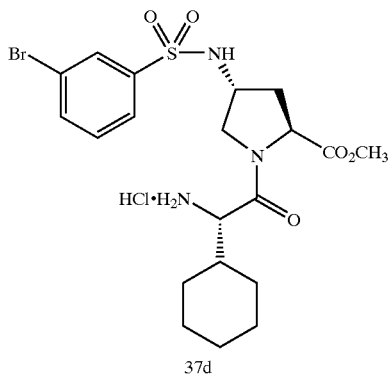

37d

The desired product 37d was obtained by the method described for Example 1, Step E. The crude material was used in the next step without purification.

Step E

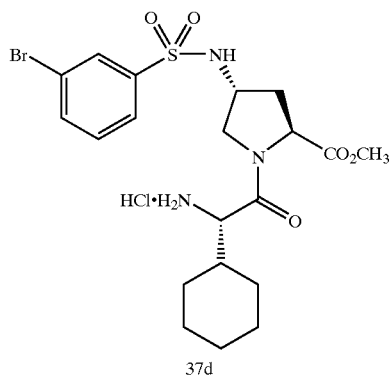

37d

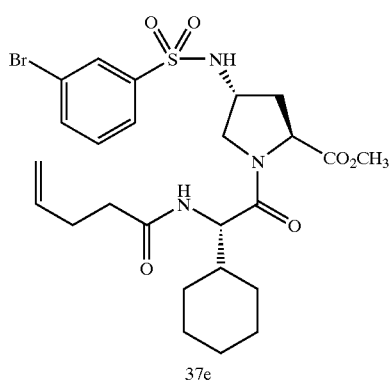

37e

The desired product 37e was obtained by the method described for Example 1, Step F using pentenoic acid as the coupling partner. Purification of the residue by column chromatography using 90/10 to 80/20 dichloromethane/EtOAc provided 35% yield of 37e. HRMS (FAB) Calcd for $C_{25}H_{35}N_3O_6SBr$: 586.1409 (M+H)$^+$. Found: 586.1423.

Step F

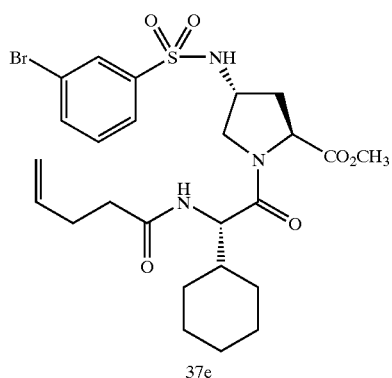

37e

-continued

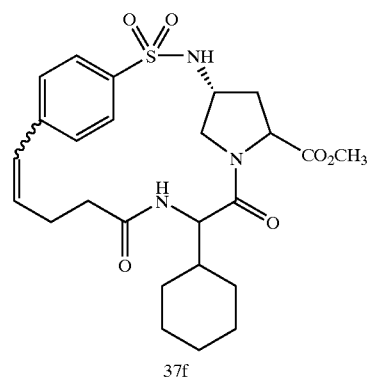

37f

To a stirred solution of 37e (660 mg, 1.13 mmol) in DMF (10 mL) under nitrogen atmosphere was added triethylamine (3.61 mL, 32.77 mmol), potassium carbonate (780 mg, 5.65 mmol), tetrabutylammonium bromide (730 mg, 2.26 mmol), and palladium (II) acetate (33 mg, 0.15 mmol). the mixture was heated at 100° C. for 2 hrs. The reaction mixture was cooled to room temperature, diluted with EtOAc and washed with 5% phosphoric acid solution. The organic layer was separated, dried (Na$_2$SO$_4$) and concentrated to provide 280 mg (49% yield) of 37f as a mixture of diastereomers. This material was pure enough to be carried to the next step. HRMS (FAB) Calcd for $C_{25}H_{34}N_3O_6S$: 504.2168 (M+H)$^+$. Found: 504.2155.

Step G

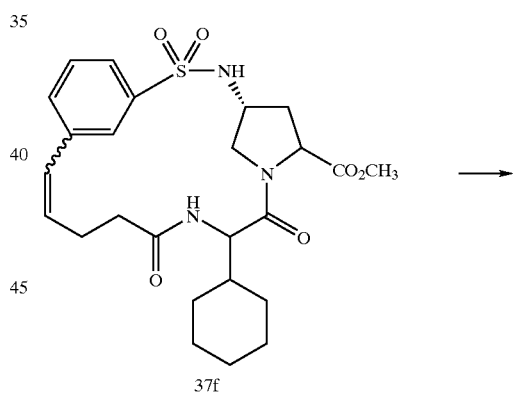

37f

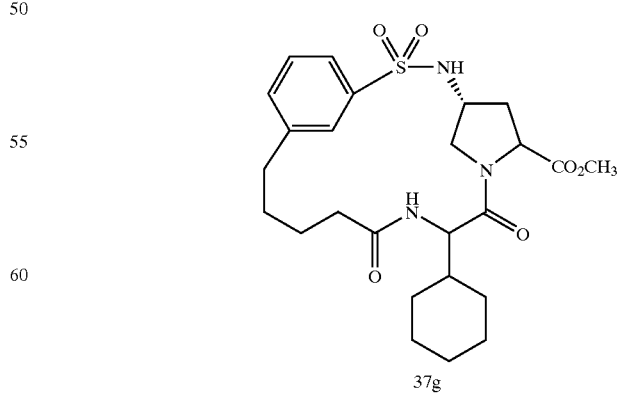

37g

The desired product 37g was obtained by the hydrogenation procedure described for Example 1, Step G in 73% yield. The material was sufficiently pure for further studies. HRMS (FAB) Calcd for $C_{25}H_{36}N_3O_6S$: 506.2325 $(M+H)^+$. Found: 506.2314.

Step H

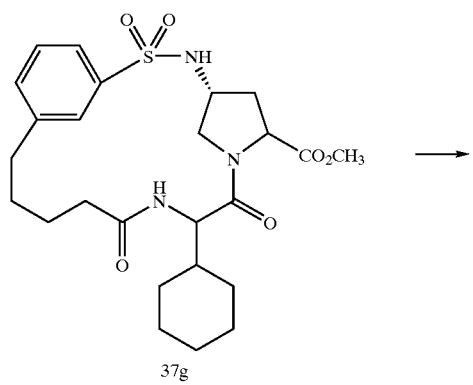

37g

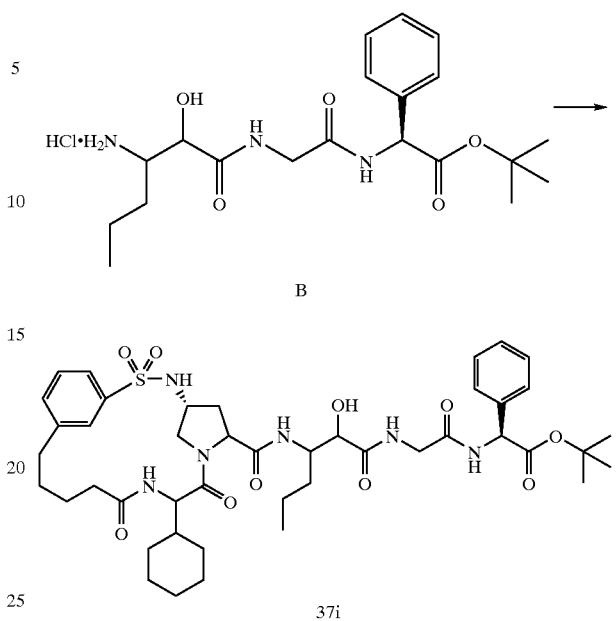

B

37i

The expected product 37i was obtained by the procedure described for Example 2, Step A in 90% yield. The crude material was sufficiently pure for further studies. HRMS (FAB) Calcd for $C_{44}H_{63}N_6O_{10}S$: 867.4326 $(M+H)^+$. Found: 867.4342.

Step J

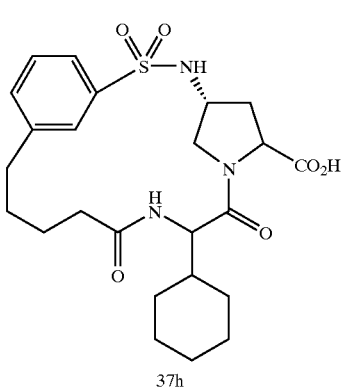

37h

The desired product 37h was obtained by the procedure described for Example 1, Step H in 84% yield. HRMS (FAB) Calcd for $C_{24}H_{34}N_3O_6S$: 492.2168 $(M+H)^+$. Found: 492.2175.

Step I

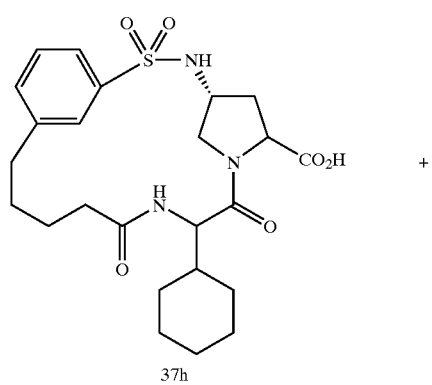

37h

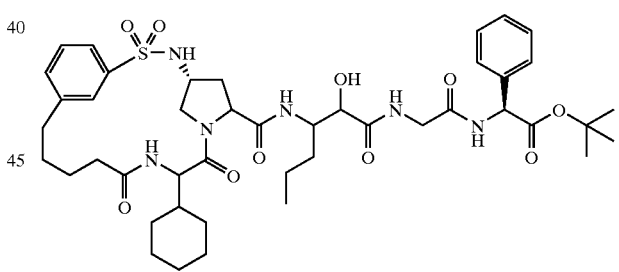

37i

↓

37A

+

245
-continued

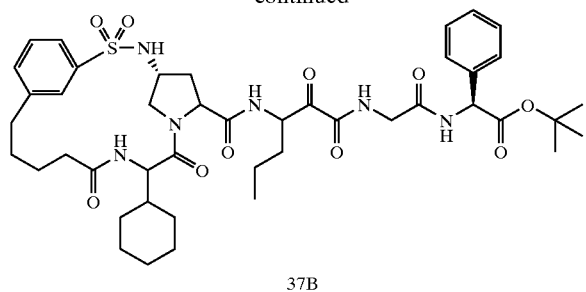
37B

The desired materials 37A and 37B were synthesized by the oxidation protocol described for Example 2, Step B. Purification of the residue using 98/2 to 96/4 dichloromethane/MeOH afforded 37A (61%, less polar) and 37B (15%, more polar) as a mixture of diastereomers. HRMS (FAB) Calcd for $C_{44}H_{61}N_6O_{10}S$: 865.4170 (M+H)$^+$. Found: 865.4190 (37A), 865.4181 (37B).

Example 38

Preparation of Compound 38

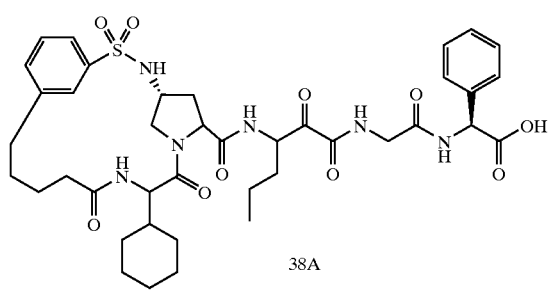
38A

Step B

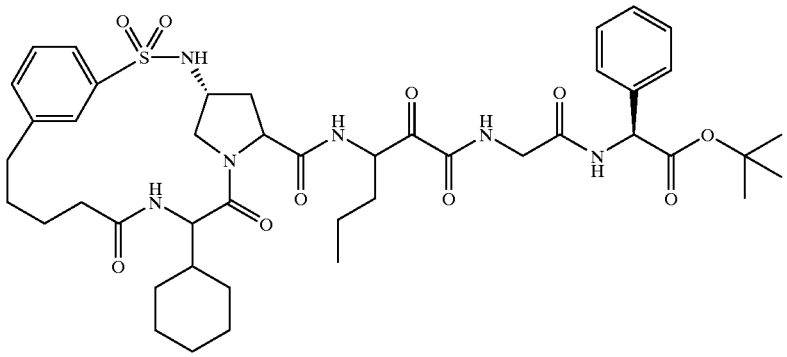
37B

246
-continued

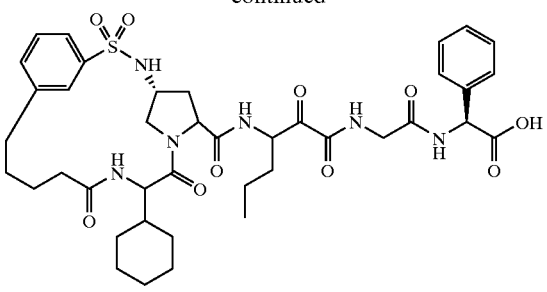
38B

Step A

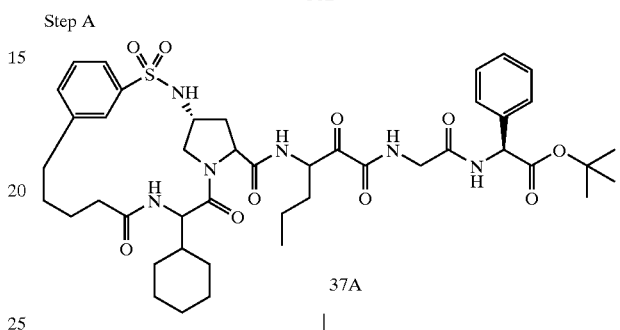
37A

↓

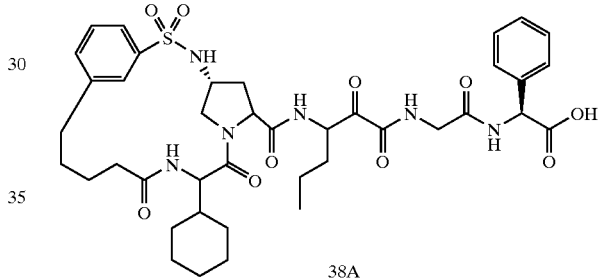
38A

The desired material 38A was synthesized as described for Example 3, Step A in 91% yield.

-continued

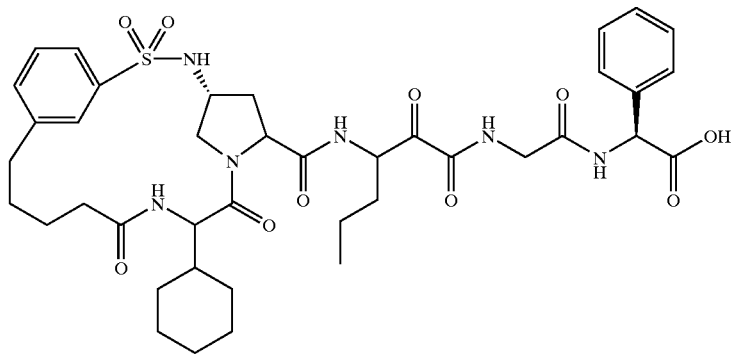

38B

The desired material 38B was synthesized as described for Example 3, Step A in 83% yield. HRMS (FAB) Calcd for $C_{40}H_{53}N_6O_{10}S$: 809.3544 $(M+H)^+$. Found: 809.3547.

Example 39

Preparation of Compound 39

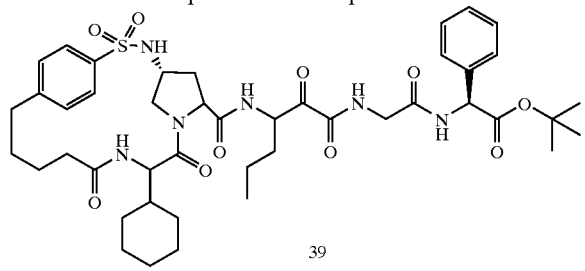

39

Step A

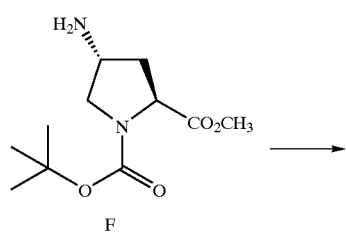

F

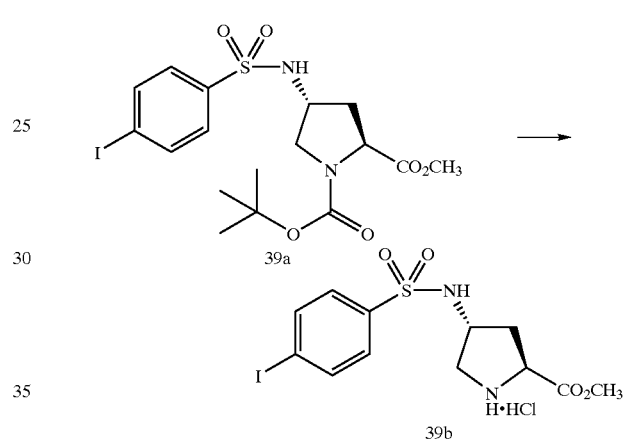

39a

The desired product 39a was obtained by the method described for Example 37, Step A using pipsyl chloride instead of 3-bromobenzenesulfonyl chloride. Purification of the residue by column chromatography using 95/5 to 90/10 dichloromethane/EtOAc provided 75% yield of 39a. HRMS (FAB) Calcd for $C_{17}H_{24}N_2O_6SI$: 511.0400 $(M+H)^+$. Found: 511.0386.

Step B

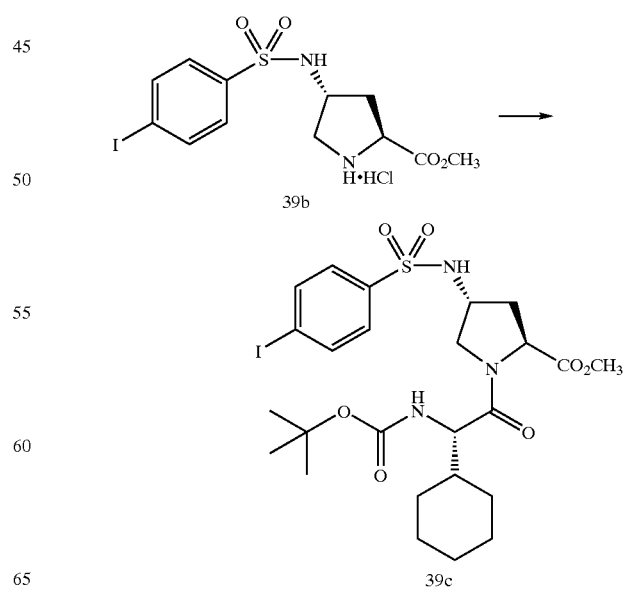

39b

The desired product 39b was obtained by the method described for Example 1, Step C. The crude material was used in the next step without purification.

Step C

39c

The desired product 39c was obtained by the method described for Example 1, Step D. Purification of the residue by column chromatography using 90/10 to 80/20 dichloromethane/EtOAc provided 68% yield of 39c. HRMS (FAB) Calcd for $C_{25}H_{37}N_3O_7SI$: 650.1397 (M+H)$^+$. Found: 650.1398.

Step D

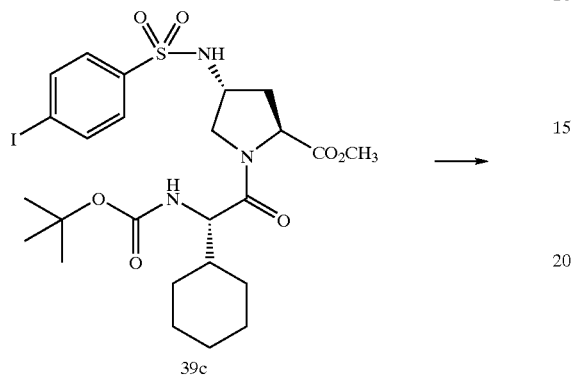

39c

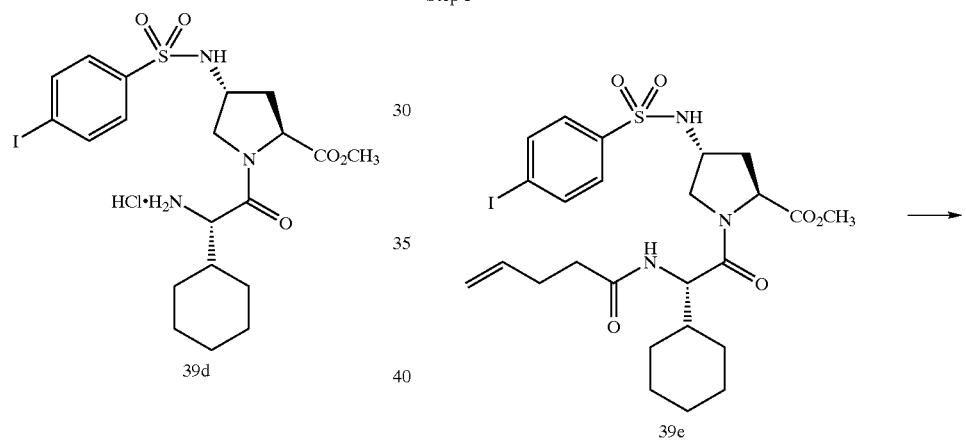

39d

The desired product 39d was obtained by the method described for Example 1, Step E. The crude material was used in the next step without purification.

Step E

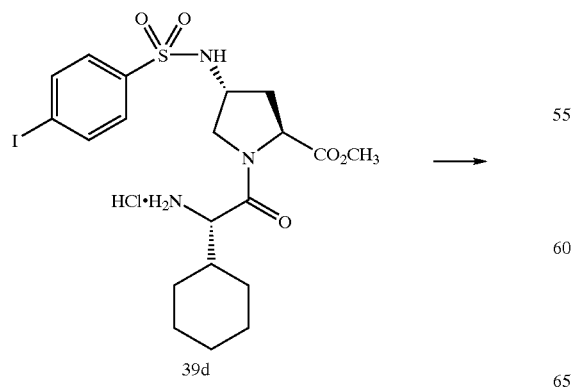

39d

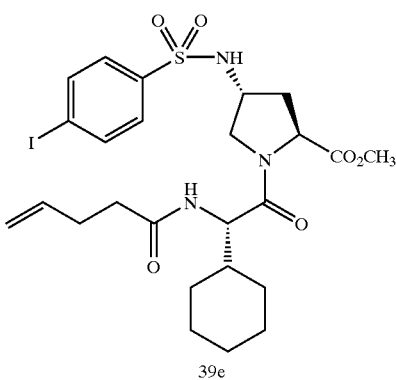

39e

The desired product 39e was obtained by the method described for Example 1, Step F using pentenoic acid as the coupling partner. Purification of the residue by column chromatography using 98/2 dichloromethane/MeOH provided 76% yield of 39e.

Step F

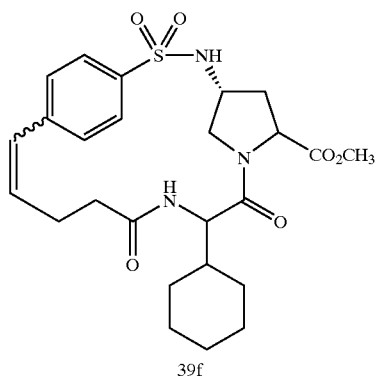

39f

The desired product 39f was obtained by the method described for Example 37, Step F. Purification of the residue by column chromatography using 98/2 dichloromethane/MeOH provided 28% yield of 39f as a mixture of diastereomers. HRMS (FAB) Calcd for $C_{25}H_{34}N_3O_6S$: 504.2168 (M+H)$^+$. Found: 504.2160.

Step G

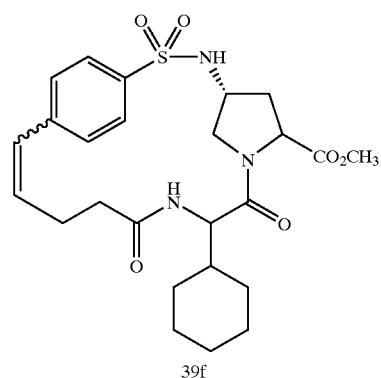

Step H

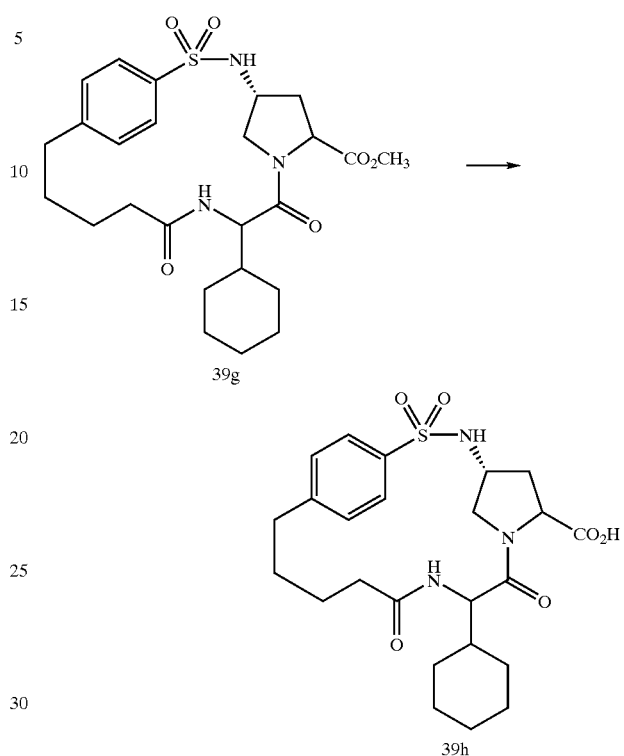

Found: 506.2314.

The desired product 39g was obtained by the hydrogenation procedure described for example 1, Step G in 84% yield. The material was sufficiently pure for further studies. HRMS (FAB) Calcd for $C_{25}H_{36}N_3O_6S$: 506.2325 (M+H)$^+$.

the desired product 39h was obtained by the procedure described for Example 1, Step H in quantitative yield. HRMS (FAB) Calcd for $C_{24}H_{34}N_3O_6S$: 492.2168 (M+H)$^+$. Found: 492.2175.

Step I

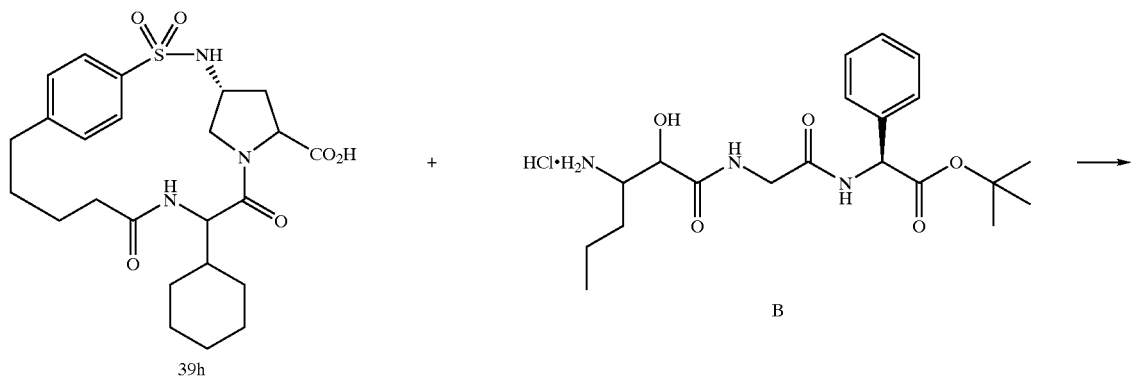

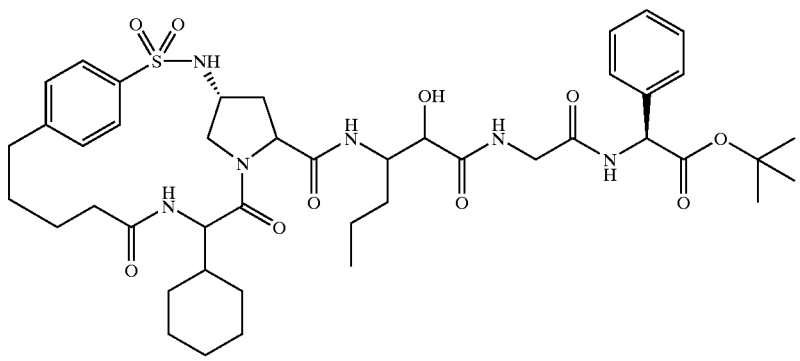

39i

The expected product 39i was obtained by the method described for Example 2, Step A in 36% yield. The crude material was sufficiently pure for further studies. HRMS (FAB) Calcd for $C_{44}H_{63}N_6O_{10}S$: 867.4326 (M+H)$^+$. Found: 867.4342.

Step J

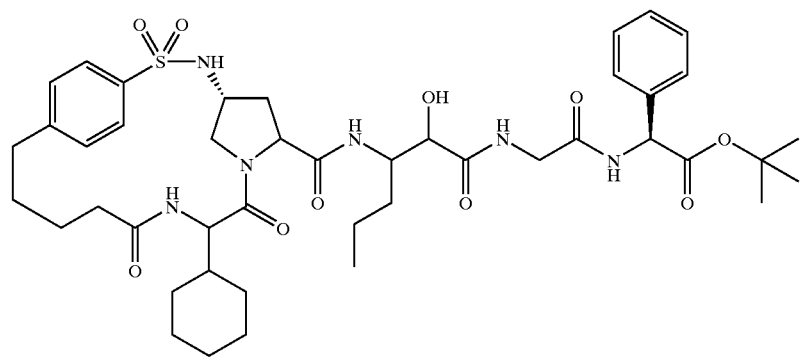

39i

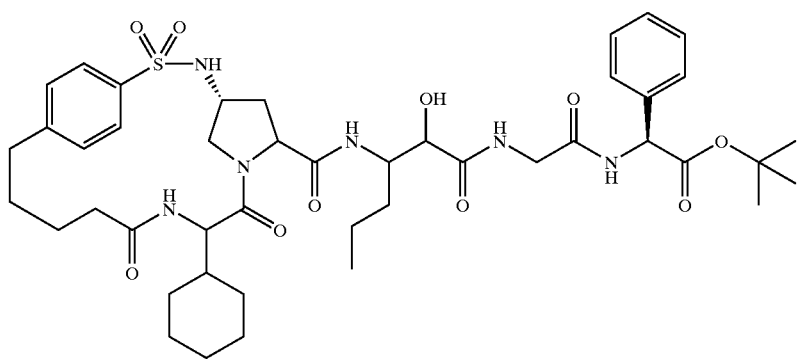

39

The desired material 39 was obtained by the oxidation protocol described for Example 2, Step B. Purification of the residue using 98/2 dichloromethane/MeOH afforded 39 in 24% yield as a mixture of diastereomers. HRMS (FAB) Calcd for $C_{44}H_{61}N_6O_{10}S$: 865.4170 (M+H)$^+$. Found: 865.4181.

Example 40

Preparation of Compound 40

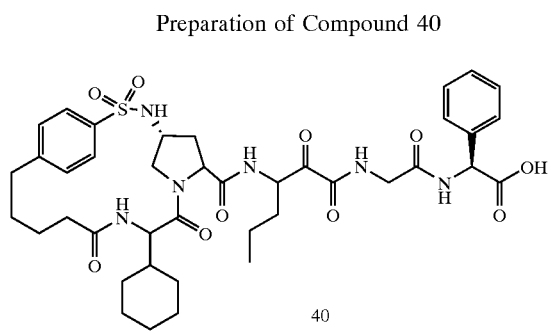

Step A

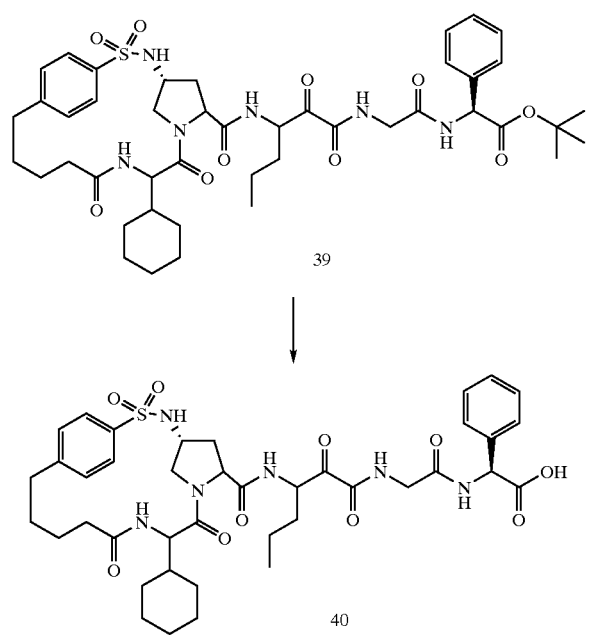

The desired material 40 was obtained by the procedure described for Example 3, Step A in 93% yield as a mixture of diastereomers. HRMS (FAB) Calcd for $C_{40}H_{53}N_6O_{10}S$: 809.3544 (M+H)$^+$. Found: 809.3544.

Example 41

Preparation of Compound 41

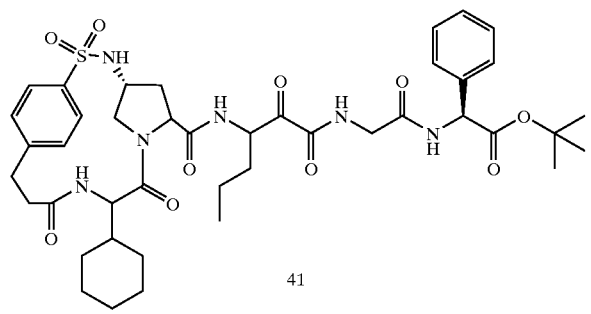

Step A

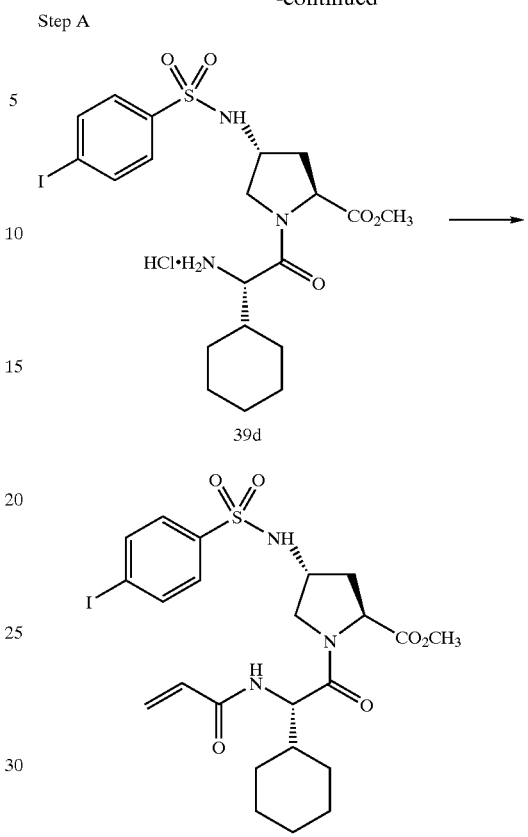

To a 25 mL addition funnel was added benzene (5 mL), DMF (0.32 mL, 4.1 mmol), and thionyl chloride (0.33 mL, 4.5 mmol). After 5 minutes two layers appeared. The lower layer was separated and added slowly to a cooled (0–5° C.) solution of acrylic acid (0.19 mL, 2.8 mmol) in dichloromethane. The mixture was maintained at that temperature for 10 minutes. Then triethylamine (0.77 mL, 5.5 mmol) was added followed by 39d (1.13 g, 2.1 mmol). The reaction mixture was warmed to ambient temperature over 5 hrs and quenched with saturated $NaHCO_3$. The organic layer was separated, washed with 5% $H_3PO_4$ solution and brine. The dichloromethane layer was dried ($Na_2SO_4$), and concentrated. The crude material was purified by flash column chromatography using 98/2 dichloromethane/MeOH to provide 870 mg of 41a (67% yield). HRMS (FAB) Calcd for $C_{23}H_{31}N_3O_6SI$: 604.0978 (M+H)$^+$. Found: 604.0964.

Step B

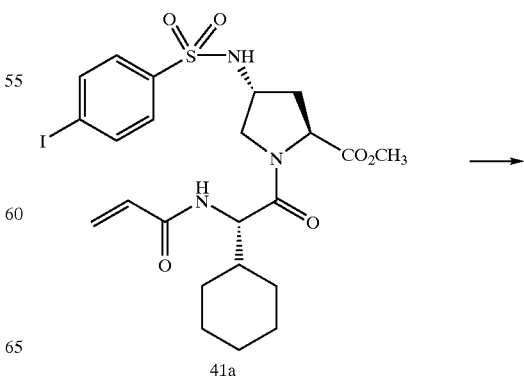

-continued

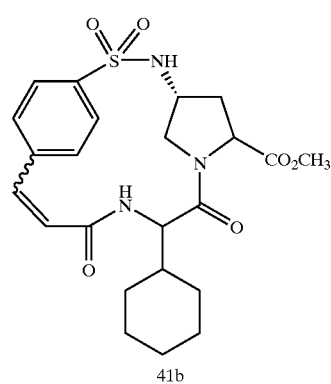
41b

The desired product 41b was obtained by the method described for Example 37, Step F. The residue was purified using 97/3 dichloromethane/MeOH to afford 41b in 26% yield. HRMS (FAB) Calcd for $C_{23}H_{30}N_3O_6S$: 476.1855 $(M+H)^+$. Found: 476.1858.

Step C

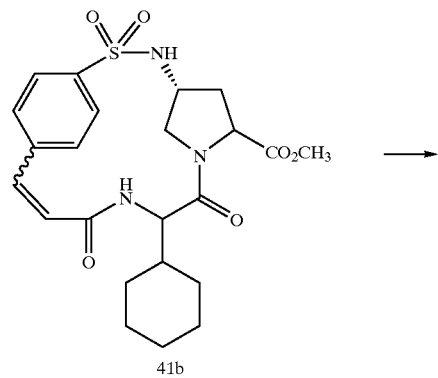
41b

→

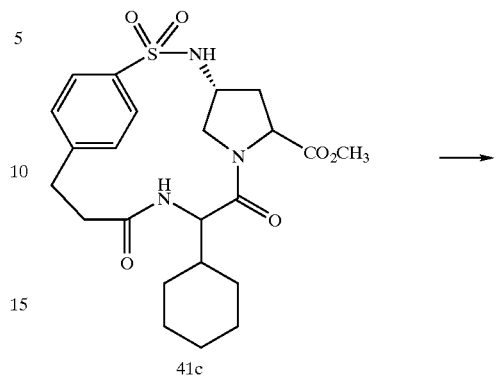
41c

The desired product 41c was obtained by the hydrogenation method described for Example 1, Step D in 75% yield. The material was sufficiently pure for further studies.

Step D

41c

→

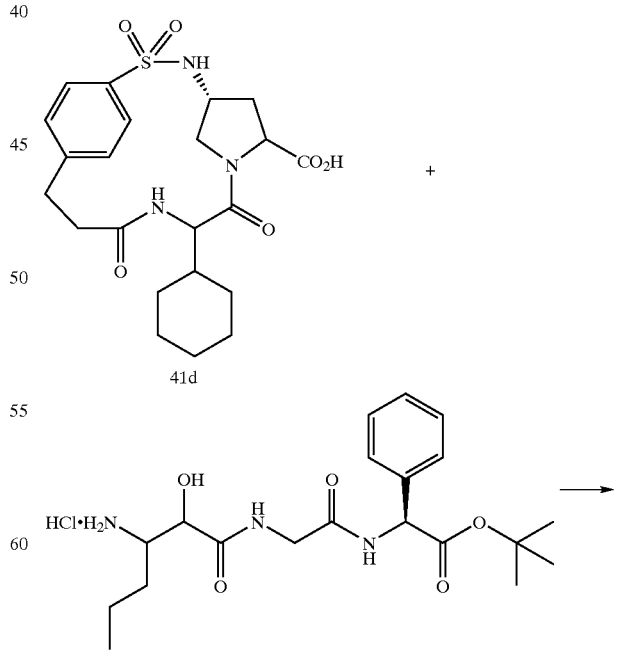
41d

The desired product 41d was obtained by the method described for Example 1, Step E. The crude material was used in the next step without purification.

Step E

41d

+

B

-continued

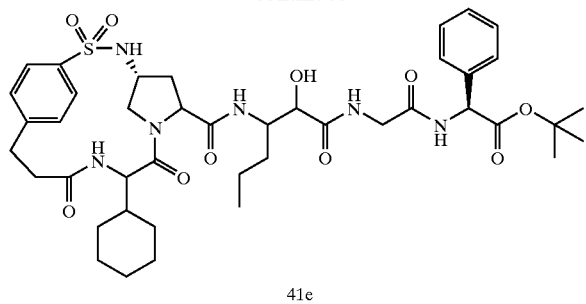

41e

The expected product 41e was obtained by the method described for Example 2, Step A in 63% yield. The crude material was sufficiently pure for further studies.

Step F

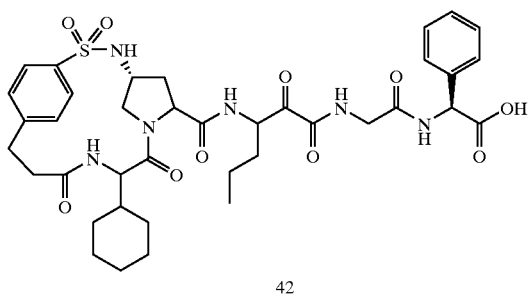

41e

↓

41

The desired material 41 was obtained by the oxidation protocol described for Example 2, Step B. Purification of the residue using 98/2 to 95/5 dichloromethane/MeOH afforded 41 in 52% yield as a mixture of diastereomers.

Example 42

Preparation of Compound 42

42

-continued

Step A

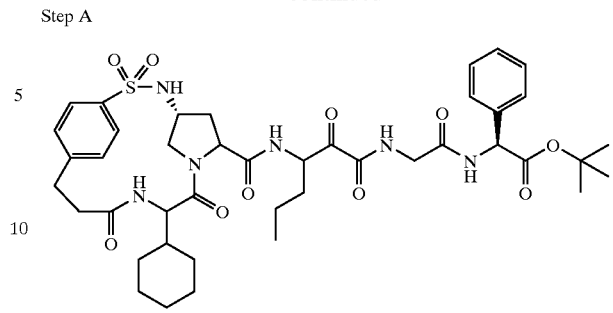

41

↓

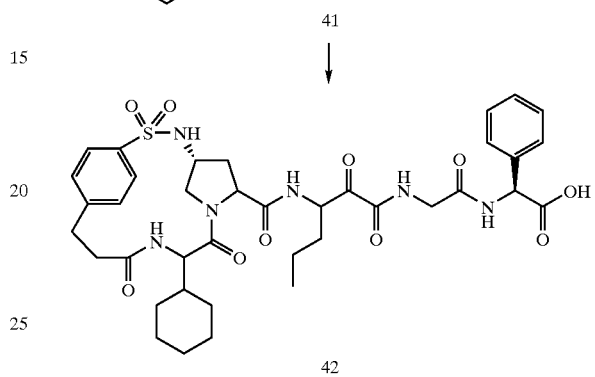

42

The desired material 42 was obtained by the procedure described for Example 3, Step A in quantitative yield as a mixture of diastereomers. HRMS (FAB) Calcd for $C_{38}H_{49}N_6O_{10}S$: 781.3231 $(M+H)^+$. Found: 781.3233.

Example 43

Preparation of Compound 43

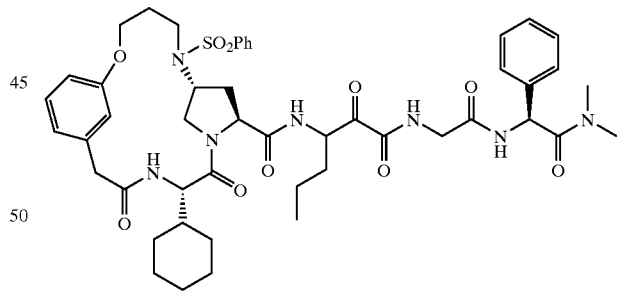

43

Step A

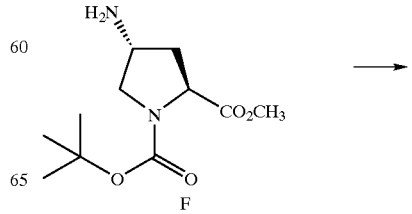

F

-continued

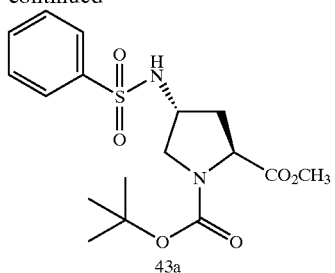
43a

To a cold (0° C.) solution of F (5.4 g, 22.1 mmol) in dichloromethane (50 mL) was added triethylamine (6.8 mL, 48.6 mmol), DMAP (few crystals) and benzenesulfonyl chloride (3.29 g, 24.1 mmol). The reaction mixture was left standing in the refrigerator (0–5° C.) overnight. The reaction mixture was washed with saturated $NaHCO_3$, and 10% citric acid solution. The organic layer was dried ($Na_2SO_4$) and concentrated. The residue was purified by flash chromatography using 95/5 dichloromethane/EtOAc to afford 5.0 g (59% yield) of 43a.

Step B

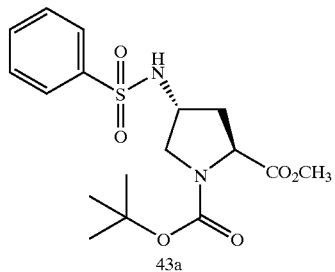
43a

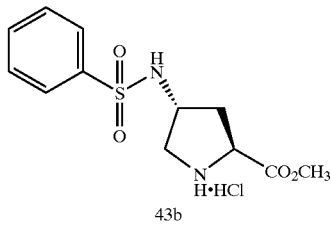
43b

The desired product 43b was obtained by the method described for Example 1, Step C. The crude material was used in the next step without purification.

Step C

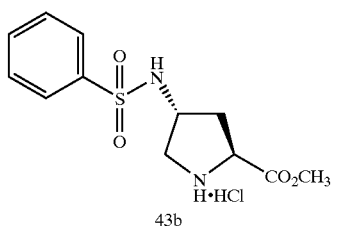
43b

-continued

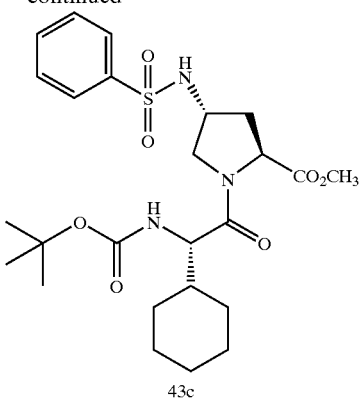
43c

The desired product 43c was obtained by the method described for Example 1, Step D. Purification of the residue by column chromatography using 99/1 dichloromethane/MeOH provided 60% yield of 43c.

Step D

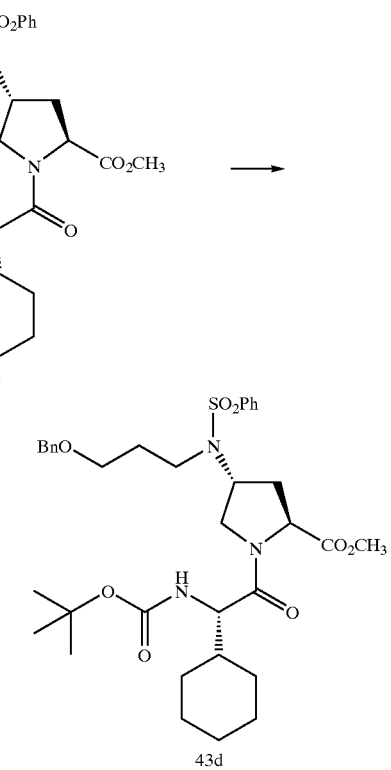

Argon gas was bubbled into a cold (20° C.) solution of 43c (1.72 g, 3.28 mmol) in dichloromethane (40 mL) for 20–30 min. ADDP (2.5 g, 9.84 mmol) was added followed by triphenylphosphine (2.6 g, 9.84 mmol) and 3-benzyloxypropanol (0.57 mL, 3.61 mmol). The reaction was warmed to ambient temperature and left standing for 2 days. Concentrated the reaction mixture and added $Et_2O$ (50 mL). The precipitated solid material was filtered off. Repeated this operation twice to remove most of the side products. The filtrate was concentrated and purified by flash chromatography using 90/10 to 85/15 dichloromethane/

EtOAc to provide 330 mg of 43d. The recovered starting materials, along with some triphenylphosphine oxide, was resubjected to the above described conditions to provide additional 420 mg of 43d. Combined yield=34%. HRMS (FAB) Calcd for $C_{35}H_{50}N_3O_8S$: 672.3319 $(M+H)^+$. Found: 672.3330.

Step E

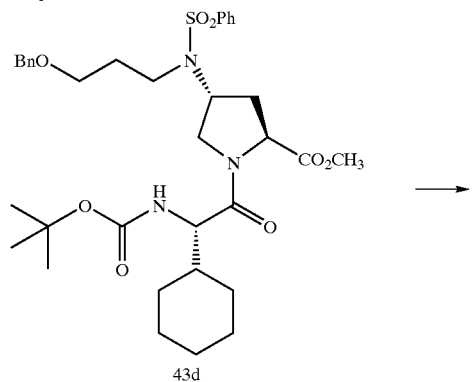

43d

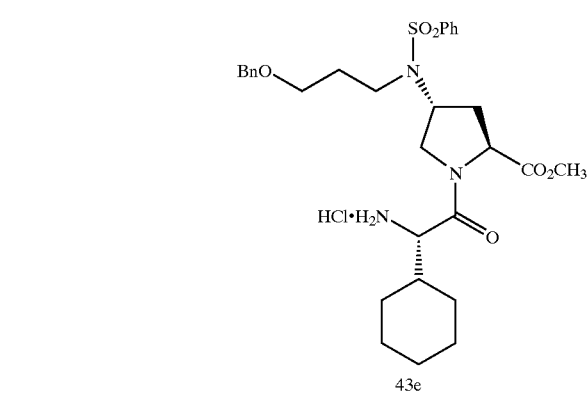

43e

The desired product 43e was obtained by the method described for Example 1, Step E. The crude product was carried to the next step.

Step F

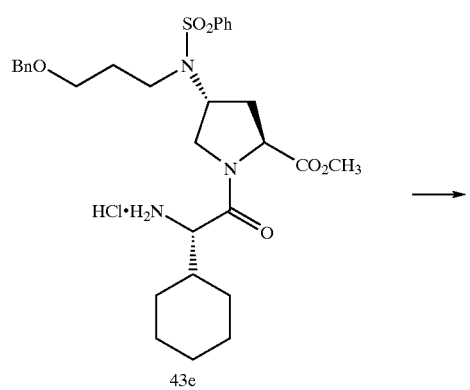

43e

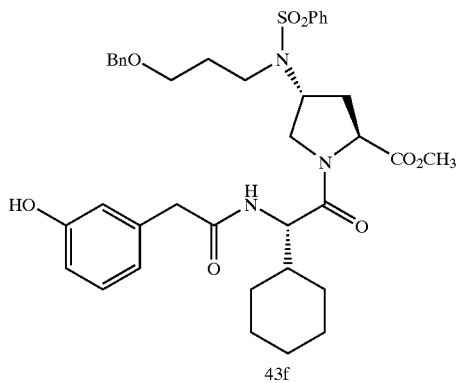

43f

The desired compound 43f was prepared by the protocol described for Example 1, step F. Purification by flash chromatography was carried out with 60/40 to 50/50 dichloromethane/EtOAc tp provide 43f in quantitative yield. HRMS (FAB) Calcd for $C_{38}H_{48}N_3O_8S$: 706.3162 $(M+H)^+$. Found 706.3157.

Step G

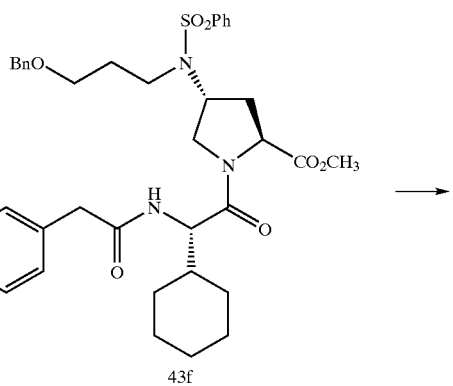

43f

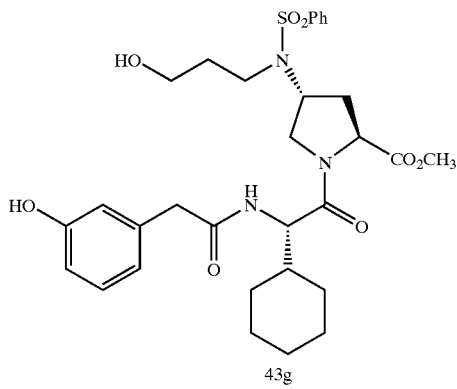

43g

The desired product 43g was obtained by the procedure described for Example 1, Step G. The material was sufficiently pure for further studies.

Step H

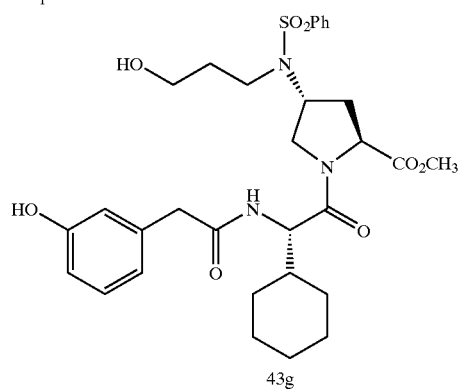

43g

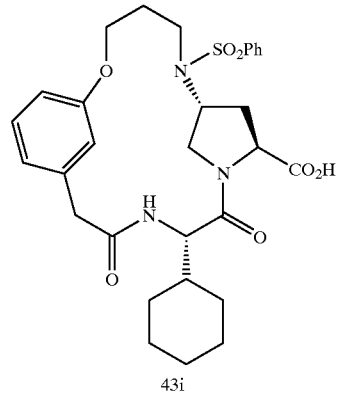

43i

The expected product 43i was obtained by the procedure described for Example 1, Step I in 92% yield.

Step J

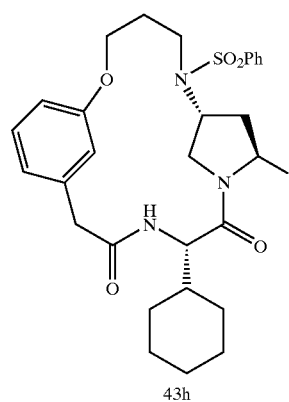

43h

The desired product 43h was obtained by the procedure described for Example 1, Step H. After completion of reaction, the solvent was evaporated. Et$_2$O (50 mL) was added and the solids were filtered off. The filtrate was concentrated and Et2O/EtOAc (50 mL/50 mL) was added. The precipitated solids were filtered off and the filtrate was concentrated. The residue was purified by flash chromatography using 85/15 to 80/20 dichloromethane/EtOAc to afford pure 43h in 20% yield. HRMS (FAB) Calcd for C$_{31}$H$_{40}$N$_3$O$_7$S: 598.2587 (M+H)$^+$. Found: 598.2581.

Step I

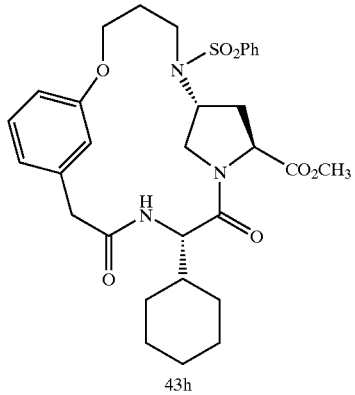

43h

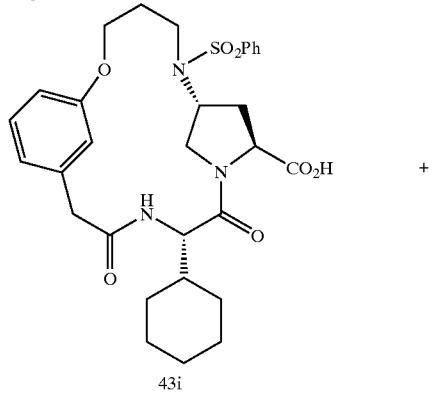

43i

A

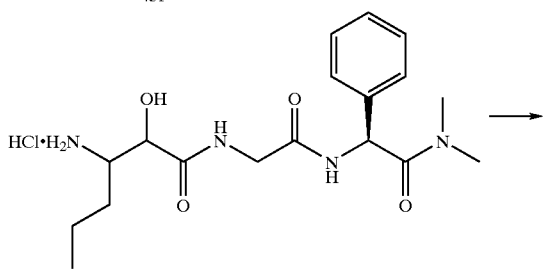

43j

The desired material 43j was synthesized as described for Example 1, Step J. The crude product was of sufficient purity to be carried forward.

Step K

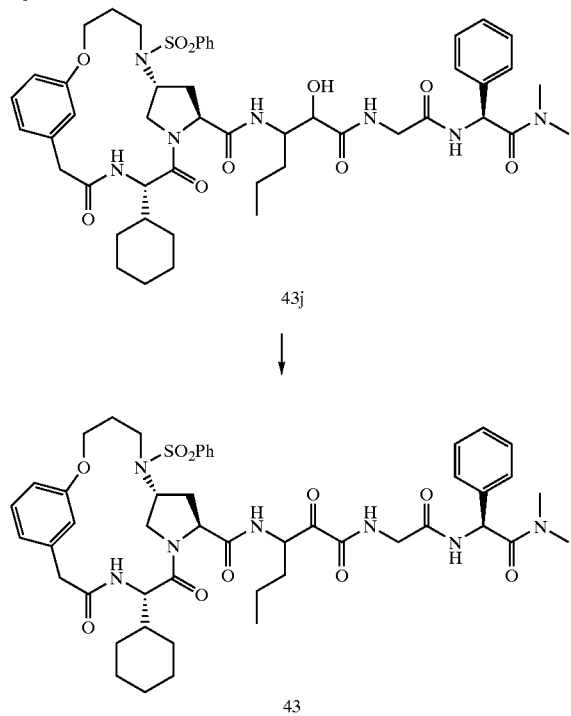

The expected product 43 was obtained by the oxidation protocol described previously for Example 1, Step K. Purification by flash column chromatography using 97/3 dichloromethane/MeOH afforded 43 as a mixture of diastereomers. Combined yield =60% (for 2 steps). HRMS (FAB) Calcd for $C_{48}H_{62}N_7O_{10}S$: 928.4279 $(M+H)^+$. Found: 928.4290.

Example 44

Preparation of Compound 44

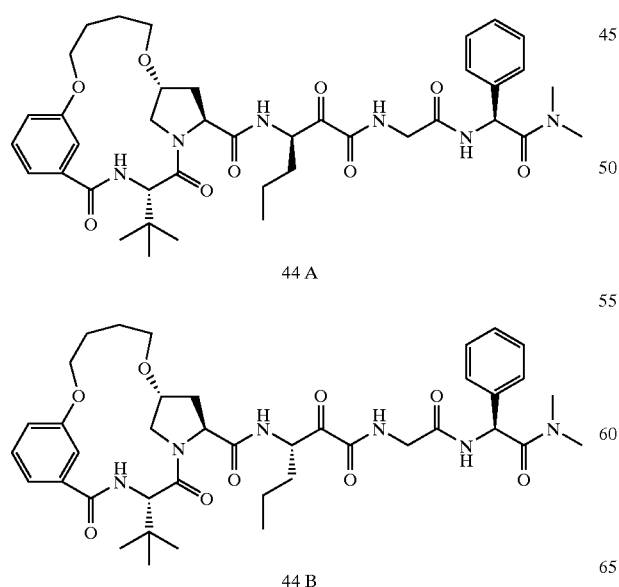

Step A

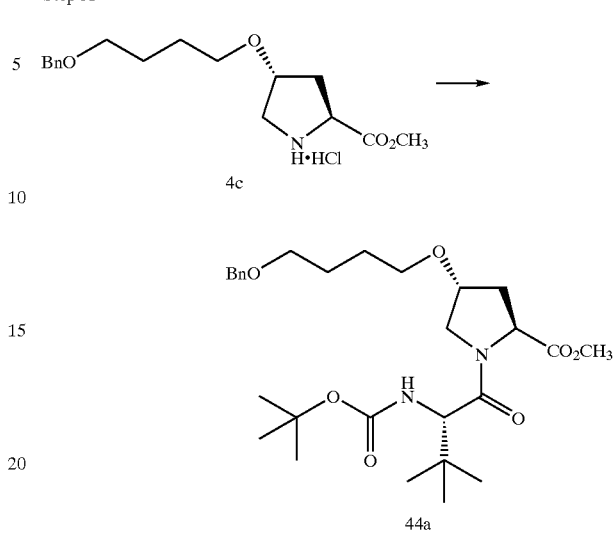

The desired product 44a was obtained by the method described for Example 1, Step D using N-boc-tert-butylglycine as the coupling partner. The material after work-up was sufficiently pure to be carried to the next step.

Step B

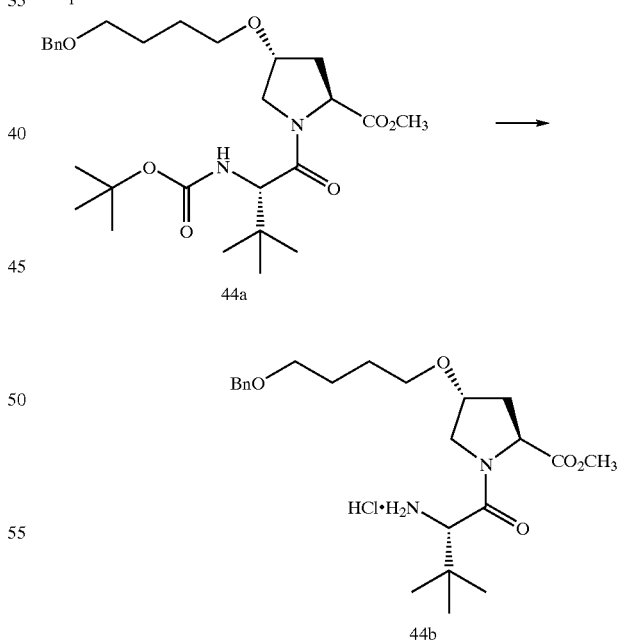

The desired product 44b was obtained by the method described for Example 1, Step E. The crude material was carried forward without purification.

Step C

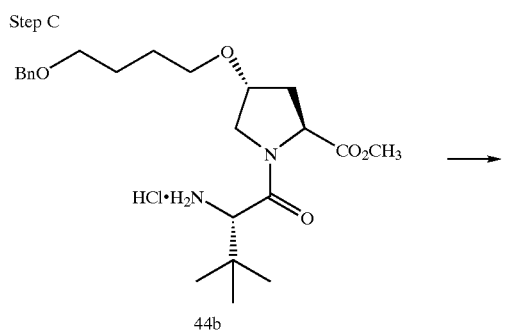

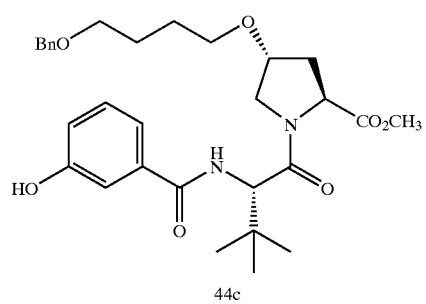

The desired product was obtained by the method described for Example 1, Step F, using 3-hydroxybenzoic acid. The material was purified by flash column chromatography using 85/15 to 65/35 dichloromethane/ethyl acetate to provide 44c in 81% yield.

Step D

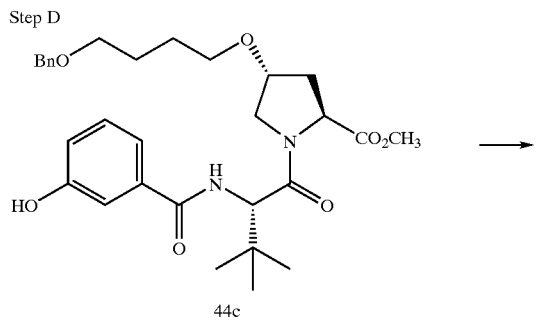

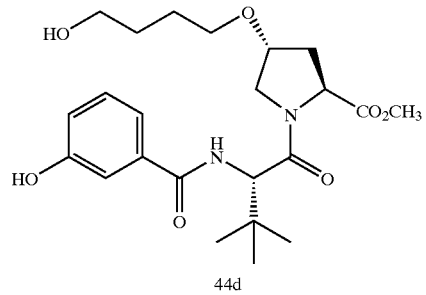

The desired product 44d was obtained by the method described for Example 1, Step G. The residue after workup was sufficiently pure for further manipulation.

Step E

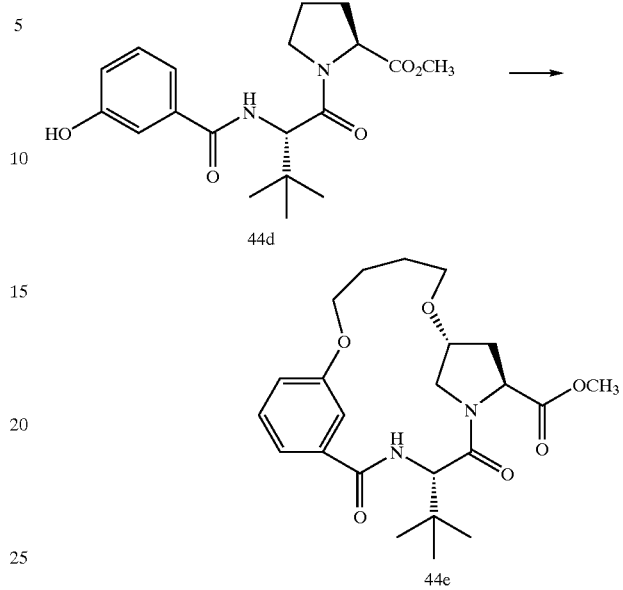

The desired product 44e was obtained by the method described for Example 1, Step H. The crude residue after concentration was taken in hexanes/EtOAc (1/1) and the solid material was filtered off. This operation was performed again to remove some of the side products. Purification by column chromatography using 80/20 dichloromethane/EtOAc afforded 44e along with triphenylphosphine oxide. This mixture was taken to the next step Step F

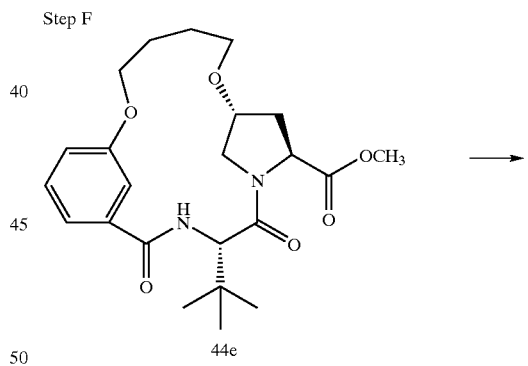

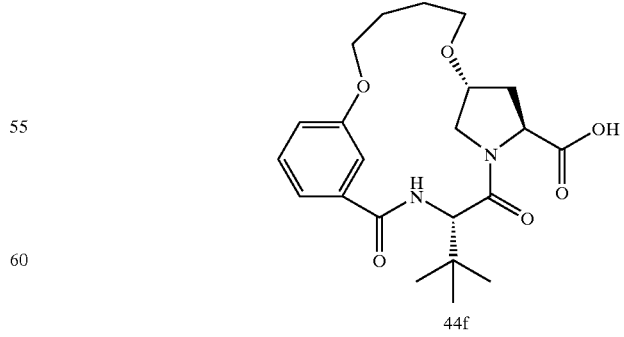

The desired product 44f was obtained by the method described for Example 1, Step I. Yield of 44f (for 2 steps)= 11%.

Step G

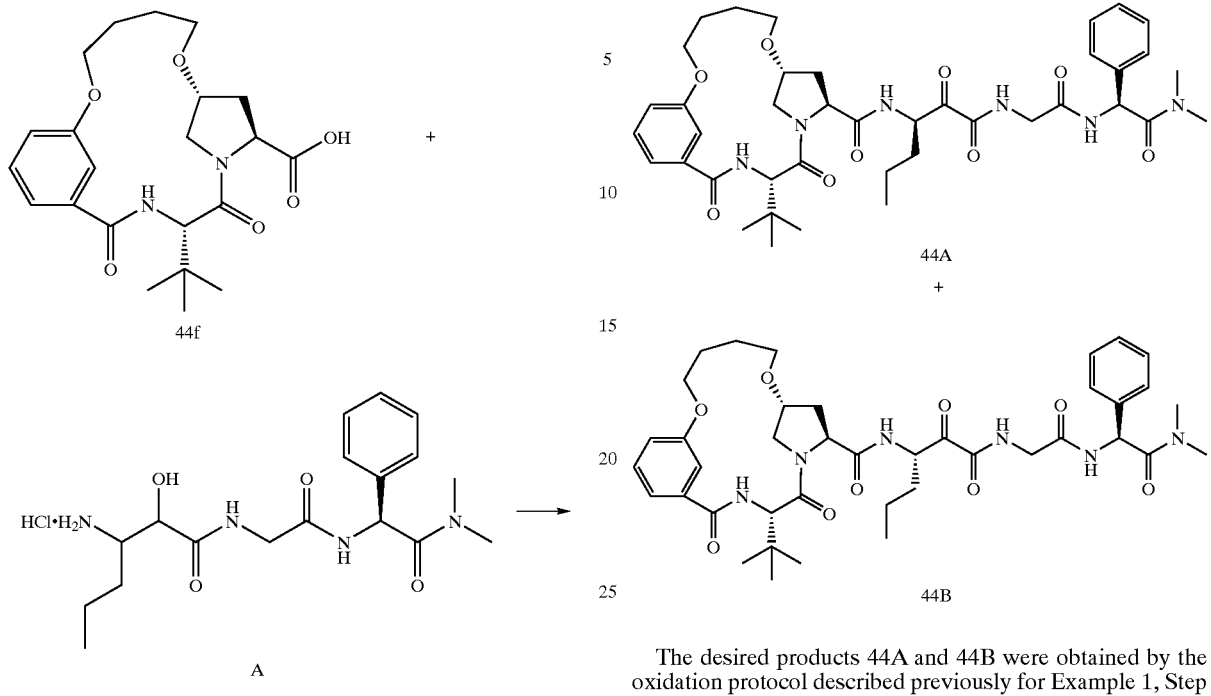

The desired products 44A and 44B were obtained by the oxidation protocol described previously for Example 1, Step K. Purification by flash column chromatography using 97/3 to 96/4 dichloromethane/methanol afforded equal amount of separate isomers 44A and 44B. Combined yield=58% (for 2 steps).

Example 45
Preparation of Compound 45

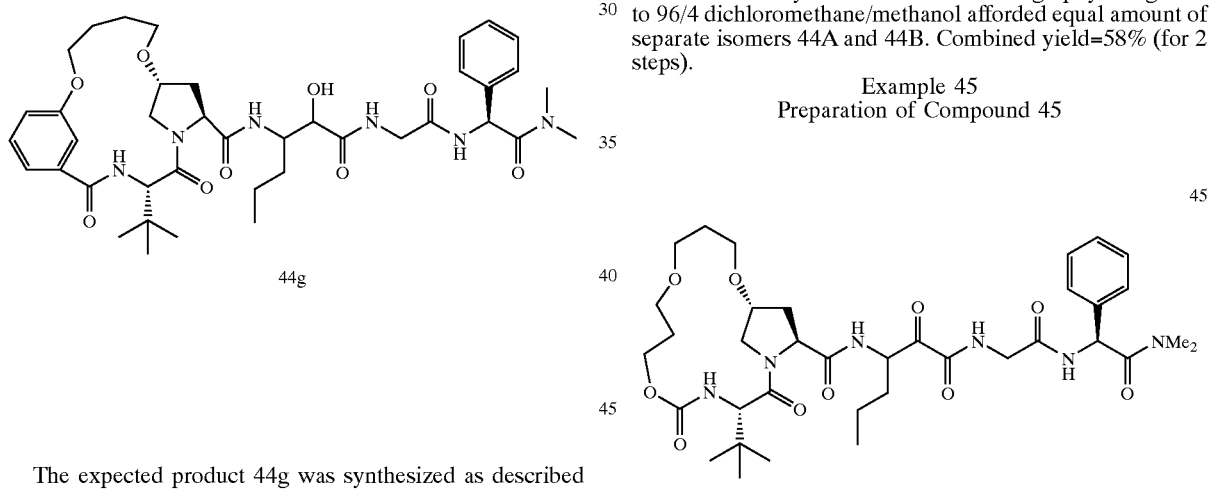

The expected product 44g was synthesized as described earlier for the Example 1, Step J. The material after work-up was carried forward to the next step.

Step A

Step H

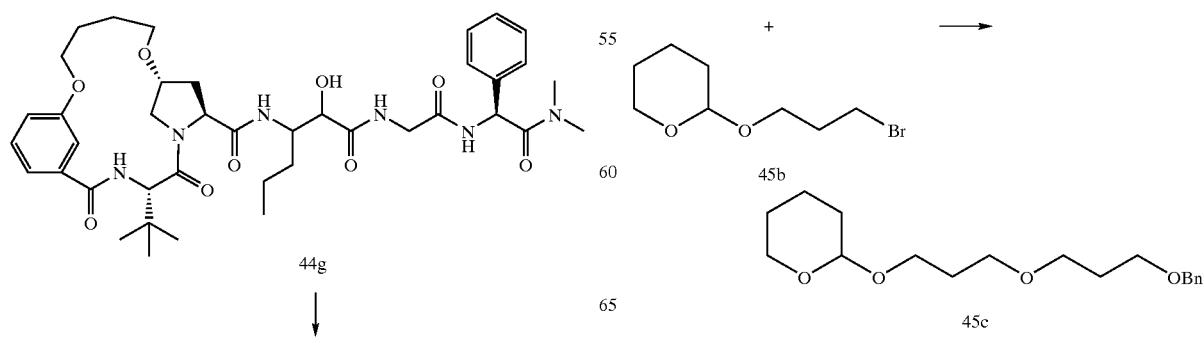

Alkylation of 45a with 45b was carried out using the procedure described for Example 1 Step A. The crude product was purified using 85/0/15 to 85/5/10 hexanes/EtOAc/dichloromethane to provide 45c in 37% yield. HRMS (FAB) Calcd for $C_{18}H_{29}O_4$: 309.2066 $(M+H)^+$. Found: 309.2060.

Step B

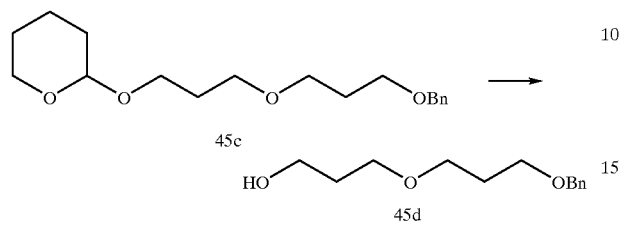

To a solution of 45c (4.8 g, 15.5 mmol) in MeOH (30 mL) was added pyridinium p-toluenesulfonate (780 mg, 3.1 mmol) and refluxed for 3 hrs when all the starting material was consumed. The reaction mixture was concentrated. The residue was dissolved in EtOAc, washed with saturated NaHCO$_3$, dried (Na2SO4) and the organic layer was concentrated to afford 3.2 g of 45d (92% yield). This material was sufficiently pure for further studies. HRMS (FAB) Calcd for $C_{13}H_{21}O_3$: 225.1491 $(M+H)^+$. Found: 225.1486.

Step C

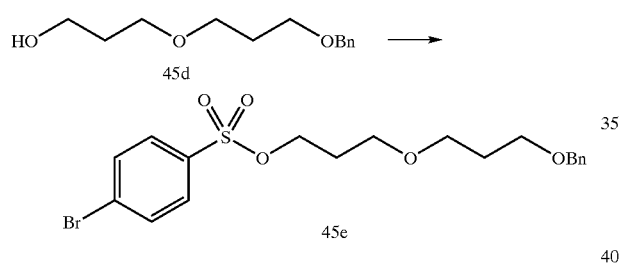

The desired product 45e was obtained by the procedure described for Example 10 Step A using 45d as the starting material. The crude product was purified using 90/10 hexanes/EtOAc to provide 45e in 70% yield. HRMS (FAB) Calcd for $C_{19}H_{24}O_5SBr$: 443.0528 $(M+H)^+$. Found: 443.0552.

Step D

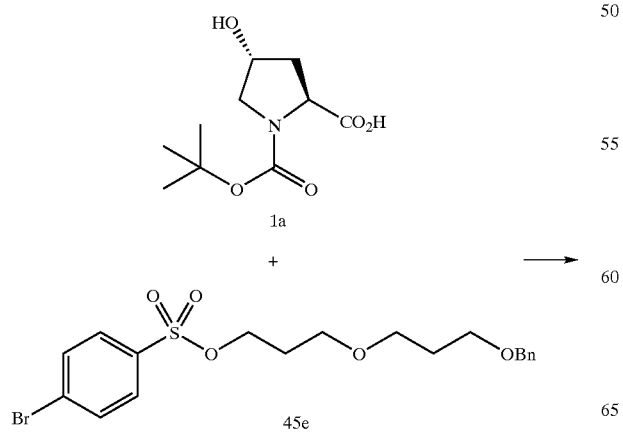

-continued

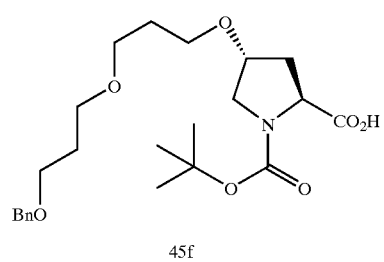

The desired product 45f was obtained by the procedure described for Example 1 Step A using 45e as the starting material. The crude product was carried further without purification.

Step E

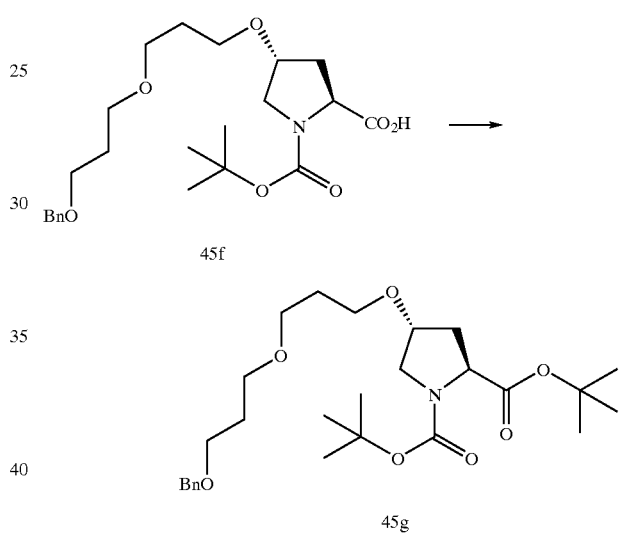

The desired product 45g was obtained by the procedure described for Example 18 Step B using 45f as the starting material. The residue was purified by flash chromatography using 90/10 dichloromethane/EtOAc to provide 45g in 61% yield (for 2 steps). HRMS (FAB) Calcd for $C_{27}H_{44}NO_7$: 494.3118 $(M+H)^+$. Found: 494.3107.

Step F

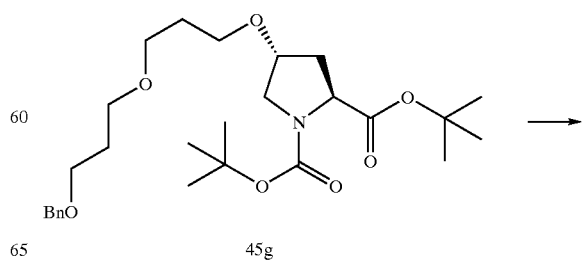

-continued

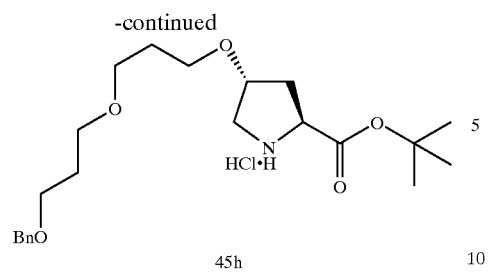

45h

The desired compound 45h was prepared by the protocol described for Example 1 Step C. The material was carried forward.

Step G

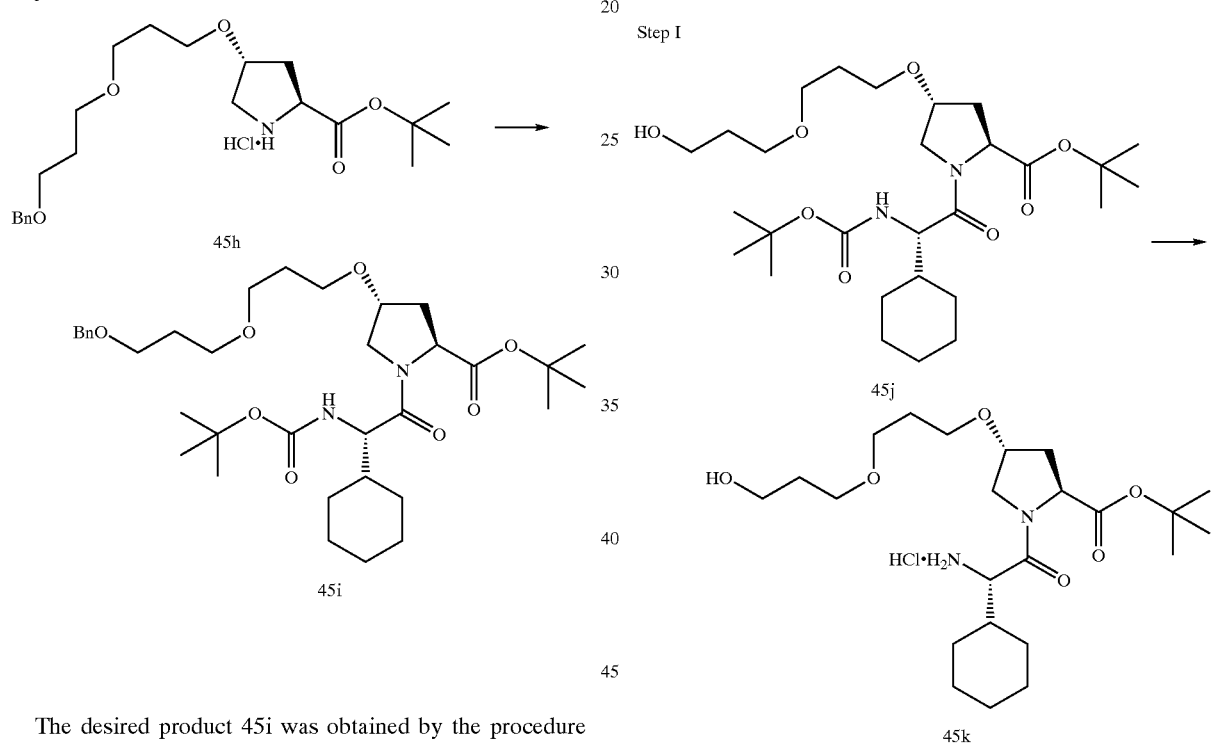

45h

45i

The desired product 45i was obtained by the procedure described for Example 1 Step D. The residue was purified by flash chromatography using 90/10 to 85/15 dichloromethane/EtOAc to provide 45i in 41% yield.

Step H

45i

-continued

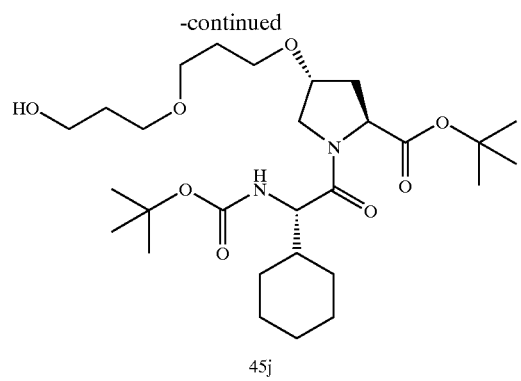

45j

The desired product 45j is obtained by the hydrogenation protocol described previously for Example 1 Step G.

Step I

45j

45k

The desired product 45k is obtained by the procedure described previously for Example 1 Step C.

Step J

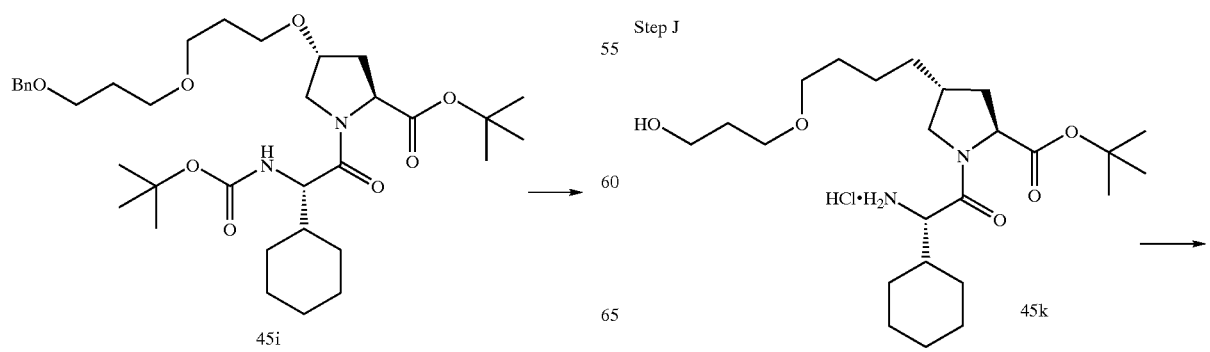

45k

Step L

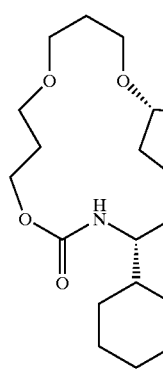
45l

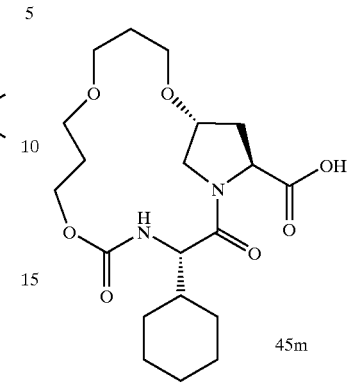
45m

+

To a cold (0° C.) solution of 45k in dichloromethane is added triethylamine followed by carbonyldiimidazole. Slow warming to ambient temperature overnight is expected to provide the required product 45l. This product can be purified using conventional flash column chromatography to afford pure 45l.

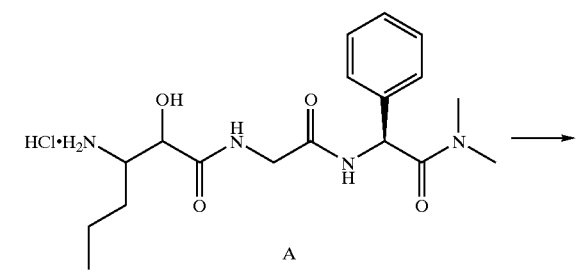
A

Step K

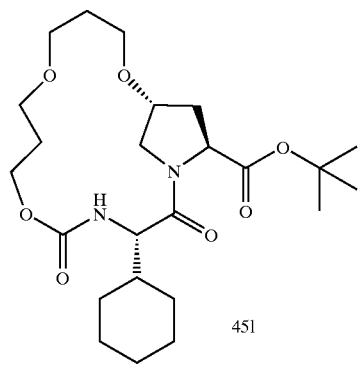
45l

→

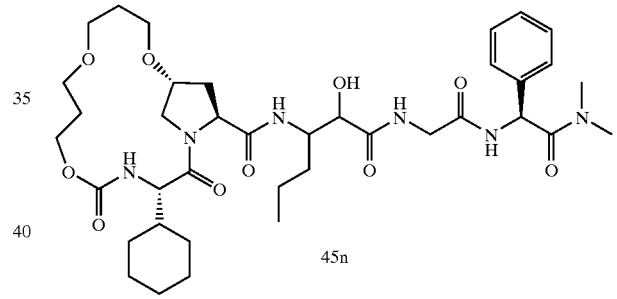
45n

The expected product 45n is synthesized as described earlier for Example 1 Step J.

Step M

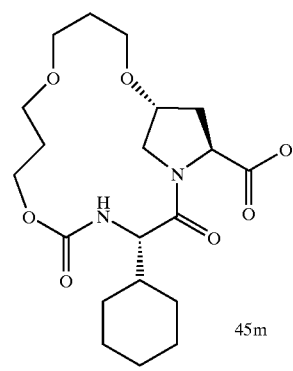
45m

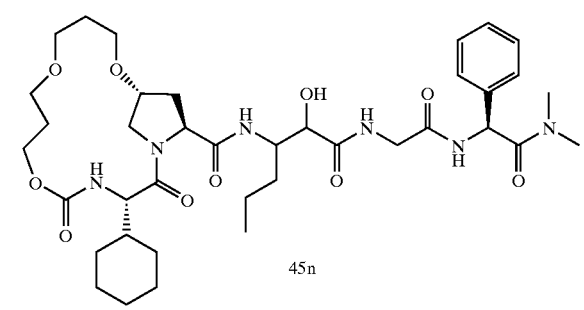
45n

↓

The desired product 45m is obtained by the producer described previously for Example 3 Step A.

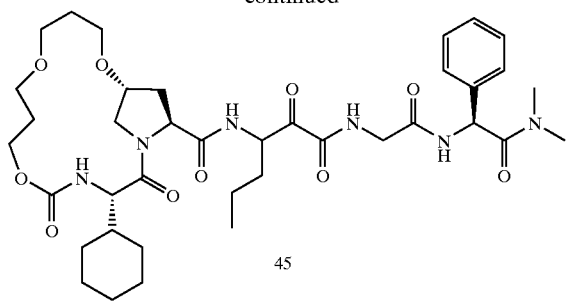

45

The desired product 45 is obtained by the oxidation protocol described previously for Example 1 Step K. Purification by flash column chromatography will afford pure 45.

Example 46

Preparation of Compound 46

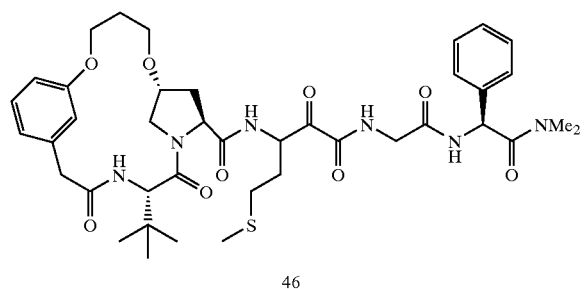

46

Step A

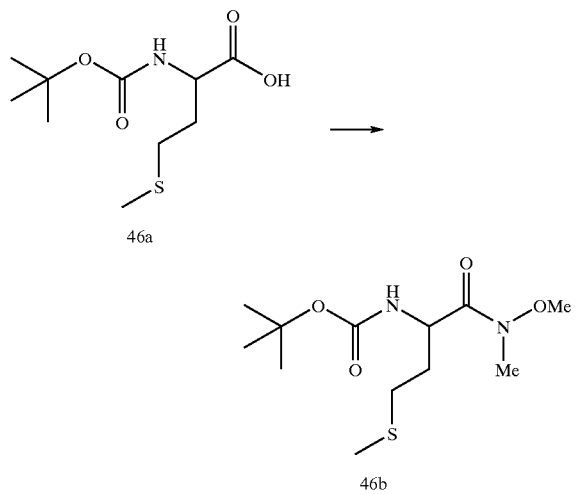

To a solution of 46a (10.0 g, 42.9 mmol) in dichloromethane (100 mL) was added BOP (22.75 g, 51.5 mmol) and stirred at room temperature for 10 minutes. N,O-dimethylhydroxylamine hydrochloride (4.18 g, 42.9 mmol) was then added followed by triethylamine (18.1 mL, 128.7 mmol). The reaction mixture was stirred at ambient temperature for 3 hours and then washed with 3N HCl, saturated NaHCO$_3$, and brine. The organic layer was dried (Na$_2$SO$_4$) and concentrated. The crude material, 46b, was used in the following step without purification.

Step B

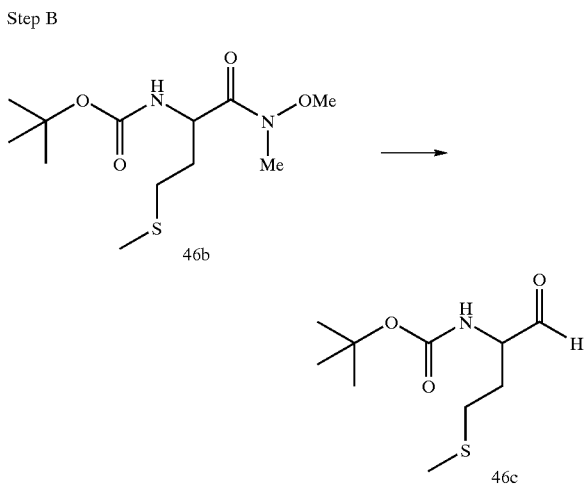

To a cold (0° C.) solution of 46b in THF (60 mL) was added a solution of LAH (1M in THF, 50 mL, 50 mmol) under nitrogen atmosphere. Reaction was kept at that temperature for 30 min. The reaction mixture was quenched (slow addition) with aqueous 10% potassium hydrogen phosphate solution (30 mL). The mixture was extracted with EtOAc twice. The combined organic layer was washed with 3N HCl, saturated NaHCO$_3$, and brine. Dried the EtOAc layer over sodium sulfate and concentrated. The residue was purified by flash column chromatography using 10/90 to 30/70 EtOAc/dichloromethane to provide 4.2 g of 46c (45% yield—for 2 steps). HRMS (FAB) Calcd for C$_{10}$H$_{20}$NO$_3$S: 234.1164 (M+H)$^+$. Found: 234.1168.

Step C

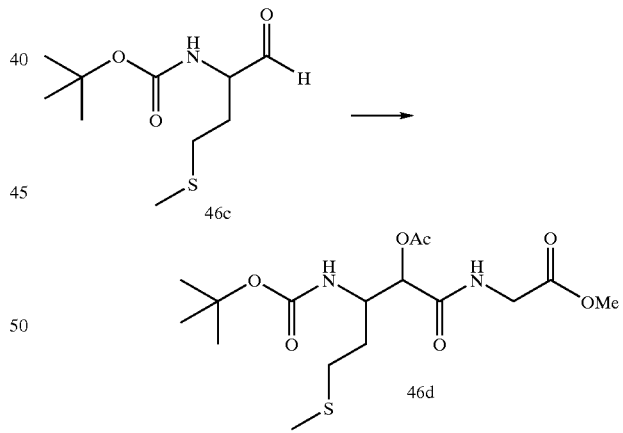

To a cold (−15° C.) solution of 46c (4.2 g, 19.4 mmol) in dichloromethane was added acetic acid (2.14 mL, 38.8 mmol) followed by methyl isocyanoacetate (1.76 mL, 19.4 mmol). The reaction mixture was warmed to room temperature and let stand for 16 hrs. Diluted the reaction with EtOAc and washed with saturated NaHCO$_3$, brine and water. The organic layer was dried (Na2SO$_4$) and concentrated. Purification by flash column chromatography using 30/70 EtOAc/dichloromethane afforded pure 46d (6.5 g) as a white solid in 92% yield. HRMS (FAB) Calcd for C$_{16}$H$_{29}$N$_2$O$_7$S: 393.1695 (M+H)$^+$. Found: 393.1692.

Step D

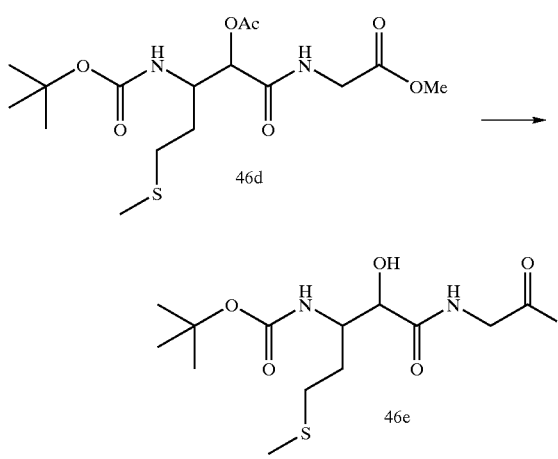

To a solution of 46d (6.5 g, 16.6 mmol) in MeOH (30 mL) was added a solution of lithium hydroxide (1.19 g, 50 mmol) in water (30 mL). After 45 minutes the reaction mixture was concentrated. Aqueous citric acid solution was added till acidic pH (3) and the product was extracted into EtOAc. Concentration of the organic layer resulted in the acid 46e (5.6 g, 90% yield). HRMS (FAB) Calcd for $C_{13}H_{25}N_2O_6S$: 337.1433 (M+H)$^+$. Found: 337.1430.

Step E

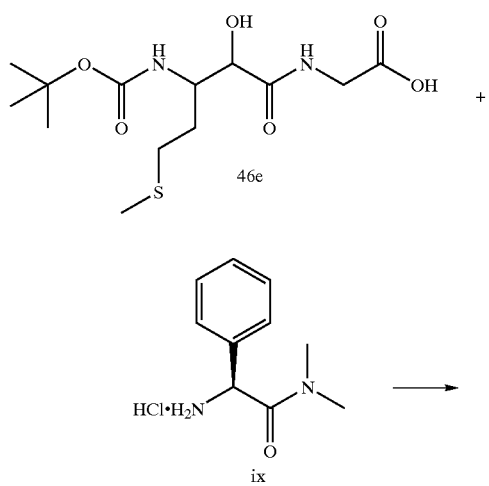

The desired product 46f was obtained by the method described for Intermediate A, Step 3. Purification of the residue by column chromatography using 20/0/80 to 50/5/45 of EtOAc/NH$_3$ in MeOH/dichloromethane afforded 3.0 g of 46f (51%). HRMS (FAB) Calcd for $C_{23}H_{37}N_4O_6S$: 497.2434 (M+H)$^+$. Found: 497.2439.

Step F

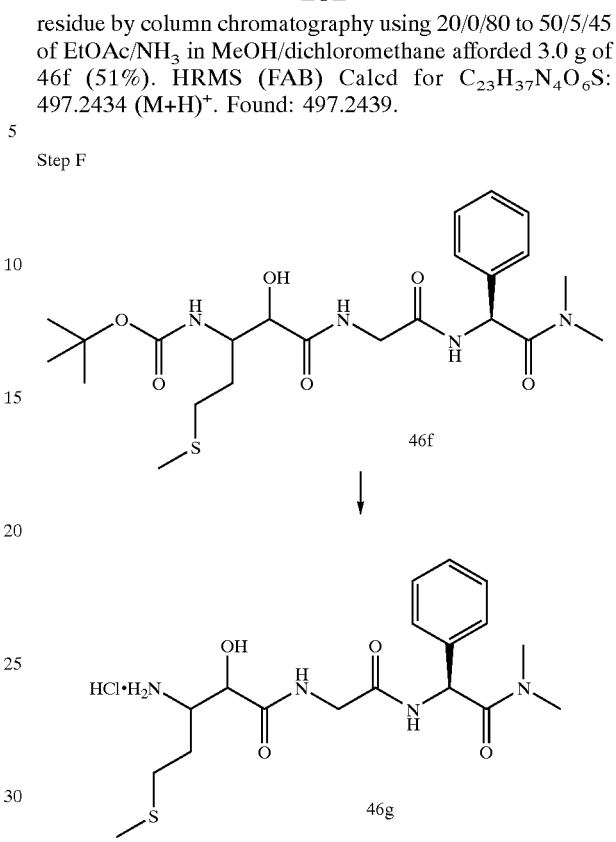

The desired compound 46g was prepared by the protocol described for Intermediate A, Step 4. The material was carried forward for further studies.

Step G

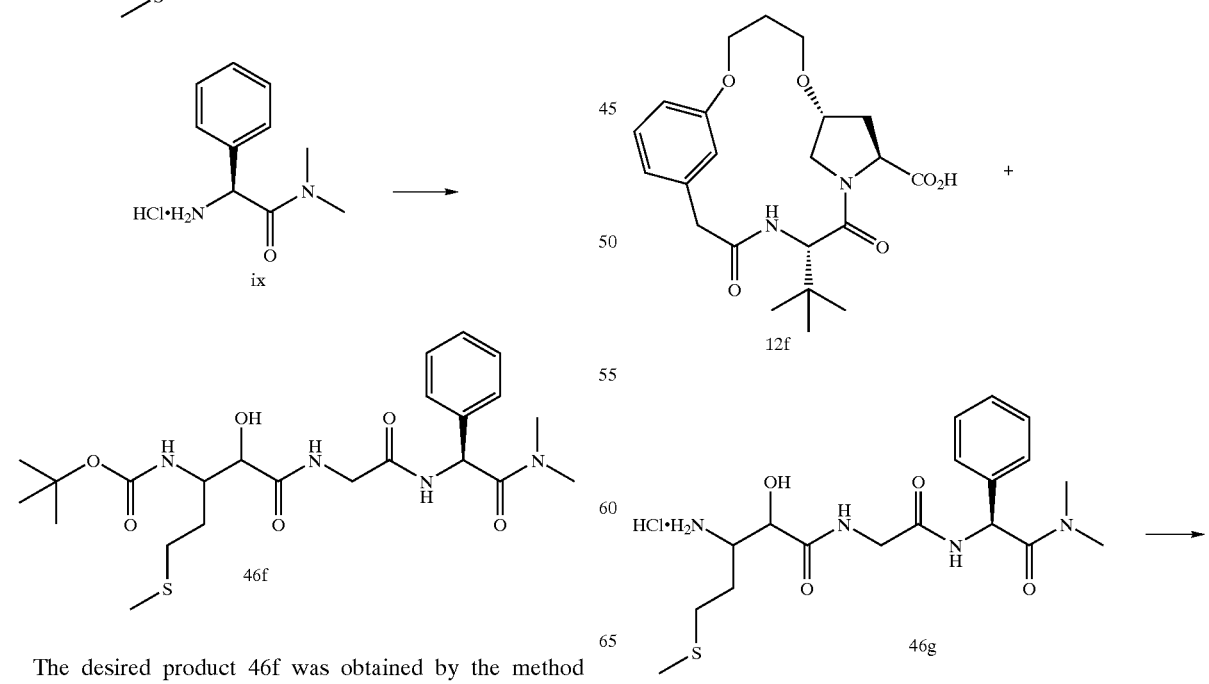

283
-continued

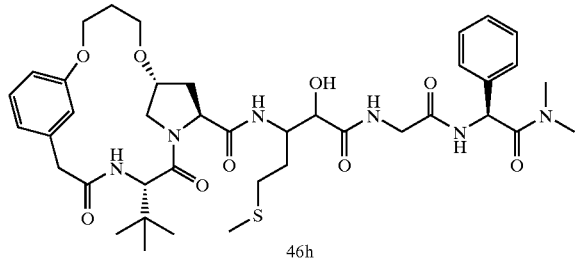

46h

Step H

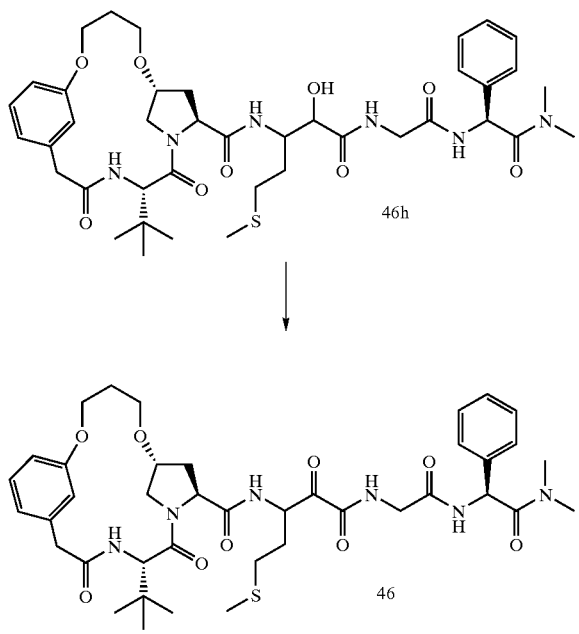

The desired product 46h was obtained by the procedure described for Example 1, Step J. The crude material was sufficiently pure for further manipulations. HRMS (FAB) Calcd for $C_{40}H_{57}N_6O_9S$: 797.3908 (M+H)$^+$. Found: 797.3896.

The desired product 46 was obtained by the oxidation protocol described previously for Example 10, Step J. The reaction took 4 days to go to completion. Purification of the residue by flash column chromatography (twice) and preparative TLC using 98/2 dichloromethane/MeOH afforded 46 as a mixture of diastereomers in 12% yield (for 2 steps). HRMS (FAB) Calcd for $C_{40}H_{55}N_6O_9S$: 795.3751 (M+H)$^+$. Found: 795.3761.

284

Example 47

Preparation of Compound 47

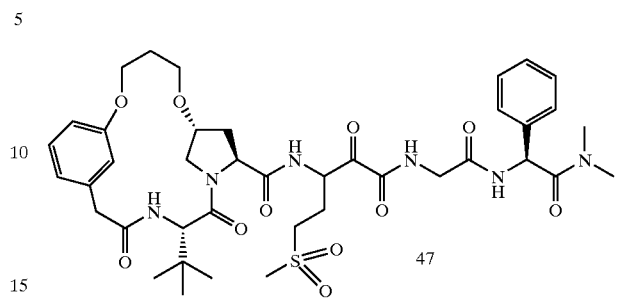

Step A

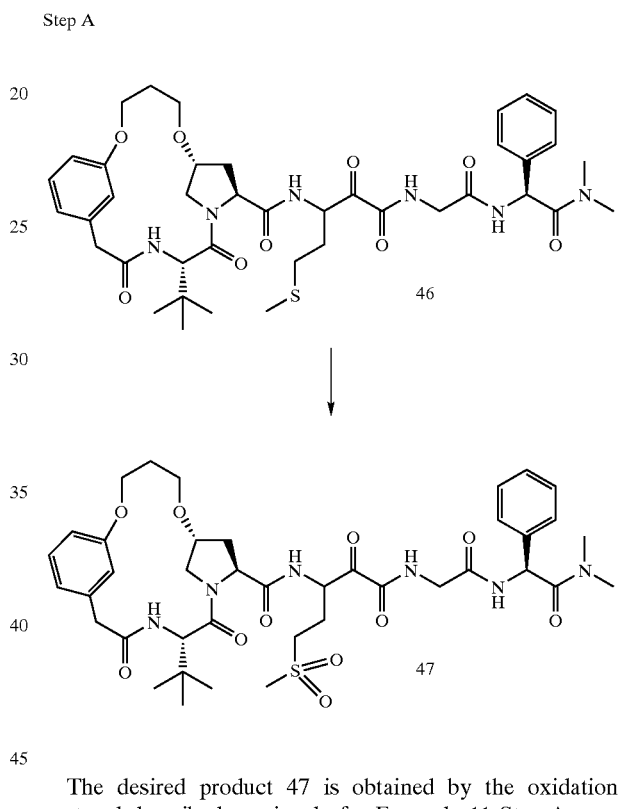

The desired product 47 is obtained by the oxidation protocol described previously for Example 11 Step A.

Example 48

Preparation of Compound 48

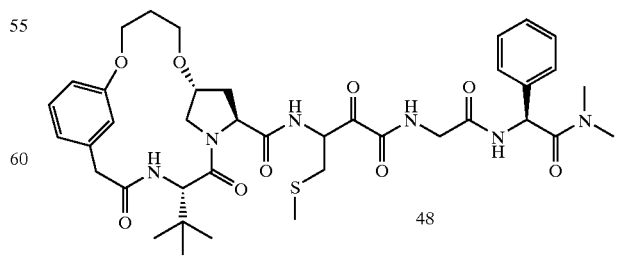

Step A

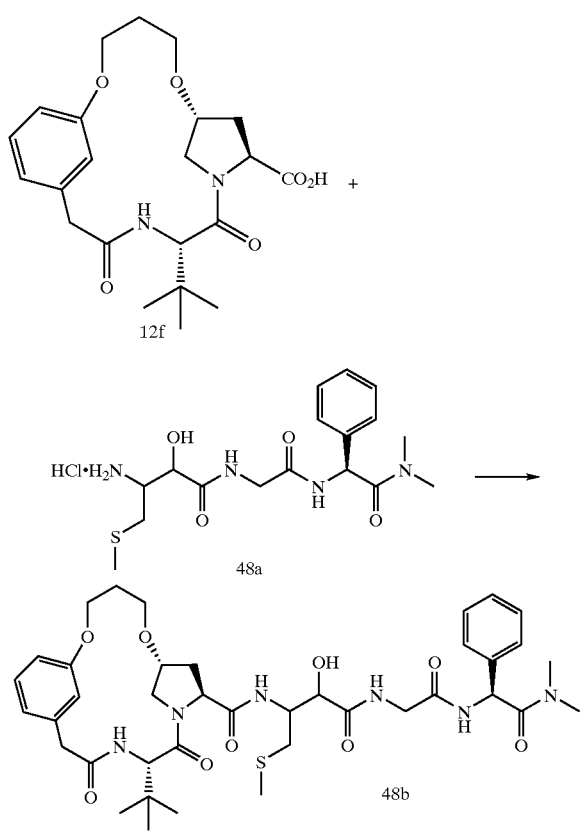

The desired product 48b was obtained by the procedure described for Example 1 Step J. The crude material was sufficiently pure for further manipulations. (Note: The precursor 48a was obtained from commercially available Nboc-S-methylcysteine by similar procedures described for 46g)

Step B

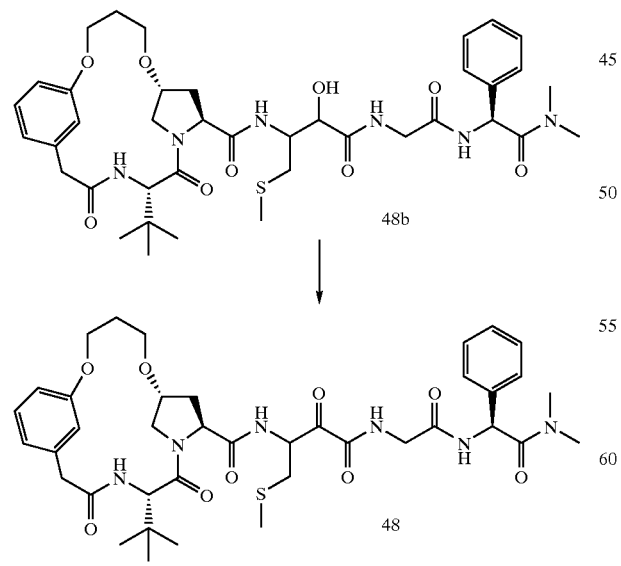

The desired product 48 was obtained by the oxidation protocol described previously for Example 10 Step J. Purification by flash column chromatography using 98/2 dichloromethane/MeOH afforded 48 as a mixture of diastereomers in 21% yield (for 2 steps).

Example 49

Preparation of Compound 49

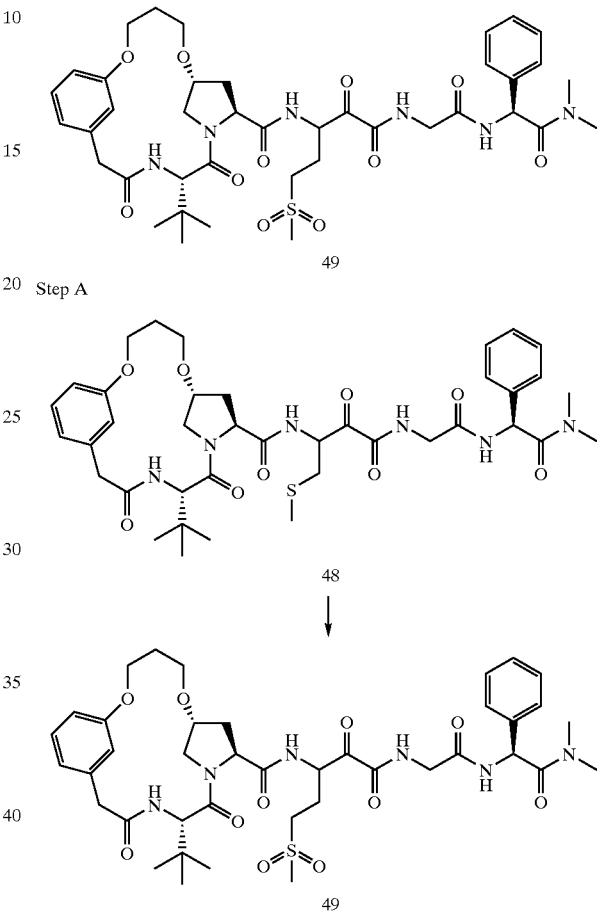

The desired product 49 is obtained by the oxidation protocol described previously for Example 11 Step A.

Example 50

Preparation of Compound 50

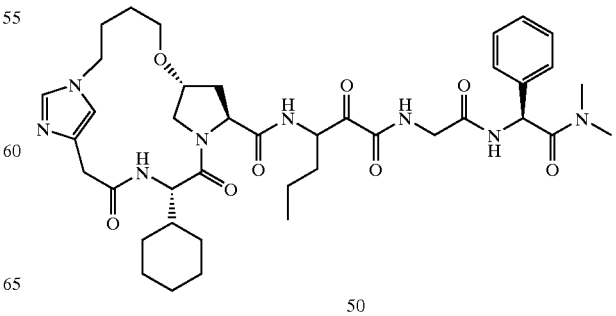

Step A

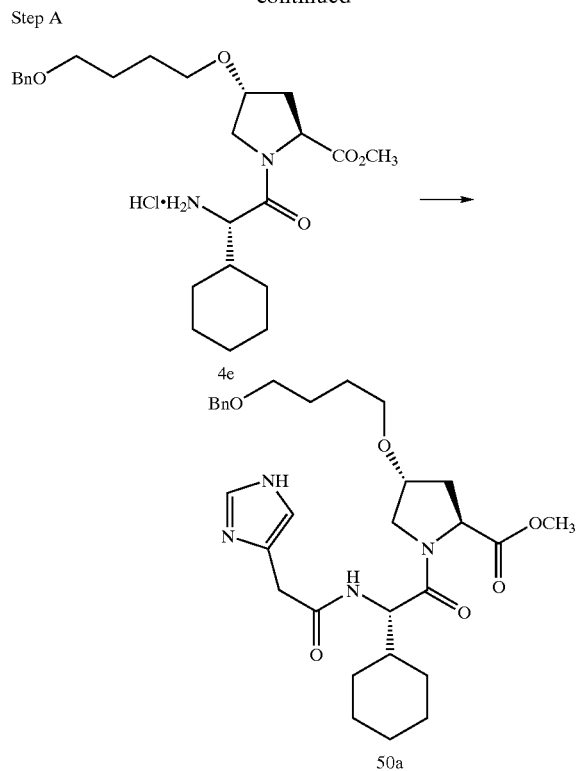

The desired product 50a is obtained by the method described for Example 1 Step F, using imidazole-4-acetic acid as the coupling partner.

Step B

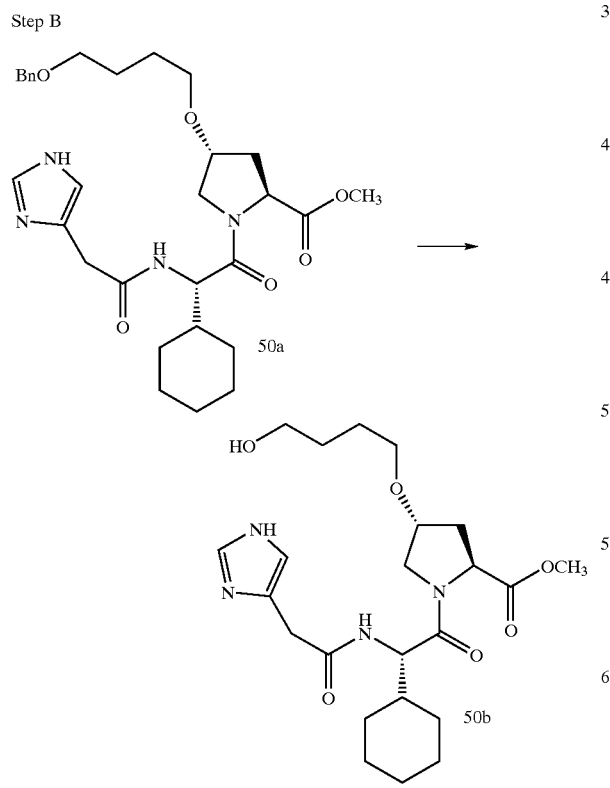

The desired product 50b is obtained by the method described for Example 1 Step G.

Step C

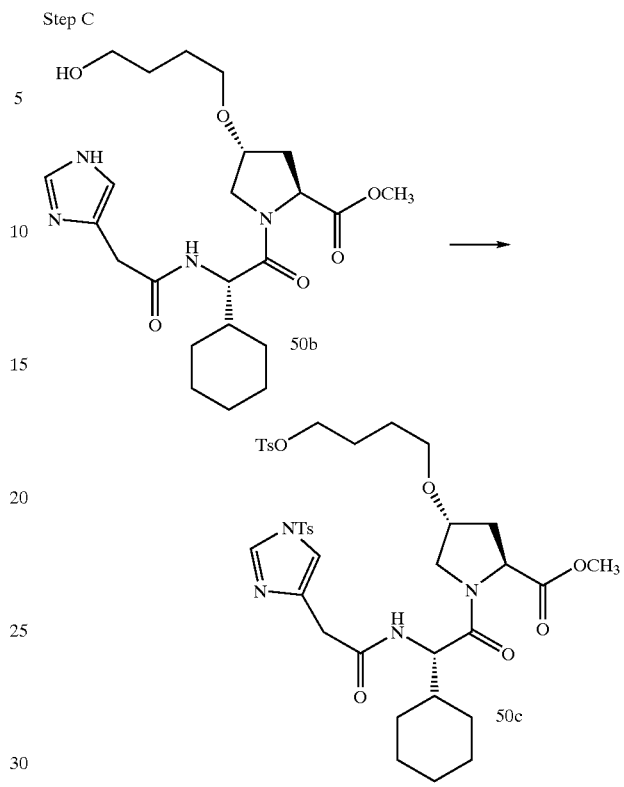

The desired product 50c is obtained by the method described for Example 10 Step A using p-toluenesulfonyl chloride as the starting material.

Step D

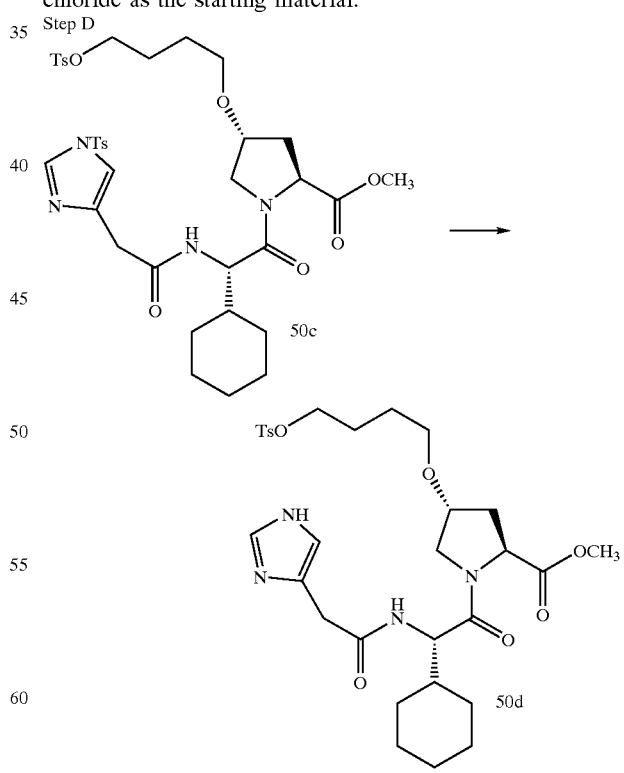

The desired product 50d is obtained by the treating 50c with HOBt in THF at ambient temperature over several hrs.

Step E

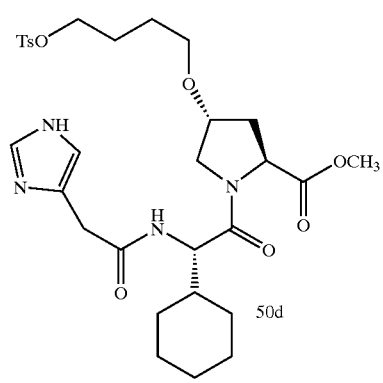

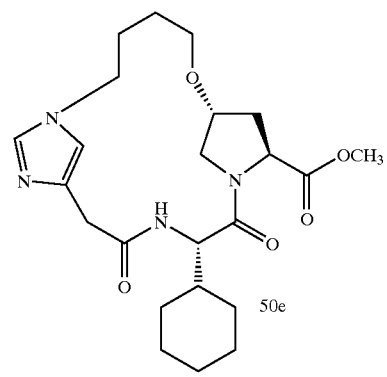

The expected product 50e is synthesized by heating of 50d with sodium carbonate, and sodium iodide in acetone at 50° C. over several hrs. The product can be purified by conventional flash chromatography.

Step F

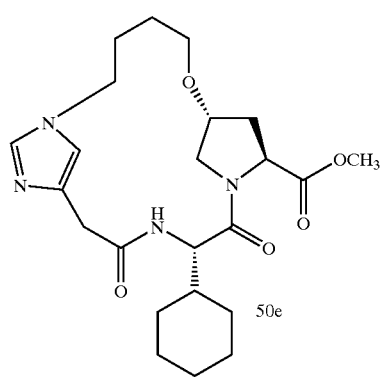

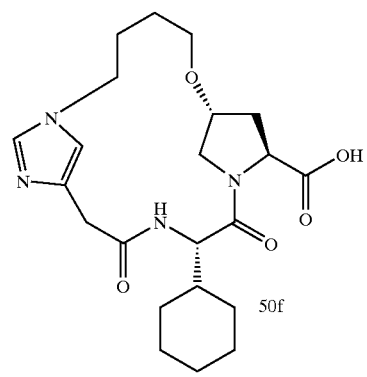

The desired products 50f is obtained by the hydrolysis protocol described previously for Example 1 Step I.

Step G

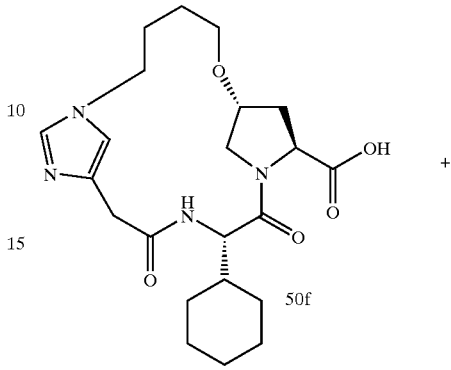

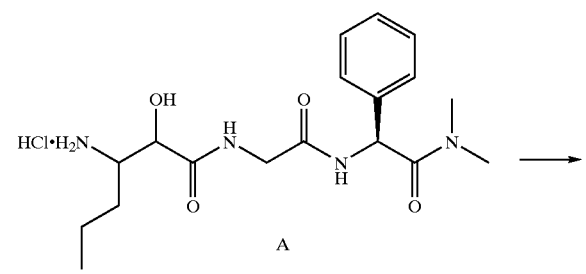

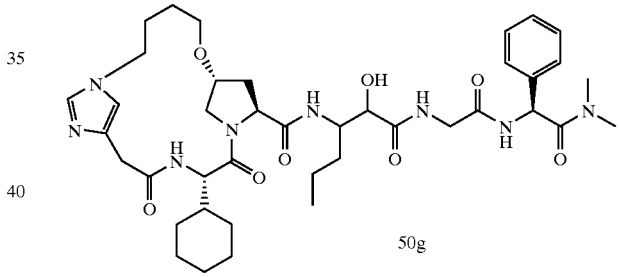

The expected product 50g is synthesized as described earlier for Example 1 Step J.

Step M

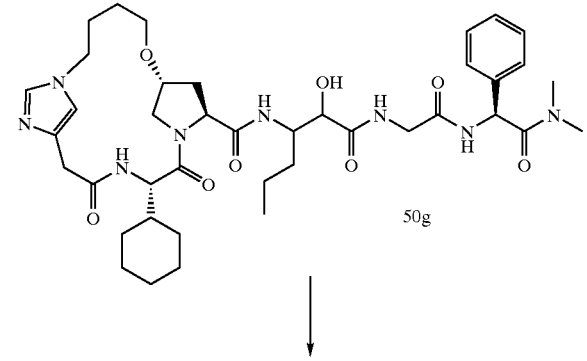

291

-continued

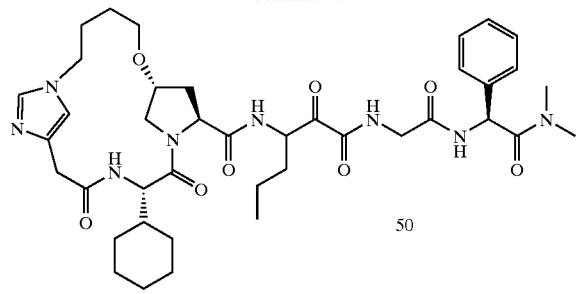

50

292

-continued

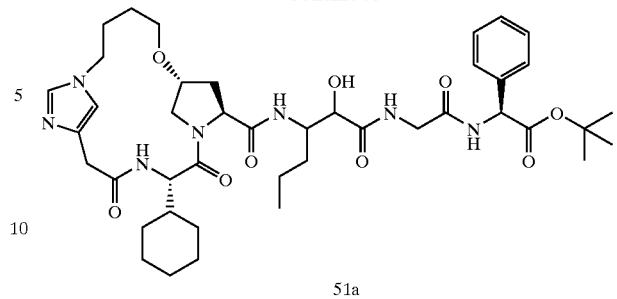

51a

The desired product 50 is obtained by the oxidation protocol described previously for Example 1 Step K. Purification by flash column chromatography will afford pure 50.

The expected product 51a is synthesized as described earlier for Example 2 Step A.

Step B

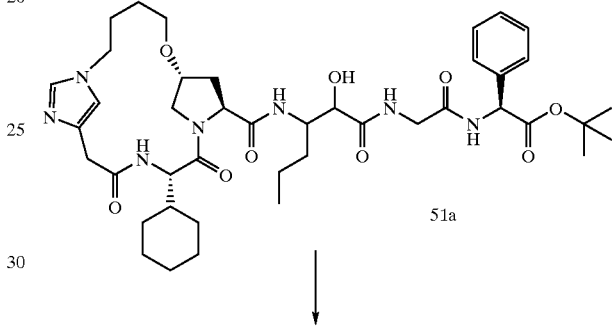

51a

↓

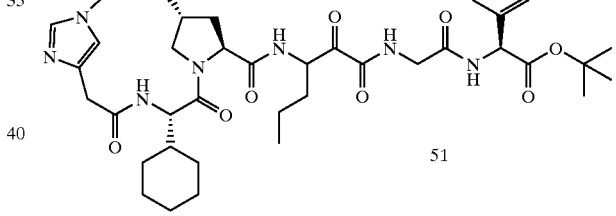

51

Example 51

Preparation of Compound 51

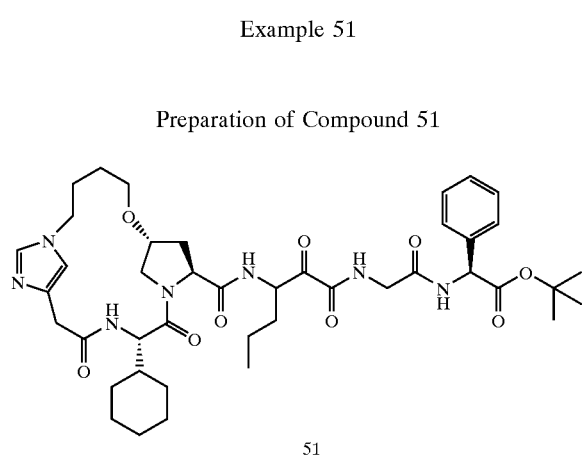

51

Step A

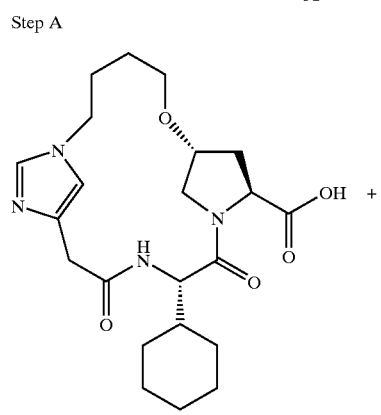

50f

+

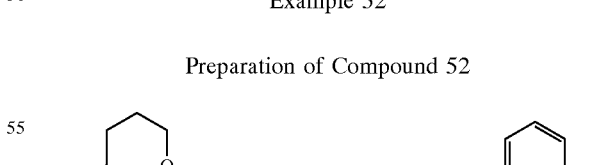

B

The desired product 51 is obtained by the oxidation protocol described previously for Example 2 Step B. Purification by flash column chromatography will afford pure 51.

Example 52

Preparation of Compound 52

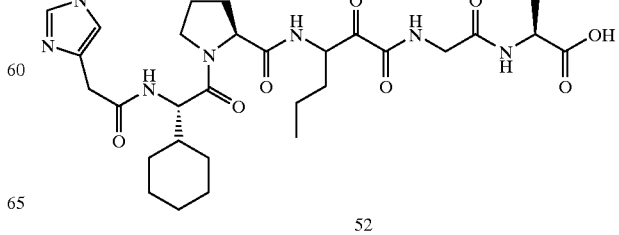

52

293
-continued
Step A
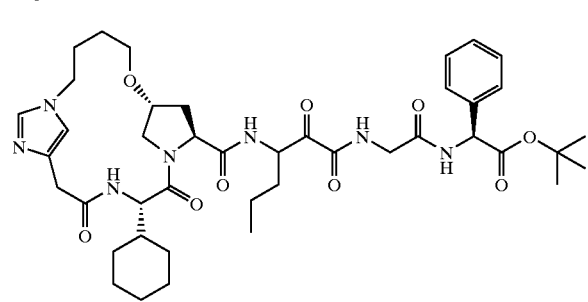
51
↓
294
-continued
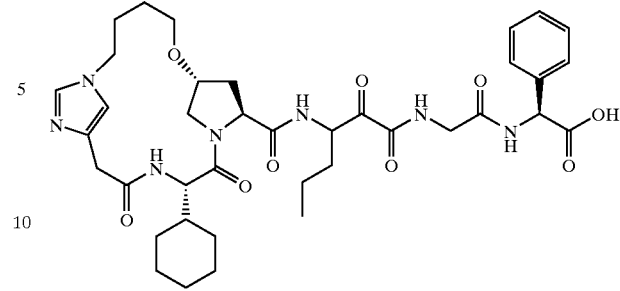
52
The desired product 52 is obtained by the procedure described previously for Example 3, Step A.
Example 53
Preparation of Compounds of Formulas 53A and 53B
53A
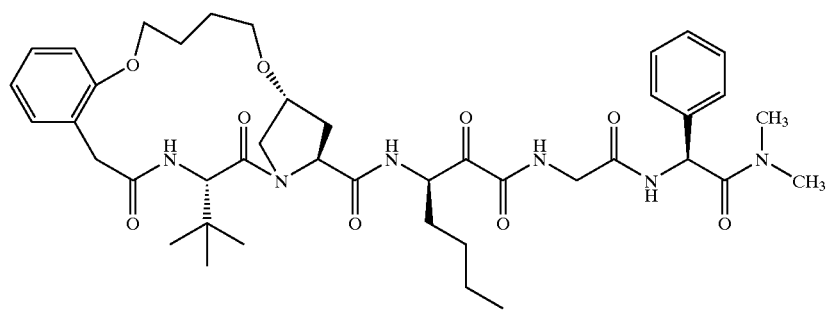
53B
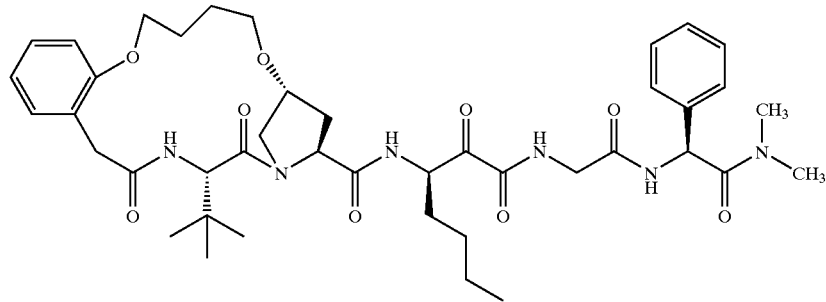
Step A:
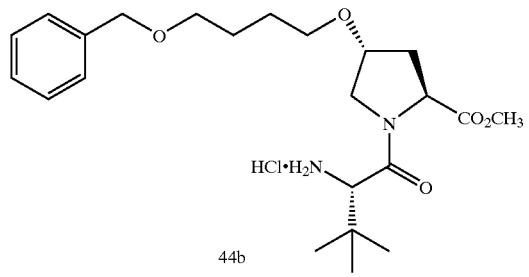 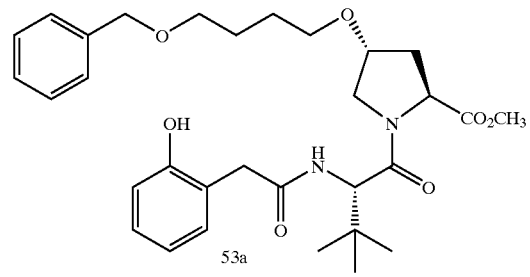

The desired product 53a was obtained by the method described in Example 1, Step F. The material was purified by flash column chromatography using 80/20 to 60/40 dichloromethane/ethyl acetate to provide 53a.

Step B:

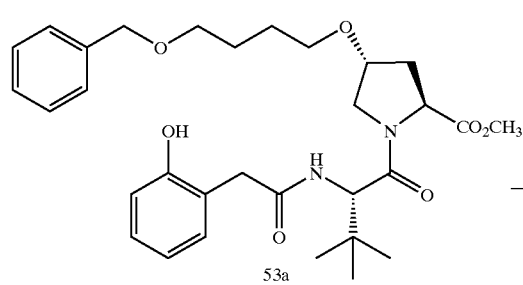

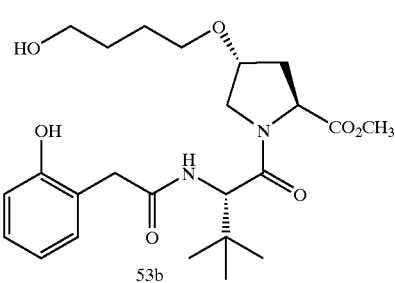

The desired product 53b was obtained by the method described in Example 1, Step G. The crude material was carried to the next step as is.

Step C:

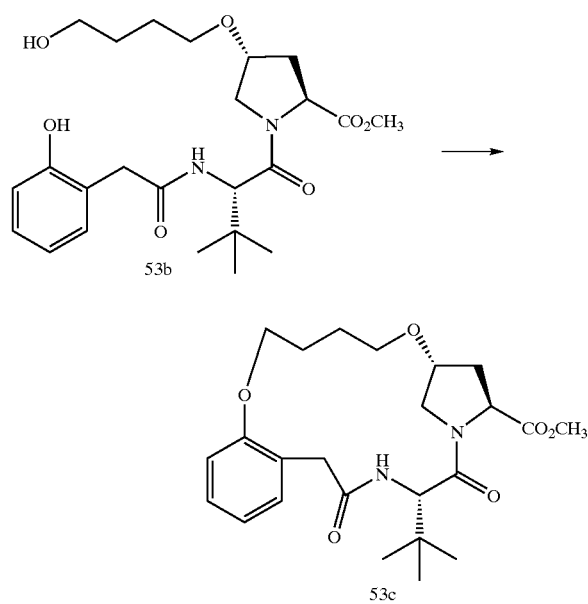

The desired product 53c was obtained by the method described in Example 1, Step H. Purification by column chromatography using 99/1 dichloromethane/methanol afforded 53c along with triphenylphosphine oxide. This mixture was taken to the next step.

Step D:

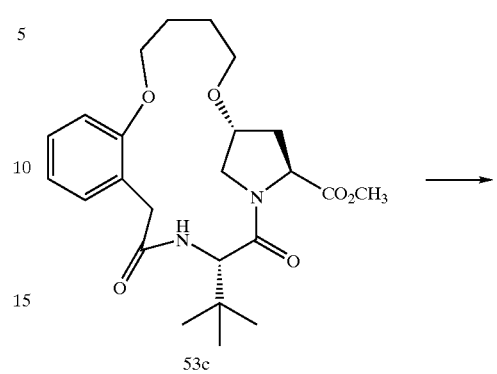

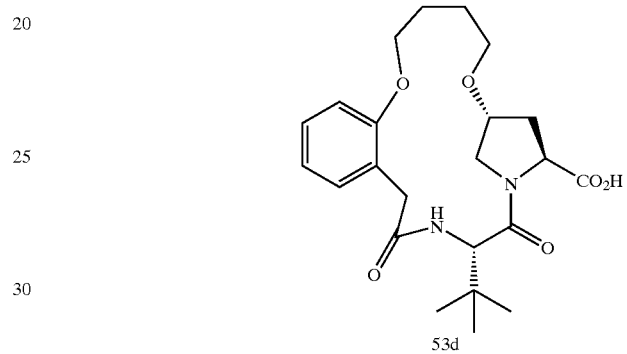

The desired product was obtained by the method described in Example 1, Step 1.

Step E:

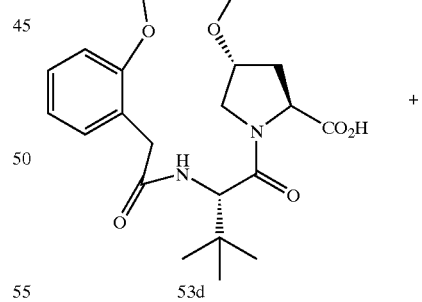

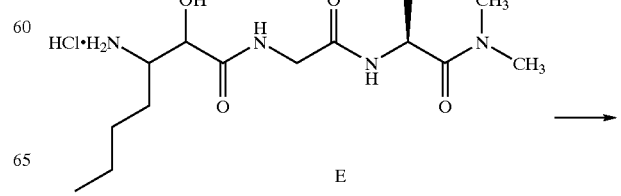

-continued

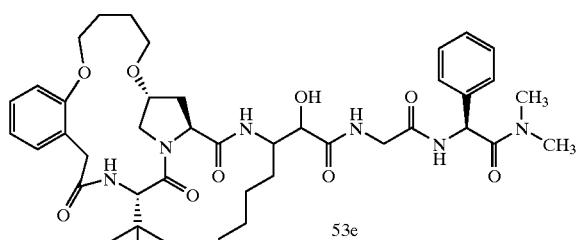

53e

The expected product 53e was synthesized as described earlier for the Example 1, Step J. The material after work-up was of sufficient purity to be carried forward to the next step.

Step F:

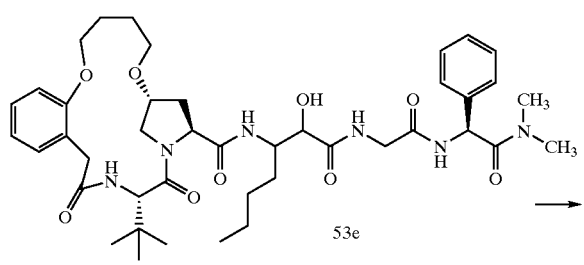

53e

↓

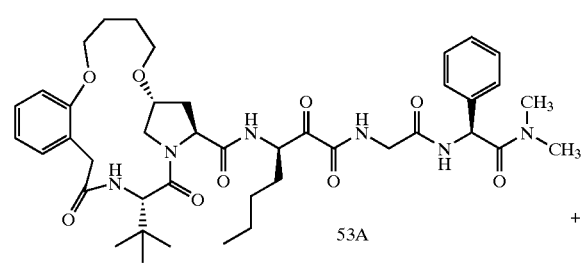

53A

+

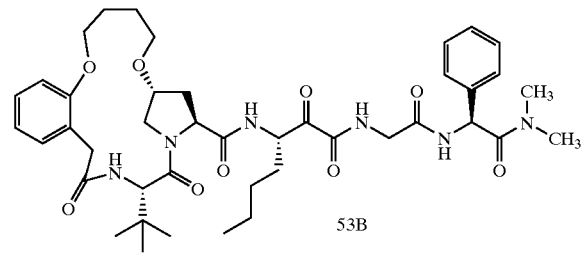

53B

The desired products 53A and 53B were obtained by the oxidation protocol described previously for Example 1, Step K. Purification by flash column chromatography using 100/0 to 99/1 dichloromethane/methanol afforded separate isomers 53A and 53B, and some mixture.

Example 54
Preparation of Compound 54

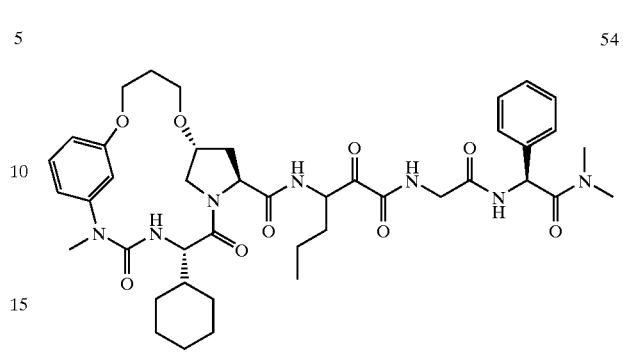

54

Step A

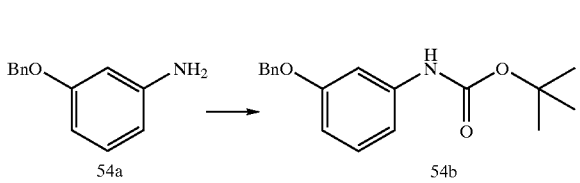

54a → 54b

Commercially available 54a was converted to the desired product 54b using the procedure described for Intermediate A Step 3 in quantitative yield.

Step B

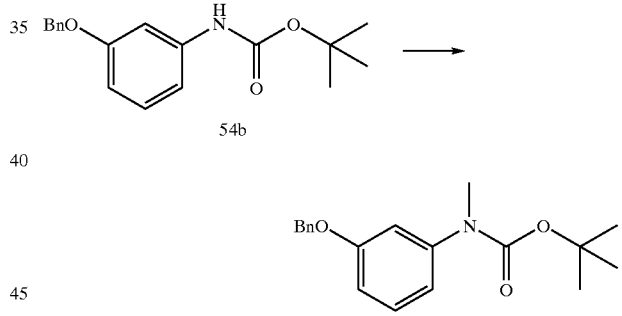

54b

↓

54c

To a cold (0° C.) solution of 54b (8 g, 26.8 mmol) in DMF (100 mL) was added sodium hydride (60% dispersion in oil, 1.3 g, 32.16 mmol). After 10 minutes iodomethane (2.8 mL, 42.8 mmol) was added and the reaction was warmed to ambient temperature over 2 hrs. The reaction mixture was quenched with aqueous $NH_4Cl$ solution and extracted with EtOAc. The organic layer was separated, dried ($Na_2SO_4$) and concentrated to afford 54c which was sufficiently pure for further studies.

Step C

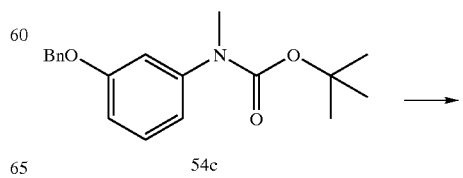

54c

-continued

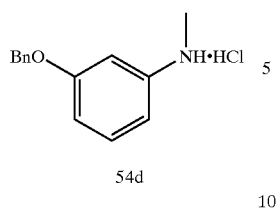

54d

The desired product 54d was obtained by the procedure described for Example 1 Step C. The crude product was used without further purification.

Step D

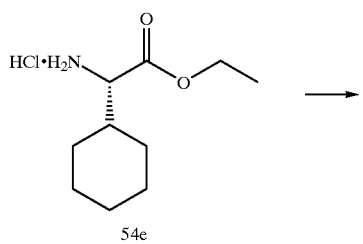

54e

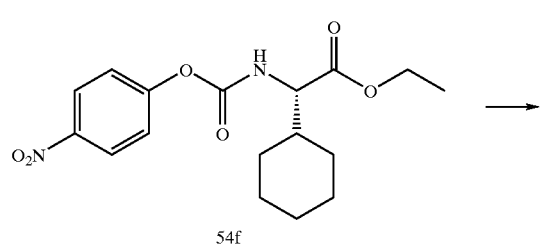

54f

The desired product 54f was obtained by the procedure described for Example 26 Step A using 54e as the starting material. The crude product was purified by flash chromatography using 80/20 to 100/0 dichloromethane/hexanes to afford 54f.

Step E

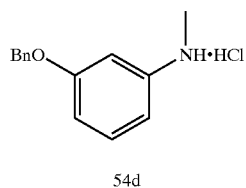

54d

+

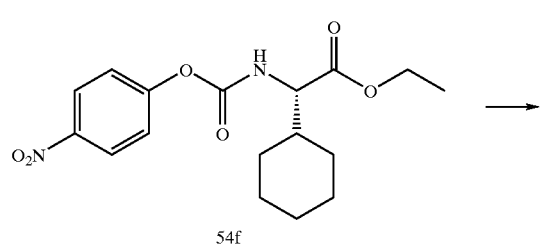

54f

-continued

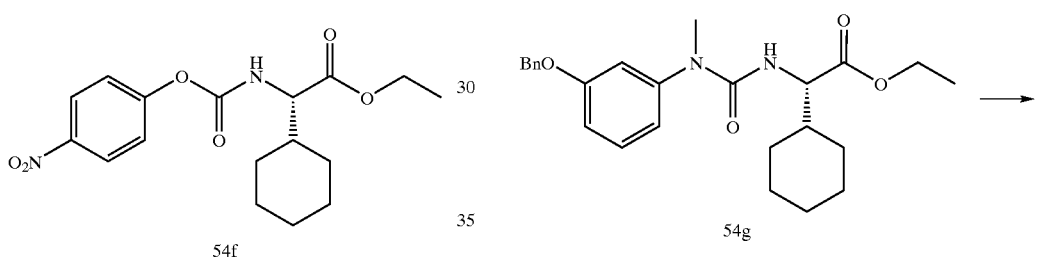

54g

The desired product 54g was obtained by the procedure described for Example 26 Step B using 54d and 54f as the starting materials. The reaction was carried out in chloroform at 50° C. The residue was purified by flash chromatography using 85/15 hexanes/EtOAc to provide 54g in 56% yield. HRMS (FAB) Calcd for $C_{25}H_{33}N_2O_4$: 425.2440 (M+H)$^+$. Found: 425.2424.

Step F

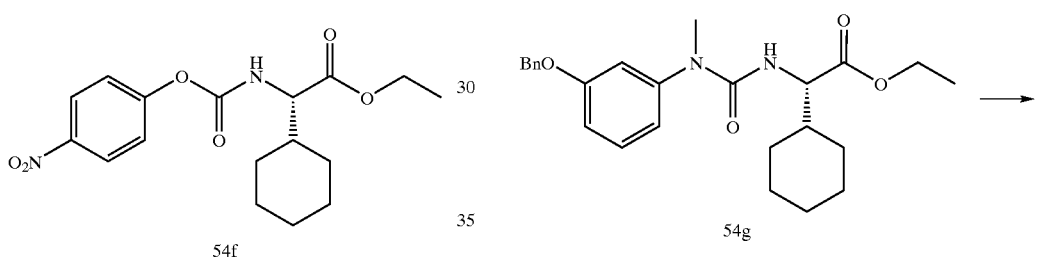

54g

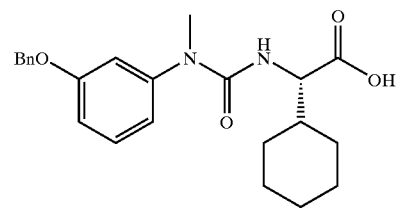

54h

The desired compound 54h was obtained by the procedure described earlier for Example 1 Step I using EtOH as the solvent.

Step G

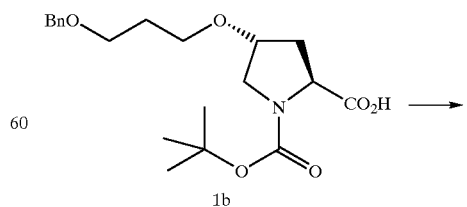

1b

-continued

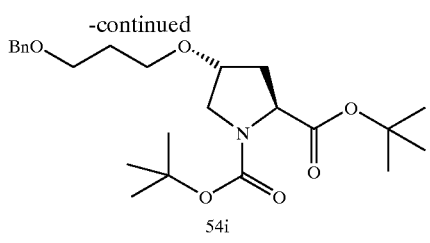

The desired compound 54i was prepared by the protocol described for Example 18 Step B.

Step H

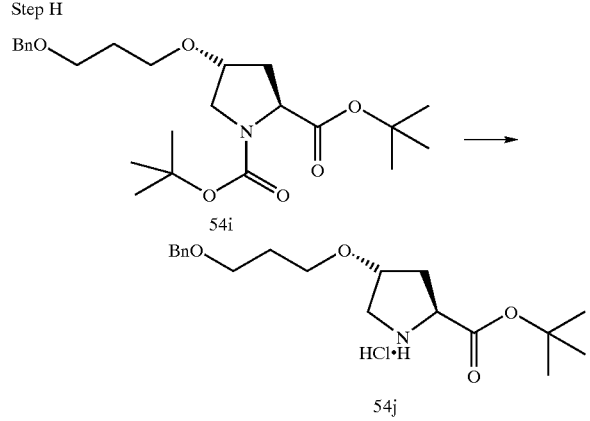

The desired product 54j was obtained by the procedure described for Example 1 Step C. The crude material was used without purification.

Step I

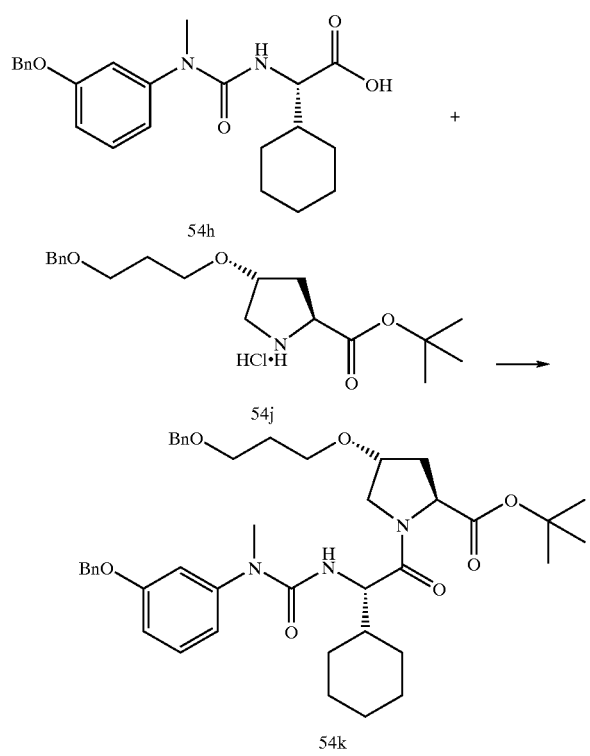

The desired product 54k was obtained by the coupling protocol described previously for Example 1 Step D.

Step J

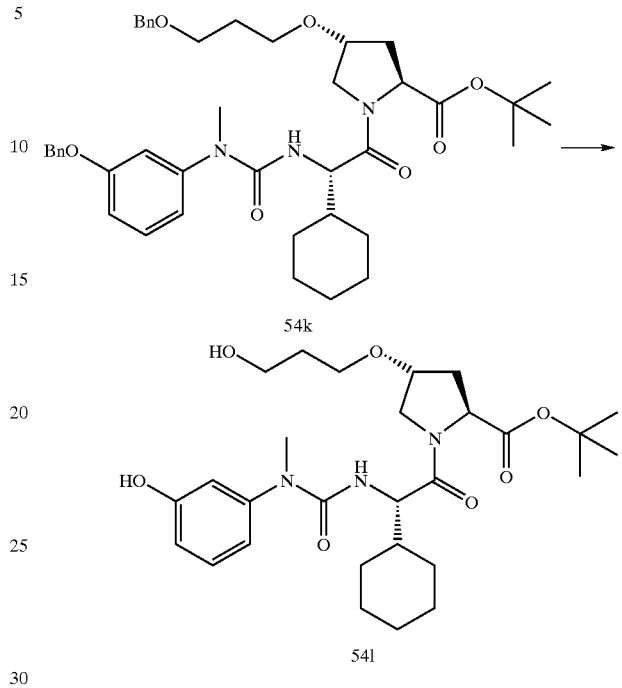

The desired product 54l is obtained by the hydrogenation procedure described previously for Example 1 Step G.

Step K

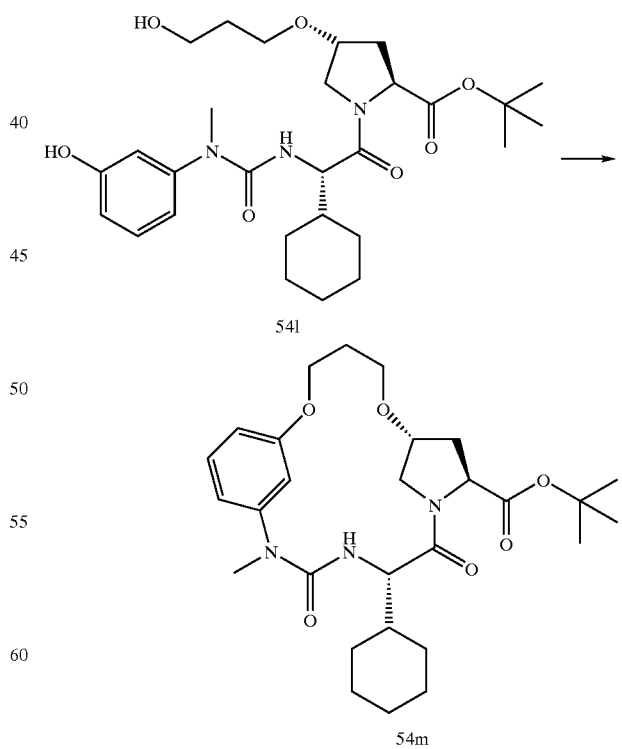

The desired product 54m is obtained by the cyclization protocol described for Example 1 Step H.

Step L

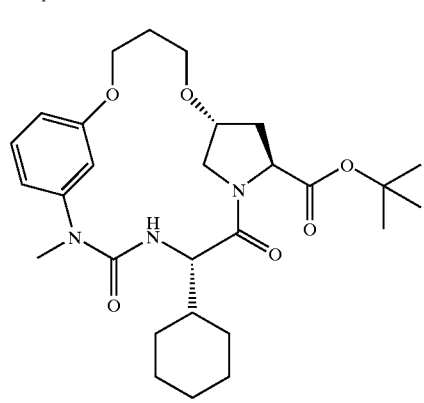

54m

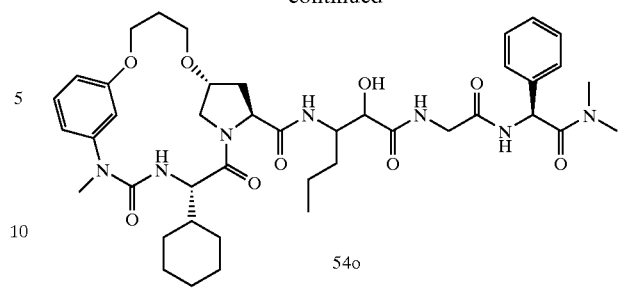

54o

The expected product 54o is synthesized as described earlier for Example 1 Step J.

Step N

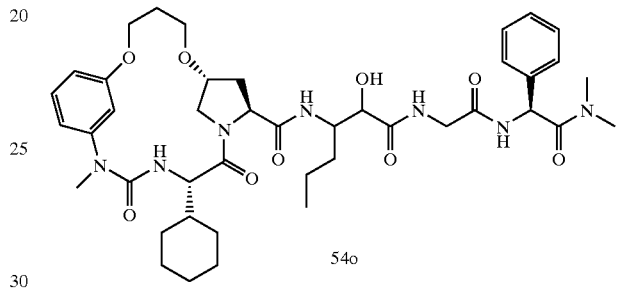

54o

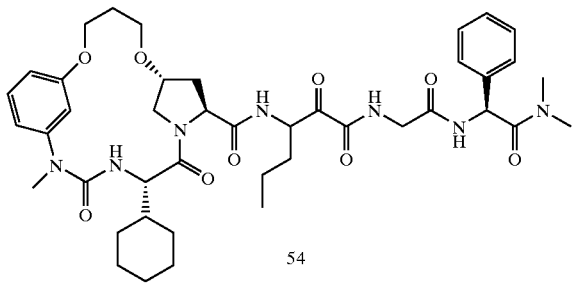

54

The desired product 54 is obtained by the oxidation protocol described previously for Example 1 Step K. Purification by flash column chromatography will afford pure 54.

Example 55

Preparation of Compound 55

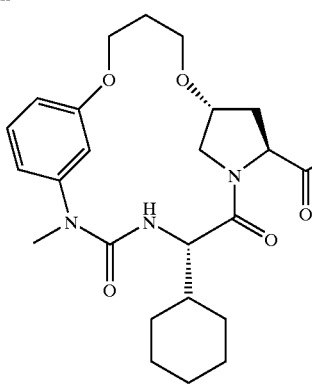

54n

The desired product 54n is obtained by the producer described previously for Example 3 Step A.

Step M

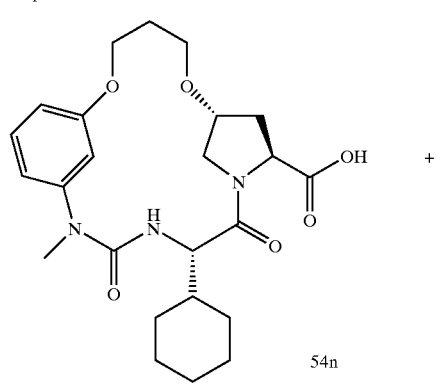

54n +

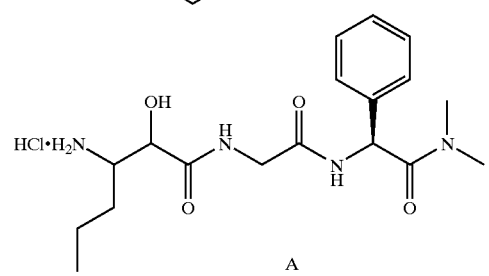

A

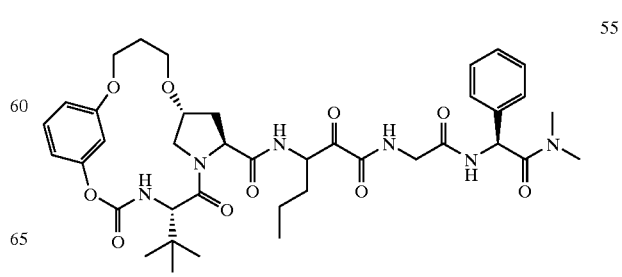

55

305
-continued

Step A

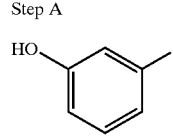

55a

→

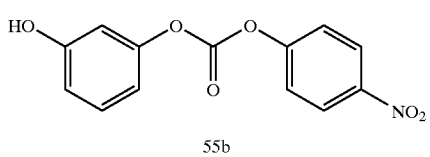

55b

Commercially available 55a was converted to the desired product 55b using the procedure described for Example 26 Step A in 41% yield.

Step B

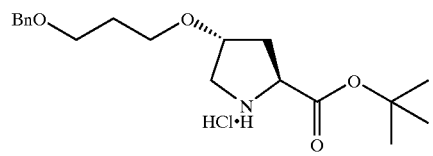

54j

→

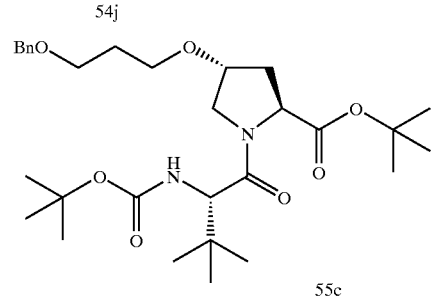

55c

The desired product 55c was obtained by the coupling protocol described previously for Example 1 Step D using N-boc-t-butylglycine as the coupling partner. Purification using 95/5 dichloromethane/EtOAc afforded 55c in 57% yield.

Step C

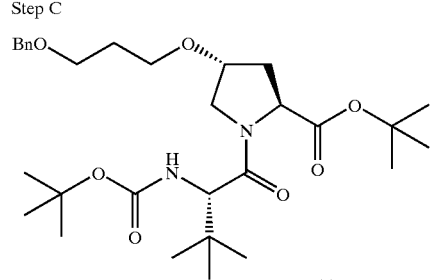

55c

→

306
-continued

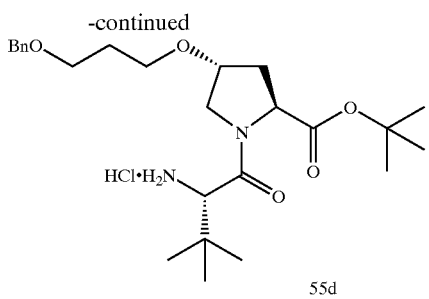

55d

The desired product 55d was obtained by the procedure described previously for Example 1 Step C. The crude material was carried further.

Step D

55b

+

55d

→

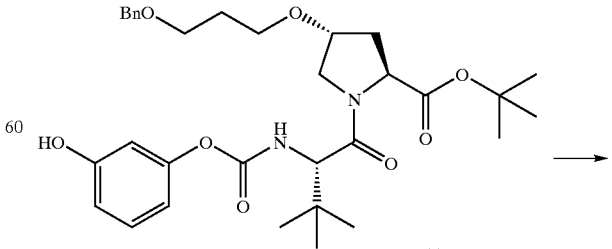

55e

The desired product 55e was obtained by the protocol described for Example 26 Step B. Purification using 80/20 dichloromethane/EtOAc afforded 55e in 20% yield. HRMS (FAB) Calcd for $C_{32}H_{45}N_2O_8$: 585.3176 (M+H)$^+$. Found: 585.3177.

Step E

55e

→

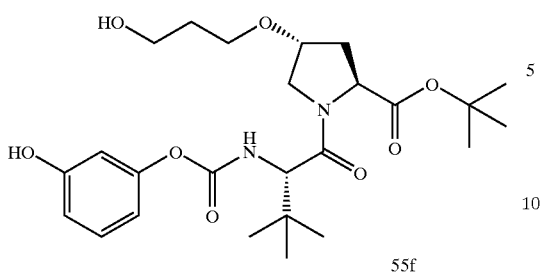

55f

The desired product 55f was obtained by the producer described previously for Example 1 Step G. HRMS (FAB) Calcd for $C_{25}H_{39}N_2O_8$: 495.2706 $(M+H)^+$. Found: 495.2704.

Step F

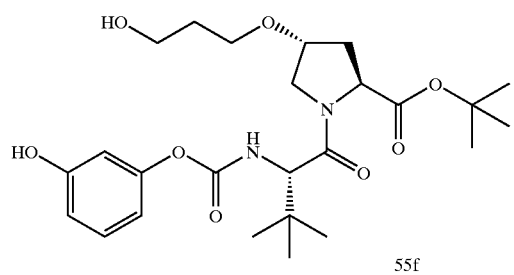

55f

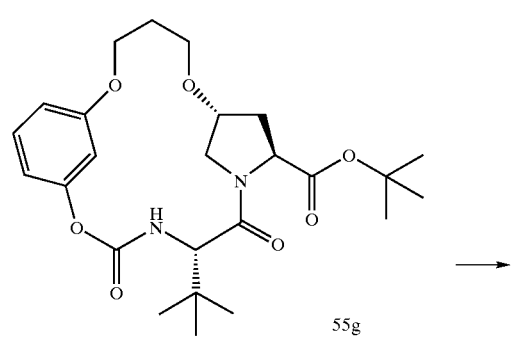

55g

The expected product 55g was synthesized as described earlier for Example 1 Step H. Purification by flash chromatography using 85/15 dichloromethane/EtOAc provided 55g in 10% yield.

Step G

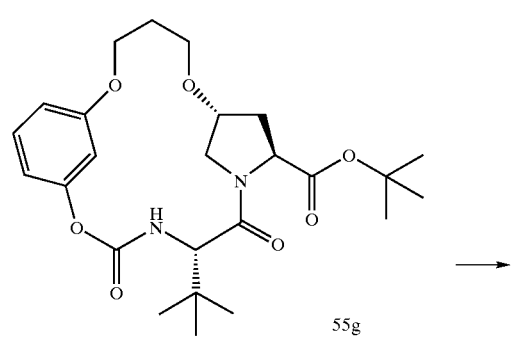

55g

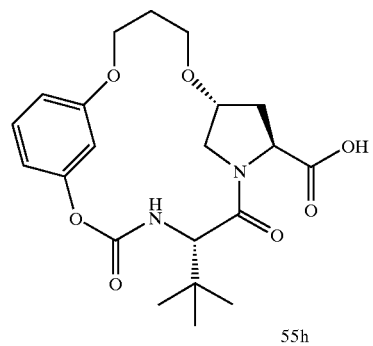

55h

The desired product 55h was obtained by the method described previously for Example 3 Step A. The crude material was carried further without purification.

Step H

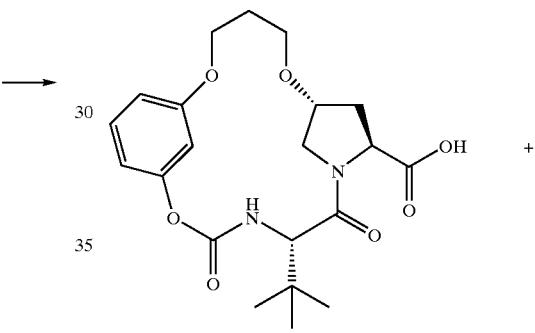

55h

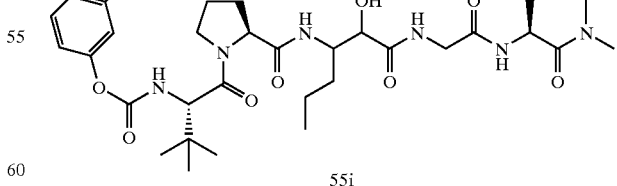

A

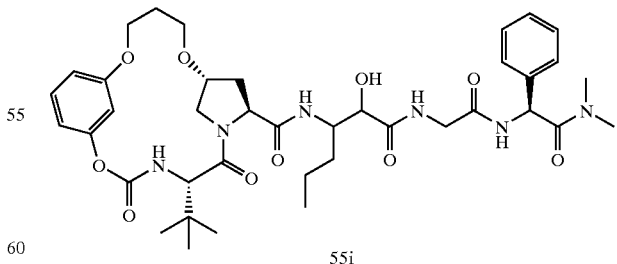

55i

The expected product 55i was synthesized as described earlier for Example 1 Step J. The crude material was carried further without purification.

Step I

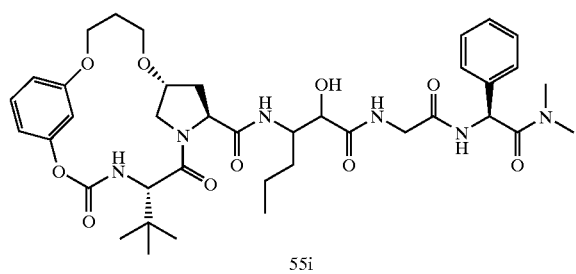

55i

↓

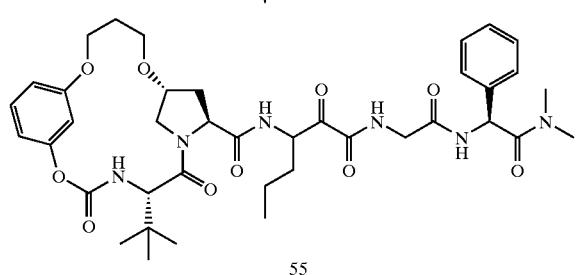

55

The desired product 55 was obtained by the oxidation protocol described previously for Example 1 Step K. Purification by flash column chromatography using 98/2 dichloromethane/MeOH afforded 55.

Example 56

Preparation of Compound 56

56 A

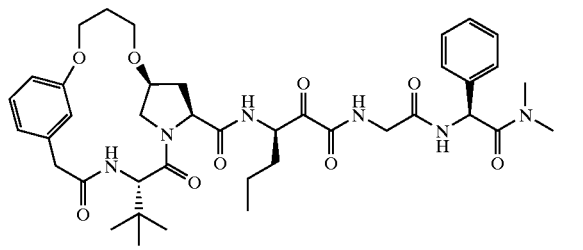

56 B

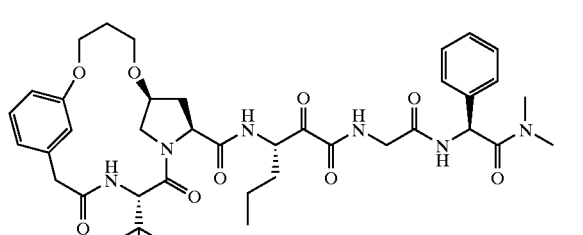

Step A

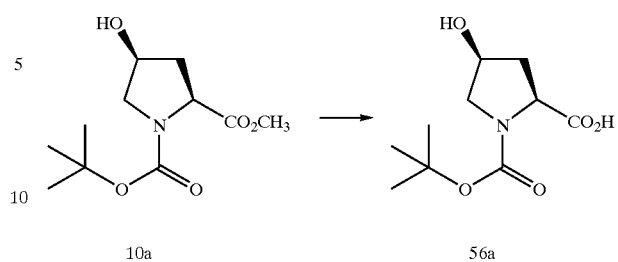

10a                                    56a

To a solution of commercially available methyl ester 10a (5.0 g, 20.4 mmol) in MeOH (20 mL) was added a solution of LiOH (730 mg, 30.6 mmol) in water (20 mL). The reaction mixture was stirred at ambient temperature for 2 hrs. TLC indicated consumption of starting material. The reaction mixture was concentrated and acidified with 10% citric acid solution. Solid NaCl was added and the aqueous layer was extracted with EtOAc several times. The combined EtOAc layer was dried ($Na_2SO_4$) and concentrated to provide 56a in quantitative yield. HRMS (FAB) Calcd for $C_{10}H_{18}N_1O_5$: 232.1185 $(M+H)^+$. Found: 232.1189.]

Step B

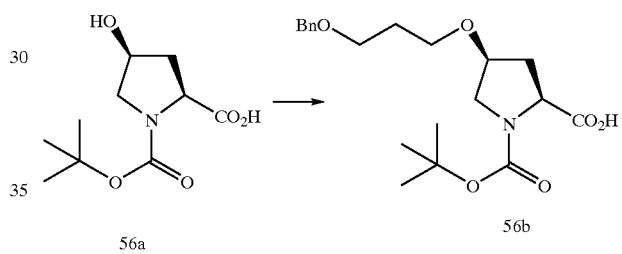

56a                                    56b

The desired product 56b was obtained by the method described for Example 1, Step A. The crude material was converted to the methyl ester without purification.

Step C

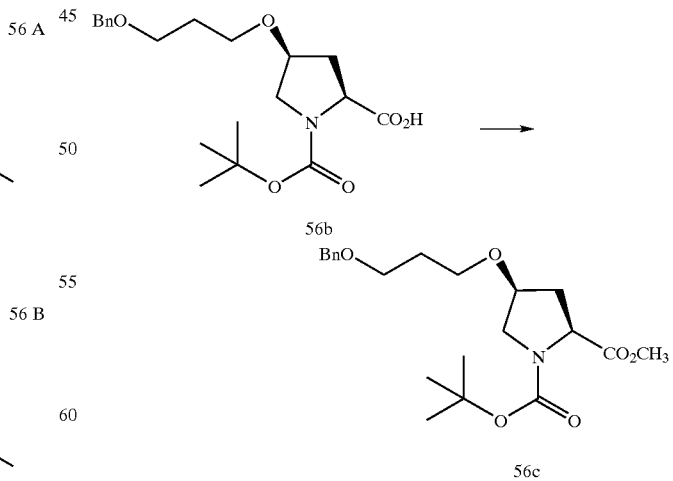

The desired product 56c was obtained by the method described for Example 1, Step B. Purification of the residue by column chromatography using 80/20 to 50/50 hexanes/

EtOAc and then 70/30 to 40/60 dichloromethane/EtOAc afforded 13% of 56c. HRMS (FAB) Calcd for $C_{21}H_{31}NO_6$: 394.2230 (M+H)$^+$. Found: 394.2224.

Step D

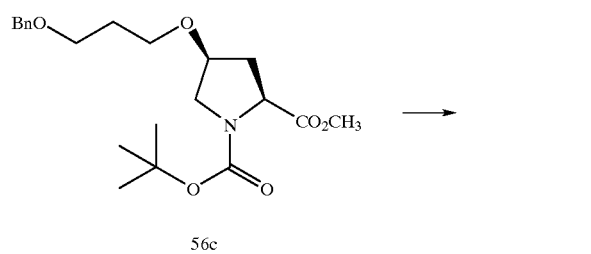

56c

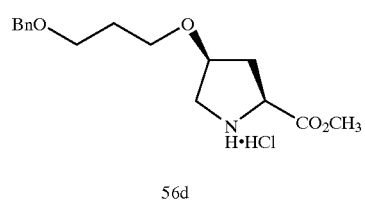

56d

The desired product 56d was obtained by the method described for Example 1, Step C. The crude material was used without purification.

Step E

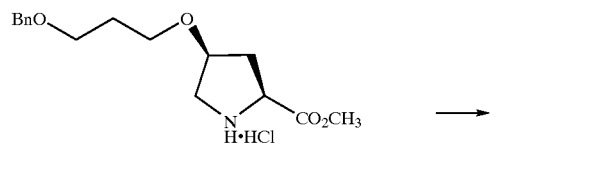

56d

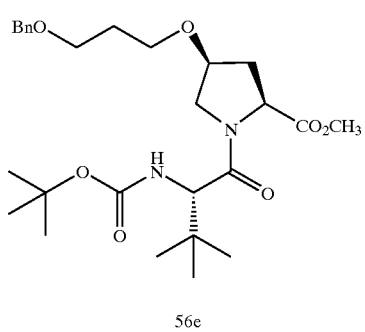

56e

The desired product 56e was obtained by the method described for Example 1, Step D, using N-boc-tert-butyl glycine as the coupling partner. Purification of the residue by column chromatography using 90/10 dichloromethane/EtOAc afforded 86% of 56e. HRMS (FAB) Calcd for $C_{27}H_{43}N_2O_7$: 507.3070 (M+H)$^+$. Found: 507.3072.

Step F

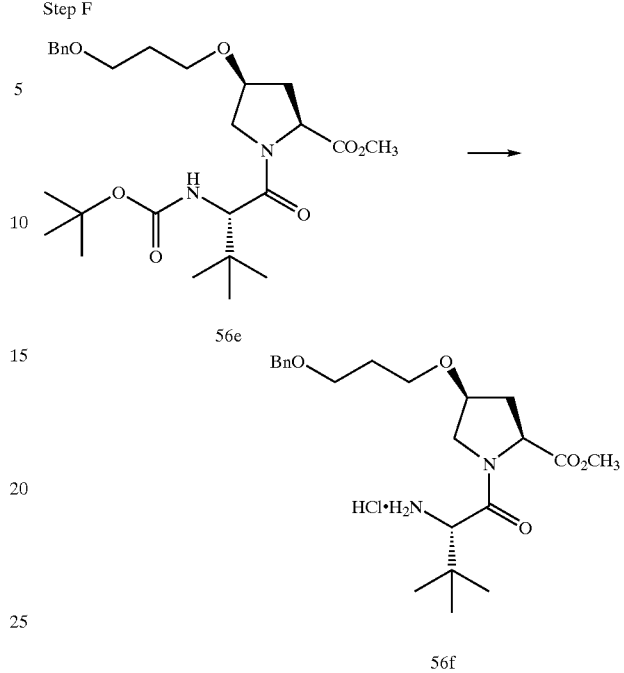

The desired compound 56f was prepared by the protocol described for Example 1, Step E. The material was carried forward as it was.

Step G

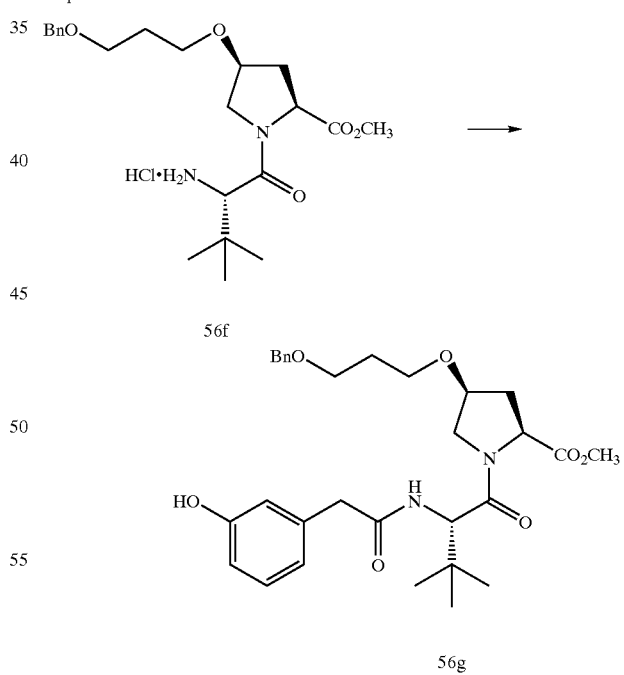

The desired product 56g was obtained by the procedure described for Example 1, Step F. The material was purified by flash column chromatography using 98/2 dichloromethane/MeOH to yield 56g in 78% as a white foam. HRMS (FAB) Calcd for $C_+H_{41}N_2O_7$: 541.2914 (M+H)$^+$. Found: 541.2916.

Step H

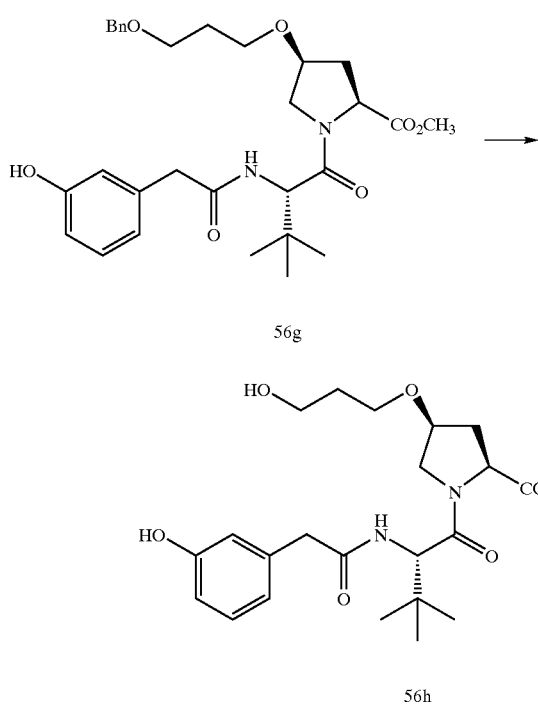

The desired product 56h was obtained by the procedure described for Example 1, Step G. The product obtained after filtering off the catalyst was pure enough for subsequent manipulations. HRMS (FAB) Calcd for $C_{23}H_{35}N_2O_7$: 451.2444 (M+H)$^+$. Found: 451.2449.

Step I

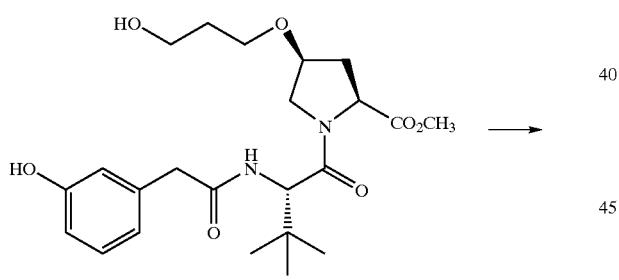

The desired product 56i was obtained by the procedure described for Example 1, Step H. Purification of the crude residue using 75/25 hexanes/acetone provided a mixture of the product 56i along with triphenylphosphine oxide. HRMS (FAB) Calcd for $C_{23}H_{33}N_2O_6$: 433.2339 (M+H)$^+$. Found: 433.2343.

Step J

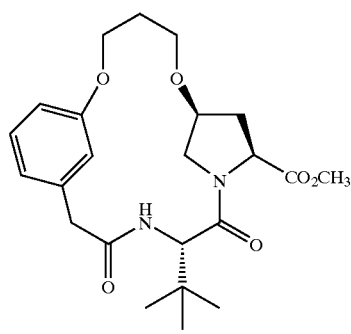

The expected product 56j was synthesized as described for Example 1, Step I. Yield for two steps=16%. HRMS (FAB) Calcd for $C_{22}H_{31}N_2O_6$: 419.2182 (M+H)$^+$. Found: 419.2176.

Step K

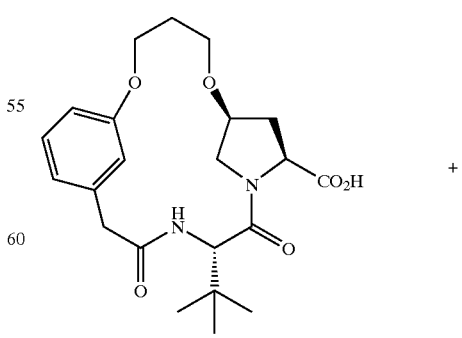

-continued

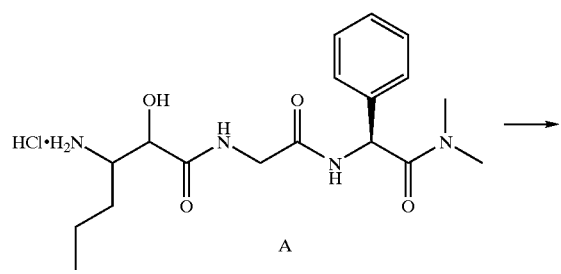

A

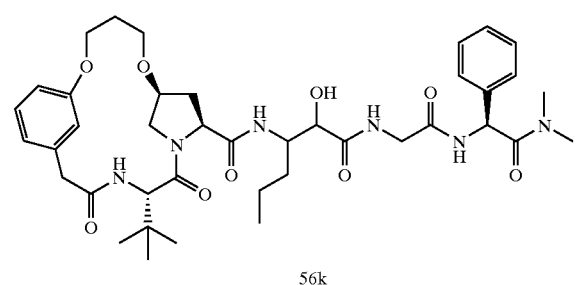

56k

The expected product 56k was synthesized as described earlier for the Example 1, Step J. The material after work-up was of sufficient purity to be carried forward to the next step. HRMS (FAB) Calcd for $C_{40}H_{57}N_6O_9$: 765.4187 $(M+H)^+$. Found: 765.4198.

Step L

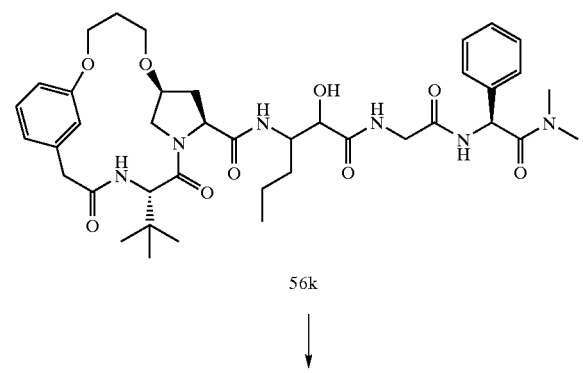

56k

↓

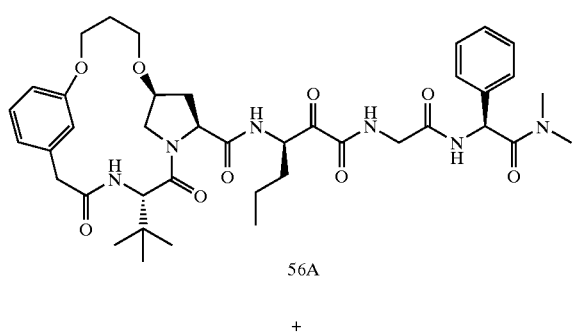

56A

+

-continued

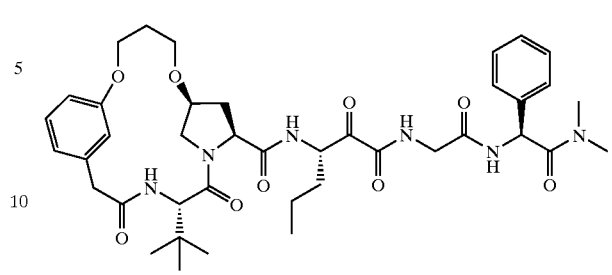

56B

The desired products 56A and 56B were obtained by the oxidation protocol described previously for Example 1, Step K. Purification by flash column chromatography using 98/2 to 96/4 dichloromethane/MeOH afforded separate isomers 56A and 56B, and some mixture. Combined yield=35% (for 2 steps). HRMS (FAB) Calcd for $C_{40}H_{55}N_6O_9$: 763.4031 $(M+H)^+$. Found: 763.4025 (56A), 763.4040 (56B).

Example 57

Preparation of Compounds of Formulas 57A and 57B

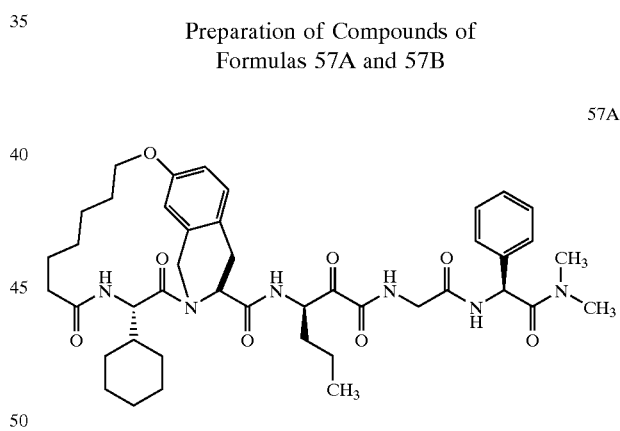

57A

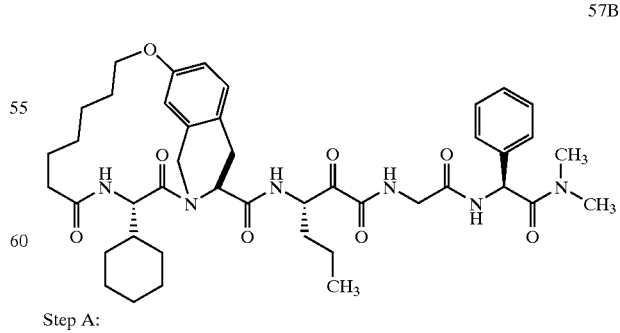

57B

Step A:

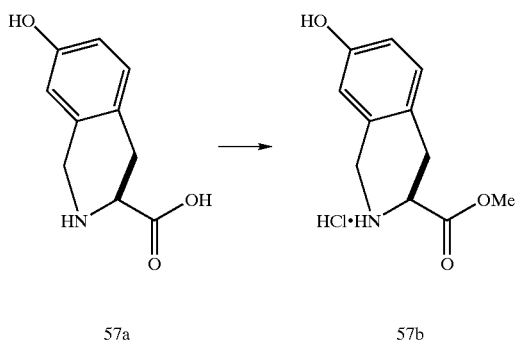

To the solution of the commercial dihydrate of the amino acid (3S)-7-hydroxy-1,2,3,4-tetrahydroisoquinoline-3-carboxylic acid 57a (5.0 g, 21.8 mmol) in methanol (180 mL) was added concentrated hydrochloric acid (5.0 mL, 60 mmol). The resulting clear solution was then heated to reflux in an oil bath for 18 h. Solvents were removed in vacuo to give methyl ester 57b as a white solid, which was used in the next reaction without further purification.

Step B:

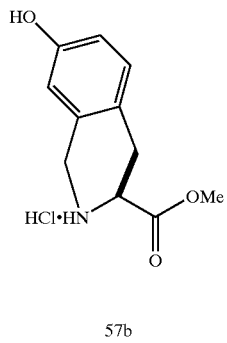

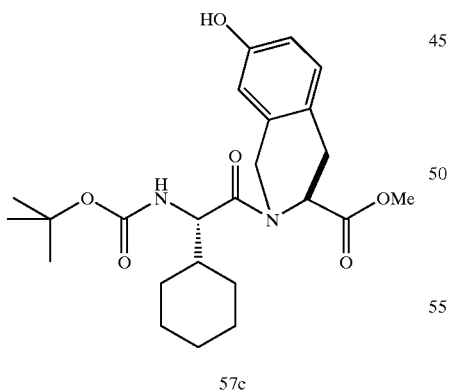

To a solution of amine hydrochloride 57b, N-Boc-cyclohexylglycine (5.95 g, 21.8 mmol), HOOBt (3.73 g, 22.9 mmol) and EDCl (5.00 g, 26.1 mmol) in anhydrous DMF (200 mL) and CH$_2$Cl$_2$ (200 mL) at −20° C. was added NMM (7.20 mL, 65.5 mmol). After stirred at this temperature for 30 min, the reaction mixture was kept in a freezer overnight (18 h), after which EtOAc (600 mL), brine (150 mL) and 5% H$_3$PO$_4$ (150 mL) were added. The separated organic solution was washed with 5% H$_3$PO$_4$ (200 mL), saturated aqueous sodium bicarbonate solution (2×200 mL), water (200 mL), and brine (200 mL), dried with magnesium sulfate, filtered and concentrated in vacuo to afford 57c (10.3 g, quant. 2 steps) as a white solid. $^1$H NMR (400 MHz, d$_6$-DMSO) δ 9.32 (s, 1H), 8.35–8.32 (m, 1H), 6.99 (d, J=8.3 Hz, 1H), 6.65–6.54 (m, 1H), 4.92 (d, J=15.5 Hz, 1H), 4.50 (d, J=15.5 Hz, 1H), 4.43–4.36 (m, 1H), 4.29–4.19 (m, 1H), 3.53 (s, 3H), 3.02–2.81 (m, 2H), 1.98–1.62 (m, 8H), 1.42–1.11 (m, 14H); $^{13}$C NMR (100 MHz, d$_6$-DMSO) δ 171.6, 171.2, 162.3, 156.0, 133.7, 128.8, 125.3, 114.1, 112.6, 78.0, 54.8, 52.4, 51.9, 45.0, 29.5, 28.1, 28.0, 25.9, 25.6, 25.5; HRMS m/z 447.2492 [calcd for C$_{24}$H$_{34}$N$_2$O$_6$, 447.2495].

Step C:

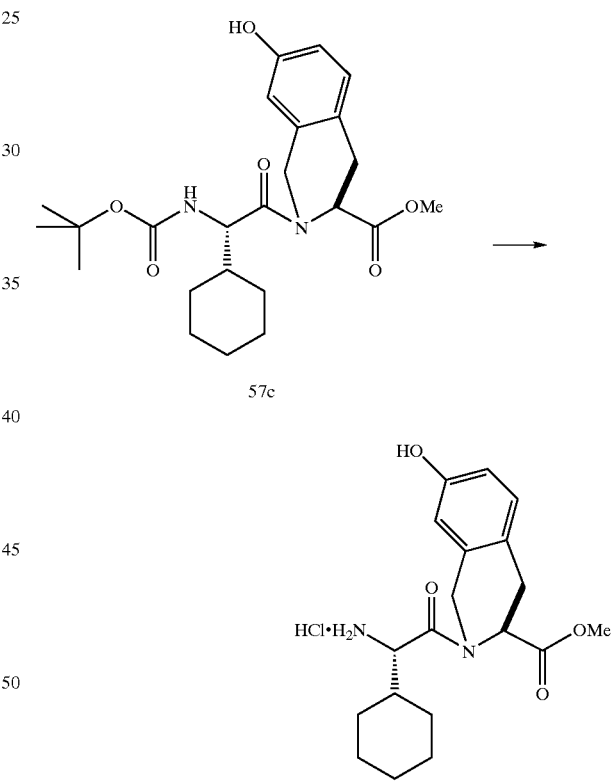

The Boc-amino methyl ester 57c (7.20 g, 16.1 mmol) was dissolved in 4 N HCl (100 mL, 400 mmol) and the resulting solution was stirred at rt. The progress of the reaction was monitored by TLC. After 4 h, the solution was concentrated in vacuo and the residue was under vacuum overnight to give 57d as a white solid which was used in the next coupling reaction without further purification.

Step D:

Step E:

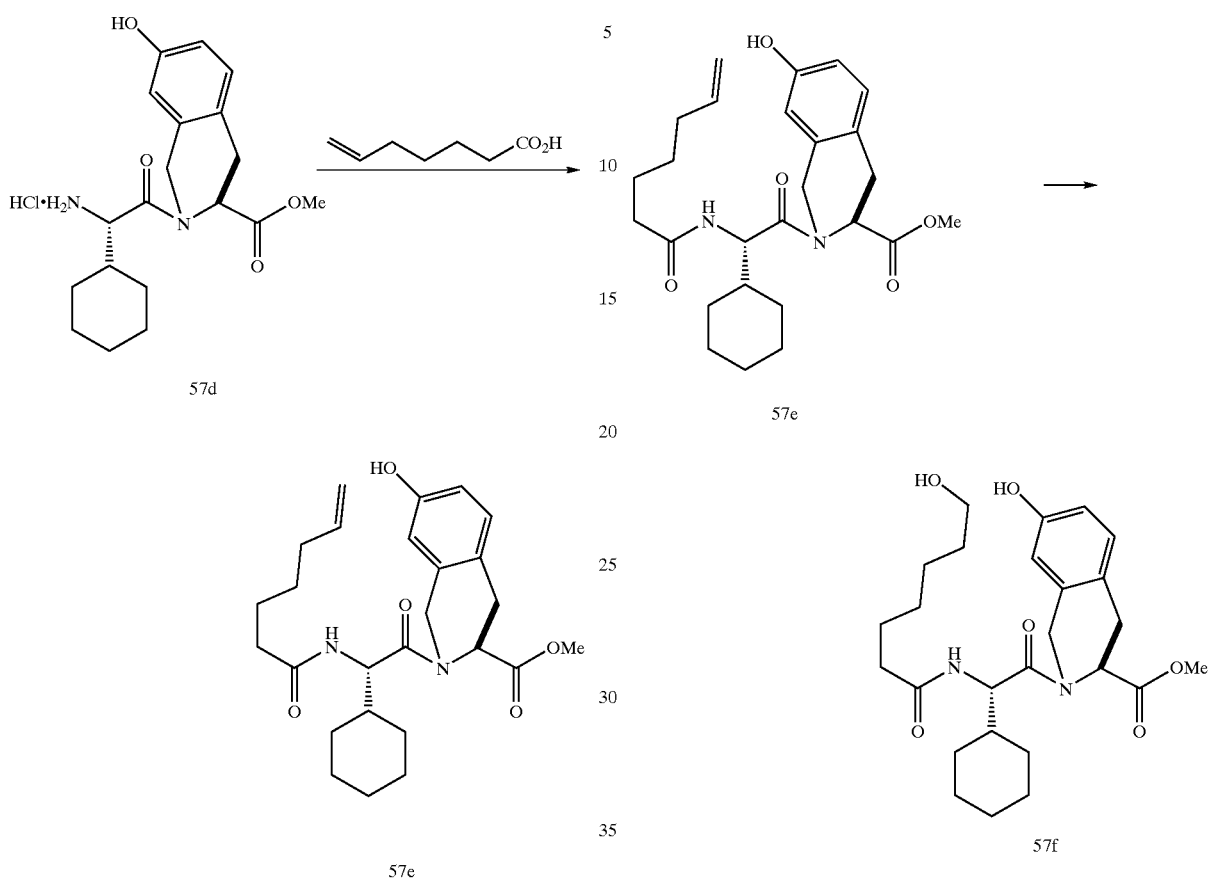

To a solution of amine hydrochloride 57d (from Step D), 6-heptenoic acid (2.90 g, 22.6 mmol), HOOBT (3.70 g, 22.7 mmol) and EDCl (4.80 g, 25.0 mmol) in anhydrous DMF (250 mL) and $CH_2Cl_2$ (150 mL) at $-20°$ C. was added NMM (7.50 mL, 68.2 mmol). After stirred at this temperature for 30 min, the reaction mixture was kept in a freezer for 2 days. It was then stirred in air and allowed to warm to rt. in 1 h. EtOAc (500 mL), brine (100 mL) and 5% $H_3PO_4$ (100 mL) were added. The separated organic solution was washed with 5% $H_3PO_4$ (100 mL), saturated aqueous sodium bicarbonate solution (2×150 mL), water (150 mL), and brine (150 mL), dried with magnesium sulfate, filtered and concentrated in vacuo. Flash chromatography (5 to 30% EtOAc-$Cl_2Cl_2$) afforded 57e (2.30 g, 5.04 mmol, 31% (2 steps)) as a white solid. $^1$H NMR (400 MHz, $d_6$-DMSO) δ 9.32 (s, 1H), 8.06–8.01 (m, 1H), 7.00–6.6.96 (m, 1H), 6.63–6.54 (m, 2H), 5.78–5.70 (m, 1H), 5.04–4.89 (m, 4H), 4.73–4.69 (m, 1H), 4.53 (d, J=15.5 Hz, 1H), 3.54 (s, 3H), 3.01–2.91 (m, 2H), 2.15–1.93 (m, 4H), 1.76–0.97 (m, 15H); $^{13}$C NMR (100 MHz, $d_6$-DMSO) δ 172.0, 171.5, 171.1, 156.0, 138.6, 134.0, 128.7, 122.5, 114.6, 114.1, 112.5, 52.9, 52.2, 51.9, 45.0, 34.5, 32.8, 32.7, 29.4, 28.7, 28.1, 27.7, 25.9, 25.5, 25.5, 24.8; HRMS m/z 457.1 [calcd for $C_{26}H_{36}N_2O_5$, 456.6].

To the solution of 57e (2.20 g, 4.82 mmol) in anhydrous THF (100 mL) under nitrogen at 0° C. was added borane-THF solution (20 mL, 1.0 M, 20 mmol) cautiously. The resulting solution was stirred at 0° C. under hydrogen for 1 h 40 min. Then ethanol (10 mL) and pH 7 buffer (15 mL) were added, followed by 30% $H_2O_2$ solution (15 mL). After stirred at 0° C. for 20 min, it was warmed to rt. and stirred for 2 h. EtOAc (400 mL) and brine (200 mL) were added and layers were separated. Aqueous solution was extracted with EtOAc (2×150 mL). Combined organic solution was dried with magnesium sulfate, filtrated, concentrated in vacuo. Flash chromatography (3 to 5% MeOH—$Cl_2Cl_2$) afforded 57f (2.18 g, 4.47 mmol, 93%) as a white solid. $^1$H NMR (400 MHz, $d_6$-DMSO) δ 9.32 (s,1H), 8.04–8.00 (m, 1H), 6.99–6.96 (m, 1H), 6.63–6.51 (m, 2H), 5.05–5.00 (m, 1H), 4.73–4.21 (m, 3H), 4.51 (d, J=15.5 Hz, 1H), 3.54 (s, 3H), 3.03–2.90 (m, 2H), 2.15–2.00 (m, 2H), 1.75–1.56 (m, 6H), 1.49–0.97 (m, 13H); $^{13}$C NMR (100 MHz, $d_6$-DMSO) δ 172.2, 171.6, 171.2, 156.0, 134.1, 128.7, 122.6, 114.2, 112.5, 60.7, 52.9, 52.3, 51.9, 45.1, 34.8, 32.4, 29.5, 28.7, 28.53, 28.47, 28.10, 25.9, 25.6, 25.5, 25.4, 25.2; HRMS m/z 475.2812 [calcd for $C_{26}H_{38}N_2O_6$, 475.2808].

Step F:

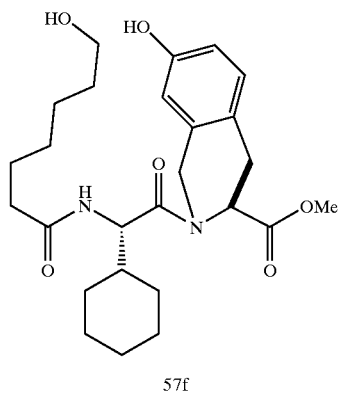

57f

A solution of phenol alcohol 57f (2.08 g, 4.38 mmol) and ADDP (3.00 g, 11.9 mmol) in anhydrous $CH_2Cl_2$ was bubbled with Argon through a frit glass bubbler for 20 min. To this solution at 0° C. was added triphenylphosphine (3.45 g, 13.2 mmol). After stirring at 0° C. for 20 min, the solution was warmed to rt. and stirred overnight (18 h) under nitrogen. TLC indicated the presence of substantial amount of starting material. A second batch of ADDP (3.00 g, 11.9 mmol) and triphenylphospine (3.45 g, 13.2 mmol) were added, and the mixture was stirred under nitrogen for 2 days and 16 h. TLC showed the complete consumption of the starting material. After removal of solvent in vacuo, the residue was partially purified by flash chromatography (1 to 2% MeOH in $Cl_2Cl_2$) to afford a mixture of the macrocycle 57 g and triphenylphosphine oxide. The macrocyclic 57 g was hydrolyzed to the corresponding acid without further purification. $^1$H NMR (400 MHz, $d_6$-DMSO) δ 8.00 (d, J=10.0 Hz, 1H), 7.17 (d, J=8.2 Hz, 1H), 6.82–6.76 (m, 2H), 5.14 (d, J=14.5 Hz, 1H), 4.79–4.74 (m, 1H), 4.39 (dd, J=11.5, 6.4 Hz, 1H), 4.25 (d, J=14.7 Hz, 1H), 4.22–4.18 (m, 1H), 4.08–4.02 (m, 1H), 3.68 (s, 3H), 3.18 (dd, J=15.1, 6.4 Hz, 1H), 2.85 (dd, J=14.7, 11.5 Hz, 1H), 2.07–2.04 (m, 2H), 1.81–1.40 (m, 10H), 1.32–0.85 (m, 9H); $^{13}$C NMR (100 MHz, $d_6$-DMSO) δ 171.9, 171.5, 170.2, 157.1, 137.0, 131.5, 126.4, 115.9, 112.6, 66.5, 54.4, 52.2, 51.9, 46.8, 44.9, 44.4, 33.6, 29.4, 29.1, 28.0, 27.3, 27.0, 26.0, 25.3, 25.2, 24.3, 24.2, 23.9; HRMS m/z 457.2707 [calcd for $C_{26}H_{36}N_2O_5$, 457.2702].

Step G:

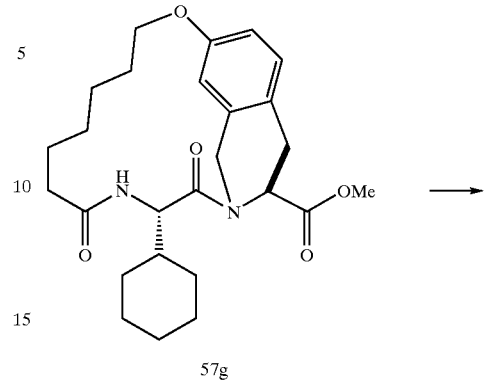

57g

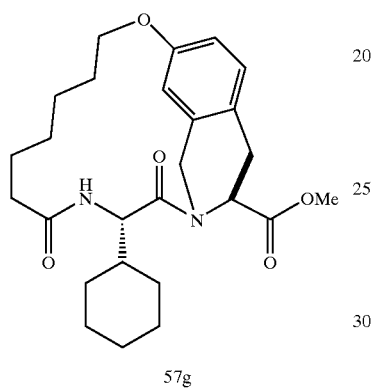

57g

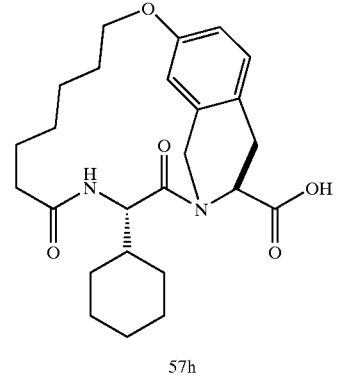

57h

An aqueous lithium hydroxide solution (0.21 g, 30 mL $H_2O$, 8.75 mmol) was added to a 0° C. solution of methyl ester 57 g (from step 12F) in THF (30 mL) and methanol (30 mL). The mixture was stirred in an ice bath and warmed to rt. along with it in 4 h. The progress of the reaction was monitored by TLC. After the volatiles were removed in vacuo, EtOAc (100 mL) and water (30 mL) were added and the two layers separated. The aqueous solution was extracted again with $CH_2Cl_2$ (100 mL), after which it was acidified to pH=1. EtOAc was then added (150 mL) and the aqueous solution was saturated with solid sodium chloride. After separation of the layers, the aqueous layer was extracted with EtOAc (2×100 mL). Organic solutions were combined, dried with magnesium sulfate, filtered and concentrated in vacuo to afford 57 h (1.23 g, 2.78 mmol, 63% (2 steps)) as a white solid.

Step H:

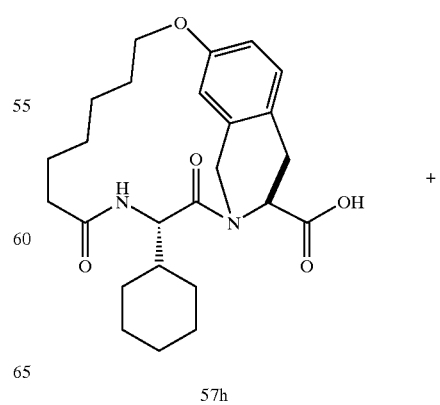

57h

+

323

-continued

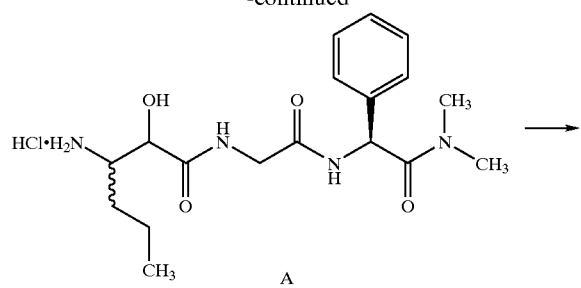

A

57i

To a solution of acid 57 h (0.390 g, 0.881 mmol), amine A (0.360 g, 0.898 mmol), HOOBt (160 mg, 0.981 mmol) and EDCl (210 mg, 1.10 mmol) in anhydrous DMF (50 mL) and $CH_2Cl_2$ (30 mL) at −20° C. was added NMM (0.40 mL, 3.64 mmol). After stirred at this temperature for 30 min, the reaction mixture was kept in a freezer for 66 h. Then EtOAc (200 mL), brine (50 mL) and 5% $H_3PO_4$ (50 mL) were added. The separated organic solution was washed, successively, with 5% $H_3PO_4$ (80 mL), saturated aqueous sodium bicarbonate solution (2×80 mL), water (80 mL), and brine (80 mL), dried with magnesium sulfate, filtered and concentrated in vacuo. Flash chromatography (2 to 5% MeOH—$Cl_2Cl_2$) afforded 57i as a mixture of four diastereomers (0.340 g, 0.431 mmol, 49%) as a white solid. $^1H$ NMR (400 MHz, $d_6$-DMSO) δ 8.56–8.46 (m, 1H), 7.96–7.82 (m, 2H), 7.40–7.25 (m, 6H), 7.15–6.99 (m, 2 H), 6.81–6.74 (m, 2H), 6.05–5.71 (m, 2H), 5.11–5.02 (m, 1H), 4.85–4.68 (m, 1 H), 4.40–3.70 (m, 8H), 3.14–3.02 (m, 1H), 2.95–2.73 (m, 7H), 2.06–2.05 (m, 2 H), 1.81–1.39 (m, 10H), 1.30–1.05 (m, 11H), 0.89–0.75 (m, 5H); $^{13}C$ NMR (100 MHz, $d_6$-DMSO) δ 172.24, 172.21, 171.87, 171.81, 171.78, 171.7, 170.8, 170.77, 170.74, 170.5, 170.4, 170.0, 169.97, 169.24, 169.22, 169.1, 169.0, 168.0, 167.9, 167.82, 167.78, 157.2, 156.9, 137.61, 137.57, 137.54, 137.47, 137.43, 137.38, 133.2, 132.2, 128.9, 128.44, 128.41, 128.37, 128.0, 127.96, 127.6, 127.4, 127.3, 127.19, 127.16, 115.7, 115.6, 115.5, 112.8, 112.77, 112.7, 112.6, 73.6, 73.39, 73.37, 72.4, 71.7, 66.9, 66.7, 55.8, 55.6, 55.09, 55.07, 53.02, 52.95, 52.9, 52.6, 51.0, 50.96, 50.91, 50.86, 50.76, 45.6, 45.5, 45.44, 45.36, 41.7, 41.6, 41.5, 41.4, 36.6, 36.55, 36.49, 35.3, 33.7, 33.6, 33.5, 33.0, 32.4, 30.7, 30.3, 30.1, 30.0, 29.8, 29.48, 29.45, 29.41, 28.3, 28.2, 28.1, 27.3, 27.2, 27.13, 27.09, 27.0, 26.9, 26.85, 26.82, 26.1, 25.4, 25.2, 24.1, 24.08, 24.03, 24.0, 23.9, 23.8, 18.8, 18.7, 18.6, 18.4, 13.9, 13.8, 13.7; HRMS m/z 789.4560 [calcd for $C_{43}H_{60}N_6O_8$, 789.4551, error=1 ppm].

324

Step I:

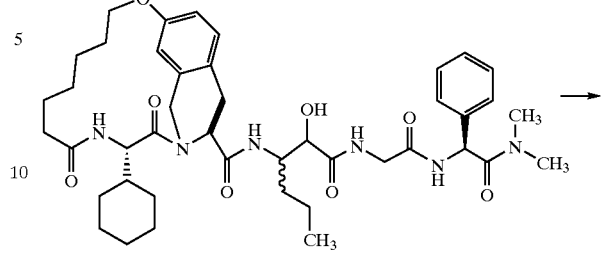

57i

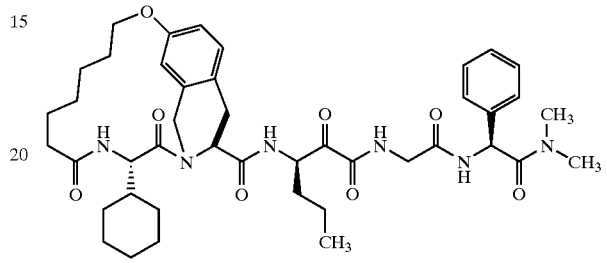

57A

57B

To the mixture of hydoxy amide 57i (0.320 g, 0.406 mmol) and Des-Martin reagent (0.400 g, 0.943 mmol) at 0° C. was added anhydrous $CH_2Cl_2$ (80 mL). The resulting white suspension was vigorously stirred at 0° C. and warmed to rt. along with the ice bath in 4 h. Saturated aqueous sodium bicarbonate and sodium bisulfite solutions (30 mL each) were added and the mixture was vigorously stirred for 10 min before layers were separated. The aqueous solution was extracted with $CH_2Cl_2$ (2×80 mL). Combined organic solution was dried with magnesium sulfate, filtered and concentrated in vacuo. Flash chromatography (2 to 5% MeOH–$Cl_2Cl_2$) afforded two stereo-isomers 57A (109 mg, 0.139 mmol) and 57B (102 mg, 0.130 mmol, 66% combined yield) as white solids.

Example 58

Preparation of Compound of Formula 58

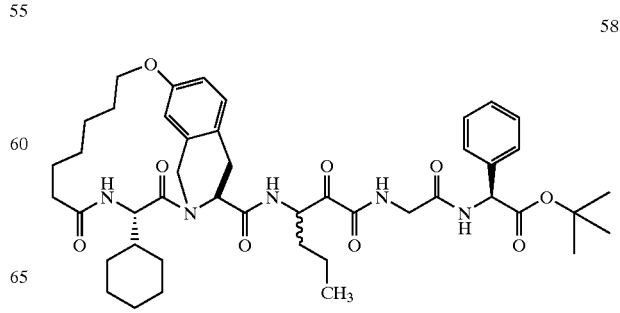

58

Step A:

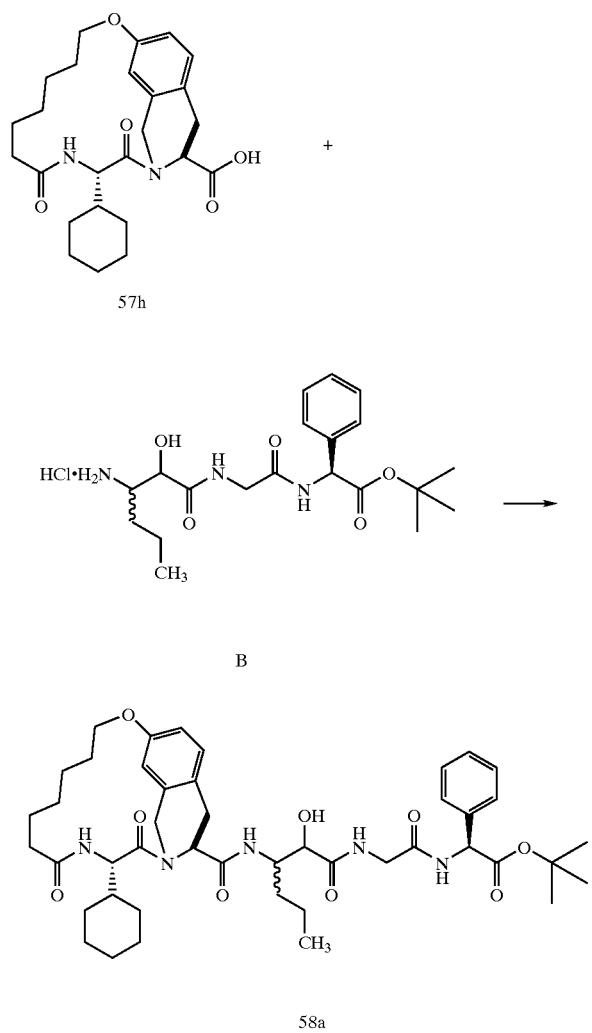

The desired compound 58a was prepared according to the method of Example 1, Step J, except substituting amine hydrochloride B for A. The hydroxy amide 58a was obtained as a mixture of inseparable diastereomers in the form of a white solid in 53% yield.

Step B:

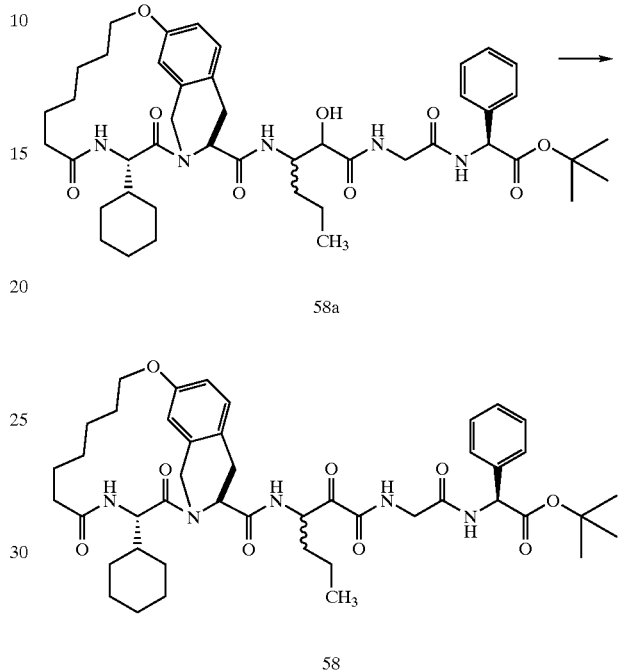

The desired compound 58 was prepared from hydroxy amide 58a according to the method of Example 2, Step B. It was obtained as a mixture of inseparable diastereomers in the form of a white solid in 88% yield.

Example 59

Preparation of Compounds of Formulas 59A and 59B

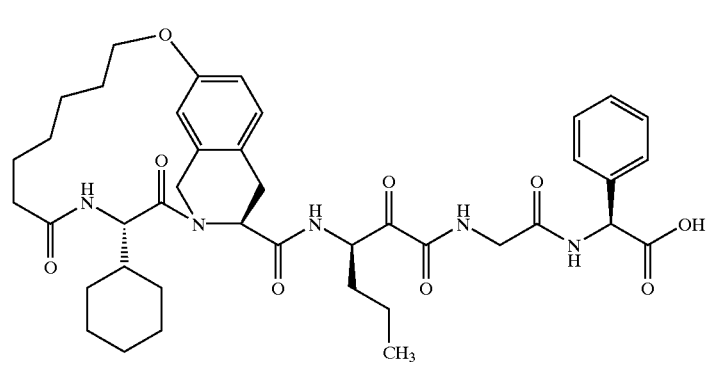

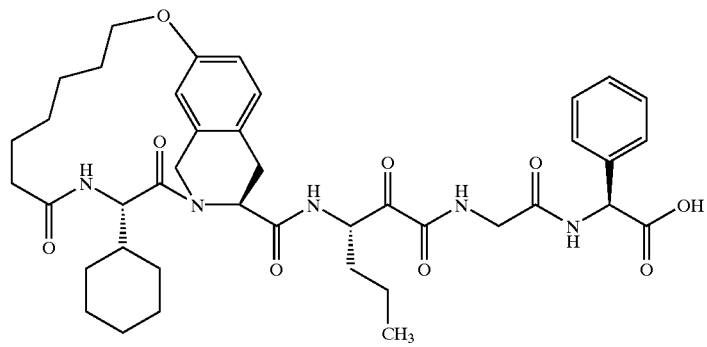
59B
Step A:
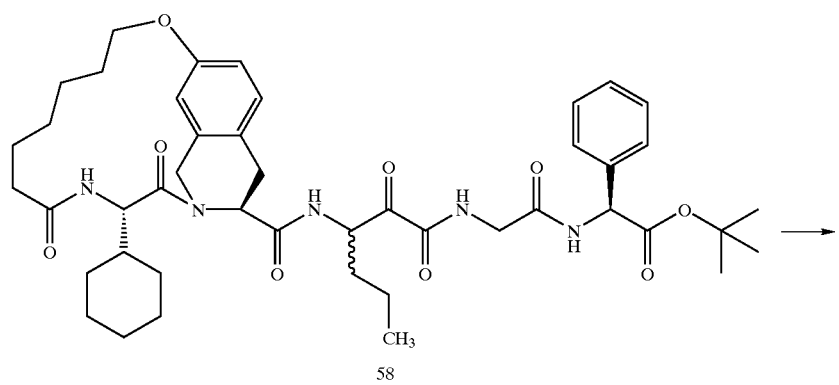
58
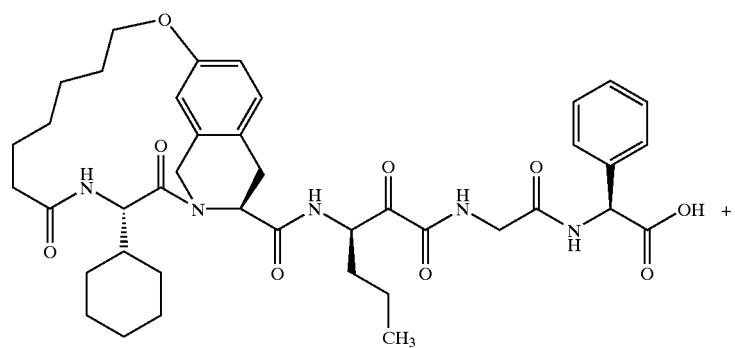
59A
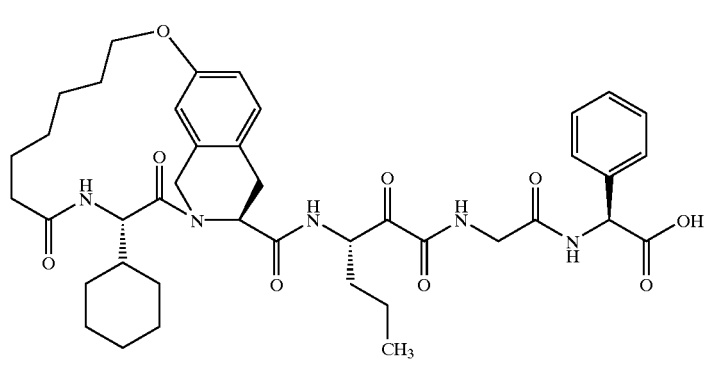
59B

A solution of the t-Butyl ester 58 (18 mg, 0.022 mmol) in trifluoroacetic acid (2 mL) and $CH_2Cl_2$ (2 mL) was stirred at rt. for 3 h. After the volatiles were removed in vacuo, the residue was dissolved in 50% MeOH—$CH_2Cl_2$ (3 mL), and concentrated to dryness in vacuo to afford an off-white solid. Flash chromatography (8–15% MeOH, 0.3–0.5% AcOH in $Cl_2Cl_2$) afforded two stereo-isomers 59A (6.5 mg, 0.0086 mmol) and 59B (6.1 mg, 0.008 mmol, 75% combined yield) as white solids. Analytical data for 59A: $^1$H NMR (400 MHz, $d_6$-DMSO) δ 8.75–8.72 (m, 1H), 8.60–8.57 (m, 1H), 8.10–8.08 (m, 1H), 7.91–7.88 (m, 1H), 7.38–7.27 (m, 5H), 7.12 (d, J=8.14 Hz, 1H), 6.81–6.73 (m, 2H), 5.24–5.22 (m, 1H), 5.06–5.01 (m, 1H), 4.77–4.73 (m, 1H), 4.39–4.17 (m, 3H), 4.07–4.01 (m, 1H), 3.92–3.79 (m, 3H), 3.15–3.05 (m, 1H), 2.78–2.72 (m, 1H), 2.08–2.05 (m, 1H), 1.78–1.45 (m, 13H), 1.41–1.22 (m, 4 H),1.18–1.03 (m,4H), 0.93–0.81 (m, 5H); $^{13}$C NMR (100 MHz, $d_6$-DMSO) δ 196.6, 171.8, 171.5, 171.9, 170.3, 167.2, 161.0, 157.1, 137.4, 128.4, 128.1, 127.7, 127.5, 127.4, 126.9, 115.6, 112.6, 66.8, 56.6, 55.1, 53.4, 52.7, 52.6, 45.4, 41.6, 33.5, 31.7, 30.0, 29.6, 28.2, 27.2, 27.1, 26.1, 25.42, 25.36, 24.0, 23.8, 18.7, 13.5; HRMS m/z 760.3915 [calcd for $C_{41}H_{53}N_5O_9$, 760.3922]. Analytical data for 59B: $^1$H NMR (400 MHz, $d_6$-DMSO) δ 8.76–8.73 (m, 1H), 8.55 (dd, J=6.9, 3.2 Hz, 1H), 8.24 (d, J=7.11 Hz, 1H), 7.93–7.88 (m, 1H), 7.37–7.25 (m, 1H), 7.15–7.11 (m, 1H), 6.82–6.74 (m, 2H), 5.23–5.20 (m, 1H), 5.09–5.01 (m, 1H), 4.75–4.71 (m, 1H), 4.38 –4.29 (m, 1H), 4.24–4.17 (m, 2 H), 4.07–4.02 (m, 1H), 3.92–3.78 (m, 2H), 3.13–3.08 (m, 1H), 2.78–2.70 (m, 1 H), 2.08–2.05 (m, 2H), 1.75–1.13 (m, 21H), 0.89–0.85 (m, 5H); $^{13}$C NMR (100 MHz, $d_6$-DMSO) δ 196.7, 171.6, 171.2, 169.9, 167.1, 160.8, 157.0, 137.5, 128.3, 128.2, 128.0, 127.97, 127.9, 127.4, 127.3, 127.1, 115.7, 115.6, 112.7, 112.6, 66.7, 56.8, 54.8, 53.3, 45.5, 41.6, 33.6, 31.8, 29.5, 28.1, 27.3, 27.0, 26.1, 25.4, 24.2, 23.9, 18.6, 13.5; HRMS m/z 760.3915 [calcd for $C_{41}H_{53}N_5O_9$, 760.3922].

Example 60

Preparation of Compound 60

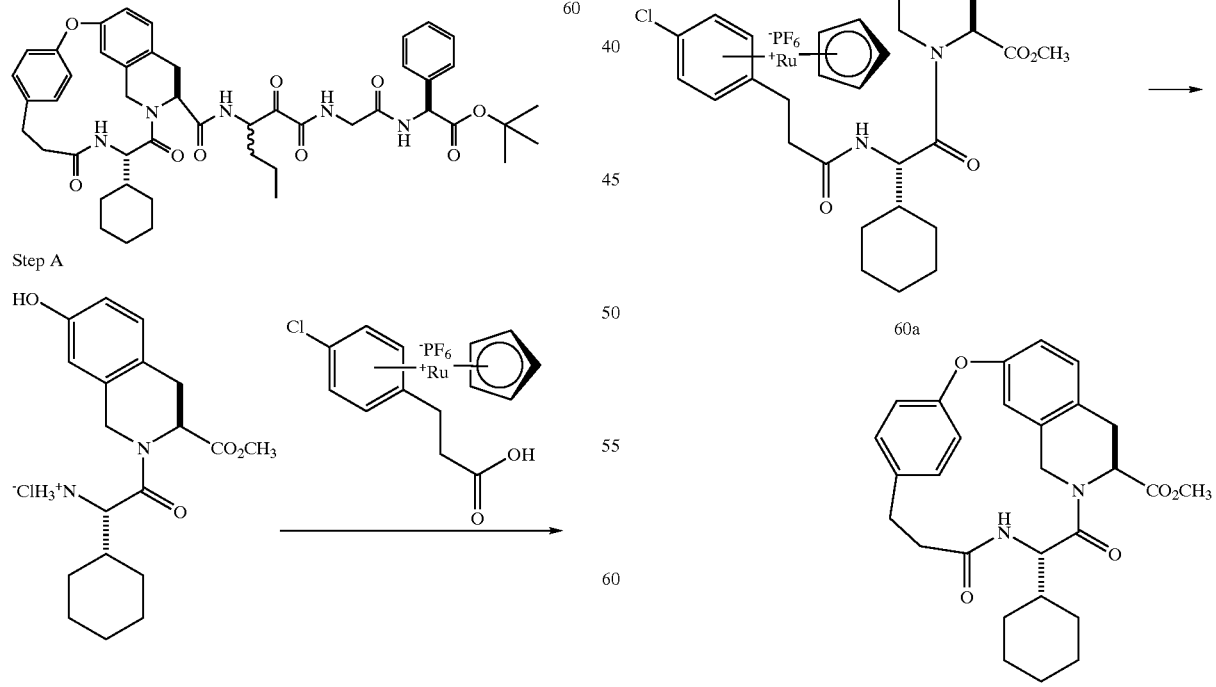

Step A

A solution of [CpRu($η^6$-4-chlorophenylpropionic acid)]$PF_6$ (4.14 g, 8.36 mmol) in dry DMF (20 mL) was treated with HOBt (1.69 g, 12.54 mmol, 1.5 equiv.) and Hunigs base (6.47 g, 9.20 mL, 50.16 mmol, 6.0 equiv.) The reaction mixture was cooled to 0° C. and treated with EDCl (2.39 g, 12.54 mmol, 1.5 equiv.) The reaction mixture was stirred at 0° C. for 30 min and the Tic-ammonium salt 57d (2.90 g, 7.6 mmol mmol, 1.0 equiv.) was added. The reaction mixture was stirred at rt. for 12 h and the DMF was distilled out in vacuo. The residue was diluted with aq. HCl (1M, 100 mL) and extracted into $CH_2Cl_2$ (3×100 mL). The combined organic layers were washed with aq. $NaHCO_3$ (1×100 mL), brine (100 mL), dried ($Na_2SO_4$), filtered, concentrated in vacuo to yield a brown solid 60a (5.2 g, 83%) which was used for cyclization. MS: (Electron spray): 647 [(M-$CH_3OH$—$PF_6$)$^+$, 100]. HRMS calcd. for $C_{32}H_{34}ClN_2O_4Ru$ [(M-$CH_3OH$—$PF_6$)]$^+$ 647.1256; Found: 647.1241.

Step B

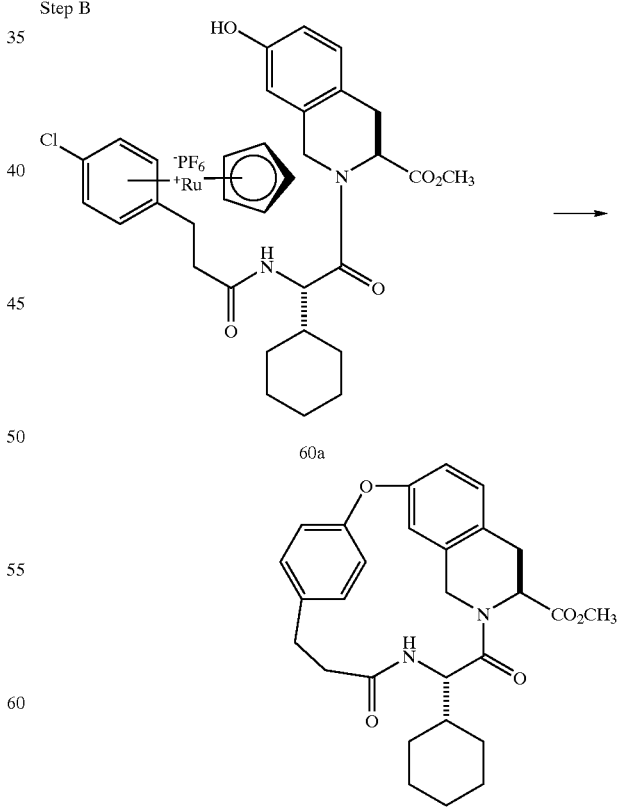

A solution of Ruthenium complex 60a (5.0 g 6.01 mmol) in dry DMF (300 mL) was degassed with dry N₂ at rt. and Cs₂CO₃ (10.0 g, 30 mmol, 5.0 equiv.) was added and stirred at rt. for 24 h. The solvent DMF was distilled off and the residue was diluted with water (100 mL) and extracted with CH₂Cl₂ (3×100 mL) and propionitrile (3×100 mL). The combined organic layers were extracted, with brine(100 mL), dried (Na₂SO₄) filtered, concentrated in vacuo and dried in vacuum overnight to yield a brown solid (5.1 g). It was used for photolytic removal of Ru without further purification. MS: (Electron spray): 643 [(M-PF$_6$)$^+$, 100].

The cyclized compound from the previous step was dissolved in CH₃CN (50 mL) and filtered into a quartz tube. The solution was degassed and photolysed in a Raynot instrument (λ=350 nm) for 48 h. The reaction mixture was concentrated in vacuo and the residue was purified by chromatography (SiO₂, EtOAc/Hexanes 3:2) to yield a tan colored solid 60b (289 mg, 20%). R$_f$: 0.73 (acetone/hexanes 3:7) $^1$H NMR (CDCl₃, 300 MHz) δ 7.18 (d, 2H, J=8.1 Hz), 7.20–7.09 (m, 2H), 6.92 (d, 2H, J=7.8 Hz), 6.86 (dd, 1H, J=2.1, 7.2 Hz), 6.76 (s, 1H), 5.41 (d, 1H, J=17.4 Hz), 4.23–4.18 (m, 2H), 4.00 (bs, 1H), 3.68 (s, 3H), 3.41 (dd, 1 H J=12, 3.9 Hz), 3.01–2.86 (m, 1H), 1.9–1.62 (m, 4H), 1.52 (bd, 1H, J=9.3 Hz), 1.36–1.07 (m, 5H); $^{13}$C NMR (CDCl₃, 100 MHz, δ) 173.2, 167.2, 163.8, 156.5, 155.1, 135.8, 132.7, 130.2, 129.2, 126.2, 119.1, 117.5, 115.8, 60.2, 55.5, 51.6, 44.2, 42.0, 35.7, 30.2, 29.3, 26.5, 26.2, 25.8, 25.7 MS: (Electron spray): 477 [(M+1)$^+$, 100], 315 (20); HRMS calcd. for C₂₈H₃₃N₂O₅ (M+1)$^+$: 477.2389; Found 477.2375; CHN Calcd. for C₂₈H₃₂N₂O₅.0.5H₂O: C 69.26% H 6.85% N 5.77%; Found: C 69.62% H 6.59% N 5.77%

Step C

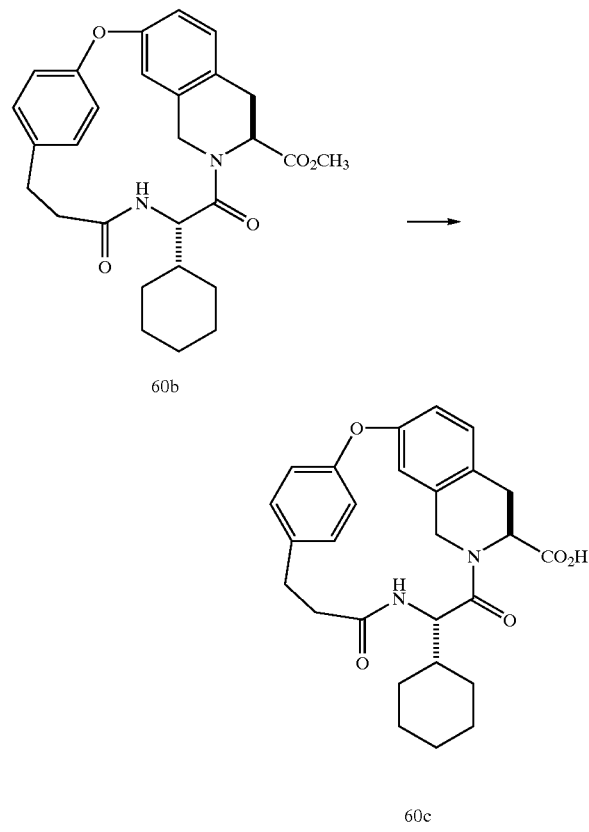

A solution of methyl ester 60b (235 mg, 0.5 mmol) of Tic-macrocycle in dioxane(10.0 mL), H₂O (10.0 mL), CH₃OH (50.0 mL) was treated with LiOH.H₂O (41 mg, 1.0 mmol, 2.0 equiv.) and stirred at rt. for 3 h. The reaction mixture was acidified and (4M HCl in Dioxane). The reaction mixture was concentrated in vacuo and the remaining water was frozen and lyophilized to obtain a colorless solid 60c used for coupling.

Step D

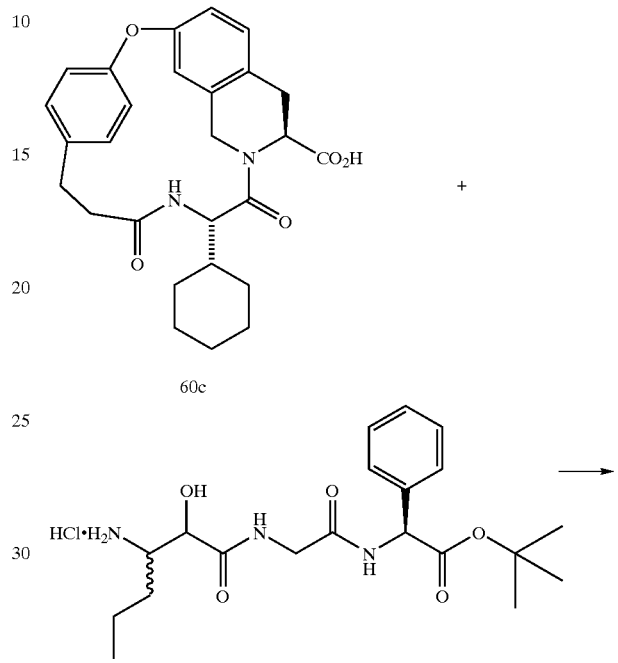

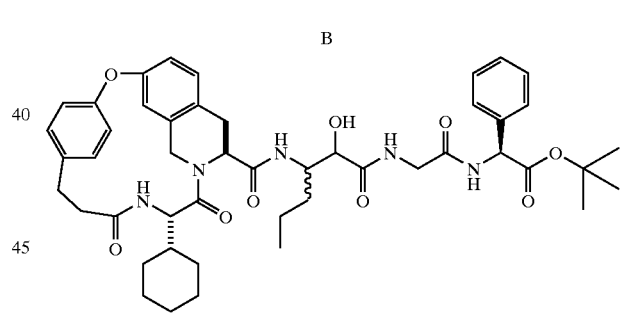

A solution of the hydrolyzed acid 60c (0.5 mmol) in dry DMF (5.0 mL) and CH₂Cl₂ (5.0 mL) was treated with HOOBt (132 mg, 0.75 mmol, 1.5 equiv.), and cooled to 0° C. and Hünigs base (258 mg, 2.0 mmol, 4.0 equiv., 369 μL) was added. To this mixture was added EDCl (143 mg, 0.75 mmol, 1.5 equiv.) and amine hydrochloride B (214 mg, 0.5 mmol, 1.0 equiv.) sequentially. The reaction mixture was stored in freezer for 48 h and concentrated in vacuo to remove DMF and CH₂Cl₂. The residue was diluted with aq. HCl (2M, 50 mL) and extracted with CH₂Cl₂ (3×30 mL) The combined organic layer was extracted with aq. HCl (1M, 2×50 mL), aq. NaOH (2M 2×30 mL), brine, dried (MgSO₄) and concentrated in vacuo. The residue 60d (172 mg) was oxidized without further purification; MS: (Electron spray): 838 [(M+1)$^+$, 50], 490 (100); HRMS calcd. for C₄₇H₆₀N₅O₉ (M+1)$^+$: 838.4391; Found: 838.4398.

Step E

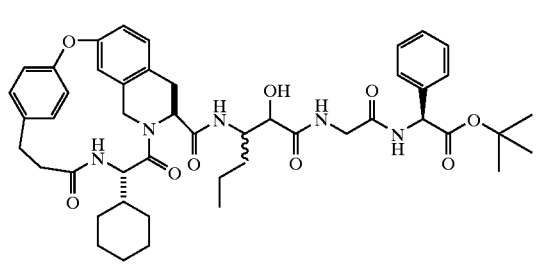

60d

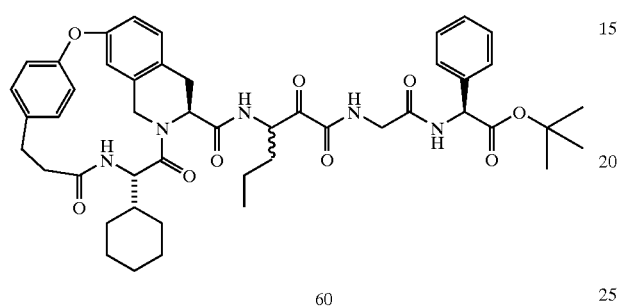

60

A solution of alcohol 60d (171 mg, 0.20 mmol) in CH$_2$Cl$_2$ (6.0 mL) was treated with Dess-Martin reagent (175 mg, 0.41 mmol, 2.0 equiv.). The reaction mixture was stirred at rt. for 4 h and diluted with aq. NaHCO$_3$ and aq. Na$_2$S$_2$O$_3$. The reaction mixture was stirred at rt. for 20 min and the reaction mixture was extracted with CH$_2$Cl$_2$ (3×30 mL). The combined organic layers were extracted with aq. Na$_2$CO$_3$, dried (Na$_2$SO$_4$), filtered concentrated in vacuo and the residue was purified by chromatography (SiO$_2$, CH$_3$OH (2M NH$_3$)/CH$_2$Cl$_2$ 1:20) to yield ketoamide 60 (56 mg, 32%) as a colorless solid. R$_f$: 0.35 (CH$_3$OH (2M NH$_3$)/CH$_2$Cl$_2$ 1:18) MS: (Electron spray, m/z relative intensity): 836 ([M+1]$^+$, 90), 490 (100). HRMS calcd. for C$_{47}$H$_{58}$N$_5$O$_9$ (M+1)$^+$ 836.4235; Found: 836.4269.

Example 61

Preparation of Compound 61

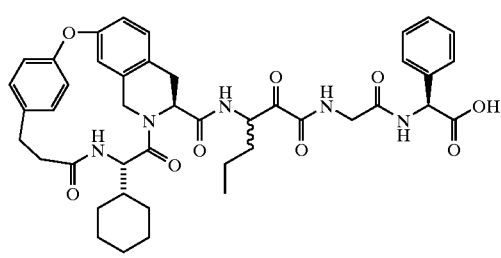

61

Step A

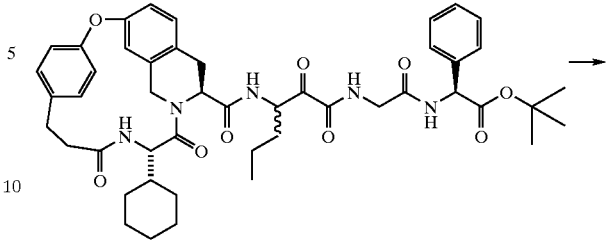

60

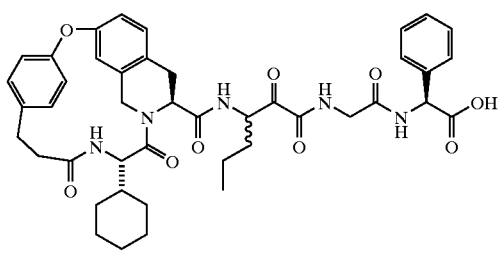

61

A solution of tert-butyl ester 60 (50 mg, 0.059 mmol) in dry CH$_2$Cl$_2$ (10.0 mL) was treated with TFA (10.0 mL) and stirred at rt. for 4 h. The disappearance of the ester to the base line was followed by TLC (CH$_3$OH/CH$_2$Cl$_2$, 1:19). The reaction mixture was concentrated in vacuo and the residue was repeatedly dissolved in heptanes/CH$_2$Cl$_2$ and concentrated in vacuo several times to yield a fine colorless solid 61 (51 mg) which was dried in vacuo.; MS (FAB) 780 [(M+1)$^+$, 85], 516 (20), 417 (20), 403 (100), 321 (20), 248 (40), 236 (40); HRMS calcd. for C$_{43}$H$_{50}$N$_5$O$_9$ (M+1)$^+$: 780.3609; found 780.3618.

Example 62

Preparation of Compound 62

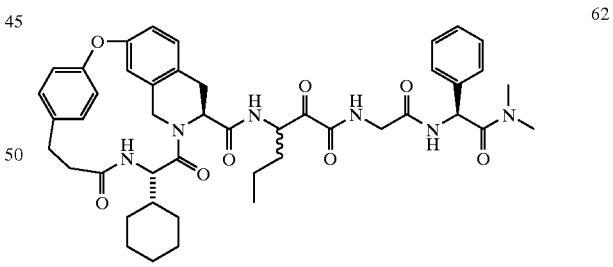

62

Step A

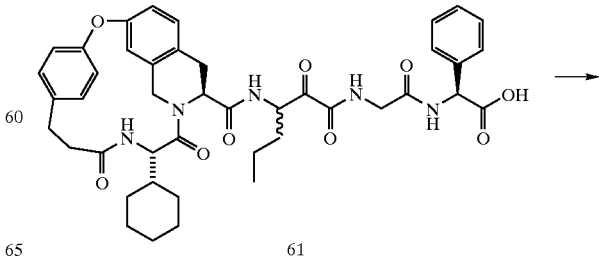

61

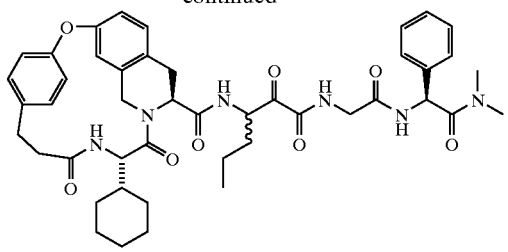

62

A solution of the acid 61 (30 mg, 0.038 mmol), dimethyl amine hydrochloride (6.2 mg, 0.076 mmol, 2.0 equiv.) in CH$_2$Cl$_2$ (1.0 mL) was treated with Hunigs base (9.1 mg, 0.076 mmol, 2.0 equiv., 15 μL), PyBrOP (35 mg, 0.076 mmol, 2.0 equiv.) and stirred at rt. for 24 h. The reaction mixture was concentrated in vacuo and purified by chromatography (SiO$_2$, acetone/Hexanes 1:1) to yield dimethyl amide 62 (14 mg, 46%) as a colorless solid; R$_f$ (0.31 acetone/Hexanes 1:1). MS (FAB) 807 [(M+1)$^+$, 100], 805 (60), 794 (60), 747 (40), 629 (40), 589 (62).

Example 63

Preparation of Compound 63

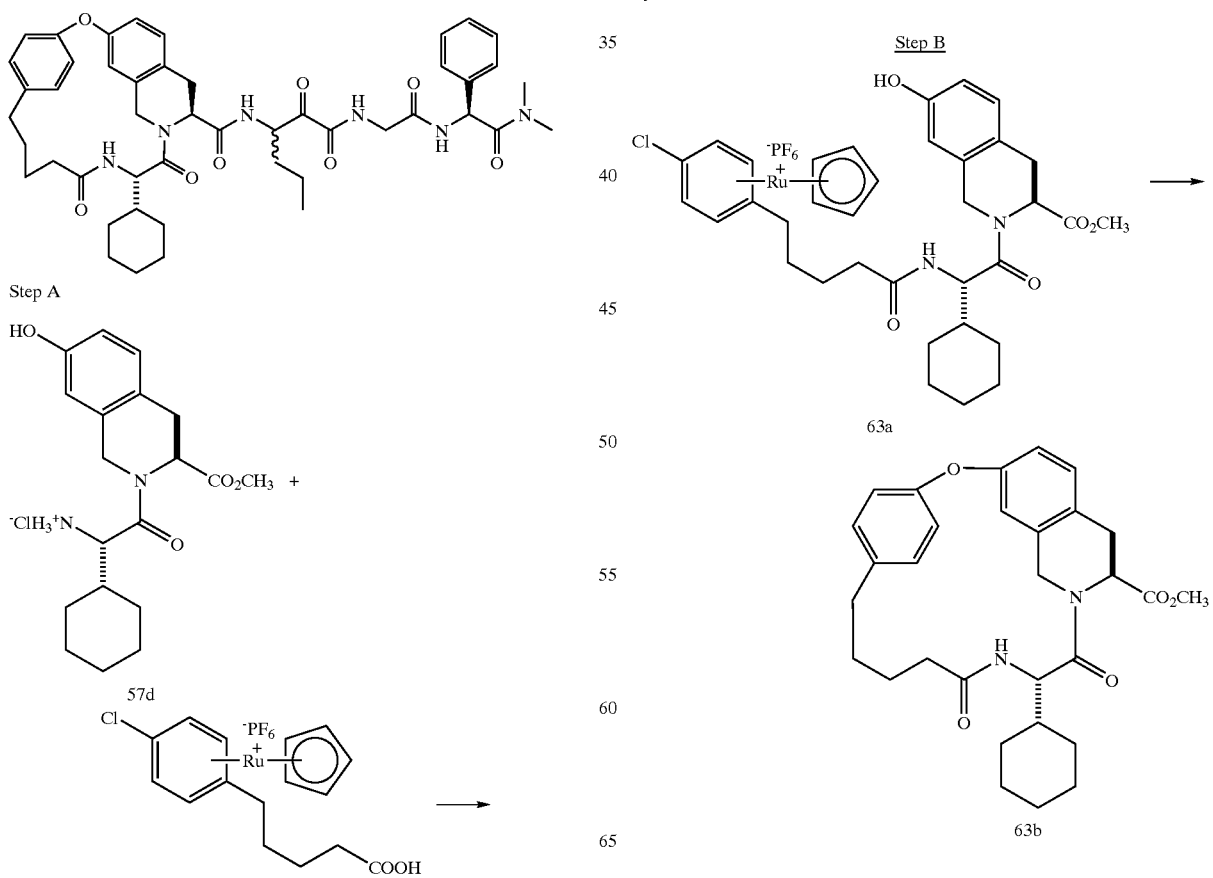

A solution of [CpRu(η$^6$-4-chlorophenylpentanoic acid)] PF$_6$ (2.2 g, 4.0 mmol) in dry DMF (10 mL) was treated with HOBt (810 mg 5.99 mmol, 1.5 equiv.) and Hünigs base (2.58 g, 3.6 mL, 19.9 mmol, 5.0 equiv.) The reaction mixture was cooled to 0° C. and treated with EDCl (1.14 g, 6.0 mmol, 1.5 equiv.) The reaction mixture was stirred at 0° C. for 30 min. and the Tic-ammonium salt 57d (1.60 g, 4.0 mmol, 1.0 equiv.) was added. The reaction mixture was stirred at rt. for 12 and the DMF was distilled out in vacuo. The residue was diluted with aq. HCl (1M, 100 mL) and extracted into CH$_2$Cl$_2$ (3×100 mL). The combined organic layers were extracted with aq. NaHCO$_3$ (1×40 mL), brine (100 mL), dried (Na$_2$SO$_4$), filtered, concentrated in vacuo to yield a brown solid 63a (2.41 g, 75%) which was used for cyclization.

Step B

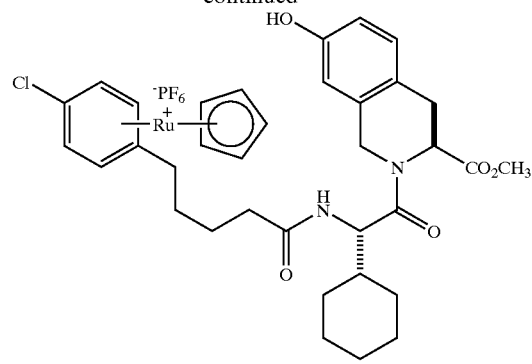

A solution of Ruthenium complex 63a (2.40 g, 2.8 mmol) in dry DMF (250 mL) was degassed with dry $N_2$ at rt. and $Cs_2CO_3$ (4.6 g, 14.0 mmol, 5.0 equiv.) was added and stirred at rt. for 14 h. The solvent DMF was distilled off and the residue was diluted with water (100 mL) and extracted with $CH_2Cl_2$ (3×100 mL). The combined organic layers were extracted, with aq. HCl (1M, 100 mL), $NaHCO_3$ (100 mL), brine(100 mL) dried ($Na_2SO_4$) filtered, concentrated in vacuo and dried in vacuum overnight to yield a brown solid (1.9 g, 79%). It was used for photolytic removal of Ru without further purification. MS: (Electron spray): 671 [$(M-PF_6)^+$, 40].

The cyclized compound from the previous step was dissolved in $CH_3CN$ (60 mL) and filtered into a quartz tube. The solution was degassed and photolyzed in a Raynot (λ=350 nm) for 48 h. The reaction mixture was concentrated in vacuo and the residue was purified by chromatography ($SiO_2$, acetone/Hexanes 3:7) to yield a tan colored solid 63b (140 mg, 13%).; $R_f$: 0.73 (acetone/hexanes 3:7); MS: (FAB): 505 [$(M+1)^+$, 80], 232 (40); HRMS calcd. for $C_{30}H_{37}N_2O_5$ $(M+1)^+$: 505.2702; Found: 505.2698.

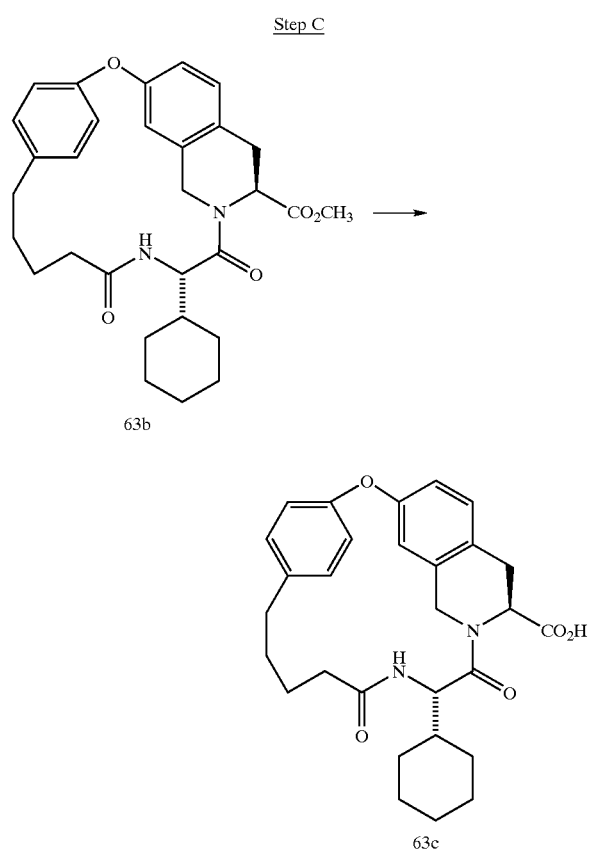

A solution of methyl ester 63b (235 mg, 0.5 mmol) of Tic-macrocycle in dioxane(10.0 mL), $H_2O$ (10.0 mL), $CH_3OH$ (50.0 mL) was treated with $LiOH.H_2O$ (41 mg, 1.0 mmol, 2.0 equiv.) and stirred at rt. for 3 h. The reaction mixture was acidified and (4M HCl in Dioxane). The reaction mixture was concentrated in vacuo and the remaining water was frozen and lyophilized to obtain a colorless solid 63c used for coupling.

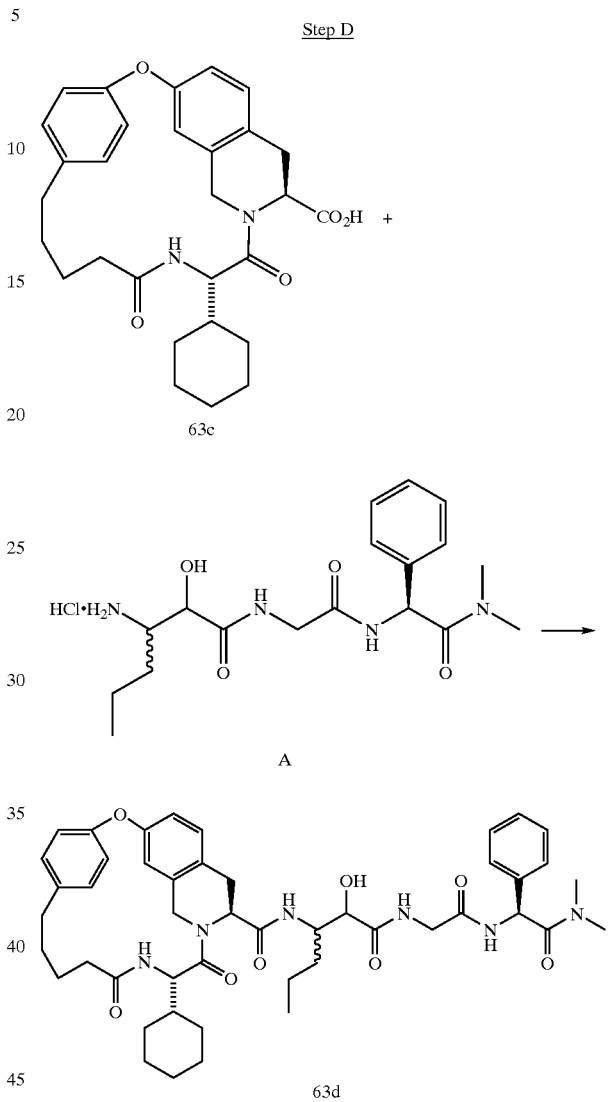

A solution of the hydrolyzed acid 63c (100 mg, 0.21. mmol) in dry DMF (4.0 mL) and $CH_2Cl_2$ (2.0 mL) was cooled to 0° C. and treated with HOOBt (53 mg, 0.32 mmol, 1.5 equiv.), Hunigs base (122 mg, 0.95 mmol, 4.5 equiv., 175 µL), EDCl (61.0 mg, 0.32 mmol, 1.5 equiv.) and stirred for 0.5 h and treated with the amine hydrochloride A (100 mg, 0.25 mmol, 1 equiv.). The reaction mixture was stirred at rt. for 16 h and concentrated in vacuo to remove DMF and $CH_2Cl_2$. The residue was diluted with aq. HCl (2M, 50 mL) and extracted with $CH_2Cl_2$ (3×50 mL) The combined organic layer was extracted with aq. HCl (1M, 100 mL), aq. NaOH (2M 100) brine, dried ($Na_2SO_4$) and concentrated in vacuo. The residue 63d (72 mg) was oxidized without further purification.

Step F

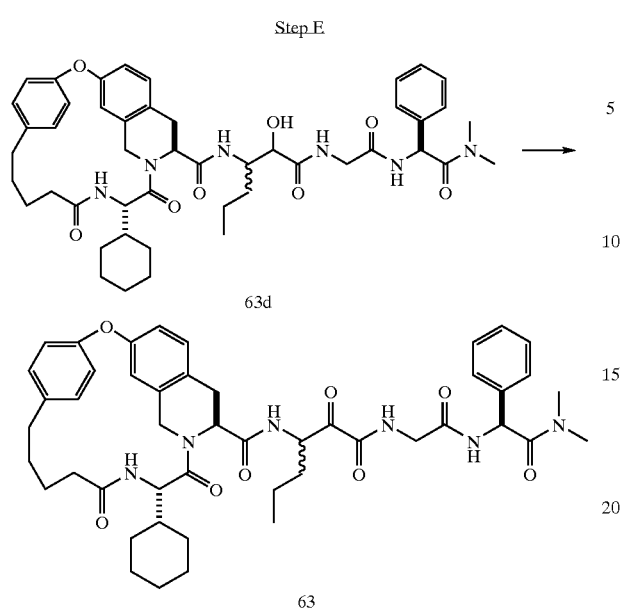

A solution of alcohol 63d (72 mg, 0.86 μmol) in CH₂Cl₂ (5.0 mL) was treated with Dess-Martin reagent (125 mg, 0.28 mmol, 3.2 equiv.). The reaction mixture was stirred at rt. for 3 h and concentrated in vacuo and the residue was purified by chromatography (SiO₂, CH₃OH/CH₂Cl₂ 1:19) to yield ketoamide 63 (11 mg, 15%) of a colorless solid; MS (FAB): 835 ([M+1]⁺, 90), 490 (100).

Example 64

Preparation of Compound 64

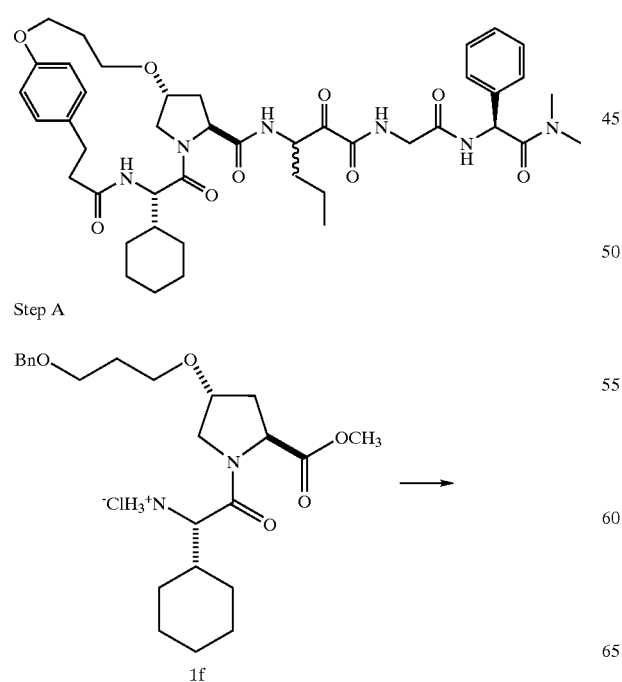

Step A

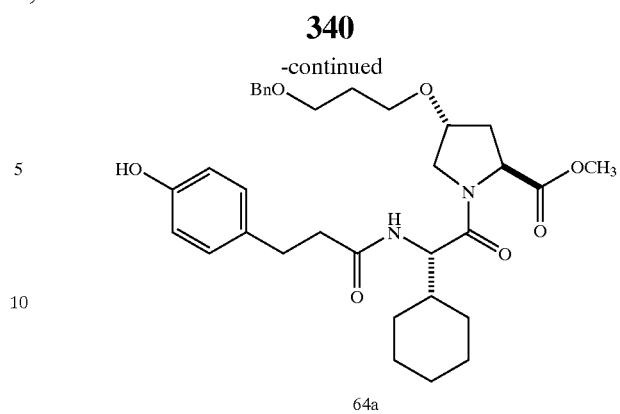

The desired product 64a was obtained by the procedure described for Example 1, Step F. The material was purified by flash column chromatography using EtOAc/Hex (7:3) to yield 64a in 80%.; $^1$H NMR (CDCl₃, δ): 7.35–7.29 (m, 5H), 7.02 (d, 2H, J=8.4 Hz), 6.72 (d, 2H, J=6.9Hz) 6.01 (d, 1H), 4.60 (t, 1H), 4.52 (s, 1H), 3.8–3.61 (m, 2H), 3.72 (s, 3 H), 3.54–3.51(m, 4H), 2.83 (t, 2H, J=7.5 Hz), 2.39 (t, 2H, J=8.1 Hz) 2.41–2.20 (m, 1H), 2.05–1.83 (m, 1H), 1.85–1.58 (m, 8H), 1.26–1.24 (m, 5H); $^{13}$C NMR (CDCl₃, δ): 172.2, 171.9, 171.0, 154.4, 138.3, 132.2, 129.4, 128.4, 127.7, 127.6, 115.4, 73.0, 66.9, 66.2, 57.9, 54.9, 52.5, 52.3, 41.0, 38.5, 34.7, 30.8, 30.0, 29.4, 27.9, 26.1, 26.0, 25.9.

Step B

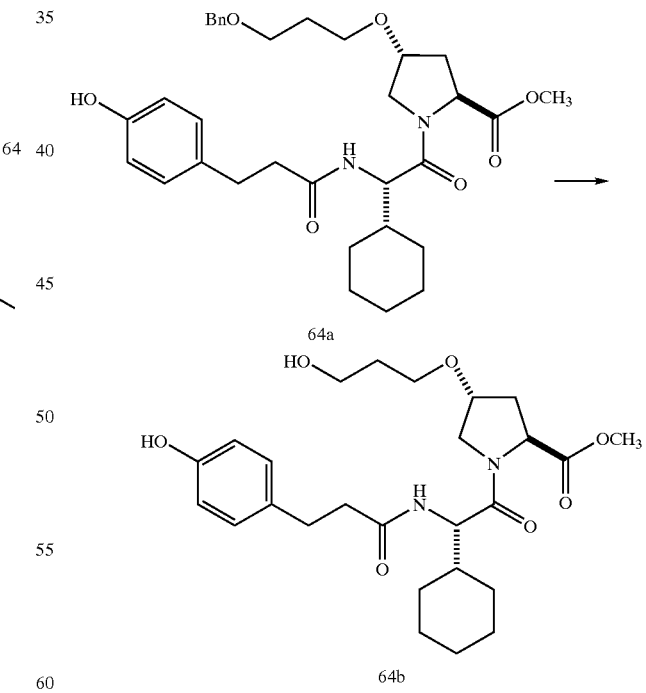

The desired product 64b was obtained by the procedure described for Example 1, Step G. The product obtained after filtering off the catalyst was pure enough for next step.

Step C

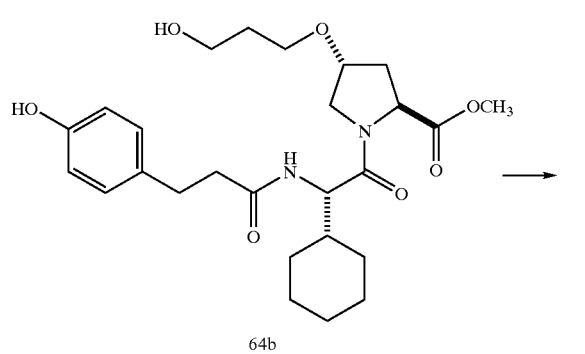

64b

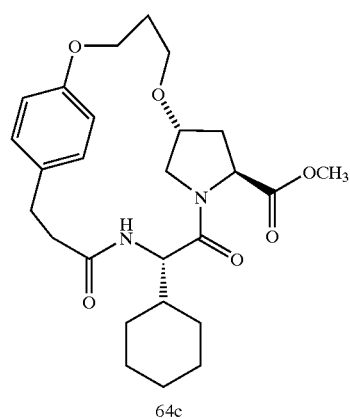

64c

The desired product 64c was obtained by the procedure described for Example 1, Step H. The crude reaction mixture was purified by SiO$_2$ gel chromatography (acetone/Hexanes 3:7) to yield 64c (64 mg, 16%) as a colorless solid.; $^{13}$C NMR (CDCl$_3$) ••172.1, 171.1, 171.0, 157.7, 131.0 129.9, 114.3, 78.1, 64.7, 63.3, 58.7, 55.3, 52.2, 52.0, 42.1, 37.9, 36.1, 30.8, 30.7, 29.7, 28.7, 28.5, 26.2, 26.0; MS (FAB) 473 (M+1)$^+$, (100), 327 (20).

Step D

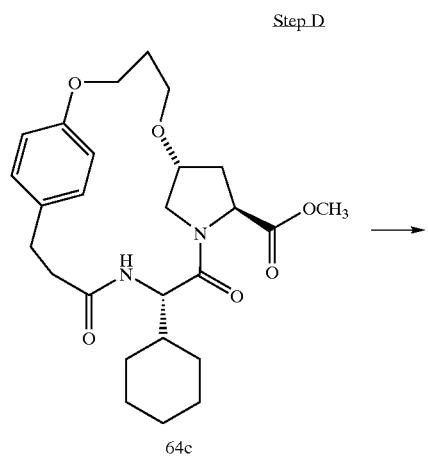

64c

-continued

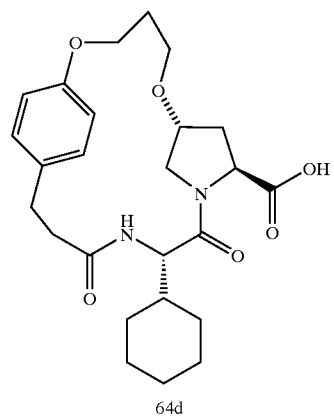

64d

The acid was synthesized as described for Example 1, Step I in quantitative yield. The crude mixture after evaporation was directly used for the next step.

Step E

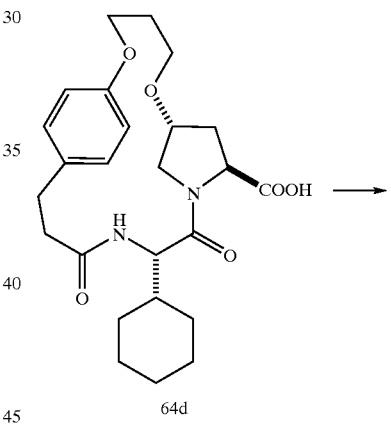

64d

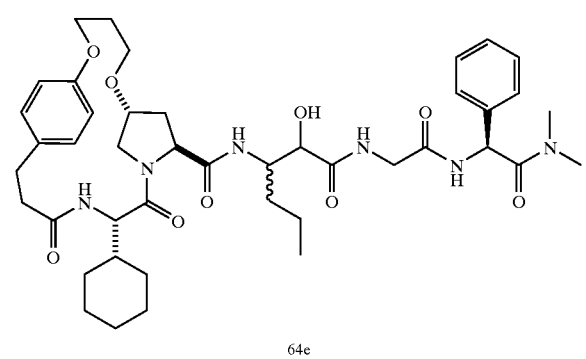

64e

The expected product 64e was synthesized as described earlier for the Example 1, Step J. The coupled material was used directly for the next step to synthesize 64.

Step F

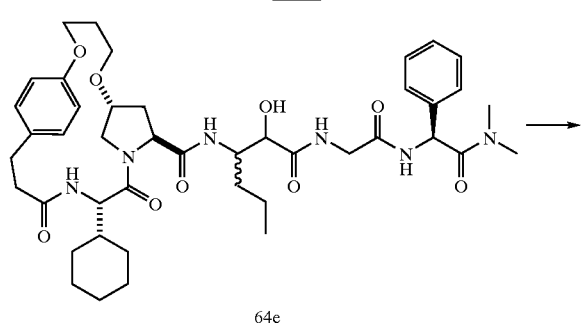

64e

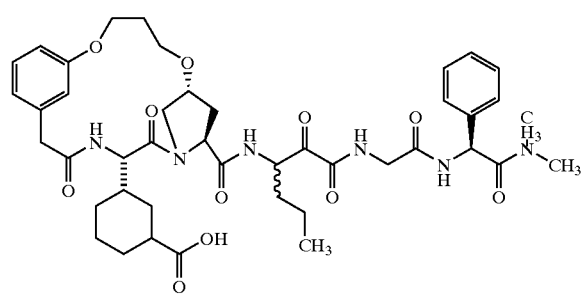

64

The desired product is obtained by the oxidation protocol described previously for Example 1, Step K.

Example 65

Preparation of Compound 65

The synthesis of Example 65 was identical to the synthesis of Example 14 except the synthesis was initiated with 3-vinylbenzoic acid. The reduction of phenyl moiety was similar to Example 14, Step C. However, a mixture of diastereomers was obtained.

Example 66

Preparation of Compounds of Formulas 66A and 66B

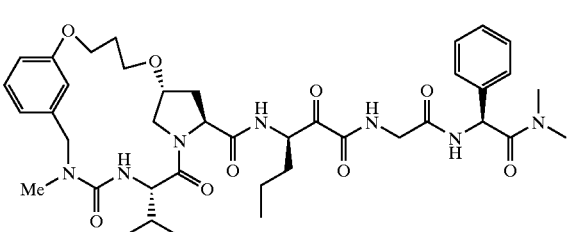

66A

66B

The synthetic sequences for Example 66 followed that described for Example 54 using suitable starting materials with appropriate modifications. The isomers 66A and 66B were separated after oxidation using column chromatography. LCMS data: 818.2 (M+H)$^+$ (for 66A and 66B).

Example 67

Preparation of Compounds of Formulas 67A and 67B

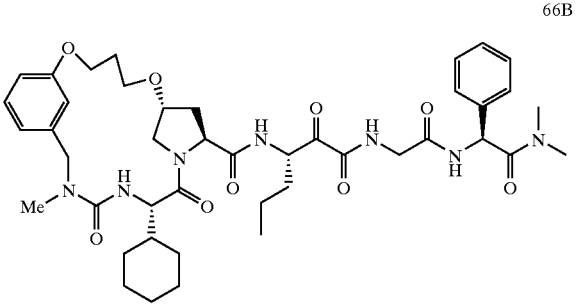

67A

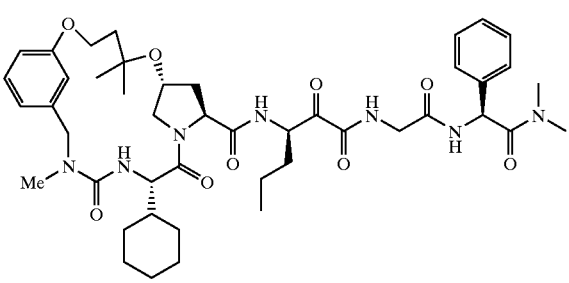

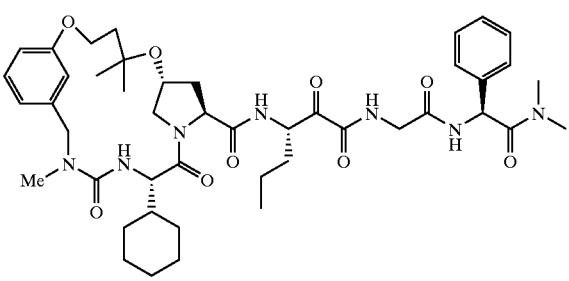

67B

The synthetic sequences for Example 67 followed that described for Example 54 using suitable starting materials with appropriate modifications. The isomers 67A and 67B were separated after oxidation using column chromatography. HRMS (FAB) Calcd for $C_{45}H_{64}N_7O_9$: 846.4766 (M+H)$^+$. Found: 846.4782 (for 67A) and 846.4774 (for 67B).

Example 68

Preparation of Compound of Formula 68

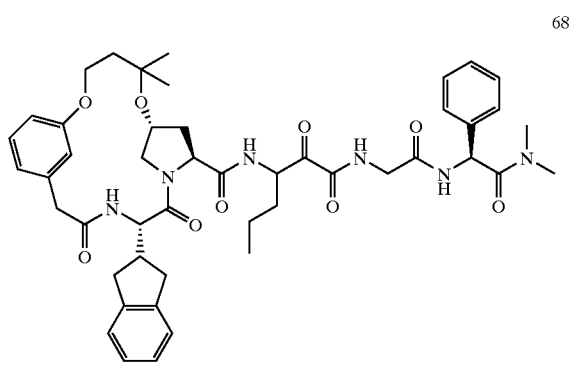

68

The synthetic sequences for Example 68 followed that described for Example 30 using suitable starting materials and appropriate modifications. After oxidation the desired product 68 was obtained as a mixture of isomers using column chromatography. HRMS (FAB) Calcd for $C_{47}H_{59}N_6O_9$: 851.4344 (M+H)$^+$. Found: 851.4149.

Example 69

Preparation of Compounds of Formula 69A and 69B

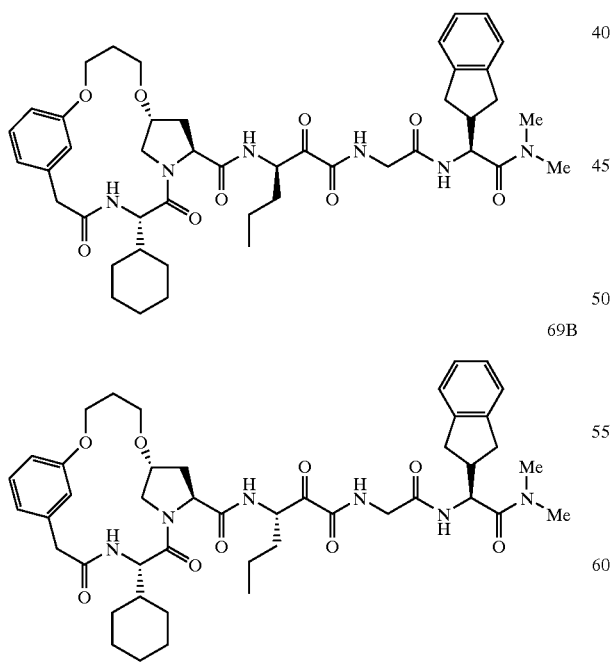

The synthetic sequences for Example 69 followed that described for Example 1 using suitable starting materials and appropriate modifications. After oxidation the isomers 69A and 69B were separated using column chromatography. LCMS data: 829.2 (M+H)$^+$ (for 69A and 69B).

Example 70

Preparation of Compounds of Formula 70A and 70B

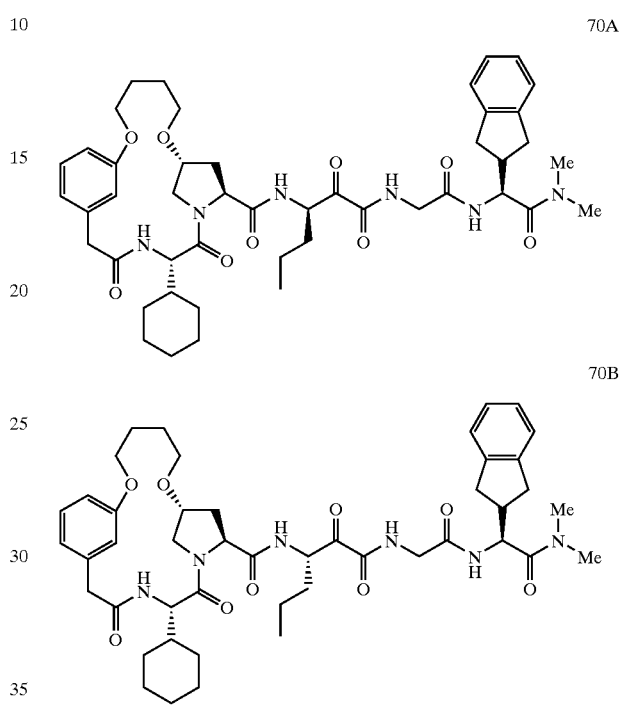

The synthetic sequences for Example 70 followed that described for Example 4 using suitable starting materials and appropriate modifications. After oxidation the isomers 70A and 70B were separated using column chromatography. LCMS data: 843.2 (M+H)$^+$ (for 70A and 70B).

Example 71

Preparation of Compound of Formula 71

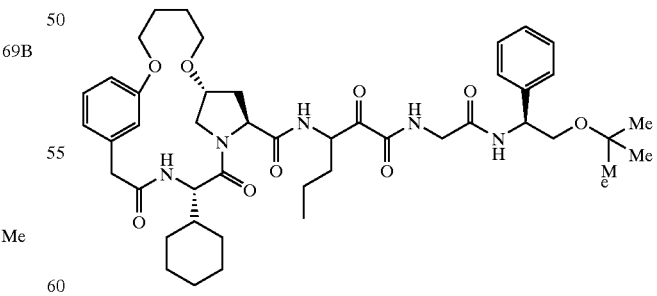

71

The synthetic sequences for Example 71 followed that described for Example 5 using suitable starting materials and appropriate modifications. After oxidation the desired product 71 was obtained as a mixture of isomers using column chromatography. LCMS data: 818.2 (M+H)$^+$.

Example 72

Preparation of Compound of Formula 72

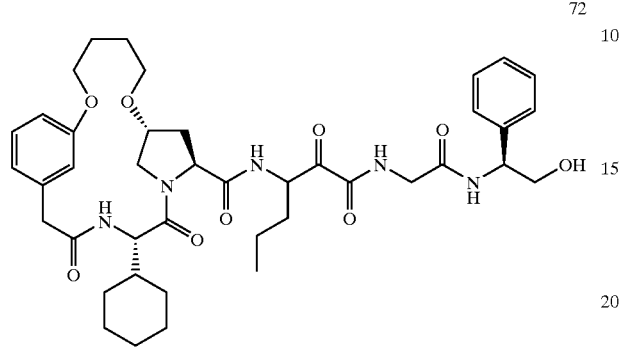

72

The synthetic sequences for Example 72 followed that described for Example 6 using suitable starting materials and appropriate modifications. After oxidation the desired product 72 was obtained as a mixture of isomers using column chromatography. LOMS data: 762.2 $(M+H)^+$.

Example 73

Preparation of Compound of Formula 73

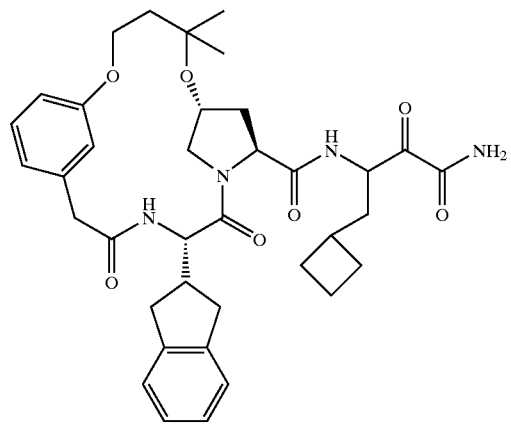

73

The synthetic sequences for Example 73 followed that described for Example 10 using suitable starting materials and appropriate modifications. After oxidation the desired product 73 was obtained as a mixture of isomers using column chromatography. LCMS data: 659.2 $(M+H)^+$.

Example 74:

Preparation of Compound 74A and 74B

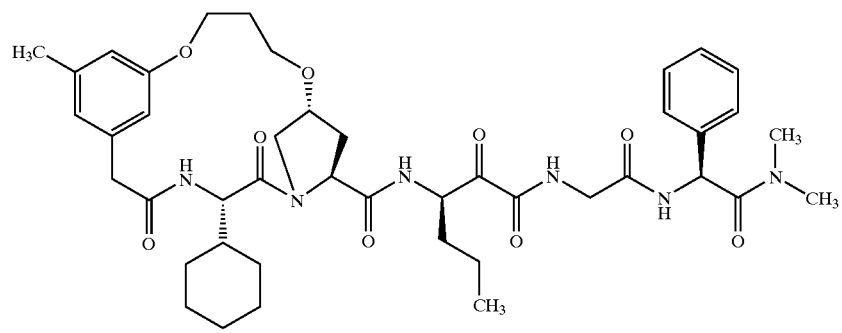

74A

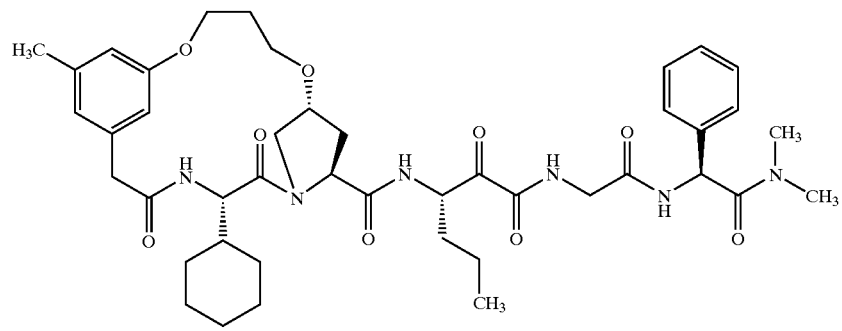

74B

The desired compounds 74A and 74B were prepared by the same method as described in the preparation of compounds 1A and 1B in Example 1, except that 5-methyl-3-hydoxy phenylacetic acid was used to substitute 3-hydroxy phenylacetic acid in Step F. LRMS (M+H)+ m/z 803.1 [calcd for $C_{43}H_{58}N_6O_9$, 802.4].

Example 75

Preparation of Compounds 75A and 75B

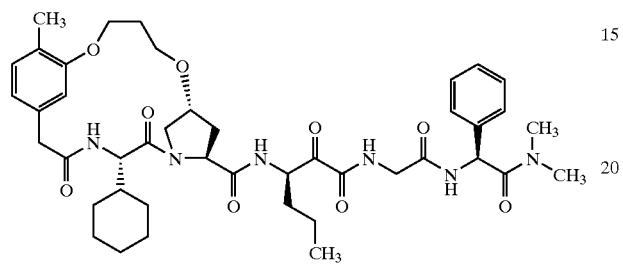

75A

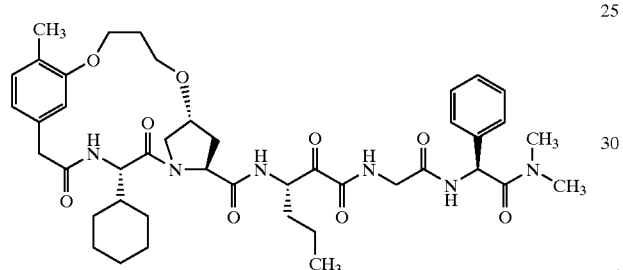

75B

The desired compounds 75A and 75B were prepared by the same method as described in the preparation of compounds 1A and 1B in Example 1, except that 4-methyl-3-hydoxy phenylacetic acid was used to substitute 3-hydroxy phenylacetic acid in Step F. LRMS (M+H)+ m/z 803.1 [calcd for $C_{43}H_{58}N_6O_9$, 802.4].

Example 76

Preparation of Compound 76

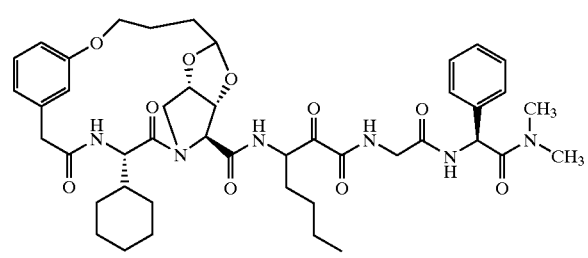

76

The desired compound 76 was prepared by the same method as described in the preparation of compounds 27A and 27B in Example 27, except that amine E was used to substitute amine A in Step J. LRMS (M+H)+ m/z 831.1 [calcd for $C_{44}H_{58}N_6O_{10}$, 830.4].

Example 77

Preparation of Compound 77

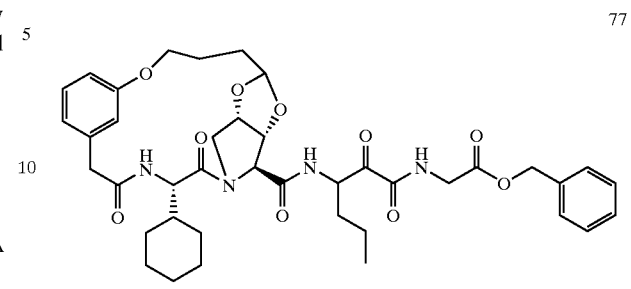

77

The desired compound 77 was prepared by the same method as described in the preparation of compounds 27A and 27B in Example 27, except that a different amine intermediate was used to substitute amine A in Step J. LRMS (M+H)+ m/z 761.1 [calcd for $C_{41}H_{52}N_4O_{10}$, 760.4].

Example 78

Preparation of Compound 78

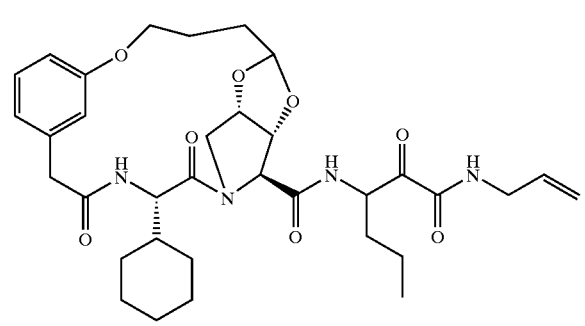

78

The desired compound 78 was prepared by the same method as described in the preparation of compounds 27A and 27B in Example 27, except that a different amine intermediate was used to substitute amine A in Step J. LRMS (M+H)+ m/z 653.1 [calcd for $C_{35}H_{48}N_4O_8$, 652.4].

Example 79

Preparation of Compound 79

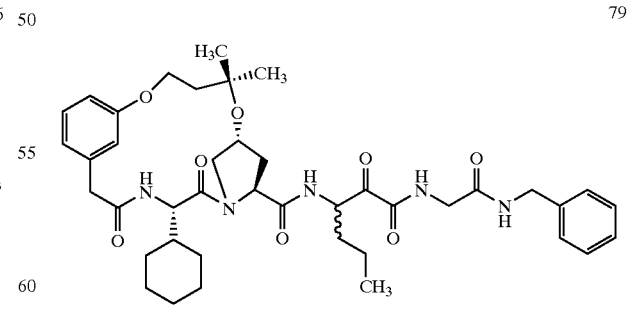

79

The desired compound 79 was prepared by the same method as described in the preparation of compound 30 in Example 30, except that a different amine intermediate was used to substitute amine A in Step I. LRMS (M+H)+ m/z 746.1 [calcd for $C_{41}H_{55}N_5O_8$, 745.4].

Example 80

Preparation of Compound 80

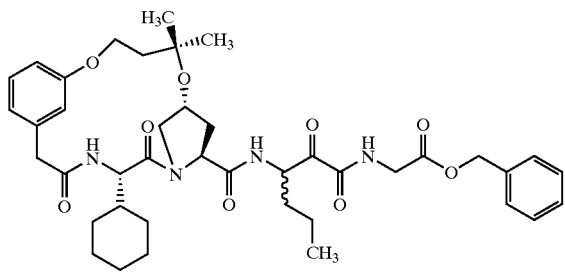

The desired compound 80 was prepared by the same method as described in the preparation of compound 30 in Example 30, except that a amine D was used to substitute amine A in Step I. LRMS (M+H)$^+$ m/z 746.1 [calcd for $C_{41}H_{55}N_5O_8$, 745.4].

Example 81

Preparation of Compound 81

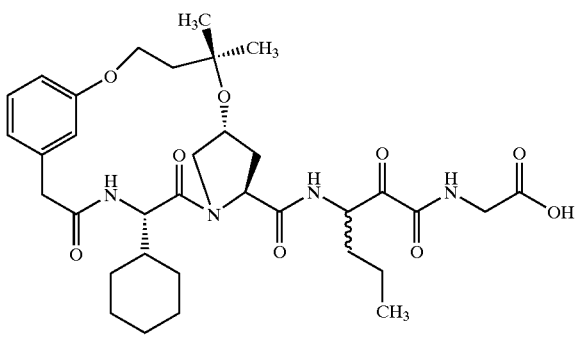

The desired compound 81 was prepared by the same method as described in the preparation of intermedaite A, Step 5. LRMS (M+H)$^+$ m/z 657.1 [calcd for $C_{34}H_{48}N_4O_9$, 656.3].

Example 82

Preparation of Compound 82

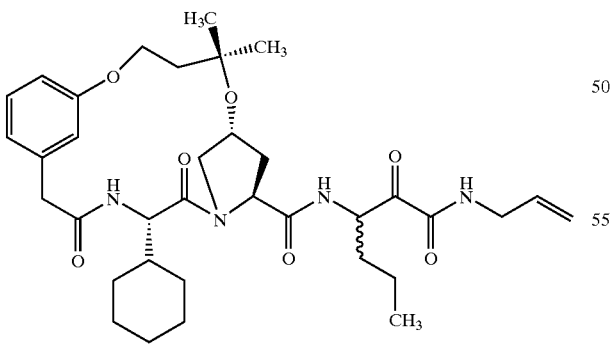

The desired compound 82 was prepared by the same method as described in the preparation of compound 30 in Example 30, except that a different amine was used to substitute amine A in Step I. LRMS (M+H)$^+$ m/z 639.1 [calcd for $C_{35}H_{50}N_4O_7$, 638.4].

Example 83

Preparation of Compound 83

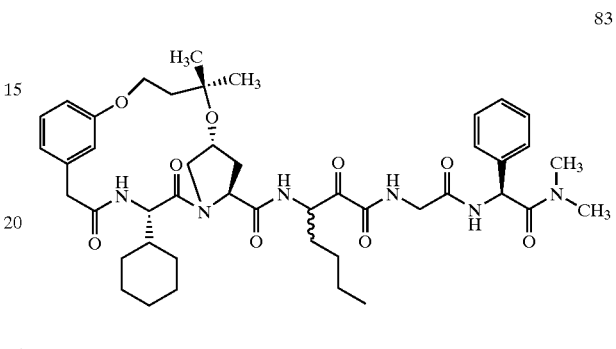

The desired compound 83 was prepared by the same method as described in the preparation of compound 30 in Example 30, except that amine E was used to substitute amine A in Step I. LRMS (M+H)$^+$ m/z 831.1 [calcd for $C_{45}H_{52}N_6O_9$, 830.5].

Example 84

Preparation of Compound 84

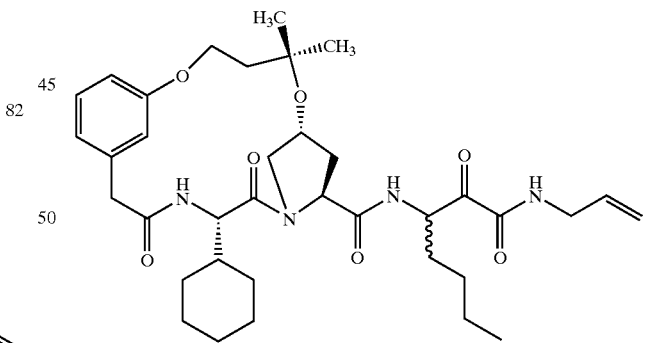

The desired compound 84 was prepared by the same method as described in the preparation of compound 30 in Example 30, except that an appropriate amine was used to substitute amine A in Step I. LRMS (M+H)$^+$ m/z 653.1 [calcd for $C_{36}H_{52}N_4O_7$, 652.4].

Example 85

Preparation of Compound 85

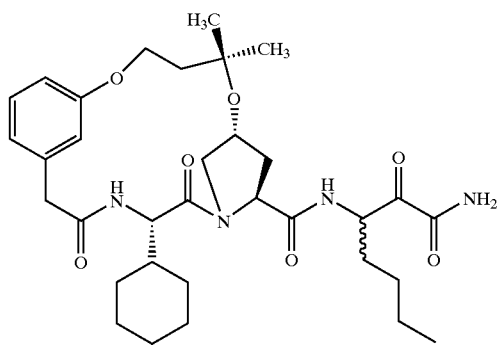

The desired compound 85 was prepared by the same method as described in the preparation of compound 30 in Example 30, except that an appropriate amine was used to substitute amine A in Step I, and that the oxidation was performed according the procedure in Example 10, Step J. LRMS (M+H)$^+$ m/z 613.1 [calcd for $C_{33}H_{48}N_4O_7$, 612.4].

Example 86

Preparation of Compound 86

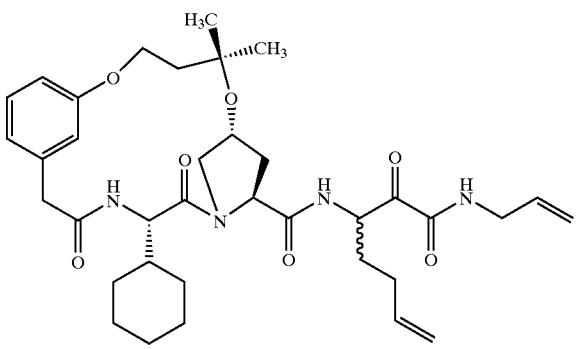

The desired compound 86 was prepared by the same method as described in the preparation of compound 30 in Example 30, except that an appropriate amine was used to substitute amine A in Step I. LRMS (M+H)$^+$ m/z 651.1 [Calcd for $C_{36}H_{50}N_4O_7$, 650.4].

Example 87

Preparation of Compound 87

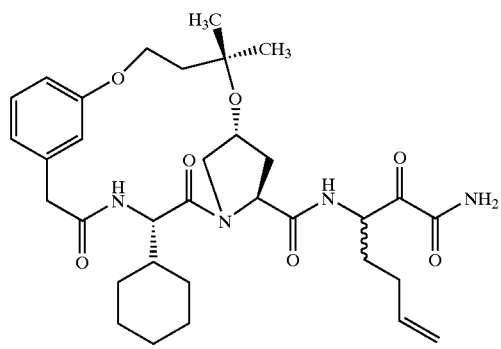

The desired compound 87 was prepared by the same method as described in the preparation of compound 30 in Example 30. Except that an appropriate amine was used to substitute amine A in Step I, and that the oxidation was performed according the procedure in Example 10, Step J. LRMS (M+H)$^+$ m/z 611.1 [calcd for $C_{33}H_{46}N_4O_7$, 610.3].

Example 88

Preparation of Compound 88

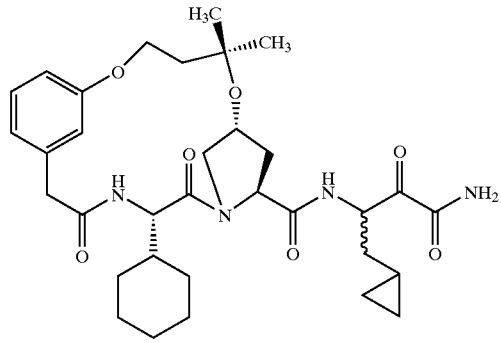

The desired compound 88 was prepared by the same method as described in the preparation of compound 30 in Example 30. Except that an appropriate amine was used to substitute amine A in Step I, and that the oxidation was performed according the procedure in Example 10, Step J. LRMS (M+H)$^+$ m/z 611.1 [calcd for $C_{33}H_{46}N_4O_7$, 610.3].

Example 89

Preparation of Compound 89

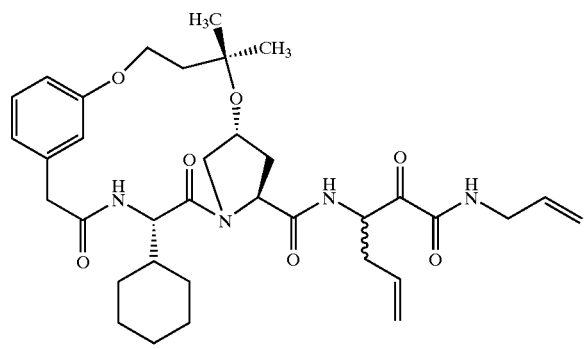

The desired compound 88 was prepared by the same method as described in the preparation of compound 30 in Example 30. Except that an appropriate amine was used to substitute amine A in Step I. LRMS (M+H)$^+$ m/z 637.1 [calcd for $C_{35}H_{48}N_4O_7$, 636.4].

Example 90

Preparation of Compound 90

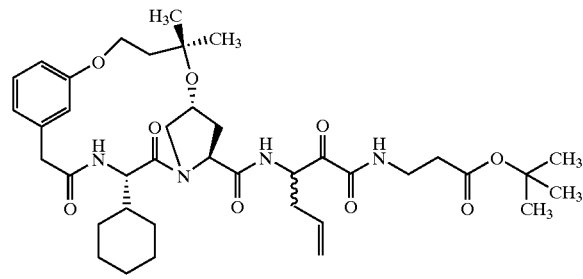

The desired compound 90 was prepared by the same method as described in the preparation of compound 30 in Example 30. Except that an appropriate amine was used to substitute amine A in Step I. LRMS (M+H)$^+$ m/z 725.1 [calcd for $C_{39}H_{56}N_4O_9$, 724.4].

Example 91

Preparation of Compound 91

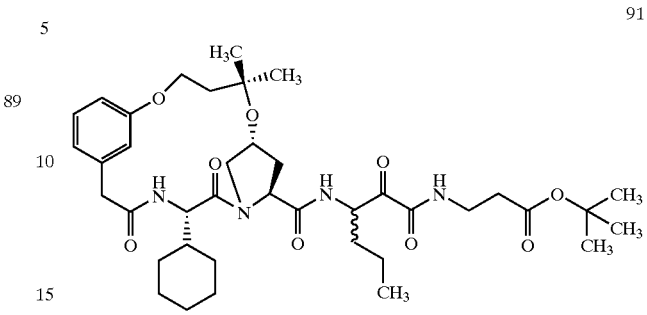

The desired compound 91 was prepared by the same method as described in the preparation of compound 30 in Example 30. Except that an appropriate amine was used to substitute amine A in Step I. LRMS (M+H)$^+$ m/z 727.1 [calcd for $C_{39}H_{58}N_4O_9$, 726.4].

Example 92

Preparation of Compound 92

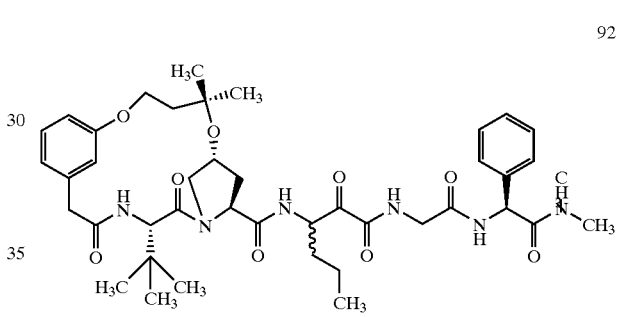

The desired compound 92 was prepared by the same method as described in the preparation of compound 30 Example 30, except that Boc-tert-butylglycine was used to substitute Boc-cyclohexylglycine in Step C. LRMS (M+H)$^+$ m/z 791.1 [calcd for $C_{42}H_{58}N_6O_9$, 790.4].

Example 93

Preparation of Compound 93

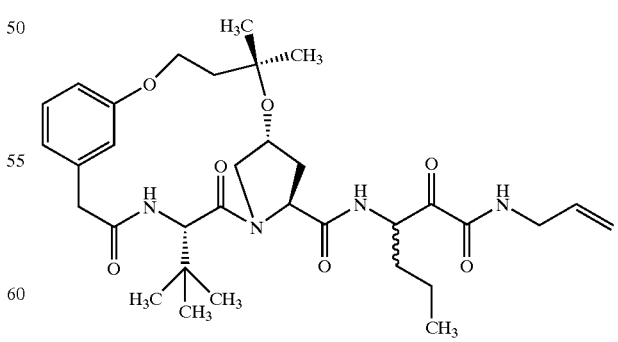

The desired compound 93 was prepared by the same method as described in the preparation of compound 92 in Example 92. Except that an appropriate amine was used to substitute amine A. LRMS (M+H)+ m/z 613.1 [calcd for $C_{33}H_{48}N_4O_7$, 612.4].

Example 94

Preparation of Compound 94

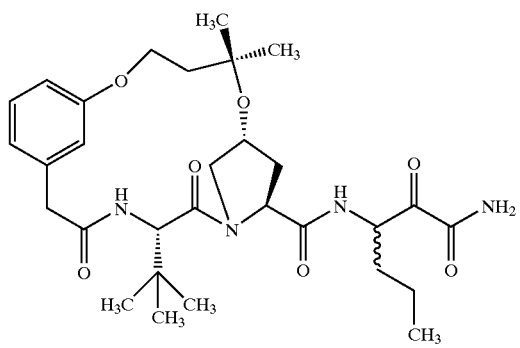

94

The desired compound 94 was prepared by the same method as described in the preparation of compound 92 in Example 92. Except that an appropriate amine was used to substitute amine A, and that the oxidation was performed according the procedure in Example 10, Step J. LRMS (M+H)+ m/z 573.1 [calcd for $C_{30}H_{44}N_4O_7$, 572.3].

Example 95

Preparation of Compound 95

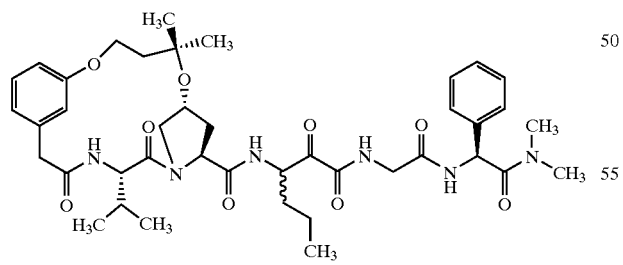

95

The desired compound 95 was prepared by the same method as described in the preparation of compound 30 Example 30, except that Boc-valine was used to substitute Boc-cyclohexylglycine in Step C. LRMS (M+H)+ m/z 777.1 [Calcd for $C_{41}H_{56}N_6O_9$, 776.4].

Example 96

Preparation of Compound 96

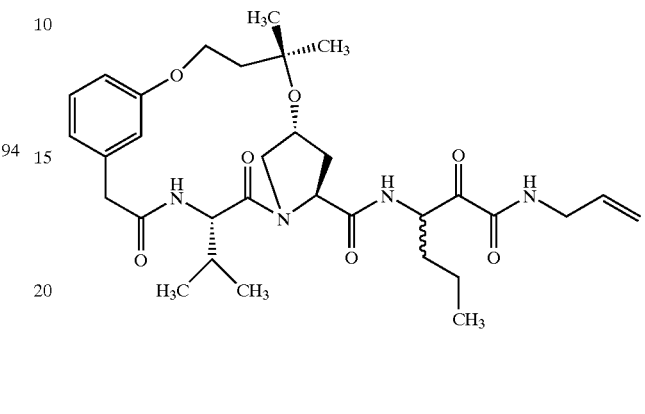

96

The desired compound 96 was prepared by the same method as described in the preparation of compound 95 in Example 95. Except that an appropriate amine was used to substitute amine A. LRMS (M+H)+ m/z 599.1 [calcd for $C_{32}H_{46}N_4O_7$, 598.3].

Example 97

Preparation of Compound 97

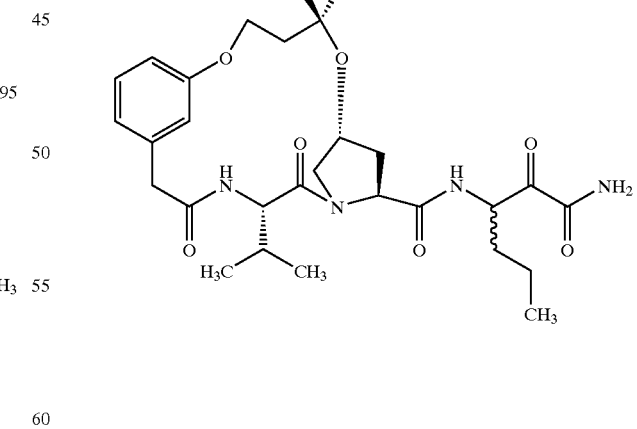

97

The desired compound 97 was prepared by the same method as described in the preparation of compound 95 in Example 95. Except that an appropriate amine was used to substitute amine A, and that the oxidation was performed according the procedure in Example 10, Step J. LRMS (M+H)+ m/z 559.1 [calcd for $C_{29}H_{42}N_4O_7$, 558.3].

Example 98

Preparation of Compound 98

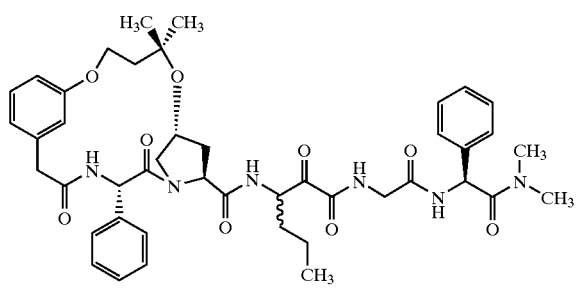

The desired compound 98 was prepared by the same method as described in the preparation of compound 30 Example 30, except that Boc-phenylglycine was used to substitute Boc-cyclohexylglycine in Step C. LRMS (M+H)+ m/z 811.1 [calcd for $C_{44}H_{54}N_6O_9$, 810.4].

Example 99

Preparation of Compound 99

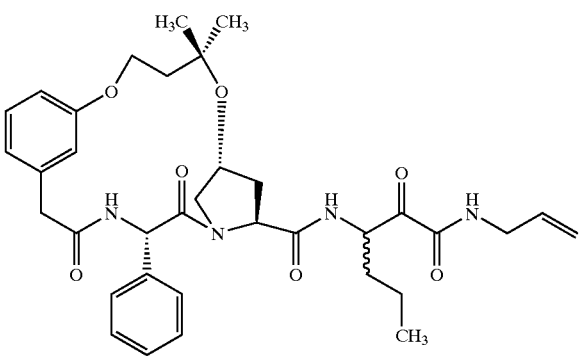

The desired compound 99 was prepared by the same method as described in the preparation of compound 98 in Example 98. Except that an appropriate amine was used to substitute amine A. LRMS (M+H)+ m/z 633.1 [calcd for $C_{35}H_{44}N_4O_7$, 632.3].

Example 100

Preparation of Compound 100

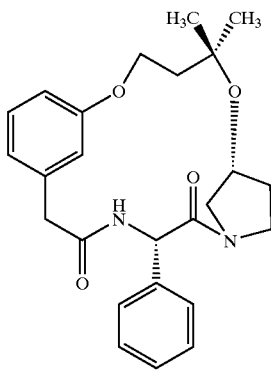

The desired compound 100 was prepared by the same method as described in the preparation of compound 98 in Example 98. Except that an appropriate amine was used to substitute amine A, and that the oxidation was performed according the procedure in Example 10, Step J. LRMS (M+H)+ m/z 593.1 [calcd for $C_{35}H_{40}N_4O_7$, 592.3].

Example 101

Preparation of Compound 101

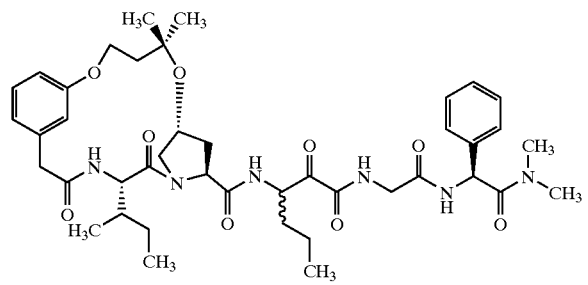

The desired compound 101 was prepared by the same method as described in the preparation of compound 30 Example 30, except that Boc-isoleucine was used to substitute Boc-cyclohexylglycine in Step C. LRMS (M+H)+ m/z 791.1 [calcd for $C_{42}H_{56}N_6O_9$, 790.4].

Example 102

Preparation of Compound 102

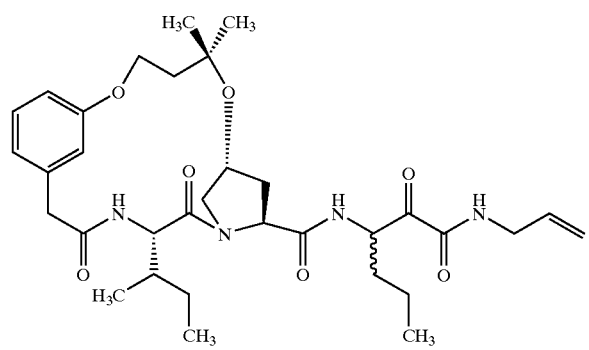

The desired compound 102 was prepared by the same method as described in the preparation of compound 101 in Example 101. Except that an appropriate amine was used to substitute amine A. LRMS (M+H)$^+$ m/z 613.1 [calcd for $C_{33}H_{48}N_4O_7$, 612.4].

Example 103

Preparation of Compound 103

The desired compound 103 was prepared by the same method as described in the preparation of compound 101 in Example 101. Except that an appropriate amine was used to substitute amine A, and that the oxidation was performed according to the procedure in Example 10, Step J. LRMS (M+H)$^+$ m/z 573.1 [calcd for $C_{30}H_{44}N_4O_7$, 572.3].

Example 104

Preparation of Compound 104

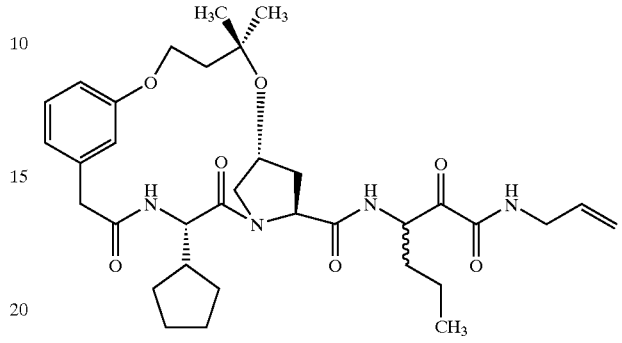

The desired compound 104 was prepared by the same method as described in the preparation of compound 30 Example 30, except that Boc-cyclopentylglycine was used to substitute Boc-cyclohexylglycine in Step C, and that an appropriate amine was used to substitute amine A in Step I. LRMS (M+H)$^+$ m/z 625.1 [calcd for $C_{34}H_{48}N_4O_7$, 624.4].

Example 105

Preparation of Compound 105

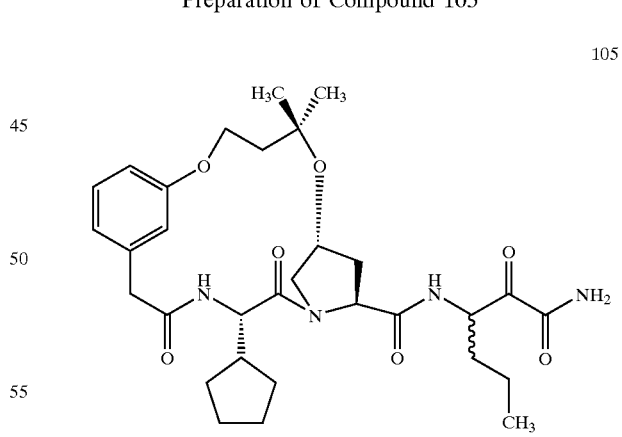

The desired compound 105 was prepared by the same method as described in the preparation of compound 104 in Example 104. Except that an appropriate amine was used to substitute amine A, and that the oxidation was performed according to the procedure in Example 10, Step J. LRMS (M+H)$^+$ m/z 585.1 [calcd for $C_{31}H_{44}N_4O_7$, 584.3].

Example 106

Preparation of Compound 106

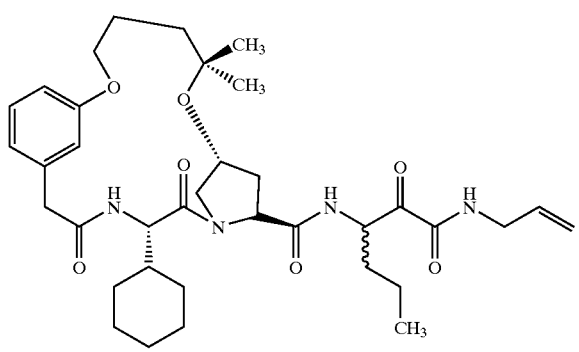

The desired compound 106 was prepared by the same method as described in the preparation of compound 30 Example 30 with the following exceptions: (a). 5-benzyloxy-2-methyl-1-pentene was used to substitute 4-benzyloxy-2-methyl-1-butene in Step A; (b). an appropriate amine was used to substitute amine A in Step I. LRMS (M+H)$^+$ m/z 653.1 [calcd for $C_{36}H_{52}N_4O_7$, 652.4].

Example 107

Preparation of Compound 107

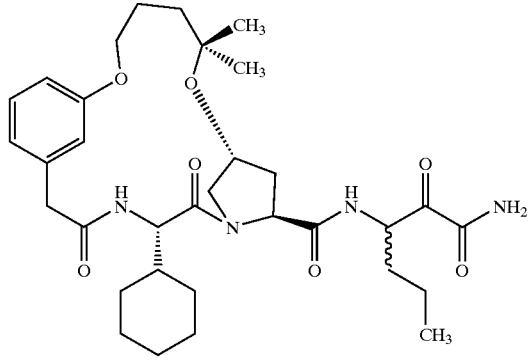

The desired compound 107 was prepared by the same method as described in the preparation of compound 106 in Example 106. Except that an appropriate amine was used to substitute amine A in Step I, and that the oxidation was performed according the procedure in Example 10, Step J. LRMS (M+H)$^+$ m/z 613.1 [calcd for $C_{33}H_{40}N_4O_7$, 612.4].

Example 108

Preparation of Compound 108

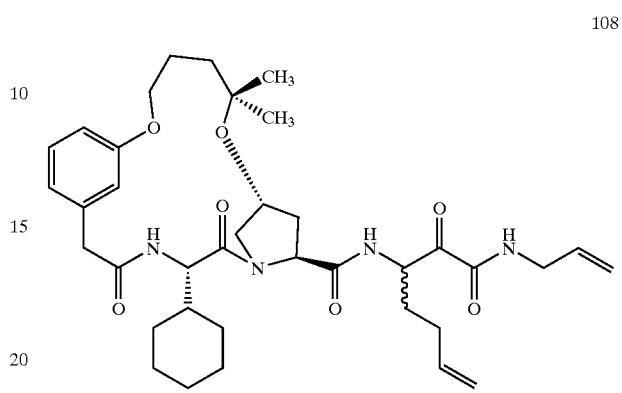

The desired compound 108 was prepared by the same method as described in the preparation of compound 106 Example 106, with the exception that an appropriate amine was used to substitute amine A in Step I. LRMS (M+H)$^+$ m/z 665.1 [calcd for $C_{37}H_{52}N_4O_7$, 664.4].

Example 109

Preparation of Compound 109

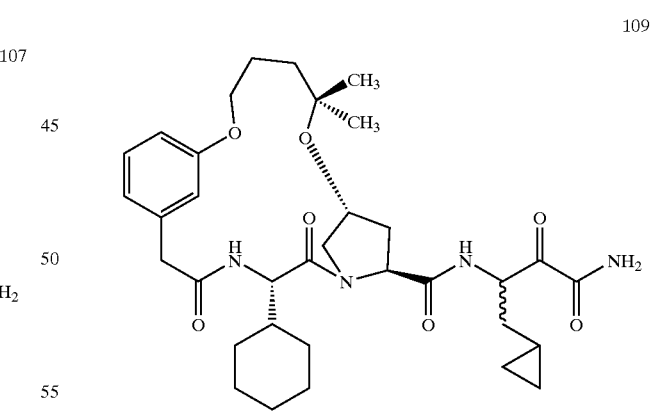

The desired compound 109 was prepared by the same method as described in the preparation of compound 106 Example 106, with the exception that an appropriate amine was used to substitute amine A in Step I, and that the oxidation was performed according the procedure in Example 10, Step J. LRMS (M+H)$^+$ m/z 625.1 [calcd for $C_{34}H_{48}N_4O_7$, 624.4].

Example 110

Preparation of Compound 110

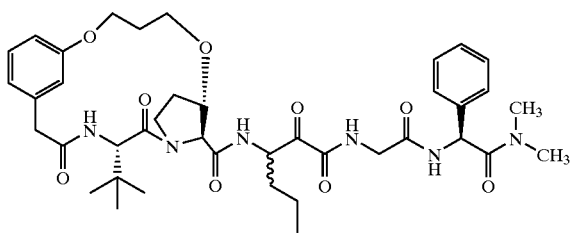

The desired compound 110 was prepared by the same method as described in the preparation of compounds 1A and 1B, Example 1, except that Boc-3-hydroxyproline was used to substitute proline 1a in Step A, and that Boc-tert-butylglycine was used to substitute Boc-cyclohexylglycine in Step D. LRMS (M+H)+ m/z 763.1 [calcd for $C_{40}H_{54}N_6O_9$, 762.4].

Example 111

Preparation of Compound 111

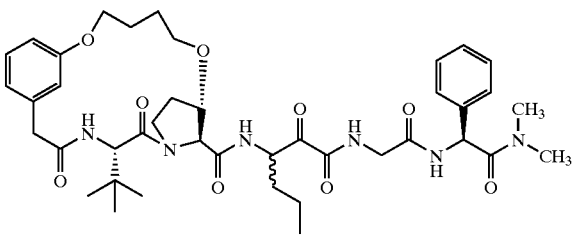

The desired compound 111 was prepared by the same method as described in the preparation of compounds 4A and 4B in Example 4, except that Boc-3-hydroxyproline was used to substitute proline 1a in Step A, and that Boc-tert-butylglycine was used to substitute Boc-cyclohexylglycine in Step D. LRMS (M+H)+ m/z 777.1 [calcd for $C_{41}H_{56}N_6O_9$, 776.4].

Assay for HCV Protease Inhibitory Activity

Spectrophotometric Assay

Spectrophotometric assays for the HCV serine protease was performed on the inventive compounds by following the procedure described by R. Zhang et al, *Analytical Biochemistry*, 270 (1999) 268–275, the disclosure of which is incorporated herein by reference. The assay based on the proteolysis of chromogenic ester substrates is suitable for the continuous monitoring of HCV NS3 protease activity. The substrates were derived from the P side of the NS5A-NS5B junction sequence (Ac-DTEDVVX(Nva), where X=A or P) whose C-terminal carboxyl groups were esterified with one of four different chromophoric alcohols (3- or 4-nitrophenol, 7-hydroxy-4-methyl-coumarin, or 4-phenylazophenol). Presented below are the synthesis, characterization and application of these novel spectrophotometric ester substrates to high throughput screening and detailed kinetic evaluation of HCV NS3 protease inhibitors.

Materials and Methods

Materials: Chemical reagents for assay related buffers were obtained from Sigma Chemical Company (St. Louis, Mo.). Reagents for peptide synthesis were from Aldrich Chemicals, Novabiochem (San Diego, Calif.), Applied Biosystems (Foster City, Calif.) and Perseptive Biosystems (Framingham, Mass.). Peptides were synthesized manually or on an automated ABI model 431A synthesizer (from Applied Biosystems). UV/VIS Spectrometer model LAMBDA 12 was from Perkin Elmer (Norwalk, Conn.) and 96-well UV plates were obtained from Corning (Corning, N.Y.). The prewarming block was from USA Scientific (Ocala, Fla.) and the 96-well plate vortexer was from Labline Instruments (Melrose Park, Ill.). A Spectramax Plus microtiter plate reader with monochrometer was obtained from Molecular Devices (Sunnyvale, Calif.).

Enzyme Preparation

Recombinant heterodimeric HCV NS3/NS4A protease (strain 1a) was prepared by using the procedures published previously (D. L. Sali et al, *Biochemistry*, 37 (1998) 3392–3401). Protein concentrations were determined by the Biorad dye method using recombinant HCV protease standards previously quantified by amino acid analysis. Prior to assay initiation, the enzyme storage buffer (50 mM sodium phosphate pH 8.0, 300 mM NaCl, 10% glycerol, 0.05% lauryl maltoside and 10 mM DTT) was exchanged for the assay buffer (25 mM MOPS pH 6.5, 300 mM NaCl, 10% glycerol, 0.05% lauryl maltoside, 5 μM EDTA and 5 μM DTT) utilizing a Biorad Bio-Spin P-6 prepacked column.

Substrate Synthesis and Purification

The synthesis of the substrates was done as reported by R. Zhang et al, (ibid.) and was initiated by anchoring Fmoc-Nva-OH to 2-chlorotrityl chloride resin using a standard protocol (K. Barlos et al, *Int. J. Pept. Protein Res.*, 37 (1991), 513–520). The peptides were subsequently assembled, using Fmoc chemistry, either manually or on an automatic ABI model 431 peptide synthesizer. The N-acetylated and fully protected peptide fragments were cleaved from the resin either by 10% acetic acid (HOAc) and 10% trifluoroethanol (TFE) in dichloromethane (DCM) for 30 min, or by 2% trifluoroacetic acid (TFA) in DCM for 10 min. The combined filtrate and DCM wash was evaporated azeotropically (or repeatedly extracted by aqueous $Na_2CO_3$ solution) to remove the acid used in cleavage. The DCM phase was dried over $Na_2SO_4$ and evaporated.

The ester substrates were assembled using standard acid-alcohol coupling procedures (K. Holmber et al, *Acta Chem. Scand.*, B33 (1979) 410–412). Peptide fragments were dissolved in anhydrous pyridine (30–60 mg/ml) to which 10 molar equivalents of chromophore and a catalytic amount (0.1 eq.) of para-toluenesulfonic acid (pTSA) were added. Dicyclohexylcarbodiimide (DCC, 3 eq.) was added to initiate the coupling reactions. Product formation was monitored by HPLC and found to be complete following 12–72 hour reaction at room temperature. Pyridine solvent was evaporated under vacuum and further removed by azeotropic evaporation with toluene. The peptide ester was deprotected with 95% TFA in DCM for two hours and extracted three times with anhydrous ethyl ether to remove excess chromophore. The deprotected substrate was purified by reversed phase HPLC on a C3 or C8 column with a 30% to 60% acetonitrile gradient (using six column volumes). The overall yield following HPLC purification was approximately 20–30%. The molecular mass was confirmed by electrospray ionization mass spectroscopy. The substrates were stored in dry powder form under desiccation.

Spectra of Substrates and Products

Spectra of substrates and the corresponding chromophore products were obtained in the pH 6.5 assay buffer. Extinction coefficients were determined at the optimal off-peak wavelength in 1-cm cuvettes (340 nm for 3-Np and HMC, 370 nm for PAP and 400 nm for 4-Np) using multiple dilutions. The optimal off-peak wavelength was defined as that wavelength yielding the maximum fractional difference in absorbance between substrate and product (product OD—substrate OD)/substrate OD).

Protease Assay

HCV protease assays were performed at 30° C. using a 200 µl reaction mix in a 96-well microtiter plate. Assay buffer conditions (25 mM MOPS pH 6.5, 300 mM NaCl, 10% glycerol, 0.05% lauryl maltoside, 5 µM EDTA and 5 µM DTT) were optimized for the NS3/NS4A heterodimer (D. L. Sali et al, ibid.)). Typically, 150 µl mixtures of buffer, substrate and inhibitor were placed in wells (final concentration of DMSO•4% v/v) and allowed to preincubate at 30° C. for approximately 3 minutes. Fifty µls of prewarmed protease (12 nM, 30° C.) in assay buffer, was then used to initiate the reaction (final volume 200 µl).The plates were monitored over the length of the assay (60 minutes) for change in absorbance at the appropriate wavelength (340 nm for 3-Np and HMC, 370 nm for PAP, and 400 nm for 4-Np) using a Spectromax Plus microtiter plate reader equipped with a monochrometer (acceptable results can be obtained with plate readers that utilize cutoff filters). Proteolytic cleavage of the ester linkage between the Nva and the chromophore was monitored at the appropriate wavelength against a no enzyme blank as a control for non-enzymatic hydrolysis. The evaluation of substrate kinetic parameters was performed over a 30-fold substrate concentration range (~6–200 µM). Initial velocities were determined using linear regression and kinetic constants were obtained by fitting the data to the Michaelis-Menten equation using non-linear regression analysis (Mac Curve Fit 1.1, K. Raner). Turnover numbers ($k_{cat}$) were calculated assuming the enzyme was fully active.

Evaluation of Inhibitors and Inactivators

The inhibition constants (K) for the competitive inhibitors Ac-D-(D-Gla)-L-I-(Cha)-C-OH (27), Ac-DTEDVVA(Nva)-OH and Ac-DTEDVVP(Nva)-OH were determined experimentally at fixed concentrations of enzyme and substrate by plotting $v_o/v_i$ vs. inhibitor concentration ($[I]_o$) according to the rearranged Michaelis-Menten equation for competitive inhibition kinetics: $v_o/v_i=1+[I]_o/(K_i(1+[S]_o/K_m))$, where $v_o$ is the uninhibited initial velocity, $v_i$ is the initial velocity in the presence of inhibitor at any given inhibitor concentration ($[I]_o$) and $[S]_o$ is the substrate concentration used. The resulting data were fitted using linear regression and the resulting slope, $1/(K_i(1+[S]_o/K_m))$, was used to calculate the $K_i$ value.

The obtained $K_i$ values for the various macrocycles of the present invention are given in the afore-mentioned Table 1 wherein the compounds have been arranged in the order of ranges of $K_i$ values. From these test results, it would be apparent to the skilled artisan that the compounds of the invention have excellent utility as NS3-serine protease inhibitors.

Cell Bioassay Method

The cell bioassays for the HCV serine protease was performed on the inventive compounds by following the procedure described by S. Agrawal et al, "Development and Characterization of Hepatitis C Virus Serine Protease Cell-based Trans-Cleavage Assay", *Hepatology* Supplement to Volume 30 (No. 4, Part 2, October 1999), Abstract No. 615 (Proceedings of AASLD 50th Annual Meeting, Dallas, Tex., Nov. 5–9, 1999), the disclosure of which is incorporated herein by reference. The assay was performed in HeLa/Huh7 cells that were co-transfected with a plasmid that expresses a reporter protein substrate containing the NS5A/5B cleavage recognition sequence and an 1BNS4A$_{21-32}$ GS-GSNS$_{3-81}$ i17K expression vector and YFPn1 as a internal standard protein to control cytotoxicity. Protease activity was measured by SDS-PAGE of total cell lysates followed by Western blot detection using a monoclonal antibody directed against the reporter substrate. Quantitation of substrate cleavage was performed by scanning the immunoblot on the phosphoimager.

Materials

Plasmid DNAs pBFP-5A/5B-GFP

The reporter gene that expresses the substrate encodes a fusion protein comprised of an N' terminal blue fluorescent protein (BFP) domain and a C' terminal green fluorescent protein (GFP) domain, separated by a 25 amino acids derived from the NS5A/5B cleavage recognition sequence. Both GFP and BFP are essentially homologous autofluorescent proteins that emit green or blue light, respectively, when excited by UV light of the appropriate wavelength. Four amino acid substitutions in the chromophore of GFP alter the emission wavelength and convert the protein to BFP.

The substrate and the resulting GFP and BFP products can be detected in cell lysates by immunologic methods using a monoclonal antibody that recognizes both proteins.

The BFP-5A/5B-GFP reporter gene contains the BFP and GFP autofluorescent protein coding sequences (Quantum Biotechnologies, Inc., Montreal, Canada) separated by the NS5A/5B cleavage recognition sequence, cloned between the Nhe I and Bam HI restriction endonuclease sites of the pQBI125 cloning vector (Quantum Biotechnologies, Inc.). Expression of the fusion protein is under the control of the CMV IE promoter-enhancer. The bovine growth hormone p (A) sequence of the vector provides the polyadenylation signal for the mRNA. The NS5A/5B cleavage sequence is: SSGADTEDVVCCSMSYTWTGALVTP. DNA sequencing was used to validate the clone.

P1BOO2: 1bNS4A21-32GS-GS NS 3-81I17K

The subtype 1b protease was cloned as an Xba1/Not1 fragment behind the CMV promoter in vector pC1 neo.

YFPn1

YFPn1 was purchased from CLONTECH (Palo Alto, Calif.). Addition of third plasmid to the transfection supplies an internal standard protein to control for cytotoxicity and does not affect percentage of protease cleavage.

Plasmid DNAs were maintained and propagated in DH5α cells (obtained from LifeTechnologies) in LB medium under the appropriate antibiotic selection, and purified using QIA-filter Plasmid Kits (Qiagen, Valencia, Calif.).

Cell Culture

HeLa cells were maintained and propagated in Eagle's Minimum Essential Media (EMEM; BioWhittaker, Walkersville, Md.) supplemented with 10% fetal calf serum (FCS), 2 mM glutamine, and 100 u/ml penicillin-streptomycin (BioWhitaker), 2% NaHCO$_3$.

Huh7 cells were maintained and propagated in Dulbecco's Modified Eagle's medium (DMEM; BioWhittaker) supplemented with 10% fetal calf serum (FCS), 100u/ml penicillin-streptomycin (BioWhitaker) and 5 ml NEAA (100×; BioWhittaker)/L.

SOP Procedure

Day Preceding Transfection

HeLa cells were seeded in 24 well plates (Falcon 3047 plates) at a density of 6×10$^4$ cells/well and grown overnight at 37° C. in a 5% CO2 incubator.

Day of Transfection

Plasmid DNAs were diluted to a final concentration of 0.05 µg/µl in nuclease free water (Promega, Madison, Wis., cat # P119C). 0.75 µg BFP-5A/5B-GFP was combined and mixed with 0.175 µg P1 B002 (0.23X) and 0.02 µg of YFPn1. The DNAs were brought to a final volume of 60 µl with EMEM lacking FBS, glutamine, and antibiotics. A ratio of 5 µl volumes of SuperFect Reagent (Qiagen, cat #301305) per total µgs of DNA was added and the mixture vortexed about 10 seconds and incubated 10 min. at room temperature to allow complex formation.

While complex formation was taking place, growth medium from cell culture plates was aspirated and cells washed 1× with 1 ml PBS without $Ca^{2+}$, $Mg^{2+}$ (BioWhitaker). 350 µl EMEM (supplemented with appropriate suplements-compleat medium) was added to the tube containing the transfection complexes and the mixture pipetted up and down 2–3 times. Total volume was transferred to one well of the 24 well culture plate. The HeLa cells were incubated with the transfection complexes for about 3 hr. at 37° C. and 5% CO2. The media containing the transfection complexes was removed from the cells by aspiration.

The cells were washed once in about 1 ml PBS, the PBS was aspirated and 495 µl of complete EMEM was added followed by 5 µl compound/well. The cells were incubated 22–24 hr. at 37° C. and 5% CO2.

Preparation of Cell Lysates

The medium from each well was aspirated and washed once 1× with DPBS. Cells were harvested in 100 µl of 1× Tris-SDS-BME sample buffer (OWL separation system, Portsmouth, N.H., cat #ER33) and transferred to microcentrifuge tubes. It was then boiled 3–5 min. to lyse cells. Loading was done at 10 µl/well on SDS-PAGE gel. The lysates were resolved by electrophoresis on 10 cm×10 cm 12.5% SDS-PAGE (Owl Scientific, cat #OG-0125B) run at 30 mamp in Tris-Glycine-SDS buffer (Owl Scientific). Prior to use, PVDF membrane (Immobilon-P; 0.45 µm pore size; Millipore, Bedford, Mass.) was soaked in 100% methanol for 10 seconds and then the blot was placed in distilled water. The proteins were transferred to PVDF filter membranes (0.45 µm, Millipore) at 108 mamp per gel for 90 minutes using a semi-dry electroblotter.

Detection of Proteins by ECF Western Blot (Amersham Pharmacia Biotech, Little Chalfont, England), catalog #RPN 5780). The PVDF filter membranes were blocked by 5% blocking reagent (from kit) in ~10 ml PBS containing 0.05% Tween 20, pH 7.4 (Sigma Chemicals, St. Louis, Mo., cat #3563) for overnight at 2–4° C. in refrigerator. The next day, the membranes were rinsed briefly twice with TPBS containing 0.05% Tween 20 washing buffer, then washed three times each time 5 min. in PBS containing 0.05% Tween 20, pH 7.4. The membranes were incubated in 12 mls of a 1:3000 dilution of anti-GFP monoclonal antibody for 30 minutes (Clontech, Palo Alto, Calif.) in PBS containing 0.05% Tween 20, pH7.4 while at the same time 1% BSA (Albumin, bovine cat #A-2153 from Sigma) was added to reduce background. The membranes were washed briefly twice with TPBS, then thrice, for 5 min. each time, in TPBS washing buffer. The membranes were incubated in 12 mls of a 1:600 dilution anti fluorescein-linked anti mouse Ig in TPBS for 30 minutes. The membranes were washed briefly with TPBS twice, then for 5 min. in TPBS washing buffer thrice. For signal amplification with ECF substrate membranes were incubated in 10 ml of 1:2500 anti fluorescein alkaline phosphatase conjugate for 30 minutes. The membranes were rinsed briefly with TPBS twice, then 5 min. in TPBS washing buffer thrice. The ECF substrate solution was prepared as per manufacturer's instructions (aliquot and freeze), membranes were incubated for 2–3 minutes, excess reagent was drained off, then were blotted with filter papers, air-dried for 9–10 minutes and then scanned.

Scanning the membrane

The blot was placed on the glass of phosphoimager Storm 860. The blue chemiluminiescent was set up, 200 pixcels size, 700 PMT voltage. The file was opened in ImageQuant and quantitated by creating squares around the bands representing the substrate (S), the product (P) and the internal control (IC). The % cleavage of the substrate was measured as $P/(S+P)\times 100$. The inhibition in cleavage due to drug was measured compared duplicate to drug controls included on each blot. A report was created Excel. The results are shown in Table 2. From these test results, it would be apparent to the skilled artisan that the compounds of the invention have excellent utility as NS3-serine protease inhibitors.

TABLE 2

| HCV Cell-based assay results: | |
|---|---|
| Example Number | Cell-Based Assay (µM) |
| 1B | 2 |
| 2 | 2 |
| 4A | 2.5 |
| 4B | 1.8 |
| 5 | 0.6 |
| 7B | 7 |
| 8 | 3.5 |
| 12B | 5.2 |
| 21 | 2 |
| 23 | 3 |
| 30 | 1 |
| 57B | 1.5 |
| 58 | 2 |

It will be apparent to those skilled in the art that many modifications, variations and alterations to the present disclosure, both to materials and methods, may be practiced. Such modifications, variations and alterations are intended to be within the spirit and scope of the present invention.

What is claimed is:

1. A macrocyclic compound, including enantiomers, stereoisomers, rotomers and tautomers of said compound, and pharmaceutically acceptable salts or solvates of said compound, said compound having the general structure shown in Formula I:

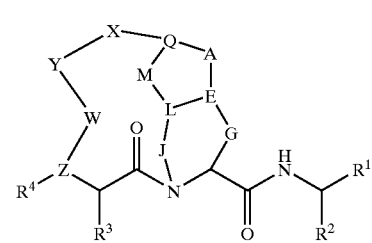

Formula I wherein the moiety;

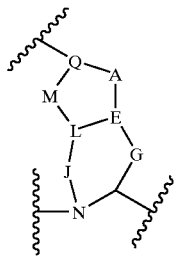

represents:

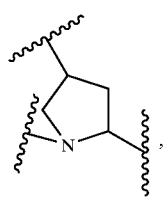 , 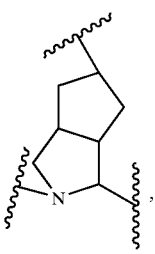 ,

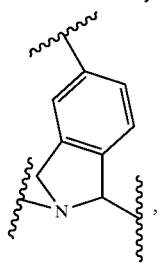 , 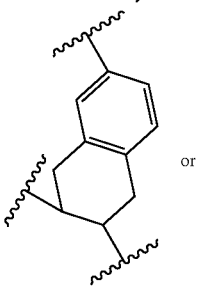 or

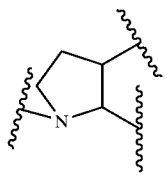 ;

X and Y are independently selected from the moieties: alkyl, alkyl-aryl, heteroalkyl, heteroaryl, aryl-heteroaryl, cycloalkyl, alkyl ether, alkyl-aryl ether, aryl ether, alkyl amino, aryl amino, alkyl-aryl amino, alkyl sulfide, alkyl-aryl sulfide, aryl sulfide, alkyl amide, alkyl-aryl amide, aryl amide, alkyl sulfonamide, alkyl-aryl sulfonamide, aryl sulfonamide, alkyl sulfonyl, aryl sulfonyl, heteroalkyl sulfonyl, heteroaryl sulfonyl, alkyl carbonyl, aryl carbonyl, heteroalkyl carbonyl, heteroaryl carbonyl, alkoxycarbonyl, aryloxycarbonyl, heteroaryloxycarbonyl, or a combination thereof, with the proviso that X and Y may optionally be additionally substituted with moieties selected from the group consisting of aromatic, alkyl, alkyl-aryl, heteroalkyl, and cycloalkyl;

$R^1$=$COR^5$, wherein $R^5$=H, OH, $OR^8$, $NR^9R^{10}$, $CF_3$, $C_2F_5$, $C_3F_7$, $CF_2R^6$, $R^6$, or COR7 wherein $R^7$=H, OH, $OR^8$, $CHR^9R^{10}$, or $NR^9R^{10}$, wherein $R^6$, $R^8$, $R^9$ and $R^{10}$ are independently selected from the group consisting of H, alkyl, aryl, heteroalkyl, heteroaryl, cycloalkyl, cycloalkyl, arylalkyl, heteroarylalkyl, $CH(R^{1'})COOR^{11}$, $CH(R^{1'})CONR^{12}R^{13}$, $CH(R^{1'})CONHCH(R^{2'})COOR^{11}$, $CH(R^{1'})CONHCH(R^{2'})CONR^{12}R^{13}$, $CH(R^{1'})CONHCH(R^{2'})R'$, $CH(R^{1'})CONHCH(R^{2'})CONHCH(R^{3'})COOR^{11}$, $CH(R^{1'})CONHCH(R^{2'})CONHCH(R^{3'})CONR^{12}R^{13}$, $CH(R^{1'})CONHCH(R^{2'})CONHCH(R^{4'})COO R^{11}$, $CH(R^{1'})CONHCH(R^{2'})CONHCH(R^{3'})CONHCH(R^{4'})CONR^{12}R^{13}$, $CH(R^{1'})CONHCH(R^{2'})CONHCH(R^{3'})CONHCH(R^{4'})CONHCH(R^{5'})COOR^{11}$, $CH(R^{1'})CONHCH(R^{2'})CONHCH(R^{3'})CONHCH(R^{4'})CONHCH(R^{5'})CONR^{12}R^{13}$, wherein $R^{1'}$, $R^{2'}$, $R^{3'}$, $R^{4'}$, $R^{5'}$, $R^{11}$, $R^{12}$, $R^{13}$, and R' are independently selected from a group consisting of H, alkyl, aryl, heteroalkyl, heteroaryl, cycloalkyl, alkyl-aryl, alkyl-heteroaryl, aryl-alkyl and heteroarylalkyl;

Z is selected from O, N, or CH;

W may be present or absent, and if W is present, W is;

$R^4$ is H, C1–C10 alkyl, C1–C10 alkenyl or C3–C8 cycloalkyl; and $R^2$, and $R^3$ are independently selected from the group consisting of H; C1–C10 alkyl; C2–C10 alkenyl; C3–C8 cycloalkyl; C3–C8 heterocycloalkyl, alkoxy, aryloxy, alkylthio, arylthio, amino, amido, ester, carboxylic acid, carbamate, urea, ketone, aldehyde, cyano, nitro; oxygen, nitrogen, sulfur, or phosphorus atoms with said oxygen, nitrogen, sulfur, or phosphorus atoms numbering zero to six;

(cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl;

with said alkyl, heteroalkyl, alkenyl, heteroalkenyl, aryl, heteroaryl, cycloalkyl and heterocycloalkyl moieties may be optionally substituted, with said term "substituted" referring to optional and suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamide, sulfoxide, sulfone, sulfonyl urea, hydrazide, and hydroxamate.

2. The compound of claim 1, wherein $R^1$=$COR^5$, and $R^5$ is H, OH, $COOR^8$, or $CONR^9R^{10}$.

3. The compound of claim 2, wherein $R^1$=$COCONR^9R^{10}$, and $R^9$ is H, $R^{10}$ is H, $CH(R^{1'})COOR^{11}$, $CH(R^{1'}) CONR^{12}R^{13}$, $CH(R^{1'})CONHCH(R^{2'})COOR^{11}$, $CH(R^{1'})CONHCH(R^{2'})CONR^{12}R^{13}$, or $CH(R^{1'})CONHCH(R^{2'})(R')$.

4. The compound of claim 3, wherein $R^{10}$=$CH(R^{1'})CONHCH(R^{2'})COOR^{11}$, $CH(R^{1'})CONHCH(R^{2'})CONR^{12}R^{13}$, or $CH(R^{1'})CONHCH(R^{2'})(R')$, wherein $R^{1'}$ is H or alkyl, and $R^{2'}$ is phenyl, substituted phenyl, hetero atom-substituted phenyl, thiophenyl, cyclohexyl, cyclopentyl, cyclopropyl, piperidyl, pyridyl and 2-indanyl.

5. The compound of claim 4, wherein $R^{1'}$ is H.

6. The compound of claim 5, wherein $R^{2'}$=phenyl, thiophenyl, cyclohexyl, 2-indanyl, cyclopentyl, pyridyl, phenyl(4-$HNSO_2NH_2$), $R^{11}$ is H or tert-butyl, $R^{12}$ and $R^{13}$ are methyl, and R' is hydroxymethyl or tert-butoxymethyl.

7. The compound of claim 1, wherein $R^2$ is selected from the group consisting of the following moieties:

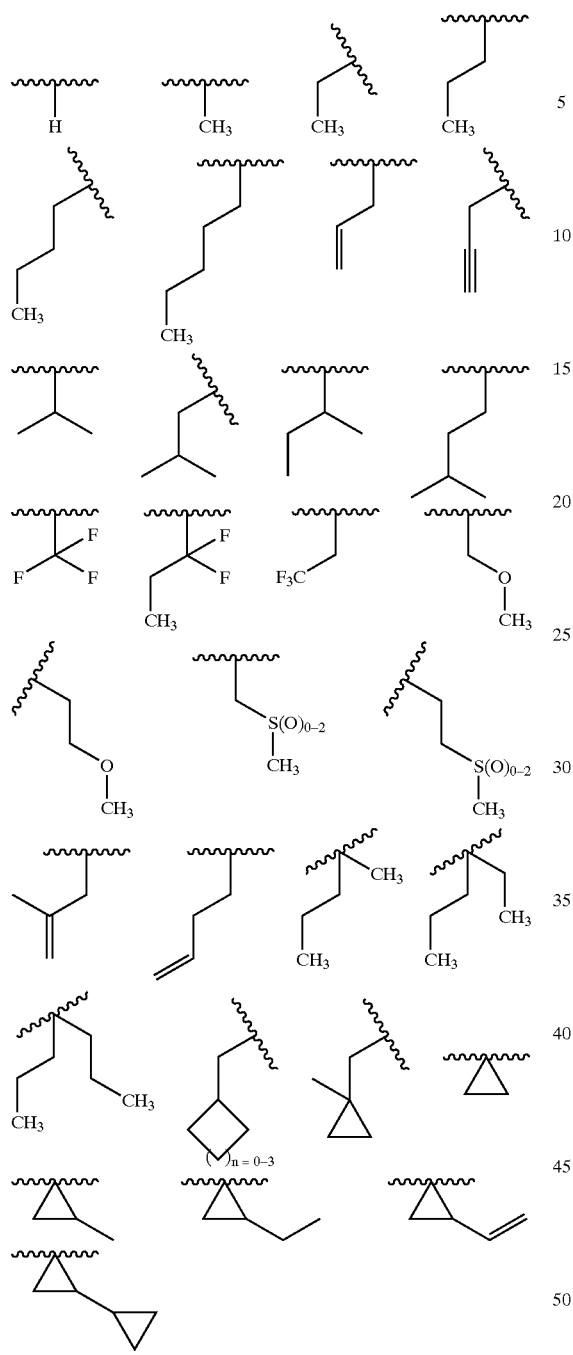

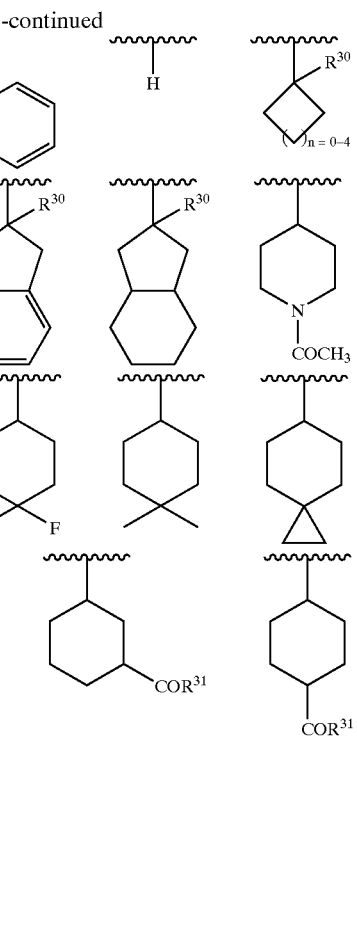

8. The compound of claim 7 wherein $R^1=COR^5$, and $R^5$ is H, OH, $COOR^8$, or $CONR^9R^{10}$.

9. The compound of claim 1, wherein $R^3$ is selected from the group consisting of:

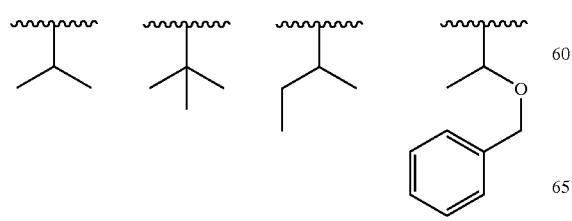

-continued wherein $R^{30}$=H, $CH_3$ or other alkyl groups;
$R^{31}$=OH, O-alkyl, $NH_2$, N-alkyl; and
$R^{32}$ and $R^{33}$ may be the same or different and are selected independently from H, F, Cl, Br and $CH_3$.

10. A compound of claim 9, wherein Z=N and $R^4$=H.

11. A compound of claim 10, wherein: X and Y are independently alkyl, alkyl-aryl, heteroaryl, alkyl ether or alkyl aryl ether.

12. A compound of claim 10, wherein the moiety X—Y is selected from the group consisting of the following structures:

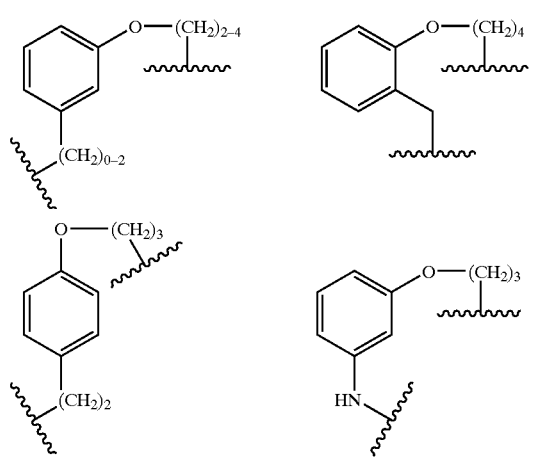

375
-continued

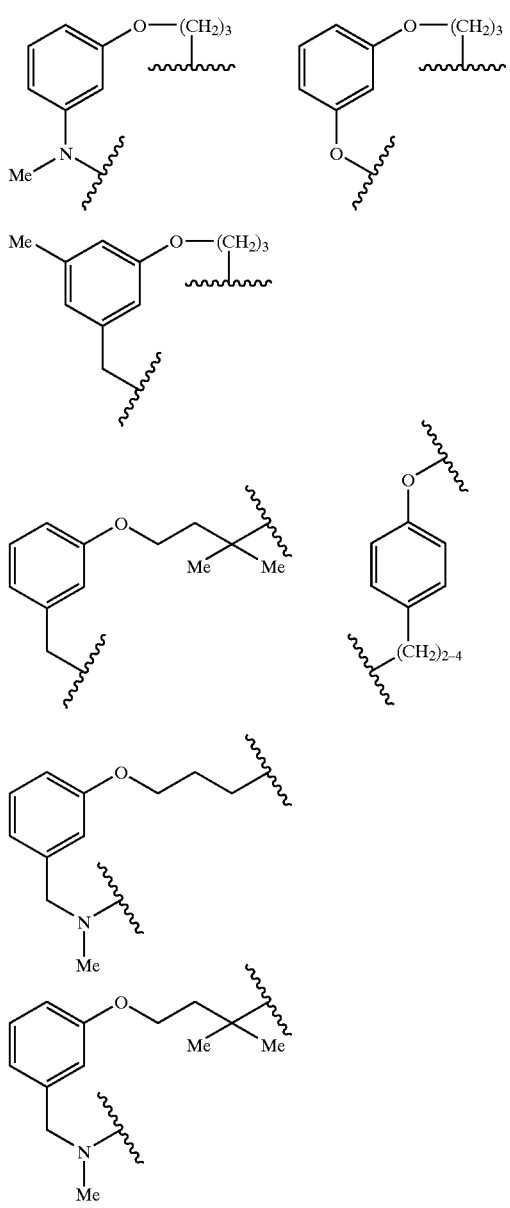

376
-continued

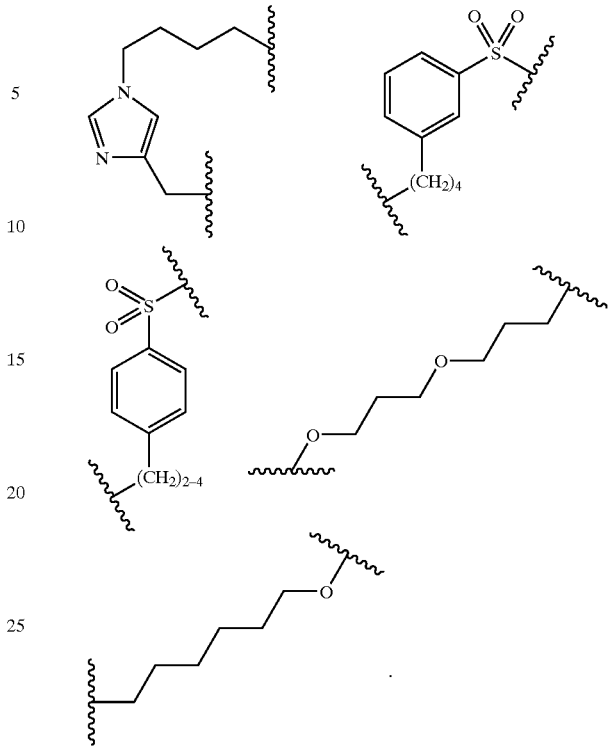

13. A pharmaceutical composition comprising as an active ingredient a compound of claim 1.

14. The pharmaceutical composition of claim 13 additionally comprising a pharmaceutically acceptable carrier.

15. A method of treating disorders associated with the Hepatitius C Virus ("HCV") protease, said method comprising administering to a patient in need of such treatment a pharmaceutical composition which comprises therapeutically effective amounts of a compound of claim 1.

16. A method of preparing a pharmaceutical composition for treating the disorders associated with the Hepatitis C Virus ("HCV") protease, said method comprising bringing into intimate contact a compound of claim 1 and a pharmaceutically acceptable carrier.

17. A compound exhibiting Hepatitis C Virus ("HCV") protease inhibitory activity, including enantiomers, stereoisomers and tautomers of said compound, and pharmaceutically acceptable salts or solvates of said compound, said compound being selected from the compounds of structures listed below:

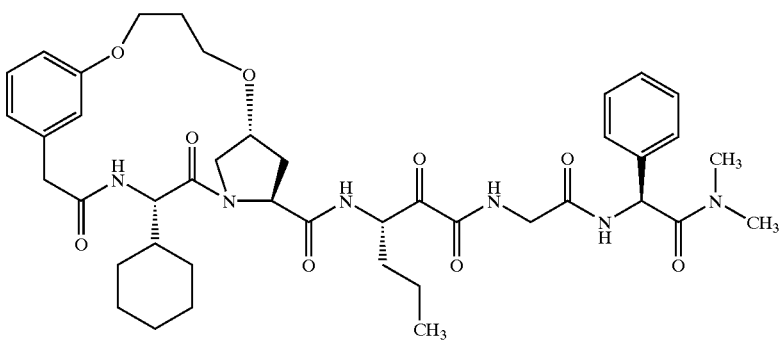

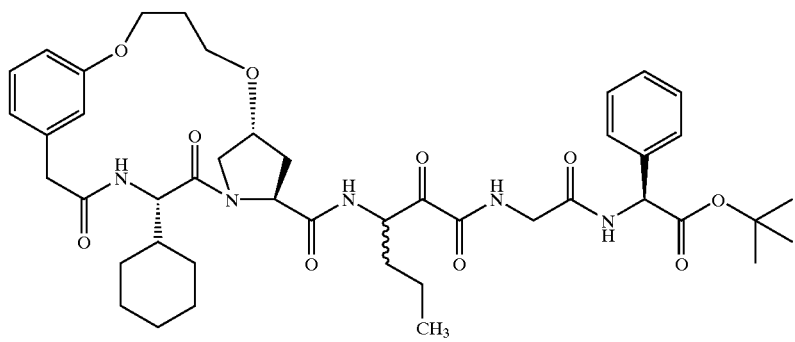
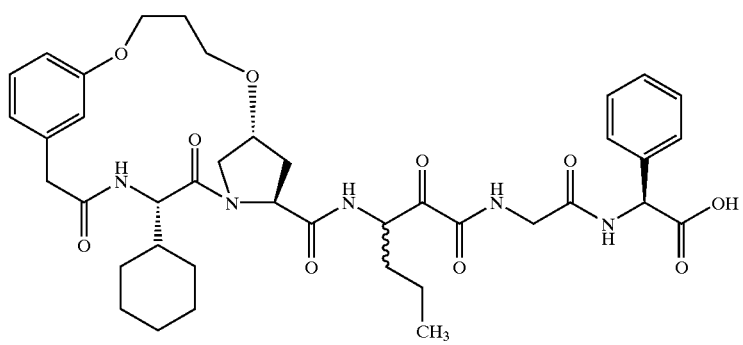
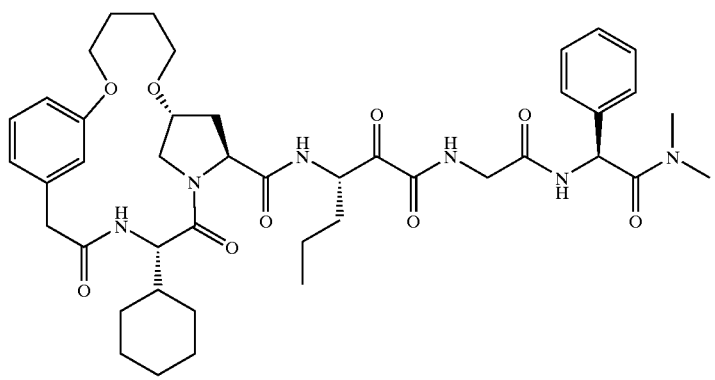
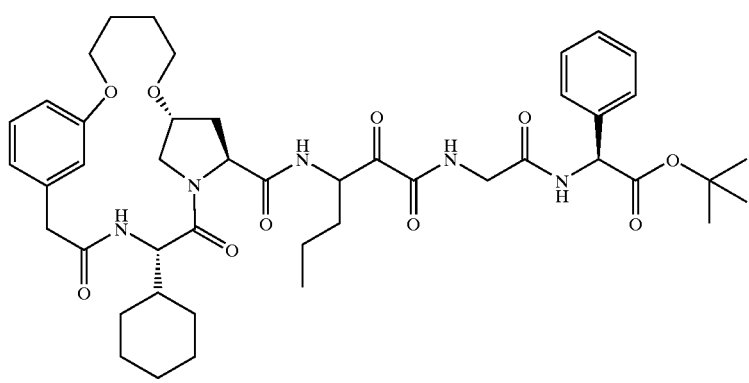

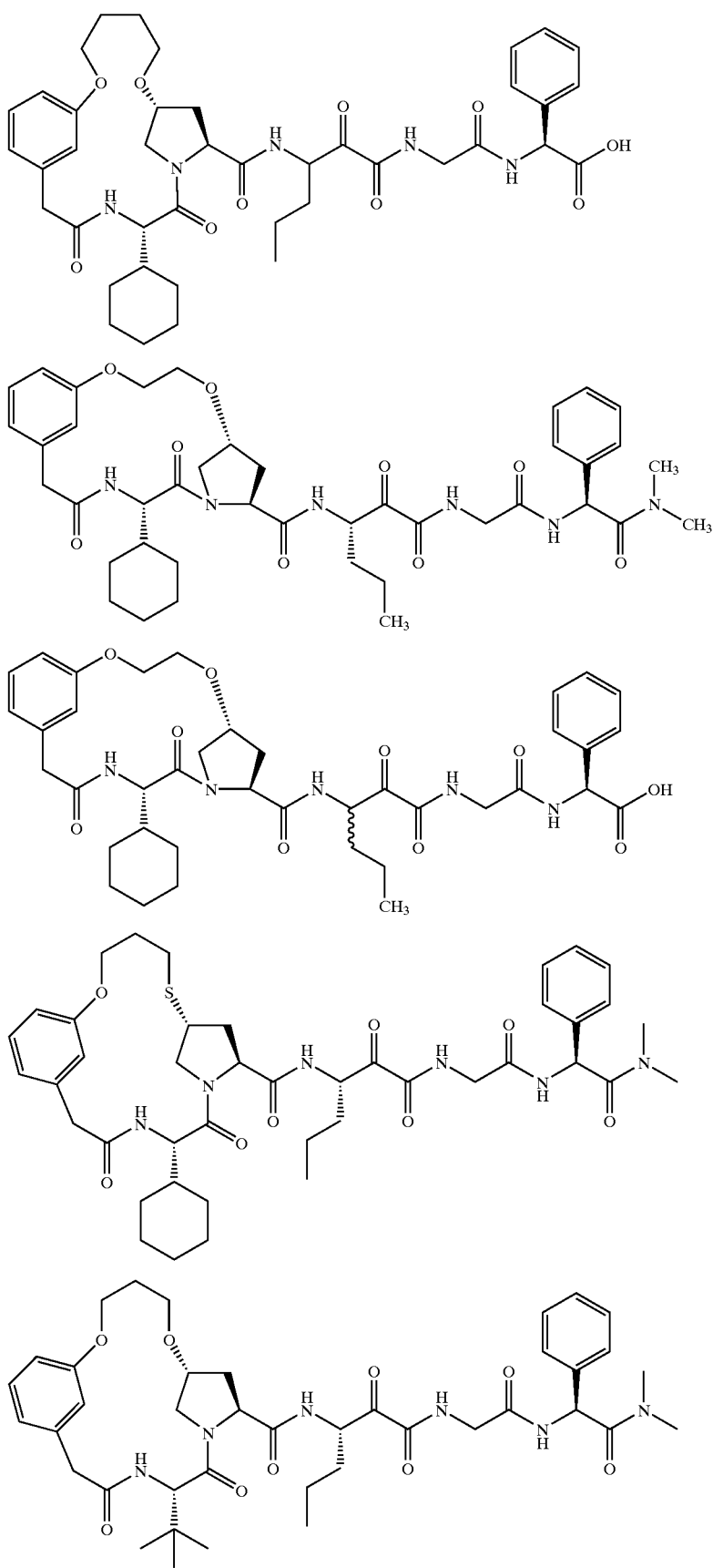

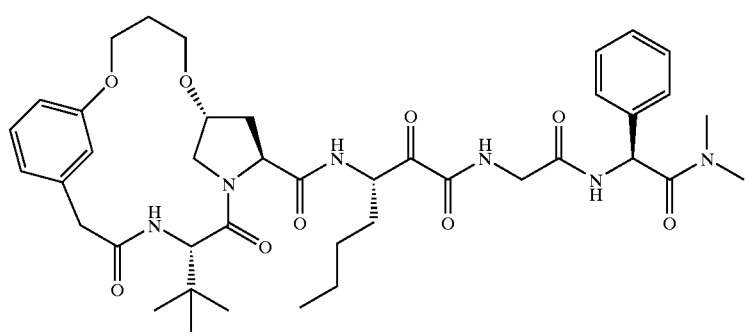
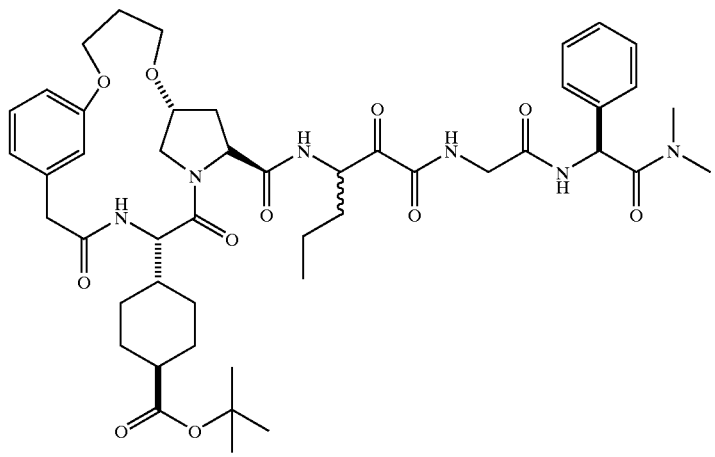
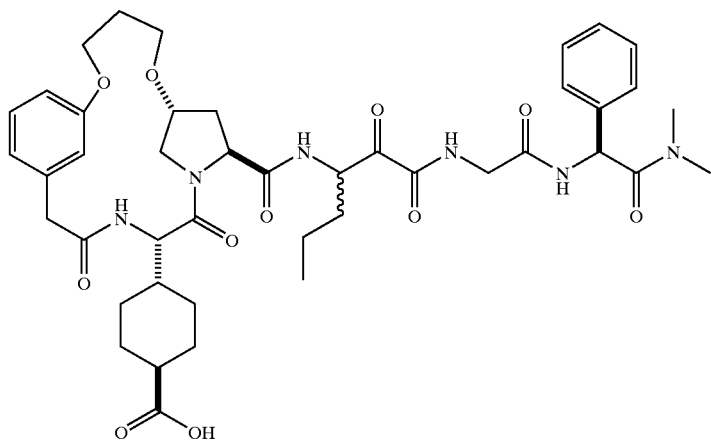
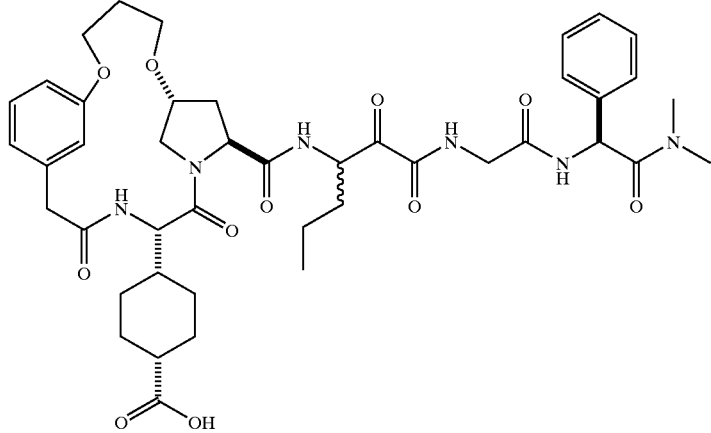

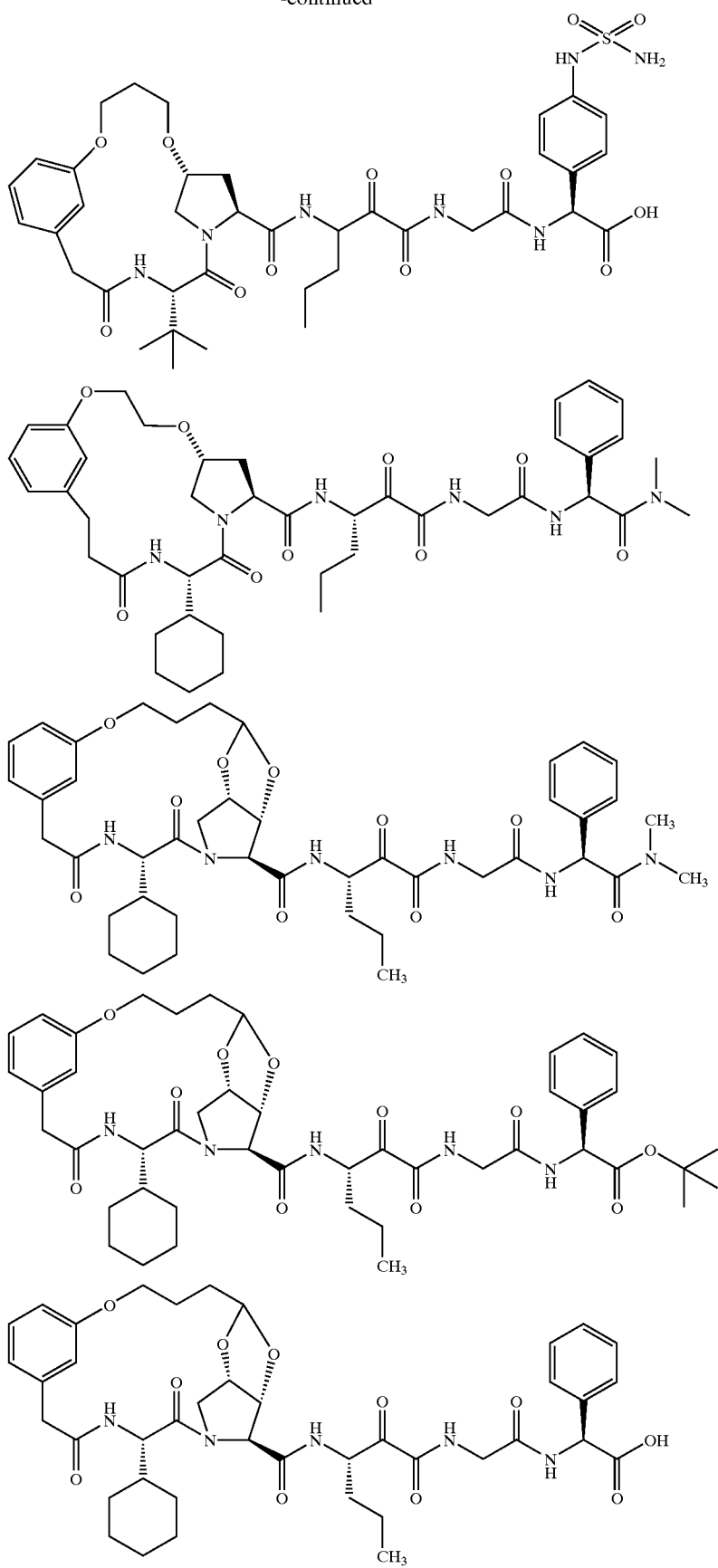

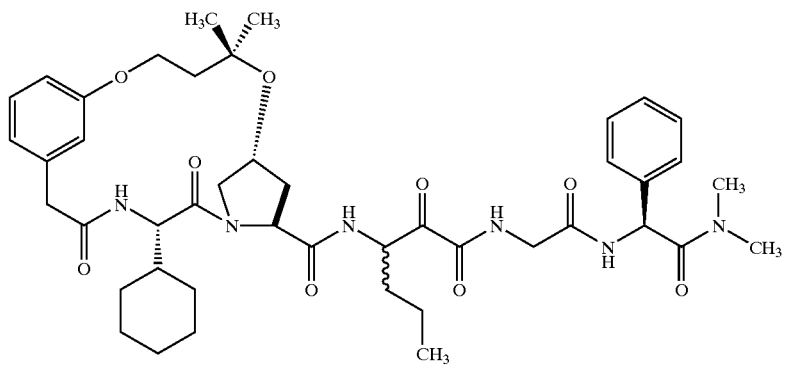
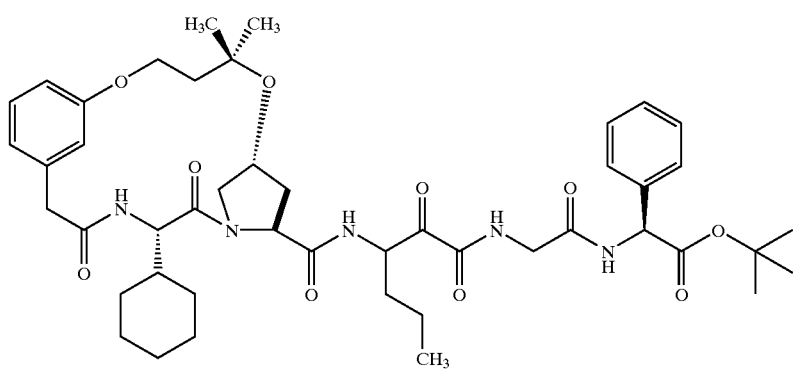
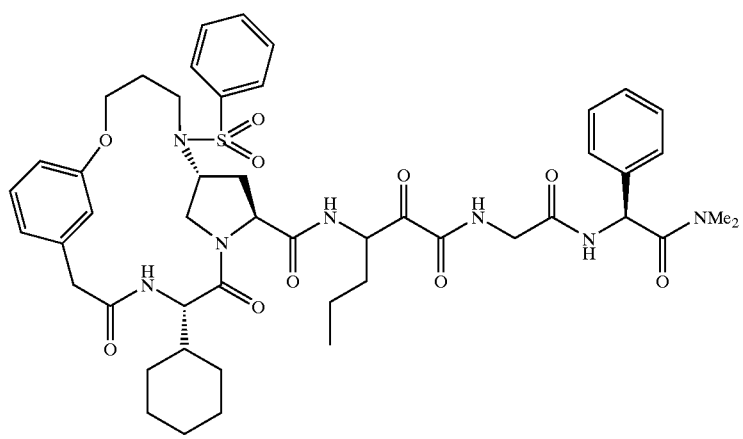
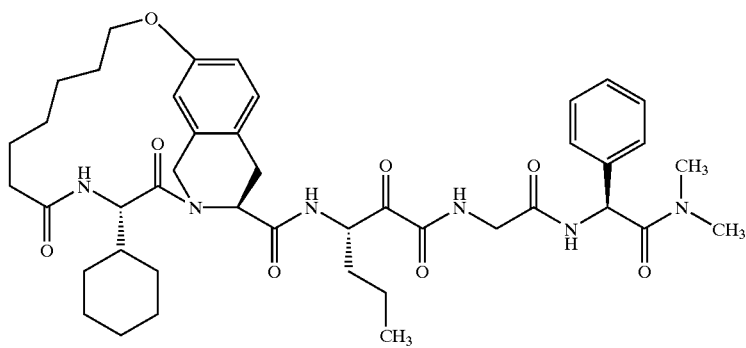

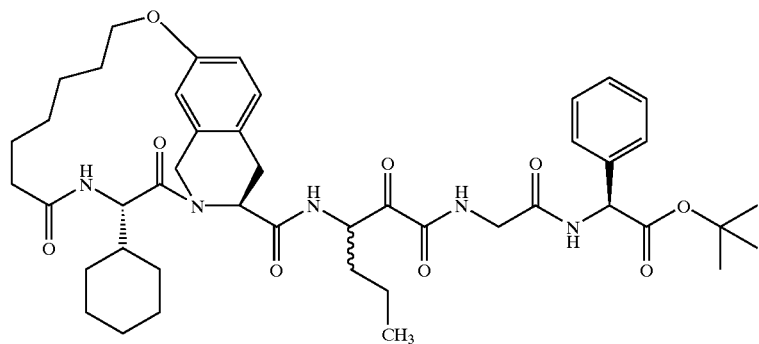
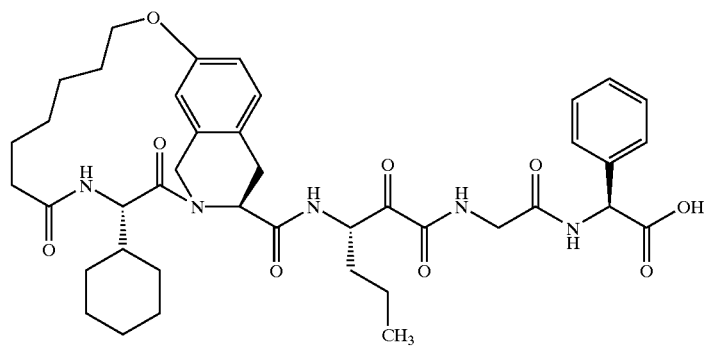
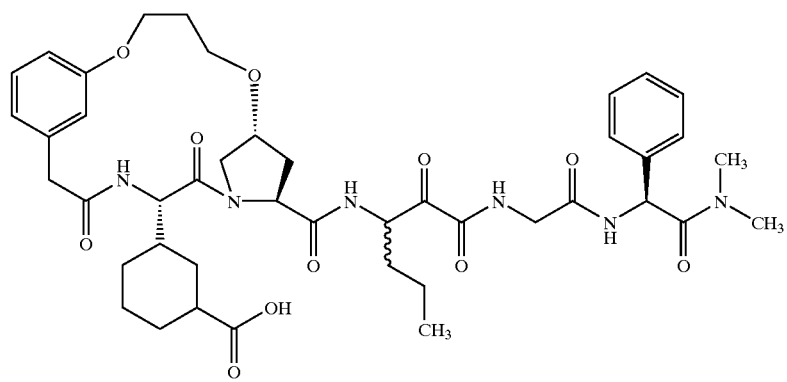
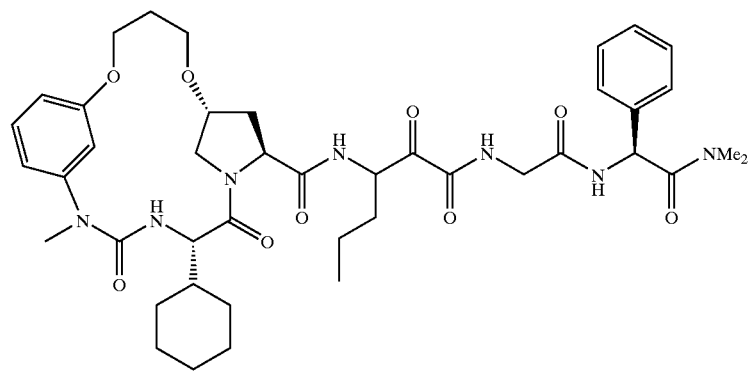

-continued
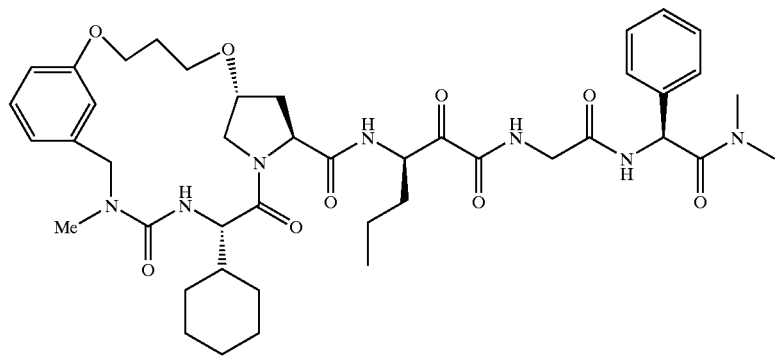
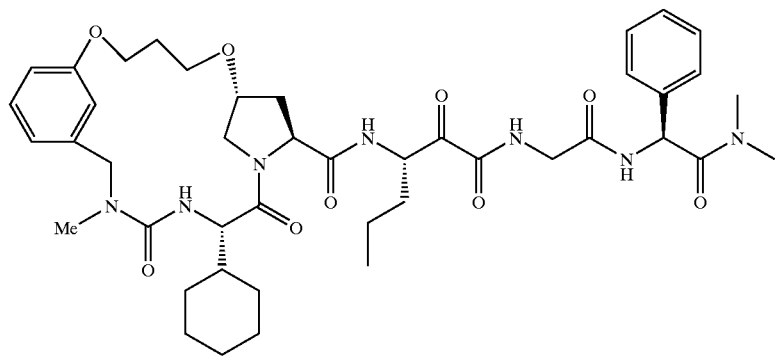
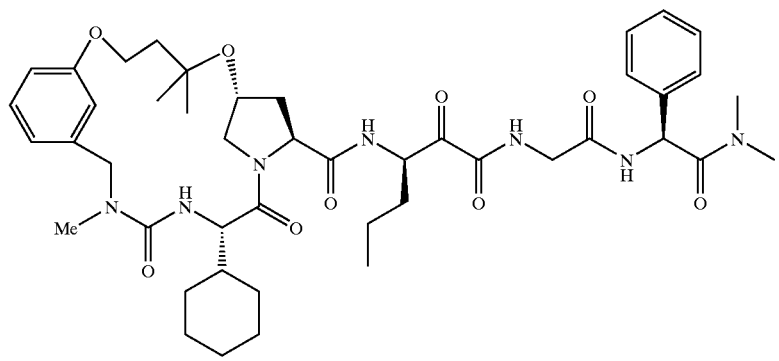
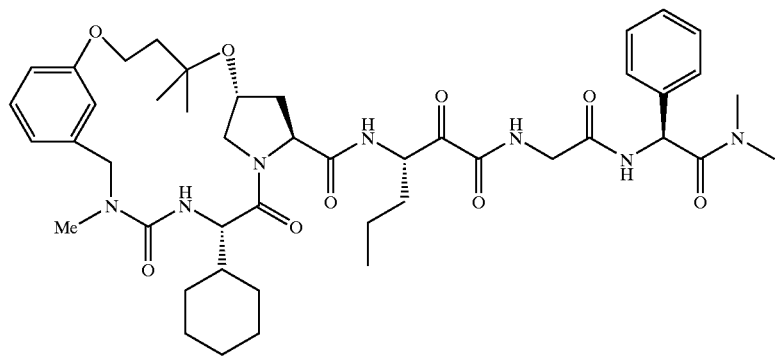

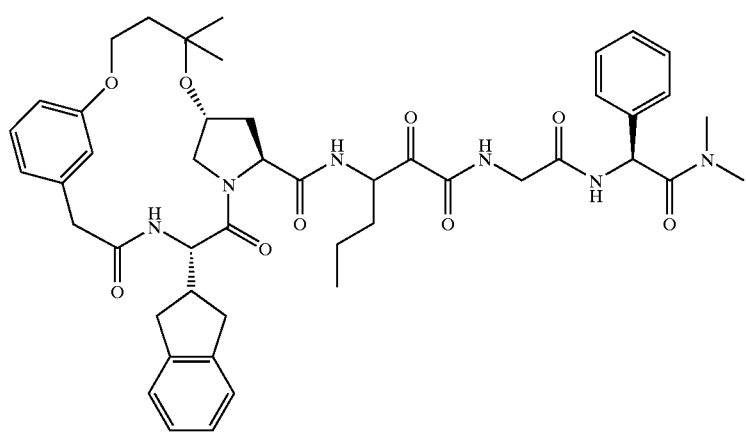
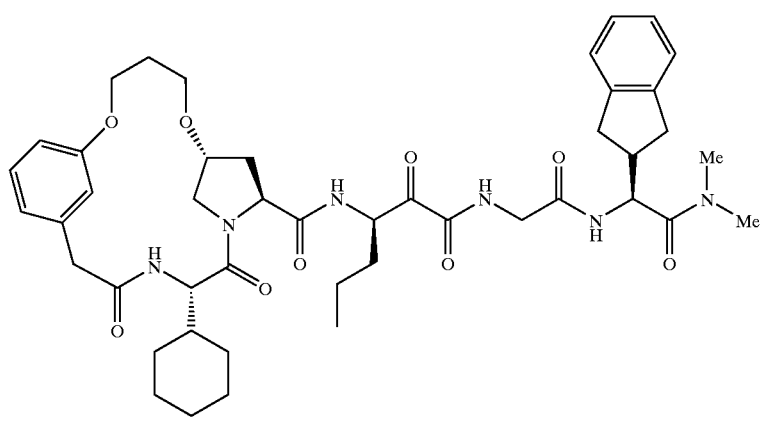
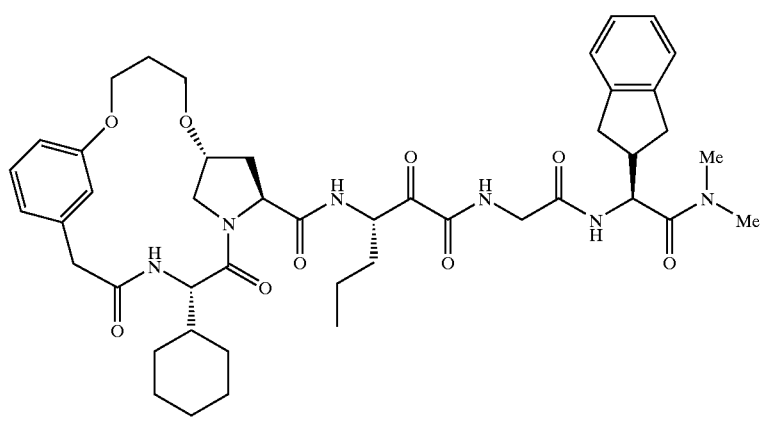
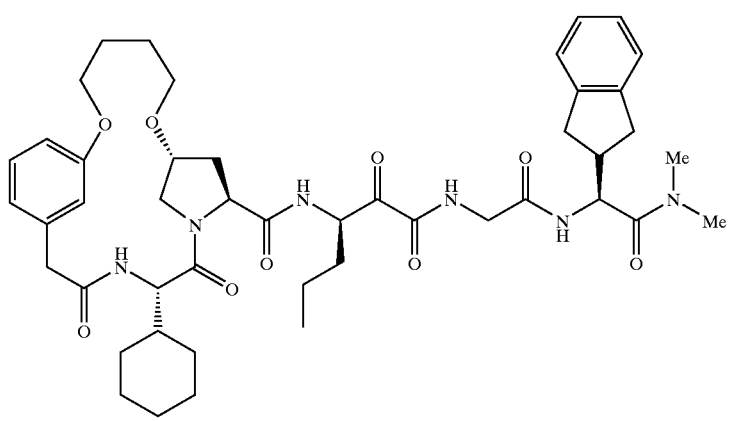

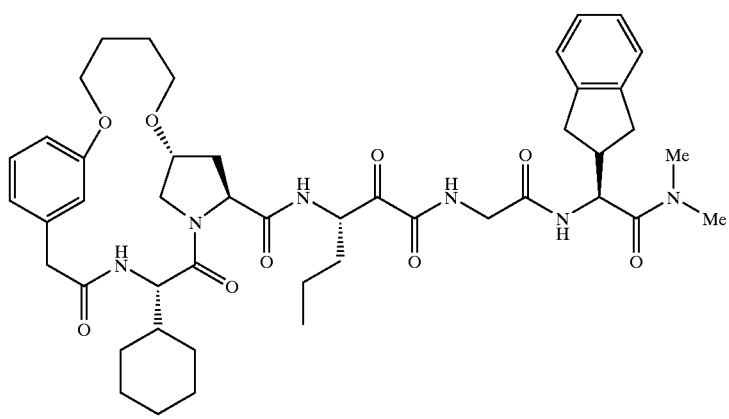
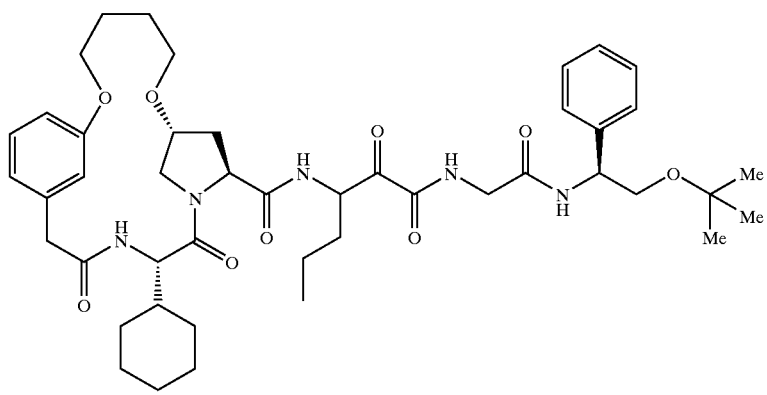
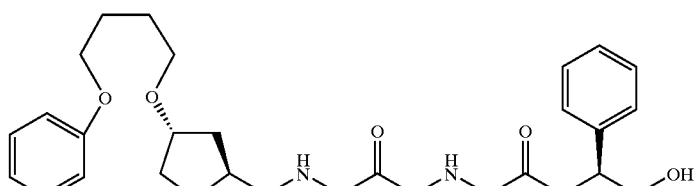
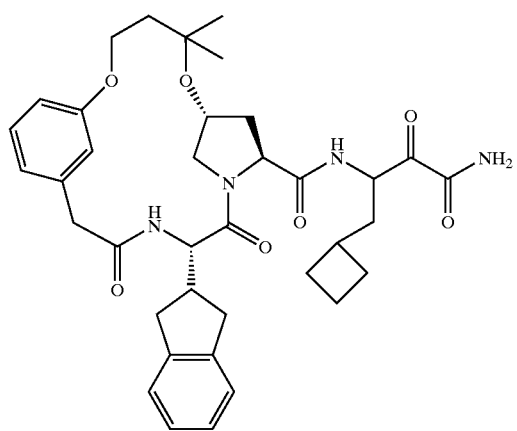

-continued
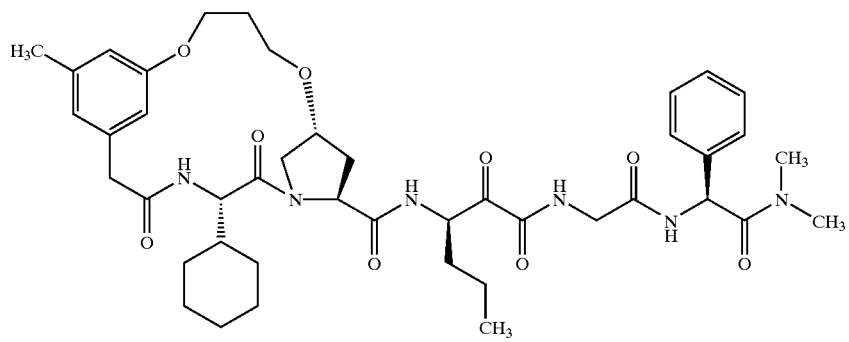
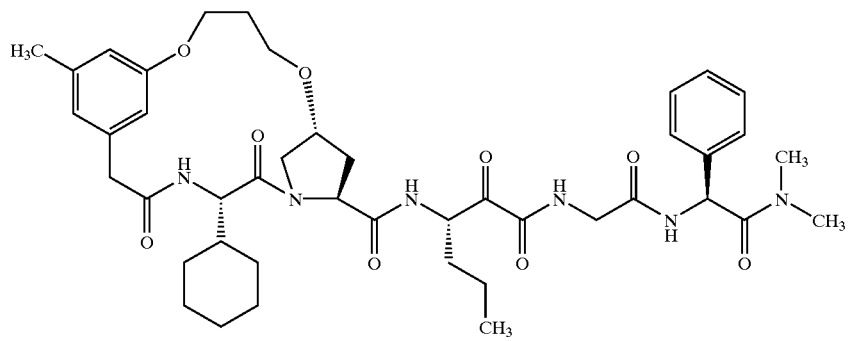
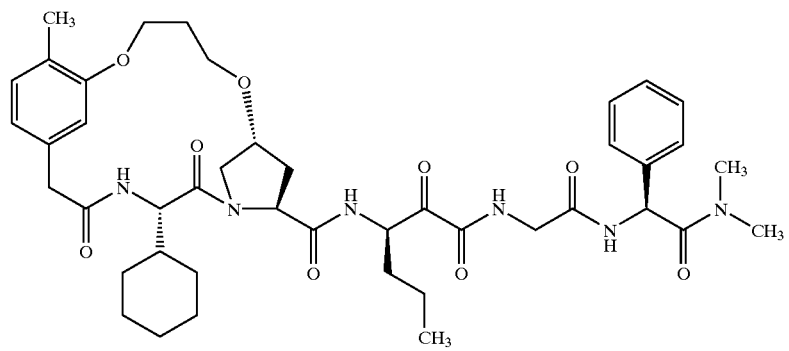
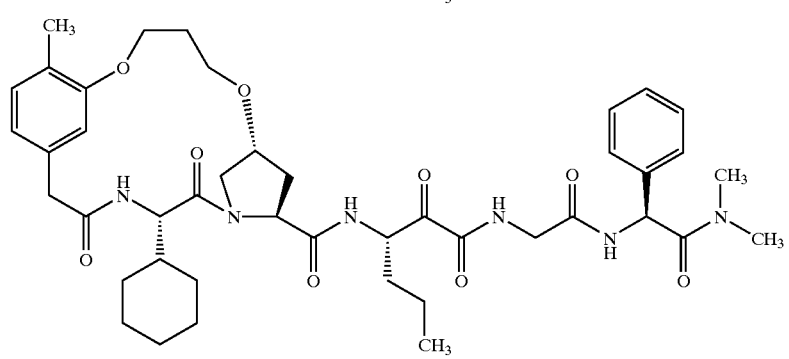
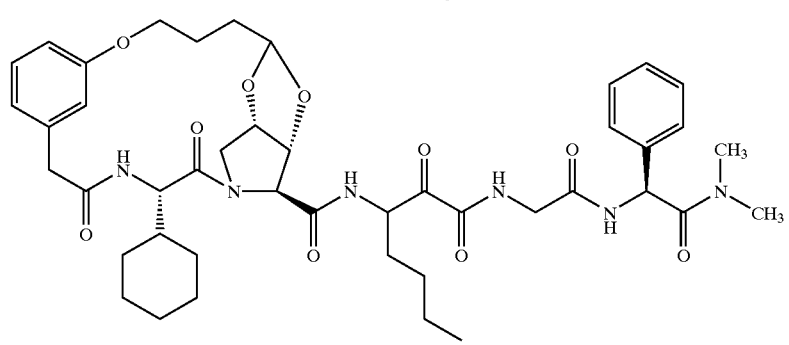

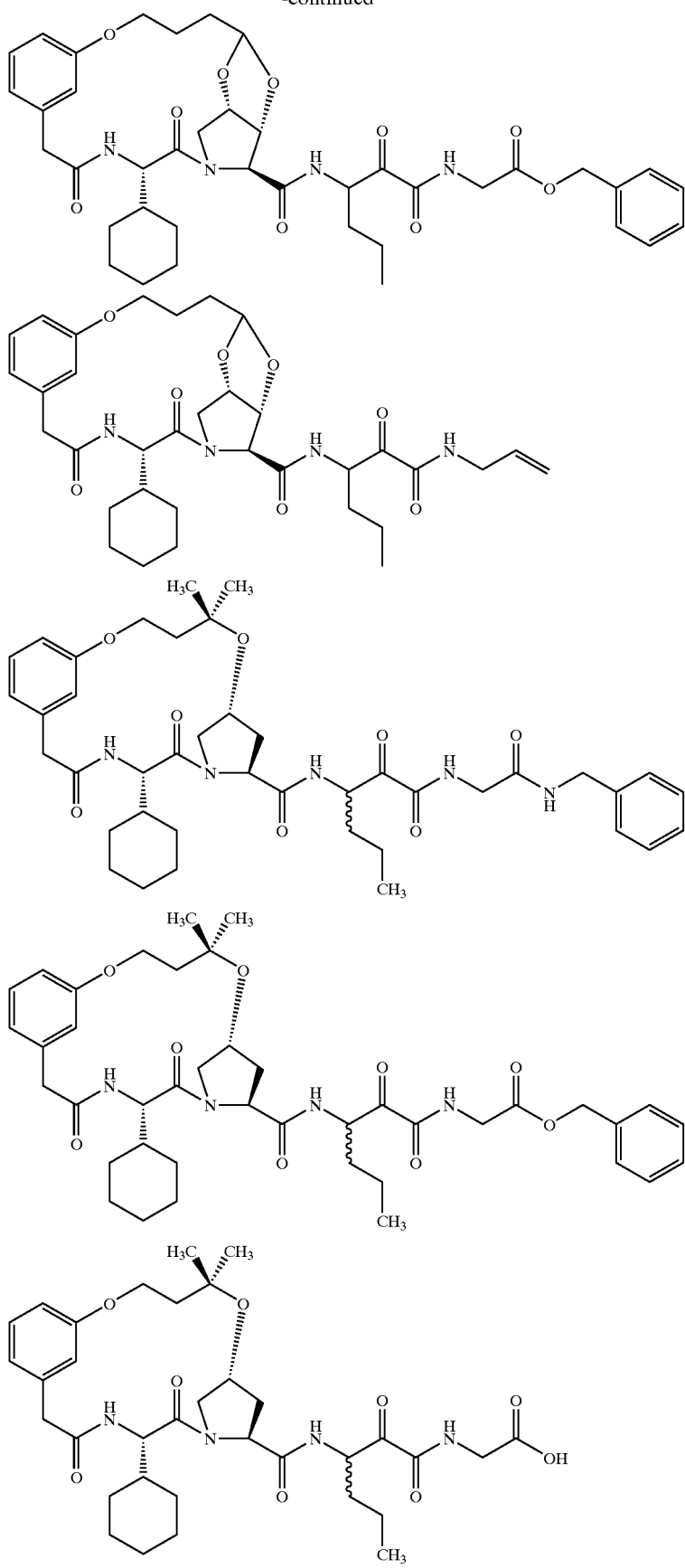

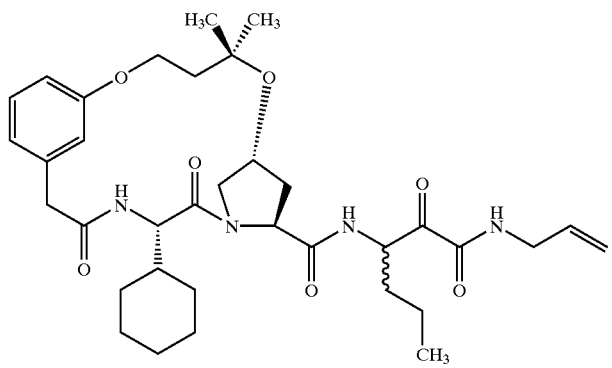
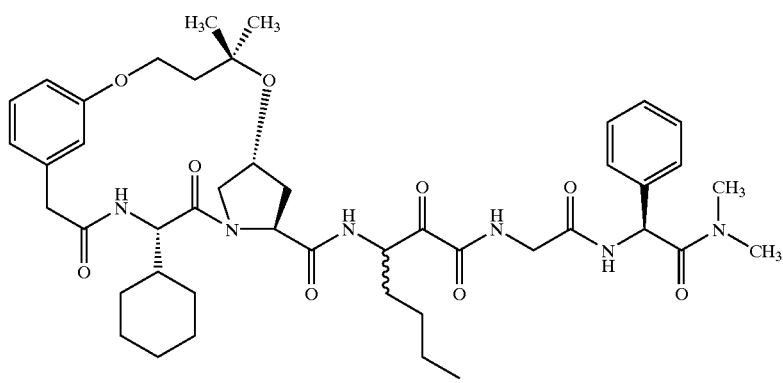
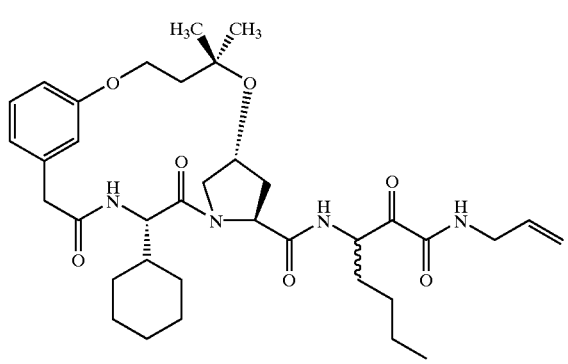
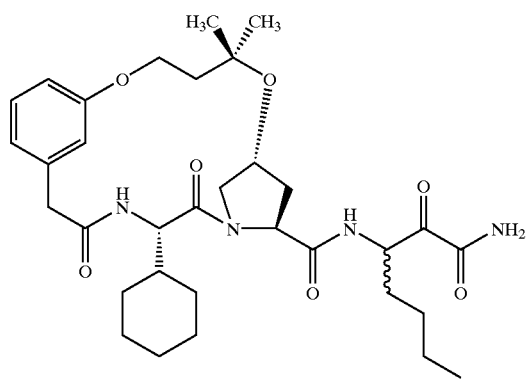
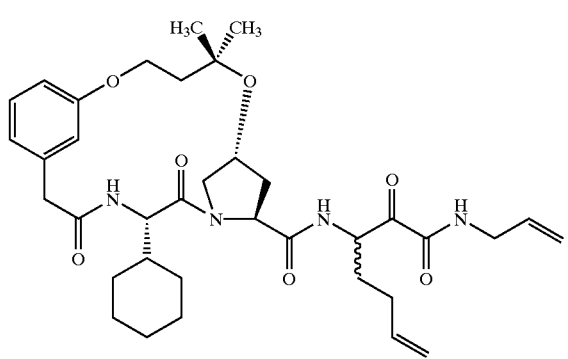
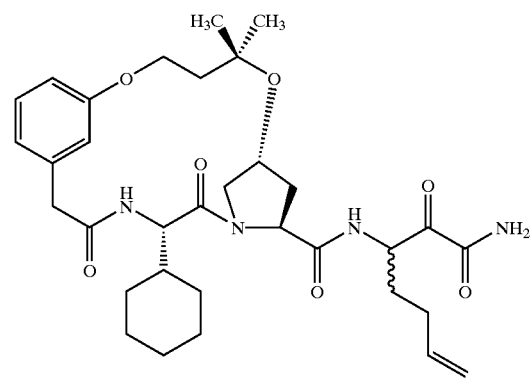

401                                    402
-continued
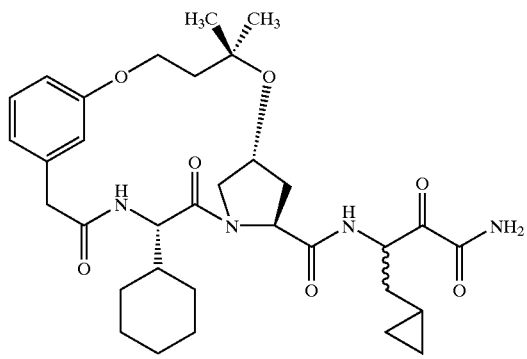
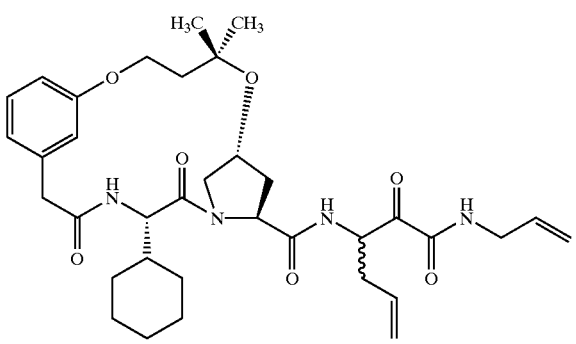
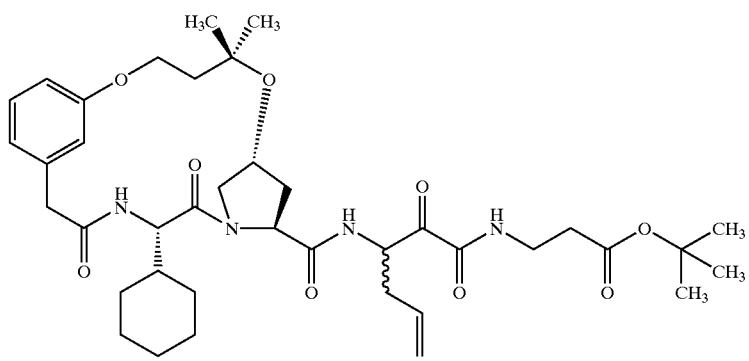
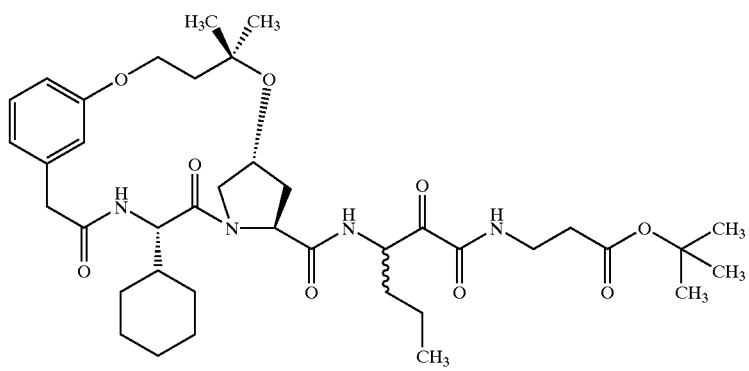
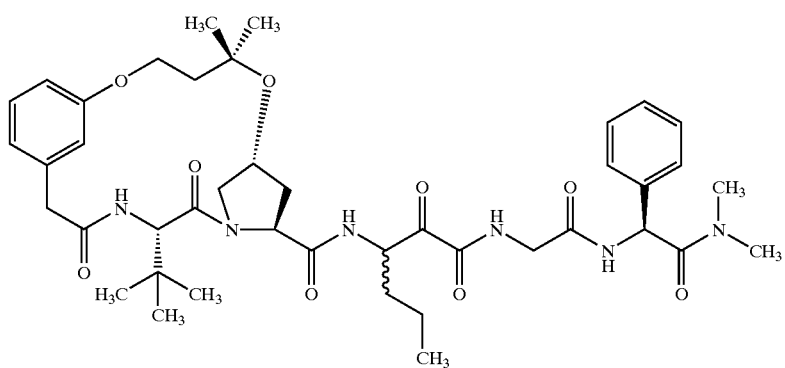

-continued
| 403 | 404 |
|---|---|
| 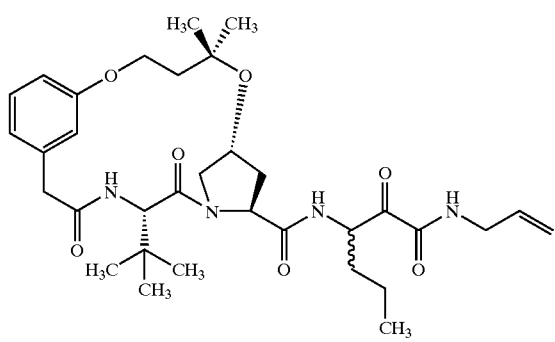 | 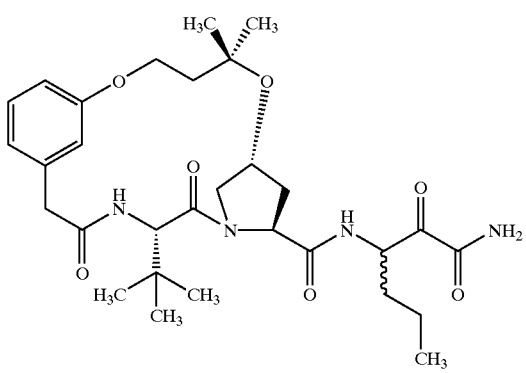 |
| 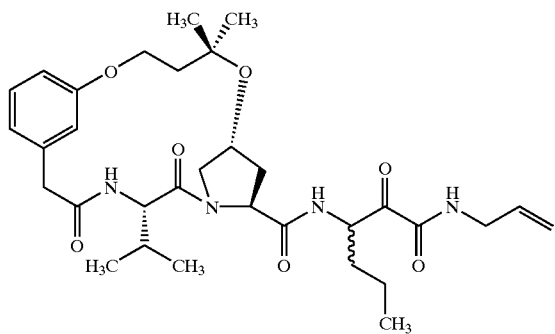 | 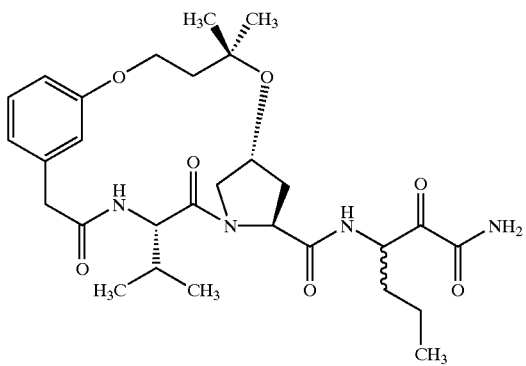 |
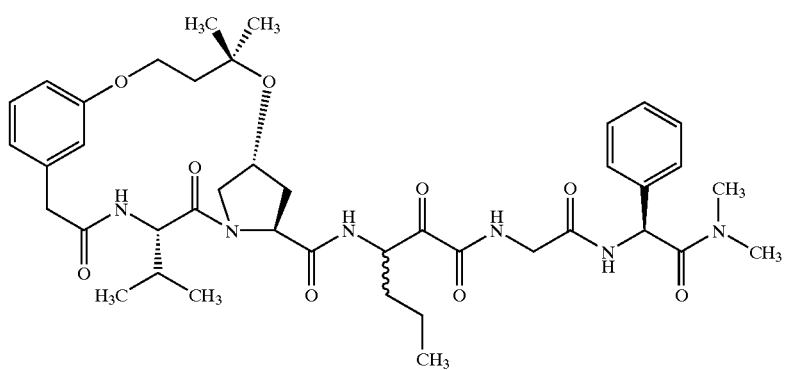
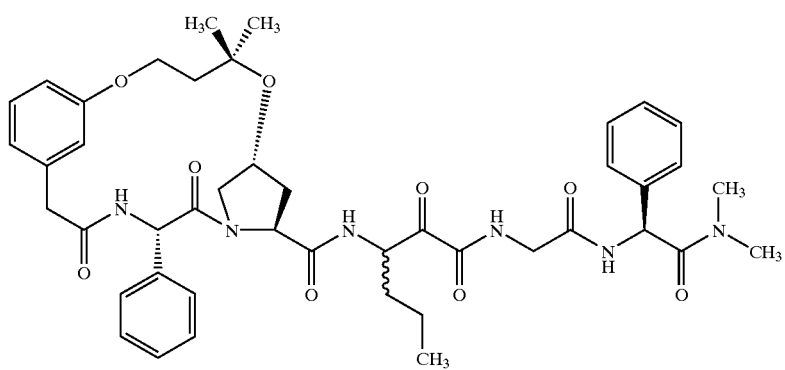

405
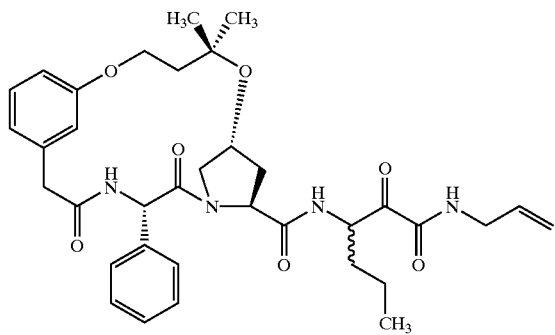
406
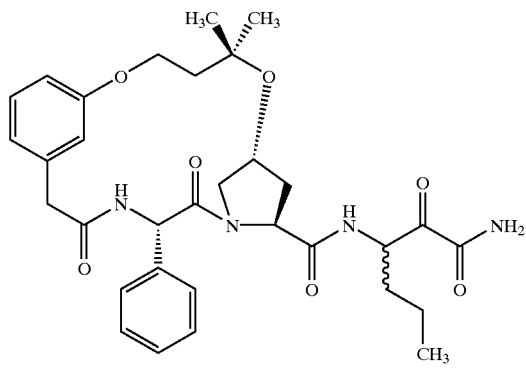
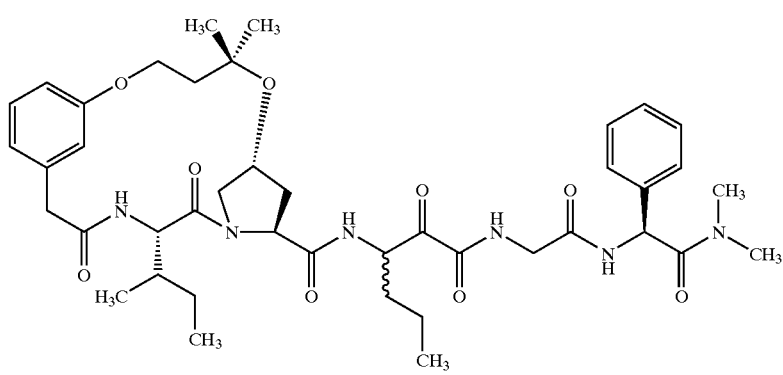
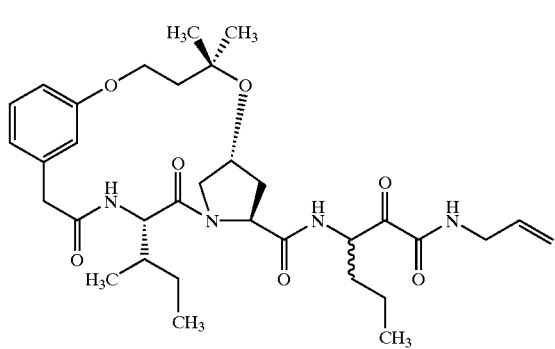
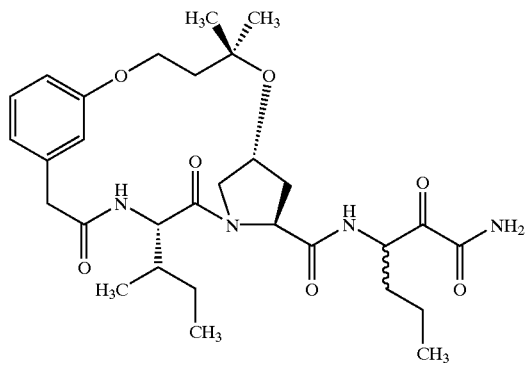
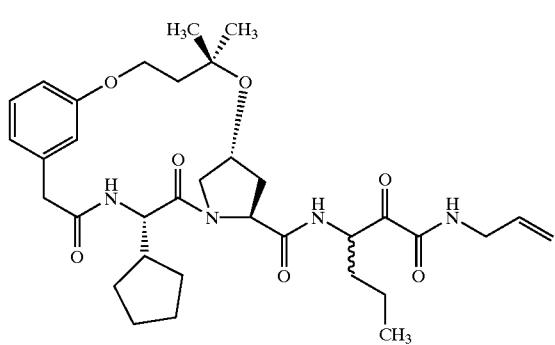
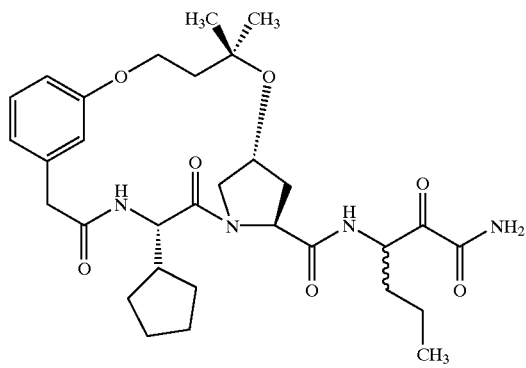

407

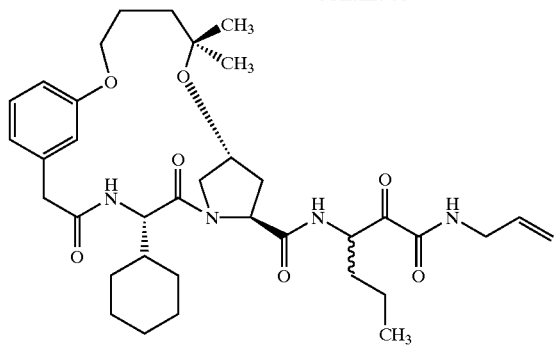

408

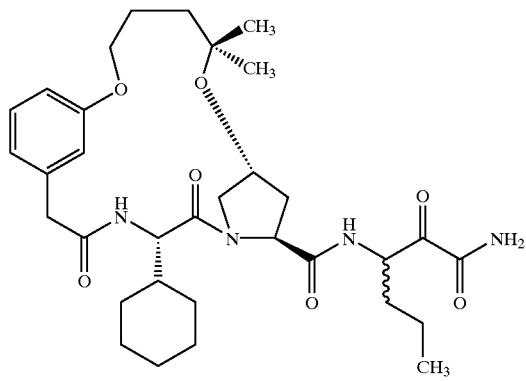

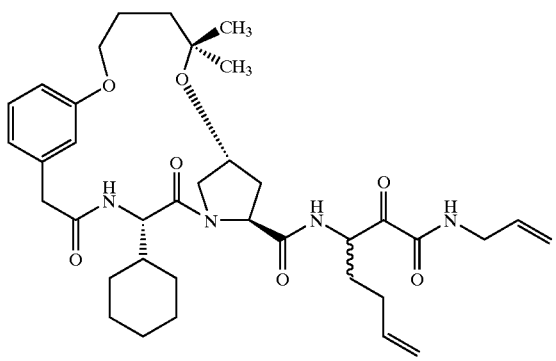

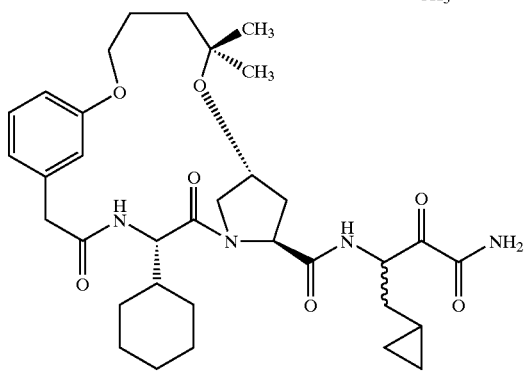

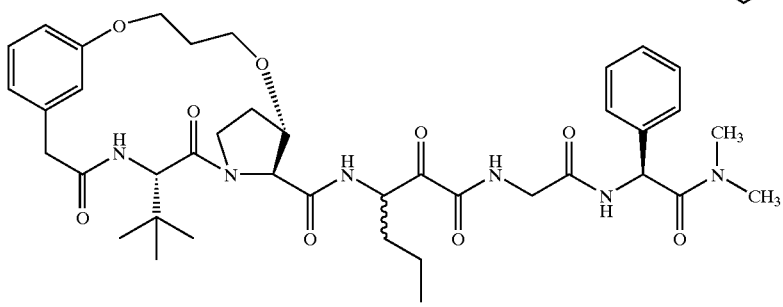

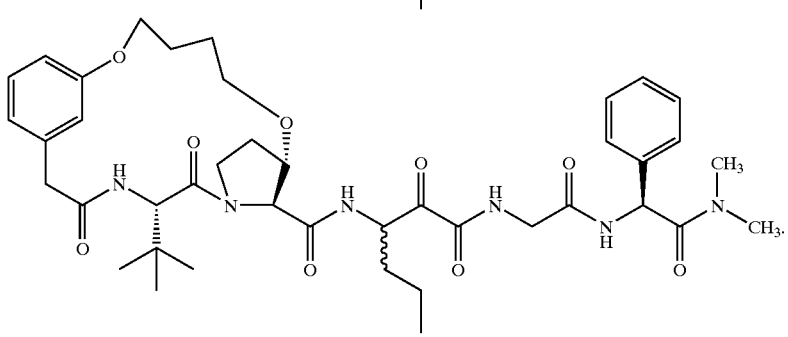

18. A pharmaceutical composition for treating disorders associated with the Hepatitis C Virus ("HCV") protease, said composition comprising therapeutically effective amount of one or more compounds in claim 17 and a pharmaceutically acceptable carrier.

19. The pharmaceutical composition of claim 18, additionally containing an antiviral agent.

20. The pharmaceutical composition of claim 18 or claim 19, additionally containing an interferon.

21. The pharmaceutical composition of claim 20, wherein said antiviral agent is ribavirin and said interferon is α-interferon.

* * * * *

UNITED STATES PATENT AND TRADEMARK OFFICE
CERTIFICATE OF CORRECTION

PATENT NO. : 6,846,802 B2
DATED : January 25, 2005
INVENTOR(S) : Kevin X. Chen et al.

It is certified that error appears in the above-identified patent and that said Letters Patent is hereby corrected as shown below:

Title page,
Item [75], Inventors, please correct inventor "George F. Njoroge" to -- F. George Njoroge --.

Column 371,
Lines 15-22, please replace the structure on the right side with the corrected structure:

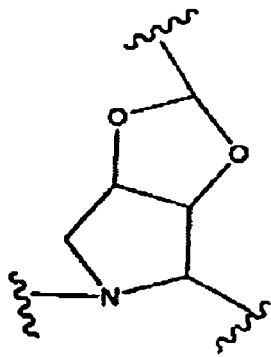

Lines 26-32, please replace the structure on the right side with the corrected structure:

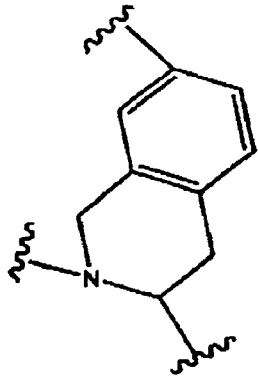

Line 60, please correct "COR7" to -- $COR^7$ --.

UNITED STATES PATENT AND TRADEMARK OFFICE
CERTIFICATE OF CORRECTION

PATENT NO. : 6,846,802 B2
DATED : January 25, 2005
INVENTOR(S) : Kevin X. Chen et al.

It is certified that error appears in the above-identified patent and that said Letters Patent is hereby corrected as shown below:

Column 372,
Line 3, please correct "COO $R^{11}$" to -- $COOR^{11}$ --.
Line 16, please correct "W is;" to -- W is C=O; --.

Column 374,
Line 44, please insert -- heteroalkyl -- between "alkyl-aryl" and "heteroaryl".

Column 376,
Line 35, please correct "Hepatitius" to -- Hepatitis --.

Signed and Sealed this

Twenty-second Day of November, 2005

JON W. DUDAS
*Director of the United States Patent and Trademark Office*